(12) United States Patent
Bradbury et al.

(10) Patent No.: US 8,003,649 B2
(45) Date of Patent: Aug. 23, 2011

(54) BICYCLIC DERIVATIVES FOR USE IN THE TREATMENT OF ANDROGEN RECEPTOR ASSOCIATED CONDITIONS-155

(75) Inventors: Robert Hugh Bradbury, Macclesfield (GB); Alfred Arthur Rabow, Macclesfield (GB); Neil James Hales, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/338,405

(22) Filed: Dec. 18, 2008

(65) Prior Publication Data

US 2010/0016279 A1   Jan. 21, 2010

Related U.S. Application Data

(60) Provisional application No. 61/015,755, filed on Dec. 21, 2007, provisional application No. 61/096,090, filed on Sep. 11, 2008, provisional application No. 61/107,804, filed on Oct. 23, 2008.

(51) Int. Cl.
| | |
|---|---|
| *A61N 31/50* | (2006.01) |
| *A61K 31/501* | (2006.01) |
| *A61K 31/41* | (2006.01) |
| *A01N 43/64* | (2006.01) |
| *C07D 487/00* | (2006.01) |
| *C07D 249/00* | (2006.01) |

(52) U.S. Cl. ............... 514/252.05; 514/360; 514/383; 544/236; 548/262.4

(58) Field of Classification Search ............ 514/252.05, 514/360, 383; 544/236; 548/262.4
See application file for complete search history.

(56) References Cited

FOREIGN PATENT DOCUMENTS

| WO | 2006039325 A2 | 4/2006 |
|---|---|---|
| WO | 2008109104 A1 | 9/2008 |

OTHER PUBLICATIONS

RN 334500-45-7 Registry file of chemical abstract services entered STN on May 3, 2001.*
RN 927049-23-8 Registry file of chemical abstract services entered STN on Mar. 18, 2007.*
RN 930466-59-4 Registry file of chemical abstract services entered STN on Apr. 17, 2007.*
RN 930503-83-6 Registry file of chemical abstract services entered STN on Apr. 17, 2007.*
RN 931060-90-1 Registry file of chemical abstract services entered STN on Apr. 19, 2007.*
Bioorg. Med. Chem. Lett. 2007; vol. 17; Issue 16, pp. 4579-4583.
Sep. 23, 2008 Novelty Search Results.
Vasaitis et. al. Androgen receptor inactivation contributes to antitumor efficacy of 17 -hydroxylase/17,20-lyase inhibitor 3 -hydroxy-17-(1H-benzimidazole-1-yl)androsta-5, 16-diene in prostate cancer; Molecular Cancer Therapeutics 2008;7(8). Aug. 2008; pp. 2348-2357.

* cited by examiner

Primary Examiner — San-Ming Hui
Assistant Examiner — Paul Zarek

(57) ABSTRACT

The invention concerns bicyclic compounds of Formula I

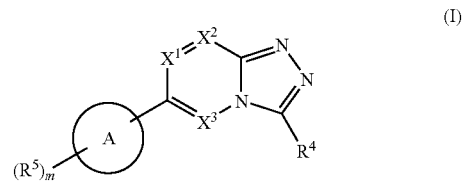

(I)

wherein the integers $X^1$, $X^2$, $X^3$, Ring A, $R^4$, $R^5$ and m are as defined in the description. The present invention also relates to processes for the preparation of such compounds, pharmaceutical compositions containing them and their use in the manufacture of a medicament for use in the prevention or treatment of androgen-receptor associated conditions.

15 Claims, 5 Drawing Sheets

X-Ray Powder Diffraction Pattern for 4-pyridin-3-yl-1-[3-(trifluoromethyl)[1,2,4]triazolo[4,3-b]pyridazin-6-yl]piperidin-4-ol Anhydrous Form A
when measured using CuKa radiation

Figure 1: X-Ray Powder Diffraction Pattern for 4-pyridin-3-yl-1-[3-(trifluoromethyl)[1,2,4]triazolo[4,3-b]pyridazin-6-yl]piperidin-4-ol Anhydrous Form A when measured using CuKa radiation
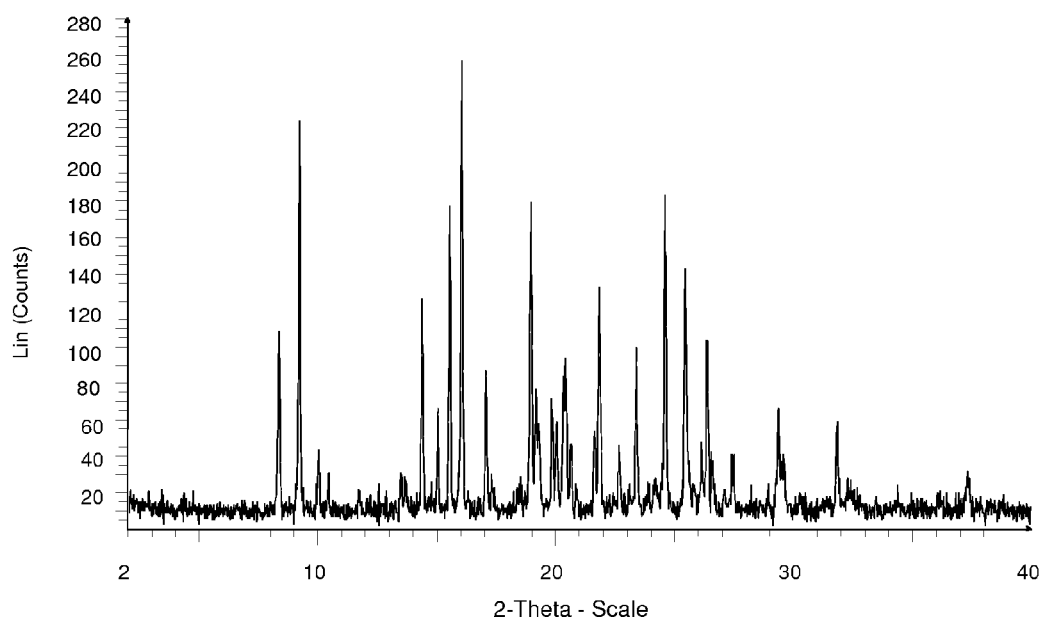

Figure 2: X-Ray Powder Diffraction Pattern for N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A when measured using CuKa radiation
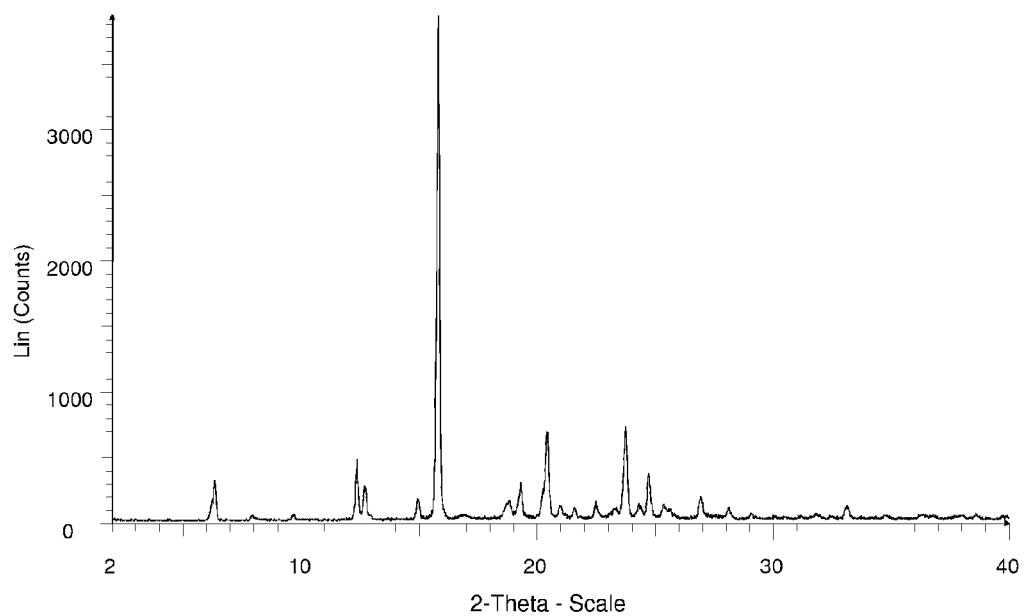

Figure 3: X-Ray Powder Diffraction Pattern for 6-[4-[4-[2-(1-Methyl-1H-pyrazol-5-yl)ethoxy]phenyl]piperidin-1-yl]-3-(trifluoromethyl)[1,2,4]triazolo[4,3-b]pyridazine Anhydrous Form A when measured using CuKa radiation
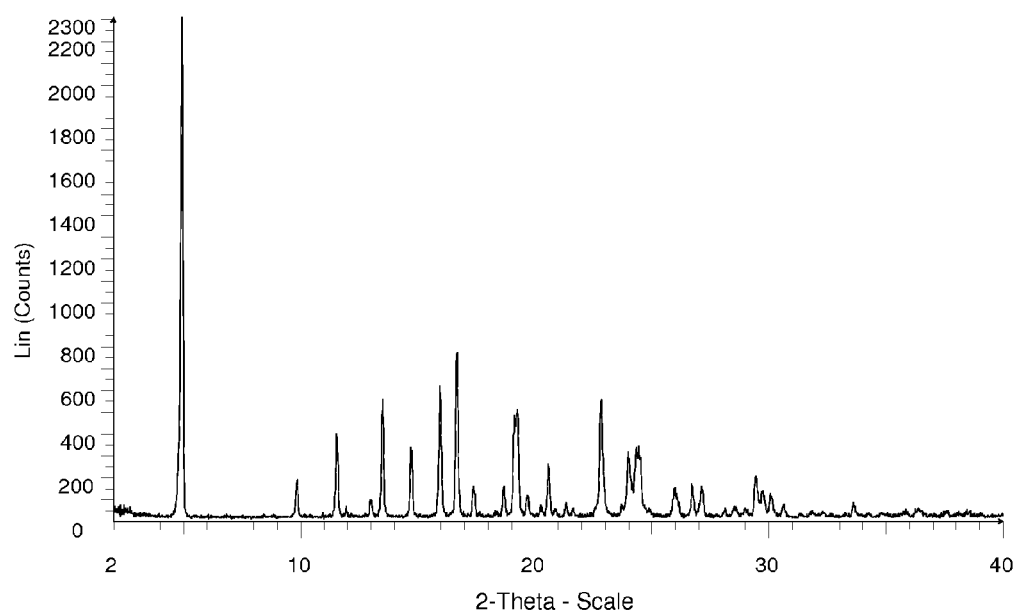

Figure 4: X-Ray Powder Diffraction Pattern for 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine Anhydrous Form A when measured using CuKa radiation
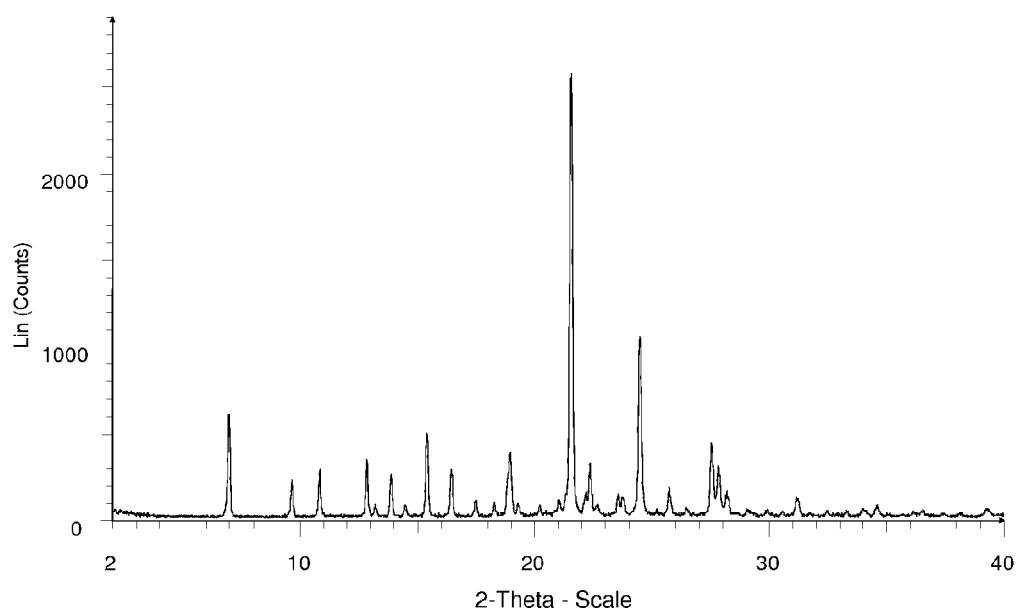

Figure 5: X-Ray Powder Diffraction Pattern for 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate when measured using CuKa radiation
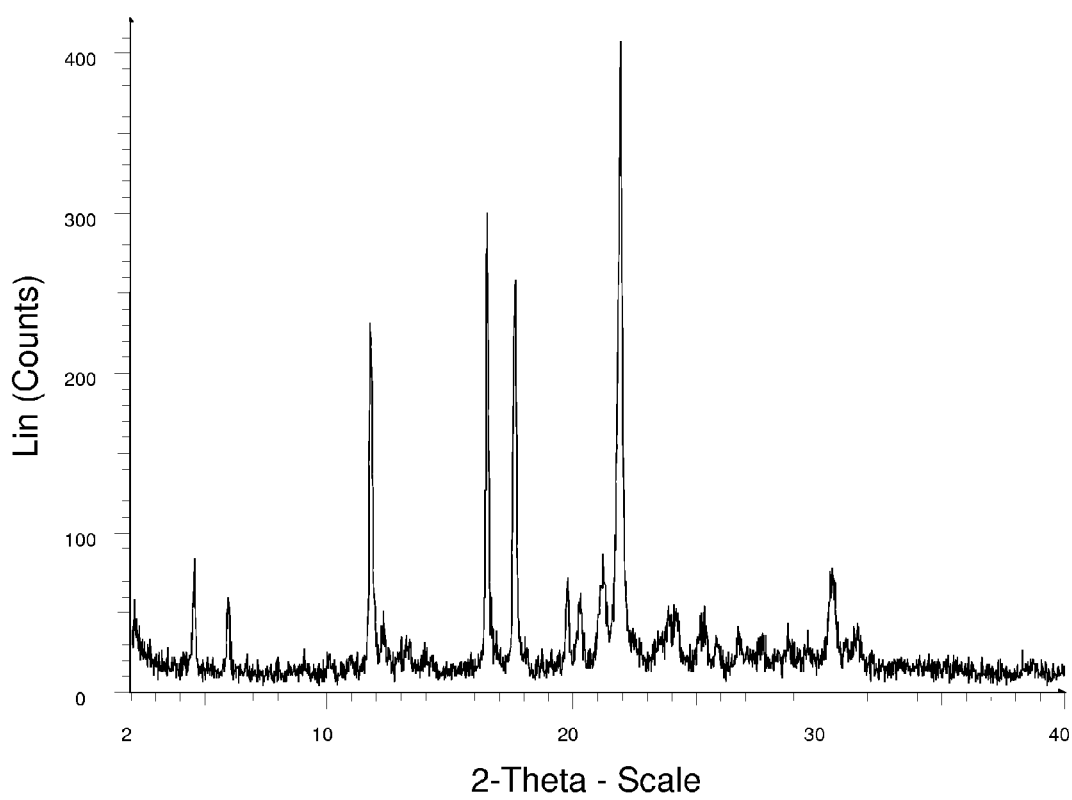

BICYCLIC DERIVATIVES FOR USE IN THE TREATMENT OF ANDROGEN RECEPTOR ASSOCIATED CONDITIONS-155

This application claims the benefit under 35 U.S.C. §119(e) of U.S. Provisional Application No. 61/015,755 (filed on 21 Dec. 2007), U.S. Provisional Application No. 61/096,090 (filed on 11 Sep. 2008), and U.S. Provisional Application No. 61/107,804 (filed on 23 Oct. 2008), the contents of each of which are hereby incorporated by reference.

This invention relates to new bicyclic derivatives and, more particularly, to bicyclic derivatives that act as ligands of the androgen receptor (AR). This invention also relates to methods for the preparation of such bicyclic derivatives, and novel intermediates in the preparation thereof, to pharmaceutical compositions containing such bicyclic derivatives, to the use of such bicyclic derivatives in the preparation of medicines, and to the use of such bicyclic derivatives in the treatment of androgen-receptor associated condition such as prostate cancer.

Prostate cancer is the second most common cause of death from cancer amongst men in developed countries. Four percent of deaths amongst men over 55 can be attributed to prostate cancer. Although the death rate is relatively low, it is currently increasing yearly at a rate of about 14%. The proportion of men for whom prostate cancer is likely to be diagnosed has risen by 30% in recent years, an increase which is attributable largely to better diagnostic methods and to a general increase in the age of the population, rather than to any increased incidence of new disease (E. J. Small, D. M. Reese, Curr. Opinion. Oncology, 2000, 12, 265-272).

The early stages of prostate cancer tumour growth are androgen-dependent. Provided that the tumour is confined to the prostate itself, it can usually be treated by surgical removal, radiation therapy and/or by chemotherapy. In more advanced cases in which the tumour is no longer confined to the prostate, but has formed metastatic tumours elsewhere in the body, the tumour may be treated palliatively by reducing blood testosterone levels. Such a reduction in blood testosterone levels may be achieved by surgical castration (orchidectomy) or medicinally by treatment with antiandrogens (Casodex, cyproterone acetate, flutamide), LHRH-Agonists (Zoladex, Buserelin), LHRH antagonists (Cetrorelix), or 5α-reductase inhibitors (Finasteride). Since adrenal androgen synthesis is unaffected by surgical castration, a recent trend has been to combine surgical and medicinal treatment. This treatment has only temporary success since after an interval of up to 2 years renewed growth of the tumour normally occurs and this renewed tumour growth is usually not hormonally dependent (L. J. Denis and K. Griffith, Seminars in Surg. Onc., 2000, 18, 52-74). Despite extensive research on this topic during the past 50 years there is still no effective treatment for the advanced stages of prostate cancer. For patients with advanced prostate cancer the 5-year survival rate is under 15%.

There is evidence that the androgen receptor plays an important role in the development and growth of prostate cancer not only in the early hormone-dependent stages but also in the advanced hormone-independent stages.

The androgen receptor belongs to the family of steroid hormone receptors, which function as transcription factors. The binding of an androgen to the androgen receptor results in the stabilisation of the receptor and protects it form undergoing a rapid proteolytic degradation. The complex of androgen and androgen receptor is transported into the nucleus, where it regulates the expression of androgen responsive genes by binding to their androgen response DNA elements in the promoter region of such androgen responsive genes (D. J. Lamb et al. Vitam. Horm. 2001, 62, 199-230).

Investigation of prostate tumours shows that in 30% of advanced cases an amplification of the androgen receptor gene locus had occurred; in other cases a range of mutations of the androgen receptor were found in various domains of the androgen receptor and that lead to androgen receptors with altered properties. Such mutated receptors can have a higher than normal affinity for androgens, can be constitutively active, can have altered ligand specificity resulting in activation by other steroid hormones or even by antiandrogens, can be activated by interaction with molecules from other growth promoting signal transduction pathways, can alter interactions with other co-factors, or can activate other target genes (J. P. Elo, T. Visakorpi, Ann. Med. 2001, 33, 130-141).

The identification of antiandrogens that would inhibit not only the natural form of the androgen receptor but also its mutated forms and thereby so alter the receptor molecule that it became unstable would be very useful in the treatment of prostate tumours at various stages of growth. Such compounds could inhibit a recurrence of tumour growth or at least prolong the disease free interval. In the case of oestrogen receptors, such ligands have been identified that destabilise the receptor and lead to a reduction in the receptor content both in vitro and in vivo (S. Dauvois et al., Proc Natl. Acad. Sci. USA, 1992, 89, 4037-41; R. A. McClelland et al. Eur. J. Cancer, 1996, 32A, 413-416).

Non-steroidal antiandrogens have been described in U.S. Pat. No. 5,411,981 (phenylimidazolidine derivatives), in WO97/00071 (specifically substituted phenyldimethyl hydantoins and their imino- and thio-derivatives), in WO00/37430 (phenylalanines, phenylhydantoins, and phenylureas), in WO01/58855 (aminopropanilides), and in EP 1122242 (substituted cyanophenylpiperazines).

A series of bicyclic derivatives capable of inducing cellular down-regulation of the androgen receptor is described herein. According to a first aspect of the present invention there is therefore provided the use of a compound of Formula (I) for the treatment of an androgen receptor associated condition;

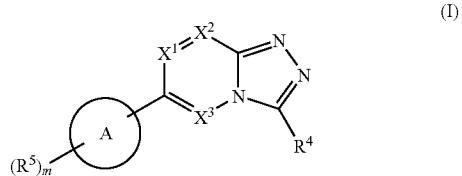

wherein
$X^1$ is selected from —N— and —C($R^1$)—;
$X^2$ is selected from —N— and —C($R^2$)—;
$X^3$ is selected from —N— and —C($R^3$)—;
Wherein at least one of $X^1$, $X^2$ and $X^3$ is not —N—;
Ring A is selected from a mono or bicyclic heterocyclic ring and a carbocyclic ring;
$R^1$, $R^2$ and $R^3$ are independently selected from hydrogen, $C_{1-6}$alkyl, $C_{1-6}$alkoxy, $C_{1-6}$alkylthio, halo and cyano wherein an alkyl chain in $R^1$, $R^2$ and $R^3$ is optionally substituted by up to three halo groups;
$R^4$ is selected from hydrogen, hydroxy, halo, cyano, amino, N—$C_{1-6}$alkylamino, N,N-di-$C_{1-6}$alkylamino, $C_{1-6}$alkyl, $C_{2-6}$alkenyl, $C_{2-6}$alkynyl, $C_{1-6}$alkoxy, $C_{1-6}$alkyl-S(O)$_n$— wherein n is an integer from 0-2 and a $C_{3-4}$carbocyclic ring, wherein a alkyl, alkenyl or alkynyl chain within $R^4$ can optionally be substituted with up to 5 groups selected from cyano, halo, amino, $C_{1-6}$alkoxy, $C_{1-4}$alkoxy$C_{1-4}$alkyl and $C_{1-6}$alkylthio and when $R^4$ comprises an alkyl chain the chain can be perfluorinated;

$R^5$ is selected from oxo or the group -$L^1$-J-$L^2$-K
wherein
  $L^1$ and $L^2$ are independently selected from a direct bond, $C_{1-6}$alkylene, $C_{2-6}$alkenylene $C_{2-6}$alkynylene, $C_{1-6}$alkylidene, wherein an alkyl, alkenyl, alkynyl or alkylidenyl chain within $L^1$ and $L^2$ can optionally be substituted with up to 3 groups selected from $R^7$ and wherein $L^1$ and $L^2$ can also be selected from one of the following groups or an alkyl, alkenyl, alkynyl or alkylidenyl chain into which is inserted one of the following groups, said groups independently selected from: —O—, —C(O)—, —C(O)—O—, —O—C(O)—, —N($R^6$)—, —N($R^6$)—C(O)—; —C(O)—N($R^6$)—, —N($R^6$)—C(O)—, —O—C(O)—N($R^6$)—, —C(O)—N($R^6$)—O—; —O—N($R^6$)—C(O)—, —N($R^6$)—C(O)—N($R^6$)—, —S(O)$_{0-2}$—, —O—S(O$_2$)—, S—(O$_2$)—O—, —N($R^6$)—S(O)$_2$— and —S(O)$_2$—N($R^6$)—;
  J is selected from a direct bond, $C_{1-4}$alkylene, aryl, heterocyclyl and heteroaryl wherein J is optionally substituted by up to five groups selected from $R^8$;
  K is selected from $C_{1-6}$alkyl, $C_{2-6}$alkenyl, $C_{2-6}$alkynyl, a carbocyclic ring, aryl, heterocyclyl and heteroaryl wherein K is optionally substituted by up to five groups selected from $R^8$;
$R^6$ is selected from hydrogen and $C_{1-6}$alkyl;
$R^7$ is selected from hydroxy, carboxy, carbamoyl, $C_{1-6}$alkyl, $C_{2-6}$alkenyl, $C_{2-6}$alkynyl, $C_{1-6}$alkoxy, $C_{1-4}$alkyloxy$C_{1-4}$alkyl, $C_{1-6}$alkoxycarbonyl, $C_{1-6}$alkyl-S(O)$_n$— wherein n is an integer from 0 to 2, aminosulphonyl, carbamoyl, N—$C_{1-4}$alkylamino, N,N-di-$C_{1-4}$alkylamino, N—$C_{1-4}$alkylaminocarbonyl, N,N-di-$C_{1-4}$alkylaminocarbonyl, N—$C_{1-4}$alkylaminosulphonyl, N,N-di-$C_{1-4}$alkylaminosulphonyl, oxo, $C_{1-6}$alkyl($C_{1-6}$alkoxy)oxophosphinyl, di$C_{1-6}$alkyloxophosphinyl, aryl, carbocyclyl, heterocyclyl, heteroaryl wherein $R^7$ is optionally substituted by up to three groups selected from hydroxy, halo, cyano, $C_{1-6}$alkyl, $C_{1-6}$alkoxy and a carbocyclic ring and an N,N-di-$C_{1-4}$alkylamino group within $R^7$ is optionally cyclized to form a ring;
$R^8$ is selected from hydroxy, oxo, cyano, halo, nitro, hydroxy, carboxy, $C_{1-6}$alkyl, $C_{1-6}$alkenyl, $C_{1-6}$alkynyl, $C_{1-6}$alkoxy, $C_{1-6}$alkoxycarbonyl, cyano$C_{1-6}$alkoxy, $C_{1-6}$alkenyloxy, $C_{1-6}$alkanoyl, $C_{1-4}$alkoxycarbonyl, $C_{1-6}$alkyl-S(O)$_n$— wherein n is an integer from 0 to 2, amino, $C_{1-6}$alkylsulphonyloxy, carbamoyl, aminosulphonyl, N—$C_{1-4}$alkylaminosulphonyl, N,N-di-$C_{1-4}$alkylaminosulphonyl, N—$C_{1-4}$alkylamino, N,N-di-$C_{1-4}$alkylamino, carbamoyl, N—$C_{1-4}$alkylaminocarbonyl, N,N-di-$C_{1-4}$alkylaminocarbonyl, aryl, carbocyclyl, heterocyclyl and heteroaryl wherein an alkyl chain or ring in $R^8$ is optionally substituted by up to five groups selected from halo, amino, hydroxy, carboxy, $C_{1-4}$alkoxy, N—$C_{1-4}$alkylamino, N,N-di-$C_{1-4}$alkylamino, carbamoyl, N—$C_{1-4}$alkylaminocarbonyl, N,N-di-$C_{1-4}$alkylaminocarbonyl and oxo and an N,N-di-$C_{1-4}$alkylamino group within $R^8$ is optionally cyclized to form a ring; and
m is an integer from 1 to 4;
or a pharmaceutically acceptable salt thereof.

According to a second aspect of the present invention there is provided the use of a compound of Formula (Ia) as a medicament;

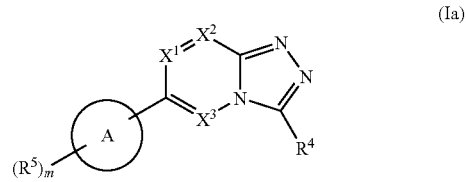

(Ia)

wherein $X^1$, $X^2$, $X^3$, Ring A, $R^1$, $R^2$, $R^3$, $R^4$ and $R^5$ are as defined above in the definition of a compound of Formula (I) with the proviso that
(i) when m is 1 then ($R^5$)$_m$ cannot be hydroxy, oxo or $C_{1-6}$alkyl and when m is 2 then ($R^5$)$_m$ cannot be dihydroxy;
(ii) -$L^1$-J-$L^2$-K cannot be trifluorophenylpiperidin-1-yl when the piperidine group is substituted by amino or $C_{1-4}$alkylcarbonylamino;
(iii) When Ring A is pyrrolidin-1-yl, m is 2 and ($R^5$)$_m$ is substituted piperidine-1-ylcarbonyl and substituted phenyl or substituted piperidine-1-ylcarbonyl and substituted pyridyl then the phenyl or pyridyl ring cannot be substituted by fluoro, chloro, cyano, trifluoromethyl or methoxy.
(iv) when Ring A is indoline and m is 1 then $R^5$ cannot be unsubstituted or substituted pyrrolidinylcarbonyl or unsubstituted or substituted piperidinylcarbonyl.
or a pharmaceutically acceptable salt thereof.

According to a third aspect of the present invention there is provided a compound of Formula (Ib);

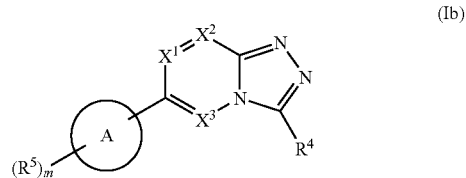

(Ib)

wherein $X^1$, $X^2$, $X^3$, Ring A, $R^1$, $R^2$, $R^3$, $R^4$ and $R^5$ are as defined above in the definition of a compound of Formula (I) the proviso that
(i) when m is 1 then ($R^5$)$_m$ cannot be hydroxy, $C_{1-6}$alkyl, oxo, acetyl, carbamoyl, ethoxycarbonyl, methylsulphonyl, methylsulphonylamino, isopropylaminocarbonylmethyl or isobutylaminocarbonylmethyl and when m is 2 ($R^5$)$_m$ cannot be dihydroxy and cannot be cyano and amino;
(ii) when $R^4$ is trifluoromethyl or methyl and Ring A is piperazin-1-yl substituted at the 4 position by phenyl, benzyl phenethyl, phenylsulphonyl, phenylcarbonyl or anilinocarbonyl then the phenyl ring cannot be unsubstituted or substituted by 2-methyl, 2,3-dimethyl, 2,4-dimethyl, 2,6-dimethyl, 2-methoxy, 4-methoxy, 3-chloro, 4-chloro, 3-fluoro, 4-fluoro, 2,6-difluoro, 3-trifluoromethyl, 2-nitro, 4-nitro or 2,3,5,6-tetrafluoro-4-trifluoromethyl;
(iii) when $R^4$ is trifluoromethyl or methyl and Ring A is piperazinyl substituted by -$L^1$-J-$L^2$-K at the 4-position and m is 1 then -$L^1$-J-$L^2$-K cannot be unsubstituted α-carbamoylbenzyl, α-phenylbenzyl, unsubstituted pyrrolidin-1-ylcarbonyl, unsubstituted morpholinocarbonylmethyl, unsubstituted thien-3-ylmethyl, unsubstituted thiazol-2-yl, unsubstituted pyridin-2-yl, unsubstituted pyridin-4-ylmethyl, unsubstituted pyrazin-2-yl, unsubstituted pyrimidin-2-yl, unsubstituted tetrazolo[1,5-b]pyridazin-6-yl, unsubstituted quinolin-8-ylmethyl, unsubstituted 1,3-benzodioxol-5-ylmethyl, 2,6-difluorophenylsulphonyl, 5-chlorothien-2-ylsulphonyl, 2-methylthiazol-4-ylmethyl, 2-(4-methoxyphenyl)thiazol-4-ylmethyl;

(iv) -$L^1$-J-$L^2$-K cannot be trifluorophenylpiperidin-1-yl when the piperidine group is substituted by amino or $C_{1-4}$alkylcarbonylamino; and (v) When Ring A is pyrrolidin-1-yl, m is 2 and $(R^5)_m$ is substituted piperidine-1-ylcarbonyl and substituted phenyl or substituted piperidine-1-ylcarbonyl and substituted pyridyl then the phenyl or pyridyl ring cannot be substituted by fluoro, chloro, cyano, trifluoromethyl or methoxy;

(vi) when Ring A is indoline and m is 1 then $R^5$ cannot be unsubstituted or substituted pyrrolidinylcarbonyl or unsubstituted or substituted piperidinylcarbonyl.

(vii) when $R^4$ is trifluoromethyl or methyl and Ring A is piperidinyl substituted by -$L^1$-J-$L^2$-K at the 4-position and m is 1 then -$L^1$-J-$L^2$-K cannot be mono or disubstituted carbamoyl;

(viii) The following compounds are excluded:
6-[2-(2,4-dimethoxyphenyl)-1-pyrrolidinyl]-3-(trifluoromethyl)-1,2,4-Triazolo[4,3-b]pyridazine;
6-[4-(7-ethyl-1H-indol-3-yl)-3,6-dihydro-1(2H)-pyridinyl]-3-(trifluoromethyl)-1,2,4-Triazolo[4,3-b]pyridazine,
6-[4-(1H-indol-3-yl)-3,6-dihydro-1(2H)-pyridinyl]-3-(trifluoromethyl)-1,2,4-Triazolo[4,3-b]pyridazine;
6,7,8,9-tetrahydro-3-[1-[3-(trifluoromethyl)-1,2,4-triazolo [4,3-b]pyridazin-6-yl]-3-piperidinyl]-5H-1,2,4-triazolo [4,3-a]azepine;
6-[4-[2-(3,5-dimethoxyphenyl)ethyl]-1-piperidinyl]-3-(trifluoromethyl)-1,2,4-triazolo[4,3-b]pyridazine;
2-thienyl[4-[3-(trifluoromethyl)-1,2,4-triazolo[4,3-b]pyridazin-6-yl]-1-piperazinyl]-methanone;
N-cyclopentyl-N-methyl-1-(3-methyl-1,2,4-triazolo[4,3-b]pyridazin-6-yl)-4-piperidinamine;
6-[4-(2-benzoxazolyl)-1-piperidinyl]-3-(trifluoromethyl)-1,2,4-triazolo[4,3-b]pyridazine
6-(3-phenylpyrrolidin-1yl)-1,2,4-triazolo[4,3-b]pyridazine; and
1-[[2,3-dihydro-1-(3-methyl-1,2,4-triazolo[4,3-b]pyridazin-6-yl)-1H-indol-2-yl]carbonyl]-3-methyl-piperidine;
or a salt thereof.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

It is to be understood that, insofar as certain of the compounds of Formula (I) defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Examples of suitable methods for separating the enantiomers of a racemic compound include chromatography using a suitable chiral stationary phase; or conversion of a racemic mixture into diastereomeric derivatives, separation of the mixture of diastereomeric derivatives into two single diastereomers, and regeneration of a separate single enantiomer from each separate single diastereomer.

Examples of suitable methods for separating a mixture of diastereomers include fractional crystallisation, normal-phase chromatography, or reverse-phase chromatography.

It is to be understood that certain compounds of Formula (I) defined above may exhibit the phenomenon of tautomerism. In particular, tautomerism may affect any heterocyclic groups that bear 1 or 2 oxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples.

It is to be understood that certain compounds of Formula (I) above may exist in unsolvated forms as well as solvated forms, such as, for example, hydrated forms. It is to be understood that the present invention encompasses all such solvated forms that possess androgen receptor ligand activity.

It is also to be understood that certain compounds of the Formula (I) may exhibit polymorphism, and that the present invention encompasses all such forms which possess androgen receptor ligand activity.

In this specification the generic term "alkyl", unless specifically specified otherwise, includes both straight-chain and branched-chain alkyl groups such as propyl, isopropyl and tert-butyl. However, references to individual alkyl groups such as "propyl" are specific for the straight-chain version only, and references to individual branched-chain alkyl groups such as "isopropyl" are specific for the branched-chain version only. The same principle also applies to generic terms "alkenyl" and "alkynyl", unless specified otherwise.

The term "fluoro$C_{1-6}$alkyl" is intended to mean a saturated carbon chain of 1 to 6 carbon atoms in length which may be straight-chained or branched wherein at least one of the hydrogen atoms have been replaced by fluorine. For example, "fluoro$C_{1-6}$alkyl" includes, but is not limited to, fluoromethyl, fluoroethyl, fluoropropyl, fluoroisopropyl, fluorobutyl, fluoroisobutyl, fluoro-tert-butyl, fluoropentyl, fluoroisopentyl, fluorohexyl, fluoroisohexyl, trifluoromethyl, pentafluoroethyl, heptafluoropropyl, nonafluorobutyl, undecafluoropentyl and tridecafluorohexyl. The term "fluoro$C_{1-4}$alkyl" should be construed accordingly.

The term "$C_{1-6}$ alkoxy" is intended to mean a saturated carbon chain of 1 to 6 carbon atoms in length, which may be straight-chained or branched, linked to oxygen. For example, "$C_{1-6}$ alkoxy" includes, but is not limited to, methoxy, ethoxy, propoxy, butoxy, pentoxy and hexoxy.

The term "$C_{2-6}$alkanoyl" is intended to mean a saturated carbon chain of 1 to 5 carbon atoms in length which may be straight-chained or branched, linked to carbonyl. For example, "$C_{2-6}$alkanoyl" includes, but is not limited to, ethanoyl, propanoyl, butanoyl, pentanoyl and hexanoyl.

The term "$C_{1-6}$alkoxy$C_{1-6}$alkyl" is intended to mean a saturated carbon chain of 1 to 6 carbon atoms in length, which may be straight-chained or branched, linked via oxygen to another saturated carbon chain of 1 to 6 carbon atoms in length, which may be straight-chained or branched. For example, "$C_{1-6}$alkoxy$C_{1-6}$alkyl" includes, but is not limited to, methoxyethyl, methoxypropyl, ethoxypropyl, propoxyethyl and butoxypropyl.

The term "hydroxy$C_{1-6}$alkyl" is intended to mean a saturated carbon chain of 1 to 6 carbon atoms in length, which may be straight-chained or branched, comprising a single hydroxyl group. For example "hydroxy$C_{1-6}$alkyl" includes, but is not limited to, hydroxymethyl, hydroxyethyl, 2-hydroxypropyl, 3-hydroxypropyl, 1-hydroxyisopropyl, 4-hydroxybutyl, hydroxypentyl, hydroxyhexyl and hydroxyisohexyl.

The term "$C_{1-6}$alkylsulphanyl" is intended to mean a saturated carbon chain of 1 to 6 carbon atoms in length, which may be straight-chained or branched, linked to sulphur. For example, "$C_{1-6}$alkylsulphanyl" includes, but is not limited to, methylsulphanyl, ethylsulphanyl, propylsulphanyl, isopropylsulphanyl, butylsulphanyl, isobutylsulphanyl, tert-butylsulphanyl, pentylsulphanyl and hexylsulphanyl.

The term "$C_{1-6}$alkylsulphinyl" is intended to mean a saturated carbon chain of 1 to 6 carbon atoms in length, which may be straight-chained or branched, linked to sulphoxide. For example, "$C_{1-6}$alkylsulphinyl" includes, but is not limited to, methylsulphinyl, ethylsulphinyl, propylsulphinyl, isopropylsulphinyl, butylsulphinyl, isobutylsulphinyl, tert-butylsulphinyl, pethylsulphinyl and hexylsulphinyl.

The term "$C_{1-16}$alkylsulphonyl" is intended to mean a saturated carbon chain of 1 to 6 carbon atoms in length, which may be straight-chained or branched, linked to sulphur dioxide. For example, "$C_{1-6}$alkylsulphonyl" includes, but is not limited to, methylsulphonyl, ethylsulphonyl, propylsulphonyl, isopropylsulphonyl, butylsulphonyl, isobutylsulphonyl, tert-butylsulphonyl, pentylsulphonyl and hexylsulphonyl.

The term "N—$C_{1-4}$alkylamino" is intended to mean a saturated carbon chain of 1 to 4 carbon atoms in length, which may be straight-chained or branched, linked to a secondary amino group. For example, "N—$C_{1-4}$alkylamino" includes, but is not limited to, methylamino, ethylamino, propylamino and butylamino.

The term "N,N-di-$C_{1-4}$alkylamino" is intended to mean a saturated carbon chain of 1 to 4 carbon atoms in length, which may be straight-chained or branched, linked to a tertiary amino group, which is in turn linked to a further saturated carbon chain of the same length. For example, "N,N-di-$C_{1-4}$alkylamino" includes, but is not limited to, N,N-dimethylamino, N,N-diethylamino, N,N-dipropylamino and N,N-dibutylamino.

The term alkylidene is used to denote an alkylidene chain which can be in either orientation within the molecule, thus for example where $L^1$ is propylidene this would cover the following two structures:

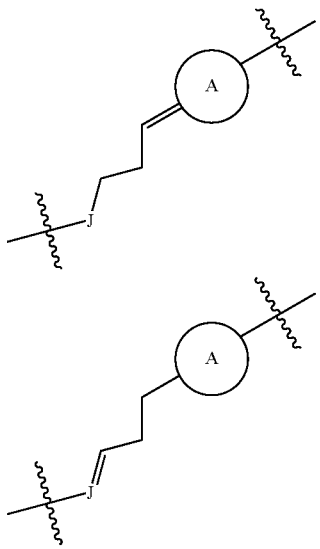

The term "halo" is used herein to denote fluoro, chloro, bromo and iodo.

The term "halo$C_{1-4}$alkyl" is intended to mean a saturated carbon chain of 1 to 4 carbon atoms in length which may be straight-chained or branched wherein at least one of the hydrogen atoms have been replaced by a halo atom. For example, "halo$C_{1-4}$alkyl" includes, but is not limited to, difluoromethyl, trifluoromethyl, chloro(difluoro)methyl, difluoroethyl and difluoropropyl.

The term "aryl" refers to phenyl or naphthyl.

The term "carbamoyl" refers to the group —C(O)NH$_2$.

Unless stated otherwise, the term "heteroaryl" refers to a 4-10 membered aromatic mono or, bicyclic ring containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. In one embodiment the term "heteroaryl" refers to a 5-10 membered aromatic mono or bicyclic ring containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. In another embodiment the term "heteroaryl" refers to a 5 or 6 membered aromatic monocyclic ring containing up to 4 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered heteroaryl rings include pyrrole, furan, imidazole, triazole, tetrazole, pyrazine, pyrazole, pyrimidine, pyridazine, pyridine, pyrrole, isoxazole, oxazole, 1,2,4 oxadiazole, isothiazole, thiazole, thiadiazole, 1,2,4-triazole and thiophene. Examples of 5/6 and 6/6 bicyclic ring systems include benzofuran, benzimidazole, benzthiophene, benzthiazole, benzisothiazole, benzoxazole, benzisoxazole, 1,3-benzodioxole, indole, pyridoimidazole, pyrimidoimidazole, quinoline, isoquinoline, quinoxaline, quinazoline, phthalazine, cinnoline and naphthyridine. This definition further comprises sulphur-containing rings wherein the sulphur atom has been oxidised to an S(O) or S(O$_2$) group.

Unless stated otherwise, the term "heterocyclyl" refers to a 4-10 membered saturated or partially saturated mono or bicyclic ring containing up to 5 heteroatoms selected from nitrogen, oxygen or sulphur linked via ring carbon atoms or ring nitrogen atoms. Examples of 'heterocyclyl' include tetrahydrofuranyl, 2,3-dihydro-4H-pyranyl, tetrahydro-2H-pyranyl, pyrrolinyl, pyrrolidinyl, 1,3-thiazolidine, morpholinyl, oxetanyl, piperidinyl, piperazinyl, dihydropyridinyl, dihydropyrimidinyl and azepane. Particular examples of 'heterocyclyl' include pyrrolinyl, pyrrolidinyl, morpholinyl, piperidinyl, piperazinyl, dihydropyridinyl and dihydropyrimidinyl. This definition further comprises sulphur-containing rings wherein the sulphur atom has been oxidised to an S(O$_2$) or S(O$_2$) group.

The term "carbocyclyl" or carbocyclic ring refers to a totally saturated or partially saturated mono, bicyclic 3-10 membered carbon ring. Examples of carbocyclic rings are cyclopropyl, cyclobutyl, cyclopentyl, cyclohexyl, bicyclo[4,2,0]octane or 2,3-dihydroindene.

Particular novel compounds of the invention include, for example, compounds of Formula (I), or pharmaceutically-acceptable salts thereof, wherein, unless otherwise stated, each of $R^1$, $R^3$, $R^4$, $R^5$, $R^6$, $R^7$, $R^8$, A, J, K, $L^1$, $L^2$ and m have any of the meanings defined hereinbefore or in paragraphs (1) to (56) hereinafter:—

(1) $X^1$ and $X^2$ and $X^3$ are all —C(H)—;
(2) $X^1$ is —C($R^1$)—, $X^2$ is —C($R^2$)— and $X^3$ is —C($R^3$)—;
(3) The ring

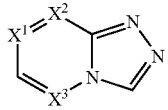

is selected from one of the following

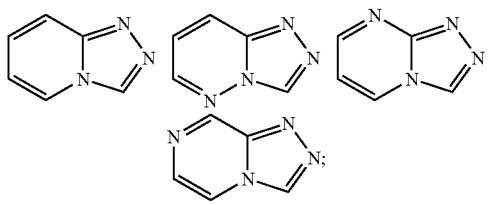

(4) $X^1$ is —C($R^1$)—, $X^2$ is —C($R^2$)— and $X^3$ is —N—;
(5) $X^1$ and $X^2$ are both C(H) and $X^3$ is —N—;
(6) Ring A is selected from pyrrolidinyl, piperidinyl, 1,2-dihydropyridyl, 1,2,5,6-tetrahydropyridyl, morpholinyl, thiomorpholinyl, oxazepanyl, thiazepanyl, azepanyl, 1,2,5,6-1H-tetrahydroazepinyl, piperazinyl, diazepanyl, tetrahydroimidazolyl, octahydro-1H-indolyl, octahydro-2H-isoindolyl, azabicyclo[2.2.1]heptanyl, azabicyclo[3.3.0]octanyl, azabicyclo[3.2.1]octanyl, triazaspirodecanyl, octahydropyrido[1,2-a]pyrazinyl, hexahydropyrrolo[3,4-c]pyrrolyl, diazabicyclo[3.2.1]octanyl and diazabicycloheptanyl;
(7) In another embodiment Ring A is selected from tetrahydrofuranyl, tetrahydropyranyl, and 5,6-dihydro-2H-pyranyl;
(8) Ring A is selected from piperidinyl, pyrrolidinyl, piperazinyl and diazepanyl;
(9) Ring A is selected from piperidinyl, piperazinyl, diazepanyl, 1,3,8-triazaspiro[4.5]decan-4-onyl, 1,3,4,6,7,8,9,9a-octahydropyrido[1,2-a]pyrazinyl, 3,3a,4,6,6a-hexahydropyrrolo[3,4-c]pyrrolyl, 3,8-diazabicyclo[3.2.1]octanyl and 2,5-diazabicyclo[2.2.1]heptanyl;
(10) Ring A is selected from piperidinyl, piperazinyl, 3,3a,4,6,6a-hexahydropyrrolo[3,4-c]pyrrolyl, and diazepanyl;
(11) Ring A is selected from piperazinyl and 3,3a,4,6,6a-hexahydropyrrolo[3,4-c]pyrrolyl;
(12) $R^1$ is $C_{1-4}$alkyl and $R^2$ is $C_{1-4}$alkyl;
(13) $R^1$ is hydrogen and $R^2$ is $C_{1-4}$alkyl;
(14) $R^1$ is $C_{1-4}$alkyl and $R^2$ is hydrogen;
(15) $R^1$ is selected from methyl and ethyl;
(16) $R^1$ is selected from hydrogen and methyl;
(17) $R^2$ is selected from hydrogen and methyl;
(18) $R^3$ is selected from hydrogen and methyl;
(19) $R^3$ is hydrogen;
(20) $R^4$ is selected from halo, $C_{1-6}$alkyl optionally substituted by up to 5 halo substituents, $C_{1-6}$alkylS(O)n- where in n is an integer from 0 to 2 and amino;
(21) $R^4$ is selected from halo, $C_{1-4}$alkyl optionally substituted by up to 5 halo substituents, $C_{1-4}$alkylthio and amino;
(22) $R^4$ is selected from chloro, difluoromethyl, trifluoromethyl, 1,1,2,2-tetrafluoroethyl, methylthio or amino;

(23) $R^5$ is the group -$L^1$-J-$L^2$-K;
(24) $R^5$ is the group -$L^1$-K;
(25) $R^5$ is the group -$L^1$-J-K;
(26) $R^5$ is the group —K;
(27) $R^5$ is the group -$L^1$-$L^2$-K;
(28) $L^1$ and $L^2$ are independently selected from a direct bond, $C_{1-6}$alkylene wherein an alkyl chain within $L^1$ and $L^2$ can optionally be substituted with up to 3 groups selected from $R^7$ and wherein $L^1$ and $L^2$ can also be selected from one of the following groups or an alkyl chain into which is inserted one of the following groups, said groups independently selected from:—O—, —C(O)—, —C(O)—O—, —O—C(O)—, —N($R^6$)—, —N($R^6$)—C(O)—, —C(O)—N($R^6$)—, —N($R^6$)—C(O)—O—, —O—C(O)—N($R^6$)—, —C(O)—N($R^6$)—O—, —O—N($R^6$)—C(O)—, —N($R^6$)—C(O)—N($R^6$)—, —S(O)$_{0-2}$—, —O—S($O_2$)—, S—($O_2$)—O—, —N($R^6$)—S(O)$_2$— and —S(O)$_2$—N($R^6$)—;
(29) $L^1$ and $L^2$ are independently selected from a direct bond, $C_{1-6}$alkylene wherein an alkyl chain within $L^1$ and $L^2$ can optionally be substituted with up to 3 groups selected from $R^7$ and wherein $L^1$ and $L^2$ can also be selected from one of the following groups or an alkyl chain into which is inserted one of the following groups, said groups independently selected from:—O—, —C(O)— and —S(O)$_{0-2}$—;
(30) $L^1$ and $L^2$ are independently selected from a direct bond, $C_{1-4}$alkylene, —O—, —C(O)—, —OC(O)—, —C(O)O—, —N($R^6$)—, —N($R^6$)C(O)—, —C(O)N($R^6$)—, —N($R^6$)C(O)O—, —S(O)$_n$— wherein n is an integer from 0 to 2, —OS(O)$_2$—, —S(O)$_2$N($R^5$)— and —N($R^5$)S(O)$_2$—;
(31) $L^1$ and $L^2$ are independently selected from a direct bond, $C_{1-4}$alkylene, —O—, —C(O)—, —C(O)O—, —N($R^6$)—, —N($R^6$)C(O)—, —C(O)N($R^6$)—, —N($R^6$)C(O)O—, —S—, —S(O)$_2$—, —OS(O)$_2$—, —S(O)$_2$N($R^6$)— and —N($R^6$)S(O)$_2$—;
(32) $L^1$ and $L^2$ are independently selected from a direct bond, $C_{1-2}$alkylene, —O—, —S(O)$_2$N($R^6$)— and —N($R^6$)S(O)$_2$—;
(33) $L^1$ is independently selected from a direct bond, $C_{1-2}$alkylene, —O—, —S(O)$_2$N($R^6$)— and —N($R^6$)S(O)$_2$— and $L^2$ is a direct bond;
(34) $L^1$ is selected from a direct bond, $C_{1-4}$alkylene, —C(O)—, —C(O)O—, —C(O)N($R^6$)—, —S(O)$_2$— and —S(O)$_2$N($R^6$)—;
(35) $L^2$ is selected from a direct bond, —O—, —C(O)O—, —N($R^6$)—, —N($R^6$)C(O)—, —C(O)N($R^6$)—, —N($R^6$)C(O)O—, —S—, —S(O)$_2$—, —OS(O)$_2$—, —($R^6$)S(O)$_2$—;
(36) $L^2$ is a direct bond;
(37) J is selected from a direct bond, aryl and heteroaryl ring wherein J is optionally substituted by up to five groups selected from $R^8$;
(38) J is selected from a direct bond, phenyl, imidazolyl and pyridyl;
(39) J is a direct bond;
(40) K is selected from aryl and heteroaryl ring wherein K is optionally substituted by up to five groups selected from $R^8$;
(41) K is selected from $C_{1-6}$alkyl, $C_{2-6}$ethenyl, cyclohexyl, phenyl, naphthyl, furanyl, pyrrolidinyl, pyrrolyl, morpholinyl, piperaziyl, thienyl, thiazolyl, thiadiazolyl, pyrazolyl, piperidinyl, pyridyl, 2,3-dihydropyridyl, pyrazinyl, pyrimidinyl, quinolinyl, quinoxalinyl, benzothiophenyl, 1-benzofuranyl, 2,3-dihydro-1-benzofuranyl, 1,2,3,4-tetrahydroquinolinyl, 1,4-dihydro-2H-

3,1-benzoxazinyl, 1,3-benzoxazolyl, 2,3-dihydro-1,4-benzodioxinyl, 1,3-benzodioxolyl, 2,3-dihydro-1,4-benzodioxinyl, 1,3-benzothiazolyl and benzimidazolyl;
(42) K is selected from methyl, ethyl, propyl, butyl, ethenyl, prop-2-enyl, cyclohexyl, phenyl, naphthyl, furanyl, pyrrolidinyl, pyrrolyl, morpholinyl, piperazinyl, thienyl, thiazolyl, thiadiazolyl, pyrazolyl, piperidinyl, pyridyl, 2,3-dihydropyridyl, pyrazinyl, pyrimidinyl, quinolinyl, quinoxalinyl, benzothiophenyl, 1-benzofuranyl, 2,3-dihydro-1-benzofuranyl, 1,2,3,4-tetrahydroquinolinyl, 1,4-dihydro-2H-3,1-benzoxazinyl, 1,3-benzoxazolyl, 2,3-dihydro-1,4-benzodioxinyl, 1,3-benzodioxolyl, 2,3-dihydro-1,4-benzodioxinyl, 1,3-benzothiazolyl and benzimidazolyl;
(43) K is selected from phenyl, naphthyl, furanyl, pyrrolyl, thienyl, thiazolyl, thiadiazolyl, pyrazolyl, piperidinyl, pyridyl, pyrazinyl, pyrimidinyl, quinolinyl, quinoxalinyl, benzothiophenyl, 1-benzofuranyl, 1,2,3,4-tetrahydroquinolinyl, 1,4-dihydro-2H-3,1-benzoxazinyl, 1,3-benzoxazolyl, 2,3-dihydro-1,4-benzodioxinyl, 1,3-benzodioxolyl, 2,3-dihydro-1,4-benzodioxinyl, 1,3-benzothiazolyl and benzimidazolyl;
(44) $R^6$ is selected from hydrogen and $C_{1-4}$alkyl;
(45) $R^6$ is selected from hydrogen, methyl;
(46) $R^7$ is selected from $C_{1-4}$alkyl, hydroxy$C_{1-4}$alkyl and phenyl;
(47) $R^7$ is selected from phenyl;
(48) $R^8$ is selected from oxo, cyano, halo, $C_{1-6}$alkyl, $C_{1-6}$alkoxy, $C_{1-6}$alkoxycarbonyl, $C_{1-6}$alkyl-S(O)$_n$— wherein n is an integer from 0 to 2, $C_{1-6}$alkylsulphonyloxy, carbamoyl, aminosulphonyl, N—$C_{1-4}$alkylaminosulphonyl, N,N-di-$C_{1-4}$alkylaminosulphonyl, N—$C_{1-4}$alkylaminocarbonyl, N,N-di-$C_{1-4}$alkylaminocarbonyl, aryl, carbocyclyl, heterocyclyl and heteroaryl wherein an alkyl chain or ring in $R^8$ is optionally substituted by up to five groups selected from halo, carboxy, $C_{1-4}$alkoxy, N,N-di-$C_{1-4}$alkylamino, carbamoyl, N—$C_{1-4}$alkylaminocarbonyl, N,N-di-$C_{1-4}$alkylaminocarbonyl and oxo and an N,N-di-$C_{1-4}$alkylamino group within $R^8$ is optionally cyclized to form a ring;
(49) $R^8$ is selected from $C_{1-6}$alkyl, $C_{1-6}$alkenyl, $C_{1-6}$alkynyl, $C_{1-6}$alkoxy, $C_{1-6}$alkoxycarbonyl, hydroxy, carbamoyl, cyano, halo, nitro, amino, N—$C_{1-4}$alkylamino, N,N-di$C_{1-4}$alkylamino and oxo wherein an alkyl, chain in $R^8$ is optionally substituted by up to 5 halo groups;
(50) $R^8$ is selected from $C_{1-6}$alkyl, $C_{1-6}$alkenyl, $C_{1-6}$alkynyl, $C_{1-6}$alkoxy, $C_{1-6}$alkoxycarbonyl, hydroxy, carbamoyl, cyano, halo, nitro, amino, N,N-di$C_{1-4}$alkylamino and oxo wherein an alkyl, chain in $R^8$ is optionally substituted by up to 5 halo groups;
(51) $R^8$ is selected from methyl, propyl, isopropyl, 2-methylpropyl, t-butyl, ethynyl, trifluoromethyl, methoxy, ethoxy, butoxy, difluoromethoxy, trifluoromethoxy, ethoxycarbonyl, hydroxy, carbamoyl, cyano, chloro, bromo, fluoro, amino, dimethylamino; diethylamino andoxo;
(52) m is an integer from 0 to 3;
(53) m is 1;
(54) m is 2;
(55) m is 3;
(56) m is 4;

Particular novel compounds of the invention include any one of the following:
6-[4-(4-nitrophenyl)piperazin-1-yl]-3-(trifluoromethyl)-[1,2,4]triazolo[4,3-b]pyridazine
6-[4-[(3-bromophenyl)methyl]piperazin-1-yl]-3-(trifluoromethyl)-[1,2,4]triazolo[4,3-b]pyridazine
6-[4-(naphthalen-1-ylmethyl)piperazin-1-yl]-3-(trifluoromethyl)-[1,2,4]triazolo[4,3-b]pyridazine
6-[4-[(3-chlorophenyl)methyl]piperazin-1-yl]-3-(trifluoromethyl)-[1,2,4]triazolo[4,3-b]pyridazine
6-[4-[3-chloro-5-(trifluoromethyl)pyridin-2-yl]-1,4-diazepan-1-yl]-3-(trifluoromethyl)-[1,2,4]triazolo[4,3-b]pyridazine
6-(4-phenethylpiperazin-1-yl)-3-(trifluoromethyl)-[1,2,4]triazolo[4,3-b]pyridazine
6-[4-(1-benzothiophen-3-ylmethyl)piperazin-1-yl]-3-(trifluoromethyl)-[1,2,4]triazolo[4,3-b]pyridazine
3-(trifluoromethyl)-6-[4-[[3-(trifluoromethyl)phenyl]methyl]piperazin-1-yl]-[1,2,4]triazolo[4,3-a]pyridine
6-[4-(3,5-dichloropyridin-4-yl)piperazin-1-yl]-3-(trifluoromethyl)-[1,2,4]triazolo[4,3-b]pyridazine
4-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]benzonitrile
3-(trifluoromethyl)-6-[4-[[3-(trifluoromethyl)phenyl]methyl]-1,4-diazepan-1-yl]-[1,2,4]triazolo[4,3-b]pyridazine
4-[[4-[3-(trifluoromethyl)-[1,2,4]triazolo[4,3-b]pyridazin-6-yl]-1,4-diazepan-1-yl]methyl]benzonitrile
6-[4-[(4-chlorophenyl)methyl]piperazin-1-yl]-3-(trifluoromethyl)-[1,2,4]triazolo[4,3-b]pyridazine
3-[[4-[3-(trifluoromethyl)-[1,2,4]triazolo[4,3-b]pyridazin-6-yl]-1,4-diazepan-1-yl]methyl]benzonitrile
6-[4-(thiophen-2-ylmethyl)piperazin-1-yl]-3-(trifluoromethyl)-[1,2,4]triazolo[4,3-b]pyridazine
3-(trifluoromethyl)-6-[4-[[3-(trifluoromethyl)phenyl]methyl]piperazin-1-yl]-[1,2,4]triazolo[4,3-b]pyridazine
6-[4-[(3-chlorophenyl)methyl]-1,4-diazepan-1-yl]-3-(trifluoromethyl)-[1,2,4]triazolo[4,3-b]pyridazine
6-[4-[(2-chlorophenyl)methyl]-1,4-diazepan-1-yl]-3-(trifluoromethyl)-[1,2,4]triazolo[4,3-b]pyridazine
6-[4-(1H-indol-6-ylmethyl)piperazin-1-yl]-3-(trifluoromethyl)-[1,2,4]triazolo[4,3-b]pyridazine
6-[4-[(2,2-difluoro-1,3-benzodioxol-4-yl)methyl]piperazin-1-yl]-3-(trifluoromethyl)-[1,2,4]triazolo[4,3-b]pyridazine
6-[4-[(2-chlorophenyl)methyl]piperazin-1-yl]-3-(trifluoromethyl)-[1,2,4]triazolo[4,3-b]pyridazine
5-[[4-[3-(trifluoromethyl)-[1,2,4]triazolo[4,3-b]pyridazin-6-yl]piperazin-1-yl]methyl]isoquinoline
6-[4-[(4-nitrophenyl)methyl]piperazin-1-yl]-3-(trifluoromethyl)-[1,2,4]triazolo[4,3-b]pyridazine
6-[4-[(4-fluorophenyl)methyl]-1,4-diazepan-1-yl]-3-(trifluoromethyl)-[1,2,4]triazolo[4,3-b]pyridazine
6-[4-(2,6-dimethylphenyl)piperazin-1-yl]-3-(trifluoromethyl)-[1,2,4]triazolo[4,3-b]pyridazine
6-[4-[(4-chlorophenyl)methyl]piperazin-1-yl]-3-(trifluoromethyl)-[1,2,4]triazolo[4,3-a]pyridine
6-[4-[(3-fluorophenyl)methyl]-1,4-diazepan-1-yl]-3-(trifluoromethyl)-[1,2,4]triazolo[4,3-b]pyridazine
3-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]benzonitrile
6-[4-[(4-chlorophenyl)methyl]-1,4-diazepan-1-yl]-3-(trifluoromethyl)-[1,2,4]triazolo[4,3-b]pyridazine
6-[4-[(3-fluorophenyl)methyl]piperazin-1-yl]-3-(trifluoromethyl)-[1,2,4]triazolo[4,3-b]pyridazine
6-[4-[(3-methylphenyl)methyl]-1,4-diazepan-1-yl]-3-(trifluoromethyl)-[1,2,4]triazolo[4,3-b]pyridazine
6-[4-[(2-fluorophenyl)methyl]-1,4-diazepan-1-yl]-3-(trifluoromethyl)-[1,2,4]triazolo[4,3-b]pyridazine
6-[4-(1H-indol-3-ylmethyl)piperazin-1-yl]-3-(trifluoromethyl)-[1,2,4]triazolo[4,3-b]pyridazine
6-[4-[(4-methylsulfonylphenyl)methyl]-1,4-diazepan-1-yl]-3-(trifluoromethyl)-[1,2,4]triazolo[4,3-b]pyridazine 3-(trifluoromethyl)-6-[4-[[2-(trifluoromethyl)phenyl]methyl]-1,4-diazepan-1-yl]-[1,2,4]triazolo[4,3-b]pyridazine
6-[4-(3-methylphenyl)piperazin-1-yl]-3-(trifluoromethyl)-[1,2,4]triazolo[4,3-b]pyridazine
6-[4-[(4-methylsulfanylphenyl)methyl]piperazin-1-yl]-3-(trifluoromethyl)-[1,2,4]triazolo[4,3-b]pyridazine
6-[4-[[3-(difluoromethoxy)phenyl]methyl]piperazin-1-yl]-3-(trifluoromethyl)-[1,2,4]triazolo[4,3-b]pyridazine
6-[4-[(4,5-dimethylfuran-2-yl)methyl]piperazin-1-yl]-3-(trifluoromethyl)-[1,2,4]triazolo[4,3-b]pyridazine
6-[4-[phenyl-[4-(trifluoromethyl)phenyl]methyl]piperazin-1-yl]-3-(trifluoromethyl)-[1,2,4]triazolo[4,3-b]pyridazine
3-[[4-[3-(trifluoromethyl)-[1,2,4]triazolo[4,3-b]pyridazin-6-yl]piperazin-1-yl]methyl]benzonitrile
3-(trifluoromethyl)-6-[4-[[2-(trifluoromethyl)phenyl]methyl]piperazin-1-yl]-[1,2,4]triazolo[4,3-b]pyridazine
6-[4-[(2-fluorophenyl)methyl]piperazin-1-yl]-3-(trifluoromethyl)-[1,2,4]triazolo[4,3-b]pyridazine
4-[[4-[3-(trifluoromethyl)-[1,2,4]triazolo[4,3-b]pyridazin-6-yl]piperazin-1-yl]methyl]benzonitrile
6-[4-[(4-methoxyphenyl)-phenylmethyl]piperazin-1-yl]-3-(trifluoromethyl)-[1,2,4]triazolo[4,3-b]pyridazine
6-[4-[(3-fluorophenyl)methyl]piperazin-1-yl]-3-(trifluoromethyl)-[1,2,4]triazolo[4,3-a]pyridine
3-(trifluoromethyl)-6-[4-[[3-(trifluoromethylsulfanyl)phenyl]methyl]piperazin-1-yl]-[1,2,4]triazolo[4,3-b]pyridazine
6-[4-[(4-fluorophenyl)methyl]piperazin-1-yl]-3-(trifluoromethyl)-[1,2,4]triazolo[4,3-b]pyridazine
6-[4-[4,4-bis(4-fluorophenyl)butyl]piperazin-1-yl]-3-(trifluoromethyl)-[1,2,4]triazolo[4,3-b]pyridazine
6-[2-[(3-chlorophenyl)methyl]-1,3,3a,4,6,6a-hexahydropyrrolo[3,4-c]pyrrol-5-yl]-3-(trifluoromethyl)-[1,2,4]triazolo[4,3-b]pyridazine
or pharmaceutically acceptable salts thereof.

According to a fourth aspect of the present invention there is provided a compound of Formula (Ic), or a pharmaceutically acceptable salt thereof, for use as a medicament:

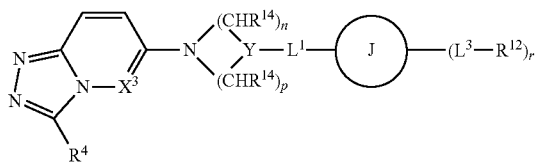

(Ic)

wherein
$X^3$ represents CH or N;
$R^4$ represents halo$C_{1-4}$alkyl;
Y represents CH, COH or N;
$R^{14}$, identically or differently on each occurrence, represents hydrogen or methyl;
n and p independently represent 1 or 2;
$L^1$ represents a direct bond, $—(CR^9R^{10})_t—$, $—(CR^9R^{10})_v—O—(CR^9R^{10})_v—$, $—N(R^{11})—(CH_2)_q—$, $—S—$, $—S(O)—$ or $—S(O)_2—$;
$R^9$ and $R^{10}$, identically or differently on each occurrence, represent hydrogen or methyl;
q, identically or differently on each occurrence, represents 0, 1, 2 or 3;
t represents 1, 2 or 3;
v, identically or differently on each occurrence, represents 0, 1 or 2;

J represents:
  aryl;
  a totally saturated monocyclic 3 to 6 membered carbocyclic ring;
  a monocyclic 4, 5, 6 or 7 membered heterocylic ring which comprises 1, 2, 3 or 4 heteroatoms independently selected from O, N or S;
  a monocyclic 5 or 6 membered heteroaryl ring which comprises 1, 2, 3 or 4 heteroatoms independently selected from O, N or S; or
  a bicyclic 9 or 10 membered heteroaryl ring system which comprises 1, 2, 3, 4 or 5 heteroatoms independently selected from O, N or S;
$L^3$ represents a direct bond, $—(CR^9R^{10})_t—$, $—C(O)N(R^{11})—(CH_2)_q—$, $—C(O)N(R^{11})—(CH_2)_q—S(O)_2—$, $—NR^{11}C(O)—(CH_2)_q—$, $—C(O)—(CH_2)_q—$, $—O—(CH_2)_q—$, $—O—(CH_2)_q—NR^{11}—(CH_2)_q—$, $—O—(CH_2)_q—C(O)NR^{11}—(CH_2)_q—$, $—S—$, $—S(O)—$ or $—S(O)_2—$;
$R^{11}$ represents hydrogen or methyl;
$R^{12}$ represents:
  halo, $C_{1-6}$alkyl, $C_{2-6}$alkenyl, $C_{2-6}$alkynyl, carboxy, $C_{1-6}$alkoxy, cyano, oxo, fluoro$C_{1-6}$alkyl, hydroxy, amino, N—$C_{1-4}$alkylamino or N,N-di-$C_{1-4}$alkylamino;
  aryl, wherein the aryl ring is optionally substituted with 1, 2 or 3 substituents selected from $R^{13}$;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^{13}$; or
  a monocyclic 4, 5, 6 or 7 membered heterocyclic ring which comprises 1, 2, 3 or 4 heteroatoms independently selected from O, N or S and wherein the heterocyclic ring is optionally substituted with 1, 2 or 3 substituents selected from $R^{13}$;
$R^{13}$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, N—$C_{1-4}$alkylamino, N,N-di-$C_{1-4}$ alkylamino or $—C(O)NR^{14}R^{15}$ wherein $R^{14}$ and $R^{15}$ independently represent hydrogen or methyl; and
r represents 0, 1, 2 or 3.

According to a fifth aspect of the present invention there is provided a compound of Formula (Ic), or a pharmaceutically acceptable salt thereof, for use in the treatment of prostate cancer:

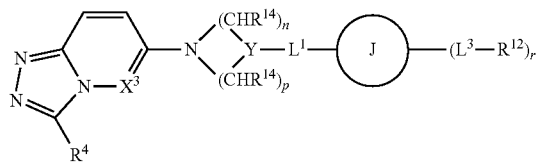

(Ic)

wherein
X³ represents CH or N;
R⁴ represents haloC₁₋₄alkyl;
Y represents CH, COH or N;
R¹⁴, identically or differently on each occurrence, represents hydrogen or methyl;
n and p independently represent 1 or 2;
L¹ represents a direct bond, —(CR⁹R¹⁰)$_t$—, —(CR⁹R¹⁰)$_v$—O—(CR⁹R¹⁰)$_v$—, —N(R¹¹)—(CH₂)$_q$—, —S—, —S(O)— or —S(O)₂—;
R⁹ and R¹⁰, identically or differently on each occurrence, represent hydrogen or methyl;
q, identically or differently on each occurrence, represents 0, 1, 2 or 3;
t represents 1, 2 or 3;
v, identically or differently on each occurrence, represents 0, 1 or 2;
J represents:
  aryl;
  a totally saturated monocyclic 3 to 6 membered carbocyclic ring;
  a monocyclic 4, 5, 6 or 7 membered heterocylic ring which comprises 1, 2, 3 or 4 heteroatoms independently selected from O, N or S;
  a monocyclic 5 or 6 membered heteroaryl ring comprising 1, 2, 3 or 4 heteroatoms independently selected from O, N or S; or
  a bicyclic 9 or 10 membered heteroaryl ring system comprising 1, 2, 3, 4 or 5 heteroatoms independently selected from O, N or S;
L³ represents a direct bond, —(CR⁹R¹⁰)$_t$—, —C(O)N(R¹¹)—(CH₂)$_q$—, —C(O)N(R¹¹)—(CH₂)$_q$—S(O)₂—, —NR¹¹C(O)—(CH₂)$_q$—, C(O)—(CH₂)$_q$—, O—(CH₂)$_q$—, —O—(CH₂)$_q$—NR¹¹—(CH₂)$_q$—, —O—(CH₂)$_q$—C(O)NR¹¹—(CH₂)$_q$—, —S—, —S(O)— or —S(O)₂—;
R¹¹ represents hydrogen or methyl;
R¹² represents:
  halo, C₁₋₆alkyl, C₂₋₆alkenyl, C₂₋₆alkynyl, carboxy, C₁₋₆alkoxy, cyano, oxo, fluoroC₁₋₆alkyl, hydroxy, amino, N—C₁₋₄alkylamino or N,N-di-C₁₋₄alkylamino;
  aryl, wherein the aryl ring is optionally substituted with 1, 2 or 3 substituents selected from R¹³;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from R¹³; or
  a monocyclic 4, 5, 6 or 7 membered heterocylic ring which comprises 1, 2, 3 or 4 heteroatoms independently selected from O, N or S and wherein the heterocyclic ring is optionally substituted with 1, 2 or 3 substituents selected from R¹³;
R¹³ represents amino, halo, C₁₋₆alkyl, C₂₋₆alkenyl, C₂₋₆alkynyl, C₁₋₆alkoxy, C₂₋₆alkanoyl, C₁₋₆alkoxyC₁₋₆alkyl, carboxy, cyano, oxo, fluoroC₁₋₆alkyl, hydroxy, hydroxyC₁₋₆alkyl, C₁₋₆alkylsulphanyl, C₁₋₆alkylsulphinyl, C₁₋₆alkylsulphonyl, N—C₁₋₄alkylamino, N,N-di-C₁₋₄alkylamino or —C(O)NR¹⁴R¹⁵ wherein R¹⁴ and R¹⁵ independently represent hydrogen or methyl; and
r represents 0, 1, 2 or 3.

According to a sixth aspect of the present invention there is provided a compound of Formula (Ic), or a pharmaceutically acceptable salt thereof:

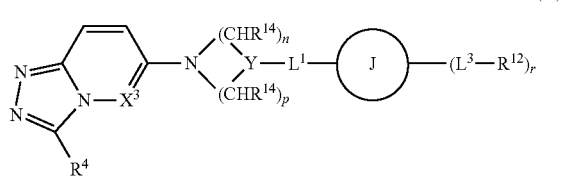

(Ic)

wherein
X³ represents CH or N;
R⁴ represents haloC₁₋₄alkyl;
Y represents CH, COH or N;
R¹⁴, identically or differently on each occurrence, represents hydrogen or methyl;
n and p independently represent 1 or 2;
L¹ represents a direct bond, —(CR⁹R¹⁰)$_t$—, —(CR⁹R¹⁰)$_v$—O—(CR⁹R¹⁰)$_v$—, —N(R¹¹)—(CH₂)$_q$—, —S—, —S(O)— or —S(O)₂—;
R⁹ and R¹⁰, identically or differently on each occurrence, represent hydrogen or methyl;
q, identically or differently on each occurrence, represents 0, 1, 2 or 3;
t represents 1, 2 or 3;
v, identically or differently on each occurrence, represents 0, 1 or 2;
J represents:
  aryl;
  a totally saturated monocyclic 3 to 6 membered carbocyclic ring;
  furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl or thiadiazolyl; or
  a bicyclic 9 membered heteroaryl ring system which comprises 1 or 2 nitrogen atoms, 1 or 2 oxygen atoms, 1 sulphur atom, or 1 nitrogen atom and 1 sulphur atom;
L³ represents a direct bond, —(CR⁹R¹⁰)$_t$—, —C(O)N(R¹¹)—(CH₂)$_q$—, —C(O)N(R¹¹)—(CH₂)$_q$—S(O)₂—, —NR¹¹C(O)—(CH₂)$_q$—, —C(O)—(CH₂)$_q$—, —O—(CH₂)$_q$—, —O—(CH₂)$_q$—NR¹¹—(CH₂)$_q$—, —O—(CH₂)$_q$—C(O)NR¹¹—(CH₂)$_q$—, —S—, —S(O)— or —S(O)₂—;
R¹¹ represents hydrogen or methyl;
R¹² represents:
  halo, C₁₋₆alkyl, C₂₋₆alkenyl, C₂₋₆alkynyl, carboxy, C₁₋₆alkoxy, cyano, oxo, fluoroC₁₋₆alkyl, hydroxy, amino, N—C₁₋₄alkylamino or N,N-di-C₁₋₄alkylamino;
  aryl, wherein the aryl ring is optionally substituted with 1, 2 or 3 substituents selected from R¹³;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from R¹³; or
  a monocyclic 4, 5, 6 or 7 membered heterocylic ring which comprises 1, 2, 3 or 4 heteroatoms independently selected from O, N or S and wherein the heterocyclic ring is optionally substituted with 1, 2 or 3 substituents selected from R¹³;
R¹³ represents amino, halo, C₁₋₆alkyl, C₂₋₆alkenyl, C₂₋₆alkynyl, C₁₋₆alkoxy, C₂₋₆alkanoyl, C₁₋₆alkoxyC₁₋₆alkyl, carboxy, cyano, oxo, fluoroC₁₋₆alkyl, hydroxy, hydroxyC₁₋₆alkyl, C₁₋₆alkylsulphanyl, C₁₋₆alkylsulphinyl, C₁₋₆alkylsulphonyl, N—C₁₋₄alkylamino, N,N-di-C₁₋₄ alkylamino or —C(O)NR$^{14}$R$^{15}$ wherein R$^{14}$ and R$^{15}$ independently represent hydrogen or methyl;

r represents 1, 2 or 3 when J represents aryl;

r represents 0 when J represents a totally saturated monocyclic 3 to 6 membered carbocyclic ring; and r represents 0, 1, 2 or 3 when J represents furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl, thiadiazolyl, or a bicyclic 9 membered heteroaryl ring system which comprises 1 or 2 nitrogen atoms, 1 or 2 oxygen atoms, 1 sulphur atom, or 1 nitrogen atom and 1 sulphur atom;

with the proviso that the compound of Formula (Ic) is other than:

4-{4-[3-(trifluoromethyl)[1,2,4]triazolo[4,3-b]pyridazin-6-yl]piperazin-1-yl}phenol;

6-[4-(pyridin-3-ylmethyl)piperazin-1-yl]-3-(trifluoromethyl)[1,2,4]triazolo[4,3-b]pyridazine;

6-[4-(2-fluorobenzyl)piperazin-1-yl]-3-(trifluoromethyl)[1,2,4]triazolo[4,3-b]pyridazine;

6-[4-(imidazo[1,2-a]pyridin-2-ylmethyl)piperazin-1-yl]-3-(trifluoromethyl)[1,2,4]triazolo[4,3-b]pyridazine;

6-[4-(3,4-dimethoxybenzyl)piperazin-1-yl]-3-(trifluoromethyl)[1,2,4]triazolo[4,3-b]pyridazine;

6-[4-(1H-indol-3-yl)piperidin-1-yl]-3-(trifluoromethyl)[1,2,4]triazolo[4,3-b]pyridazine;

6-{4-[2-(3,5-dimethoxyphenyl)ethyl]piperidin-1-yl}-3-(trifluoromethyl)[1,2,4]triazolo[4,3-b]pyridazine;

6-[4-(4-methoxybenzyl)piperazin-1-yl]-3-(trifluoromethyl)[1,2,4]triazolo[4,3-b]pyridazine;

6-[4-(3-chlorobenzyl)piperazin-1-yl]-3-(trifluoromethyl)[1,2,4]triazolo[4,3-b]pyridazine;

6-[4-(4-chlorobenzyl)piperazin-1-yl]-3-(trifluoromethyl)[1,2,4]triazolo[4,3-b]pyridazine;

6-[4-(2-methylbenzyl)piperazin-1-yl]-3-(trifluoromethyl)[1,2,4]triazolo[4,3-b]pyridazine;

6-[4-(pyridin-4-ylmethyl)piperazin-1-yl]-3-(trifluoromethyl)[1,2,4]triazolo[4,3-b]pyridazine;

6-[4-(2,6-dimethylphenyl)piperazin-1-yl]-3-(trifluoromethyl)[1,2,4]triazolo[4,3-b]pyridazine;

6-[4-(4-methoxyphenyl)piperazin-1-yl]-3-(trifluoromethyl)[1,2,4]triazolo[4,3-b]pyridazine;

6-[4-(3-chlorophenyl)piperazin-1-yl]-3-(trifluoromethyl)[1,2,4]triazolo[4,3-b]pyridazine;

6-[4-(4-fluorophenyl)piperazin-1-yl]-3-(trifluoromethyl)[1,2,4]triazolo[4,3-b]pyridazine; or 6-{4-[(2,6-difluorophenyl)sulfonyl]piperazin-1-yl}-3-(trifluoromethyl)[1,2,4]triazolo[4,3-b]pyridazine.

According to one embodiment of the sixth aspect of the present invention there is provided a compound of Formula (Ic), or a pharmaceutically acceptable salt thereof:

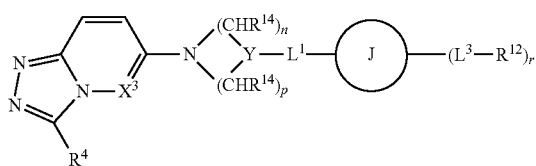

(Ic)

wherein

X$^3$ represents CH or N;

R$^4$ represents difluoromethyl, trifluoromethyl or chloro(difluoro)methyl;

Y represents CH, COH or N;

R$^{14}$, identically or differently on each occurrence, represents hydrogen or methyl;

n and p independently represent 1 or 2;

L$^1$ represents a direct bond, —(CR$^9$R$^{10}$)$_t$—, —(CR$^9$R$^{10}$)$_v$—O—(CR$^9$R$^{10}$)$_v$— or —N(R$^{11}$)—(CH$_2$)$_q$—;

R$^9$ and R$^{10}$, identically or differently on each occurrence, represent hydrogen or methyl;

q represents 0, 1, 2 or 3;

t represents 1 or 2;

v represents 0, 1 or 2;

J represents:

aryl;

a totally saturated monocyclic 3 to 6 membered carbocyclic ring;

imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl; or a bicyclic 9 membered heteroaryl ring system comprising 1 or 2 nitrogen atoms or a single sulphur atom;

L$^3$ represents a direct bond, —(CH$_2$)$_q$—, —C(O)N(R$^{11}$)—(CH$_2$)$_q$—, —NR$^{10}$C(O)—(CH$_2$)$_q$—, —C(O)—(CH$_2$)$_q$—, —O—(CH$_2$)$_q$—, —O—(CH$_2$)$_q$—NR$^{11}$—, —O—(CH$_2$)$_q$—C(O)NR$^{11}$—, —S—, —S(O)— or —S(O)$_2$—;

R$^{11}$ represents hydrogen or methyl;

R$^{12}$ represents:

halo, C$_{1-6}$alkyl, C$_{2-6}$alkenyl, C$_{2-6}$alkynyl, carboxy, C$_{1-6}$alkoxy, cyano, oxo, fluoroC$_{1-6}$alkyl, hydroxy, amino, N—C$_{1-4}$alkylamino or N,N-di-C$_{1-4}$alkylamino;

a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from R$^{13}$; or a monocyclic 4, 5, 6 or 7 membered heterocyclic ring which comprises 1, 2, 3 or 4 heteroatoms independently selected from O, N or S and wherein the heterocyclic ring is optionally substituted with 1, 2 or 3 substituents selected from R$^{13}$;

R$^{13}$ represents amino, halo, C$_{1-6}$alkyl, C$_{2-6}$alkenyl, C$_{2-6}$alkynyl, C$_{1-6}$alkoxy, C$_{2-6}$alkanoyl, C$_{1-6}$alkoxyC$_{1-6}$alkyl, carboxy, cyano, oxo, fluoroC$_{1-6}$alkyl, hydroxy, hydroxyC$_{1-6}$alkyl, C$_{1-6}$alkylsulphanyl, C$_{1-6}$alkylsulphinyl, C$_{1-6}$alkylsulphonyl, N—C$_{1-4}$alkylamino, N,N-di-C$_{1-4}$ alkylamino or —C(O)NR$^{14}$R$^{15}$ wherein R$^{14}$ and R$^{15}$ independently represent hydrogen or methyl;

r represents 1, 2 or 3 when J represents aryl;

r represents 0 when J represents a totally saturated monocyclic 3 to 6 membered carbocyclic ring; and r represents 0, 1, 2 or 3 when J represents imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl or a bicyclic 9 membered heteroaryl ring system comprising 1 or 2 nitrogen atoms or a single sulphur atom;

with the proviso that the compound of Formula (Ic) is other than:

4-{4-[3-(trifluoromethyl)[1,2,4]triazolo[4,3-b]pyridazin-6-yl]piperazin-1-yl}phenol;

6-[4-(pyridin-3-ylmethyl)piperazin-1-yl]-3-(trifluoromethyl)[1,2,4]triazolo[4,3-b]pyridazine;

6-[4-(2-fluorobenzyl)piperazin-1-yl]-3-(trifluoromethyl)[1,2,4]triazolo[4,3-b]pyridazine;

6-[4-(imidazo[1,2-a]pyridin-2-ylmethyl)piperazin-1-yl]-3-(trifluoromethyl)[1,2,4]triazolo[4,3-b]pyridazine;

6-[4-(3,4-dimethoxybenzyl)piperazin-1-yl]-3-(trifluoromethyl)[1,2,4]triazolo[4,3-b]pyridazine;

6-[4-(1H-indol-3-yl)piperidin-1-yl]-3-(trifluoromethyl)[1,2,4]triazolo[4,3-b]pyridazine;
6-{4-[2-(3,5-dimethoxyphenyl)ethyl]piperidin-1-yl}-3-(trifluoromethyl)[1,2,4]triazolo[4,3-b]pyridazine;
6-[4-(4-methoxybenzyl)piperazin-1-yl]-3-(trifluoromethyl) [1,2,4]triazolo[4,3-b]pyridazine;
6-[4-(3-chlorobenzyl)piperazin-1-yl]-3-(trifluoromethyl)[1,2,4]triazolo[4,3-b]pyridazine;
6-[4-(4-chlorobenzyl)piperazin-1-yl]-3-(trifluoromethyl)[1,2,4]triazolo[4,3-b]pyridazine;
6-[4-(2-methylbenzyl)piperazin-1-yl]-3-(trifluoromethyl)[1,2,4]triazolo[4,3-b]pyridazine;
6-[4-(pyridin-4-ylmethyl)piperazin-1-yl]-3-(trifluoromethyl)[1,2,4]triazolo[4,3-b]pyridazine;
6-[4-(2,6-dimethylphenyl)piperazin-1-yl]-3-(trifluoromethyl)[1,2,4]triazolo[4,3-b]pyridazine;
6-[4-(4-methoxyphenyl)piperazin-1-yl]-3-(trifluoromethyl) [1,2,4]triazolo[4,3-b]pyridazine; or
6-[4-(3-chlorophenyl)piperazin-1-yl]-3-(trifluoromethyl)[1,2,4]triazolo[4,3-b]pyridazine.

According to a further embodiment of the sixth aspect of the present invention there is provided a compound of Formula (If), or a pharmaceutically acceptable salt thereof:

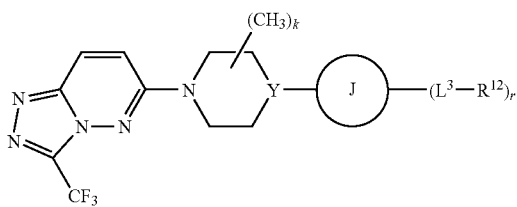

(If)

wherein
Y represents CH, COH or N;
k represents 0, 1 or 2;
J represents:
  aryl;
  a totally saturated monocyclic 3 to 6 membered carbocyclic ring;
  furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl or thiadiazolyl; or
  a bicyclic 9 membered heteroaryl ring system which comprises 1 or 2 nitrogen atoms, 1 or 2 oxygen atoms, 1 sulphur atom, or 1 nitrogen atom and 1 sulphur atom;
$L^3$ represents a direct bond, $-(CR^9R^{10})_t-$, $-C(O)N(R^{11})-(CH_2)_q-$, $-C(O)N(R^{11})-(CH_2)_q-S(O)_2-$, $-C(O)-(CH_2)_q-$, $-O-(CH_2)_q-$, $-O-(CH_2)_q-NR^{11}-(CH_2)_q-$, $-O-(CH_2)_q-C(O)NR^{11}-(CH_2)_q-$, $-S-$, $-S(O)-$ or $-S(O)_2-$;
$R^9$ and $R^{10}$, identically or differently on each occurrence, represent hydrogen or methyl; q, identically or differently on each occurrence, represents 0, 1, 2 or 3;
t represents 1, 2 or 3;
$R^{11}$ represents hydrogen or methyl;
$R^{12}$ represents:
  halo, $C_{1-6}$alkyl, $C_{2-6}$alkenyl, $C_{2-6}$alkynyl, carboxy, $C_{1-6}$alkoxy, fluoro$C_{1-6}$alkyl, hydroxy, amino, $N-C_{1-4}$alkylamino or $N,N$-di-$C_{1-4}$alkylamino;
  aryl, wherein the aryl ring is optionally substituted with 1, 2 or 3 substituents selected from $R^{13}$;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^{13}$; or
  a monocyclic 4, 5, 6 or 7 membered heterocyclic ring which comprises 1, 2, 3 or 4 heteroatoms independently selected from O, N or S and wherein the heterocyclic ring is optionally substituted with 1, 2 or 3 substituents selected from $R^{13}$;
$R^{13}$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, $N-C_{1-4}$alkylamino, $N,N$-di-$C_{1-4}$ alkylamino or $-C(O)NR^{14}R^{15}$ wherein $R^{14}$ and $R^{15}$ independently represent hydrogen or methyl;
r represents 1, 2 or 3 when J represents aryl;
r represents 0 when J represents a totally saturated monocyclic 3 to 6 membered carbocyclic ring; and
r represents 0, 1, 2 or 3 when J represents furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl, thiadiazolyl, or a bicyclic 9 membered heteroaryl ring system which comprises 1 or 2 nitrogen atoms, 1 or 2 oxygen atoms, 1 sulphur atom, or 1 nitrogen atom and 1 sulphur atom;
with the proviso that the compound of Formula (If) is other than:
  4-{4-[3-(trifluoromethyl)[1,2,4]triazolo[4,3-b]pyridazin-6-yl]piperazin-1-yl}phenol;
  6-[4-(1H-indol-3-yl)piperidin-1-yl]-3-(trifluoromethyl)[1,2,4]triazolo[4,3-b]pyridazine;
  6-[4-(2,6-dimethylphenyl)piperazin-1-yl]-3-(trifluoromethyl)[1,2,4]triazolo[4,3-b]pyridazine;
  6-[4-(4-methoxyphenyl)piperazin-1-yl]-3-(trifluoromethyl) [1,2,4]triazolo[4,3-b]pyridazine;
  6-[4-(3-chlorophenyl)piperazin-1-yl]-3-(trifluoromethyl)[1,2,4]triazolo[4,3-b]pyridazine; or
  6-[4-(4-fluorophenyl)piperazin-1-yl]-3-(trifluoromethyl)[1,2,4]triazolo[4,3-b]pyridazine.

According to a seventh aspect of the present invention there is provided a compound of Formula (Id), or a pharmaceutically acceptable salt thereof:

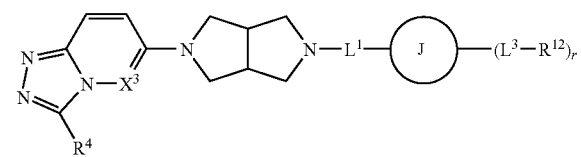

(Id)

wherein
$X^3$ represents CH or N;
$R^4$ represents halo$C_{1-4}$alkyl;
$L^1$ represents a direct bond, $-(CR^9R^{10})_t-$, $-(CR^9R^{10})_v-O-(CR^9R^{10})_v-$, $-N(R^{11})-(CH_2)_q-$, $-S-$, $-S(O)-$ or $-S(O)_2-$;
$R^9$ and $R^{10}$, identically or differently on each occurrence, represent hydrogen or methyl;

q, identically or differently on each occurrence, represents 0, 1, 2 or 3;

t represents 1, 2 or 3;

v, identically or differently on each occurrence, represents 0, 1 or 2;

J represents:
  aryl;
  a totally saturated monocyclic 3 to 6 membered carbocyclic ring;
  a monocyclic 4, 5, 6 or 7 membered heterocylic ring which comprises 1, 2, 3 or 4 heteroatoms independently selected from O, N or S;
  a monocyclic 5 or 6 membered heteroaryl ring which comprises 1, 2, 3 or 4 heteroatoms independently selected from O, N or S; or
  a bicyclic 9 or 10 membered heteroaryl ring system which comprises 1, 2, 3, 4 or 5 heteroatoms independently selected from O, N or S;

$L^3$ represents a direct bond, $-(CR^9R^{10})_t-$, $-C(O)N(R^{11})-(CH_2)_q-$, $-C(O)N(R^{11})-(CH_2)_q-S(O)_2-$, $-NR^{11}C(O)-(CH_2)_q-$, $-C(O)-(CH_2)_q-$, $-O-(CH_2)_q-$, $-O-(CH_2)_q-NR^{11}-(CH_2)_q-$, $-O-(CH_2)_q-C(O)NR^{11}-(CH_2)_q-$, $-S-$, $-S(O)-$ or $-S(O)_2-$;

$R^{11}$ represents hydrogen or methyl;

$R^{12}$ represents:
  halo, $C_{1-6}$alkyl, $C_{2-6}$alkenyl, $C_{2-6}$alkynyl, carboxy, $C_{1-6}$alkoxy, cyano, oxo, fluoro$C_{1-6}$alkyl, hydroxy, amino, $N-C_{1-4}$alkylamino or N,N-di-$C_{1-4}$alkylamino;
  aryl, wherein the aryl ring is optionally substituted with 1, 2 or 3 substituents selected from $R^{13}$;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^{13}$; or
  a monocyclic 4, 5, 6 or 7 membered heterocylic ring which comprises 1, 2, 3 or 4 heteroatoms independently selected from O, N or S and wherein the heterocyclic ring is optionally substituted with 1, 2 or 3 substituents selected from $R^{13}$;

$R^{13}$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, $N-C_{1-4}$alkylamino, N,N-di-$C_{1-4}$alkylamino or $-C(O)NR^{14}R^{15}$ wherein $R^{14}$ and $R^{15}$ independently represent hydrogen or methyl; and r represents 0, 1, 2 or 3.

According to an eighth aspect of the present invention there is provided a compound of Formula (Id) as defined hereinbefore, or a pharmaceutically acceptable salt thereof, for use as a medicament.

According to a ninth aspect of the present invention there is provided a compound of Formula (Id) as defined hereinbefore, or a pharmaceutically acceptable salt thereof, for use in the treatment of prostate cancer.

According to a tenth aspect of the present invention there is provided a compound of Formula (Ie), or a pharmaceutically acceptable salt thereof:

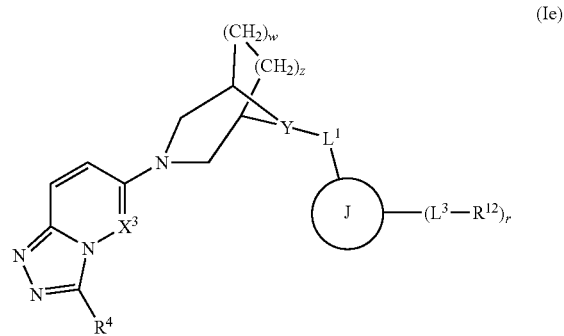

(Ie)

wherein
$X^3$ represents CH or N;
$R^4$ represents halo$C_{1-4}$alkyl;
Y represents CH, COH or N;
w and z independently represent 0 or 1;
$L^1$ represents a direct bond, $-(CR^9R^{10})_t-$, $-(CR^9R^{10})_v-O-(CR^9R^{10})_v-$, $-N(R^{11})-(CH_2)_q-$, $-S-$, $-S(O)-$ or $-S(O)_2-$;

$R^9$ and $R^{10}$, identically or differently on each occurrence, represent hydrogen or methyl;

q, identically or differently on each occurrence, represents 0, 1, 2 or 3;

t represents 1, 2 or 3;

v, identically or differently on each occurrence, represents 0, 1 or 2;

J represents:
  aryl;
  a totally saturated monocyclic 3 to 6 membered carbocyclic ring;
  a monocyclic 4, 5, 6 or 7 membered heterocylic ring which comprises 1, 2, 3 or 4 heteroatoms independently selected from O, N or S;
  a monocyclic 5 or 6 membered heteroaryl ring which comprises 1, 2, 3 or 4 heteroatoms independently selected from O, N or S; or
  a bicyclic 9 or 10 membered heteroaryl ring system which comprises 1, 2, 3, 4 or 5 heteroatoms independently selected from O, N or S;

$L^3$ represents a direct bond, $-(CR^9R^{10})_t-$, $-C(O)N(R^{11})-(CH_2)_q-$, $-C(O)N(R^{11})-(CH_2)_q-S(O)_2-$, $-NR^{11}C(O)-(CH_2)_q-$, $-C(O)-(CH_2)_q-$, $-O-(CH_2)_q-$, $-O-(CH_2)_q-NR^{11}-(CH_2)_q-$, $-O-(CH_2)_q-C(O)NR^{1"}-(CH_2)_q-$, $-S-$, $-S(O)-$ or $-S(O)_2-$;

$R^{11}$ represents hydrogen or methyl;

$R^{12}$ represents:
  halo, $C_{1-6}$alkyl, $C_{2-6}$alkenyl, $C_{2-6}$alkynyl, carboxy, $C_{1-6}$alkoxy, cyano, oxo, fluoro$C_{1-6}$alkyl, hydroxy, amino, $N-C_{1-4}$alkylamino or N,N-di-$C_{1-4}$alkylamino;
  aryl, wherein the aryl ring is optionally substituted with 1, 2 or 3 substituents selected from $R^{13}$;
  a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^{13}$; or
  a monocyclic 4, 5, 6 or 7 membered heterocylic ring which comprises 1, 2, 3 or 4 heteroatoms independently selected from O, N or S and wherein the heterocyclic ring is optionally substituted with 1, 2 or 3 substituents selected from $R^{13}$;

$R^{13}$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, N—$C_{1-4}$alkylamino, N,N-di-$C_{1-4}$ alkylamino or —C(O)NR$^{14}$R$^{15}$ wherein R$^{14}$ and R$^{15}$ independently represent hydrogen or methyl; and r represents 0, 1, 2 or 3.

According to an eleventh aspect of the present invention there is provided a compound of Formula (Ie) as defined hereinbefore, or a pharmaceutically acceptable salt thereof, for use as a medicament.

According to a twelfth aspect of the present invention there is provided a compound of Formula (Ie) as defined hereinbefore, or a pharmaceutically acceptable salt thereof, for use in the treatment of prostate cancer.

In further embodiments of the fourth, fifth, sixth, seventh, eighth, ninth, tenth, eleventh and twelfth aspects of the present invention, each of the following definitions of J, $L^1$, $L^3$, n, p, r, w, z, $R^4$, $R^9$, $R^{10}$, $R^{11}$, $R^{12}$, $R^{13}$, $X^3$ and Y in paragraphs (1) to (61) hereinafter may be used individually or in combination with one or more of the other following definitions to limit the broadest definitions of Formulae (Ic), (Id), (Ie) or (If).

(1) $X^3$ represents N;
(2) $X^3$ represents CH;
(3) $R^4$ represents difluoromethyl, trifluoromethyl, chloro(difluoro)methyl, difluoroethyl or difluoropropyl;
(4) $R^4$ represents difluoromethyl, trifluoromethyl or chloro(difluoro)methyl;
(5) $R^4$ represents difluoromethyl
(6) $R^4$ represents trifluoromethyl;
(7) $R^4$ represents chloro(difluoro)methyl;
(8) $R^{14}$ represents hydrogen;
(9) n and p both represent 2;
(10) n and p both represent 1;
(11) Y represents CH or COH;
(12) Y represents CH;
(13) Y represents COH;
(14) Y represents N;
(15) $L^1$ represents a direct bond, —(CR$^9$R$^{10}$)$_n$—, —(CR$^9$R$^{10}$)$_v$—O—(CR$^9$R$^{10}$)$_v$— or —N(R$^{11}$)—(CH$_2$)$_q$—;
(16) $L^1$ represents a direct bond, —CH$_2$—, —CH(CH$_3$)— or —O—;
(17) $L^1$ represents a direct bond;
(18) $L^1$ represents —CH$_2$—;
(19) J represents phenyl, pyridinyl, indolyl, indazolyl or pyrrolopyridinyl;
(20) J represents phenyl;
(21) J represents pyridinyl;
(22) J represents pyridin-3-yl;
(23) $L^3$ represents a direct bond;
(24) $L^3$ represents a direct bond, —(CR$^9$R$^{10}$)$_t$—, —C(O)N(R$^{11}$)—(CH$_2$)$_q$—, —NR$^{11}$C(O)—(CH$_2$)$_q$—, —C(O)—(CH$_2$)$_q$—, —O—(CH$_2$)$_q$— or —O—(CH$_2$)$_q$—C(O)NR$^{1}$"-(CH$_2$)$_q$—;
(25) $L^3$ represents —(CR$^9$R$^{10}$)$_t$—, —C(O)N(R$^{11}$)—(CH$_2$)$_q$—, —NR$^{11}$C(O)—(CH$_2$)$_q$—, —C(O)—(CH$_2$)$_q$—, —O—(CH$_2$)$_q$— or —O—(CH$_2$)$_q$—C(O)NR$^{11}$—(CH$_2$)$_q$—;
(26) $L^3$ represents —C(O)N(R$^{11}$)—(CH$_2$)$_q$—, —NR$^{11}$C(O)—(CH$_2$)$_q$—, —C(O)—(CH$_2$)$_q$—, —O—(CH$_2$)$_q$— or —O—(CH$_2$)$_q$—C(O)NR$^{1}$—(CH$_2$)$_q$—;
(27) $L^3$ represents —C(O)N(R$^{11}$)—(CH$_2$)$_q$—, —NR$^{10}$C(O)—(CH$_2$)$_q$—, —C(O)—(CH$_2$)$_q$— or —O—(CH$_2$)$_q$—;
(28) $L^3$ represents a direct bond, —C(O)N(R$^{11}$)—(CH$_2$)$_q$— or —O—(CH$_2$)$_q$—;
(29) $L^3$ represents —C(O)N(R$^{11}$)—(CH$_2$)$_q$— or —O—(CH$_2$)$_q$—;
(30) $L^3$ represents —O—(CH$_2$)$_q$—;
(31) $L^3$ represents —O—CH$_2$—CH$_2$—;
(32) $R^9$ and $R^{10}$ both represent hydrogen;
(33) $R^{11}$ represents hydrogen;
(34) $R^{11}$ represents methyl;
(35) q represents 0, 1 or 2;
(36) $R^{12}$ represents fluoro, chloro, methyl, methoxy, difluoromethyl, trifluoromethyl, cyano, hydroxy, imidazolyl, pyrrolidinyl, piperidinyl, methylsulphonyl, morpholinyl, pyrazolyl or phenyl;
(37) $R^{12}$ represents fluoro, chloro, methyl, methoxy, difluoromethyl, trifluoromethyl, hydroxy, imidazolyl, pyrrolidinyl, piperidinyl, methylsulphonyl, morpholinyl, pyrazolyl or phenyl;
(38) $R^{12}$ represents fluoro, chloro, methyl, methoxy, difluoromethyl, trifluoromethyl, cyano, hydroxy, methylsulphonyl, dimethylamino, pyrrolidinyl, piperidinyl, piperazinyl, morpholinyl or pyrazolyl;
(39) $R^{12}$ represents fluoro, chloro, methyl, methoxy, difluoromethyl, trifluoromethyl, hydroxy, methylsulphonyl, dimethylamino, pyrrolidinyl, piperidinyl, piperazinyl, morpholinyl or pyrazolyl;
(40) $R^{12}$ represents fluoro, chloro, methyl, methoxy, difluoromethyl, trifluoromethyl, cyano or hydroxy;
(41) $R^{12}$ represents fluoro, chloro, methyl, methoxy, difluoromethyl, trifluoromethyl or hydroxy;
(42) $R^{12}$ represents pyrrolidinyl, piperidinyl, methylsulphonyl, morpholinyl or pyrazolyl;
(43) $R^{12}$ represents pyrazolyl;
(44) $R^{12}$ represents pyrazol-5-yl;
(45) $R^{12}$ represents 1-methyl-1H-pyrazol-5-yl;
(46) r represents 1 or 2 when J represents aryl;
(47) r represents 1 when J represents aryl;
(48) r represents 0 or 1 when J represents imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl or a bicyclic 9 membered heteroaryl ring system comprising 1 or 2 nitrogen atoms or a single sulphur atom;
(49) r represents 1 when J represents imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl or a bicyclic 9 membered heteroaryl ring system comprising 1 or 2 nitrogen atoms or a single sulphur atom;
(50) r represents 0 when J represents imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl or a bicyclic 9 membered heteroaryl ring system comprising 1 or 2 nitrogen atoms or a single sulphur atom;
(51) r represents 1 when J represents pyrazolyl;
(52) $L^3$ represents —O—CH$_2$—CH$_2$—, $R^{12}$ represents 1-methyl-1H-pyrazol-5-yl and r represents 1;
(53) $R^{13}$ represents methyl, methoxy, oxo, hydroxy, cyano, acetyl or methylsulphonyl;
(54) $R^{13}$ represents methyl, methoxy, oxo, hydroxy, acetyl or methylsulphonyl;
(55) $R^{13}$ represents methyl, oxo or hydroxy;
(56) $R^{13}$ represents methyl;
(57) k represents 0;
(58) k represents 1;
(59) k represents 2;

(60) w and z both represent 1;
(61) w and z both represent 0.

Particular novel compounds of Formula (Ic) include, but are not limited to, the following compounds:

4-[[4-[3-(trifluoromethyl)-[1,2,4]triazolo[4,3-b]pyridazin-6-yl]piperazin-1-yl]methyl]benzonitrile;
3-(trifluoromethyl)-6-[4-[[3-(trifluoromethyl)phenyl]methyl]piperazin-1-yl]-[1,2,4]triazolo[4,3-b]pyridazine;
4-pyridin-3-yl-1-[3-(trifluoromethyl)[1,2,4]triazolo[4,3-b]pyridazin-6-yl]piperidin-4-ol;
3-(difluoromethyl)-6-{4-[(1R)-1-(4-fluorophenyl)ethyl]piperazin-1-yl}[1,2,4]triazolo[4,3-b]pyridazine;
4-(4-fluorophenyl)-1-[3-(trifluoromethyl)[1,2,4]triazolo[4,3-b]pyridazin-6-yl]piperidin-4-ol;
N-(2-methoxyethyl)-N-methyl-4-{1-[3-(trifluoromethyl)[1,2,4]triazolo[4,3-b]pyridazin-6-yl]piperidin-4-yl}benzamide;
N-(2-hydroxyethyl)-N-methyl-4-{1-[3-(trifluoromethyl)[1,2,4]triazolo[4,3-b]pyridazin-6-yl]piperidin-4-yl}benzamide;
6-(4-{4-[(4-methylpiperazin-1-yl)carbonyl]phenyl}piperidin-1-yl)-3-(trifluoromethyl)[1,2,4]triazolo[4,3-b]pyridazine;
N-[2-(2-oxopyrrolidin-1-yl)ethyl]-4-{1-[3-(trifluoromethyl)[1,2,4]triazolo[4,3-b]pyridazin-6-yl]piperidin-4-yl}benzamide;
6-[4-(1H-indazol-3-ylmethyl)piperazin-1-yl]-3-(trifluoromethyl)[1,2,4]triazolo[4,3-b]pyridazine;
N-(2-methoxyethyl)-N-methyl-3-({1-[3-(trifluoromethyl)[1,2,4]triazolo[4,3-b]pyridazin-6-yl]piperidin-4-yl}oxy)benzamide;
2-morpholin-4-yl-N-(4-{1-[3-(trifluoromethyl)[1,2,4]triazolo[4,3-b]pyridazin-6-yl]piperidin-4-yl}phenyl)acetamide;
6-(4-{4-[2-(1-methyl-1H-pyrazol-5-yl)ethoxy]phenyl}piperidin-1-yl)-3-(trifluoromethyl)[1,2,4]triazolo[4,3-b]pyridazine;
6-{4-[2-(difluoromethyl)-5-fluorobenzyl]piperazin-1-yl}-3-(trifluoromethyl)[1,2,4]triazolo[4,3-b]pyridazine;
6-{4-[(6-methylpyridin-3-yl)methyl]piperazin-1-yl}-3-(trifluoromethyl)[1,2,4]triazolo[4,3-b]pyridazine;
6-[4-(1H-pyrrolo[2,3-b]pyridin-3-yl)piperidin-1-yl]-3-(trifluoromethyl)[1,2,4]triazolo[4,3-b]pyridazine;
6-[4-(5-methoxy-1H-indol-3-yl)piperidin-1-yl]-3-(trifluoromethyl)[1,2,4]triazolo[4,3-b]pyridazine;
1-[(4-{1-[3-(trifluoromethyl)[1,2,4]triazolo[4,3-b]pyridazin-6-yl]piperidin-4-yl}phenyl)carbonyl]piperidin-4-ol;
N-methyl-N-[2-(methylsulfonyl)ethyl]-4-{1-[3-(trifluoromethyl)[1,2,4]triazolo[4,3-b]pyridazin-6-yl]piperidin-4-yl}benzamide;
6-[3-(4-methoxyphenoxy)azetidin-1-yl]-3-(trifluoromethyl)[1,2,4]triazolo[4,3-b]pyridazine;
6-(4-{4-[2-(1-methyl-1H-pyrazol-5-yl)ethoxy]phenyl}piperazin-1-yl)-3-(trifluoromethyl)[1,2,4]triazolo[4,3-b]pyridazine; and
4-[4-[2-(1-methyl-1H-pyrazol-5-yl)ethoxy]phenyl]-1-[3-(trifluoromethyl)[1,2,4]triazolo[4,3-b]pyridazin-6-yl]piperidin-4-ol;

and pharmaceutically acceptable salts thereof.

Crystalline forms of particular novel compounds of Formula (Ic), and a particular salt thereof, have also been identified.

According to the present invention there is therefore provided a crystalline form of 4-pyridin-3-yl-1-[3-(trifluoromethyl)[1,2,4]triazolo[4,3-b]pyridazin-6-yl]piperidin-4-ol, Anhydrous Form A, which has an X-ray powder diffraction pattern with at least one specific peak at a 2θ value of about 9.18°, 15.51°, 16.01°, 18.94° or 24.59° when measured using CuKa radiation, more particularly wherein said values may be plus or minus 0.5° 2θ.

According to the present invention there is therefore provided a crystalline form of 4-pyridin-3-yl-1-[3-(trifluoromethyl)[1,2,4]triazolo[4,3-b]pyridazin-6-yl]piperidin-4-ol, Anhydrous Form A, which has an X-ray powder diffraction pattern with specific peaks at 2θ values of about 9.18°, 15.51°, 16.01°, 18.94° and 24.59° when measured using CuKa radiation, more particularly wherein said values may be plus or minus 0.5° 2θ.

According to the present invention there is therefore provided a crystalline form of 4-pyridin-3-yl-1-[3-(trifluoromethyl)[1,2,4]triazolo[4,3-b]pyridazin-6-yl]piperidin-4-ol, Anhydrous Form A, which has an X-ray powder diffraction pattern with specific peaks at 2θ values of 8.30, 9.18, 9.96, 10.41, 14.35, 15.02, 15.51, 16.01, 17.03, 18.46, 18.94, 19.18, 19.82, 20.35, 20.61, 21.80, 22.65, 23.38, 24.15, 24.59, 25.43, 26.12, 26.35, 26.59, 27.43, 29.38, 31.83 and 37.33° when measured using CuKa radiation, more particularly wherein said values may be plus or minus 0.5° 2θ.

According to the present invention there is therefore provided a crystalline form of 4-pyridin-3-yl-1-[3-(trifluoromethyl)[1,2,4]triazolo[4,3-b]pyridazin-6-yl]piperidin-4-ol, Anhydrous Form A, which has an X-ray powder diffraction pattern substantially the same as the X-ray powder diffraction pattern shown in FIG. 1 when measured using CuKa radiation.

According to the present invention there is therefore provided a crystalline form of N-(2-methoxyethyl)-N-methyl-4-[1-[3-(trifluoromethyl)[1,2,4]triazolo[4,3-b]pyridazin-6-yl]piperidin-4-yl]benzamide, Anhydrous Form A, which has an X-ray powder diffraction pattern with at least one specific peak at a 2θ value of about 12.34°, 15.78°, 20.42°, 23.75° or 24.73° when measured using CuKa radiation, more particularly wherein said values may be plus or minus 0.5° 2θ.

According to the present invention there is therefore provided a crystalline form of N-(2-methoxyethyl)-N-methyl-4-[1-[3-(trifluoromethyl)[1,2,4]triazolo[4,3-b]pyridazin-6-yl]piperidin-4-yl]benzamide, Anhydrous Form A, which has an X-ray powder diffraction pattern with specific peaks at 2θ values of about 12.34°, 15.78°, 20.42°, 23.75° and 24.73° when measured using CuKa radiation, more particularly wherein said values may be plus or minus 0.5° 2θ.

According to the present invention there is therefore provided a crystalline form of N-(2-methoxyethyl)-N-methyl-4-[1-[3-(trifluoromethyl)[1,2,4]triazolo[4,3-b]pyridazin-6-yl]piperidin-4-yl]benzamide, Anhydrous Form A, which has an X-ray powder diffraction pattern with specific peaks at 2θ values of 6.28, 7.92, 9.65, 12.34, 12.69, 14.92, 15.78, 16.89, 18.78, 19.28, 20.42, 20.99, 21.57, 22.49, 23.31, 23.75, 24.34, 24.73, 25.38, 26.93, 28.14, 29.08, 31.16, 31.86, 32.50, 33.14, 34.79, 36.34, 36.78, 38.01 and 38.64° when measured using CuKa radiation, more particularly wherein said values may be plus or minus 0.5° 2θ.

According to the present invention there is therefore provided a crystalline form of N-(2-methoxyethyl)-N-methyl-4-[1-[3-(trifluoromethyl)[1,2,4]triazolo[4,3-b]pyridazin-6-yl]piperidin-4-yl]benzamide, Anhydrous Form A, which has an X-ray powder diffraction pattern substantially the same as the X-ray powder diffraction pattern shown in FIG. 2 when measured using CuKa radiation.

According to the present invention there is therefore provided a crystalline form of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine, Anhydrous Form A, which has an X-ray powder diffraction pattern with at least one specific peak at a 2θ value of about 4.90°, 13.47°, 15.93°, 16.64° or 22.83° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine, Anhydrous Form A, which has an X-ray powder diffraction pattern with specific peaks at 2θ values of about 4.90°, 13.47°, 15.93°, 16.64° and 22.83° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine, Anhydrous Form A, which has an X-ray powder diffraction pattern with specific peaks at 2θ values of 4.90, 9.784, 11.50, 11.94, 12.97, 13.47, 14.72, 15.93, 16.64, 17.36, 18.32, 18.67, 19.195, 19.67, 20.26, 20.58, 20.87, 21.33, 21.64, 22.83, 23.7, 24, 24.40, 25.99, 26.75, 27.15, 28.10, 28.55, 29.02, 29.46, 29.74, 30.12, 30.65, 31.37, 31.85, 33.66, 34.28, 35.85, 36.42, 37.62 and 38.53° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine, Anhydrous Form A, which has an X-ray powder diffraction pattern substantially the same as the X-ray powder diffraction pattern shown in FIG. 3 when measured using CuKa radiation.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine, Anhydrous Form A, which has an X-ray powder diffraction pattern with at least one specific peak at a 2θ value of about 6.90°, 15.38°, 21.55°, 24.48° or 27.56° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine, Anhydrous Form A, which has an X-ray powder diffraction pattern with specific peaks at 2θ values of about 6.90°, 15.38°, 21.55°, 24.48° and 27.56° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine, Anhydrous Form A, which has an X-ray powder diffraction pattern with specific peaks at 2θ values of 6.90, 9.6, 10.78, 12.82, 13.16, 13.85, 14.44, 15.38, 16.44, 17.46, 18.25, 18.92, 19.27, 20.18, 21.03, 21.55, 22.36, 22.63, 23.55, 23.76, 24.48, 25.2, 25.76, 26.47, 27.56, 27.83, 28.21, 29.10, 29.93, 30.59, 31.20, 32.49, 33.33, 34.04, 34.62, 36.18, 36.54, 37.45, 38.17 and 39.32° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine, Anhydrous Form A, which has an X-ray powder diffraction pattern substantially the same as the X-ray powder diffraction pattern shown in FIG. 4 when measured using CuKa radiation.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate which has an X-ray powder diffraction pattern with at least one specific peak at a 2θ value of about 11.72°, 16.46°, 17.58° or 21.89° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate which has an X-ray powder diffraction pattern with specific peaks at 2θ values of about 11.72°, 16.46°, 17.58° and 21.89° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate which has an X-ray powder diffraction pattern with specific peaks at 2θ values of 4.51, 5.90, 11.72, 12.22, 13.23, 16.46, 17.58, 19.74, 20.26, 21.18, 21.89, 23.86, 24.17, 25.83, 26.75, 28.78, 30.54 and 31.51° when measured using CuKa radiation, more particularly wherein said values may be plus or minus 0.5° 2θ.

According to the present invention there is therefore provided a crystalline form of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate which has an X-ray powder diffraction pattern substantially the same as the X-ray powder diffraction pattern shown in FIG. 5 when measured using CuKa radiation.

Reference herein to a compound of Formula (I) should be understood to refer equally to a compound of Formula (Ic), (Id), (Ie) and (If).

A suitable pharmaceutically-acceptable salt of a compound of the Formula (I) is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

A suitable pharmaceutically-acceptable solvate of a compound of the Formula I is, for example, a hydrate such as a hemi-hydrate, a mono-hydrate, a di-hydrate or a tri-hydrate or an alternative quantity thereof.

The compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a carboxy group is, for example, an in vivo cleavable ester thereof. An in vivo cleavable ester of a compound of the Formula (I) containing a carboxy group is, for example, a pharmaceutically-acceptable ester which is cleaved in the human or animal body to produce the parent acid. Suitable pharmaceutically-acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically-acceptable pro-drug of a compound of the Formula (I) that possesses a hydroxy group is, for example, an in vivo cleavable ester or ether thereof. An in vivo cleavable ester or ether of a compound of the Formula (I) containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N-[di-$C_{1-4}$alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$C_{1-4}$alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula (I) that possesses a carboxy group is, for example, an in vivo cleavable amide thereof, for example an amide formed with an amine such as ammonia, a $C_{1-4}$alkylamine such as methylamine, a di-$C_{1-4}$alkylamine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically-acceptable pro-drug of a compound of the Formula (I) that possesses an amino group is, for example, an in vivo cleavable amide derivative thereof. Suitable pharmaceutically-acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$)alkylpiperazin-1-ylmethyl.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

An example of a metabolite of a compound of the Formula (I) is 3-[4-hydroxy-1-[3-(trifluoromethyl)-[1,2,4]triazolo[4,3-b]pyridazin-6-yl]piperidin-4-yl]pyridine 1-oxide which is a metabolite of 4-pyridin-3-yl-1-[3-(trifluoromethyl)[1,2,4]triazolo[4,3-b]pyridazin-6-yl]piperidin-4-ol.

The compounds of Formula (I) can be prepared by a process comprising a step selected from (1) to (10) as follows, these processes are provided as a further feature of the invention:—

Preparation of Compounds of Formula (I)

1. A process for the manufacture of compounds of Formula (I) comprises reacting a compound of formula (II), wherein G is a leaving group such as halogen, alkane sulfonyloxy, or arylsulfonyloxy and $R^4$, $X^1$, $X^2$, and $X^3$ are as defined above, with a monocyclic or bicyclic amine of Formula (III), wherein $R^5$ and m are as defined above.

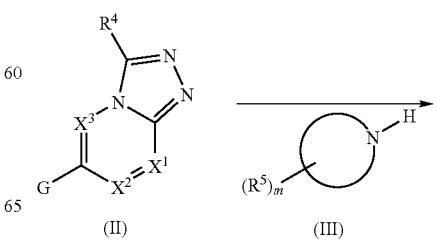

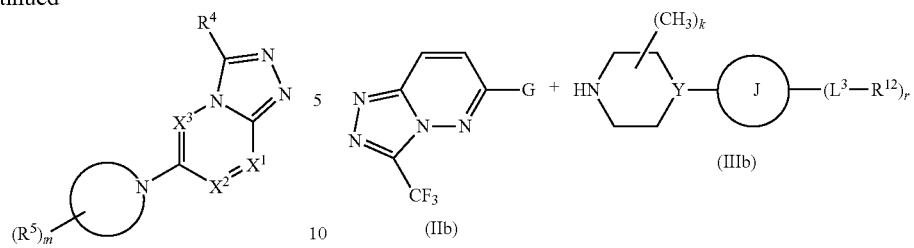

The reaction may be carried out by combining the components in an inert solvent such as ethanol, xylene, or N-methylpyrrolidone at temperatures between 25° C. and 250° C., preferably between 50° C. and 150° C. The reaction may be advantageously catalyzed by bases such as organic bases, for instance diisopropylethylamine or by low-valent transition metal catalysts such as Pd(0), for instance bis(dibenzylideneacetone) palladium(0). The reaction may be heated by a conventional heat source, such as an oil bath or a heating block, or by microwave heating.

In one embodiment of the invention, there is provided a process for the preparation of compounds of Formula (Ic) which comprises reacting a compound of Formula (IIa), wherein G is a suitable leaving group such as halogen, for example chloro, and $R^4$ and $X^3$ are as defined hereinbefore in relation to Formula (Ic), with an amine of Formula (IIIa), wherein J, Y, $L^1$, $L^3$, $R^{12}$, $R^{14}$, n, p and r are as defined hereinbefore in relation to Formula (Ic):

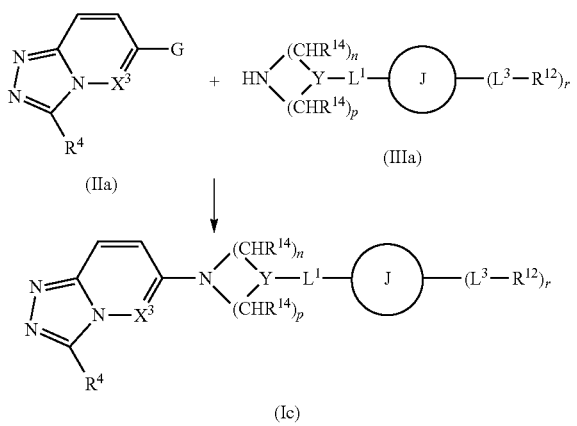

and thereafter, if necessary:
(i) converting a functional group of one compound of the invention into another functional group;
(ii) introducing a new functional group into one compound of the invention;
(iii) removing any protecting groups;
(iv) for compounds of the invention in the form of a single enantiomer separating a racemic compound of the invention into separate enantiomers;
(v) preparing a pharmaceutically acceptable salt thereof, and/or
(vi) preparing a crystalline form thereof.

In a further embodiment of the invention, there is provided a process for the preparation of compounds of Formula (If) which comprises reacting a compound of Formula (IIb), wherein G represents halogen, with an amine of Formula (IIIb), wherein Y, J, $L^3$, $R^{12}$, k and r are as defined hereinbefore in relation to Formula (If):

and thereafter, if necessary:
(i) converting a functional group of one compound of the invention into another functional group;
(ii) introducing a new functional group into one compound of the invention;
(iii) removing any protecting groups;
(iv) for compounds of the invention in the form of a single enantiomer separating a racemic compound of the invention into separate enantiomers;
(v) preparing a pharmaceutically acceptable salt thereof, and/or
(vi) preparing a crystalline form thereof.

The above reactions may be carried out by combining the components of formula (IIa) and (IIIa) or (IIb) and (IIIb) in a suitable solvent, for example dimethylformamide or dimethylacetamide, at a suitable temperature, for example between 25° C. and 250° C., more particularly between 50° C. and 150° C., in the presence of a suitable base, for example diisopropylethylamine. The reaction may be heated by a conventional heat source, such as an oil bath or a heating block, or by microwave heating.

Compounds of formula (II), (IIa) or (IIb) may be made by methods well-known to those skilled in the art including methods according to or analogous to methods described in the chemical literature, for instance as described in W. L. Mosby, *Heterocyclic Compounds*, Vol. 15 Part 1 and Part 2, *Systems with Bridgehead Nitrogen*, Interscience, 1961; R. N. Castle, *Heterocyclic Compounds*, Vol. 27, *Condensed Pyridazines*, Wiley, 1973; and *Heterocyclic Chemistry*, Vol. 35, *Condensed Pyrazines*, G. W. H. Cheeseman and R. F. Cookson, Wiley, 1979 and references therein.

Amines of formula (III), (IIIa) or (IIIb) may be made by methods well-known to those skilled in the art including methods according to or analogous to methods described in the chemical literature, for instance J. R. Malpass, *Aliphatic and Cyclic Amines in Comprehensive Organic Chemistry*, Volume 2, p 3, D. Barton and D. Ollis Eds, Pergamon, 1979, J. M. J. Gladych and D. Hartley, *Polyfunctional Amines in Comprehensive Organic Chemistry*, Volume 2, p 61, D. Barton and D. Ollis Eds, Pergamon, 1979; *Houben-Weyl Meth-* ods of Organic Chemistry, Vol E 23 e Cyclic Compounds I (1999) to Vol E 23 j Cyclic Compounds VI (2000) and references therein and modified as required by functional group transformations well-known to those skilled in the art including methods according to or analogous to methods described in the chemical literature, for instance Comprehensive Functional Group Transformations, A. R. Katritzky, O. Meth-Cohn, and C. W. Rees Eds., Pergamon, 1995, and references therein.

2. A process for the manufacture of compounds of Formula (I) comprises reacting a compound of formula (II), wherein G is a leaving group such as iodide, bromide, chloride, alkane sulfonyloxy, or arylsulfonyloxy and $R^4$, $X^1$, $X^2$, and $X^3$ are as defined above, with a monocyclic or bicyclic organometallic compound such as an organozinc compound of formula (IV) wherein $R^5$ and m are as defined above and M is a suitable metal such as Zn—W wherein W is one or more inert ligand or ligands, such as bromide or iodide.

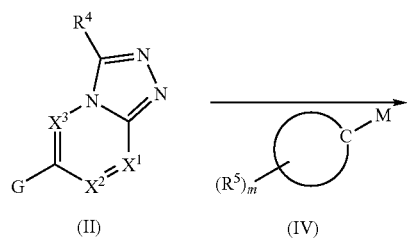

(II)            (IV)

The reaction may be advantageously catalysed by low-valent transition metal catalysts such as Pd(0), for instance bisdiphenylphosphinoferrocene)palladium(II) dichloride (dppf). The reaction may be carried out by combining the components in an inert solvent such as xylene or tetrahydrofuran at temperatures between 0° C. and 150° C., preferably between 25° C. and 100° C. The reaction may be heated by a conventional heat source, such as an oil bath or a heating block, or by microwave heating.

Organometallic reagents of formula (IV) may be made by methods well-known to those skilled in the art including methods according to or analogous to methods described in the chemical literature, for instance E. Nakamura, Organozinc Chemistry p 590 in Organometallics in Synthesis, M. Schlosser Ed., Wiley, 2002 and references therein.

3. A process for the manufacture of compounds of Formula (I) comprises reacting a compound of formula (II), wherein G is a leaving group such as iodide, bromide, chloride, alkane sulfonyloxy, or arylsulfonyloxy and $R^4$, $X^1$, $X^2$, and $X^3$ are as defined above, with a monocyclic or bicyclic organometallic compound such as an organoborane compound of formula (V) wherein M is an organometallic residue such as $B(OH)_2$ and wherein $R^5$ and m are as defined above.

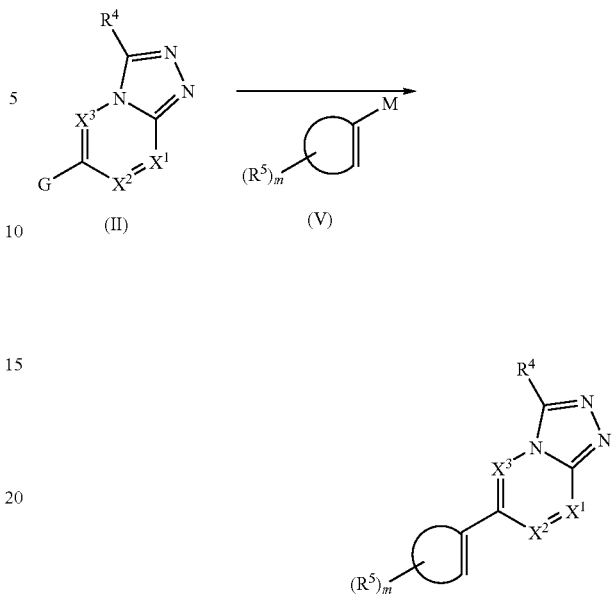

(II)            (V)

Alternatively, M is a leaving group such as iodide, bromide, chloride, alkane sulfonyloxy, or arylsulfonyloxy and $R^4$, $X^1$, $X^2$, and $X^3$ are as defined above and G is an organometallic compound such as an organostannane and wherein $R^5$ and m are as defined above.

The reaction may be advantageously catalysed by low-valent transition metal catalysts such as Pd(0), for instance bis(dibenzylideneacetone)palladium/triphenylarsine. The reaction may be carried out by combining the components in an inert solvent such as xylene or tetrahydrofuran or N-methylpyrrolidone at temperatures between 0° C. and 150° C., preferably between 25° C. and 100° C. The reaction may be heated by a conventional heat source, such as an oil bath or a heating block, or by microwave heating.

For further details of such coupling reactions see for instance Organometallics in Synthesis, M. Schlosser Ed., Wiley, 2002, and references therein. Organometallic reagents of formula (V) may be made by methods well-known to those skilled in the art including methods according to or analogous to methods described in the chemical literature, for instance Comprehensive Organometallic Chemistry, G. Wilkinson and F. G. A. Stone, Eds., Pergamon, 1982, and Organometallics in Synthesis, M. Schlosser Ed., Wiley, 2002, and references therein 4. A process for the manufacture of compounds of Formula (I) comprises reacting a compound of formula VI with an acylating agent, such as a carboxylic acid or a reactive derivative thereof wherein $R^4$, $X^1$, $X^2$, and $X^3$, $R^5$, and m are as defined above. Suitable acylating reagents RC(Z)G are for instance carboxylic acid derivatives wherein G= is selected from Cl, O—C(=O)R, O-Alkyl, S-Alkyl and Z is selected from O, S, N-Alkyl or N-Aryl, or wherein Z and G taken together with the carbon atom to which they are attached form a nitrile or an orthoester or an orthoamide.

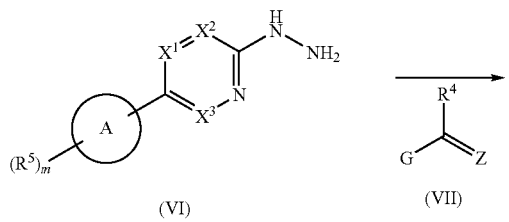

(VI)   (VII)

The reaction may be carried out by combining the components in the absence of a solvent or in an inert solvent such as ortho-dichlorobenzene at temperatures between 25° C. and 250° C., preferably between 50° C. and 150° C. The reaction may be heated by a conventional heat source, such as an oil bath or a heating block, or by microwave heating.

Compounds of formula (VI) may be made by methods well-known to those skilled in the art including methods according to or analogous to methods described in the chemical literature, for instance as described in in W. L. Mosby, *Heterocyclic Compounds*, Vol. 15 Part 1 and Part 2, *Systems with Bridgehead Nitrogen*, Interscience, 1961; R. N. Castle, *Heterocyclic Compounds*, Vol. 27, *Condensed Pyridazines*, Wiley, 1973; and *Heterocyclic Chemistry*, Vol. 35, *Condensed Pyrazines*, G. W. H. Cheeseman and R. F. Cookson, Wiley, 1979 and references therein.

5. A process for the manufacture of compounds of Formula (I) wherein $X^1$ and $X^2$ are $C(R^1)$ and $C(R^2)$ respectively and $X^3$ is nitrogen comprises reacting an N-amino-1,2,4-triazole (VIII) wherein $R^4$ is as defined above with an unsaturated ketone or unsaturated ester (IX) wherein G is a leaving group such as alkoxy or dialkylamino and $R^1$, $R^2$, $R^5$. and m are as defined above

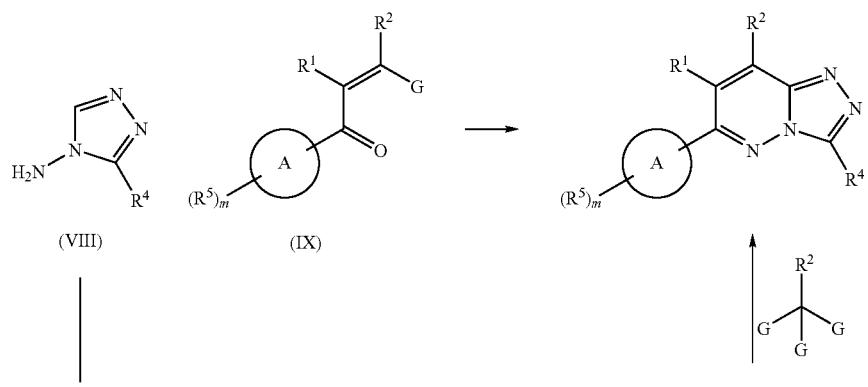

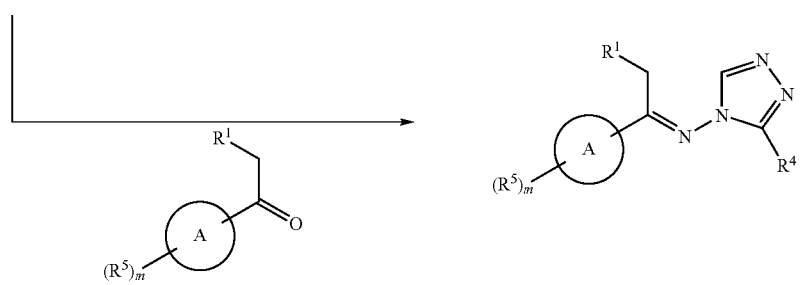

The reaction may be carried out in one or two steps as shown and the last step takes place in a solvent such as acetic acid at temperatures between 25° C. and 250° C., preferably between 50° C. and 150° C. for instance according to the procedure of D. F. Lieberman and J. D. Albright, *J. Het. Chem.*, 1988, 827.

Other useful and related processes for the manufacture of compounds of Formula (I) or for the preparation of starting materials for the manufacture of compounds of Formula (I) are disclosed in the literature for instance in W. L. Mosby, *Heterocyclic Compounds*, Vol. 15 Part 1 and Part 2, *Systems with Bridgehead Nitrogen*, Interscience, 1961; R. N. Castle, *Heterocyclic Compounds*, Vol. 27, Condensed Pyridazines, Wiley, 1973; and *Heterocyclic Chemistry*, Vol. 35, *Condensed Pyrazines*, G. W. H. Cheeseman and R. F. Cookson, Wiley, 1979 and references therein.

6. A process for the manufacture of compounds of Formula (I) comprises introducing a group $R^5$ by reacting a compound of formula (X) wherein Z is a replaceable group such as a hydrogen of a primary or secondary amine, or Z is a leaving group such as halogen or alkyl or aryl sulfonyloxy, or Z is a counterion such as sodium(I) or magnesium(II) with a compound of formula (XI) wherein $R^5$ is as defined above and Q is a replaceable group such as a hydrogen of a primary or secondary amine, or Q is a leaving group such as halogen or alkyl or aryl sulfonyloxy, or Q is a counterion such as sodium(I) or magnesium(II).

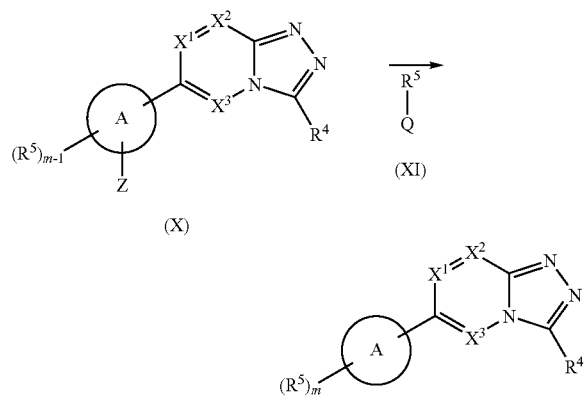

Examples of reactions of this type include alkylations, acylations, and sulfonylations. Alternatively, if Z is the hydrogen of a secondary amine, preferably a cyclic secondary amine and $R^5$-Q is an aldehyde, the $m^{th}$ group $R^5$ may be introduced by reductive amination, for instance by reducing the mixture of aldehyde and secondary amine with sodium cyanoborohydride.

7. A process for the manufacture of compounds of Formula (I) comprises converting a functional group of one compound of the invention into another functional group using standard chemical reactions well-known to those skilled in the art to produce another compound of the invention. Such methods are described for instance in *Comprehensive Organic Chemistry*, Volume 2, p 3, D. Barton and D. Ollis Eds, Pergamon, 1979, *Comprehensive Functional Group Transformations*, A. R. Katritzky, O. Meth-Cohn, and C. W. Rees Eds., Pergamon, 1995, and by various authors in *Houben-Weyl, Methods of Organic Chemistry*, Verlag Chemie, various years, and references therein.

8. A process for the manufacture of compounds of the invention comprises introducing a new functional group into one compound of the invention using standard chemical reactions well-known to those skilled in the art to produce another compound of the invention. Such methods are described for instance in *Comprehensive Organic Chemistry*, Volume 2, p 3, D. Barton and D. Ollis Eds, Pergamon, 1979, *Comprehensive Functional Group Transformations*, A. R. Katritzky, O. Meth-Cohn, and C. W. Rees Eds., Pergamon, 1995, and by various authors in *Houben-Weyl, Methods of Organic Chemistry*, Verlag Chemie, various years, and references therein.

9. A process for the manufacture of compounds of the invention in the form of a single enantiomer comprises separating a racemic compound of the invention into separate enantiomers.

Examples of suitable methods for separating the enantiomers of a racemic compound include chromatography using a suitable chiral stationary phase; or conversion of a racemic mixture into diastereomeric derivatives, separation of the mixture of diastereomeric derivatives into two single diastereomers, and regeneration of a separate single enantiomer from each separate single diastereomer; or selective chemical reaction of one of the enantiomers of a racemic compound (kinetic resolution) using a diastereoselective reaction catalysed by a microbiological agent or an enzyme.

Examples of suitable methods for separating a mixture of diastereomers include fractional crystallisation, normal-phase chromatography or reverse-phase chromatography.

Examples of suitable diastereomeric derivatives where $R^5$ contains an hydroxy- or amino-group include esters formed by acylation of $R^5$ using an activated derivative of a single enantiomer of a carboxylic acid. An example of a suitable carboxylic acid is camphanic acid.

Examples of suitable diastereomeric derivatives where $R^5$ contains a carboxylic acid include esters or amides formed by acylation of a single enantiomer of an alcohol or amine using an activated derivative of a compound of Formula (I) wherein at least one of $R^5$ contains a carboxylic acid. An example of a suitable amine is 1-phenylethylamine and an example of a suitable alcohol is menthol.

Examples of suitable agents to carry out a kinetic resolution of a racemic mixture of compounds of the invention include Hog Liver Esterase and Baker's Yeast.

10. A process for the manufacture of a compound of the invention in the form of a single enantiomer comprises carrying out one of the processes described in the preceding sections using chiral intermediates in resolved form.

It will be appreciated by a person skilled in the art that it may be necessary/desirable to protect any sensitive groups in the compounds in some of the processes/reactions mentioned herein. The instances where protection is necessary or desirable, and suitable methods for providing such protection are known to those skilled in the art. Conventional protecting groups may be used in accordance with standard practice (for illustration see P. G. M. Wuts and T. W. Green, *Protective Groups in Organic Synthesis*, 4th Edition, John Wiley and Sons, 2002). Thus, if reactants include groups such as amino, carboxy or hydroxy it may be desirable to protect the group in some of the reactions mentioned herein.

Any protecting groups utilised in the processes described herein may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A suitable protecting group for an amino or alkylamino group is, for example, an acyl group, for example an alkanoyl group such as trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl or heteroaroyl group, for example picolinoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable acid such as hydrochloric, sulphuric, or phosphoric acid or trifluoroacetic acid or a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Biological Assays

The ability of compounds to reduce Androgen Receptor (AR) numbers was assessed in a cell based immuno-fluorescence assay using the LNCaP prostate epithelial cell line.

a) LNCaP Androgen Receptor Down-regulation Cell Assay

This immunofluorescence end point assay measures the ability of a test compound to down-regulate and reduce measured levels of the AR in the LNCaP prostate carcinoma cell line (LNCaP clone FGC (CRL-1740) obtained from the American Type Culture Collection (ATCC)).

LNCaP cells were cultured in Growth Medium (phenol red free Roswell Park Memorial Institute (RPMI) 1640 (Invitrogen Code no. 11835-063) containing 2 mM L-Glutamine (Invitrogen Code no. 25030-024) and 1% (v/v) Penicillin/Streptomycin (10000 units/ml Penicillin and 10000 µg/ml of Streptomycin utilising penicillin G (sodium salt) and streptomycin sulphate: prepared in normal saline, Invitrogen Code no. 15140122) and 10% (v/v) foetal bovine serum (FBS)) in a 5% $CO_2$ air incubator at 37° C. Cells for assay were harvested from T175 stock flasks by washing once in PBS (phosphate buffered saline, pH 7.4) (Invitrogen Code no. 14190-094) and harvested using 5 mls of 1× Trypsin/ethylaminediaminetetraacetic acid (EDTA) (10× Trypsin-EDTA, 5.0 g/L Trypsin, 2.0 g/L of EDTA·4Na and 8.5 g/L of NaCl, without Phenol Red, Invitrogen Code no. 15400-054) diluted in PBS solution. A 5 ml volume of Growth Medium was added to each flask (as above except that 5% (v/v) charcoal stripped FBS (HyClone Code no. SH30068.03) was included instead of 10% (v/v) FBS). Cells were syringed at least twice using a sterile 18G×1.5" (1.2×40 mm) broad gauge needle and cell density was measured using a haemocytometer. Cells were further diluted in Growth Medium plus 5% (v/v) charcoal stripped FBS and seeded at a density of $6.5×10^3$ cells per well (in 90 ul) into transparent, black, tissue culture treated 96 well plates (Packard, No. 6005182).

Test data reported herein was generated using two different compounds preparation and dosing methods. In method (1) a 10 mM compound stock solution in 100% (v/v) DMSO was serially diluted in 4-fold steps in 100% (v/v) DMSO using a Thermo Scientific Matrix SerialMate. The diluted compounds were then further diluted 1 in 30 in assay media using a Thermo Scientific Matrix PlateMate and a 10 µl aliquot of this dilution was dosed to cells manually using a multi-channel pipette. In method (2) starting with a 10 mM compound stock solution, the Labcyte Echo 550 was used to generate a compound concentration response set diluted in 30 µl of assay media. The Echo 550 is a liquid handler that uses acoustic technology to perform direct microplate-to-microplate transfers of DMSO compound solutions. The system can be programmed to transfer volumes as low as 2.5 mL in multiple increments between microplates and in so doing generates a serial dilution of compound which is then back-filled to normalise the DMSO concentration across the dilution range. A 10 µl volume of diluted compound is then dosed to cells using a Thermo Scientific Matrix PlateMate.

Plates were incubated overnight at 37° C., 5% $CO_2$. Wells were then dosed with compound prepared by one of the 2 methods above and further incubated for 20-22 hours at 37° C., 5% $CO_2$. Plates were fixed by the addition of 20 µl of 10% (v/v) formaldehyde solution (in PBS) to each well (final formaldehyde conc.=1.67% (v/v)) and left at room temperature for 10 mins. This fixative solution was removed and cells were washed with 250 µl of PBS/0.05% (v/v) Tween 20 (PBST) using an automated plate washer. This process was then repeated twice more.

Immunostaining was performed at room temperature. Cells were permeabilised by the addition of 35 μl of PBS containing 0.5% Tween 20 and incubated for 1 hour at room temperature. Permeabilisation solution was removed and cells were washed with 250 μl of PBST using an automated plate washer. This process was then repeated twice more. 35 μl of Blocking Solution (PBST containing 3% (w/v) Marvel dried skimmed milk (Nestle)) was added to each well and plates were incubated at room temperature for a minimum of 1 hour. Following removal of the Blocking Solution with a plate washer, 35 μl of mouse anti-human AR monoclonal antibody (clone AR441) (immunogen-synthetic peptide corresponding to amino acids 229-315 of the human AR coupled to keyhole limpet hemocyanin, DAKO, Code No. M3562), diluted 1:500 in Blocking Solution, was added to each well and incubated for 1 hour. Then this primary antibody solution was removed from the wells followed by 3×100 μl PBST washes using a plate washer. Then 35 μl of Alexa-Fluor 488 goat anti-mouse IgG secondary antibody (Invitrogen, Code No. A-11001), diluted 1:500 in Blocking Solution, was added to each well. Henceforth, wherever possible, plates were protected from light exposure. The plates were incubated for 1 hour and then the secondary antibody solution was removed from the wells followed by 3×100 ul PBST washes using a plate washer. Then 50 μl of PBST was added to each well and plates were covered with a black plate seal and stored at 4° C. before being read. Plates were read within six hours of completing the immunostaining.

The Green Fluorescent AR-associated signal in each well was measured using an Acumen Explorer HTS Reader (TTP Labtech Ltd., Cambridge). AR-associated fluorescence emission can be detected at 530 nm following excitation at 488 nm. The instrument is a laser-scanning fluorescence microplate cytometer which samples the well at regular intervals and uses threshold algorithms to identify all fluorescent intensities above the solution background without the need to generate and analyse an image. These fluorescent objects can be quantified and provide a measure of the AR levels in cells. Fluorescence dose response data obtained with each compound was exported into a suitable software package (such as Origin) to perform curve fitting analysis. Down-regulation of AR levels was expressed as an $IC_{50}$ value. This was determined by calculation of the concentration of compound that was required to give a 50% reduction of the AR signal.

The following table discloses biological data for compounds of the present invention using the aforementioned down-regulation assay.

| Example Number | Androgen Receptor Down-regulation Assay (a) $IC_{50}/\mu M$ |
|---|---|
| 1 | 3.4 |
| 2 | 8.3 |
| 3 | 11 |
| 4 | 2.5 |
| 5 | 1.6 |
| 6 | 7.5 |
| 7 | 18 |
| 8 | 1.7 |
| 9 | 1.7 |
| 10 | 14 |
| 11 | 2.5 |
| 12 | 4.3 |
| 13 | 8.4 |
| 14 | 0.69 |
| 15 | 2.5 |
| 16 | 0.77 |
| 17 | 2.5 |
| 18 | 1.2 |
| 19 | 0.52 |
| 20 | 1.8 |
| 21 | 0.27 |
| 22 | 1.4 |
| 23 | 0.45 |
| 24 | >26 |
| 25 | 1.1 |
| 26 | 1.0 |
| 27 | 1.2 |
| 28 | 2.8 |
| 29 | 4.2 |
| 30 | 0.38 |
| 31 | 2.1 |
| 32 | 1.6 |
| 33 | 0.68 |
| 34 | 20 |
| 35 | 3.0 |
| 36 | 0.99 |
| 37 | 1.4 |
| 38 | 1.2 |
| 39 | 5.0 |
| 40 | 3.3 |
| 41 | 28 |
| 42 | 12.0 |
| 43 | 1.5 |
| 44 | 1.3 |
| 45 | 1.4 |
| 46 | 1.3 |
| 47 | 1.5 |
| 48 | 1.5 |
| 49 | 3.2 |
| 50 | 1.4 |
| 51 | 8.4 |
| 52 | 1.3 |
| 53 | 7.9 |
| 54 | 6.7 |
| 55 | 8.8 |
| 56 | 2.1 |
| 57 | 4.3 |
| 58 | 3.1 |
| 59 | 2.7 |
| 60 | 0.61 |
| 61 | 7.4 |
| 62 | 0.72 |
| 63 | 1.5 |
| 64 | 2.5 |
| 65 | 0.76 |
| 66 | 0.33 |
| 67 | 1.0 |
| 68 | 1.20 |
| 69 | 1.4 |
| 70 | 0.64 |
| 71 | 1.4 |
| 72 | 1.0 |
| 73 | 12 |
| 74 | 5.6 |
| 75 | 2.3 |
| 76 | 2.3 |
| 77 | 1.4 |
| 78 | 1.20 |
| 79 | 2.4 |
| 80 | 16 |
| 81 | 7.2 |
| 82 | 1.6 |
| 83 | 2.5 |
| 84 | 1.8 |
| 85 | 1.6 |
| 86 | 1.2 |

-continued

| Example Number | Androgen Receptor Down-regulation Assay (a) IC$_{50}$/μM |
|---|---|
| 87 | 5.2 |
| 88 | 1.5 |
| 89 | 23 |
| 90 | 3.2 |
| 91 | 1.2 |
| 92 | 12 |
| 93 | 1.3 |
| 94 | 0.93 |
| 95 | 0.67 |
| 96 | >1.3 |
| 97 | 0.36 |
| 98 | 2.3 |
| 99 | 2.9 |
| 100 | 1.8 |
| 101 | 1.7 |
| 102 | 2.9 |
| 103 | 6.2 |
| 104 | 9.5 |
| 105 | 3.2 |
| 106 | 4.4 |
| 107 | 7.2 |
| 108 | 2.3 |
| 109 | 7.2 |
| 110 | 1.3 |
| 111 | 0.77 |
| 112 | 4.7 |
| 113 | 7.1 |
| 114 | 6.5 |
| 115 | 2.5 |
| 116 | 1.1 |
| 117 | 1.7 |
| 118 | 0.30 |
| 119 | 2.2 |
| 120 | 1.7 |
| 121 | 4.8 |
| 122 | 4.3 |
| 123 | 4.1 |
| 124 | 1.7 |
| 125 | 1.9 |
| 126 | 2.0 |
| 127 | 1.5 |
| 128 | 2.3 |
| 129 | 0.99 |
| 130 | 1.8 |
| 131 | 4.1 |
| 132 | 2.6 |
| 133 | 1.3 |
| 134 | 1.8 |
| 135 | 4.9 |
| 136 | 1.2 |
| 137 | 1.5 |
| 138 | 13 |
| 139 | 2.0 |
| 140 | 7.1 |
| 141 | 9.7 |
| 142 | 5.1 |
| 143 | 8.8 |
| 144 | 4.9 |
| 145 | 1.2 |
| 146 | 7.3 |
| 147 | 2.5 |
| 148 | 3.4 |
| 149 | 7.9 |
| 150 | 7.6 |
| 151 | 3.1 |
| 152 | 6.7 |
| 153 | 7.9 |
| 154 | 1.6 |
| 155 | 18 |
| 156 | 11 |
| 157 | 2.4 |
| 158 | 3.0 |
| 159 | 1.4 |

-continued

| Example Number | Androgen Receptor Down-regulation Assay (a) IC$_{50}$/μM |
|---|---|
| 160 | 6.6 |
| 161 | 1.4 |
| 162 | 1.0 |
| 163 | 3.6 |
| 164 | 1.7 |
| 165 | 1.7 |
| 166 | 0.93 |
| 167 | 2.4 |
| 168 | 1.6 |
| 169 | 0.92 |
| 170 | 0.61 |
| 171 | 0.62 |
| 172 | 0.81 |
| 173 | 1.2 |
| 174 | 0.94 |
| 175 | 0.68 |
| 176 | 0.85 |
| 177 | 0.77 |
| 178 | 0.88 |
| 179 | 0.59 |
| 180 | 1.2 |
| 181 | 2.1 |
| 182 | 1.2 |
| 183 | 1.2 |
| 184 | 14 |
| 185 | 0.68 |
| 186 | 2.8 |
| 187 | 4.7 |
| 188 | 2.2 |
| 189 | 1.1 |
| 190 | 0.79 |
| 191 | 2.1 |
| 192 | 8.7 |
| 193 | 2.0 |
| 194 | 2.4 |
| 195 | 4.0 |
| 196 | 1.5 |
| 197 | 0.82 |
| 198 | 1.2 |
| 199 | 1.9 |
| 200 | 1.3 |
| 201 | 1.7 |
| 202 | 11 |
| 203 | 1.7 |
| 204 | 1.5 |
| 205 | 0.53 |
| 206 | 2.0 |
| 207 | 7.6 |
| 208 | 13 |
| 209 | 12 |
| 210 | 1.8 |
| 211 | 8.2 |
| 212 | 3.7 |
| 213 | 4.5 |
| 214 | 15 |
| 215 | 7.4 |
| 216 | 6.8 |
| 217 | 3.7 |
| 218 | >7.3 |
| 219 | 3.5 |
| 220 | 3.6 |
| 221 | 3.1 |
| 222 | 2.6 |
| 223 | 4.7 |
| 224 | 12 |
| 225 | 9.2 |
| 226 | 11 |
| 227 | 13 |
| 228 | 15 |
| 229 | 1.9 |
| 230 | 2.1 |
| 231 | 2.1 |
| 232 | 3.6 |

| Example Number | Androgen Receptor Down-regulation Assay (a) IC$_{50}$/μM |
|---|---|
| 233 | 1.5 |
| 234 | 2 |
| 235 | 1.9 |
| 236 | 5.3 |
| 237 | 5.3 |
| 238 | 5 |
| 239 | 2.8 |
| 240 | 3 |
| 241 | 13 |
| 242 | 7.4 |
| 243 | 3.7 |
| 244 | 15 |
| 245 | 17 |
| 246 | 23 |
| 247 | 12 |
| 248 | 1.7 |
| 249 | 6.3 |
| 250 | 4.9 |
| 251 | 9.3 |
| 252 | 8.9 |
| 253 | 3.7 |
| 254 | 1.3 |
| 255 | 1.8 |
| 256 | 7.4 |
| 257 | 9 |
| 258 | 6.4 |
| 259 | 4.8 |
| 260 | 5.6 |
| 261 | 7.9 |
| 262 | 25 |
| 263 | 11 |
| 264 | 0.95 |
| 265 | 3.8 |
| 266 | 0.63 |
| 267 | 0.85 |
| 268 | 0.91 |
| 269 | 2 |
| 270 | 10 |
| 271 | 1.8 |
| 272 | 1.8 |
| 273 | 10 |
| 274 | 6.1 |
| 275 | 6 |
| 276 | 15 |
| 277 | 2 |
| 278 | 0.65 |
| 279 | 13 |
| 280 | 0.78 |
| 281 | 0.8 |
| 282 | 2.4 |
| 283 | 0.78 |
| 284 | 0.98 |
| 285 | 2.7 |
| 286 | 8.5 |
| 287 | 2 |
| 288 | 3.3 |
| 289 | 2.7 |
| 290 | 5.8 |
| 291 | >9.7 |
| 292 | 7 |
| 293 | 11 |
| 294 | 9.5 |
| 295 | 3.4 |
| 296 | 2.1 |
| 297 | 15 |
| 298 | 5.7 |
| 299 | 0.84 |
| 300 | 1 |
| 301 | 1.8 |
| 302 | 1.1 |
| 303 | 5.8 |
| 304 | 1.8 |
| 305 | 4 |
| 306 | 1.3 |
| 307 | 3.4 |
| 308 | 1.4 |
| 309 | 1.6 |
| 310 | 3.2 |
| 311 | 5 |
| 312 | 2.6 |
| 313 | 1.8 |
| 314 | 4.6 |
| 315 | 2 |
| 316 | 12 |
| 317 | 4.1 |
| 318 | 3.7 |
| 319 | 11 |
| 320 | 8.6 |
| 321 | 8 |
| 322 | 9.6 |
| 323 | >8.1 |
| 324 | 5.9 |
| 325 | >1.2 |
| 326 | 2 |
| 327 | 1 |
| 328 | 0.75 |
| 329 | 3.6 |
| 330 | 3.7 |
| 331 | 16 |
| 332 | 16 |
| 333 | 2.7 |
| 334 | 1.1 |
| 335 | 1.5 |
| 336 | 2.4 |
| 337 | 1.5 |
| 338 | 8.5 |
| 339 | 0.77 |
| 340 | 1.5 |
| 341 | 1.3 |
| 342 | 2.1 |
| 343 | 1.7 |
| 344 | 0.29 |
| 345 | 1.1 |
| 346 | 8.5 |
| 347 | 0.97 |
| 348 | 1 |
| 349 | 1.7 |
| 350 | 0.74 |
| 351 | 1.9 |
| 352 | 0.57 |
| 353 | 0.69 |
| 354 | 2.7 |
| 355 | 0.72 |
| 356 | 2.2 |
| 357 | 2.1 |
| 358 | 6.7 |
| 359 | 2.6 |
| 360 | 1 |
| 361 | 4.7 |
| 362 | 1 |
| 363 | 22 |
| 364 | 16 |
| 365 | 19 |
| 366 | >33 |
| 367 | 4.1 |
| 368 | 3.4 |
| 369 | 8.7 |
| 370 | 11 |
| 371 | 6.2 |
| 372 | 1.3 |
| 373 | 4 |
| 374 | 0.93 |
| 375 | 11 |
| 376 | 3 |
| 377 | 5.9 |
| 378 | 11 |

| Example Number | Androgen Receptor Down-regulation Assay (a) IC$_{50}$/μM |
|---|---|
| 379 | 18 |
| 380 | 4.2 |
| 381 | 2.1 |
| 382 | 1.8 |
| 383 | 1.3 |
| 384 | 2.9 |
| 385 | 2.1 |
| 386 | 2.4 |
| 387 | 1.1 |
| 388 | 1.6 |
| 389 | 1.5 |
| 390 | 1.7 |
| 391 | 2.7 |
| 392 | 4.5 |
| 393 | 1.9 |
| 394 | 5.6 |
| 395 | 10 |
| 396 | 1.8 |
| 397 | 3.9 |
| 398 | 1.9 |
| 399 | 3.7 |
| 400 | 1.8 |
| 401 | 1.6 |
| 402 | 2.8 |
| 403 | 4.8 |
| 404 | 2.7 |
| 405 | 3 |
| 406 | 6.3 |
| 407 | 5.7 |
| 408 | 1.7 |
| 409 | 3.9 |
| 410 | 2.1 |
| 411 | 2.2 |
| 412 | 9.1 |
| 413 | 1.9 |
| 414 | >10 |
| 415 | 1.4 |
| 416 | 2.7 |
| 417 | 4.6 |
| 418 | >14 |
| 419 | 4 |
| 420 | 5.9 |
| 421 | 4 |
| 422 | 4.2 |
| 423 | 7.4 |
| 424 | 2.2 |
| 425 | 3.6 |
| 426 | 2.2 |
| 427 | 4.3 |
| 428 | 15 |
| 429 | 2.6 |
| 430 | 1.7 |
| 431 | 1.5 |
| 432 | 1.2 |
| 433 | 0.9 |
| 434 | 0.83 |
| 435 | 0.98 |
| 436 | 0.75 |
| 437 | 0.53 |
| 438 | 1.6 |
| 439 | 0.48 |
| 440 | 2.3 |
| 441 | 0.22 |
| 442 | 0.44 |
| 443 | 1.5 |
| 444 | 1.2 |
| 445 | 1.6 |
| 446 | 0.7 |
| 447 | 16 |
| 448 | 6.3 |
| 449 | 4.8 |
| 450 | 8.2 |
| 451 | 9.7 |
| 452 | 16 |
| 453 | 5.7 |
| 454 | 9.2 |
| 455 | 10 |
| 456 | 21 |
| 457 | 11 |
| 458 | 21 |
| 459 | 15 |
| 460 | 5.1 |
| 461 | 13 |
| 462 | 7.7 |
| 463 | 0.98 |
| 464 | 1.4 |
| 465 | 4 |
| 466 | >19 |
| 467 | 4.9 |
| 468 | >11 |
| 469 | 1.8 |
| 470 | 4.6 |
| 471 | 2 |
| 472 | 3.9 |
| 473 | 3.2 |
| 474 | 0.96 |
| 475 | >15 |
| 476 | 3.5 |
| 477 | 6.3 |
| 478 | 1.3 |
| 479 | 17 |
| 480 | 9.6 |
| 481 | 6.6 |
| 482 | 1.8 |
| 483 | >30 |
| 484 | >14 |
| 485 | 10 |
| 486 | >13 |
| 487 | 16 |
| 488 | 3.1 |
| 489 | 3.6 |
| 490 | 5.9 |
| 491 | 7.2 |
| 492 | >30 |
| 493 | 18 |
| 494 | 0.43 |
| 495 | 0.35 |
| 496 | 11 |
| 497 | 2.8 |
| 498 | 2.4 |
| 499 | 1.7 |
| 500 | >18 |
| 501 | 1.2 |
| 502 | 2.2 |
| 503 | 4.3 |
| 504 | 1.9 |
| 505 | >19 |
| 506 | 9.8 |
| 507 | 0.53 |
| 508 | 2.2 |
| 509 | 1.8 |
| 510 | 3.7 |
| 511 | 10 |
| 512 | 0.87 |
| 513 | 0.24 |
| 514 | 0.87 |
| 515 | 1.4 |
| 516 | 1.4 |
| 517 | 1.5 |
| 518 | 11 |
| 519 | 1.2 |
| 520 | 1.4 |
| 521 | 5.4 |
| 522 | 3.9 |
| 523 | 1 |
| 524 | 3.2 |

-continued

| Example Number | Androgen Receptor Down-regulation Assay (a) IC$_{50}$/μM |
|---|---|
| 525 | 5.2 |
| 526 | 2.5 |
| 527 | 0.67 |
| 528 | 2.2 |
| 529 | 1.9 |
| 530 | 1.6 |
| 531 | 1.8 |
| 532 | 0.98 |
| 533 | 2.3 |
| 534 | 2.3 |
| 535 | 1.9 |
| 536 | 1.4 |
| 537 | 3 |
| 538 | 2.3 |
| 539 | 1.5 |
| 540 | 1.5 |
| 541 | 4 |
| 542 | 2.6 |
| 543 | 3.2 |
| 544 | 2.9 |
| 545 | 3.6 |
| 546 | 1.7 |
| 547 | 1.2 |
| 548 | 2.2 |
| 549 | 1.6 |
| 550 | 7.2 |
| 551 | 4 |
| 552 | 7.8 |
| 553 | 2.6 |
| 554 | 4.9 |
| 555 | 1.4 |
| 556 | 4.4 |
| 557 | 3.1 |
| 558 | 2.6 |
| 559 | 2 |
| 560 | 8.8 |
| 561 | 2.9 |
| 562 | 2 |
| 563 | 1.3 |
| 564 | 6.7 |
| 565 | 3.5 |
| 566 | 16 |
| 567 | >16 |
| 568 | 3.3 |
| 569 | 2.7 |
| 570 | 4.5 |
| 571 | 0.96 |
| 572 | 3.4 |
| 573 | 10 |
| 574 | 4 |
| 575 | 2.5 |
| 576 | 5 |
| 577 | 5 |
| 578 | 2.5 |
| 579 | 4.1 |
| 580 | 2 |
| 581 | 3.3 |
| 582 | 2.4 |
| 583 | 4.1 |
| 584 | 2.8 |
| 585 | 1.5 |
| 586 | 2.1 |
| 587 | >17 |
| 588 | 5.3 |
| 589 | 4.8 |
| 590 | 22 |
| 591 | 20 |
| 592 | 9.6 |
| 593 | 7.2 |
| 594 | 22 |
| 595 | 6.8 |
| 596 | 4.2 |
| 597 | 2.9 |

-continued

| Example Number | Androgen Receptor Down-regulation Assay (a) IC$_{50}$/μM |
|---|---|
| 598 | 4.2 |
| 599 | 5.8 |
| 600 | 0.85 |
| 601 | 2.2 |
| 602 | 1.6 |
| 603 | 3.5 |
| 604 | 1.7 |
| 605 | 5 |
| 606 | 2.7 |
| 607 | 7.4 |
| 608 | 2.7 |
| 609 | 6.6 |
| 610 | 3.2 |
| 611 | 1.6 |
| 612 | >13 |
| 613 | 3.3 |
| 614 | >12 |
| 615 | 0.88 |
| 616 | 1.7 |
| 617 | 4.3 |
| 618 | >4 |
| 619 | 4.5 |
| 620 | >13 |
| 621 | 2.3 |
| 622 | 7.4 |
| 623 | 0.89 |
| 624 | 3.1 |
| 625 | 1.4 |
| 626 | 1.1 |
| 627 | 1.7 |
| 628 | 2.7 |
| 629 | 1.3 |
| 630 | 2.4 |
| 631 | 1.1 |
| 632 | 1.2 |
| 633 | 1.9 |
| 634 | 1.1 |
| 635 | 2.9 |
| 636 | 20 |
| 637 | 1.8 |
| 638 | 0.9 |
| 639 | 1.2 |
| 640 | 0.92 |
| 641 | 1.4 |
| 642 | 1.4 |
| 643 | 6 |
| 644 | 1.5 |
| 645 | 2.3 |
| 646 | 6.1 |
| 647 | 1.7 |
| 648 | 2.1 |
| 649 | 2.3 |
| 650 | 3.1 |
| 651 | 1.9 |
| 652 | 3.1 |
| 653 | 1 |
| 654 | 2.6 |
| 655 | 1.1 |
| 656 | 1.1 |
| 657 | 3.2 |
| 658 | 0.94 |
| 659 | 1 |
| 660 | 0.63 |
| 661 | 0.65 |
| 662 | 5.4 |
| 663 | 2.7 |
| 664 | 3.6 |
| 665 | 0.82 |
| 666 | 0.94 |
| 667 | 1 |
| 668 | 1.1 |
| 669 | 0.6 |
| 670 | 0.67 |

| Example Number | Androgen Receptor Down-regulation Assay (a) IC$_{50}$/μM |
|---|---|
| 671 | 1.6 |
| 672 | 0.58 |
| 673 | 0.73 |
| 674 | 1.1 |
| 675 | 1.5 |
| 676 | 0.56 |
| 677 | 4.5 |
| 678 | 15 |
| 679 | 0.58 |
| 680 | 0.6 |
| 681 | 1.3 |
| 682 | 0.58 |
| 683 | 0.49 |
| 684 | 0.69 |
| 685 | 5.7 |
| 686 | 4.2 |
| 687 | 3.8 |
| 688 | 6.6 |
| 689 | 4.1 |
| 690 | 17 |
| 691 | >28 |
| 692 | 4.2 |
| 693 | 2.3 |
| 694 | 3.2 |
| 695 | 3.3 |
| 696 | 4.2 |
| 697 | >22 |
| 698 | 5.6 |
| 699 | 2.1 |
| 700 | 7.1 |
| 701 | 14 |
| 702 | >12 |
| 703 | 5.5 |
| 704 | 4.2 |
| 705 | 5.3 |
| 706 | 2.9 |
| 707 | 7.9 |
| 708 | 6.2 |
| 709 | 1.7 |
| 710 | 2.1 |
| 711 | 2.5 |
| 712 | 3 |
| 713 | 0.81 |
| 714 | >9.9 |
| 715 | 1.2 |
| 716 | 0.81 |
| 717 | 2.9 |
| 718 | 3.6 |
| 719 | 3.5 |
| 720 | 2.7 |
| 721 | 2.9 |
| 722 | 4.1 |
| 723 | 0.9 |
| 724 | 0.69 |
| 725 | 1.2 |
| 726 | 1.4 |
| 727 | 1.2 |
| 728 | 1.5 |
| 729 | 0.92 |
| 730 | 0.72 |
| 731 | 1.1 |
| 732 | 1.1 |
| 733 | 0.6 |
| 734 | 2.5 |
| 735 | 1.9 |
| 736 | 0.4 |
| 737 | 0.74 |
| 738 | 3.3 |
| 739 | 3.2 |
| 740 | 2 |
| 741 | 2.2 |
| 742 | 17 |
| 743 | 14 |
| 744 | 9.6 |
| 745 | 3.4 |
| 746 | 3.3 |
| 747 | 23 |
| 748 | 5.6 |
| 749 | >22 |
| 750 | 2.6 |
| 751 | 6.3 |
| 752 | 18 |
| 753 | 2.1 |
| 754 | 2.5 |
| 755 | 2.2 |
| 756 | 3.2 |
| 757 | >12 |
| 758 | 1.3 |
| 759 | 3.9 |
| 760 | >3.1 |
| 761 | 1.5 |
| 762 | 1.2 |
| 763 | >9.8 |
| 764 | 2.5 |
| 765 | 8.8 |
| 766 | >17 |
| 767 | >12 |
| 768 | 4.7 |
| 769 | 11 |
| 770 | 6.3 |
| 771 | 3.1 |
| 772 | 14 |
| 773 | 3.1 |
| 774 | 8 |
| 775 | 6.8 |
| 776 | 6.9 |
| 777 | 4.6 |
| 778 | 2.6 |
| 779 | 0.54 |
| 780 | 0.51 |
| 781 | 0.82 |
| 782 | 2 |
| 783 | 0.84 |
| 784 | 2.2 |
| 785 | 1.7 |
| 786 | 8.4 |
| 787 | 1.3 |
| 788 | 2.2 |
| 789 | 2.1 |
| 790 | 2 |
| 791 | 0.96 |
| 792 | 16 |
| 793 | 1.6 |
| 794 | 1.1 |
| 795 | 2.4 |
| 796 | 0.63 |
| 797 | 2.4 |
| 798 | 1 |
| 799 | 1.6 |
| 800 | 1.1 |
| 801 | 1.3 |
| 802 | 1.2 |
| 803 | 7 |
| 804 | 1.3 |
| 805 | 1 |
| 806 | 2.3 |
| 807 | 7.5 |
| 808 | 1 |
| 809 | |
| 810 | 1.9 |
| 811 | 1.2 |
| 812 | 2.1 |
| 813 | 6.8 |
| 814 | 1.8 |
| 815 | >17 |
| 816 | 9.3 |

| Example Number | Androgen Receptor Down-regulation Assay (a) IC$_{50}$/μM |
|---|---|
| 817 | 5.6 |
| 818 | 3.8 |
| 819 | >18 |
| 820 | 4 |
| 821 | 2 |
| 822 | 1.7 |
| 823 | 4.7 |
| 824 | 1.9 |
| 825 | 1.9 |
| 826 | 1.4 |
| 827 | 1 |
| 828 | 9.5 |
| 829 | 13 |
| 830 | 0.85 |
| 831 | 3.1 |
| 832 | 1.4 |
| 833 | >12 |
| 834 | 4.4 |
| 835 | 20 |
| 837 | 1.6 |
| 838 | 7.6 |
| 839 | 1.1 |
| 840 | 2.6 |
| 841 | 2.9 |
| 842 | 1.1 |
| 843 | 0.93 |
| 844 | 0.78 |
| 845 | 0.9 |
| 846 | 0.27 |
| 847 | 3.1 |
| 848 | 3.5 |
| 849 | 0.68 |
| 850 | 0.56 |
| 851 | 0.92 |
| 852 | 0.29 |
| 853 | 1.3 |
| 854 | Not tested |
| 855 | 0.44 |
| 856 | 2.2 |
| 857 | >33 |
| 858 | >33 |
| 859 | >33 |
| 860 | 0.8 |
| 861 | Not tested |
| 862 | Not tested |
| 863 | Not tested |
| 864 | Not tested | b) Androgen Receptor—Ligand Binding Domain Competitive Binding Assay

The ability of compounds to bind to isolated Androgen Receptor Ligand binding domain (AR-LBD) was assessed in competition assays using either a Fluorescence Polarisation (FP) or a LanthaScreen™ Time-Resolved Fluorescence Resonance Energy Transfer (TR-FRET) detection end-point.

For the FP test, an assay test kit was purchased from Invitrogen and used to measure compound binding to the isolated rat AR-LBD which shares 100% sequence identity to the human AR-LBD. The Invitrogen PolarScreen™ Androgen Receptor Competitor Assay Red (Product Code No. PV4293), is a fluorescence polarisation (FP)-based competition assay which measures if test compound can displace a fluorescently-labelled tracer compound. If the test compound binds to the AR-LBD it will prevent the formation of the receptor/tracer complex, which will result in a low polarisation value. If the test compound does not bind the receptor, it will have no effect on formation of the receptor/tracer complex, and the measured polarisation value of the tracer will remain high. The assay was performed as essentially described in the Invitrogen method with the exception that the final assay volume was 12 μl and this required an appropriate low volume black 384 well microtitre plate. Compounds were dosed directly from a compound source microplate containing serially diluted compound (4 wells containing 10 mM, 0 mM, 1 μM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range. FP dose response data obtained with each compound was exported into a suitable software package (such as Origin) to perform curve fitting analysis. Competitive AR binding was expressed as an IC$_{50}$ value. This was determined by calculation of the concentration of compound that was required to give a 50% reduction in tracer compound binding to AR-LBD.

The following table discloses various biological data for a representative selection of compounds of the present invention using the aforementioned FP ligand binding assay.

| Example Number | Androgen Receptor FP Ligand-Binding Assay IC$_{50}$/μM |
|---|---|
| 4 | 20.18 |
| 41 | 19.55 |
| 166 | 6.085 |
| 174 | 16.3 |
| 183 | 14.37 |
| Other Examples within the range Example 1-Example 215 show Androgen Receptor Ligand-Binding IC50 greater than 20 μM | |

For LanthaScreen™ TR-FRET, a suitable fluorophore (Product code PV4294) and rat GST-tagged AR-LBD were purchased from Invitrogen and used to measure compound binding. The assay principle is that AR-LBD is added to a fluorescent ligand to form a receptor/fluorophore complex. A terbium-labelled anti-GST antibody is used to indirectly label the receptor by binding to a GST tag, and competitive binding is detected by a test compounds' ability to displace the fluorescent ligand resulting in a loss of TR-FRET signal between the Tb-anti-GST antibody and the tracer. The assay was performed as follows with all reagent additions carried out using the Thermo Scientific Matrix PlateMate:—

1. Acoustic dispense 120 nl of the test compound into a black low volume 384 well assay plates.
2. Dispense 6 μl of the 2× Fluorophore reagent into each well of the assay plate
3. Dispense 6 μl of the 2×AR-LBD/Tb-anti-GST Ab into each well of the assay plate
4. Cover the assay plate to protect the reagents from light and evaporation, and incubate at room temperature for 1 hour.
5. Excite at 340 nM and measure the fluorescent emission signal of each well at 495 nm and 570 nm using the BMG PheraSTAR.

Compounds were dosed directly from a compound source microplate containing serially diluted compound (4 wells containing 10 mM, 0.1 mM, 1 μM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then backfilled to normalise the DMSO concentration across the dilution range. In total 120 nL of compound plus DMSO is added to each well and compounds were tested in a 12-point concentration response format over a final compound concentration range of 100, 30, 10, 3, 1, 0.3, 0.1, 0.03, 0.01, 0.003, 0.001, 0.0001 μM, respectively. TR-FRET dose response data obtained with each compound was exported into a suitable software package (such as Origin) to perform curve fitting analysis. Competitive AR binding was expressed as an $IC_{50}$ value. This was determined by calculation of the concentration of compound that was required to give a 50% reduction in tracer compound binding to AR-LBD.

| Table of Results - LanthaScreen ™ AR Binding Assay | | |
|---|---|---|
| | Example Number | |
| | 511 | 513 |
| $IC_{50}$ (μM) | >100 (n = 2) | 1.3 (n = 2) |

According to a further aspect of the invention there is provided a pharmaceutical composition which comprises a compound of the Formula (I), or a pharmaceutically acceptable salt thereof, as defined hereinbefore in association with a pharmaceutically-acceptable diluent or carrier. The composition may be in a form suitable for oral administration, for example as a tablet or capsule; for parenteral injection (including intravenous, subcutaneous, intramuscular, intravascular or infusion) as a sterile solution, suspension or emulsion; for topical administration as an ointment or cream; or for rectal administration as a suppository.

In general the above compositions may be prepared in a conventional manner using conventional excipients. For preclinical in vivo applications simple formulations and suspensions may be used. For example, 4-pyridin-3-yl-1-[3-(trifluoromethyl)[1,2,4]triazolo[4,3-b]pyridazin-6-yl]piperidin-4-ol may be formulated as a simple aqueous suspensions in 1% w/v Polysorbate 80 or 0.67% w/v PVP (Polyvinylpyrrolidone)/0.33% w/v Aerosol AOT (sodium 1,2-bis(2-ethylhexoxycarbonyl)ethanesulphonate). Formulations of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine and 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine may be prepared as suspensions with reduced particle size (mean particle size less than 1 micro-meter) as follows. The required amount of compound is vortexed and/or magnetically stirred in vehicle (water containing 1% w/v Pluronic F127) in order to break down any large aggregates, wet the compound and displace any air from the surface. The resultant slurry is transferred to a zirconia milling pot containing about one third of 0.6-0.8 mm diameter zirconia milling beads. Additional zirconia milling beads are added to the pot until the level of slurry and beads is approximately equal and the top of the pot closed. The pot is then sealed with a teflon ring and zirconia lid and placed on a suitable mill, for example, a Fritsch P7 planetary micromill. The pot is rotatated in the mill for 4×30 minute cycles at a rotation speed of 800 rpm with 15 minutes cooling period between each cycle. At the end of the 4 cycles the pot is allowed to cool to room temperature. The milled suspension is removed from the pot using a suitable pipette and transferred to a suitable vessel. Finally the milled suspension is made to volume with vehicle (water containing 1% w/v Pluronic F127) to produce the suspension at the required concentration.

The compound of Formula (I) will normally be administered to a warm-blooded animal at a unit dose within the range 5-5000 mg/m² body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient. For example, 4-pyridin-3-yl-1-[3-(trifluoromethyl)[1,2,4]triazolo[4,3-b]pyridazin-6-yl]piperidin-4-ol could be administered to a human patient at a dose of 500 to 1500 mg BID (twice a day), more particularly about 1000 mg BID, and 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine could be administered to a human patient at a dose of 165 to 660 mg BID, more particularly about 430 mg BID. The predicted human doses for 4-pyridin-3-yl-1-[3-(trifluoromethyl)[1,2,4]triazolo[4,3-b]pyridazin-6-yl]piperidin-4-ol and 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine are based on a standard human weighing 70 kg and BID doses are per dose (i.e. half the total daily dose).

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

We have found that the compounds defined in the present invention, or a pharmaceutically acceptable salt thereof, or pharmaceutical compositions containing them, are effective modulators of the androgen-receptor.

Accordingly, the compounds of the present invention are expected to be potentially useful agents in the treatment of diseases or medical conditions mediated alone or in part by the androgen receptor. Compounds of the invention may induce down-regulation of the androgen receptor and/or be selective agonists, partial agonists, antagonists or partial antagonists of the androgen receptor.

The compound of the invention are useful in the treatment of androgen receptor-associated conditions. An "androgen receptor-associated condition," as used herein, denotes a condition or disorder which can be treated by modulating the function or activity of an androgen receptor in a subject, wherein treatment comprises prevention, partial alleviation or cure of the condition or disorder. Modulation may occur locally, for example, within certain tissues of the subject, or more extensively throughout a subject being treated for such a condition or disorder.

In one embodiment, compounds of the present invention can be administered to animals, for example humans, for the treatment of a variety of conditions and disorders, including, but not limited to the treatment of androgen-sensitive diseases or disorders whose progress or onset is aided by activation of the androgen receptor or androgen receptor modulators. Examples of particular androgen-sensitive diseases or disorders include, but are not limited to, androgen-sensitive cancers such as prostate cancer and other cancers composed of malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; and androgen sensitive disorders such as benign prostatic hyperplasia and prostamegaly, acne (acne vulgaris), seborrhoea, hirsutism (hypertrichosis), androgenic alopecia and male pattern baldness, precocious puberty, endometriosis, polycystic ovarian syndrome, treatment of spermatogenesis, conteracting preeclampsia, eclampsia of pregnancy and preterm labor, treatment of premenstrual syndrome, treatment of vaginal dryness, sexual perversion, virilisation, and the like. Compounds of the invention may also be used to improve ovulation in a domestic animal.

In another embodiment, compounds of the present invention can be administered to animals, for example humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular-24 dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; age related decreased testosterone levels in men, male menopause, hypogonadism, male hormone replacement, male and female sexual dysfunction (e.g., erectile dysfunction, decreased sex drive, sexual well-being, decreased libido), urinary incontinence, male and female contraception, hair loss, and the enhancement of bone and muscle performance/strength.

The term treatment is also intended to include prophylactic treatment.

In addition, the conditions, diseases, and maladies collectively referenced to as "Syndrome X" or Metabolic Syndrome as detailed in Johannsson J. Clin. Endocrinol. Metab., 82, 727-34 (1997), may be treated employing the compounds of the invention.

In one embodiment the androgen-receptor associated conditions include prostate cancer, benign prostatic hyperplasia and prostamegaly, acne (acne vulgaris), seborrhoea, hirsutism (hypertrichosis), androgenic alopecia and male pattern baldness, precocious puberty, polycystic ovarian syndrome, sexual perversion, virilisation, and the like. Compounds of the invention may also be used to improve ovulation in a domestic animal.

Accordingly, the present invention relates to a method of treating any one of the aforementioned androgen-receptor associated condition in a warm-blooded animal, such as man, in need of such treatment which comprises administering to said animal an effective amount of a compound of the Formula (I), or a pharmaceutically acceptable salt thereof, as defined hereinbefore.

According to a further aspect the present invention relates to the use of compound of Formula (I), or a pharmaceutically acceptable salt thereof, as hereinbefore defined in the manufacture of a medicament for the treatment of any one of the aforementioned androgen-receptor associated condition.

According to another aspect of the present invention there is provided a compound of the Formula (I), or a pharmaceutically acceptable salt or pro-drug thereof, as defined hereinbefore for use in the treatment of any one of the aforementioned androgen-receptor associated condition.

According to another aspect of the present invention there is provided a compound of the Formula (Ia), or a pharmaceutically acceptable salt thereof, as defined hereinbefore for use in a method of treatment of the human or animal body by therapy.

According to a further aspect of the invention there is provided the use of a compound of the Formula (I), or a pharmaceutically acceptable salt or pro-drug thereof, as defined hereinbefore in the manufacture of a medicament for use in the production of an anti-androgenic effect in a warm-blooded animal such as man.

According to a further feature of this aspect of the invention there is provided a method for producing an anti-androgenic effect in a warm-blooded animal, such as man, in need of such treatment which comprises administering to said animal an effective amount of a compound of the Formula (I), or a pharmaceutically acceptable salt thereof, as defined hereinbefore.

The term "anti-androgenic effect" is used herein to mean the inhibition and/or down regulation of androgen receptors.

According to a further aspect of the invention there is provided the use of a compound of the Formula (I), or a pharmaceutically acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a compound of the Formula (I), or a pharmaceutically acceptable salt thereof, as defined hereinbefore.

According to an additional feature of this aspect of the invention there is provided a method of treating androgen-sensitive cancers in a warm-blooded animal, such as man, in need of such treatment which comprises administering to said animal an effective amount of a compound of the Formula (I), or a pharmaceutically acceptable salt thereof, as defined hereinbefore.

According to a further feature of the invention there is provided a compound of the Formula (I), or a pharmaceutically acceptable salt thereof, as defined hereinbefore for use in the treatment of androgen-sensitive cancers.

According to a further feature of the invention there is provided the use of a compound of the Formula (I), or a pharmaceutically acceptable salt thereof, as defined hereinbefore in the manufacture of a medicament for use in the treatment of androgen-sensitive cancers.

According to an additional feature of this aspect of the invention there is provided a method of treating prostate cancer in a warm-blooded animal, such as man, in need of such treatment which comprises administering to said animal an effective amount of a compound of the Formula (I), or a pharmaceutically acceptable salt thereof, as defined hereinbefore. In one embodiment of this aspect of the invention, the prostate cancer is hormone resistant.

According to a further feature of the invention there is provided a compound of the Formula (I), or a pharmaceutically acceptable salt thereof, as defined hereinbefore for use in the treatment of prostate cancer, more particularly hormone resistant prostate cancer.

According to a further feature of the invention there is provided the use of a compound of the Formula (I), or a pharmaceutically acceptable salt thereof, as defined hereinbefore in the manufacture of a medicament for use in the treatment of prostate cancer, more particularly hormone resistant prostate cancer.

Hormone resistant prostate cancer (HRPC) arises when the prostate cancer progresses to the hormone-independent stage of the disease.

According to an additional feature of this aspect of the invention there is provided a method of treating any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation; in a warm-blooded animal, such as man, in need of such treatment which comprises administering to said animal an effective amount of a compound of the Formula (I), or a pharmaceutically acceptable salt thereof, as defined hereinbefore.

According to a further feature of the invention there is provided a compound of the Formula (I), or a pharmaceutically acceptable salt thereof, as defined hereinbefore for use in the treatment of any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation.

According to a further feature of the invention there is provided the use of a compound of the Formula (I), or a pharmaceutically acceptable salt thereof, as defined hereinbefore in the manufacture of a medicament for use in the treatment of any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The androgen receptor ligands of the present invention may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment, in addition to the androgen receptor ligand treatment defined hereinbefore, may be: surgery, radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZDO530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN 107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH$_{66336}$)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of Formula (I) or a pharmaceutically acceptable salt thereof in combination with an anti-tumour agent selected from one listed under (i)-(x) herein above, in association with a pharmaceutically acceptable diluent or carrier.

According to a further aspect of the invention there is provided a pharmaceutical composition which comprises a compound of Formula (I) or a pharmaceutically acceptable salt thereof in combination with an anti-tumour agent selected from one listed under (i)-(x) herein above, in association with a pharmaceutically acceptable diluent or carrier for use in the treatment of an androgen sensitive disorder.

According to a further aspect of the invention there is provided a pharmaceutical composition which comprises a compound of Formula (I) or a pharmaceutically acceptable salt thereof in combination with an anti-tumour agent selected from one listed under (i)-(x) herein above, in association with a pharmaceutically acceptable diluent or carrier for use in the treatment of cancer, such as prostate cancer.

According to another feature of the invention there is provided the use of a compound of the Formula (I) or a pharmaceutically acceptable salt thereof in combination with an anti-tumour agent selected from one listed under (i)-(x) herein above, in the manufacture of a medicament for use in the treatment of an androgen sensitive disorder in a warm-blooded animal, such as man.

According to another feature of the invention there is provided the use of a compound of the Formula (I) or a pharmaceutically acceptable salt thereof in combination with an anti-tumour agent selected from one listed under (i)-(x) herein above, in the manufacture of a medicament for use in the treatment of cancer, such as prostate cancer, in a warm-blooded animal, such as man.

According to another feature of the invention there is provided a compound of the Formula (I) or a pharmaceutically acceptable salt thereof in combination with an anti-tumour agent selected from one listed under (i)-(x) herein above for use in treatment of an androgen-sensitive disorder in a warm-blooded animal, such as man.

According to another feature of the invention there is provided a compound of the Formula (I) or a pharmaceutically acceptable salt thereof in combination with an anti-tumour agent selected from one listed under (i)-(x) herein above for use in treatment of cancer, such as prostate cancer in a warm-blooded animal, such as man.

Therefore in an additional feature of the invention, there is provided a method of treating an androgen-sensitive disorder in a warm-blooded animal, such as man, in need of such treatment which comprises administering to said animal an effective amount of a compound of Formula (I) or a pharmaceutically acceptable salt thereof in combination with an anti-tumour agent selected from one listed under (i)-(x) herein above.

Therefore in an additional feature of the invention, there is provided a method of treating cancer, such as prostate cancer, in a warm-blooded animal, such as man, in need of such treatment which comprises administering to said animal an effective amount of a compound of Formula (I) or a pharmaceutically acceptable salt thereof in combination with an anti-tumour agent selected from one listed under (i)-(x) herein above.

According to a further aspect of the present invention there is provided a kit comprising a compound of Formula (I) or a pharmaceutically acceptable salt thereof in combination with an anti-tumour agent selected from one listed under (i)-(x) herein above.

According to a further aspect of the present invention there is provided a kit comprising:
a) a compound of Formula (I) or a pharmaceutically acceptable salt thereof in a first unit dosage form;
b) an anti-tumour agent selected from one listed under (i)-(ix) herein above; in a second unit dosage form; and
c) container means for containing said first and second dosage forms.

In particular, the compounds of the invention may be used for the treatment of various hormone dependent cancers including without limitation prostate cancer in combination with one or more of the following agents: gonadotrophin agonists (GnRH) (LH-RH agonists); inhibitors of gonadotrophin secretion; 5-alpha reductase inhibitors; antiprogestins; antiestrogens; aromatase inhibitors; progestins; estrogens; cytostatic agents; cytotoxic agents; inhibitors of cell growth signalling pathways, including without limitation kinase inhibitors such as VEGF kinase inhibitors; antibodies including without limitation antibodies directed at cell-growth signalling factors such as EGF antibodies; antisense oligonucleotides; immunological modifiers such as interferons, interleukins, growth hormones, and other cytokines; and other hormonal therapies.

The compounds of the invention man also be used for the treatment of various hormone dependent diseases and disorders, such as prostate cancer in combination with one or more of the following agents: antibiotics; anti-inflammatory agents; potassium channel openers; synthetic thyroid hormone replacements; protein kinase C inhibitors (PKC inhibitors); and immunophilin inhibitors or antagonists.

According to this aspect of the invention there is provided a pharmaceutical composition comprising a compound of the Formula (I) as defined hereinbefore and an additional anti-tumour substance as defined hereinbefore for the conjoint treatment of cancer.

In addition to their use in therapeutic medicine, the compounds of Formula (I) and their pharmaceutically acceptable salts thereof, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The invention will now be illustrated in the following Examples in which, generally:
(i) temperatures are given in degrees Celsius (° C.); operations were carried out at room or ambient temperature, that is, at a temperature in the range of 18 to 25° C.;
(ii) organic solutions were dried over anhydrous magnesium sulfate or anhydrous sodium sulfate; evaporation of solvent was carried out using a rotary evaporator under reduced pressure (600 to 4000 Pascals; 4.5 to 30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and/or analytical LC-MS, and reaction times where given are for illustration only.
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; bs, broad singlet;
(viii) chemical symbols have their usual meanings; SI units and symbols are used;
(ix) Mass spectra (MS) and LC-MS data were generated on an LC-MS system where the HPLC component comprised generally either an Agilent 1100, Waters Alliance HT (2790 & 2795) equipment or an HP1100 pump and Diode Array with CTC autosampler and was run on a Phenomenex Gemini C18 5 μm, 50×2 mm column (or similar) eluting with either acidic eluent (for example, using a gradient between 0-95% water/acetonitrile with 5% of a 1% formic acid in 50:50 water:acetonitrile (v/v) mixture), or basic eluent (for example, using a gradient between 0-95% water/acetonitrile with 5% of a 0.1% 880 Ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the (M+H)+ for positive ion mode and (M−H)− for negative ion mod;
(x) unless stated otherwise compounds containing an asymmetrically substituted carbon and/or sulfur atom have not been resolved;

(xi) any microwave reactions were carried out in either a Biotage Optimizer EXP, or a CEM Explorer microwave;
(xii) preparative high performance liquid chromatography (HPLC) was performed on a Gilson instrument using the following conditions:—
Column: C18 reversed-phase silica, for example, Waters 'Xbridge', 5 μm silica, 19×100 mm, or 30×100 mm, using decreasingly polar solvent mixtures as eluent (decreasing ratio of Solvent A to Solvent B)
Solvent A: Water with 1% ammonium hydroxide
Solvent B: Acetonitrile
Flow rate: 28 ml/min or 61 ml/min
Gradient: Tailored to suit each compound—generally 7-10 min in length
Wavelength: 254 nm
(xiii) Strong cation exchange (SCX) chromatography was performed on pre-packed cartridges (for example, ISOLUTE SCX-2 propyl sulfonic acid-based cartridges supplied by International Sorbent Technology), using a basic eluent (for example, 2M ammonia in methanol);
(xiv) the following abbreviations have been used herein, where necessary:—
DMF N,N-dimethylformamide
DCM dichloromethane
DME 1,2-dimethoxyethane
DMSO dimethylsulphoxide
THF tetrahydrofuran
HATU O-(7-Azabenzotriazol-1-yl)-N,N,N',N'-tetramethyluronium hexafluorophosphate
EDCI 1-(3-Dimethylaminopropyl)-3-ethylcarbodiimide
DCCI 1,3-Dicyclohexylcarbodiimide
PYBOP Benzotriazole-1-yl-oxy-trispyrrolidinonophosphonium hexafluorophosphate DEAD Diethyl azodicarboxylate
DIAD Diisopropyl azodicarboxylate
DTAD Di-tert-butyl azodicarboxylate
DIPEA N,N-Diisopropylethylamine
MeOH Methanol
TFA Trifluoroacetic acid
m-CPBA m-Chloroperoxybenzoic acid
AcOH Acetic acid
DMA N,N-Dimethylacetamide
EtOAc Ethyl acetate
EtOH Ethanol
MeCN Acetonitrile
MTBE Methyl tert-butyl ether
CAS Chemical Abstracts Service
X-Ray Powder Diffraction (XRPD)

The X-ray powder diffraction patterns of the crystal forms were determined by mounting a sample of the crystalline material on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 Angstroms using a Bruker D5000 powder X-ray diffractometer (Bruker AXS, Banner Lane Coventry CV4 9 GH). The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in continuous scan theta-theta mode. The instrument was equipped with a scintillation counter as detector. Control and data capture was by means of a Dell Optiplex 686 NT 4.0 Workstation operating with Diffrac+software.

The skilled person is aware that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, the skilled person will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form is not limited to the crystals that provide X-ray powder diffraction patterns identical to the X-ray powder diffraction patterns shown in FIGS. A to D and any crystals providing X-ray powder diffraction patterns substantially the same as that shown in FIGS. A to D fall within the scope of the present invention. A person skilled in the art of X-ray powder diffraction is able to judge the substantial identity of X-ray powder diffraction patterns.

Differential Scanning Calorimetry (DSC)

DSC was recorded using a Thermal Analysis Q1000 system. Typically less than 5 mg of material, contained in an aluminium pan fitted with a sealed lid, was heated over the temperature range 25° C. to 300° C. at a constant heating rate of 10° C. per minute. A nitrogen purge gas was used with flow rate 50 ml per minute.

General Synthetic Method 1

General Procedure for the Reaction of a 6-chloro-3-(fluorinated-alkyl)-[1,2,4]-triazolo[4,3-b]pyridazine with a cyclic amine A solution of the cyclic amine (1.47 mmol; 3 equivalents) in ethanol (1 mL) was added to the 6-chloro-3-(fluorinated-alkyl)-[1,2,4]-triazolo[4,3-b]pyridazine (0.49 mmol) (see below for preparation of novel starting materials) and the reaction was heated and shaken at 70° C. overnight. The reaction mixture was evaporated to dryness and purified by hplc using an Waters X Bridge C18 column (5μ silica, 19 mm diameter, 100 mm length) eluted with decreasingly polar mixtures of water (containing 5% aqueous ammonia) and acetonitrile to give the corresponding 6-cyclicamino-3-(fluorinated-alkyl)-[1,2,4]-triazolo[4,3-b]pyridazine.

6-Chloro-3-difluoromethyl-[1,2,4]-triazolo[4,3-b]pyridazine used as starting material for General Synthetic Method 1 was prepared according to the following procedure:

6-Chloro-3-difluoromethyl-[1,2,4]-triazolo[4,3-b]pyridazine

A mixture of 3-chloropyridazin-6-yl hydrazine (5.0 g, 34.72 mmol) and difluoroacetic acid (21.93 mL; ca. 347 mmol) was heated at 100° C. for 3 hours and then evaporated to dryness. The involatile residue was dissolved in ethyl acetate (200 mL) and washed sequentially with saturated aqueous sodium carbonate and then saturated brine. The organic phase was dried over $MgSO_4$, filtered, and evaporated to give 6-chloro-3-difluoromethyl-[1,2,4]-triazolo[4,3-b]pyridazine (6.0 g, 84.7%) as a white solid that was used without further purification.

$^1$H NMR (300.13 MHz, DMSO-$d_6$) δ 7.68 (1H, t), 7.72 (1H, t, $J_{HF}$=51.2 Hz), 8.59-8.62 (1H, m); m/z 205.38 (M+1)$^+$.

6-Chloro-3-(3,3,3-trifluoroethyl)-[1,2,4]-triazolo[4,3-b]pyridazine used as starting material for General Synthetic Method 1 was prepared according to the following procedure:

6-Chloro-3-(3,3,3-trifluoroethyl)-[1,2,4]-triazolo[4,3-b]pyridazine

A mixture of 3-chloropyridazin-6-yl hydrazine (5.0 g, 34.72 mmol) and trifluoropropionic acid (44.4 g, 347 mmol) was heated at 100° C. for 3 hours and then evaporated to dryness. The involatile residue was extracted with boiling ethyl acetate (200 mL), the hot ethyl acetate extract was filtered and allowed to cool to room temperature, and the product was isolated by filtration to give 6-chloro-3-(3,3,3-trifluoroethyl)-[1,2,4]-triazolo[4,3-b]pyridazine (2.0 g, 24%) as an off-white solid that was used without further purification.

$^1$H NMR (300.13 MHz, DMSO-$d_6$) δ 4.37-4.40 (2H, m), 7.56-7.59 (1H, m), 8.51-8.54 (1H, m); m/z 237.42 (M+1)$^+$.

6-Chloro-3-(2,2,3,3-tetrafluoroethyl)-[1,2,4]-triazolo[4,3-b]pyridazine used as starting material for General Synthetic Method 1 was prepared according to the following procedure:

6-Chloro-3-(2,2,3,3-tetrafluoroethyl)-[1,2,4]-triazolo[4,3-b]pyridazine

A mixture of 3-chloropyridazin-6-yl hydrazine (5.0 g, 34.72 mmol) and tetrafluoropropionic acid (32.5 mL; ca. 347 mmol) was heated at 100° C. for 3 hours and then evaporated to dryness. The involatile residue was dissolved in ethyl acetate (200 mL) and washed sequentially with saturated aqueous sodium carbonate and then saturated brine. The organic phase was dried over MgSO$_4$, filtered, and evaporated to give 6-chloro-3-(2,2,3,3-tetrafluoroethyl)-[1,2,4]-triazolo[4,3-b]pyridazine (4.2 g, 48.8%) as a white solid that was used without further purification.

$^1$H NMR (300.13 MHz, DMSO-$d_6$) δ 7.21 (1H, t), 7.73-7.77 (1H, m), 8.65-8.68 (1H, m); m/z 255.28 (M+1)$^+$.

General Synthetic Method 2

General Procedure for the Reaction of a 6-chloro-3-(heteroatom)-[1,2,4]triazolo[4,3-b]pyridazine with a cyclic amine A solution of the cyclic amine (1.10 mmol; 3 equivalents) in ethanol (2 mL) was added to the 6-chloro-3-(heteroatom)-[1,2,4]-triazolo[4,3-b]pyridazine (0.37 mmol) (see below for preparation of novel starting materials) and the reaction was heated and shaken at 70° C. overnight. The reaction mixture was evaporated to dryness and purified by hplc using a Waters X Bridge C18 column (5μ silica, 19 mm diameter, 100 mm length) eluted with decreasingly polar mixtures of water (containing 5% aqueous ammonia) and acetonitrile to give the corresponding 6-(cyclicamino)-3-(heteroatom)-[1,2,4]-triazolo[4,3-b]pyridazine.

General Synthetic Method 3

General Procedure for the Reaction of a 6-chloro-3-trifluoromethyl-[1,2,4]-triazolo[4,3-b]pyridazine with a Cyclic Amine A solution of the cyclic amine (0.55 mmol) in ethanol (1 mL) was added to 6-chloro-3-(trifluoromethyl)-[1,2,4]triazolo[3,4-f]pyridazine (0.050 g, 0.22 mmol) and the mixture was heated at 70° C. for 16 hours or until analytical hplc-ms indicated that reaction was complete. The reaction mixture was evaporated to leave an involatile residue that was purified by preparative reverse phase chromatography to give the corresponding 6-(cyclicamino)-3-trifluoromethyl-[1,2,4]-triazolo[4,3-b]pyridazine.

General Synthetic Method 4

General Procedure for the Reaction of a 6-chloro-3-trifluoromethyl-[1,2,4]-triazolo[4,3-b]pyridazine with the Acid Salt of a Cyclic Amine A solution of the acid salt of a cyclic amine (0.55 mmol) in ethanol (1 mL) was added to 6-chloro-3-(trifluoromethyl)-[1,2,4]triazolo[3,4-f]pyridazine (0.050 g, 0.22 mmol). The reaction mixture was treated with diisopropylethylamine (1 equivalent/acid salt) and the mixture was heated at 70° C. for 16 hours or until analytical hplc-ms indicated that reaction was complete. The reaction mixture was evaporated to leave an involatile residue that was purified by preparative reverse phase chromatography to give the corresponding 6-(cyclicamino)-3-trifluoromethyl-[1,2,4]-triazolo[4,3-b]pyridazine.

General Synthetic Method 5

General Procedure for the Reductive Amination of 6-(piperazin-1-yl)-3-(trifluoromethyl)-[1,2,4]triazolo[4,3-b]pyridazine with an aldehyde (Polystyrylmethyl)trimethylammonium cyanoborohydride (4.1 mmol/g, 0.049 g, 0.2 mmol) was added to the aldehyde (0.2 mmol) followed by a solution of 6-(piperazin-1-yl)-3-(trifluoromethyl)-[1,2,4]triazolo[4,3-b]pyridazine (0.05 g, 0.184 mmol) in a mixture of acetic acid and dichloromethane (1:9; 2 mL). The mixture was shaken for 40 hours and then filtered. The filtrate was evaporated and the involatile residue was purified by preparative reverse phase chromatography to yield the corresponding 6-(4-(substituted-methyl)-piperazin-1-yl)-3-(trifluoromethyl)-[1,2,4]triazolo[4,3-b]pyridazine.

The 6-(piperazin-1-yl)-3-(trifluoromethyl)-[1,2,4]triazolo[4,3-b]pyridazine used as starting material was prepared as follows:—

Preparation of tert-butyl 4-(3-(trifluoromethyl)-[1,2,4]triazolo[4,3-b]pyridazin-6-yl)piperazine-1-carboxylate A mixture of tert-butyl piperazine-1-carboxylate (8.29 g, 44.5 mmol) and ethanol (90 mL) was added to a mixture of diisopropylethylamine (9.16 mL, 52.6 mmol) and 6-chloro-3-(trifluoromethyl)-[1,2,4]triazolo[3,4-f]pyridazine (9.0 g, 40.4 mmol) in ethanol (90 mL) The mixture was heated at 70° C. for 11 hours and then allowed to cool to ambient temperature to give a precipitate. The precipitate was collected by filtration, washed with chilled ethanol and then with water, and dried under vacuum to afford tert-butyl 4-(3-(trifluoromethyl)-[1,2,4]triazolo[4,3-b]pyridazin-6-yl)piperazine-1-carboxylate (13.64 g, 90.6%) as a white solid that was used without further purification.

1H NMR (300.132 MHz, DMSO) d 1.43 (s, 9H), 3.48 (m, 4H), 3.62 (m, 4H), 7.58 (d, 1H), 8.28 (d, 1H); m/z 373 (M+H)$^+$.

Preparation of 6-(piperazin-1-yl)-3-(trifluoromethyl)-[1,2,4]triazolo[4,3-b]pyridazine Trifluoroacetic acid (25 mL, 324.49 mmol) was added to a mixture of tert-butyl 4-(3-(trifluoromethyl)-[1,2,4]triazolo[4,3-b]pyridazin-6-yl)piperazine-1-carboxylate (6.7 g, 17.99 mmol) and dichloromethane (100 mL) at ambient temperature and the resulting solution was stirred at ambient temperature for 1 hour. The reaction mixture was evaporated to give an involatile residue that was treated with saturated aqueous sodium bicarbonate solution (100 mL) and then extracted with dichloromethane (4×200 mL). The organic phases were combined and dried over Na$_2$SO$_4$, filtered, and evaporated to give 6-(piperazin-1-yl)-3-(trifluoromethyl)-[1,2,4]triazolo[4,3-b]pyridazine (4.78 g, 98%) as a white solid that was used without further purification.

1H NMR (300.132 MHz, DMSO) δ 2.43 (s, 1H), 2.74-2.87 (m, 4H), 3.45-3.59 (m, 4H), 7.57 (d, 1H), 8.22 (d, 1H); m/z 273 (M+H)$^+$.

General Synthetic Method 6

General Procedure for the Reductive Amination of 6-(piperazin-1-yl)-3-(trifluoromethyl)-[1,2,4]triazolo[4,3-b]pyridazine with an aldehyde A solution of the aldehyde (0.2 mmol) in dichloromethane (0.5 mL) was added to a mixture of (polystyrylmethyl)trimethylammonium cyanoborohydride (4.1 mmol/g, 0.049 g, 0.2 mmol), 6-(piperazin-1-yl)-3-(trifluoromethyl)-[1,2,4]triazolo[4,3-b]pyridazine (0.05 g, 0.184 mmol) and a mixture of acetic acid and dichloromethane (1:9; 2 mL). The reaction mixture was shaken for 16 hours and then filtered. The filtrate was evaporated and the involatile residue was purified by preparative reverse phase chromatography to yield the corresponding 6-(4-(substituted-methyl)-piperazin-1-yl)-3-(trifluoromethyl)-[1,2,4]triazolo[4,3-b]pyridazine.

General Synthetic Method 7

General Procedure for the Reductive Amination of 6-(piperazin-1-yl)-3-(trifluoromethyl)-[1,2,4]triazolo[4,3-b]pyridazine with an aldehyde (Polystyrylmethyl)trimethylammonium cyanoborohydride (4.1 mmol/g, 0.061 g, 0.25 mmol) was added to the aldehyde (0.25 mmol) followed by a solution of 6-(piperazin-1-yl)-3-(trifluoromethyl)-[1,2,4]triazolo[4,3-b]pyridazine (0.05 g, 0.184 mmol) in a mixture of acetic acid and dichloromethane (1:9; 2 mL). The mixture was shaken for 4 days and then filtered. The filtrate was evaporated and the involatile residue was purified by preparative reverse phase chromatography to yield the corresponding 6-(4-(substituted-methyl)-piperazin-1-yl)-3-(trifluoromethyl)-[1,2,4]triazolo[4,3-b]pyridazine.

General Synthetic Method 8

General Procedure for the Reductive Amination of 6-(1,4-diazepan-1-yl)-3-(trifluoromethyl)-[1,2,4]triazolo[4,3-b]pyridazine with an aldehyde (Polystyrylmethyl)trimethylammonium cyanoborohydride (4.1 mmol/g, 0.049 g, 0.2 mmol) was added to the aldehyde (0.2 mmol) followed by a solution of 6-(1,4-diazepan-1-yl)-3-(trifluoromethyl)-[1,2,4]triazolo[3,4-f]pyridazine (0.053 g, 0.184 mmol) in a mixture of acetic acid and dichloromethane (1:9; 2 mL). The mixture was shaken for 16 hours and then filtered. The filtrate was evaporated and the residue was purified by preparative reverse phase chromatography to yield the corresponding 6-(4-(substituted-methyl)-1,4-diazepan-1-yl)-3-(trifluoromethyl)-[1,2,4]triazolo[4,3-b]pyridazine.

The 6-(1,4-diazepan-1-yl)-3-(trifluoromethyl)-[1,2,4]triazolo[3,4-f]pyridazine used as starting material was prepared as follows:—

Preparation of tert-butyl 4-[3-(trifluoromethyl)-[1,2,4]triazolo[3,4-f]pyridazin-6-yl]-1,4-diazepane-1-carboxylate tert-Butyl 1,4-diazepane-1-carboxylate (4.00 g, 20.0 mmol) was added to a mixture of diisopropylethylamine (4.11 mL, 23.7 mmol) and 6-chloro-3-(trifluoromethyl)-[1,2,4]triazolo[3,4-f]pyridazine (4.0 g, 18.2 mmol) in ethanol (80 mL). The mixture was heated under reflux for 6 hours and then allowed to cool to ambient temperature to give a precipitate. The precipitate was collected by filtration, washed with ethanol, and dried under vacuum to afford tert-butyl 4-[3-(trifluoromethyl)-[1,2,4]triazolo[3,4-f]pyridazin-6-yl]-1,4-diazepane-1-carboxylate (5.94 g, 85.4%) as a white solid. 1H NMR (300.132 MHz, DMSO) δ 1.15 (9H, d), 1.72-1.93 (2H, m), 3.27-3.39 (2H, m), 3.50-3.63 (2H, m), 3.66-3.75 (2H, m), 3.83 (2H, t), 7.46-7.56 (1H, m), 8.19-8.31 (1H, m); apparently as a mixture of rotamers; m/z 387 (M+H)$^+$.

Preparation of 6-(1,4-diazepan-1-yl)-3-(trifluoromethyl)-[1,2,4]triazolo[3,4-f]pyridazine Trifluoroacetic acid (8 mL, 103.68 mmol) was added to a mixture of tert-butyl 4-[3-(trifluoromethyl)-[1,2,4]triazolo[3,4-f]pyridazin-6-yl]-1,4-diazepane-1-carboxylate (5.9 g, 15.3 mmol) and dichloromethane (80 mL) at ambient temperature and the resulting solution was stirred at ambient temperature for 6 hours. The reaction mixture was evaporated to give an involatile residue that was treated with saturated aqueous sodium bicarbonate solution (100 mL) and then extracted with dichloromethane (4×200 mL). The organic phases were combined and dried over Na$_2$SO$_4$, filtered, and evaporated to give 6-(1,4-diazepan-1-yl)-3-(trifluoromethyl)-[1,2,4]triazolo[3,4-f]pyridazine (3.8 g, 86.9%) as a white solid. 1H NMR (300.132 MHz, DMSO) δ 1.68-1.84 (m, 2H), 2.69 (t, 2H), 2.88 (t, 2H), 3.60-3.79 (m, 4H), 7.46 (d, 1H), 8.19 (d, 1H); m/z. 287 (M+H)$^+$.

General Synthetic Method 9

General Procedure for the Reductive Amination of 6-(piperazin-1-yl)-3-(trifluoromethyl)-[1,2,4]triazolo[4,3-a]pyridine with an aldehyde (Polystyrylmethyl)trimethylammonium cyanoborohydride (4.1 mmol/g, 0.061 g, 0.25 mmol) was added to the aldehyde (0.25 mmol) followed by a solution of 6-(piperazin-1-yl)-3-(trifluoromethyl)-[1,2,4]triazolo[4,3-a]pyridine (0.050 g, 0.184 mmol) in a mixture of acetic acid and dichloromethane (1:9; 2 mL). The mixture was shaken for 40 hours and then filtered. The filtrate was evaporated and the involatile residue was purified by preparative reverse phase chromatography yield the corresponding 6-(4-(substituted-methyl)-piperazin-1-yl)-3-(trifluoromethyl)-[1,2,4]triazolo[4,3-a]pyridine.

The 6-(piperazin-1-yl)-3-(trifluoromethyl)-[1,2,4]triazolo[4,3-a]pyridine used as starting material was prepared as follows:—

Preparation of 6-bromo-3-(trifluoromethyl)-[1,2,4]triazolo[4,3-a]pyridine

A mixture of polyphosphoric acid (20 mL, 175 mmol) and N'-(5-bromopyridin-2-yl)-2,2,2-trifluoroacetohydrazide (1.9 g, 6.69 mmol) was stirred at 120° C. for 20 hours and then poured in to water. The mixture was then basified with saturated aqueous sodium bicarbonate solution and extracted with dichloromethane (3×250 mL). The organic phases were combined and washed with brine (1×100 mL), dried with MgSO$_4$ and evaporated to give an involatile residue. The residue was purified by flash chromatography on silica-gel using an increasing gradient of ethyl acetate in isohexane as eluant to give 6-bromo-3-(trifluoromethyl)-[1,2,4]triazolo[4,3-a]pyridine (1.39 g, 78%) as a beige solid.

1H NMR (300.132 MHz, DMSO) δ 7.74-7.81 (m, 1H), 8.00-8.07 (m, 1H), 8.92 (s, 1H); m/z 266 and 268 (M+H$^+$).

Preparation of tert-butyl 4-(3-(trifluoromethyl)-[1,2,4]triazolo[4,3-a]pyridin-6-yl)piperazine-1-carboxylate A solution of tert-butyl piperazine-1-carboxylate (1.30 g, 6.99 mmol)], 6-bromo-3-(trifluoromethyl)-[1,2,4]triazolo[4,3-a]pyridine (0.93 g, 3.50 mmol), bis(dibenzylideneacetone) palladium (0.101 g, 0.17 mmol), rac-2,2'-bis(diphenylphosphino)-1,1'-binaphthyl (0.163 g, 0.26 mmol) and sodium tert-butoxide (0.84 g, 8.74 mmol) in xylenes (30 mL) was sealed into a microwave tube and degassed for 10 minutes. The reaction mixture was heated at 100° C. for 30 minutes and then cooled to ambient temperature. The reaction mixture was diluted with water (20 mL) and then extracted with ethyl acetate (2×40 mL). The organic phases were combined, dried over $Na_2SO_4$, filtered, and evaporated to give an involatile residue. The residue was purified by flash chromatography on silica-gel using an increasing gradient of ethyl acetate in isohexane as eluant to give tert-butyl 4-(3-(trifluoromethyl)-[1,2,4]triazolo[4,3-a]pyridin-6-yl)piperazine-1-carboxylate (0.86 g, 66.2%) as a yellow solid.

1H NMR (300.132 MHz, DMSO) δ 1.43 (s, 9H), 3.12-3.20 (m, 4H), 3.46-3.54 (m, 4H), 7.59 (s, 1H), 7.69-7.78 (m, 1H), 7.95 (d, 1H); m/z 372 (M+H$^+$).

Preparation of 6-(piperazin-1-yl)-3-(trifluoromethyl)-[1,2,4]triazolo[4,3-a]pyridine Trifluoroacetic acid (5 mL, 64.90 mmol) was added to a mixture of tert-butyl 4-(3-(trifluoromethyl)-[1,2,4]triazolo[4,3-a]pyridin-6-yl)piperazine-1-carboxylate (0.86 g, 2.32 mmol) and dichloromethane (20 mL). The resulting solution was stirred at 20° C. for 90 minutes and then evaporated to leave an involatile residue. The residue was purified by ion-exchange chromatography on an SCX column using aqueous ammonia (7M) in methanol as eluant to give 6-(piperazin-1-yl)-3-(trifluoromethyl)-[1,2,4]triazolo[4,3-a]pyridine (0.540 g, 86%) as a yellow solid that was used without further purification.

1H NMR (300.132 MHz, DMSO) δ 2.79-2.92 (m, 4H), 3.03-3.13 (m, 4H), 7.49 (s, 1H), 7.67-7.76 (m, 1H), 7.91 (d, 1H); m/z 272 (M+H$^+$).

General Synthetic Method 10
General Procedure for the Reductive Amination of 6-(hexahydropyrrolo[3,4-c]pyrrol-2(1H)-yl)-3-(trifluoromethyl)-[1,2,4]triazolo[4,3-b]pyridazine with an aldehyde (Polystyrylmethyl)trimethylammonium cyanoborohydride (4.1 mmol/g, 0.061 g, 0.25 mmol) was added to the aldehyde (0.25 mmol) followed by a solution of 6-(hexahydropyrrolo[3,4-c]pyrrol-2(1H)-yl)-3-(trifluoromethyl)-[1,2,4]triazolo[4,3-b]pyridazine (0.055 g, 0.184 mmol) in a mixture of acetic acid and dichloromethane (1:9; 2 mL). The mixture was shaken for 16 hours and then filtered. The filtrate was evaporated and the involatile residue was purified by preparative reverse phase chromatography to yield the corresponding 6-(2-(substituted methyl)-1,3,3a,4,6,6a-hexahydropyrrolo[3,4-c]pyrrol-5-yl)-3-(trifluoromethyl)-[1,2,4]triazolo[4,3-b]pyridazine.

The 6-(hexahydropyrrolo[3,4-c]pyrrol-2(1H)-yl)-3-(trifluoromethyl)-[1,2,4]triazolo[4,3-b]pyridazine used as starting material was prepared as follows:—

Preparation of 6-(hexahydropyrrolo[3,4-c]pyrrol-2(1H)-yl)-3-(trifluoromethyl)-[1,2,4]triazolo[4,3-b]pyridazine Trifluoroacetic acid (15 mL, 194.70 mmol) was added to a mixture of tert-butyl 5-(3-(trifluoromethyl)-[1,2,4]triazolo[4,3-b]pyridazin-6-yl)hexahydropyrrolo[3,4-c]pyrrole-2(1H)-carboxylate (3 g, 7.53 mmol) and dichloromethane (60 mL). The resulting solution was stirred at ambient temperature for 1 hour and then evaporated to leave an involatile residue. The residue was purified by ion-exchange chromatography on an SCX column using aqueous ammonia (7M) in methanol as eluant to give 6-(hexahydropyrrolo[3,4-c]pyrrol-2(1H)-yl)-3-(trifluoromethyl)-[1,2,4]triazolo[4,3-b]pyridazine (2.200 g, 98%) as a white solid that was used without further purification.

1H NMR (300.132 MHz, DMSO) δ 2.61-2.74 (m, 2H), 2.82-2.96 (m, 4H), 3.27-3.38 (m under $H_2O$, 2H), 3.67-3.80 (m, 2H), 7.27 (d, 1H), 8.20 (d, 1H); m/z 299 (M+H$^+$).

EXAMPLE 1

Preparation of 6-(4-benzhydrylpiperazin-1-yl)-3-(1,1,2,2-tetrafluoroethyl)-[1,2,4]triazolo[4,3-b]pyridazine A mixture of 1-benzhydrylpiperazine and 6-chloro-3-(2,2,3,3-tetrafluoroethyl)-1,2,4-triazolo[4,3-b]pyridazine was allowed to react by General Synthetic Method 1 to give 6-(4-benzhydrylpiperazin-1-yl)-3-(1,1,2,2-tetrafluoroethyl)-[1,2,4]triazolo[4,3-b]pyridazine.

1H NMR (700.03 MHz, DMSO-d6) δ 2.46 (4H, t), 3.63 (4H, t), 4.39 (1H, s), 7.07-7.23 (3H, m), 7.33 (4H, t), 7.48 (4H, d), 7.51-7.52 (1H, m), 8.23 (1H, d); m/z=471 [M+H]+.

EXAMPLE 2

Preparation of 6-(4-benzyl-1,4-diazepan-1-yl)-3-(1,1,2,2-tetrafluoroethyl)-[1,2,4]triazolo[4,3-b]pyridazine A mixture of 1-benzyl-1,4-diazepane and 6-chloro-3-(2,2,3,3-tetrafluoroethyl)-1,2,4-triazolo[4,3-b]pyridazine was allowed to react by General Synthetic Method 1 to give 6-(4-benzyl-1,4-diazepan-1-yl)-3-(1,1,2,2-tetrafluoroethyl)-[1,2,4]triazolo[4,3-b]pyridazine.

1H NMR (700.03 MHz, DMSO-d6) δ 1.85-1.90 (2H, m), 2.61 (2H, t), 2.72-2.76 (2H, m), 3.63 (2H, s), 3.73 (2H, t), 3.76 (2H, t), 7.05-7.21 (1H, m), 7.21-7.24 (1H, m), 7.24-7.27 (4H, m), 7.46 (1H, d), 8.19 (1H, d); m/z=409 [M+H]+.

EXAMPLE 3

Preparation of 6-piperidin-1-yl-3-(2,2,2-trifluoroethyl)-[1,2,4]triazolo[4,3-b]pyridazine A mixture of piperidine and 6-chloro-3-(3,3,3-trifluoroethyl)-1,2,4-triazolo[4,3-b]pyridazine was allowed to react by General Synthetic Method 1 to give 6-piperidin-1-yl-3-(2,2,2-trifluoroethyl)-[1,2,4]triazolo[4,3-b]pyridazine.

1H NMR (700.03 MHz, DMSO-d6) δ 1.59-1.62 (4H, m), 1.65 (2H, d), 3.60 (4H, t), 4.20 (2H, q), 7.43 (1H, d), 8.06 (1H, d); m/z=286 [M+H]+.

EXAMPLE 4

Preparation of 6-(4-benzhydrylpiperazin-1-yl)-3-(2,2,2-trifluoroethyl)-[1,2,4]triazolo[4,3-b]pyridazine A mixture of 1-benzhydrylpiperazine and 6-chloro-3-(3,3,3-trifluoroethyl)-1,2,4-triazolo[4,3-b]pyridazine was allowed to react by General Synthetic Method 1 to give 6-(4-benzhydrylpiperazin-1-yl)-3-(2,2,2-trifluoroethyl)-[1,2,4]triazolo[4,3-b]pyridazine.

1H NMR (700.03 MHz, DMSO-d6) δ 2.46 (4H, t), 3.62 (4H, t), 4.19 (2H, q), 4.39 (1H, s), 7.22 (2H, t), 7.33 (4H, t), 7.37 (1H, d), 7.48 (4H, d), 8.11 (1H, d); m/z=453 [M+H]+.

EXAMPLE 5

Preparation of 6-(4-benzhydrylpiperazin-1-yl)-3-(difluoromethyl)-[1,2,4]triazolo[4,3-b]pyridazine A mixture of 1-benzhydrylpiperazine and 6-chloro-3-difluoromethyl-1,2,4-triazolo[4,3-b]pyridazine was allowed to react by General Synthetic Method 1 to give 6-(4-benzhydrylpiperazin-1-yl)-3-(difluoromethyl)-[1,2,4]triazolo[4,3-b]pyridazine.

1H NMR (700.03 MHz, DMSO-d6) δ 2.46 (4H, t), 3.63 (4H, t), 4.40 (1H, s), 7.21-7.23 (2H, m), 7.33 (4H, t), 7.28-7.57 (1H, m), 7.45-7.49 (5H, m), 8.18-8.19 (1H, m); m/z=421 [M+H]+.

EXAMPLE 6

Preparation of 6-(4-benzyl-1,4-diazepan-1-yl)-3-(difluoromethyl)-[1,2,4]triazolo[4,3-b]pyridazine A mixture of 1-benzyl-1,4-diazepane and 6-chloro-3-difluoromethyl-1,2,4-triazolo[4,3-b]pyridazine was allowed to react by General Synthetic Method 1 to give 6-(4-benzyl-1,4-diazepan-1-yl)-3-(difluoromethyl)-[1,2,4]triazolo[4,3-b]pyridazine.

1H NMR (700.03 MHz, DMSO-d6) δ 1.86-1.90 (2H, m), 2.61 (2H, t), 2.74 (2H, t), 3.63 (2H, s), 3.73 (2H, t), 3.75 (2H, t), 7.21-7.24 (1H, m), 7.26 (4H, t), 7.41 (1H, d), 7.40-7.55 (1H, m), 8.14 (1H, d); m/z=359 [M+H]+.

EXAMPLE 7

Preparation of 6-piperidin-1-yl-[1,2,4]triazolo[4,3-b]pyridazin-3-amine

A mixture of piperidine and 3-amino-6-chloro-1,2,4-triazolo[4,3-b]pyridazine was allowed to react by General Synthetic Method 2 to give 6-piperidin-1-yl-[1,2,4]triazolo[4,3-b]pyridazin-3-amine.

1H NMR (700.03 MHz, DMSO-d6) δ 1.58-1.63 (6H, m), 3.53 (4H, t), 6.00 (2H, s), 7.07 (1H, d), 7.72 (1H, d); m/z=219 [M+H]+.

EXAMPLE 8

Preparation of 6-(4-benzhydrylpiperazin-1-yl)-3-chloro-[1,2,4]triazolo[4,3-b]pyridazine A mixture of 1-benzhydrylpiperazine and 3,6-dichloro-1,2,4-triazolo[4,3-b]pyridazine was allowed to react by General Synthetic Method 2 to give 6-(4-benzhydrylpiperazin-1-yl)-3-chloro-[1,2,4]triazolo[4,3-b]pyridazine.

1H NMR (700.03 MHz, DMSO-d6) δ 2.46 (4H, t), 3.63 (4H, t), 4.40 (1H, s), 7.21-7.23 (2H, m), 7.33 (4H, t), 7.41 (1H, d), 7.47 (4H, d), 8.11 (1H, d); m/z=405 [M+H]+.

EXAMPLE 9

Preparation of 6-(4-benzhydrylpiperazin-1-yl)-3-methylsulfanyl-[1,2,4]triazolo[4,3-b]pyridazine A mixture of 1-benzhydrylpiperazine and 6-chloro-3-methylsulfanyl-1,2,4-triazolo[4,3-b]pyridazine was allowed to react by General Synthetic Method 2 to give 6-(4-benzhydrylpiperazin-1-yl)-3-methylsulfanyl-[1,2,4]triazolo[4,3-b]pyridazine.

1H NMR (700.03 MHz, DMSO-d6) δ 2.46 (4H, t), 2.68 (3H, s), 3.58 (4H, t), 4.39 (1H, s), 7.21-7.23 (2H, m), 7.31 (1H, d), 7.33 (4H, t), 7.47 (4H, d), 8.05 (1H, d); m/z=417 [M+H]+.

EXAMPLE 10

Preparation of 6-(4-benzyl-1,4-diazepan-1-yl)-3-methylsulfanyl-[1,2,4]triazolo[4,3-b]pyridazine A mixture of 1-benzyl-1,4-diazepane and 6-chloro-3-methylsulfanyl-1,2,4-triazolo[4,3-b]pyridazine was allowed to react by General Synthetic Method 2 to give 6-(4-benzyl-1,4-diazepan-1-yl)-3-methylsulfanyl-[1,2,4]triazolo[4,3-b]pyridazine.

1H NMR (700.03 MHz, DMSO-d6) δ 1.86-1.90 (2H, m), 2.60 (2H, t), 2.67 (3H, s), 2.74 (2H, t), 3.63 (2H, s), 3.72 (2H, t), 3.74 (2H, t), 7.22-7.24 (1H, m), 7.25 (1H, d), 7.26-7.28 (4H, m), 8.01 (1H, d); m/z=355 [M+H]+.

EXAMPLE 11

Preparation of 6-[4-(5-bromopyridin-2-yl)piperazin-1-yl]-3-(trifluoromethyl)-[1,2,4]triazolo[4,3-b]pyridazine A mixture of 1-(5-bromopyridin-2-yl)piperazine and 6-chloro-3-(trifluoromethyl)-[1,2,4]triazolo[4,3-b]pyridazine in ethanol (7 mL) was stirred at 80° C. for 20 hours. The reaction mixture was concentrated and partitioned between dichloromethane (50 mL) and saturated aqueous sodium bicarbonate solution (25 mL). The aqueous phase was extracted twice with dichloromethane (2×50 mL). The organic phases were combined, washed with water (100 mL), and concentrated to give a residue that was purified by flash chromatography on silica-gel using ethyl acetate as eluant to give 6-[4-(5-bromopyridin-2-yl)piperazin-1-yl]-3-(trifluoromethyl)-[1,2,4]triazolo[4,3-b]pyridazine 0.353 g, 73.4%)

1H NMR (300.132 MHz, DMSO) δ 3.64-3.77 (8H, m), 6.90 (1H, d), 7.65 (1H, d), 7.71-7.76 (1H, m), 8.20-8.22 (1H, m), 8.29 (1H, d); m/z=430 not assigned (Br).

EXAMPLE 12

Preparation of 4-((4-(8-Methyl-3-(trifluoromethyl)-[1,2,4]triazolo[4,3-b]pyridazin-6-yl)piperazin-1-yl)methyl)benzonitrile A mixture of 1-(4-cyanobenzyl)-piperazine (0.158 g, 0.79 mmol) and 6-chloro-8-methyl-3-(trifluoromethyl)-[1,2,4]triazolo[4,3-b]pyridazine 0.062 g, 0.26 mmol) in ethanol (5 mL) was heated to 70° C. for 20 hours. The reaction mixture was allowed to cool and then concentrated to give an involatile residue that was purified by flash chromatography on silica-gel using an increasing gradient of ethyl acetate in dichloromethane to give 4-((4-(8-methyl-3-(trifluoromethyl)-[1,2,4]triazolo[4,3-b]pyridazin-6-yl)piperazin-1-yl)methyl)benzonitrile (0.0676 g, 64.3%) as a white solid; 1H NMR spectrum (CDCl$_3$) δ 2.47-2.55 (4H, m), 2.61 (3H, d), 3.50-3.60 (6H, m), 6.72-6.76 (1H, m), 7.42 (2H, d), 7.57 (2H, d); m/z 402.69 (M+1)$^+$.

The 6-chloro-8-methyl-3-(trifluoromethyl)-[1,2,4]triazolo[4,3-b]pyridazine used as starting material was prepared as follows Preparation of a mixture of
6-chloro-4-methylpyridazin-3-yl hydrazine and
6-chloro-5-methylpyridazin-3-yl hydrazine Hydrazine hydrate (1.79 mL, 36.81 mmol) was added to a stirred suspension of 3,6-dichloro-4-methylpyridazine (0.50 g, 3.07 mmol) in water (10 mL) and the reaction mixture was heated at 80° C. for 4 hours. The reaction mixture was allowed to cool and evaporated under rescued pressure to give a mixture of 3-chloro-6-hydrazinyl-4-methylpyridazine compound and 6-chloro-3-hydrazinyl-4-methylpyridazine (0.452 g) as an off-white solid that was used without further purification. m/z 159.41 (M+1)+.

Preparation of 6-chloro-7-methyl-3-(trifluoromethyl)-[1,2,4]triazolo[4,3-b]pyridazine and 6-chloro-8-methyl-3-(trifluoromethyl)-[1,2,4]triazolo[4,3-b]pyridazine A suspension of a mixture of 3-chloro-6-hydrazinyl-4-methylpyridazine compound and 6-chloro-3-hydrazinyl-4-methylpyridazine (0.200 g) in trifluoroacetic acid (10 mL) was heated under reflux for 20 hours. The reaction mixture was allowed to cool and then concentrated to give an involatile residue that was purified by flash chromatography on silica-gel using dichloromethane as eluant to give pure fractions of:
6-chloro-8-methyl-3-(trifluoromethyl)-[1,2,4]triazolo[4,3-b]pyridazine (0.0620 g) as a white solid. 1H NMR (CDCl$_3$) δ 2.74 (3H, d), 7.05 (1H, q); m/z 237.37 (M+1)$^+$; and
6-chloro-7-methyl-3-(trifluoromethyl)-[1,2,4]triazolo[4,3-b]pyridazine (0.078 g) as a white solid. 1H NMR (CDCl$_3$) δ 2.49 (3H, d), 7.97 (1H, q); m/z 237.37 (M+1)+.

EXAMPLE 13

Preparation of 4-((4-(7-Methyl-3-(trifluoromethyl)-[1,2,4]triazolo[4,3-b]pyridazin-6-yl)piperazin-1-yl)methyl)benzonitrile The method of Example 12 was repeated using a mixture of 6-chloro-7-methyl-3-(trifluoromethyl)-[1,2,4]triazolo[4,3-b]pyridazine (0.078 g, 0.33 mmol) and 1-(4-cyanobenzyl)-piperazine (0.199 g, 0.99 mmol) to give 4-((4-(7-methyl-3-(trifluoromethyl)-[1,2,4]triazolo[4,3-b]pyridazin-6-yl)piperazin-1-yl)methyl)benzonitrile (0.099 g, 75%).
1H NMR (CDCl$_3$) δ 2.37 (3H, d), 2.53-2.63 (4H, m), 3.23-3.32 (4H, m), 3.57 (2H, s), 7.42 (2H, d), 7.57 (2H, d), 7.73-7.76 (1H, m); m/z 402.71 (M+1)+.
The 6-chloro-7-methyl-3-(trifluoromethyl)-[1,2,4]triazolo[4,3-b]pyridazine used as starting material was prepared as described in Example 12.

EXAMPLE 14

Preparation of 6-[4-[(4-chlorophenyl)methyl]piperazin-1-yl]-3-(trifluoromethyl)-[1,2,4]triazolo[4,3-b]pyridazine A mixture of 1-[(4-chlorophenyl)methyl]piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-[(4-chlorophenyl)methyl]piperazin-1-yl]-3-(trifluoromethyl)-[1,2,4]triazolo[4,3-b]pyridazine.
1H NMR (499.802 MHz, DMSO-d6) δ 2.48-2.51 (4H, m), 3.52 (2H, s), 3.56-3.62 (4H, m), 7.37 (4H, q), 7.57 (1H, d), 8.23 (1H, d) (Signal at 2.5 obscured by DMSO); m/z=397 [M+H]+.

EXAMPLE 15

Preparation of 6-[4-[(4-methoxyphenyl)methyl]piperazin-1-yl]-3-(trifluoromethyl)-[1,2,4]triazolo[4,3-b]pyridazine A mixture of 1-[(4-methoxyphenyl)methyl]piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-[(4-methoxyphenyl)methyl]piperazin-1-yl]-3-(trifluoromethyl)-[1,2,4]triazolo[4,3-b]pyridazine.
1H NMR (499.802 MHz, DMSO-d6) δ 2.44-2.51 (4H, m), 3.47 (2H, s), 3.57-3.64 (4H, m), 3.75 (3H, s), 6.91 (2H, d), 7.25 (2H, d), 7.58 (1H, d), 8.24 (1H, d) (Signal at 2.5 partially obscured by DMSO); m/z=393 [M+H]+.

EXAMPLE 16

Preparation of 6-[4-(2,6-dimethylphenyl)piperazin-1-yl]-3-(trifluoromethyl)-[1,2,4]triazolo[4,3-b]pyridazine A mixture of 1-(2,6-dimethylphenyl)piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-(2,6-dimethylphenyl)piperazin-1-yl]-3-(trifluoromethyl)-[1,2,4]triazolo[4,3-b]pyridazine.
1H NMR (700.03 MHz, DMSO-d6) δ 2.31 (6H, s), 3.17 (4H, t), 3.73 (4H, t), 6.95-6.97 (1H, m), 7.00 (2H, d), 7.66 (1H, d), 8.27 (1H, d); m/z=377 [M+H]+.

EXAMPLE 17

Preparation of 1-[4-[4-[3-(trifluoromethyl)-[1,2,4]triazolo[4,3-b]pyridazin-6-yl]piperazin-1-yl]phenyl]ethanone A mixture of 1-(4-piperazin-1-ylphenyl)ethanone and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 1-[4-[4-[3-(trifluoromethyl)-[1,2,4]triazolo[4,3-b]pyridazin-6-yl]piperazin-1-yl]phenyl]ethanone.
1H NMR (700.03 MHz, DMSO-d6) δ 2.47 (3H, s), 3.56 (4H, t), 3.79 (4H, t), 7.03-7.04 (2H, m), 7.66 (1H, d), 7.84-7.86 (2H, m), 8.30 (1H, d); m/z=391 [M+H]+.

EXAMPLE 18

Preparation of 6-[4-[4,4-bis(4-fluorophenyl)butyl]piperazin-1-yl]-3-(trifluoromethyl)-[1,2,4]triazolo[4,3-b]pyridazine A mixture of 1-[4,4-bis(4-fluorophenyl)butyl]piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-[4,4-bis(4-fluorophenyl)butyl]piperazin-1-yl]-3-(trifluoromethyl)-[1,2,4]triazolo[4,3-b]pyridazine.

1H NMR (700.03 MHz, DMSO-d6) δ 1.34-1.38 (2H, m), 2.02 (2H, q), 2.34 (2H, t), 2.42 (4H, t), 3.57 (4H, t), 4.01 (1H, t), 7.09-7.13 (4H, m), 7.32-7.35 (4H, m), 7.58 (1H, d), 8.23 (1H, d); m/z=517 [M+H]+.

EXAMPLE 19

Preparation of 6-[4-(3,5-dichloropyridin-4-yl)piperazin-1-yl]-3-(trifluoromethyl)-[1,2,4]triazolo[4,3-b]pyridazine A mixture of 1-(3,5-dichloropyridin-4-yl)piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-(3,5-dichloropyridin-4-yl)piperazin-1-yl]-3-(trifluoromethyl)-[1,2,4]triazolo[4,3-b]pyridazine.

1H NMR (700.03 MHz, DMSO-d6) δ 3.45-3.46 (4H, m), 3.78 (4H, t), 7.67 (1H, d), 8.30 (1H, d), 8.50 (2H, s); m/z=418 [M+H]+.

EXAMPLE 20

Preparation of 1-phenyl-8-[3-(trifluoromethyl)-[1,2,4]triazolo[4,3-b]pyridazin-6-yl]-1,3,8-triazaspiro[4.5]decan-4-one A mixture of 1-phenyl-1,3,8-triazaspiro[4.5]decan-4-one and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 1-phenyl-8-[3-(trifluoromethyl)-[1,2,4]triazolo[4,3-b]pyridazin-6-yl]-1,3,8-triazaspiro[4.5]decan-4-one.

1H NMR (700.03 MHz, DMSO-d6) δ 1.79-1.81 (2H, m), 2.55 (2H, d), 3.79 (2H, d), 4.19-4.22 (2H, m), 4.63 (2H, s), 6.67 (2H, d), 6.71 (1H, t), 7.07-7.09 (2H, m), 7.66 (1H, d), 8.29 (1H, d), 8.81 (1H, s); m/z=418 [M+H]+.

EXAMPLE 21

Preparation of 6-[4-(4-nitrophenyl)piperazin-1-yl]-3-(trifluoromethyl)-[1,2,4]triazolo[4,3-b]pyridazine A mixture of 1-(4-nitrophenyl)piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-(4-nitrophenyl)piperazin-1-yl]-3-(trifluoromethyl)-[1,2,4]triazolo[4,3-b]pyridazine.

1H NMR (300.132 MHz, DMSO-d6) δ 3.66-3.74 (4H, m), 3.76-3.85 (4H, m), 7.06 (2H, d), 7.64 (1H, d), 8.10 (2H, d), 8.30 (1H, d); m/z=394 [M+H]+.

EXAMPLE 22

Preparation of 6-(4-benzhydrylpiperazin-1-yl)-3-(trifluoromethyl)-[1,2,4]triazolo[4,3-b]pyridazine A mixture of 1-benzhydrylpiperazine and 6-chloro-3-(trifluoromethyl)-[1,2,4]triazolo[4,3-b]pyridazine was allowed to react by General Synthetic Method 3. The crude product was purified by hplc using a Phenomenex Luna C18 100A column (10µ silica, 21 mm diameter, 150 mm length) eluted with decreasingly polar mixtures of water (containing 0.1% aqueous ammonia) and acetonitrile as eluents to give 6-(4-benzhydrylpiperazin-1-yl)-3-(trifluoromethyl)-[1,2,4]triazolo[4,3-b]pyridazine.

1H NMR (700.03 MHz, DMSO-d6) δ 2.46 (4H, t), 3.63 (4H, t), 4.40 (1H, s), 7.21-7.23 (2H, m), 7.32-7.34 (4H, m), 7.46-7.48 (4H, m), 7.54 (1H, d), 8.25 (1H, d); m/z=439 [M+H]+.

EXAMPLE 23

Preparation of 6-(4-phenethylpiperazin-1-yl)-3-(trifluoromethyl)-[1,2,4]triazolo[4,3-b]pyridazine A mixture of 1-phenethylpiperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-(4-phenethylpiperazin-1-yl)-3-(trifluoromethyl)-[1,2,4]triazolo[4,3-b]pyridazine.

1H NMR (700.03 MHz, DMSO-d6) δ 2.58-2.60 (6H, m), 2.79 (2H, t), 3.62 (4H, t), 7.18-7.21 (1H, m), 7.25-7.26 (2H, m), 7.28-7.30 (2H, m), 7.61 (1H, d), 8.25 (1H, d); m/z=377 [M+H]+.

EXAMPLE 24

Preparation of 1-piperidin-1-yl-2-[4-[3-(trifluoromethyl)-[1,2,4]triazolo[4,3-b]pyridazin-6-yl]piperazin-1-yl]ethanone A mixture of 2-piperazin-1-yl-1-piperidin-1-ylethanone and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 1-piperidin-1-yl-2-[4-[3-(trifluoromethyl)-[1,2,4]triazolo[4,3-b]pyridazin-6-yl]piperazin-1-yl]ethanone.

1H NMR (700.03 MHz, DMSO-d6) δ 1.44 (2H, s), 1.53 (2H, d), 1.58-1.61 (2H, m), 2.58 (4H, t), 3.21 (2H, s), 3.42 (2H, t), 3.48 (2H, t), 3.61 (4H, t), 7.60 (1H, d), 8.26 (1H, d); m/z=398 [M+H]+.

EXAMPLE 25

Preparation of 6-[4-[(4-methoxyphenyl)-phenylmethyl]piperazin-1-yl]-3-(trifluoromethyl)-[1,2,4]triazolo[4,3-b]pyridazine A mixture of 1-[(4-methoxyphenyl)-phenylmethyl]piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-[(4-methoxyphenyl)-phenylmethyl]piperazin-1-yl]-3-(trifluoromethyl)-[1,2,4]triazolo[4,3-b]pyridazine.

1H NMR (700.03 MHz, DMSO-d6) δ 2.45 (4H, t), 3.62 (4H, t), 3.72 (3H, s), 4.34 (1H, s), 6.88-6.90 (2H, m), 7.20-7.24 (1H, m), 7.31-7.33 (2H, m), 7.35-7.37 (2H, m), 7.44-7.45 (2H, m), 7.54 (1H, d), 8.25 (1H, d); m/z=469 [M+H]+.

EXAMPLE 26

Preparation of 6-[4-[phenyl-[4-(trifluoromethyl)phenyl]methyl]piperazin-1-yl]-3-(trifluoromethyl)-[1,2,4]triazolo[4,3-b]pyridazine A mixture of 1-[phenyl-[4-(trifluoromethyl)phenyl]methyl]piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-[phenyl-[4-(trifluoromethyl)phenyl]methyl]piperazin-1-yl]-3-(trifluoromethyl)-[1,2,4]triazolo[4,3-b]pyridazine.

1H NMR (700.03 MHz, DMSO-d6) δ 2.45-2.49 (4H, m), 3.64 (4H, t), 4.57 (1H, s), 7.24-7.26 (1H, m), 7.35 (2H, t), 7.47-7.48 (2H, m), 7.54 (1H, d), 7.69-7.73 (4H, m), 8.26 (1H, d); m/z=507 [M+H]+.

EXAMPLE 27

Preparation of 6-[4-(6-bromonaphthalen-2-yl)sulfonylpiperazin-1-yl]-3-(trifluoromethyl)-[1,2,4]triazolo[4,3-b]pyridazine A mixture of 1-(6-bromonaphthalen-2-yl)sulfonylpiperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-(6-bromonaphthalen-2-yl)sulfonylpiperazin-1-yl]-3-(trifluoromethyl)-[1,2,4]triazolo[4,3-b]pyridazine.

1H NMR (700.03 MHz, DMSO-d6) δ 3.16 (4H, t), 3.72 (4H, t), 7.49 (1H, d), 7.81-7.83 (1H, m), 7.84-7.86 (1H, m), 8.16 (1H, d), 8.19 (1H, d), 8.21 (1H, d), 8.39 (1H, d), 8.52 (1H, d); m/z=543 not assigned (Br).

EXAMPLE 28

Preparation of N-[[(9aR)-2-[3-(trifluoromethyl)-[1,2,4]triazolo[4,3-b]pyridazin-6-yl]-1,3,4,6,7,8,9,9a-octahydropyrido[1,6-a]pyrazin-7-yl]methyl]-2-methylquinolin-4-amine A mixture of N-[[(9aR)-2,3,4,6,7,8,9,9a-octahydro-1H-pyrido[1,6-a]pyrazin-7-yl]methyl]-2-methylquinolin-4-amine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give N-[[(9aR)-2-[3-(trifluoromethyl)-[1,2,4]triazolo[4,3-b]pyridazin-6-yl]-1,3,4,6,7,8,9,9a-octahydropyrido[1,6-a]pyrazin-7-yl]methyl]-2-methylquinolin-4-amine.

1H NMR (700.03 MHz, DMSO-d6) δ 1.06-1.10 (1H, m), 1.24-1.26 (1H, m), 1.69-1.71 (1H, m), 1.79 (1H, d), 1.91-1.94 (1H, m), 1.96 (1H, d), 2.09-2.12 (1H, m), 2.17-2.21 (1H, m), 2.47 (3H, s), 2.70 (1H, d), 2.85-2.87 (1H, m), 2.98 (1H, d), 3.02-3.06 (1H, m), 3.15 (2H, t), 4.13 (1H, d), 4.19 (1H, d), 6.37 (1H, s), 7.05 (1H, s), 7.33-7.36 (1H, m), 7.56 (1H, d), 7.62 (1H, d), 7.68-7.69 (1H, m), 8.19 (1H, d), 8.25 (1H, d); m/z=497 [M+H]+.

EXAMPLE 29

Preparation of 6-[4-(2,4-difluorophenyl)piperazin-1-yl]-3-(trifluoromethyl)-[1,2,4]triazolo[4,3-b]pyridazine A mixture of 1-(2,4-difluorophenyl)piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-(2,4-difluorophenyl)piperazin-1-yl]-3-(trifluoromethyl)-[1,2,4]triazolo[4,3-b]pyridazine.

1H NMR (700.03 MHz, DMSO-d6) δ 3.13 (4H, t), 3.78 (4H, t), 7.01-7.04 (1H, m), 7.12-7.16 (1H, m), 7.22-7.25 (1H, m), 7.66 (1H, d), 8.29 (1H, d); m/z=385 [M+H]+.

EXAMPLE 30

Preparation of 6-[4-[3-chloro-5-(trifluoromethyl)pyridin-2-yl]-1,4-diazepan-1-yl]-3-(trifluoromethyl)-[1,2,4]triazolo[4,3-b]pyridazine A mixture of 1-[3-chloro-5-(trifluoromethyl)pyridin-2-yl]-1,4-diazepane and 6-chloro-3-(trifluoromethyl)-[1,2,4]triazolo[4,3-b]pyridazine was allowed to react by General Synthetic Method 3. The crude product was purified by hplc using a Waters XTerra C18 column (5µ silica, 19 mm diameter, 100 mm length) eluted with decreasingly polar mixtures of water (containing 0.1% aqueous ammonia) and acetonitrile as eluents to give 6-[4-[3-chloro-5-(trifluoromethyl)pyridin-2-yl]-1,4-diazepan-1-yl]-3-(trifluoromethyl)-[1,2,4]triazolo[4,3-b]pyridazine.

1H NMR (700.03 MHz, DMSO-d6) δ 2.04 (2H, d), 3.76 (2H, t), 3.80 (2H, t), 3.96 (2H, d), 4.02 (2H, s), 7.52 (1H, d), 7.96 (1H, s), 8.20 (1H, d), 8.29 (1H, d); m/z=466 [M+H]+.

EXAMPLE 31

Preparation of 6-[4-[4-(4-fluorophenyl)-5-(2-methoxypyrimidin-4-yl)imidazol-1-yl]piperidin-1-yl]-3-(trifluoromethyl)-[1,2,4]triazolo[4,3-b]pyridazine A mixture of 4-[5-(4-fluorophenyl)-3-piperidin-4-ylimidazol-4-yl]-2-methoxypyrimidine and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-[4-(4-fluorophenyl)-5-(2-methoxypyrimidin-4-yl)imidazol-1-yl]piperidin-1-yl]-3-(trifluoromethyl)-[1,2,4]triazolo[4,3-b]pyridazine.

1H NMR (700.03 MHz, DMSO-d6) δ 2.07-2.13 (2H, m), 2.19-2.21 (2H, m), 3.13 (2H, d), 3.98 (3H, s), 4.43-4.45 (2H, m), 4.76-4.79 (1H, m), 6.96 (1H, d), 7.16 (2H, d), 7.42-7.44 (2H, m), 7.67 (1H, d), 8.17 (1H, s), 8.29 (1H, d), 8.56 (1H, d); m/z=540 [M+H]+.

EXAMPLE 32

Preparation of 6-[4-(2-methylphenyl)piperazin-1-yl]-3-(trifluoromethyl)-[1,2,4]triazolo[4,3-b]pyridazine A mixture of 1-(2-methylphenyl)piperazine and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-(2-methylphenyl)piperazin-1-yl]-3-(trifluoromethyl)-[1,2,4]triazolo[4,3-b]pyridazine.

1H NMR (700.03 MHz, DMSO-d6) δ 2.32 (3H, s), 3.00 (4H, t), 3.77 (4H, t), 6.99-7.01 (1H, m), 7.06 (1H, d), 7.16-7.18 (1H, m), 7.20 (1H, d), 7.66 (1H, d), 8.28 (1H, d); m/z=363 [M+H]+.

EXAMPLE 33

Preparation of 6-[4-[(2-chlorophenyl)methyl]-1,4-diazepan-1-yl]-3-(trifluoromethyl)-[1,2,4]triazolo[4,3-b]pyridazine A mixture of 1-[(2-chlorophenyl)methyl]-1,4-diazepane and 6-chloro-3-(trifluoromethyl)-[1,2,4]triazolo[4,3-b]pyridazine was allowed to react by General Synthetic Method 3. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-[(2-chlorophenyl)methyl]-1,4-diazepan-1-yl]-3-(trifluoromethyl)-[1,2,4]triazolo[4,3-b]pyridazine.

1H NMR (499.802 MHz, DMSO-d6) δ 1.81-1.92 (2H, m), 2.65-2.70 (2H, m), 2.77-2.83 (2H, m), 3.70 (2H, s), 3.71-3.76 (2H, m), 3.76-3.80 (2H, m), 7.18-7.27 (2H, m), 7.34 (1H, d), 7.41 (1H, d), 7.49 (1H, d), 8.21 (1H, d); m/z=411 [M+H]+.

EXAMPLE 34

Preparation of 1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]butan-1-one A mixture of 1-(2,3,3a,4,6,6a-hexahydro-1H-pyrrolo[3,4-c]pyrrol-5-yl)butan-1-one and 6-chloro-3-(trifluoromethyl)-[1,2,4]triazolo[4,3-b]pyridazine was allowed to react by General Synthetic Method 3. The crude product was purified by hplc using a Waters XBridge Prep C18 OBD column (5μ silica, 19 mm diameter, 100 mm length) eluted with decreasingly polar mixtures of water (containing 0.2% aqueous ammonia) and acetonitrile as eluents to give 1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]butan-1-one.

1H NMR (300.132 MHz, DMSO-d6) δ 0.88 (3H, t), 1.51 (2H, sextet), 2.16-2.25 (2H, m), 2.94-3.19 (2H, m), 3.25-3.34 (1H, m), 3.35-3.50 (3H, m), 3.54-3.64 (1H, m), 3.66-3.83 (3H, m), 7.24 (1H, d), 8.22 (1H, d) (Signal at 3.3 partially obscured by water); m/z=369 [M+H]+.

EXAMPLE 35

Preparation of tert-butyl (1S,5R)-3-[3-(trifluoromethyl)-[1,2,4]triazolo[4,3-b]pyridazin-6-yl]-3,8-diazabicyclo[3.2.1]octane-8-carboxylate A mixture of tert-butyl (1S,5R)-3,8-diazabicyclo[3.2.1]octane-8-carboxylate and 6-chloro-3-(trifluoromethyl)-[1,2,4]triazolo[4,3-b]pyridazine was allowed to react by General Synthetic Method 3. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give tert-butyl (1S,5R)-3-[3-(trifluoromethyl)-[1,2,4]triazolo[4,3-b]pyridazin-6-yl]-3,8-diazabicyclo[3.2.1]octane-8-carboxylate.

1H NMR (300.132 MHz, DMSO-d6) δ 1.37 (9H, s), 1.59-1.69 (2H, m), 1.76-1.89 (2H, m), 3.00-3.10 (2H, m), 3.84-3.95 (2H, m), 4.18-4.25 (2H, m), 7.47 (1H, d), 8.20 (1H, d); m/z=399 [M+H]+.

EXAMPLE 36

Preparation of 6-[4-(3-methylphenyl)piperazin-1-yl]-3-(trifluoromethyl)-[1,2,4]triazolo[4,3-b]pyridazine A mixture of 1-(3-methylphenyl)piperazine dihydrochloride and 6-chloro-3-(trifluoromethyl)-[1,2,4]triazolo[4,3-b]pyridazine was allowed to react by General Synthetic Method 4. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-(3-methylphenyl)piperazin-1-yl]-3-(trifluoromethyl)-[1,2,4]triazolo[4,3-b]pyridazine.

1H NMR (700.03 MHz, DMSO-d6) δ 2.28 (3H, s), 3.76 (4H, t), 6.65 (1H, d), 6.80-6.81 (1H, m), 6.83 (1H, s), 7.13 (1H, t), 7.67 (1H, d), 8.29 (1H, d) (Some peaks obscured by solvent); m/z=363 [M+H]+.

EXAMPLE 37

Preparation of 6-[4-(2-chlorophenyl)piperazin-1-yl]-3-(trifluoromethyl)-[1,2,4]triazolo[4,3-b]pyridazine A mixture of 1-(2-chlorophenyl)piperazine hydrate hydrochloride and 6-chloro-3-(trifluoromethyl)-[1,2,4]triazolo[4,3-b]pyridazine was allowed to react by General Synthetic Method 4. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-(2-chlorophenyl)piperazin-1-yl]-3-(trifluoromethyl)-[1,2,4]triazolo[4,3-b]pyridazine.

1H NMR (700.03 MHz, DMSO-d6) δ 3.15 (4H, t), 3.79 (4H, t), 7.08-7.11 (1H, m), 7.21-7.22 (1H, m), 7.32-7.35 (1H, m), 7.45-7.47 (1H, m), 7.67 (1H, d), 8.30 (1H, d); m/z=383 [M+H]+.

EXAMPLE 38

Preparation of 6-[4-(6-chloronaphthalen-2-yl)sulfonylpiperazin-1-yl]-3-(trifluoromethyl)-[1,2,4]triazolo[4,3-b]pyridazine A mixture of 1-(6-chloronaphthalen-2-yl)sulfonylpiperazine hydrochloride and 6-chloro-3-(trifluoromethyl)-[1,2,4]triazolo[4,3-b]pyridazine was allowed to react by General Synthetic Method 4. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 6-[4-(6-chloronaphthalen-2-yl)sulfonylpiperazin-1-yl]-3-(trifluoromethyl)-[1,2,4]triazolo[4,3-b]pyridazine.

1H NMR (700.03 MHz, DMSO-d6) δ 3.16 (4H, t), 3.72 (4H, t), 7.49 (1H, d), 7.71-7.72 (1H, m), 7.85-7.86 (1H, m), 8.16 (1H, d), 8.21 (1H, d), 8.23 (1H, d), 8.27 (1H, d), 8.53 (1H, d); m/z=497 [M+H]+.

EXAMPLE 39

Preparation of 1-[1-[3-(trifluoromethyl)-[1,2,4]triazolo[4,3-b]pyridazin-6-yl]piperidin-4-yl]-4H-3,1-benzoxazin-2-one A mixture of 1-piperidin-4-yl-4H-3,1-benzoxazin-2-one hydrochloride and 6-chloro-3-(trifluoromethyl)-[1,2,4]triazolo[4,3-b]pyridazine was allowed to react by General Synthetic Method 4. The crude product was purified by hplc using a Waters XTerra C18 column (5μ silica, 19 mm diameter, 100 mm length) eluted with decreasingly polar mixtures of water (containing 0.1% aqueous ammonia) and acetonitrile as eluents to give 1-[1-[3-(trifluoromethyl)-[1,2,4]triazolo[4,3-b]pyridazin-6-yl]piperidin-4-yl]-4H-3,1-benzoxazin-2-one.

1H NMR (700.03 MHz, DMSO-d6) δ 1.95-1.97 (2H, m), 2.53-2.57 (2H, m), 3.22 (1H, d), 4.25-4.28 (1H, m), 4.41-4.43 (2H, m), 5.16 (2H, s), 7.12-7.15 (1H, m), 7.30-7.31 (1H, m), 7.37 (1H, d), 7.39-7.41 (1H, m), 7.67 (1H, d), 8.26 (1H, d) (Some peaks obscured by solvent); m/z=419 [M+H]+.

EXAMPLE 40

Preparation of 1-[1-[3-(trifluoromethyl)-[1,2,4]triazolo[4,3-b]pyridazin-6-yl]piperidin-4-yl]-3,4-dihydroquinolin-2-one A mixture of 1-piperidin-4-yl-3,4-dihydroquinolin-2-one hydrochloride and 6-chloro-3-(trifluoromethyl)-[1,2,4]triazolo[4,3-b]pyridazine was allowed to react by General Synthetic Method 4. The crude product was purified by hplc using a Phenomenex Luna C18 100A column (10μ silica, 21 mm diameter, 150 mm length) eluted with decreasingly polar mixtures of water (containing 0.1% aqueous ammonia) and acetonitrile as eluents to give 1-[1-[3-(trifluoromethyl)-[1,2,4]triazolo[4,3-b]pyridazin-6-yl]piperidin-4-yl]-3,4-dihydroquinolin-2-one.

1H NMR (700.03 MHz, DMSO-d6) δ 1.83-1.85 (2H, m), 2.43-2.45 (2H, m), 2.61-2.67 (2H, m), 2.80 (2H, t), 3.15-3.18 (2H, m), 4.32-4.36 (1H, m), 4.39-4.41 (2H, m), 7.01-7.03 (1H, m), 7.23-7.26 (2H, m), 7.31 (1H, d), 7.66 (1H, d), 8.26 (1H, d); m/z=417 [M+H]+.

EXAMPLE 41

Preparation of 6-(5-benzyl-2,5-diazabicyclo[2.2.1]heptan-2-yl)-3-(trifluoromethyl)-[1,2,4]triazolo[4,3-b]pyridazine A mixture of (1R,4R)-6-benzyl-3,6-diazabicyclo[2.2.1]heptane dihydrobromide and 6-chloro-3-(trifluoromethyl)-[1,2,4]triazolo[4,3-b]pyridazine was allowed to react by General Synthetic Method 4. The crude product was purified by hplc using a Waters XBridge Prep C18 OBD column (5μ silica, 19 mm diameter, 100 mm length) eluted with decreasingly polar mixtures of water (containing 0.2% aqueous ammonia) and acetonitrile as eluents to give 6-(5-benzyl-2,5-diazabicyclo[2.2.1]heptan-2-yl)-3-(trifluoromethyl)-[1,2,4]triazolo[4,3-b]pyridazine.

1H NMR (700.03 MHz, DMSO-d6) δ 1.83-1.84 (1H, m), 2.00 (1H, d), 2.88 (1H, d), 3.63 (2H, s), 3.73 (2H, s), 7.23 (1H, d), 7.29-7.31 (2H, m), 7.32 (3H, t), 8.21 (1H, d) (Some peaks obscured by solvent); m/z=375 [M+H]+.

EXAMPLE 42

Preparation of 6-[4-(pyridin-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with pyridine-2-carbaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-(pyridin-2-ylmethyl)piperazin-1-yl]-3-(trifluoromethyl)-[1,2,4]triazolo[4,3-b]pyridazine.

1H NMR (499.802 MHz, DMSO-d6) δ 2.55-2.62 (4H, m), 3.61-3.66 (4H, m), 3.68 (2H, s), 7.26-7.32 (1H, m), 7.49 (1H, d), 7.59 (1H, d), 7.76-7.82 (1H, m), 8.25 (1H, d), 8.52 (1H, d); m/z=364 [M+H]+.

EXAMPLE 43

Preparation of 3-[[4-[3-(trifluoromethyl)-[1,2,4]triazolo[4,3-b]pyridazin-6-yl]piperazin-1-yl]methyl]benzonitrile Reductive amination of 6-(piperazin-1-yl)-3-(trifluoromethyl)-[1,2,4]triazolo[4,3-b]pyridazine with 3-formylbenzonitrile was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 3-[[4-[3-(trifluoromethyl)-[1,2,4]triazolo[4,3-b]pyridazin-6-yl]piperazin-1-yl]methyl]benzonitrile.

1H NMR (499.802 MHz, DMSO-d6) δ 2.51-2.57 (4H, m), 3.60-3.66 (6H, m), 7.54-7.62 (2H, m), 7.71 (1H, d), 7.76 (1H, d), 7.79 (1H, s), 8.26 (1H, d) (Signal at 2.5 partially obscured by DMSO); m/z=388 [M+H]+.

EXAMPLE 44

Preparation of 4-[[4-[3-(trifluoromethyl)-[1,2,4]triazolo[4,3-b]pyridazin-6-yl]piperazin-1-yl]methyl]benzonitrile Reductive amination of 6-(piperazin-1-yl)-3-(trifluoromethyl)-[1,2,4]triazolo[4,3-b]pyridazine with 4-formylbenzonitrile was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 4-[[4-[3-(trifluoromethyl)-[1,2,4]triazolo[4,3-b]pyridazin-6-yl]piperazin-1-yl]methyl]benzonitrile.

1H NMR (499.802 MHz, DMSO-d6) δ 2.51-2.56 (4H, m), 3.59-3.68 (6H, m), 7.53-7.62 (3H, m), 7.82 (2H, d), 8.26 (1H, d) (Signal at 2.5 partially obscured by DMSO); m/z=388 [M+H]+.

EXAMPLE 45

Preparation of 6-[4-[(4-fluorophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-fluorobenzaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-[(4-fluorophenyl)methyl]piperazin-1-yl]-3-(trifluoromethyl)-[1,2,4]triazolo[4,3-b]pyridazine.

1H NMR (499.802 MHz, DMSO-d6) δ 2.48-2.52 (4H, m), 3.53 (2H, s), 3.58-3.66 (4H, m), 7.17 (2H, t), 7.34-7.41 (2H, m), 7.58 (1H, d), 8.25 (1H, d) (Signal at 2.5 partially obscured by DMSO); m/z=381 [M+H]+.

EXAMPLE 46

Preparation of 6-[4-[(2-methylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2-methylbenzaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-[(2-methylphenyl)methyl]piperazin-1-yl]-3-(trifluoromethyl)-[1,2,4]triazolo[4,3-b]pyridazine.

1H NMR (499.802 MHz, DMSO-d6) δ 2.33 (3H, s), 2.49-2.53 (4H, m), 3.48 (2H, s), 3.56-3.61 (4H, m), 7.12-7.18 (3H, m), 7.25 (1H, d), 7.57 (1H, d), 8.23 (1H, d) (Signal at 2.5 partially obscured by DMSO); m/z=377 [M+H]+.

EXAMPLE 47

Preparation of 6-[4-[(4-methylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-methylbenzaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-[(4-methylphenyl)methyl]piperazin-1-yl]-3-(trifluoromethyl)-[1,2,4]triazolo[4,3-b]pyridazine.

1H NMR (499.802 MHz, DMSO-d6) δ 2.30 (3H, s), 2.45-2.51 (4H, m), 3.50 (2H, s), 3.56-3.65 (4H, m), 7.15 (2H, d), 7.22 (2H, d), 7.58 (1H, d), 8.24 (1H, d) (Signal at 2.5 partially obscured by DMSO); m/z=377 [M+H]+.

EXAMPLE 48

Preparation of 6-[4-(1,3-benzothiazol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-benzothiazole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1,3-benzothiazol-2-ylmethyl)piperazin-1-yl]-3-(trifluoromethyl)-[1,2,4]triazolo[4,3-b]pyridazine.

1H NMR (499.802 MHz, DMSO) δ 2.73 (4H, t), 3.66 (4H, t), 4.04 (2H, s), 7.40-7.43 (1H, m), 7.46-7.51 (1H, m), 7.60 (1H, d), 7.94 (1H, d), 8.06 (1H, d), 8.25 (1H, d); m/z=420 [M+H]+.

EXAMPLE 49

Preparation of 6-[4-(1,3-benzoxazol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-benzoxazole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1,3-benzoxazol-2-ylmethyl)piperazin-1-yl]-3-(trifluoromethyl)-[1,2,4]triazolo[4,3-b]pyridazine.

1H NMR (499.802 MHz, DMSO) δ 2.72 (4H, t), 3.65 (4H, t), 3.97 (2H, s), 7.36-7.44 (2H, m), 7.59 (1H, d), 7.72-7.77 (2H, m), 8.25 (1H, d); m/z=404 [M+H]+.

EXAMPLE 50

Preparation of 4-[[4-[3-(trifluoromethyl)-[1,2,4]triazolo[4,3-b]pyridazin-6-yl]piperazin-1-yl]methyl]quinoline Reductive amination of 6-(piperazin-1-yl)-3-(trifluoromethyl)-[1,2,4]triazolo[4,3-b]pyridazine with quinoline-4-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 4-[[4-[3-(trifluoromethyl)-[1,2,4]triazolo[4,3-b]pyridazin-6-yl]piperazin-1-yl]methyl]quinoline.
1H NMR (499.802 MHz, DMSO) δ 2.65 (4H, t), 3.64 (4H, t), 4.04 (2H, s), 7.56 1H, d), 7.60 (1H, d), 7.63-7.67 (1H, m), 7.75-7.80 (1H, m), 8.05 (1H, d), 8.26 (1H, d), 8.33 (1H, d), 8.88 (1H, d); m/z=414 [M+H]+.

EXAMPLE 51

Preparation of 6-[4-(1,3-thiazol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-thiazole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1,3-thiazol-2-ylmethyl)piperazin-1-yl]-3-(trifluoromethyl)-[1,2,4]triazolo[4,3-b]pyridazine.
1H NMR (499.802 MHz, DMSO) δ 2.64 (4H, t), 3.63 (4H, t), 3.91 (2H, s), 7.58 (1H, d), 7.67 (1H, d), 7.73 (1H, d), 8.24 (1H, d); m/z=370 [M+H]+.

EXAMPLE 52

Preparation of 6-[4-(1-benzothiophen-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-benzothiophene-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1-benzothiophen-2-ylmethyl)piperazin-1-yl]-3-(trifluoromethyl)-[1,2,4]triazolo[4,3-b]pyridazine.
1H NMR (499.802 MHz, DMSO) δ 2.62 (4H, t), 3.65 (4H, t), 3.88 (2H, s), 7.30-7.38 (3H, m), 7.60 (1H, d), 7.78 (1H, d), 7.91 (1H, d), 8.25 (1H, d); m/z=419 [M+H]+.

EXAMPLE 53

Preparation of 6-[4-(thiadiazol-4-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with thiadiazole-4-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(thiadiazol-4-ylmethyl)piperazin-1-yl]-3-(trifluoromethyl)-[1,2,4]triazolo[4,3-b]pyridazine.
1H NMR (499.802 MHz, DMSO) δ 2.62 (4H, t), 3.63 (4H, t), 4.13 (2H, s), 7.59 (1H, d), 8.25 (1H, d), 9.10 (1H, s); m/z=371 [M+H]+.

EXAMPLE 54

Preparation of 6-[4-[(1-methylbenzimidazol-2-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-methylbenzimidazole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(1-methylbenzimidazol-2-yl)methyl]piperazin-1-yl]-3-(trifluoromethyl)-[1,2,4]triazolo[4,3-b]pyridazine.
1H NMR (499.802 MHz, DMSO) δ 2.62 (4H, t), 3.62 (4H, t), 3.85-3.89 (5H, m), 7.16-7.22 (1H, m), 7.22-7.28 (1H, m), 7.54 (1H, d), 7.57-7.62 (2H, m), 8.25 (1H, d); m/z=417 [M+H]+.

EXAMPLE 55

Preparation of 6-[4-(pyrazin-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with pyrazine-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(pyrazin-2-ylmethyl)piperazin-1-yl]-3-(trifluoromethyl)-[1,2,4]triazolo[4,3-b]pyridazine.
1H NMR (499.802 MHz, DMSO) δ 2.61 (4H, t), 3.64 (4H, t), 3.75 (2H, s), 7.60 (1H, d), 8.26 (1H, d), 8.57 (1H, d), 8.60-8.62 (1H, m), 8.74 (1H, d); m/z=365 [M+H]+.

EXAMPLE 56

Preparation of 2-[[4-[3-(trifluoromethyl)-[1,2,4]triazolo[4,3-b]pyridazin-6-yl]piperazin-1-yl]methyl]quinoline Reductive amination of 6-(piperazin-1-yl)-3-(trifluoromethyl)-[1,2,4]triazolo[4,3-b]pyridazine with quinoline-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 2-[[4-[3-(trifluoromethyl)-[1,2,4]triazolo[4,3-b]pyridazin-6-yl]piperazin-1-yl]methyl]quinoline.

1H NMR (499.802 MHz, DMSO) δ 2.61 (4H, t), 3.63 (4H, t), 3.83 (2H, s), 7.55-7.60 (2H, m), 7.67 (1H, d), 7.71-7.76 (1H, m), 7.96 (2H, t), 8.23 (1H, d), 8.34 (1H, d); m/z=414 [M+H]+.

EXAMPLE 57

Preparation of 6-[4-[(2-methylsulfonylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2-methylsulfonylbenzaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-[(2-methylsulfonylphenyl)methyl]piperazin-1-yl]-3-(trifluoromethyl)-[1,2,4]triazolo[4,3-b]pyridazine.

1H NMR (499.802 MHz, DMSO) δ 2.60 (4H, t), 3.44 (3H, s), 3.62 (4H, t), 3.96 (2H, s), 7.58-7.67 (3H, m), 7.70-7.75 (1H, m), 7.99-8.02 (1H, m), 8.27 (1H, d); m/z=441 [M+H]+.

EXAMPLE 58

Preparation of 6-[[4-[3-(trifluoromethyl)-[1,2,4]triazolo[4,3-b]pyridazin-6-yl]piperazin-1-yl]methyl]quinoxaline Reductive amination of 6-(piperazin-1-yl)-3-(trifluoromethyl)-[1,2,4]triazolo[4,3-b]pyridazine with quinoxaline-6-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[[4-[3-(trifluoromethyl)-[1,2,4]triazolo[4,3-b]pyridazin-6-yl]piperazin-1-yl]methyl]quinoxaline.

1H NMR (499.802 MHz, DMSO) δ 2.59 (4H, t), 3.63 (4H, t), 3.81 (2H, s), 7.57 (1H, d), 7.86-7.89 (1H, m), 8.02 (1H, s), 8.07 (1H, d), 8.23 (1H, d), 8.91 (1H, d), 8.93 (1H, d); m/z=415 [M+H]+.

EXAMPLE 59

Preparation of 2-[[4-[3-(trifluoromethyl)-[1,2,4]triazolo[4,3-b]pyridazin-6-yl]piperazin-1-yl]methyl]benzonitrile Reductive amination of 6-(piperazin-1-yl)-3-(trifluoromethyl)-[1,2,4]triazolo[4,3-b]pyridazine with 2-formylbenzonitrile was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 2-[[4-[3-(trifluoromethyl)-[1,2,4]triazolo[4,3-b]pyridazin-6-yl]piperazin-1-yl]methyl]benzonitrile.

1H NMR (499.802 MHz, DMSO) δ 2.59 (4H, t), 3.63 (4H, t), 3.74 (2H, s), 7.50 (1H, t), 7.60 (1H, d), 7.64 (1H, d), 7.69-7.74 (1H, m), 7.84 (1H, d), 8.26 (1H, d); m/z=388 [M+H]+.

EXAMPLE 60

Preparation of 6-[4-(1-benzothiophen-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-benzothiophene-3-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(1-benzothiophen-3-ylmethyl)piperazin-1-yl]-3-(trifluoromethyl)-[1,2,4]triazolo[4,3-b]pyridazine.

1H NMR (499.802 MHz, DMSO) δ 2.59 (4H, t), 3.62 (4H, t), 3.81 (2H, s), 7.36-7.44 (2H, m), 7.58 (1H, d), 7.63 (1H, s), 7.99 (1H, d), 8.03 (1H, d), 8.25 (1H, d); m/z=419 [M+H]+.

EXAMPLE 61

Preparation of 6-[4-(1,3-thiazol-4-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-thiazole-4-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(1,3-thiazol-4-ylmethyl)piperazin-1-yl]-3-(trifluoromethyl)-[1,2,4]triazolo[4,3-b]pyridazine.

1H NMR (499.802 MHz, DMSO) δ 2.59 (4H, t), 3.62 (4H, t), 3.75 (2H, s), 7.56-7.61 (2H, m), 8.25 (1H, d), 9.06 (1H, d); m/z=370 [M+H]+.

EXAMPLE 62

Preparation of 6-[4-[(2-chlorophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2-chlorobenzaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-[(2-chlorophenyl)methyl]piperazin-1-yl]-3-(trifluoromethyl)-[1,2,4]triazolo[4,3-b]pyridazine.

1H NMR (499.802 MHz, DMSO) δ 2.59 (4H, t), 3.61-3.67 (6H, m), 7.30-7.34 (1H, m), 7.34-7.39 (1H, m), 7.44-7.47 (1H, m), 7.53-7.57 (1H, m), 7.60 (1H, d), 8.26 (1H, d); m/z=397 [M+H]+.

EXAMPLE 63

Preparation of 6-[4-(1H-indol-7-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-indole-7-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1H-indol-7-ylmethyl)piperazin-1-yl]-3-(trifluoromethyl)-[1,2,4]triazolo[4,3-b]pyridazine.

1H NMR (499.802 MHz, DMSO) δ 2.58 (4H, t), 3.64 (4H, t), 3.82 (2H, s), 6.44-6.46 (1H, m), 6.94-7.03 (2H, m), 7.33 (1H, t), 7.48 (1H, d), 7.58 (1H, d), 8.25 (1H, d), 10.84 (1H, s); m/z=402 [M+H]+.

EXAMPLE 64

Preparation of 3-[[4-[3-(trifluoromethyl)[1,2,4]triazolo[4,3-b]pyridazin-6-yl]piperazin-1-yl]methyl]quinoline Reductive amination of 6-(piperazin-1-yl)-3-(trifluoromethyl)-[1,2,4]triazolo[4,3-b]pyridazine with quinoline-3-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 3-[[4-[3-(trifluoromethyl)-[1,2,4]triazolo[4,3-b]pyridazin-6-yl]piperazin-1-yl]methyl]quinoline.

1H NMR (499.802 MHz, DMSO) δ 2.58 (4H, t), 3.63 (4H, t), 3.76 (2H, s), 7.55-7.62 (2H, m), 7.71-7.76 (1H, m), 7.97 (1H, d), 8.01 (1H, d), 8.21-8.26 (2H, m), 8.88 (1H, d); m/z=414 [M+H]+.

EXAMPLE 65

Preparation of 5-[[4-[3-(trifluoromethyl)-[1,2,4]triazolo[4,3-b]pyridazin-6-yl]piperazin-1-yl]methyl]isoquinoline Reductive amination of 6-(piperazin-1-yl)-3-(trifluoromethyl)-[1,2,4]triazolo[4,3-b]pyridazine with isoquinoline-5-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 5-[[4-[3-(trifluoromethyl)-[1,2,4]triazolo[4,3-b]pyridazin-6-yl]piperazin-1-yl]methyl]isoquinoline.

1H NMR (499.802 MHz, DMSO) δ 2.58 (4H, t), 3.58 (4H, t), 3.95 (2H, s), 7.56 (1H, d), 7.61-7.66 (1H, m), 7.74 (1H, d), 8.06 (1H, d), 8.13 (1H, d), 8.23 (1H, d), 8.53 (1H, d), 9.31 (1H, s); m/z=414 [M+H]+.

EXAMPLE 66

Preparation of 6-[4-(naphthalen-1-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with naphthalene-1-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(naphthalen-1-ylmethyl)piperazin-1-yl]-3-(trifluoromethyl)-[1,2,4]triazolo[4,3-b]pyridazine.

1H NMR (499.802 MHz, DMSO) δ 2.58 (4H, t), 3.58 (4H, t), 3.94 (2H, s), 7.43-7.58 (5H, m), 7.83-7.88 (1H, m), 7.90-7.94 (1H, m), 8.23 (1H, d), 8.29 (1H, d); m/z=413 [M+H]+.

EXAMPLE 67

Preparation of 3-(trifluoromethyl)-6-[4-[[2-(trifluoromethyl)phenyl]methyl]piperazin-1-yl]-[1,2,4]triazolo[4,3-b]pyridazine Reductive amination of 6-(piperazin-1-yl)-3-(trifluoromethyl)-[1,2,4]triazolo[4,3-b]pyridazine with 2-(trifluoromethyl)benzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 3-(trifluoromethyl)-6-[4-[[2-(trifluoromethyl)phenyl]methyl]piperazin-1-yl]-[1,2,4]triazolo[4,3-b]pyridazine.

1H NMR (499.802 MHz, DMSO) δ 2.56 (4H, t), 3.64 (4H, t), 3.71 (2H, s), 7.50 (1H, t), 7.60 (1H, d), 7.67-7.75 (2H, m), 7.84 (1H, d), 8.26 (1H, d); m/z=431 [M+H]+.

EXAMPLE 68

Preparation of 6-[4-[(2,2-difluoro-1,3-benzodioxol-4-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2,2-difluoro-1,3-benzodioxole-4-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(2,2-difluoro-1,3-benzodioxol-4-yl)methyl]piperazin-1-yl]-3-(trifluoromethyl)-[1,2,4]triazolo[4,3-b]pyridazine.

1H NMR (499.802 MHz, DMSO) δ 2.56 (4H, t), 3.62 (4H, t), 3.67 (2H, s), 7.19-7.25 (2H, m), 7.32-7.35 (1H, m), 7.59 (1H, d), 8.25 (1H, d); m/z=443 [M+H]+.

EXAMPLE 69

Preparation of 6-[4-[(1-methylindol-2-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-methylindole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(1-methylindol-2-yl)methyl]piperazin-1-yl]-3-(trifluoromethyl)-[1,2,4]triazolo[4,3-b]pyridazine.

1H NMR (499.802 MHz, DMSO) δ 2.56 (4H, t), 3.59 (4H, t), 3.70 (2H, s), 3.78 (3H, s), 6.36 (1H, s), 6.99 (1H, t), 7.09-7.13 (1H, m), 7.40 (1H, d), 7.48 (1H, d), 7.57 (1H, d), 8.23 (1H, d); m/z=416 [M+H]+.

EXAMPLE 70

Preparation of 6-[4-(thiophen-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with thiophene-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(thiophen-2-ylmethyl)piperazin-1-yl]-3-(trifluoromethyl)-[1,2,4]triazolo[4,3-b]pyridazine.

1H NMR (499.802 MHz, DMSO) δ 2.55 (4H, t), 3.62 (4H, t), 3.77 (2H, s), 6.98-7.02 (2H, m), 7.45-7.47 (1H, m), 7.59 (1H, d), 8.25 (1H, d); m/z=369 [M+H]+.

EXAMPLE 71

Preparation of 6-[4-[(1-methylindol-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-methylindole-3-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(1-methylindol-3-yl)methyl]piperazin-1-yl]-3-(trifluoromethyl)-[1,2,4]triazolo[4,3-b]pyridazine.

1H NMR (499.802 MHz, DMSO) δ 2.55 (4H, t), 3.60 (4H, t), 3.70 (2H, s), 3.77 (3H, s), 7.04 (1H, t), 7.15 (1H, t), 7.26 (1H, s), 7.40 (1H, d), 7.56 (1H, d), 7.67 (1H, d), 8.23 (1H, d) (Signal at 2.55 partially under DMSO); m/z=416 [M+H]+.

EXAMPLE 72

Preparation of 6-[4-[(2-fluorophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2-fluorobenzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(2-fluorophenyl)methyl]piperazin-1-yl]-3-(trifluoromethyl)-[1,2,4]triazolo[4,3-b]pyridazine.

1H NMR (499.802 MHz, DMSO) δ 2.55 (4H, t), 3.59-3.65 (6H, m), 7.16-7.23 (2H, m), 7.32-7.38 (1H, m), 7.43-7.48 (1H, m), 7.58 (1H, d), 8.25 (1H, d) (Signal at 2.55 partially under DMSO); m/z=381 [M+H]+.

EXAMPLE 73

Preparation of 6-[4-(pyridin-4-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with pyridine-4-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(pyridin-4-ylmethyl)piperazin-1-yl]-3-(trifluoromethyl)-[1,2,4]triazolo[4,3-b]pyridazine.

1H NMR (499.802 MHz, DMSO) δ 2.54 4H, t), 3.60 (2H, s), 3.64 (4H, t), 7.37 (2H, m), 7.59 (1H, d), 8.26 (1H, d), 8.52-8.55 (2H, m) (Signal at 2.54 partially obscured by DMSO); m/z=364 [M+H]+.

EXAMPLE 74

Preparation of 6-[4-[(3-methylsulfonylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-methylsulfonylbenzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(3-methylsulfonylphenyl)methyl]piperazin-1-yl]-3-(trifluoromethyl)-[1,2,4]triazolo[4,3-b]pyridazine.

1H NMR (499.802 MHz, DMSO) δ 2.53 (4H, t), 3.21 (3H, s), 3.62 (4H, t), 3.66 (2H, s), 7.57 (1H, d), 7.63 (1H, t), 7.69 (1H, d), 7.83 (1H, d), 7.88 (1H, s), 8.24 (1H, d); m/z=441 [M+H]+.

EXAMPLE 75

Preparation of 6-[4-[(2-methoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2-methoxybenzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(2-methoxyphenyl)methyl]piperazin-1-yl]-3-(trifluoromethyl)-[1,2,4]triazolo[4,3-b]pyridazine.

1H NMR (499.802 MHz, DMSO) δ 2.52 (4H, t), 3.53 (2H, s), 3.60 (4H, t), 3.77 (3H, s), 6.90-6.95 (1H, m), 6.98 (1H, d), 7.21-7.26 (1H, m), 7.31-7.35 (1H, m), 7.56 (1H, d), 8.22 (1H, d); m/z=393 [M+H]+.

EXAMPLE 76

Preparation of 6-[4-(2,3-dihydro-1,4-benzodioxin-5-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2,3-dihydro-1,4-benzodioxine-5-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(2,3-dihydro-1,4-benzodioxin-5-ylmethyl)piperazin-1-yl]-3-(trifluoromethyl)-[1,2,4]triazolo[4,3-b]pyridazine.

1H NMR (499.802 MHz, DMSO) δ 2.52 (4H, t), 3.50 (2H, s), 3.59 (4H, t), 4.19-4.25 (4H, m), 6.73-6.80 (2H, m), 6.87-6.89 (1H, m), 7.56 (1H, d), 8.22 (1H, d); m/z=421 [M+H]+.

EXAMPLE 77

Preparation of 6-[4-(1H-indol-5-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-indole-5-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(1H-indol-5-ylmethyl)piperazin-1-yl]-3-(trifluoromethyl)-[1,2,4]triazolo[4,3-b]pyridazine.

1H NMR (499.802 MHz, DMSO) δ 2.52-2.54 (4H, m), 3.58-3.63 (6H, m), 6.38-6.41 (1H, m), 7.06-7.10 (1H, m), 7.32 (1H, t), 7.35 (1H, d), 7.47 (1H, s), 7.58 (1H, d), 8.24 (1H, d), 11.02 (1H, s) (Signal at 2.52 under DMSO); m/z=402 [M+H]+.

EXAMPLE 78

Preparation of 6-[4-(1H-indol-6-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-indole-6-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(1H-indol-6-ylmethyl)piperazin-1-yl]-3-(trifluoromethyl)-[1,2,4]triazolo[4,3-b]pyridazine.

1H NMR (499.802 MHz, DMSO) δ 2.51-2.55 (4H, m), 3.60-3.64 (6H, m), 6.38-6.41 (1H, m), 6.96-7.00 (1H, m), 7.31 (1H, t), 7.35 (1H, s), 7.49 (1H, d), 7.58 (1H, d), 8.24 (1H, d), 10.99 (1H, s) (Signal at 2.51 under DMSO); m/z=402 [M+H]+.

EXAMPLE 79

Preparation of 6-[4-(furan-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with furan-2-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(furan-2-ylmethyl)piperazin-1-yl]-3-(trifluoromethyl)-[1,2,4]triazolo[4,3-b]pyridazine.

1H NMR (499.802 MHz, DMSO) δ 2.51-2.55 (4H, m), 3.58 (2H, s), 3.61 (4H, t), 6.33 (1H, d), 6.40-6.44 (1H, m), 7.58 (1H, d), 7.60-7.62 (1H, m), 8.25 (1H, d) (Signal at 2.51 partially obscured by DMSO); m/z=353 [M+H]+.

EXAMPLE 80

Preparation of 6-[4-(1H-pyrazol-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-pyrazole-3-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(1H-pyrazol-3-ylmethyl)piperazin-1-yl]-3-(trifluoromethyl)-[1,2,4]triazolo[4,3-b]pyridazine.

1H NMR (499.802 MHz, DMSO) δ 2.51-2.54 (4H, m), 3.51-3.65 (6H, m), 6.18 (1H, s), 7.41 (0H, s), 7.55-7.70 (2H, m), 8.24 (1H, d) (Signal at 2.51 obscured by DMSO); m/z=353 [M+H]+.

EXAMPLE 81

Preparation of 6-[4-(pyridin-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with pyridine-3-carbaldehyde was carried out according to General Synthetic Method 5. The crude product was purified by hplc using a Waters XBridge Prep C18 OBD column (5µ silica, 19 mm diameter, 100 mm length) eluted with decreasingly polar mixtures of water (containing 1% aqueous ammonia) and acetonitrile as eluents to give 6-[4-(pyridin-3-ylmethyl)piperazin-1-yl]-3-(trifluoromethyl)-[1,2,4]triazolo[4,3-b]pyridazine.

1H NMR (499.802 MHz, DMSO) δ 2.50-2.53 (4H, m), 3.57 (2H, s), 3.60 (4H, t), 7.34-7.39 (1H, m), 7.57 (1H, d), 7.71-7.76 (1H, m), 8.23 (1H, d), 8.46-8.49 (1H, m), 8.52 (1H, d) (Signal at 2.5 obscured by DMSO peak); m/z=364 [M+H]+.

EXAMPLE 82

Preparation of 6-[4-[(3-methoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-methoxybenzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(3-methoxyphenyl)methyl]piperazin-1-yl]-3-(trifluoromethyl)-[1,2,4]triazolo[4,3-b]pyridazine.

1H NMR (499.802 MHz, DMSO) δ 2.49-2.51 (4H, m), 3.50 (2H, s), 3.60 (4H, t), 3.74 (3H, s), 6.81-6.84 (1H, m), 6.87-6.91 (2H, m), 7.24 (1H, t), 7.56 (1H, d), 8.23 (1H, d) (Signal at 2.49 obscured by DMSO); m/z=393 [M+H]+.

EXAMPLE 83

Preparation of 6-[4-(1H-pyrrol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-pyrrole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1H-pyrrol-2-ylmethyl)piperazin-1-yl]-3-(trifluoromethyl)-[1,2,4]triazolo[4,3-b]pyridazine.

1H NMR (499.802 MHz, DMSO) δ 2.48 (4H, t), 3.48 (2H, s), 3.60 (4H, t), 5.89-5.92 (1H, m), 5.94 (1H, q), 6.64-6.67 (1H, m), 7.58 (1H, d), 8.24 (1H, d), 10.68 (1H, s) (Signal at 2.48 partially obscured by DMSO); m/z=352 [M+H]+.

EXAMPLE 84

Preparation of 6-[4-(2,3-dihydro-1-benzofuran-5-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2,3-dihydro-1-benzofuran-5-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(2,3-dihydro-1-benzofuran-5-ylmethyl)piperazin-1-yl]-3-(trifluoromethyl)-[1,2,4]triazolo[4,3-b]pyridazine.

1H NMR (499.802 MHz, DMSO) δ 2.47-2.51 (4H, m), 3.17 (2H, t), 3.45 (2H, s), 3.60 (4H, t), 4.51 (2H, t), 6.71 (1H, d), 7.02 (1H, d), 7.19 (1H, s), 7.58 (1H, d), 8.25 (1H, d) (Signal at 2.47 partially obscured by DMSO); m/z=405 [M+H]+.

EXAMPLE 85

Preparation of 6-[4-(1,3-benzodioxol-5-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-benzodioxole-5-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(1,3-benzodioxol-5-ylmethyl)piperazin-1-yl]-3-(trifluoromethyl)-[1,2,4]triazolo[4,3-b]pyridazine.

1H NMR (499.802 MHz, DMSO) δ 2.47-2.50 (4H, m), 3.46 (2H, s), 3.61 (4H, t), 6.00 (2H, s), 6.77-6.80 (1H, m), 6.86 (1H, d), 6.90 (1H, d), 7.58 (1H, d), 8.25 (1H, d) (Signal at 2.47 partially obscured by DMSO); m/z=407 [M+H]+.

EXAMPLE 86

Preparation of 6-[4-(thiophen-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with thiophene-3-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(thiophen-3-ylmethyl)piperazin-1-yl]-3-(trifluoromethyl)-[1,2,4]triazolo[4,3-b]pyridazine.

1H NMR (499.802 MHz, DMSO) δ 2.47-2.49 (4H, m), 3.54 (2H, s), 3.59 (4H, t), 7.05-7.08 (1H, m), 7.32-7.35 (1H, m), 7.47-7.50 (1H, m), 7.56 (1H, d), 8.23 (1H, d) (Signal at 2.47 partially under DMSO); m/z=369 [M+H]+.

EXAMPLE 87

Preparation of 6-[4-[(1-methylpyrrol-2-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-methylpyrrole-2-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(1-methylpyrrol-2-yl)methyl]piperazin-1-yl]-3-(trifluoromethyl)-[1,2,4]triazolo[4,3-b]pyridazine.

1H NMR (499.802 MHz, DMSO) δ 2.46 (4H, t), 3.44 (2H, s), 3.57 (4H, t), 3.60 (3H, s), 5.86-5.90 (2H, m), 6.67 (1H, t), 7.56 (1H, d), 8.23 (1H, d) (Signal at 2.46 partially obscured by DMSO); m/z=366 [M+H]+.

EXAMPLE 88

Preparation of 6-[4-(2,3-dihydro-1,4-benzodioxin-6-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2,3-dihydro-1, 4-benzodioxine-6-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(2,3-dihydro-1,4-benzodioxin-6-ylmethyl)piperazin-1-yl]-3-(trifluoromethyl)-[1,2,4]triazolo[4,3-b]pyridazine.

1H NMR (499.802 MHz, DMSO) δ 2.46 (4H, t), 3.40 (2H, s), 3.58 (4H, t), 4.21 (4H, s), 6.74-6.77 (1H, m), 6.78 (1H, s), 6.79 (1H, d), 7.56 (1H, d), 8.22 (1H, d) (Signal at 2.46 partially under DMSO); m/z=421 [M+H]+.

EXAMPLE 89

Preparation of 6-[4-[(3-methylimidazol-4-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-methylimidazole-4-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(3-methylimidazol-4-yl)methyl]piperazin-1-yl]-3-(trifluoromethyl)-[1,2,4]triazolo[4,3-b]pyridazine.

1H NMR (499.802 MHz, DMSO) δ 2.46-2.50 (4H, m), 3.49 (2H, s), 3.58 (4H, t), 3.62 (3H, s), 6.77 (1H, s), 7.55 (1H, s), 7.57 (1H, d), 8.23 (1H, d) (Signal at 2.46 under DMSO); m/z=367 [M+H]+.

EXAMPLE 90

Preparation of 6-[4-(furan-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with furan-3-carbaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(furan-3-ylmethyl)piperazin-1-yl]-3-(trifluoromethyl)-[1,2,4]triazolo[4,3-b]pyridazine.

1H NMR (499.802 MHz, DMSO) δ 2.46-2.49 (4H, m), 3.39 (2H, s), 3.59 (4H, t), 6.43-6.45 (1H, m), 7.56 (1H, s), 7.57-7.59 (1H, m), 7.61 (1H, t), 8.23 (1H, d) (Signal at 2.46 obscured by DMSO); m/z=353 [M+H]+.

EXAMPLE 91

Preparation of 6-[4-[(3-methylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-methylbenzaldehyde was carried out according to General Synthetic Method 5. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(3-methylphenyl)methyl]piperazin-1-yl]-3-(trifluoromethyl)-[1,2,4]triazolo[4,3-b]pyridazine.

1H NMR (499.802 MHz, DMSO) δ 2.29 (3H, s), 2.47 (4H, t), 3.48 (2H, s), 3.59 (4H, t), 7.06 (1H, d), 7.10 (1H, d), 7.13 (1H, s), 7.21 (1H, t), 7.56 (1H, d), 8.22 (1H, d) (Signal at 2.29 obscured by DMSO); m/z=377 [M+H]+.

EXAMPLE 92

Preparation of 6-[4-(1H-benzimidazol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-benzimidazole-2-carbaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-(1H-benzimidazol-2-ylmethyl)piperazin-1-yl]-3-(trifluoromethyl)-[1,2,4]triazolo[4,3-b]pyridazine.

1H NMR (300.132 MHz, DMSO-d6) δ 2.60-2.67 (4H, m), 3.61-3.69 (4H, m), 3.81 (2H, s), 7.09-7.21 (2H, m), 7.43-7.48 (1H, m), 7.53-7.62 (2H, m), 8.25 (1H, d), 12.33 (1H, s); m/z=403 [M+H]+.

EXAMPLE 93

Preparation of 6-[4-(1-benzofuran-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1-benzofuran-2-carbaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-(1-benzofuran-2-ylmethyl)piperazin-1-yl]-3-(trifluoromethyl)-[1,2,4]triazolo[4,3-b]pyridazine.

1H NMR (300.132 MHz, DMSO-d6) δ 2.58-2.67 (4H, m), 3.59-3.68 (4H, m), 3.76 (2H, s), 6.82 (1H, s), 7.18-7.32 (2H, m), 7.52-7.63 (3H, m), 8.24 (1H, d); m/z=403 [M+H]+.

EXAMPLE 94

Preparation of 6-[4-(1H-indol-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-indole-3-carbaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 6-[4-(1H-indol-3-ylmethyl)piperazin-1-yl]-3-(trifluoromethyl)-[1,2,4]triazolo[4,3-b]pyridazine.

1H NMR (300.132 MHz, DMSO-d6) δ 2.51-2.59 (4H, m), 3.54-3.65 (4H, m), 3.71 (2H, s), 6.95-7.03 (1H, m), 7.04-7.12 (1H, m), 7.26 (1H, d), 7.36 (1H, d), 7.56 (1H, d), 7.66 (1H, d), 8.22 (1H, d), 10.94 (1H, s) (Signal at 2.5 partially obscured by DMSO); m/z=402 [M+H]+.

EXAMPLE 95

Preparation of 3-(trifluoromethyl)-6-[4-[[3-(trifluoromethyl)phenyl]methyl]piperazin-1-yl]-[1,2,4]triazolo[4,3-b]pyridazine Reductive amination of 6-(piperazin-1-yl)-3-(trifluoromethyl)-[1,2,4]triazolo[4,3-b]pyridazine with 3-(trifluoromethyl)benzaldehyde was carried out according to General Synthetic Method 5. The crude product was purified by hplc using a Waters XBridge Prep C18 OBD column, 5μ silica, 19 mm diameter, 100 mm length eluted with decreasingly polar mixtures of water (containing 1% aqueous ammonia) and acetonitrile as eluents to give 3-(trifluoromethyl)-6-[4-[[3-(trifluoromethyl)phenyl]methyl]piperazin-1-yl]-[1,2,4]triazolo[4,3-b]pyridazine.

1H NMR (300.132 MHz, DMSO-d6) δ 2.50-2.57 (4H, m), 3.57-3.69 (6H, m), 7.54-7.71 (5H, m), 8.25 (1H, d) (Signal at 2.5 partially obscured by DMSO); m/z=431 [M+H]+.

EXAMPLE 96

Preparation of 6-[4-[(3-fluorophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-fluorobenzaldehyde was carried out according to General Synthetic Method 5. The crude product was purified by hplc using a Waters XBridge Prep C18 OBD column (5μ silica, 21 mm diameter, 100 mm length) eluted with decreasingly polar mixtures of water (containing 0.05% aqueous ammonia) and acetonitrile as eluents to give 6-[4-[(3-fluorophenyl)methyl]piperazin-1-yl]-3-(trifluoromethyl)-[1,2,4]triazolo[4,3-b]pyridazine.

1H NMR (300.132 MHz, DMSO-d6) δ 2.50-2.56 (4H, m), 3.57 (2H, s), 3.59-3.66 (4H, m), 7.05-7.21 (3H, m), 7.34-7.44 (1H, m), 7.58 (1H, d), 8.25 (1H, d) (Signal at 2.5 partially obscured by DMSO); m/z=381 [M+H]+.

EXAMPLE 97

Preparation of 6-[4-[(3-chlorophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-chlorobenzaldehyde was carried out according to General Synthetic Method 5. The crude product was purified by hplc using a Waters XBridge Prep C18 OBD column, 5μ silica, 21 mm diameter, 100 mm length eluted with decreasingly polar mixtures of water (containing 0.05% aqueous ammonia) and acetonitrile as eluents to give 6-[4-[(3-chlorophenyl)methyl]piperazin-1-yl]-3-(trifluoromethyl)-[1,2,4]triazolo[4,3-b]pyridazine.

1H NMR (300.132 MHz, DMSO-d6) δ 2.50-2.54 (4H, m), 3.56 (2H, s), 3.59-3.66 (4H, m), 7.27-7.43 (4H, m), 7.58 (1H, d), 8.25 (1H, d) (Signal at 2.5 partially obscured by DMSO); m/z=397 [M+H]+.

EXAMPLE 98

Preparation of 6-[4-[(4,5-dimethylfuran-2-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4,5-dimethylfuran-2-carbaldehyde was carried out according to General Synthetic Method 6. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-[(4,5-dimethylfuran-2-yl)methyl]piperazin-1-yl]-3-(trifluoromethyl)-[1,2,4]triazolo[4,3-b]pyridazine.

1H NMR (700.03 MHz, DMSO-d6) δ 1.88 (3H, s), 2.15 (3H, s), 3.45 (2H, s), 3.60 (4H, t), 6.07 (1H, s), 7.58 (1H, d), 8.24 (1H, d) (Some peaks obscured by solvent); m/z=381 [M+H]+.

EXAMPLE 99

Preparation of 6-[4-(cyclohexylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with cyclohexanecarbaldehyde was carried out according to General Synthetic Method 6. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 6-[4-(cyclohexylmethyl)piperazin-1-yl]-3-(trifluoromethyl)-[1,2,4]triazolo[4,3-b]pyridazine.

1H NMR (700.03 MHz, DMSO-d6) δ 0.84-0.89 (2H, m), 1.15-1.18 (1H, m), 1.20-1.26 (2H, m), 1.51-1.54 (1H, m), 1.63-1.69 (3H, m), 1.76 (2H, d), 2.14 (2H, d), 2.46 (4H, t), 3.60 (4H, t), 7.59 (1H, d), 8.24 (1H, d); m/z=369 [M+H]+.

EXAMPLE 100

Preparation of 6-[4-[(2,2-difluoro-1,3-benzodioxol-5-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 2,2-difluoro-1,3-benzodioxole-5-carbaldehyde was carried out according to General Synthetic Method 7. The crude product was purified by hplc using a Phenomenex Luna C18 100A, 10 m silica, 21 mm diameter, 150 mm length eluted with decreasingly polar mixtures of water (containing 0.1% aqueous ammonia) and acetonitrile as eluents to give 6-[4-[(2,2-difluoro-1,3-benzodioxol-5-yl)methyl]piperazin-1-yl]-3-(trifluoromethyl)-[1,2,4]triazolo[4,3-b]pyridazine.

1H NMR (300.132 MHz, DMSO-d6) δ 2.50-2.55 (4H, m), 3.56 (2H, s), 3.58-3.65 (4H, m), 7.14-7.20 (1H, m), 7.33-7.40 (2H, m), 7.58 (1H, d), 8.25 (1H, d) (Signal at 2.5 obscured by DMSO); m/z=443 [M+H]+.

EXAMPLE 101

Preparation of 6-[4-(1H-indol-2-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-indole-2- carbaldehyde was carried out according to General Synthetic Method 7. The crude product was purified by hplc using a Waters XBridge Prep C18 OBD column, 5μ silica, 21 mm diameter, 100 mm length eluted with decreasingly polar mixtures of water (containing 0.05% aqueous ammonia) and acetonitrile as eluents to give 6-[4-(1H-indol-2-ylmethyl)piperazin-1-yl]-3-(trifluoromethyl)-[1,2,4]triazolo[4,3-b]pyridazine.

1H NMR (500.133 MHz, DMSO-d6) δ 2.52-2.58 (4H, m), 3.58-3.65 (4H, m), 3.68 (2H, s), 6.29 (1H, s), 6.93 (1H, t), 7.02 (1H, t), 7.31 (1H, d), 7.44 (1H, d), 7.57 (1H, d), 8.22 (1H, d), 11.00 (1H, s); m/z=402 [M+H]+.

EXAMPLE 102

Preparation of 6-[4-(1,3-benzodioxol-4-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1,3-benzodioxole-4-carbaldehyde was carried out according to General Synthetic Method 7. The crude product was purified by hplc using a Waters XBridge Prep C18 OBD column, 5μ silica, 21 mm diameter, 100 mm length eluted with decreasingly polar mixtures of water (containing 0.05% aqueous ammonia) and acetonitrile as eluents to give 6-[4-(1,3-benzodioxol-4-ylmethyl)piperazin-1-yl]-3-(trifluoromethyl)-[1,2,4]triazolo[4,3-b]pyridazine.

1H NMR (500.133 MHz, DMSO-d6) δ 2.49-2.54 (4H, m), 3.51 (2H, s), 3.57-3.61 (4H, m), 5.98 (2H, s), 6.79-6.86 (3H, m), 7.56 (1H, d), 8.22 (1H, d) (Signal at 2.5 partially obscured by DMSO); m/z=407 [M+H]+.

EXAMPLE 103

Preparation of 5-[[4-[3-(trifluoromethyl)[1,2,4]triazolo[4,3-b]pyridazin-6-yl]piperazin-1-yl]methyl]quinoxaline Reductive amination of 6-(piperazin-1-yl)-3-(trifluoromethyl)-[1,2,4]triazolo[4,3-b]pyridazine with quinoxaline-5-carbaldehyde was carried out according to General Synthetic Method 7. The crude product was purified by hplc using a Waters XBridge Prep C18 OBD column, 5μ silica, 21 mm diameter, 100 mm length eluted with decreasingly polar mixtures of water (containing 0.05% aqueous ammonia) and acetonitrile as eluents to give 5-[[4-[3-(trifluoromethyl)-[1,2,4]triazolo[4,3-b]pyridazin-6-yl]piperazin-1-yl]methyl]quinoxaline.

1H NMR (500.133 MHz, DMSO-d6) δ 2.60-2.66 (4H, m), 3.60-3.66 (4H, m), 4.24 (2H, s), 7.57 (1H, d), 7.85-7.90 (1H, m), 7.95 (1H, d), 8.03 (1H, s), 8.23 (1H, d), 8.96 (2H, s); m/z=415 [M+H]+.

EXAMPLE 104

Preparation of 6-[4-(1H-pyrrol-3-ylmethyl)piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 1H-pyrrole-3-carbaldehyde was carried out according to General Synthetic Method 7. The crude product was purified by hplc using a Waters XBridge Prep C18 OBD column, 5μ silica, 21 mm diameter, 100 mm length eluted with decreasingly polar mixtures of water (containing 0.05% aqueous ammonia) and acetonitrile as eluents to give 6-[4-(1H-pyrrol-3-ylmethyl)piperazin-1-yl]-3-(trifluoromethyl)-[1,2,4]triazolo[4,3-b]pyridazine.

1H NMR (500.133 MHz, DMSO-d6) δ 2.43-2.48 (4H, m), 3.36 (2H, s), 3.54-3.60 (4H, m), 5.96 (1H, s), 6.63 (1H, s), 6.65-6.68 (1H, m), 7.56 (1H, d), 8.21 (1H, d), 10.57 (1H, s); m/z=352 [M+H]+.

EXAMPLE 105

Preparation of 6-[4-[[3-(4-methylphenoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-(4-methylphenoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[3-(4-methylphenoxy)phenyl]methyl]piperazin-1-yl]-3-(trifluoromethyl)-[1,2,4]triazolo[4,3-b]pyridazine.

1H NMR (499.8 MHz, DMSO-d6) δ 2.30 (3H, s), 2.49-2.52 (4H, m), 3.53 (2H, s), 3.60 (4H, t), 6.86-6.88 (1H, m), 6.92-6.94 (2H, m), 6.96 (1H, s), 7.08 (1H, d), 7.21 (2H, d), 7.34 (1H, t), 7.58 (1H, d), 8.25 (1H, d) (Signal at 2.5 partially obscured by DMSO); m/z=469 [M+H]+.

EXAMPLE 106

Preparation of N,N-dimethyl-4-[[4-[3-(trifluoromethyl)-[1,2,4]triazolo[4,3-b]pyridazin-6-yl]piperazin-1-yl]methyl]aniline Reductive amination of 6-(piperazin-1-yl)-3-(trifluoromethyl)-[1,2,4]triazolo[4,3-b]pyridazine with 4-dimethylaminobenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give N,N-dimethyl-4-[[4-[3-(trifluoromethyl)-[1,2,4]triazolo[4,3-b]pyridazin-6-yl]piperazin-1-yl]methyl]aniline.

1H NMR (499.8 MHz, DMSO-d6) δ 2.45-2.49 (4H, t), 2.88 (6H, s), 3.31 (2H, s), 3.60 (4H, t), 6.70 (2H, d), 7.13 (2H, d), 7.58 (1H, d), 8.24 (1H, d) (Benzyl signal obscured by water); m/z=406 [M+H]+.

EXAMPLE 107

Preparation of N-[4-[[4-[3-(trifluoromethyl)-[1,2,4]triazolo[4,3-b]pyridazin-6-yl]piperazin-1-yl]methyl]phenyl]acetamide Reductive amination of 6-(piperazin-1-yl)-3-(trifluoromethyl)-[1,2,4]triazolo[4,3-b]pyridazine with N-(4-formylphenyl)acetamide was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give N-[4-[[4-[3-

(trifluoromethyl)-[1,2,4]triazolo[4,3-b]pyridazin-6-yl]piperazin-1-yl]methyl]phenyl]acetamide.

1H NMR (499.8 MHz, DMSO-d6) δ 2.04 (3H, s), 2.50 (4H, t), 3.48 (2H, s), 3.61 (4H, t), 7.24 (2H, d), 7.54 (2H, d), 7.58 (1H, d), 8.25 (1H, d), 9.90 (1H, s) (Signal at 2.5 partially obscured by DMSO); m/z=420 [M+H]+.

EXAMPLE 108

Preparation of 6-[4-[(4-ethoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-ethoxybenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-ethoxyphenyl)methyl]piperazin-1-yl]-3-(trifluoromethyl)-[1,2,4]triazolo[4,3-b]pyridazine.

1H NMR (499.8 MHz, DMSO-d6) δ 1.33 (3H, t), 2.48 (4H, t), 3.47 (2H, s), 3.60 (4H, t), 4.02 (2H, q), 6.89 (2H, d), 7.23 (2H, d), 7.58 (1H, d), 8.24 (1H, d); m/z=407 [M+H]+.

EXAMPLE 109

Preparation of 6-[4-[(4-butoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-butoxybenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-butoxyphenyl)methyl]piperazin-1-yl]-3-(trifluoromethyl)-[1,2,4]triazolo[4,3-b]pyridazine.

1H NMR (499.8 MHz, DMSO-d6) δ 0.94 (3H, t), 1.41-1.48 (2H, m), 1.67-1.73 (2H, m), 2.48 (4H, t), 3.47 (2H, s), 3.60 (4H, t), 3.96 (2H, t), 6.89 (2H, d), 7.22 (2H, d), 7.58 (1H, d), 8.24 (1H, d); m/z=435 [M+H]+.

EXAMPLE 110

Preparation of 6-[4-[(3-nitrophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-nitrobenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(3-nitrophenyl)methyl]piperazin-1-yl]-3-(trifluoromethyl)-[1,2,4]triazolo[4,3-b]pyridazine.

1H NMR (499.8 MHz, DMSO-d6) δ 2.57 (4H, t), 3.62 (4H, t), 3.71 (2H, s), 7.57 (1H, d), 7.64 (1H, t), 7.80 (1H, d), 8.12-8.15 (1H, m), 8.21 (1H, s), 8.24 (1H, d); m/z=408 [M+H]+.

EXAMPLE 111

Preparation of 6-[4-[(4-nitrophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-nitrobenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-nitrophenyl)methyl]piperazin-1-yl]-3-(trifluoromethyl)-[1,2,4]triazolo[4,3-b]pyridazine.

1H NMR (499.8 MHz, DMSO-d6) δ 2.56 (4H, t), 3.64 (4H, t), 3.71 (2H, s), 7.60 (1H, d), 7.65 (2H, d), 8.23 (2H, d), 8.26 (1H, d); m/z=408 [M+H]+.

EXAMPLE 112

Preparation of N,N-dimethyl-3-[4-[[4-[3-(trifluoromethyl)-[1,2,4]triazolo[4,3-b]pyridazin-6-yl]piperazin-1-yl]methyl]phenoxy]propan-1-amine Reductive amination of 6-(piperazin-1-yl)-3-(trifluoromethyl)-[1,2,4]triazolo[4,3-b]pyridazine with 4-(3-dimethylaminopropoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give N,N-dimethyl-3-[4-[[4-[3-(trifluoromethyl)-[1,2,4]triazolo[4,3-b]pyridazin-6-yl]piperazin-1-yl]methyl]phenoxy]propan-1-amine.

1H NMR (499.8 MHz, DMSO-d6) δ 1.81-1.87 (2H, m), 2.15 (6H, s), 2.36 (2H, t), 2.49 (4H, t), 3.47 (2H, s), 3.60 (4H, t), 3.98 (2H, t), 6.89 (2H, d), 7.23 (2H, d), 7.58 (1H, d), 8.25 (1H, d) (Signal at 2.49 partially obscured by DMSO); m/z=464 [M+H]+.

EXAMPLE 113

Preparation of 6-[4-[(4-pyrrolidin-1-ylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-pyrrolidin-1-ylbenzaldehyde was carried out according to General Synthetic Method 7. The crude product was purified by hplc using a Phenomenex Luna C18 100A, 10 m silica, 21 mm diameter, 150 mm length eluted with decreasingly polar mixtures of water (containing 0.1% aqueous ammonia) and acetonitrile as eluents to give 6-[4-[(4-pyrrolidin-1-ylphenyl)methyl]piperazin-1-yl]-3-(trifluoromethyl)-[1,2,4]triazolo[4,3-b]pyridazine.

1H NMR (300.13 MHz, DMSO-d6) δ 1.92-1.97 (4H, m), 2.46 (4H, t), 3.21 (4H, t), 3.40 (2H, s), 3.59 (4H, t), 6.50 (2H, d), 7.10 (2H, d), 7.57 (1H, d), 8.23 (1H, d); m/z=432 [M+H]+.

EXAMPLE 114

Preparation of 6-[4-[[4-[(2-methylpropan-2-yl)oxy]phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-[(2-methylpropan-2-yl)oxy]benzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[[4-[(2-methylpropan-2-yl)oxy]phenyl]methyl]piperazin-1-yl]-3-(trifluoromethyl)-[1,2,4]triazolo[4,3-b]pyridazine.

1H NMR (499.8 MHz, DMSO-d6) δ 1.30 (9H, s), 2.48-2.52 (4H, m), 3.50 (2H, s), 3.61 (4H, t), 6.94 (2H, d), 7.24 (2H, d), 7.58 (1H, d), 8.25 (1H, d) (Signal at 2.50 partially obscured by DMSO); m/z=435 [M+H]+.

EXAMPLE 115

Preparation of 6-[4-[(4-propan-2-yloxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-propan-2-yloxybenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-propan-2-yloxyphenyl)methyl]piperazin-1-yl]-3-(trifluoromethyl)-[1,2,4]triazolo[4,3-b]pyridazine.

1H NMR (499.8 MHz, DMSO-d6) δ 1.27 (6H, d), 2.49 (4H, t), 3.46 (2H, s), 3.61 (4H, t), 4.56-4.61 (1H, m), 6.88 (2H, d), 7.22 (2H, d), 7.58 (1H, d), 8.25 (1H, d) (Signal at 2.49 partially obscured by DMSO); m/z=421 [M+H]+.

EXAMPLE 116

Preparation of 3-(trifluoromethyl)-6-[4-[[3-(trifluoromethylsulfanyl)phenyl]methyl]piperazin-1-yl]-[1,2,4]triazolo[4,3-b]pyridazine Reductive amination of 6-(piperazin-1-yl)-3-(trifluoromethyl)-[1,2,4]triazolo[4,3-b]pyridazine with 3-(trifluoromethylsulfanyl)benzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 3-(trifluoromethyl)-6-[4-[[3-(trifluoromethylsulfanyl)phenyl]methyl]piperazin-1-yl]-[1,2,4]triazolo[4,3-b]pyridazine.

1H NMR (499.8 MHz, DMSO-d6) δ 2.52-2.55 (4H, m), 3.63 (6H, d), 7.54 (1H, t), 7.59 (2H, d), 7.64 (1H, d), 7.70 (1H, s), 8.26 (1H, d) (Signal at 2.54 partially obscured by DMSO); m/z=463 [M+H]+.

EXAMPLE 117

Preparation of 6-[4-[(4-pyridin-3-ylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-pyridin-3-ylbenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-pyridin-3-ylphenyl)methyl]piperazin-1-yl]-3-(trifluoromethyl)-[1,2,4]triazolo[4,3-b]pyridazine.

1H NMR (499.8 MHz, DMSO-d6) δ 2.56 (4H, t), 3.62 (2H, s), 3.64 (4H, t), 7.48-7.51 (3H, m), 7.59 (1H, d), 7.72 (2H, d), 8.07-8.10 (1H, m), 8.26 (1H, d), 8.57-8.58 (1H, m), 8.91 (1H, d); m/z=440 [M+H]+.

EXAMPLE 118

Preparation of 6-[4-[(3-bromophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-bromobenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(3-bromophenyl)methyl]piperazin-1-yl]-3-(trifluoromethyl)-[1,2,4]triazolo[4,3-b]pyridazine.

1H NMR (499.8 MHz, DMSO-d6) δ 2.50-2.54 (4H, m), 3.56 (2H, s), 3.63 (4H, t), 7.32 (1H, t), 7.35-7.37 (1H, m), 7.47-7.49 (1H, m), 7.55 (1H, s), 7.59 (1H, d), 8.25 (1H, d) (Signal at 2.52 partially obscured by DMSO); m/z=441 not assigned (Br).

EXAMPLE 119

Preparation of 6-[4-[[3-(4-chlorophenoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-(4-chlorophenoxy)benzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[[3-(4-chlorophenoxy)phenyl]methyl]piperazin-1-yl]-3-(trifluoromethyl)-[1,2,4]triazolo[4,3-b]pyridazine.

1H NMR (499.8 MHz, DMSO-d6) δ 2.51-2.53 (4H, m), 3.56 (2H, s), 3.61 (4H, t), 6.94-6.96 (1H, m), 7.03-7.06 (3H, m), 7.15 (1H, d), 7.38 (1H, d), 7.43-7.46 (2H, m), 7.59 (1H, d), 8.25 (1H, d) (Signal at 2.52 partially obscured by DMSO); m/z=489 [M+H]+.

EXAMPLE 120

Preparation of 6-[4-[[3-(4-methoxyphenoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-(4-methoxyphenoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[3-(4-methoxyphenoxy)phenyl]methyl]piperazin-1-yl]-3-(trifluoromethyl)-[1,2,4]triazolo[4,3-b]pyridazine.

1H NMR (499.8 MHz, DMSO-d6) δ 2.49-2.51 (4H, m), 3.52 (2H, s), 3.60 (4H, t), 3.76 (3H, s), 6.81-6.83 (1H, m), 6.93 (1H, s), 6.96-6.98 (2H, m), 7.01-7.02 (2H, m), 7.05 (1H, d), 7.31 (1H, t), 7.58 (1H, d), 8.25 (1H, d) (Signal at 2.50 partially obscured by DMSO); m/z=485 [M+H]+.

EXAMPLE 121

Preparation of methyl 4-[[4-[3-(trifluoromethyl)-[1,2,4]triazolo[4,3-b]pyridazin-6-yl]piperazin-1-yl]methyl]benzoate Reductive amination of 6-(piperazin-1-yl)-3-(trifluoromethyl)-[1,2,4]triazolo[4,3-b]pyridazine with methyl 4-formylbenzoate was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give methyl 4-[[4-[3-(trifluoromethyl)-[1,2,4]triazolo[4,3-b]pyridazin-6-yl]piperazin-1-yl]methyl]benzoate.

1H NMR (499.8 MHz, DMSO-d6) δ 2.53 (4H, t), 3.62-3.64 (6H, m), 3.86 (3H, s), 7.51 (2H, d), 7.59 (1H, d), 7.95 (2H, d), 8.25 (1H, d) (Signal at 2.53 partially obscured by DMSO); m/z=421 [M+H]+.

EXAMPLE 122

Preparation of 6-[4-[(4-tert-butylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-tert-butylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-tert-butylphenyl)methyl]piperazin-1-yl]-3-(trifluoromethyl)-[1,2,4]triazolo[4,3-b]pyridazine.

1H NMR (499.8 MHz, DMSO-d6) δ 1.29 (9H, s), 2.49-2.51 (4H, m), 3.51 (2H, s), 3.61 (4H, t), 7.26 (2H, d), 7.37 (2H, d), 7.58 (1H, d), 8.25 (1H, d) (Signal at 2.50 partially obscured by DMSO); m/z=419 [M+H]+.

EXAMPLE 123

Preparation of 6-[4-[[4-(2-methylpropyl)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(2-methylpropyl)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[4-(2-methylpropyl)phenyl]methyl]piperazin-1-yl]-3-(trifluoromethyl)-[1,2,4]triazolo[4,3-b]pyridazine.

1H NMR (499.8 MHz, DMSO-d6) δ 0.87 (6H, d), 1.81-1.86 (1H, m), 2.44 (2H, d), 2.48-2.51 (4H, m), 3.51 (2H, s), 3.61 (4H, t), 7.13 (2H, d), 7.24 (2H, d), 7.58 (1H, d), 8.25 (1H, d) (Signal at 2.49 partially obscured by DMSO); m/z=419 [M+H]+.

EXAMPLE 124

Preparation of 6-[4-[[6-(4-methylphenyl)sulfanylpyridin-3-yl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-(4-methylphenyl)sulfanylpyridine-3-carbaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[6-(4-methylphenyl)sulfanylpyridin-3-yl]methyl]piperazin-1-yl]-3-(trifluoromethyl)-[1,2,4]triazolo[4,3-b]pyridazine.

1H NMR (499.8 MHz, DMSO-d6) δ 2.38 (3H, s), 2.48-2.51 (4H, m), 3.51 (2H, s), 3.60 (4H, t), 6.89 (1H, d), 7.32 (2H, d), 7.48 (2H, d), 7.59 (2H, d), 8.25 (1H, d), 8.34-8.34 (1H, m) (Signal at 2.50 partially obscured by DMSO); m/z=486 [M+H]+.

EXAMPLE 125

Preparation of 6-[4-[[3-(4-fluorophenyl)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-(4-fluorophenyl)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[3-(4-fluorophenyl)phenyl]methyl]piperazin-1-yl]-3-(trifluoromethyl)-[1,2,4]triazolo[4,3-b]pyridazine.

1H NMR (499.8 MHz, DMSO-d6) δ 2.56 (4H, t), 3.63-3.64 (6H, m), 7.28-7.32 (2H, m), 7.35 (1H, d), 7.45 (1H, t), 7.57 (3H, d), 7.70-7.73 (2H, m), 8.25 (1H, d); m/z=457 [M+H]+.

EXAMPLE 126

Preparation of 6-[4-[[4-(4-fluorophenoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(4-fluorophenoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[4-(4-fluorophenoxy)phenyl]methyl]piperazin-1-yl]-3-(trifluoromethyl)-[1,2,4]triazolo[4,3-b]pyridazine.

1H NMR (499.8 MHz, DMSO-d6) δ 2.51-2.53 (4H, m), 3.52 (2H, s), 3.62 (4H, t), 6.97 (2H, d), 7.05-7.09 (2H, m), 7.21-7.26 (2H, m), 7.34 (2H, d), 7.59 (1H, d), 8.26 (1H, d) (Signal at 2.51 partially obscured by DMSO); m/z=473 [M+H]+.

EXAMPLE 127

Preparation of 6-[4-[(4-bromophenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-bromobenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-bromophenyl)methyl]piperazin-1-yl]-3-(trifluoromethyl)-[1,2,4]triazolo[4,3-b]pyridazine.

1H NMR (499.8 MHz, DMSO-d6) δ 2.49-2.52 (4H, m), 3.53 (2H, s), 3.62 (4H, t), 7.31 (2H, d), 7.54 (2H, d), 7.58 (1H, d), 8.25 (1H, d) (Signal at 2.50 partially obscured by DMSO); m/z=443 not assigned (Br).

EXAMPLE 128

Preparation of N,N-diethyl-4-[[4-[3-(trifluoromethyl)-[1,2,4]triazolo[4,3-b]pyridazin-6-yl]piperazin-1-yl]methyl]aniline Reductive amination of 6-(piperazin-1-yl)-3-(trifluoromethyl)-[1,2,4]triazolo[4,3-b]pyridazine with 4-diethylaminobenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give N,N-diethyl-4-[[4-[3-(trifluoromethyl)-[1,2,4]triazolo[4,3-b]pyridazin-6-yl]piperazin-1-yl]methyl]aniline.

1H NMR (499.8 MHz, DMSO-d6) δ 1.09 (6H, t), 2.47 (4H, t), 3.39 (2H, s), 3.60 (4H, t), 6.62 (2H, d), 7.09 (2H, d), 7.58 (1H, d), 8.24 (1H, d) (Aminomethylene signals obscured by water); m/z=434 [M+H]+.

EXAMPLE 129

Preparation of 6-[4-[(4-methylsulfanylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-methylsulfanylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-methylsulfanylphenyl)methyl]piperazin-1-yl]-3-(trifluoromethyl)-[1,2,4]triazolo[4,3-b]pyridazine.

1H NMR (499.8 MHz, DMSO-d6) δ 2.48 (3H, s), 2.49-2.51 (4H, m), 3.51 (2H, s), 3.61 (4H, t), 7.25 (2H, d), 7.29 (2H, d), 7.58 (1H, d), 8.25 (1H, d) (Signal at 2.50 partially obscured by DMSO); m/z=409 [M+H]+.

EXAMPLE 130

Preparation of 6-[4-[(4-propan-2-ylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-propan-2-ylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-propan-2-ylphenyl)methyl]piperazin-1-yl]-3-(trifluoromethyl)-[1,2,4]triazolo[4,3-b]pyridazine.

1H NMR (499.8 MHz, DMSO-d6) δ 1.21 (6H, d), 2.48-2.51 (4H, m), 2.86-2.91 (1H, m), 3.50 (2H, s), 3.61 (4H, t), 7.21 (2H, d), 7.25 (2H, d), 7.58 (1H, d), 8.25 (1H, d) (Signal at 2.49 partially obscured by DMSO); m/z=405 [M+H]+.

EXAMPLE 131

Preparation of 6-[4-[[4-(trifluoromethoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(trifluoromethoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[4-(trifluoromethoxy)phenyl]methyl]piperazin-1-yl]-3-(trifluoromethyl)-[1,2,4]triazolo[4,3-b]pyridazine.

1H NMR (499.8 MHz, DMSO-d6) δ 2.51-2.54 (4H, m), 3.58 (2H, s), 3.62 (4H, t), 7.34 (2H, d), 7.48 (2H, d), 7.59 (1H, d), 8.26 (1H, d) (Signal at 2.52 partially obscured by DMSO); m/z=447 [M+H]+.

EXAMPLE 132

Preparation of 6-[4-[[4-(4-chlorophenoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(4-chlorophenoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[4-(4-chlorophenoxy)phenyl]methyl]piperazin-1-yl]-3-(trifluoromethyl)-[1,2,4]triazolo[4,3-b]pyridazine.

1H NMR (499.8 MHz, DMSO-d6) δ 2.51-2.54 (4H, m), 3.54 (2H, s), 3.62 (4H, t), 7.01-7.04 (4H, m), 7.36-7.38 (2H, m), 7.42-7.45 (2H, m), 7.59 (1H, d), 8.26 (1H, d) (Signal at 2.52 partially obscured by DMSO); m/z=489 [M+H]+.

EXAMPLE 133

Preparation of 6-[4-[(4-ethynylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-ethynylbenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-ethynylphenyl)methyl]piperazin-1-yl]-3-(trifluoromethyl)-[1,2,4]triazolo[4,3-b]pyridazine.

1H NMR (499.8 MHz, DMSO-d6) δ 2.50-2.53 (4H, m), 3.57 (2H, s), 3.62 (4H, t), 7.36 (2H, d), 7.46 (2H, d), 7.59 (1H, d), 8.25 (1H, d) (Signal at 2.52 obscured by DMSO); m/z=387 [M+H]+.

EXAMPLE 134

Preparation of 6-[4-[(4-pyridin-2-ylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-pyridin-2-ylbenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-pyridin-2-ylphenyl)methyl]piperazin-1-yl]-3-(trifluoromethyl)-[1,2,4]triazolo[4,3-b]pyridazine.

1H NMR (499.8 MHz, DMSO-d6) δ 2.56 (4H, t), 3.62 (2H, s), 3.64 (4H, t), 7.34-7.37 (1H, m), 7.47 (2H, d), 7.60 (1H, d), 7.87-7.91 (1H, m), 7.96 (1H, d), 8.07 (2H, d), 8.25 (1H, d), 8.67-8.68 (1H, m); m/z=440 [M+H]+.

EXAMPLE 135

Preparation of 6-[4-[(4-ethylsulfonylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-ethylsulfonylbenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-ethylsulfonylphenyl)methyl]piperazin-1-yl]-3-(trifluoromethyl)-[1,2,4]triazolo[4,3-b]pyridazine.

1H NMR (499.8 MHz, DMSO-d6) δ 1.12 (3H, t), 2.55 (4H, t), 3.24-3.29 (2H, m), 3.64 (4H, t), 3.68 (2H, s), 7.59 (1H, d), 7.64 (2H, d), 7.87 (2H, d), 8.26 (1H, d) (Signal at 3.27 partially obscured water); m/z=455 [M+H]+.

EXAMPLE 136

Preparation of 6-[4-[(3-prop-2-enoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-prop-2-enoxybenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(3-prop-2-enoxyphenyl)methyl]piperazin-1-yl]-3-(trifluoromethyl)-[1,2,4]triazolo[4,3-b]pyridazine.

1H NMR (499.8 MHz, DMSO-d6) δ 2.50-2.53 (4H, m), 3.52 (2H, s), 3.62 (4H, t), 4.56-4.58 (2H, m), 5.25-5.28 (1H, m), 5.38-5.43 (1H, m), 6.02-6.09 (1H, m), 6.85-6.87 (1H, m), 6.92 (2H, d), 7.25 (1H, t), 7.59 (1H, d), 8.25 (1H, d) (Signal at 2.51 obscured by DMSO); m/z=419 [M+H]+.

EXAMPLE 137

Preparation of 6-[4-[(6-chloropyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-chloropyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-chloropyridin-3-yl)methyl]piperazin-1-yl]-3-(trifluoromethyl)-[1,2,4]triazolo[4,3-b]pyridazine.

1H NMR (499.8 MHz, DMSO-d6) δ 2.52-2.55 (4H, m), 3.60 (2H, s), 3.62 (4H, t), 7.51 (1H, d), 7.59 (1H, d), 7.82-7.84 (1H, m), 8.25 (1H, d), 8.37 (1H, d) (Signal at 2.53 partially obscured by DMSO); m/z=398 [M+H]+.

EXAMPLE 138

Preparation of N-[3-[[4-[3-(trifluoromethyl)-[1,2,4]triazolo[4,3-b]pyridazin-6-yl]piperazin-1-yl]methyl]phenyl]acetamide Reductive amination of 6-(piperazin-1-yl)-3-(trifluoromethyl)-[1,2,4]triazolo[4,3-b]pyridazine with N-(3-formylphenyl)acetamide was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give N-[3-[[4-[3-(trifluoromethyl)-[1,2,4]triazolo[4,3-b]pyridazin-6-yl]piperazin-1-yl]methyl]phenyl]acetamide.

1H NMR (499.8 MHz, DMSO-d6) δ 2.04 (3H, s), 2.50-2.53 (4H, m), 3.51 (2H, s), 3.62 (4H, t), 7.00 (1H, d), 7.25 (1H, t), 7.51 (1H, d), 7.56-7.61 (2H, m), 8.25 (1H, d), 9.90 (1H, s) (Signal at 2.51 obscured by DMSO); m/z=420 [M+H]+.

EXAMPLE 139

Preparation of 6-[4-[(4-prop-2-enoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-prop-2-enoxybenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-prop-2-enoxyphenyl)methyl]piperazin-1-yl]-3-(trifluoromethyl)-[1,2,4]triazolo[4,3-b]pyridazine.

1H NMR (499.8 MHz, DMSO-d6) δ 2.49 (4H, t), 3.47 (2H, s), 3.61 (4H, t), 4.55-4.57 (2H, m), 5.25-5.28 (1H, m), 5.38-5.42 (1H, m), 6.02-6.09 (1H, m), 6.92 (2H, d), 7.24 (2H, d), 7.58 (1H, d), 8.25 (1H, d); m/z=419 [M+H]+.

EXAMPLE 140

Preparation of N,N-dimethyl-2-[4-[[4-[3-(trifluoromethyl)-[1,2,4]triazolo[4,3-b]pyridazin-6-yl]piperazin-1-yl]methyl]phenoxy]ethanamine Reductive amination of 6-(piperazin-1-yl)-3-(trifluoromethyl)-[1,2,4]triazolo[4,3-b]pyridazine with 4-(2-dimethylaminoethoxy)benzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give N,N-dimethyl-2-[4-[[4-[3-(trifluoromethyl)-[1,2,4]triazolo[4,3-b]pyridazin-6-yl]piperazin-1-yl]methyl]phenoxy]ethanamine.

1H NMR (499.8 MHz, DMSO-d6) δ 2.22 (6H, s), 2.47-2.51 (4H, m), 2.62 (2H, t), 3.47 (2H, s), 3.61 (4H, t), 4.04 (2H, t), 6.91 (2H, d), 7.23 (2H, d), 7.58 (1H, d), 8.25 (1H, d); m/z=450 [M+H]+.

EXAMPLE 141

Preparation of N,N-dimethyl-4-[[4-[3-(trifluoromethyl)-[1,2,4]triazolo[4,3-b]pyridazin-6-yl]piperazin-1-yl]methyl]benzamide Reductive amination of 6-(piperazin-1-yl)-3-(trifluoromethyl)-[1,2,4]triazolo[4,3-b]pyridazine with 4-formyl-N,N-dimethylbenzamide was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give N,N-dimethyl-4-[[4-[3-(trifluoromethyl)-[1,2,4]triazolo[4,3-b]pyridazin-6-yl]piperazin-1-yl]methyl]benzamide.

1H NMR (499.8 MHz, DMSO-d6) δ 2.52-2.55 (4H, m), 2.90-3.02 (6H, m), 3.59 (2H, s), 3.63 (4H, t), 7.37-7.41 (4H, m), 7.59 (1H, d), 8.25 (1H, d) (Signal at 2.53 partially obscured by DMSO); m/z=434 [M+H]+.

EXAMPLE 142

Preparation of 6-[4-[(6-methoxypyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-methoxypyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-methoxypyridin-3-yl)methyl]piperazin-1-yl]-3-(trifluoromethyl)-[1,2,4]triazolo[4,3-b]pyridazine.

1H NMR (499.8 MHz, DMSO-d6) δ 2.49-2.52 (4H, m), 3.50 (2H, s), 3.61 (4H, t), 3.85 (3H, s), 6.81 (1H, d), 7.59 (1H, d), 7.66-7.68 (1H, m), 8.09 (1H, d), 8.25 (1H, d) (Signal at 2.50 partially obscured by DMSO); m/z=394 [M+H]+.

EXAMPLE 143

Preparation of 6-[4-[(6-morpholin-4-ylpyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-morpholin-4-ylpyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-morpholin-4-ylpyridin-3-yl)methyl]piperazin-1-yl]-3-(trifluoromethyl)-[1,2,4]triazolo[4,3-b]pyridazine.

1H NMR (499.8 MHz, DMSO-d6) δ 2.47-2.51 (4H, m), 3.41-3.45 (6H, m), 3.60 (4H, t), 3.70 (4H, t), 6.83 (1H, d), 7.51-7.54 (1H, m), 7.58 (1H, d), 8.05 (1H, d), 8.25 (1H, d) (Signal at 2.49 partially obscured by DMSO. Some signals distorted by water); m/z=449 [M+H]+.

EXAMPLE 144

Preparation of 6-[4-[(6-phenoxypyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-phenoxypyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-phenoxypyridin-3-yl)methyl]piperazin-1-yl]-3-(trifluoromethyl)-[1,2,4]triazolo[4,3-b]pyridazine.

1H NMR (499.8 MHz, DMSO-d6) δ 2.51-2.54 (4H, m), 3.54 (2H, s), 3.62 (4H, t), 7.02 (1H, d), 7.12-7.14 (2H, m), 7.20-7.23 (1H, m), 7.41-7.44 (2H, m), 7.59 (1H, d), 7.81-7.83

(1H, m), 8.09 (1H, d), 8.25 (1H, d) (Signal at 2.52 partially obscured by DMSO); m/z=456 [M+H]+.

EXAMPLE 145

Preparation of 6-[4-[(3-ethynylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-ethynylbenzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(3-ethynylphenyl)methyl]piperazin-1-yl]-3-(trifluoromethyl)-[1,2,4]triazolo[4,3-b]pyridazine.

1H NMR (499.8 MHz, DMSO-d6) δ 2.50-2.53 (4H, m), 3.55 (2H, s), 3.62 (4H, t), 4.17 (1H, s), 7.37-7.41 (3H, m), 7.45 (1H, s), 7.58 (1H, d), 8.25 (1H, d) (Signal at 2.52 partially obscured by DMSO.); m/z=387 [M+H]+.

EXAMPLE 146

Preparation of tert-butyl N-[4-[[4-[3-(trifluoromethyl)-[1,2,4]triazolo[4,3-b]pyridazin-6-yl]piperazin-1-yl]methyl]phenyl]carbamate Reductive amination of 6-(piperazin-1-yl)-3-(trifluoromethyl)-[1,2,4]triazolo[4,3-b]pyridazine with tert-butyl N-(4-formylphenyl)carbamate was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give tert-butyl N-[4-[[4-[3-(trifluoromethyl)-[1,2,4]triazolo[4,3-b]pyridazin-6-yl]piperazin-1-yl]methyl]phenyl]carbamate.

1H NMR (499.8 MHz, DMSO-d6) δ 1.48 (9H, s), 2.48 (4H, t), 3.46 (2H, s), 3.61 (4H, t), 7.20 (2H, d), 7.42 (2H, d), 7.58 (1H, d), 8.24 (1H, d), 9.29 (1H, s); m/z=478 [M+H]+.

EXAMPLE 147

Preparation of 6-[4-[(6-ethoxypyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-ethoxypyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-ethoxypyridin-3-yl)methyl]piperazin-1-yl]-3-(trifluoromethyl)-[1,2,4]triazolo[4,3-b]pyridazine.

1H NMR (499.8 MHz, DMSO-d6) δ 1.32 (3H, t), 2.48-2.51 (4H, m), 3.49 (2H, s), 3.61 (4H, t), 4.30 (2H, q), 6.78 (1H, d), 7.59 (1H, d), 7.64-7.67 (1H, m), 8.06 (1H, d), 8.25 (1H, d) (Signal at 2.49 partially obscured by DMSO); m/z=408 [M+H]+.

EXAMPLE 148

Preparation of 6-[4-[(6-propan-2-yloxypyridin-3-yl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 6-propan-2-yloxypyridine-3-carbaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(6-propan-2-yloxypyridin-3-yl)methyl]piperazin-1-yl]-3-(trifluoromethyl)-[1,2,4]triazolo[4,3-b]pyridazine.

1H NMR (499.8 MHz, DMSO-d6) δ 1.29 (6H, d), 2.49-2.52 (4H, m), 3.48 (2H, s), 3.61 (4H, t), 5.21-5.26 (1H, m), 6.72 (1H, d), 7.59 (1H, d), 7.62-7.65 (1H, m), 8.06 (1H, d), 8.25 (1H, d) (Signal at 2.50 partially obscured by DMSO); m/z=422 [M+H]+.

EXAMPLE 149

Preparation of [3-[[4-[3-(trifluoromethyl)-[1,2,4]triazolo[4,3-b]pyridazin-6-yl]piperazin-1-yl]methyl]phenyl]methanol Reductive amination of 6-(piperazin-1-yl)-3-(trifluoromethyl)-[1,2,4]triazolo[4,3-b]pyridazine with 3-(hydroxymethyl)benzaldehyde was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give [3-[[4-[3-(trifluoromethyl)-[1,2,4]triazolo[4,3-b]pyridazin-6-yl]piperazin-1-yl]methyl]phenyl]methanol.

1H NMR (499.8 MHz, DMSO-d6) δ 2.50-2.53 (4H, m), 3.54 (2H, s), 3.62 (4H, t), 4.51 (2H, d), 5.15 (1H, t), 7.21 (2H, t), 7.28-7.32 (2H, m), 7.59 (1H, d), 8.25 (1H, d) (Signal at 2.51 partially obscured by DMSO); m/z=393 [M+H]+.

EXAMPLE 150

Preparation of N-[3-[[4-[3-(trifluoromethyl)-[1,2,4]triazolo[4,3-b]pyridazin-6-yl]piperazin-1-yl]methyl]phenyl]methanesulfonamide Reductive amination of 6-(piperazin-1-yl)-3-(trifluoromethyl)-[1,2,4]triazolo[4,3-b]pyridazine with N-(3-formylphenyl)methanesulfonamide was carried out according to General Synthetic Method 7. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give N-[3-[[4-[3-(trifluoromethyl)-[1,2,4]triazolo[4,3-b]pyridazin-6-yl]piperazin-1-yl]methyl]phenyl]methanesulfonamide.

1H NMR (499.8 MHz, DMSO-d6) δ 2.51-2.54 (4H, m), 2.99 (3H, s), 3.53 (2H, s), 3.62 (4H, t), 7.08 (1H, d), 7.13 (1H, d), 7.22 (1H, s), 7.31 (1H, t), 7.59 (1H, d), 8.25 (1H, d), 9.69 (1H, s) (Signal at 2.52 partially obscured by DMSO); m/z=456 [M+H]+.

EXAMPLE 151

Preparation of [3-[[4-[3-(trifluoromethyl)-[1,2,4] triazolo[4,3-b]pyridazin-6-yl]piperazin-1-yl]methyl] phenyl]methanesulfonate Reductive amination of 6-(piperazin-1-yl)-3-(trifluoromethyl)-[1,2,4]triazolo[4,3-b]pyridazine with (3-formylphenyl)methanesulfonate was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give [3-[[4-[3-(trifluoromethyl)-[1, 2,4]triazolo[4,3-b]pyridazin-6-yl]piperazin-1-yl]methyl] phenyl]methanesulfonate.

1H NMR (499.8 MHz, DMSO-d6) δ 2.52-2.56 (4H, m), 3.36 (3H, s), 3.61-3.64 (6H, m), 7.26-7.28 (1H, m), 7.34 (1H, s), 7.37 (1H, d), 7.47 (1H, t), 7.59 (1H, d), 8.25 (1H, d) (Signal at 2.54 partially obscured by DMSO. Methyl signal distorted by water); m/z=457 [M+H]+.

EXAMPLE 152

Preparation of [4-[[4-[3-(trifluoromethyl)-[1,2,4] triazolo[4,3-b]pyridazin-6-yl]piperazin-1-yl]methyl] phenyl]methanesulfonate Reductive amination of 6-(piperazin-1-yl)-3-(trifluoromethyl)-[1,2,4]triazolo[4,3-b]pyridazine with (4-formylphenyl)methanesulfonate was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give [4-[[4-[3-(trifluoromethyl)-[1, 2,4]triazolo[4,3-b]pyridazin-6-yl]piperazin-1-yl]methyl] phenyl] methanesulfonate.

1H NMR (499.8 MHz, DMSO-d6) δ 2.51-2.55 (4H, m), 3.38 (3H, s), 3.58 (2H, s), 3.63 (4H, t), 7.32-7.34 (2H, m), 7.46 (2H, d), 7.59 (1H, d), 8.26 (1H, d) (Signal at 2.53 partially obscured by DMSO); m/z=457 [M+H]+.

EXAMPLE 153

Preparation of 2-[4-[[4-[3-(trifluoromethyl)-[1,2,4] triazolo[4,3-b]pyridazin-6-yl]piperazin-1-yl]methyl] phenoxy]acetamide Reductive amination of 6-(piperazin-1-yl)-3-(trifluoromethyl)-[1,2,4]triazolo[4,3-b]pyridazine with 2-(4-formylphenoxy)acetamide was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 2-[4-[[4-[3-(trifluoromethyl)-[1,2,4]triazolo[4,3-b]pyridazin-6-yl]piperazin-1-yl]methyl] phenoxy]acetamide.

1H NMR (499.8 MHz, DMSO-d6) δ 2.48-2.51 (4H, m), 3.48 (2H, s), 3.61 (4H, t), 4.42 (2H, s), 6.93 (2H, d), 7.26 (2H, d), 7.36 (1H, s), 7.49 (1H, s), 7.58 (1H, d), 8.25 (1H, d) (Signal at 2.50 partially obscured by DMSO); m/z=436 [M+H]+.

EXAMPLE 154

Preparation of 2-[4-[[4-[3-(trifluoromethyl)-[1,2,4] triazolo[4,3-b]pyridazin-6-yl]piperazin-1-yl]methyl] phenoxy]acetonitrile Reductive amination of 6-(piperazin-1-yl)-3-(trifluoromethyl)-[1,2,4]triazolo[4,3-b]pyridazine with 2-(4-formylphenoxy)acetonitrile was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 2-[4-[[4-[3-(trifluoromethyl)-[1,2,4]triazolo[4,3-b]pyridazin-6-yl]piperazin-1-yl]methyl] phenoxy]acetonitrile.

1H NMR (499.8 MHz, DMSO-d6) δ 2.49-2.52 (4H, m), 3.51 (2H, s), 3.61 (4H, t), 5.16 (2H, s), 7.05 (2H, d), 7.33 (2H, d), 7.58 (1H, d), 8.25 (1H, d) (Signal at 2.51 partially obscured by DMSO); m/z=418 [M+H]+.

EXAMPLE 155

Preparation of 6-[4-[[4-(4-methylpiperazin-1-yl) phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(4-methylpiperazin-1-yl)benzaldehyde was carried out according to General Synthetic Method 7. The crude product was purified by hplc using a Phenomenex Luna C18 100A, 10 m silica, 21 mm diameter, 150 mm length eluted with decreasingly polar mixtures of water (containing 0.1% aqueous ammonia) and acetonitrile as eluents to give 6-[4-[[4-(4-methylpiperazin-1-yl)phenyl]methyl]piperazin-1-yl]-3-(trifluoromethyl)-[1,2, 4]triazolo[4,3-b]pyridazine.

1H NMR (300.13 MHz, DMSO-d6) δ 2.23 (3H, s), 2.43-2.51 (8H, m), 3.12 (4H, t), 3.43 (2H, s), 3.56-3.62 (4H, m), 6.89 (2H, d), 7.15 (2H, d), 7.57 (1H, d), 8.24 (1H, d) (Signal at 2.46 partially obscured by DMSO); m/z=461 [M+H]+.

EXAMPLE 156

Preparation of N,N-dimethyl-3-[[4-[3-(trifluoromethyl)-[1,2,4]triazolo[4,3-b]pyridazin-6-yl]piperazin-1-yl]methyl]benzamide Reductive amination of 6-(piperazin-1-yl)-3-(trifluoromethyl)-[1,2,4]triazolo[4,3-b]pyridazine with 3-formyl-N,N-dimethylbenzamide was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give N,N-dimethyl-3-[[4-[3-(trifluoromethyl)-[1,2,4]triazolo[4,3-b]pyridazin-6-yl]piperazin-1-yl]methyl]benzamide.

1H NMR (499.8 MHz, DMSO-d6) δ 2.51-2.55 (4H, m), 2.90-3.01 (6H, m), 3.59 (2H, s), 3.63 (4H, t), 7.29-7.32 (1H, m), 7.36 (1H, s), 7.39-7.43 (2H, m), 7.59 (1H, d), 8.25 (1H, d) (Signal at 2.53 partially obscured by DMSO); m/z=434 [M+H]+.

EXAMPLE 157

Preparation of 6-[4-[(3-butoxyphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-butoxybenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(3-butoxyphenyl)methyl]piperazin-1-yl]-3-(trifluoromethyl)-[1,2,4]triazolo[4,3-b]pyridazine.

1H NMR (499.8 MHz, DMSO-d6) δ 0.94 (3H, t), 1.41-1.49 (2H, m), 1.67-1.73 (2H, m), 2.50-2.53 (4H, m), 3.52 (2H, s), 3.62 (4H, t), 3.97 (2H, t), 6.82-6.84 (1H, m), 6.90 (2H, t), 7.25 (1H, t), 7.59 (1H, d), 8.25 (1H, d) (Signal at 2.52 obscured by DMSO); m/z=435 [M+H]+.

EXAMPLE 158

Preparation of 6-[4-[(4-propylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-propylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-propylphenyl)methyl]piperazin-1-yl]-3-(trifluoromethyl)-[1,2,4]triazolo[4,3-b]pyridazine.

1H NMR (499.8 MHz, DMSO-d6) δ 0.90 (3H, t), 1.56-1.63 (2H, m), 2.48-2.51 (4H, m), 2.55 (2H, t), 3.51 (2H, s), 3.61 (4H, t), 7.16 (2H, d), 7.24 (2H, d), 7.58 (1H, d), 8.25 (1H, d) (Signal at 2.49 partially obscured by DMSO); m/z=405 [M+H]+.

EXAMPLE 159

Preparation of 6-[4-[(4-ethylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-ethylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-ethylphenyl)methyl]piperazin-1-yl]-3-(trifluoromethyl)-[1,2,4]triazolo[4,3-b]pyridazine.

1H NMR (499.8 MHz, DMSO-d6) δ 1.19 (3H, t), 2.48-2.51 (4H, m), 2.60 (2H, q), 3.50 (2H, s), 3.61 (4H, t), 7.18 (2H, d), 7.24 (2H, d), 7.58 (1H, d), 8.25 (1H, d) (Signal at 2.49 partially obscured by DMSO); m/z=391 [M+H]+.

EXAMPLE 160

Preparation of 6-[4-[(4-morpholin-4-ylphenyl)methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-morpholin-4-ylbenzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[(4-morpholin-4-ylphenyl)methyl]piperazin-1-yl]-3-(trifluoromethyl)-[1,2,4]triazolo[4,3-b]pyridazine.

1H NMR (499.8 MHz, DMSO-d6) δ 2.48 (4H, t), 3.09 (4H, t), 3.45 (2H, s), 3.60 (4H, t), 3.74 (4H, t), 6.91 (2H, d), 7.18 (2H, d), 7.58 (1H, d), 8.24 (1H, d); m/z=448 [M+H]+.

EXAMPLE 161

Preparation of 6-[4-[[4-(difluoromethoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 4-(difluoromethoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[4-(difluoromethoxy)phenyl]methyl]piperazin-1-yl]-3-(trifluoromethyl)-[1,2,4]triazolo[4,3-b]pyridazine.

1H NMR (499.8 MHz, DMSO-d6) δ 2.49-2.52 (4H, m), 3.54 (2H, s), 3.62 (4H, t), 7.16 (2H, d), 7.22 (1H, t), 7.39 (2H, d), 7.58 (1H, d), 8.25 (1H, d) (Signal at 2.49 partially obscured by DMSO); m/z=429 [M+H]+.

EXAMPLE 162

Preparation of 6-[4-[[3-(difluoromethoxy)phenyl]methyl]piperazin-1-yl]-3-(trifluoromethyl)-[1,2,4]triazolo[4,3-b]pyridazine Reductive amination of 6-(piperazin-1-yl)-3-(trifluoromethyl)-[1,2,4]triazolo[4,3-b]pyridazine with 3-(difluoromethoxy)benzaldehyde was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[4-[[3-(difluoromethoxy)phenyl]methyl]piperazin-1-yl]-3-(trifluoromethyl)-[1,2,4]triazolo[4,3-b]pyridazine.

1H NMR (499.8 MHz, DMSO-d6) δ 2.51-2.55 (4H, m), 3.58 (2H, s), 3.63 (4H, t), 7.07-7.11 (1H, m), 7.16 (1H, s), 7.23 (1H, d), 7.24 (1H, t), 7.41 (1H, t), 7.59 (1H, d), 8.26 (1H, d) (Signal at 2.49 partially obscured by DMSO); m/z=429 [M+H]+.

EXAMPLE 163

Preparation of ethyl (E)-3-[4-[[4-[3-(trifluoromethyl)-[1,2,4]triazolo[4,3-b]pyridazin-6-yl]piperazin-1-yl]methyl]phenyl]prop-2-enoate Reductive amination of 6-(piperazin-1-yl)-3-(trifluoromethyl)-[1,2,4]triazolo[4,3-b]pyridazine with ethyl (E)-3-(4- formylphenyl)prop-2-enoate was carried out according to General Synthetic Method 7. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give ethyl (E)-3-[4-[[4-[3-(trifluoromethyl)-[1,2,4]triazolo[4,3-b]pyridazin-6-yl]piperazin-1-yl]methyl]phenyl]prop-2-enoate.

1H NMR (499.8 MHz, DMSO-d6) δ 1.27 (3H, t), 2.51-2.54 (4H, m), 3.59 (2H, s), 3.63 (4H, t), 4.21 (2H, q), 6.62 (1H, d), 7.40 (2H, d), 7.59 (1H, d), 7.64-7.67 (1H, m), 7.70 (2H, d), 8.25 (1H, d) (Signal at 2.52 partially obscured by DMSO); m/z=461 [M+H]+.

EXAMPLE 164

Preparation of 6-[4-[(2-methylsulfonylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 2-methylsulfonylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(2-methylsulfonylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.86-1.92 (2H, m), 2.67 (2H, t), 2.79-2.83 (2H, m), 3.27 (3H, s), 3.74 (2H, t), 3.78 (2H, t), 4.03 (2H, s), 7.51 (1H, d), 7.55-7.60 (3H, m), 7.95 (1H, d), 8.23 (1H, d); m/z=455 [M+H]+.

EXAMPLE 165

Preparation of 6-[4-[(3-methylsulfonylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-methylsulfonylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(3-methylsulfonylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.86-1.92 (2H, m), 2.64 (2H, t), 2.77-2.81 (2H, m), 3.18 (3H, s), 3.73-3.78 (6H, m), 7.50 (1H, d), 7.53 (1H, d), 7.61 (1H, d), 7.80 (1H, d), 7.84 (1H, s), 8.22 (1H, d); m/z=455 [M+H]+.

EXAMPLE 166

Preparation of 6-[4-[(4-methylsulfonylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-methylsulfonylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(4-methylsulfonylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.86-1.92 (2H, m), 2.64 (2H, t), 2.77 (2H, t), 3.19 (4H, s), 3.73-3.78 (6H, m), 7.50 (1H, d), 7.53 (2H, d), 7.81 (2H, d), 8.23 (1H, d); m/z=455 [M+H]+.

EXAMPLE 167

Preparation of 6-[4-[(2-methoxyphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 2-methoxybenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(2-methoxyphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.85-1.92 (2H, m), 2.63 (2H, t), 2.76 (2H, t), 3.61 (2H, s), 3.70-3.74 (5H, m), 3.76 (2H, t), 6.83 (1H, t), 6.94 (1H, d), 7.19 (1H, t), 7.26 (1H, d), 7.49 (1H, d), 8.21 (1H, d); m/z=407 [M+H]+.

EXAMPLE 168

Preparation of 3-(trifluoromethyl)-6-[4-[[4-(trifluoromethyl)phenyl]methyl]-1,4-diazepan-1-yl]-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-(trifluoromethyl)benzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 3-(trifluoromethyl)-6-[4-[[4-(trifluoromethyl)phenyl]methyl]-1,4-diazepan-1-yl]-[1,2,4]triazolo[4,3-b]pyridazine.

1H NMR (499.8 MHz, DMSO-d6) δ 1.85-1.91 (2H, sm), 2.65 (2H, t), 2.75 (2H, t), 3.73-3.77 (6H, m), 7.46 (2H, d), 7.50 (1H, d), 7.58 (2H, d), 8.23 (1H, d); m/z=445 [M+H]+.

EXAMPLE 169

Preparation of 6-[4-[(2-fluorophenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 2-fluorobenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(2-fluorophenyl)methyl]-1,4-diazepan-1-yl]-3-(trifluoromethyl)-[1,2,4]triazolo[4,3-b]pyridazine.

1H NMR (499.8 MHz, DMSO-d6) δ 1.85-1.91 (2H, m), 2.64 (2H, t), 2.76 (2H, t), 3.68 (2H, s), 3.71 (2H, t), 3.76 (2H, t), 7.06-7.11 (2H, m), 7.25-7.28 (1H, m), 7.36 (1H, t), 7.48 (1H, d), 8.21 (1H, d); m/z=395 [M+H]+.

EXAMPLE 170

Preparation of 4-[[4-[3-(trifluoromethyl)-[1,2,4]triazolo[4,3-b]pyridazin-6-yl]-1,4-diazepan-1-yl]methyl]benzonitrile Reductive amination of 6-(1,4-diazepan-1-yl)-3-(trifluoromethyl)-[1,2,4]triazolo[4,3-b]pyridazine with 4-formylbenzonitrile was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 4-[[4-[3-(trifluoromethyl)-[1,2,4]triazolo[4,3-b]pyridazin-6-yl]-1,4-diazepan-1-yl]methyl]benzonitrile.

1H NMR (499.8 MHz, DMSO-d6) δ 1.84-1.91 (2H, m), 2.63 (2H, t), 2.75 (2H, t), 3.72 (2H, s), 3.73-3.79 (4H, m), 7.45 (2H, d), 7.49 (1H, d), 7.69 (2H, d), 8.23 (1H, d); m/z=402 [M+H]+.

EXAMPLE 171

Preparation of 3-[[4-[3-(trifluoromethyl)[1,2,4]triazolo[4,3-b]pyridazin-6-yl]-1,4-diazepan-1-yl]methyl]benzonitrile Reductive amination of 6-(1,4-diazepan-1-yl)-3-(trifluoromethyl)-[1,2,4]triazolo[4,3-b]pyridazine with 3-formylbenzonitrile was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 3-[[4-[3-(trifluoromethyl)-[1,2,4]triazolo[4,3-b]pyridazin-6-yl]-1,4-diazepan-1-yl]methyl]benzonitrile.

1H NMR (499.8 MHz, DMSO-d6) δ 1.84-1.91 (2H, m), 2.63 (2H, t), 2.75 (2H, t), 3.69 (2H, s), 3.72-3.77 (4H, m), 7.45 (1H, t), 7.50 (1H, d), 7.59 (1H, d), 7.69 (2H, d), 8.22 (1H, d); m/z=402 [M+H]+.

EXAMPLE 172

Preparation of 6-[4-[(3-fluorophenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-fluorobenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(3-fluorophenyl)methyl]-1,4-diazepan-1-yl]-3-(trifluoromethyl)-[1,2,4]triazolo[4,3-b]pyridazine.

1H NMR (499.8 MHz, DMSO-d6) δ 1.84-1.90 (2H, m), 2.63 (2H, t), 2.75 (2H, t), 3.65 (2H, s), 3.73 (2H, t), 3.76 (2H, t), 7.01-7.04 (2H, m), 7.08 (1H, d), 7.26-7.30 (1H, m), 7.49 (1H, d), 8.22 (1H, d); m/z=395 [M+H]+.

EXAMPLE 173

Preparation of 6-[4-[(3-methoxyphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-methoxybenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(3-methoxyphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.84-1.90 (2H, m), 2.61 (2H, t), 2.74 (2H, t), 3.60 (2H, s), 3.67 (3H, s), 3.73-3.77 (4H, m), 6.77-6.82 (3H, m), 7.16 (1H, t), 7.49 (1H, d), 8.21 (1H, d); m/z=407 [M+H]+.

EXAMPLE 174

Preparation of 3-(trifluoromethyl)-6-[4-[[2-(trifluoromethyl)phenyl]methyl]-1,4-diazepan-1-yl]-[1,2,4]triazolo[4,3-b]pyridazine Reductive amination of 6-(1,4-diazepan-1-yl)-3-(trifluoromethyl)-[1,2,4]triazolo[4,3-b]pyridazine with 2-(trifluoromethyl)benzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 3-(trifluoromethyl)-6-[4-[[2-(trifluoromethyl)phenyl]methyl]-1,4-diazepan-1-yl]-[1,2,4]triazolo[4,3-b]pyridazine.

1H NMR (499.8 MHz, DMSO-d6) δ 1.83-1.90 (2H, m), 2.65 (2H, t), 2.77 (2H, t), 3.76 (6H, d), 7.42 (1H, t), 7.45-7.52 (2H, m), 7.65 (2H, t), 8.22 (1H, d); m/z=445 [M+H]+.

EXAMPLE 175

Preparation of 6-[4-[(3-chlorophenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-chlorobenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(3-chlorophenyl)methyl]-1,4-diazepan-1-yl]-3-(trifluoromethyl)-[1,2,4]triazolo[4,3-b]pyridazine.

1H NMR (499.8 MHz, DMSO-d6) δ 1.83-1.90 (2H, m), 2.64 (2H, t), 2.75 (2H, t), 3.64 (2H, s), 3.73 (2H, t), 3.76 (2H, t), 7.19-7.21 (1H, m), 7.24-7.28 (3H, m), 7.49 (1H, d), 8.22 (1H, d); m/z=411 [M+H]+.

EXAMPLE 176

Preparation of 6-[4-[(4-chlorophenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-chlorobenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(4-chlorophenyl)methyl]-1,4-diazepan-1-yl]-3-(trifluoromethyl)-[1,2,4]triazolo[4,3-b]pyridazine.

1H NMR (499.8 MHz, DMSO-d6) δ 1.83-1.90 (2H, m), 2.61 (2H, t), 2.73 (2H, t), 3.62 (2H, s), 3.71-3.76 (4H, m), 7.25-7.30 (4H, m), 7.49 (1H, d), 8.22 (1H, d); m/z=411 [M+H]+.

EXAMPLE 177

Preparation of 6-[4-[(4-fluorophenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-fluorobenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(4-fluorophenyl)methyl]-1,4-diazepan-1-yl]-3-(trifluoromethyl)-[1,2,4]triazolo[4,3-b]pyridazine.

1H NMR (499.8 MHz, DMSO-d6) δ 1.83-1.90 (2H, m), 2.61 (2H, t), 2.72 (2H, t), 3.61 (2H, s), 3.71-3.75 (4H, m), 7.05 (2H, t), 7.26-7.29 (2H, m), 7.49 (1H, d), 8.22 (1H, d); m/z=395 [M+H]+.

EXAMPLE 178

Preparation of 6-[4-[(3-methylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-methylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(3-methylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.83-1.90 (2H, m), 2.22 (3H, s), 2.61 (2H, t), 2.73 (2H, t), 3.58 (2H, s), 3.70-3.77 (4H, m), 7.03 (3H, d), 7.13 (1H, t), 7.49 (1H, d), 8.22 (1H, d); m/z=391 [M+H]+.

EXAMPLE 179

Preparation of 3-(trifluoromethyl)-6-[4-[[3-(trifluoromethyl)phenyl]methyl]-1,4-diazepan-1-yl]-[1,2,4]triazolo[4,3-b]pyridazine Reductive amination of 6-(1,4-diazepan-1-yl)-3-(trifluoromethyl)-[1,2,4]triazolo[4,3-b]pyridazine with 3-(trifluoromethyl)benzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 3-(trifluoromethyl)-6-[4-[[3-(trifluoromethyl)phenyl]methyl]-1,4-diazepan-1-yl]-[1,2,4]triazolo[4,3-b]pyridazine.

1H NMR (499.8 MHz, DMSO-d6) δ 1.83-1.89 (2H, m), 2.65 (2H, t), 2.77 (2H, t), 3.71-3.79 (6H, m), 7.45-7.51 (2H, m), 7.53-7.59 (3H, m), 8.22 (1H, d); m/z=445 [M+H]+.

EXAMPLE 180

Preparation of 2-[[4-[3-(trifluoromethyl)-[1,2,4]triazolo[4,3-b]pyridazin-6-yl]-1,4-diazepan-1-yl]methyl]benzonitrile Reductive amination of 6-(1,4-diazepan-1-yl)-3-(trifluoromethyl)-[1,2,4]triazolo[4,3-b]pyridazine with 2-formylbenzonitrile was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 2-[[4-[3-(trifluoromethyl)-[1,2,4]triazolo[4,3-b]pyridazin-6-yl]-1,4-diazepan-1-yl]methyl]benzonitrile.

1H NMR (499.8 MHz, DMSO-d6) δ 1.82-1.89 (2H, m), 2.69 (2H, t), 2.80 (2H, t), 3.71-3.78 (6H, m), 7.42 (1H, t), 7.46-7.51 (2H, m), 7.57 (1H, t), 7.70 (1H, d), 8.20 (1H, d); m/z=402 [M+H]+.

EXAMPLE 181

Preparation of 6-[4-[(4-methoxyphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-methoxybenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(4-methoxyphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.82-1.89 (2H, m), 2.59 (2H, t), 2.71 (2H, t), 3.54 (2H, s), 3.70-3.74 (7H, m), 6.79 (2H, d), 7.14 (2H, d), 7.48 (1H, d), 8.21 (1H, d); m/z=407 [M+H]+.

EXAMPLE 182

Preparation of 6-[4-[(4-methylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 4-methylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(4-methylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.82-1.89 (2H, m), 2.26 (3H, s), 2.60 (2H, t), 2.71 (2H, t), 3.57 (2H, s), 3.70-3.74 (4H, m), 7.03 (2H, d), 7.11 (2H, d), 7.48 (1H, d), 8.21 (1H, d); m/z=391 [M+H]+.

EXAMPLE 183

Preparation of 6-[4-[(2-methylphenyl)methyl]-1,4-diazepan-1-yl]-3-(trifluoromethyl)-[1,2,4]triazolo[4,3-b]pyridazine Reductive amination of 6-(1,4-diazepan-1-yl)-3-(trifluoromethyl)-[1,2,4]triazolo[4,3-b]pyridazine with 2-methylbenzaldehyde was carried out according to General Synthetic Method 8. The crude product was purified by hplc using a Waters XBridge Prep C18 OBD column (5μ silica, 19 mm diameter, 100 mm length) eluted with decreasingly polar mixtures of water (containing 0.05% aqueous ammonia) and acetonitrile as eluents to give 6-[4-[(2-methylphenyl)methyl]-1,4-diazepan-1-yl]-3-(trifluoromethyl)-[1,2,4]triazolo[4,3-b]pyridazine.

1H NMR (499.8 MHz, DMSO-d6) δ 1.78-1.85 (2H, m), 2.15 (3H, s), 2.61 (2H, t), 2.71-2.77 (2H, m), 3.55 (2H, s), 3.71 (2H, t), 3.75 (2H, t), 7.04-7.09 (2H, m), 7.08-7.15 (1H, m), 7.16-7.18 (1H, m), 7.48 (1H, d), 8.20 (1H, d); m/z=391 [M+H]+.

EXAMPLE 184

Preparation of 3-(trifluoromethyl)-6-[4-[[6-(trifluoromethyl)pyridin-3-yl]methyl]piperazin-1-yl]-[1,2,4]triazolo[4,3-a]pyridine Reductive amination of 6-(piperazin-1-yl)-3-(trifluoromethyl)-[1,2,4]triazolo[4,3-a]pyridine with 6-(trifluoromethyl)pyridine-3-carbaldehyde was carried out according to General Synthetic Method 9. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 3-(trifluoromethyl)-6-[4-[[6-(trifluoromethyl)pyridin-3-yl]methyl]piperazin-1-yl]-[1,2,4]triazolo[4,3-a]pyridine.

1H NMR (499.8 MHz, DMSO-d6) δ 2.60 (4H, t), 3.22 (4H, t), 3.73 (2H, s), 7.54 (1H, s), 7.72-7.75 (1H, m), 7.90-7.94 (2H, m), 8.05-8.07 (1H, m), 8.75 (1H, s); m/z=431 [M+H]+.

EXAMPLE 185

Preparation of 3-(trifluoromethyl)-6-[4-[[3-(trifluoromethyl)phenyl]methyl]piperazin-1-yl]-[1,2,4]triazolo[4,3-a]pyridine Reductive amination of 6-(piperazin-1-yl)-3-(trifluoromethyl)-[1,2,4]triazolo[4,3-a]pyridine with 3-(trifluoromethyl)benzaldehyde was carried out according to General Synthetic Method 9. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 3-(trifluoromethyl)-6-[4-[[3-(trifluoromethyl)phenyl]methyl]piperazin-1-yl]-[1,2,4]triazolo[4,3-a]pyridine.

1H NMR (499.8 MHz, DMSO-d6) δ 2.58 (4H, t), 3.22 (4H, t), 3.68 (2H, s), 7.54 (1H, s), 7.60 (1H, t), 7.66 (2H, d), 7.70 (1H, s), 7.72-7.74 (1H, m), 7.93 (1H, d); m/z=430 [M+H]+.

EXAMPLE 186

Preparation of 3-(trifluoromethyl)-6-[4-[[4-(trifluoromethyl)phenyl]methyl]piperazin-1-yl]-[1,2,4]triazolo[4,3-a]pyridine Reductive amination of 6-(piperazin-1-yl)-3-(trifluoromethyl)-[1,2,4]triazolo[4,3-a]pyridine with 4-(trifluoromethyl)benzaldehyde was carried out according to General Synthetic Method 9. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 3-(trifluoromethyl)-6-[4-[[4-(trifluoromethyl)phenyl]methyl]piperazin-1-yl]-[1,2,4]triazolo[4,3-a]pyridine.

1H NMR (499.8 MHz, DMSO-d6) δ 2.58 (4H, t), 3.22 (4H, t), 3.67 (3H, s), 7.54 (1H, s), 7.58-7.60 (2H, m), 7.71-7.74 (3H, m), 7.92-7.94 (1H, m); m/z=430 [M+H]+.

EXAMPLE 187

Preparation of 4-[[4-[3-(trifluoromethyl)-[1,2,4]triazolo[4,3-a]pyridin-6-yl]piperazin-1-yl]methyl]benzonitrile Reductive amination of 6-(piperazin-1-yl)-3-(trifluoromethyl)-[1,2,4]triazolo[4,3-a]pyridine with 4-formylbenzonitrile was carried out according to General Synthetic Method 9. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 4-[[4-[3-(trifluoromethyl)-[1,2,4]triazolo[4,3-a]pyridin-6-yl]piperazin-1-yl]methyl]benzonitrile.

1H NMR (499.8 MHz, DMSO-d6) δ 2.58 (4H, t), 3.22 (4H, t), 3.67 (2H, s), 7.54 (1H, s), 7.57 (2H, d), 7.72-7.74 (1H, m), 7.83 (2H, d), 7.93 (1H, d); m/z=387 [M+H]+.

EXAMPLE 188

Preparation of 3-[[4-[3-(trifluoromethyl)-[1,2,4]triazolo[4,3-a]pyridin-6-yl]piperazin-1-yl]methyl]benzonitrile Reductive amination of 6-(piperazin-1-yl)-3-(trifluoromethyl)-[1,2,4]triazolo[4,3-a]pyridine with 3-formylbenzonitrile was carried out according to General Synthetic Method 9. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 3-[[4-[3-(trifluoromethyl)-[1,2,4]triazolo[4,3-a]pyridin-6-yl]piperazin-1-yl]methyl]benzonitrile.

1H NMR (499.8 MHz, DMSO-d6) δ 2.57 (4H, t), 3.22 (4H, t), 3.64 (2H, s), 7.54 (1H, s), 7.58 (1H, t), 7.72-7.74 (2H, m), 7.75-7.77 (1H, m), 7.80 (1H, s), 7.93 (1H, d); m/z=387 [M+H]+.

EXAMPLE 189

Preparation of 6-[4-[(3-fluorophenyl)methyl]piperazin-1-yl]-3-(trifluoromethyl)-[1,2,4]triazolo[4,3-a]pyridine Reductive amination of 6-(piperazin-1-yl)-3-(trifluoromethyl)-[1,2,4]triazolo[4,3-a]pyridine with 3-fluorobenzaldehyde was carried out according to General Synthetic Method 9. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(3-fluorophenyl)methyl]piperazin-1-yl]-3-(trifluoromethyl)-[1,2,4]triazolo[4,3-a]pyridine.

1H NMR (499.8 MHz, DMSO-d6) δ 2.57 (4H, t), 3.21 (4H, t), 3.60 (2H, s), 7.08-7.12 (1H, m), 7.16-7.21 (2H, m), 7.38-7.42 (1H, m), 7.54 (1H, s), 7.72-7.74 (1H, m), 7.93 (1H, d); m/z=380 [M+H]+.

EXAMPLE 190

Preparation of 6-[4-[(4-chlorophenyl)methyl]piperazin-1-yl]-3-(trifluoromethyl)-[1,2,4]triazolo[4,3-a]pyridine Reductive amination of 6-(piperazin-1-yl)-3-(trifluoromethyl)-[1,2,4]triazolo[4,3-a]pyridine with 4-chlorobenzaldehyde was carried out according to General Synthetic Method 9. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-chlorophenyl)methyl]piperazin-1-yl]-3-(trifluoromethyl)-[1,2,4]triazolo[4,3-a]pyridine.

1H NMR (499.8 MHz, DMSO-d6) δ 2.55 (4H, t), 3.20 (4H, t), 3.56 (2H, s), 7.39 (4H, d), 7.53 (1H, s), 7.71-7.74 (1H, m), 7.93 (1H, d); m/z=396 [M+H]+.

EXAMPLE 191

Preparation of 6-[4-[(4-fluorophenyl)methyl]piperazin-1-yl]-3-(trifluoromethyl)-[1,2,4]triazolo[4,3-a]pyridine Reductive amination of 6-(piperazin-1-yl)-3-(trifluoromethyl)-[1,2,4]triazolo[4,3-a]pyridine with 4-fluorobenzaldehyde was carried out according to General Synthetic Method 9. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-fluorophenyl)methyl]piperazin-1-yl]-3-(trifluoromethyl)-[1,2,4]triazolo[4,3-a]pyridine.

1H NMR (499.8 MHz, DMSO-d6) δ 2.55 (4H, t), 3.20 (4H, t), 3.55 (2H, s), 7.18 (2H, t), 7.37-7.40 (2H, m), 7.53 (1H, s), 7.71-7.74 (1H, m), 7.93 (1H, d); m/z=380 [M+H]+.

EXAMPLE 192

Preparation of 6-[4-[(4-methoxyphenyl)methyl]piperazin-1-yl]-3-(trifluoromethyl)-[1,2,4]triazolo[4,3-a]pyridine Reductive amination of 6-(piperazin-1-yl)-3-(trifluoromethyl)-[1,2,4]triazolo[4,3-a]pyridine with 4-methoxybenzaldehyde was carried out according to General Synthetic Method 9. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[4-[(4-methoxyphenyl)methyl]piperazin-1-yl]-3-(trifluoromethyl)-[1,2,4]triazolo[4,3-a]pyridine.

1H NMR (499.8 MHz, DMSO-d6) δ 2.53 (4H, t), 3.19 (4H, t), 3.49 (2H, s), 3.76 (3H, s), 6.88-6.92 (2H, m), 7.25 (2H, d), 7.53 (1H, s), 7.71-7.73 (1H, m), 7.92 (1H, d); m/z=392 [M+H]+.

EXAMPLE 193

Preparation of 6-[2-(pyridin-4-ylmethyl)-1,3,3a,4,6,6a-hexahydropyrrolo[3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with pyridine-4-carbaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[2-(pyridin-4-ylmethyl)-1,3,3a,4,6,6a-hexahydropyrrolo[3,4-c]pyrrol-5-yl]-3-(trifluoromethyl)-[1,2,4]triazolo[4,3-b]pyridazine.

1H NMR (499.8 MHz, DMSO-d6) δ 2.98 (2H, s), 3.42 (1H, d), 3.62 (2H, s), 3.75-3.78 (2H, m), 7.30-7.33 (3H, m), 8.23 (1H, d), 8.48 (2H, q) (Some peaks obscured by solvent); m/z=390 [M+H]+.

EXAMPLE 194

Preparation of 6-[2-[(3-methoxyphenyl)methyl]-1,3,3a,4,6,6a-hexahydropyrrolo[3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 3-methoxybenzaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[2-[(3-methoxyphenyl)methyl]-1,3,3a,4,6,6a-hexahydropyrrolo[3,4-c]pyrrol-5-yl]-3-(trifluoromethyl)-[1,2,4]triazolo[4,3-b]pyridazine.

1H NMR (499.8 MHz, DMSO-d6) δ 2.96 (2H, s), 3.55 (2H, s), 3.70 (3H, s), 3.72-3.76 (2H, m), 6.79-6.81 (1H, m), 6.85-6.86 (2H, m), 7.21 (1H, t), 7.31 (1H, d), 8.22 (1H, d) (Some peaks obscured by solvent); m/z=419 [M+H]+.

EXAMPLE 195

Preparation of 6-[2-[(4-methoxyphenyl)methyl]-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 4-methoxybenzaldehyde was carried out according to General Synthetic Method 10. The crude product was purified by hplc using a Waters XBridge Prep C18

OBD column, 5µ silica, 30 mm diameter, 100 mm length eluted with decreasingly polar mixtures of water (containing 0.1% aqueous ammonia) and acetonitrile as eluents to give 6-[2-[(4-methoxyphenyl)methyl]-1,3,3a,4,6,6a-hexahydropyrrolo[3,4-c]pyrrol-5-yl]-3-(trifluoromethyl)-[1,2,4]triazolo[4,3-b]pyridazine.

1H NMR (499.8 MHz, DMSO-d6) δ 2.94-2.95 (2H, m), 3.40 (2H, s), 3.50 (2H, s), 3.73 (5H, s), 6.85 (2H, d), 7.19 (2H, d), 7.30 (1H, d), 8.22 (1H, d) (Some peaks obscured by solvent); m/z=419 [M+H]+.

EXAMPLE 196

Preparation of 3-(trifluoromethyl)-6-[2-[[3-(trifluoromethyl)phenyl]methyl]-1,3,3a,4,6,6a-hexahydropyrrolo[3,4-c]pyrrol-5-yl]-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 3-(trifluoromethyl)benzaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 3-(trifluoromethyl)-6-[2-[[3-(trifluoromethyl)phenyl]methyl]-1,3,3a,4,6,6a-hexahydropyrrolo[3,4-c]pyrrol-5-yl]-[1,2,4]triazolo[4,3-b]pyridazine.

1H NMR (499.8 MHz, DMSO-d6) δ 2.61-2.64 (2H, m), 2.97-2.98 (2H, m), 3.34 (1H, s), 3.68 (2H, s), 3.72-3.75 (2H, m), 7.31 (1H, d), 7.54 (1H, t), 7.59-7.67 (3H, m), 8.22 (1H, d) (Some peaks obscured by solvent); m/z=457 [M+H]+.

EXAMPLE 197

Preparation of 3-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]benzonitrile Reductive amination of 6-(hexahydropyrrolo[3,4-c]pyrrol-2(1H)-yl)-3-(trifluoromethyl)-[1,2,4]triazolo[4,3-b]pyridazine with 3-formylbenzonitrile was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 3-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]benzonitrile.

1H NMR (499.8 MHz, DMSO-d6) δ 2.60-2.63 (2H, m), 2.97-2.98 (2H, m), 3.64 (2H, s), 3.73-3.77 (2H, m), 7.31 (1H, d), 7.53 (1H, t), 7.65 (1H, d), 7.71 (2H, d), 8.22 (1H, d) (Some peaks obscured by solvent); m/z=414 [M+H]+.

EXAMPLE 198

Preparation of 6-[2-[(3-chlorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 3-chlorobenzaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[2-[(3-chlorophenyl)methyl]-1,3,3a,4,6,6a-hexahydropyrrolo[3,4-c]pyrrol-5-yl]-3-(trifluoromethyl)-[1,2,4]triazolo[4,3-b]pyridazine.

1H NMR (499.8 MHz, DMSO-d6) δ 2.59-2.62 (2H, m), 2.97 (2H, d), 3.32-3.35 (245H, m), 3.59 (2H, s), 3.72-3.76 (2H, m), 7.25-7.35 (5H, m), 8.22 (1H, d) (Some peaks obscured by solvent); m/z=423 [M+H]+.

EXAMPLE 199

Preparation of 3-(trifluoromethyl)-6-[2-[[4-(trifluoromethyl)phenyl]methyl]-1,3,3a,4,6,6a-hexahydropyrrolo[3,4-c]pyrrol-5-yl]-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 4-(trifluoromethyl)benzaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 3-(trifluoromethyl)-6-[2-[[4-(trifluoromethyl)phenyl]methyl]-1,3,3a,4,6,6a-hexahydropyrrolo[3,4-c]pyrrol-5-yl]-[1,2,4]triazolo[4,3-b]pyridazine.

1H NMR (499.8 MHz, DMSO-d6) δ 2.59-2.62 (1H, m), 2.97-3.01 (2H, m), 3.67 (2H, s), 3.74-3.77 (2H, m), 7.31 (1H, d), 7.52 (2H, d), 7.66 (2H, d), 8.22 (1H, d) (Some peaks obscured by solvent); m/z=457 [M+H]+.

EXAMPLE 200

Preparation of 6-[2-[(3-fluorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 3-fluorobenzaldehyde was carried out according to General Synthetic Method 10. The crude product was purified by hplc using a Waters XBridge Prep C18 OBD column, 5µ silica, 30 mm diameter, 100 mm length eluted with decreasingly polar mixtures of water (containing 0.1% aqueous ammonia) and acetonitrile as eluents to give 6-[2-[(3-fluorophenyl)methyl]-1,3,3a,4,6,6a-hexahydropyrrolo[3,4-c]pyrrol-5-yl]-3-(trifluoromethyl)-[1,2,4]triazolo[4,3-b]pyridazine.

1H NMR (499.8 MHz, DMSO-d6) δ 2.58-2.65 (1H, m), 2.97 (2H, d), 3.60 (2H, s), 3.73-3.77 (2H, m), 7.03-7.07 (1H, m), 7.11 (1H, d), 7.13 (1H, d), 7.30 (1H, t), 7.33-7.36 (1H, m), 8.22 (1H, d) (Some peaks obscured by solvent); m/z=407 [M+H]+.

EXAMPLE 201

Preparation of 3-(trifluoromethyl)-6-[2-[[6-(trifluoromethyl)pyridin-3-yl]methyl]-1,3,3a,4,6,6a-hexahydropyrrolo[3,4-c]pyrrol-5-yl]-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 6-(trifluoromethyl)pyridine-3-carbaldehyde was carried out according to General Synthetic Method 10.

The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 3-(trifluoromethyl)-6-[2-[[6-(trifluoromethyl) pyridin-3-yl]methyl]-1,3,3a,4,6,6a-hexahydropyrrolo[3,4-c] pyrrol-5-yl]-[1,2,4]triazolo[4,3-b]pyridazine.

1H NMR (499.8 MHz, DMSO-d6) δ 2.58-2.64 (4H, m), 2.98-3.02 (2H, m), 3.34 (1H, s), 3.73-3.75 (4H, m), 3.77 (1H, s), 7.31 (1H, d), 7.84 (1H, d), 7.99 (1H, d), 8.22 (1H, d), 8.69 (1H, s) (Some peaks obscured by solvent); m/z=458 [M+H]+.

EXAMPLE 202

Preparation of 4-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]-1H-pyridin-2-one Reductive amination of 6-(hexahydropyrrolo[3,4-c]pyrrol-2(1H)-yl)-3-(trifluoromethyl)-[1,2,4]triazolo[4,3-b]pyridazine with 2-hydroxypyridine-4-carbaldehyde was carried out according to General Synthetic Method 10. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 4-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]-1H-pyridin-2-one.

1H NMR (499.8 MHz, DMSO-d6) δ 2.58-2.59 (2H, m), 2.98-2.99 (2H, m), 3.78 (2H, t), 6.11 (1H, d), 6.21 (1H, s), 7.25 (1H, d), 7.32 (1H, d), 8.22 (1H, d) (Some peaks obscured by solvent); m/z=406 [M+H]+.

EXAMPLE 203

Preparation of 6-[2-[(4-fluorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 4-fluorobenzaldehyde was carried out according to General Synthetic Method 10. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[2-[(4-fluorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine.

1H NMR (499.8 MHz, DMSO-d6) δ 2.56-2.59) (2H, m), 2.96 (2H, s), 3.56 (2H, s), 3.73-3.76 (2H, m), 7.11 (2H, t), 7.31 (1H, d), 7.32 (2H, t), 8.22 (1H, d) (Some peaks obscured by solvent); m/z=407 [M+H]+.

EXAMPLE 204

Preparation of 6-[2-[(4-chlorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with 4-chlorobenzaldehyde was carried out according to General Synthetic Method 10. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[2-[(4-chlorophenyl)methyl]-1,3,3a,4,6,6a-hexahydropyrrolo [3,4-c]pyrrol-5-yl]-3-(trifluoromethyl)-[1,2,4]triazolo[4,3-b]pyridazine.

1H NMR (499.8 MHz, DMSO-d6) δ 2.56-2.59 (2H, m), 2.96 (2H, s), 3.57 (2H, s), 3.74 (1H, d), 3.77 (1H, s), 7.29-7.36 (5H, m), 8.21-8.23 (1H, m) (Some peaks obscured by solvent); m/z=423 [M+H]+.

EXAMPLE 205

Preparation of 4-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl]benzonitrile Reductive amination of 6-(hexahydropyrrolo[3,4-c]pyrrol-2(1H)-yl)-3-(trifluoromethyl)-[1,2,4]triazolo[4,3-b]pyridazine with 4-formylbenzonitrile was carried out according to General Synthetic Method 10. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 4-[[5-[3-(trifluoromethyl)-[1,2,4]triazolo[4,3-b]pyridazin-6-yl]-1,3,3a,4,6,6a-hexahydropyrrolo[3,4-c]pyrrol-2-yl]methyl] benzonitrile.

1H NMR (499.8 MHz, DMSO-d6) δ 2.54-2.62 (4H, m), 2.97-2.98 (2H, m), 3.67 (2H, s), 3.78-3.74 (2H, m), 7.31 (1H, d), 7.50 (2H, d), 8.22 (1H, d) (Some peaks obscured by solvent); m/z=414 [M+H]+.

EXAMPLE 206

Preparation of 6-[2-(pyridin-3-ylmethyl)-1,3,3a,4,6,6a-hexahydropyrrolo [3,4-c]pyrrol-5-yl]-3-(trifluoromethyl)-[1,2,4]triazolo[4,3-b]pyridazine Reductive amination of 6-(hexahydropyrrolo[3,4-c]pyrrol-2(1H)-yl)-3-(trifluoromethyl)-[1,2,4]triazolo[4,3-b]pyridazine with pyridine-3-carbaldehyde was carried out according to General Synthetic Method 10. The crude product was purified by hplc using a Waters XBridge Prep C18 OBD column, 5μ silica, 30 mm diameter, 100 mm length eluted with decreasingly polar mixtures of water (containing 0.1% aqueous ammonia) and acetonitrile as eluents to give 6-[2-(pyridin-3-ylmethyl)-1,3,3a,4,6,6a-hexahydropyrrolo [3,4-c]pyrrol-5-yl]-3-(trifluoromethyl)-[1,2,4]triazolo[4,3-b]pyridazine.

1H NMR (499.8 MHz, DMSO-d6) δ 2.53-2.56 (2H, m), 2.59-2.62 (2H, m), 2.93-3.01 (2H, m), 3.61 (2H, s), 3.72-3.76 (2H, m), 7.28-7.31 (1H, m), 7.33 (1H, d), 7.68-7.70 (1H, m), 8.22 (1H, d), 8.45-8.46 (1H, m), 8.49 (1H, d) (Some peaks obscured by solvent); m/z=390 [M+H]+.

EXAMPLE 207

Preparation of (3-methoxyphenyl)-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]methanone The amine 6-(hexahydropyrrolo[3,4-c]pyrrol-2(1H)-yl)-3-(trifluoromethyl)-[1,2,4]triazolo[4,3-b]pyridazine was acylated with 3-methoxybenzoyl chloride by General Synthetic Method 11. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give (3-methoxyphenyl)-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]methanone.

1H NMR (300.132 MHz, DMSO-d6) δ 2.96-3.17 (2H, m), 3.34-3.60 (4H, m), 3.62-3.90 (7H, m), 6.98-7.11 (3H, m), 7.23 (1H, d), 7.34 (1H, t), 8.23 (1H, d); m/z=433 [M+H]+.

EXAMPLE 208

Preparation of 2-methyl-1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]propan-1-one The amine 6-(hexahydropyrrolo[3,4-c]pyrrol-2(1H)-yl)-3-(trifluoromethyl)-[1,2,4]triazolo[4,3-b]pyridazine was acylated with 2-methylpropanoyl chloride by General Synthetic Method 11. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 2-methyl-1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]propan-1-one.

1H NMR (300.132 MHz, DMSO-d6) δ 0.94-1.05 (6H, m), 2.59-2.70 (1H, m), 2.95-3.19 (2H, m), 3.24-3.29 (1H, m), 3.35-3.54 (3H, m), 3.55-3.64 (1H, m), 3.71-3.83 (3H, m), 7.24 (1H, d), 8.22 (1H, d) (Signal at 3.3 partially obscured by water); m/z=369 [M+H]+.

EXAMPLE 209

Preparation of 3-methyl-1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]butan-1-one The amine 6-(hexahydropyrrolo[3,4-c]pyrrol-2(1H)-yl)-3-(trifluoromethyl)-[1,2,4]triazolo[4,3-b]pyridazine was acylated with 3-methylbutanoyl chloride by General Synthetic Method 11. The crude product was purified by hplc using a Waters XBridge Prep C18 OBD column (5μ silica, 19 mm diameter, 100 mm length) eluted with decreasingly polar mixtures of water (containing 1% aqueous ammonia) and acetonitrile as eluents to give 3-methyl-1-[2-[3-(trifluoromethyl)-[1,2,4]triazolo[4,3-b]pyridazin-6-yl]-1,3,3a,4,6,6a-hexahydropyrrolo[3,4-c]pyrrol-5-yl]butan-1-one.

1H NMR (300.132 MHz, DMSO-d6) δ 0.84-0.94 (6H, m), 1.92-2.06 (1H, m), 2.09-2.15 (2H, m), 2.92-3.18 (2H, m), 3.24-3.35 (1H, m), 3.35-3.48 (3H, m), 3.54-3.64 (1H, m), 3.67-3.82 (3H, m), 7.24 (1H, d), 8.22 (1H, d) (Signal at 3.3 partially obscured by water); m/z=383 [M+H]+.

EXAMPLE 210

Preparation of 6-(5-benzyl-1,3,3a,4,6,6a-hexahydropyrrolo[3,4-c]pyrrol-2-yl)-3-(trifluoromethyl)-[1,2,4]triazolo[3,4-f]pyridazine 2-Benzyl-3,3a,4,5,6,6a-hexahydro-1H-pyrrolo[3,4-c]pyrrole hydrochloride (0.129 g, 0.54 mmol) and then diisopropylethylamine (0.070 g, 0.54 mmol) were added sequentially to a solution of 6-chloro-3-(trifluoromethyl)-[1,2,4]triazolo[3,4-f]pyridazine (0.080 g, 0.36 mmol) in ethanol (2 mL). The reaction mixture was heated at 70° C. for 4 hours and then evaporated to leave an involatile residue. The residue was purified by preparative hplc using a Phenomenex Luna C18 100A column (10% silica, 21 mm diameter, 150 mm length) eluted with decreasingly polar mixtures of water (containing 0.1% trifluoroacetic acid) and acetonitrile as eluents to give a partially purified product that was further purified by ion exchange chromatography an SCX column eluted with 7M aqueous ammonia in methanol as eluents to give 6-(5-benzyl-1,3,3a,4,6,6a-hexahydropyrrolo[3,4-c]pyrrol-2-yl)-3-(trifluoromethyl)-[1,2,4]triazolo[3,4-f]pyridazine (0.116 g, 83%) as a white solid.

1H NMR (300.132 MHz, CDCl3) 2.57-2.71 (4H, m), 2.96-3.09 (2H, m), 3.39-3.49 (2H, m), 3.61 (2H, s), 3.74-3.86 (2H, m), 6.87 (1H, d), 7.20-7.34 (5H, m), 7.89 (1H, d); m/z=389 [M+H]+.

EXAMPLE 211

Preparation of tert-butyl 5-(3-(trifluoromethyl)-[1,2,4]triazolo[4,3-b]pyridazin-6-yl)hexahydropyrrolo[3,4-c]pyrrole-2(1H)-carboxylate tert-Butyl hexahydropyrrolo[3,4-c]pyrrole-2(1H)-carboxylate (3.15 g, 14.83 mmol) was added to a mixture of 6-chloro-3-(trifluoromethyl)-[1,2,4]triazolo[4,3-b]pyridazine (3 g, 13.48 mmol) and diisopropyethylamine (4.66 mL, 26.96 mmol) and ethanol (50 mL). The mixture was warmed to 70° C. over a period of 10 minutes, stirred at 70° C. for 1 hour, and then allowed to cool to ambient temperature to give a precipitate. The precipitate was collected by filtration, washed with ethanol (50 mL), and dried under vacuum to afford tert-butyl 5-(3-(trifluoromethyl)-[1,2,4]triazolo[4,3-b]pyridazin-6-yl)hexahydropyrrolo[3,4-c]pyrrole-2(1H)-carboxylate (3.00 g, 55.9%) as a white solid.

1H NMR (300.132 MHz, DMSO) d 1.39 (s, 9H), 2.96-3.09 (m, 2H), 3.16-3.26 (m, 2H), 3.35-3.47 (m, 2H), 3.48-3.60 (m, 2H), 3.67-3.80 (m, 2H), 7.23 (d, 1H), 8.22 (d, 1H); m/z 399 (M+H+)

EXAMPLE 212

Preparation of 4-((4-(3-(trifluoromethyl)-[1,2,4]triazolo[4,3-b]pyridazin-6-yl)piperazin-1-yl)methyl)aniline A mixture of trifluoroacetic acid (0.5 mL, 0.15 mmol) and tert-butyl 4-((4-(3-(trifluoromethyl)-[1,2,4]triazolo[4,3-b]pyridazin-6-yl)piperazin-1-yl)methyl)phenylcarbamate (0.072 g, 0.15 mmol) in dichloromethane (2 mL) was stirred at ambient temperature for 2 hours and then evaporated to give an involatile residue. The residue was purified by hplc using a Phenomenex Luna C18 100A column (10μ silica, 21 mm diameter, 150 mm length) eluted with decreasingly polar mixtures of water (containing 0.1% TFA) and acetonitrile as eluents to give a partially purified product that was further purified by ion exchange chromatography using an SCX column eluted 7M aquous ammonia in methanol to give 4-((4-(3-(trifluoromethyl)-[1,2,4]triazolo[4,3-b]pyridazin-6-yl)piperazin-1-yl)methyl)aniline (0.032 g, 56.2%) as a white solid.

1H NMR (300.132 MHz, DMSO-d6) δ 2.24-2.32 (4H, m), 3.18 (2H, s), 3.35-3.49 (4H, m), 4.79 (2H, s), 6.36 (2H, d), 6.79 (2H, d), 7.41 (1H, d), 8.07 (1H, d); m/z=378 [M+H]+.

The tert-butyl 4-((4-(3-(trifluoromethyl)-[1,2,4]triazolo[4,3-b]pyridazin-6-yl)piperazin-1-yl)methyl)phenylcarbamate used as starting material was prepared as follows:—

Preparation of tert-butyl 4-((4-(3-(trifluoromethyl)-[1,2,4]triazolo[4,3-b]pyridazin-6-yl)piperazin-1-yl)methyl)phenylcarbamate A solution of 6-(piperazin-1-yl)-3-(trifluoromethyl)-[1,2,4]triazolo[4,3-b]pyridazine (0.079 g, 0.29 mmol) in a mixture of acetic acid and dichloromethane (1:9; 3 mL) was added to a mixture of (polystyrylmethyl)trimethylammonium cyanoborohydride (4.1 mmol/g, 0.097 g, 0.4 mmol) and N-(4-formylphenyl)carbamic acid tert-butyl ester (0.088.4 g, 0.4 mmol). The reaction mixture was shaken for 4 days and then filtered. The filtrate was evaporated and the and the involatile residue was purified by hplc using a Waters XBridge Prep C18 OBD column (5μ silica, 21 mm diameter, 100 mm length) eluted with decreasingly polar mixtures of water (containing 0.05% aqueous ammonia) and acetonitrile as eluents to give tert-butyl 4-((4-(3-(trifluoromethyl)-[1,2,4]triazolo[4,3-b]pyridazin-6-yl)piperazin-1-yl)methyl)phenylcarbamate (0.0722 g, 52%) as a white solid, which was used without further purification.

EXAMPLE 213

N-(4-fluorophenyl)-2-[3-(trifluoromethyl)-[1,2,4]triazolo[3,4-f]pyridazin-6-yl]-1,3,3a,4,6,6a-hexahydropyrrolo[3,4-c]pyrrole-5-carboxamide 1-Fluoro-4-isocyanatobenzene (0.026 g, 0.19 mmol) was added to a suspension of 6-(hexahydropyrrolo[3,4-c]pyrrol-2(1H)-yl)-3-(trifluoromethyl)-[1,2,4]triazolo[4,3-b]pyridazine (0.05 g, 0.17 mmol) in toluene (1.5 mL). The reaction mixture was heated at 70° C. for 1 hour and evaporated to give an involatile residue. The residue was purified by hplc using a Phenomenex Luna C18 100A column (10μ silica, 21 mm diameter, 150 mm length) eluted with decreasingly polar mixtures of water (containing 0.1% trifluoroacetic acid) and acetonitrile as eluents to give N-(4-fluorophenyl)-2-[3-(trifluoromethyl)-[1,2,4]triazolo[3,4-f]pyridazin-6-yl]-1,3,3a,4,6,6a-hexahydropyrrolo[3,4-c]pyrrole-5-carboxamide (0.0309 g, 42%) as a white solid.

EXAMPLE 214

N,N-dimethyl-2-[3-(trifluoromethyl)-[1,2,4]triazolo[3,4-f]pyridazin-6-yl]-1,3,3a,4,6,6a-hexahydropyrrolo[3,4-c]pyrrole-5-sulfonamide N,N-Dimethylsulfamoyl chloride (0.027 g, 0.19 mmol) and then dichloromethane were added sequentially to a mixture of diisopropylethylamineamine (0.044 g, 0.34 mmol) and 6-(hexahydropyrrolo[3,4-c]pyrrol-2(1H)-yl)-3-(trifluoromethyl)-[1,2,4]triazolo[4,3-b]pyridazine (0.05 g, 0.17 mmol) in toluene (1.5 mL). The reaction mixture was stirred for 1 hour and evaporated to give an involatile residue. The residue was purified by preparative hplc using a Phenomenex Luna C18 100A column (10μ silica, 21 mm diameter, 150 mm length) eluted with decreasingly polar mixtures of water (containing 0.1% trifluoroacetic acid) and acetonitrile as eluents to give N,N-dimethyl-2-[3-(trifluoromethyl)-[1,2,4]triazolo[3,4-f]pyridazin-6-yl]-1,3,3a,4,6,6a-hexahydropyrrolo[3,4-c]pyrrole-5-sulfonamide (0.0206 g, 30%) as a white solid.

1H NMR (300.132 MHz, DMSO-d6) δ 2.75 (6H, s), 3.05-3.15 (2H, m), 3.17-3.24 (2H, m), 3.40-3.55 (4H, m), 3.72-3.81 (2H, m), 7.27 (1H, d), 8.23 (1H, d); m/z=406 [M+H]+.

EXAMPLE 215

6-(5-ethylsulfonyl-1,3,3a,4,6,6a-hexahydropyrrolo[3,4-c]pyrrol-2-yl)-3-(trifluoromethyl)-[1,2,4]triazolo[3,4-f]pyridazine Ethanesulfonyl chloride (0.024 g, 0.19 mmol) and then dichloromethane (0.5 mL) were added sequentially to a mixture of diisopropylethylamine (0.044 g, 0.34 mmol) and 6-(hexahydropyrrolo[3,4-c]pyrrol-2(1H)-yl)-3-(trifluoromethyl)-[1,2,4]triazolo[4,3-b]pyridazine (0.050 g, 0.17 mmol) in toluene (1.5 mL). The reaction mixture was stirred for 1 hour at ambient temperature and then for 1.5 hours at 50° C. and then evaporated to give an involatile residue. The residue was purified by preparative hplc using a Phenomenex Luna C18 100A column (10μ silica, 21 mm diameter, 150 mm length) eluted with decreasingly polar mixtures of water (containing 0.1% trifluoroacetic acid) and acetonitrile as eluents to give 6-(5-ethylsulfonyl-1,3,3a,4,6,6a-hexahydropyrrolo[3,4-c]pyrrol-2-yl)-3-(trifluoromethyl)-[1,2,4]triazolo[3,4-f]pyridazine (0.0143 g, 22%) as a white solid.

1H NMR (300.132 MHz, DMSO-d6) δ 2.75 (6H, s), 3.05-3.15 (2H, m), 3.17-3.24 (2H, m), 3.40-3.55 (4H, m), 3.72-3.81 (2H, m), 7.27 (1H, d), 8.23 (1H, d); m/z=406 [M+H]+.

EXAMPLE 216

Preparation of 6-[(2R,5S)-4-benzyl-2,5-dimethylpiperazin-1-yl]-3-(trifluoromethyl)[1,2,4]triazolo[4,3-b]pyridazine

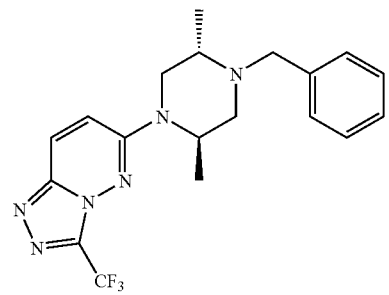

A stirred solution of 6-chloro-3-(trifluoromethyl)-[1,2,4]triazolo[4,3-b]pyridazine (4.45 g, 20 mmol), (2S,5R)-1-benzyl-2,5-dimethylpiperazine (4.90 g, 24.00 mmol) and DIPEA (5.14 mL, 30.00 mmol) in DMF (40 mL) was heated at 125° C. for 2 hours. The reaction mixture was evaporated to dryness, redissolved in DCM and washed sequentially with 1M aqueous $K_2CO_3$, water and saturated brine. The organic layer was dried over MgSO4, filtered and evaporated. The crude product was purified by MPLC silica chromatography, eluting with 75% EtOAc/isohexane. Pure fractions were evaporated to dryness to afford 6-[(2R,5S)-4-benzyl-2,5-dimethylpiperazin-1-yl]-3-(trifluoromethyl)[1,2,4]triazolo[4,3-b]pyridazine (6.16 g, 79%) as a tan gum.

1H NMR (399.9 MHz, DMSO-d6) δ 1.01-1.03 (3H, m), 1.26 (3H, d), 2.34-2.37 (1H, m), 2.80-2.84 (1H, m), 3.11 (1H, t), 3.44-3.48 (1H, m), 3.53 (1H, d), 3.66 (1H, d), 3.93 (1H, d), 4.42 (1H, s), 7.24-7.30 (1H, m), 7.31-7.41 (4H, m), 7.56-7.59 (1H, m), 8.22-8.26 (1H, m); m/z=391 [M+H]+.

EXAMPLE 217

Preparation of 6-[(2R,5S)-2,5-dimethyl-4-(pyridin-3-ylmethyl)piperazin-1-yl]-3-(trifluoromethyl)[1,2,4]triazolo[4,3-b]pyridazine

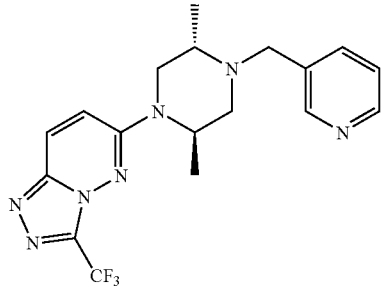

A mixture of pyridine-3-carboxaldehyde and 6-[(2R,5S)-2,5-dimethylpiperazin-1-yl]-3-(trifluoromethyl)-[1,2,4]triazolo[4,3-b]pyridazine was allowed to react by General Synthetic Method 5 to give 6-[(2R,5S)-2,5-dimethyl-4-(3-pyridylmethyl)piperazin-1-yl]-3-(trifluoromethyl)-[1,2,4]triazolo[4,3-b]pyridazine in 84% yield.

1H NMR (399.9 MHz, CDCl3) δ 1.09-1.11 (3H, m), 1.33 (3H, d), 2.36-2.40 (1H, m), 2.88-2.95 (1H, m), 3.15-3.18 (1H, m), 3.53-3.59 (2H, m), 3.69 (1H, d), 3.84 (1H, d), 4.31 (1H, s), 7.03 (1H, d), 7.28-7.30 (1H, m), 7.71-7.74 (1H, m), 7.91 (1H, d), 8.52-8.54 (1H, m), 8.60 (1H, d); m/z=392 [M+H]+.

The 6-[(2R,5S)-2,5-dimethylpiperazin-1-yl]-3-(trifluoromethyl)-[1,2,4]triazolo[4,3-b]pyridazine used as starting material was prepared as follows:—

A solution of 6-[(2R,5S)-4-benzyl-2,5-dimethylpiperazin-1-yl]-3-(trifluoromethyl)[1,2,4]triazolo[4,3-b]pyridazine (6.1 g, 15.62 mmol) in ethanol (150 mL) and 5M hydrochloric acid (9.37 mL, 46.87 mmol) was hydrogenated over 10% palladium on charcoal (1 g, 9.40 mmol) under hydrogen at 1 atmosphere for 3 days. The catalyst was filtered off and the filtrate was evaporated. The residue was taken into DCM and washed with 2M aqueous K₂CO₃. The organic phase was dried over MgSO4 and evaporated. The crude product was purified by MPLC silica chromatography, elution gradient 2 to 5% methanolic ammonia in DCM. Product fractions were evaporated to near dryness and crystallised from ether to afford 6-[(2R,5S)-2,5-dimethylpiperazin-1-yl]-3-(trifluoromethyl)-[1,2,4]triazolo[4,3-b]pyridazine (1.430 g, 30.5%) as a white crystalline solid.

1H NMR (400.1 MHz, CDCl3) δ 1.23-1.25 (3H, m), 1.33 (3H, d), 2.71-2.75 (1H, m), 3.32-3.39 (2H, m), 3.47 (1H, d), 3.59-3.64 (1H, m), 4.15-4.19 (1H, m), 7.04 (1H, d), 7.92 (1H, d); m/z=301 [M+H]+

EXAMPLES 218-222

The following compounds were prepared in 73-82% yield by General Synthetic Method 5, starting from 6-[(2R,5S)-2,5-dimethylpiperazin-1-yl]-3-(trifluoromethyl)-[1,2,4]triazolo[4,3-b]pyridazine and the appropriate aldehyde:—

| Ex. | R | 1H NMR (399.9 MHz, CDCl3) | m/z [M + H]+ |
|---|---|---|---|
| 218 | 4-CN | δ 1.09-1.10 (3H, m), 1.35 (3H, d), 2.33-2.36 (1H, m), 2.90-2.94 (1H, m), 3.16 (1H, d), 3.58 (2H, d), 3.72-3.75 (1H, m), 3.85 (1H, d), 4.32 (1H, s), 7.03 (1H, d), 7.51 (2H, d), 7.63 (2H, d), 7.92 (1H, d) | 416 |
| 219 | 3,4-di-F | δ 1.07 (3H, d), 1.33-1.35 (3H, m), 2.35-2.38 (1H, m), 2.87-2.91 (1H, m), 3.13-3.16 (1H, m), 3.50 (1H, d), 3.53-3.57 (1H, m), 3.62 (1H, d), 3.84 (1H, d), 4.31 (1H, s), 7.02-7.15 (3H, m), 7.21-7.30 (1H, m), 7.91 (1H, d) | 427 |
| 220 | 3,5-di-F | δ 1.07-1.09 (3H, m), 1.36 (3H, d), 2.36-2.40 (1H, m), 2.89-2.93 (1H, m), 3.14-3.17 (1H, m), 3.51-3.59 (2H, m), 3.66 (1H, d), 3.85 (1H, d), 4.32 (1H, d), 6.68-6.74 (1H, m), 6.91-6.95 (2H, m), 7.04 (1H, d), 7.92 (1H, d) | 427 |
| 221 | 4-F | δ 1.07 (3H, d), 1.32 (3H, d), 2.35-2.39 (1H, m), 2.86-2.90 (1H, m), 3.13-3.16 (1H, m), 3.50-3.56 (2H, m), 3.63 (1H, d), 3.83 (1H, d), 4.30 (1H, t), 7.00-7.05 (3H, m), 7.32-7.35 (2H, m), 7.89-7.91 (1H, m) | 409 |
| 222 | 3-CN, 4-F | δ 1.09 (3H, d), 1.34 (3H, d), 2.31-2.35 (1H, m), 2.89-2.93 (1H, m), 3.12-3.16 (1H, m), 3.52-3.58 (1H, m), 3.65-3.69 (1H, m), 3.84-3.87 (1H, m), 4.33 (1H, s), 7.04 (1H, d), 7.20 (1H, t), 7.60-7.67 (2H, m), 7.92 (1H, d) | 434 |

EXAMPLE 223

Preparation of 6-[(2S,5R)-2,5-dimethyl-4-(pyridin-3-ylmethyl)piperazin-1-yl]-3-(trifluoromethyl)[1,2,4]triazolo[4,3-b]pyridazine

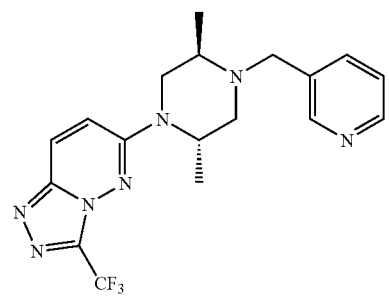

A mixture of pyridine-3-carboxaldehyde and 6-[(2S,5R)-2,5-dimethylpiperazin-1-yl]-3-(trifluoromethyl)-[1,2,4]triazolo[4,3-b]pyridazine was allowed to react by General Synthetic Method 5 to give 6-[(2S,5R)-2,5-dimethyl-4-(pyridin-3-ylmethyl)piperazin-1-yl]-3-(trifluoromethyl)[1,2,4]triazolo[4,3-b]pyridazine in 84% yield.

1H NMR (399.9 MHz, CDCl3) δ 1.09-1.11 (3H, m), 1.33 (3H, d), 2.36-2.40 (1H, m), 2.88-2.95 (1H, m), 3.15-3.18 (1H, m), 3.53-3.59 (2H, m), 3.69 (1H, d), 3.84 (1H, d), 4.31 (1H, s), 7.03 (1H, d), 7.28-7.30 (1H, m), 7.71-7.74 (1H, m), 7.91 (1H, d), 8.52-8.54 (1H, m), 8.60 (1H, d); m/z=392 [M+H]+.

The 6-[(2S,5R)-2,5-dimethylpiperazin-1-yl]-3-(trifluoromethyl)-[1,2,4]triazolo[4,3-b]pyridazine used as starting material was prepared as follows:—

Preparation of (2R,5S)-tert-butyl 2,5-dimethyl-4-[3-(trifluoromethyl)-[1,2,4]triazolo[4,3-b]pyridazin-6-yl]piperazine-1-carboxylate A stirred solution of 6-chloro-3-(trifluoromethyl)-[1,2,4]triazolo[4,3-b]pyridazine (4.45 g, 20 mmol), (2R,5S)-tert-butyl 2,5-dimethylpiperazine-1-carboxylate (5.14, 24 mmol) and DIPEA (5.14 mL, 30.00 mmol) in DMF (40.0 mL) was heated at 125° C. for 2.5 hours. The reaction mixture was evaporated to dryness, redissolved in DCM and washed sequentially with 1M aqueous K₂CO₃, water and saturated brine. The organic layer was dried over MgSO4, filtered and evaporated. The crude product was purified by MPLC silica chromatography, eluting with EtOAc. Product fractions were evaporated and triturated with ether. The solid was collected by filtration, washed with ether and dried under vacuum to afford (2R,5S)-tert-butyl 2,5-dimethyl-4-[3-(trifluoromethyl)-[1,2,4]triazolo[4,3-b]pyridazin-6-yl]piperazine-1-carboxylate (6.09 g, 76%) as a white crystalline solid.

1H NMR (399.9 MHz, DMSO-d6) δ 1.14-1.21 (6H, m), 1.44 (9H, s), 3.36-3.42 (2H, m), 3.71 (1H, d), 3.88 (1H, d), 4.25-4.35 (1H, m), 4.47 (1H, s), 7.59 (1H, d), 8.28 (1H, d); m/z=401 [M+H]+.

Preparation of 6-[(2S,5R)-2,5-dimethylpiperazin-1-yl]-3-(trifluoromethyl)-[1,2,4]triazolo[4,3-b]pyridazine (2R,5S)-tert-Butyl 2,5-dimethyl-4-[3-(trifluoromethyl)-[1,2,4]triazolo[4,3-b]pyridazin-6-yl]piperazine-1-carboxylate (6.01 g, 15 mmol) was added in portions to stirred TFA (25 mL) over 5 minutes. There was a moderate exotherm and the reaction mixture was allowed to stir for a further 15 minutes. The bulk of the TFA was evaporated and the residue was basified with 1M aqueous K₂CO₃. It was extracted thoroughly with DCM (4×200 mL) and the combined organic phase was dried over MgSO4 and evaporated to give an oil which rapidly crystallised. The solid was collected by filtration and dried under vacuum to give 6-[(2S,5R)-2,5-dimethylpiperazin-1-yl]-3-(trifluoromethyl)-[1,2,4]triazolo[4,3-b]pyridazine (3.52 g, 78%) as a white crystalline solid.

1H NMR (400.1 MHz, CDCl3) δ 1.23-1.25 (3H, m), 1.33 (3H, d), 2.71-2.75 (1H, m), 3.32-3.39 (2H, m), 3.47 (1H, d), 3.59-3.64 (1H, m), 4.15-4.19 (1H, m), 7.04 (1H, d), 7.92 (1H, d); m/z=301 [M+H]+.

EXAMPLES 224-228

The following compounds were prepared in 63-84% yield by General Synthetic Method 5, starting from 6-[(2S,5R)-2,5-dimethylpiperazin-1-yl]-3-(trifluoromethyl)-[1,2,4]triazolo[4,3-b]pyridazine and the appropriate aldehyde:—

| Ex. | R | 1H NMR (399.9 MHz, CDCl3) | m/z [M + H]+ |
|---|---|---|---|
| 224 | 3,4-di-F | δ 1.07 (3H, d), 1.33-1.35 (3H, m), 2.35-2.38 (1H, m), 2.87-2.91 (1H, m), 3.13-3.16 (1H, m), 3.50 (1H, d), 3.53-3.57 (1H, m), 3.62 (1H, d), 3.84 (1H, d), 4.31 (1H, s), 7.02-7.15 (3H, m), 7.21-7.30 (1H, m), 7.91 (1H, d) | 427 |
| 225 | 3,5-di-F | δ 1.07-1.09 (3H, m), 1.36 (3H, d), 2.36-2.40 (1H, m), 2.89-2.93 (1H, m), 3.14-3.17 (1H, m), 3.51-3.59 (2H, m), 3.66 (1H, d), 3.85 (1H, d), 4.32 (1H, d), 6.68-6.74 (1H, m), 6.91-6.95 (2H, m), 7.04 (1H, d), 7.92 (1H, d) | 426 |
| 226 | 4-F | δ 1.07 (3H, d), 1.32 (3H, d), 2.35-2.39 (1H, m), 2.86-2.90 (1H, m), 3.13-3.16 (1H, m), 3.50-3.56 (2H, m), 3.63 (1H, d), 3.83 (1H, d), 4.30 (1H, t), 7.00-7.05 (3H, m), 7.32-7.35 (2H, m), 7.89-7.91 (1H, m) | 408 |
| 227 | 3-CN, 4-F | δ 1.09 (3H, d), 1.34 (3H, d), 2.31-2.35 (1H, m), 2.89-2.93 (1H, m), 3.12-3.16 (1H, m), 3.52-3.58 (2H, m), 3.65-3.69 (1H, m), 3.84-3.87 (1H, m), 4.33 (1H, s), 7.04 (1H, d), 7.20 (1H, t), 7.60-7.67 (2H, m), 7.92 (1H, d) | 434 |
| 228 | 4-CN | δ 1.10 (3H, d), 1.35 (3H, d), 2.33-2.36 (1H, m), 2.90-2.94 (1H, m), 3.14-3.17 (1H, m), 3.54-3.62 (2H, m), 3.72-3.75 (1H, m), 3.85 (1H, s), 4.33 (1H, d), 7.04 (1H, d), 7.50-7.52 (2H, m), 7.63-7.65 (2H, m), 7.92 (1H, d). | 416 |

EXAMPLE 229

Preparation of 6-[4-[2-(2-fluorophenyl)ethyl]piperazin-1-yl]-3-(trifluoromethyl)[1,2,4]triazolo[4,3-b]pyridazine

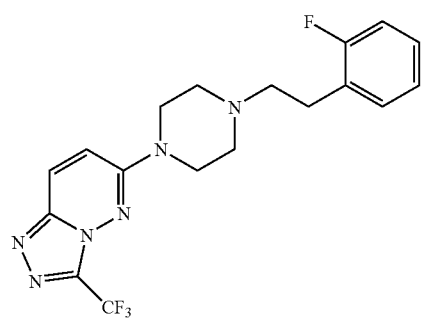

A stirred solution of 6-(piperazin-1-yl)-3-(trifluoromethyl)-[1,2,4]triazolo[4,3-b]pyridazine dihydrochloride (0.173 g, 0.5 mmol), DIPEA (0.300 mL, 1.75 mmol) and 2-fluorophenethyl bromide (0.084 mL, 0.60 mmol) in DMF (2 mL) was heated at 100° C. for 2.5 hours. The reaction was incomplete and further DIPEA (0.300 mL, 1.75 mmol) and 2-fluorophenethyl bromide (0.084 mL, 0.60 mmol) were added. The solution was stirred at 100° C. for a further 90 minutes. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[2-(2-fluorophenyl)ethyl]piperazin-1-yl]-3-(trifluoromethyl)[1,2,4]triazolo[4,3-b]pyridazine (0.131 g, 66.4%) as a crisp foam.

1H NMR (399.9 MHz, DMSO-d6) δ 2.53-2.61 (6H, m), 2.81-2.85 (2H, m), 3.61 (4H, t), 7.12-7.17 (2H, m), 7.23-7.27 (1H, m), 7.34-7.39 (1H, m), 7.61 (1H, d), 8.25 (1H, d); m/z=395 [M+H]+.

EXAMPLES 230-235

The following compounds were prepared in 24-64% yield by an analogous method to Example 229, starting from 6-(piperazin-1-yl)-3-(trifluoromethyl)-[1,2,4]triazolo[4,3-b]pyridazine and the appropriate phenethyl bromide:—

| Ex. | R | 1H NMR (399.9 MHz, CDCl3) | m/z [M + H]+ |
|---|---|---|---|
| 230 | 4-F | δ 2.63-2.67 (6H, m), 2.79-2.83 (2H, m), 3.65 (4H, t), 6.96-7.01 (2H, m), 7.07 (1H, d), 7.15-7.19 (2H, m), 7.93 (1H, d) | 395 |
| 231 | 4-Cl | δ 2.63-2.67 (6H, m), 2.79-2.82 (2H, m), 3.64 (4H, t), 7.06 (1H, d), 7.13-7.16 (2H, m), 7.25-7.28 (2H, m), 7.93 (1H, d) | 411 |
| 232 | 2-Cl | δ 2.66-2.71 (6H, m), 2.95-2.99 (2H, m), 3.66 (4H, t), 7.07 (1H, d), 7.14-7.22 (2H, m), 7.25 (1H, d), 7.34-7.36 (1H, m), 7.93 (1H, d) | 411 |
| 233 | 3-Cl | δ 2.64-2.68 (6H, m), 2.79-2.83 (2H, m), 3.65 (4H, t), 7.05-7.11 (2H, m), 7.18-7.25 (3H, m), 7.93 (1H, s) | 411 |
| 234 | 3-F | δ 2.64-2.70 (6H, m), 2.82-2.86 (2H, m), 3.65 (4H, t), 6.88-6.95 (2H, m), 6.99 (1H, s), 7.07 (1H, d), 7.23-7.28 (1H, m), 7.93 (1H, d) | 395 |
| 235 | 4-CN | δ 2.64-2.70 (6H, m), 2.87-2.91 (2H, m), 3.64 (4H, t), 7.06 (1H, d), 7.32-7.34 (2H, m), 7.58-7.61 (2H, m), 7.93 (1H, d) | 402 |

EXAMPLES 236-247

The following compounds were prepared in 33-89% yield by an analogous method to Example 216, starting from the appropriate 3-substituted 6-chloro-[1,2,4]triazolo[4,3-b]pyridazine (obtained as described in the corresponding footnote) and the appropriate benzyl piperazine:—

| Ex. | Note | R1 | R2 | 1H NMR (399.9 MHz, CDCl3) | m/z [M + H]+ |
|---|---|---|---|---|---|
| 236 | [1] | 4-F | H | δ 2.57 (4H, t), 3.54 (2H, s), 3.61 (4H, t), 6.99-7.05 (3H, m), 7.12 (1H, t), 7.25-7.33 (2H, m), 7.88-7.91 (1H, m) | 363 |
| 237 | [1] | 4-CN | H | δ 2.59 (4H, t), 3.62-3.64 (6H, m), 7.02 (1H, d), 7.12 (1H, t), 7.49 (2H, d), 7.62-7.65 (2H, m), 7.91 (1H, d) | 370 |
| 238 | [1] | 3-CN | H | δ 2.59 (4H, t), 3.60 (2H, s), 3.63 (4H, t), 7.03 (1H, d), 7.12 (1H, t), 7.45 (1H, t), 7.57-7.60 (2H, m), 7.69 (1H, t), 7.91 (1H, d) | 370 |
| 239 | [1] | 3-F | H | δ 2.59 (4H, t), 3.57 (2H, s), 3.63 (4H, t), 6.95-6.99 (1H, m), 7.02 (1H, d), 7.08-7.12 (2H, m), 7.12 (1H, t), 7.25-7.32 (1H, m), 7.90 (1H, d) | 363 |
| 240 | [2] | 4-F | Me | δ 2.30 (3H, t), 2.57 (4H, t), 3.53 (2H, s), 3.60 (4H, t), 6.98-7.01 (1H, m), 7.00-7.05 (2H, m), 7.29-7.32 (2H, m), 7.88 (1H, d) | 377 |
| 241 | [2] | 4-CN | Me | δ 2.30 (3H, t), 2.59 (4H, t), 3.61-3.63 (6H, m), 7.00 (1H, d), 7.48 (2H, d), 7.62-7.65 (2H, m), 7.90 (1H, d) | 384 |
| 242 | [2] | 3-CN | Me | δ 2.30 (3H, t), 2.59 (4H, t), 3.60 (2H, s), 3.63 (4H, t), 7.00 (1H, d), 7.45 (1H, t), 7.56-7.60 (2H, m), 7.69-7.69 (1H, m), 7.90 (1H, d) | 384 |
| 243 | [2] | 3-F | Me | δ 2.30 (3H, t), 2.59 (4H, t), 3.56 (2H, s), 3.62 (4H, t), 6.94-6.99 (1H, m), 7.00 (1H, d), 7.08-7.11 (2H, m), 7.26-7.32 (1H, m), 7.89 (1H, d) | 377 |
| 244 | [3] | 4-F | Et | δ 1.18 (3H, t), 2.56-2.70 (6H, m), 3.53 (2H, s), 3.60 (4H, t), 6.98-7.01 (1H, m), 6.99-7.05 (2H, m), 7.28-7.32 (2H, m), 7.87-7.89 (1H, m) | 391 |
| 245 | [3] | 4-CN | Et | δ 1.18 (3H, t), 2.60 (4H, q), 2.56-2.70 (2H, m), 3.57-3.62 (4H, m), 3.60-3.63 (2H, m), 7.00 (1H, d), 7.48 (2H, d), 7.62-7.65 (2H, m), 7.90 (1H, d) | 398 |
| 246 | [3] | 3-CN | Et | δ 1.18 (3H, t), 2.59-2.61 (2H, m), 2.56-2.70 (4H, m), 3.60 (2H, s), 3.62 (4H, t), 7.00 (1H, d), 7.45 (1H, t), 7.57-7.60 (2H, m), 7.68-7.69 (1H, m), 7.90 (1H, d) | 398 |
| 247 | [3] | 3-F | Et | δ 1.18 (3H, t), 2.56-2.70 (6H, m), 3.56 (2H, s), 3.61 (4H, t), 6.94-7.00 (1H, m), 7.00 (1H, d), 7.08-7.11 (2H, m), 7.27-7.32 (1H, m), 7.89 (1H, d) | 391 |

[1] Starting from 6-chloro-3-difluoromethyl-[1,2,4]-triazolo[4,3-b]pyridazine, obtained as described in General Synthetic Method 1, preparation of starting materials. [2] Starting from 6-chloro-3-(1,1-difluoroethyl)-[1,2,4]-triazolo[4,3-b]pyridazine, obtained in 66% yield by an analogous method to General Synthetic Method 1, preparation of starting materials, starting from 3-chloropyridazin-6-yl hydrazine and 2,2-difluoropropanoic acid.

1H NMR (399.9 MHz, CDCl3) δ 2.37 (3H, t), 7.25 (1H, d), 8.15 (1H, d); m/z=219 [M+H]+.

[3] Starting from 6-chloro-3-(1,1-difluoropropyl)-[1,2,4]-triazolo[4,3-b]pyridazine, obtained in 52% yield by an analogous method to General Synthetic Method 1, preparation of starting materials, starting from 3-chloropyridazin-6-yl hydrazine and 2,2-difluorobutanoic acid.

1H NMR (399.9 MHz, CDCl3) δ 1.23 (3H, t), 2.60-2.74 (2H, m), 7.24 (1H, d), 8.15 (1H, d); m/z=274 [M+H]+.

EXAMPLES 248-263

The following compounds were prepared in 35-83% yield by General Synthetic Method 5, starting from 3-(difluoromethyl)-6-(piperazin-1-yl)-[1,2,4]triazolo[4,3-b]pyridazine and the appropriate aldehyde:—

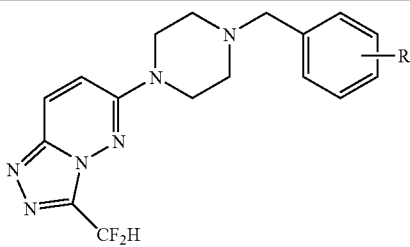

| Ex. | R | 1H NMR (399.9 MHz, CDCl3) | m/z [M + H]+ |
|---|---|---|---|
| 248 | 3-Cl | δ 2.60 (4H, d), 3.55 (2H, s), 3.63 (4H, t), 7.02 (1H, d), 6.99-7.25 (1H, m), 7.22-7.31 (3H, m), 7.37 (1H, s), 7.90 (1H, d) | 379 |
| 249 | 2,4-di-F | δ 2.63 (4H, s), 3.62 (3H, s), 3.63 (3H, s), 6.79-6.84 (1H, m), 6.85-6.90 (1H, m), 7.02 (1H, d), 7.12 (1H, t), 7.38 (1H, q), 7.90 (1H, d) | 381 |
| 250 | 3,4-di-F | δ 2.59 (4H, s), 3.53 (2H, s), 3.63 (4H, t), 7.02 (1H, d), 7.06-7.13 (2H, m), 6.99-7.25 (1H, m), 7.15-7.24 (1H, m), 7.90 (1H, d) | 381 |
| 251 | 3,5-di-F | δ 2.60 (4H, s), 3.55 (2H, s), 3.64 (4H, s), 6.70-6.75 (1H, m), 6.90-6.92 (2H, m), 7.03 (1H, d), 7.12 (1H, t), 7.91 (1H, d) | 381 |
| 252 | 2,6-di-F | δ 2.66 (4H, s), 3.62 (4H, t), 3.79 (2H, s), 6.89-6.94 (2H, m), 6.99 (1H, t), 6.98-7.24 (1H, m), 7.23-7.31 (1H, m), 7.88 (1H, s) | 381 |
| 253 | 2-F, 4-OMe | δ 2.61-2.62 (4H, m), 3.60-3.63 (6H, m), 3.80 (3H, s), 6.60-6.64 (1H, m), 6.68-6.70 (1H, m), 7.01 (1H, d), 6.99-7.25 (1H, m), 7.24-7.28 (1H, m), 7.89 (1H, d) | 393 |
| 254 | 3-Br | δ 2.59 (4H, s), 3.55 (2H, s), 3.63 (4H, s), 7.02 (1H, d), 7.12 (1H, t), 7.19-7.23 (1H, m), 7.28-7.31 (1H, m), 7.42 (1H, d), 7.52-7.53 (1H, m), 7.90 (1H, d) | 423 |
| 255 | 3-CF3 | δ 2.61 (4H, s), 3.63 (6H, s), 7.02 (1H, d), 7.12 (1H, t), 7.46 (1H, t), 7.55 (2H, d), 7.63 (1H, s), 7.89-7.92 (1H, m) | 413 |
| 256 | 2,3-di-F | δ 2.64 (4H, t), 3.63 (4H, t), 3.68 (2H, s), 7.02 (1H, d), 7.06-7.16 (3H, m), 7.12 (1H, t), 7.90 (1H, d) | 381 |
| 257 | 3-OMe, 4-F | δ 2.58 (4H, t), 3.51 (2H, d), 3.62 (4H, t), 3.91 (3H, s), 6.82-6.86 (1H, m), 6.99-7.05 (3H, m), 7.12 (1H, t), 7.89-7.91 (1H, m) | 393 |
| 258 | 2-F, 5-OMe | δ 2.64 (4H, t), 3.63 (4H, t), 3.64 (2H, s), 3.80 (3H, s), 6.75-6.79 (1H, m), 6.93-6.96 (1H, m), 6.97-6.99 (1H, m), 7.02 (1H, d), 6.99-7.25 (1H, m), 7.89 (1H, d) | 393 |
| 259 | 2,5-di-F | δ 2.65 (4H, s), 3.63 (6H, s), 6.92-6.99 (1H, m), 7.01-7.04 (2H, m), 7.25 (1H, t), 7.12-7.18 (1H, m), 7.90 (1H, s) | 381 |
| 260 | 3-CN, 4-F | δ 2.59 (4H, t), 3.56 (2H, s), 3.63 (4H, t), 7.03 (1H, d), 7.12 (1H, t), 7.20 (1H, t), 7.58-7.62 (1H, m), 7.64-7.66 (1H, m), 7.91 (1H, d) | 388 |
| 261 | 3-F, 4-OMe | δ 2.57 (4H, t), 3.50 (2H, d), 3.62 (4H, t), 3.89 (3H, s), 6.92 (1H, t), 7.02 (2H, d), 7.10-7.13 (1H, m), 7.12 (1H, t), 7.89 (1H, d) | 393 |

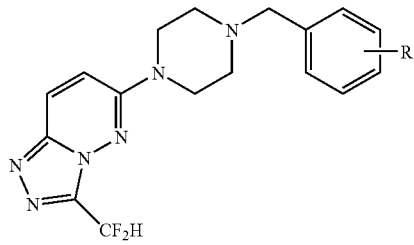

| Ex. | R | 1H NMR (399.9 MHz, CDCl3) | m/z [M + H]+ |
|---|---|---|---|
| 262 | 2-F, 4-CN | δ 2.64 (4H, t), 3.63 (4H, t), 3.69 (2H, s), 7.02 (1H, d), 7.12 (1H, t), 7.35-7.38 (1H, m), 7.46-7.48 (1H, m), 7.61 (1H, t), 7.91 (1H, d) | 388 |
| 263 | 2,6-di-F, 4-CN | δ 2.65 (4H, t), 3.60-3.62 (4H, m), 3.78 (2H, t), 7.00 (1H, t), 7.12 (1H, t), 7.24-7.25 (2H, m), 7.89 (1H, d) | 406 |

The 3-(difluoromethyl)-6-(piperazin-1-yl)-[1,2,4]triazolo[4,3-b]pyridazine used as starting material was prepared as follows:—

Preparation of tert-butyl 4-[3-(difluoromethyl)-[1,2,4]triazolo[4,3-b]pyridazin-6-yl]piperazine-1-carboxylate A stirred solution of 6-chloro-3-(difluoromethyl)-[1,2,4]triazolo[4,3-b]pyridazine (3.07 g, 15 mmol), tert-butyl piperazine-1-carboxylate (3.35 g, 18.00 mmol) and DIPEA (3.85 mL, 22.50 mmol) in DMF (25 mL) was heated at 100° C. for 1 hour. The reaction mixture was evaporated to dryness, redissolved in DCM and washed sequentially with 1M aqueous K2CO3, water and saturated brine. The organic layer was dried over MgSO4, filtered and evaporated. The crude product was triturated with ether and the solid was collected by filtration, washed with ether and dried under vacuum to afford tert-butyl 4-[3-(difluoromethyl)-[1,2,4]triazolo[4,3-b]pyridazin-6-yl]piperazine-1-carboxylate (5.05 g, 95%) as a white crystalline solid.

1H NMR (399.9 MHz, CDCl3) δ 1.49 (9H, s), 3.60 (8H, s), 7.04 (1H, d), 7.13 (1H, t), 7.94 (1H, d); m/z=355 [M+H]+.

Preparation of 3-(difluoromethyl)-6-(piperazin-1-yl)-[1,2,4]triazolo[4,3-b]pyridazine 4M Hydrogen chloride in dioxan (10.58 mL, 42.33 mmol) was added to a stirred partial solution of tert-butyl 4-[3-(difluoromethyl)-[1,2,4]triazolo[4,3-b]pyridazin-6-yl]piperazine-1-carboxylate (5.0 g, 14.11 mmol) in 1,4-dioxan (14.11 mL) at ambient temperature and the mixture was stirred for 1 hour. During this time it gave a clear solution that precipitated a gum, which crystallised on further stirring. The precipitate was collected by filtration, washed with ether and dried giving the dihydrochloride salt. This was dissolved in MeOH and adsorbed onto a SCX cartridge, then eluted with 2M ammonia in methanol. The product crystallised on evaporation and was triturated with ether. The solid was collected by filtration, washed with ether and dried under vacuum to afford 3-(difluoromethyl)-6-(piperazin-1-yl)-[1,2,4]triazolo[4,3-b]pyridazine (3.28 g, 91%) as a white crystalline solid.

1H NMR (399.9 MHz, CDCl3) δ 3.01-3.03 (4H, m), 3.59 (4H, t), 7.02-7.05 (1H, m), 7.13 (1H, t), 7.90 (1H, d); m/z=255 [M+H]+.

EXAMPLES 264-265

The following compounds were both prepared in 78% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and the appropriate aldehyde:—

[Structure]

| Ex. | X | 1H NMR (399.9 MHz, CDCl3) | m/z [M + H]+ |
|---|---|---|---|
| 264 | S | δ 2.65 (4H, t), 3.62 (4H, t), 3.83 (2H, s), 7.00-7.03 (1H, m), 7.25 (1H, t), 7.32 (1H, d), 7.35-7.41 (2H, m), 7.85-7.91 (2H, m), 7.98-8.02 (1H, m) | 401 |
| 265 | NH | δ 2.64 (4H, t), 3.61 (4H, t), 3.79 (2H, d), 7.00 (1H, d), 6.98-7.25 (1H, m), 7.12-7.16 (2H, m), 7.20-7.24 (1H, m), 7.37-7.40 (1H, m), 7.75-7.78 (1H, m), 7.87 (1H, d), 8.13 (1H, s) | 384 |

EXAMPLE 266

Preparation of 3-(difluoromethyl)-6-[4-(1H-indol-3-yl)piperidin-1-yl][1,2,4]triazolo[4,3-b]pyridazine

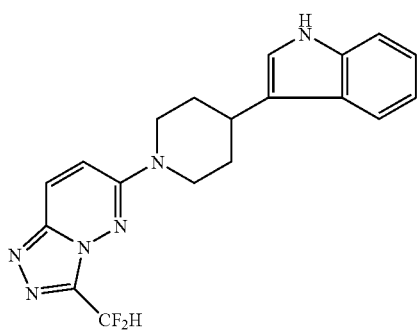

A mixture of 3-(piperidin-4-yl)-1H-indole and 3-(difluoromethyl)-6-(piperazin-1-yl)-[1,2,4]triazolo[4,3-b]pyridazine was allowed to react by an analogous method to Example 216 to give 3-(difluoromethyl)-6-[4-(1H-indol-3-yl)piperidin-1-yl][1,2,4]triazolo[4,3-b]pyridazine in 85% yield.

1H NMR (399.9 MHz, CDCl3) δ 1.81-1.92 (2H, m), 2.23-2.26 (2H, m), 3.17 (1H, t), 3.18-3.25 (2H, m), 4.36 (2H, s), 6.99-6.99 (1H, m), 7.09-7.15 (2H, m), 7.15 (1H, t), 7.19-7.23 (1H, m), 7.38-7.40 (1H, m), 7.65 (1H, s), 7.90 (1H, s), 8.04 (1H, s); m/z=369 [M+H]+.

EXAMPLES 267-268

The following compounds were prepared in 83-89% yield by an analogous method to Example 216, starting from 3-(difluoromethyl)-6-(piperazin-1-yl)-[1,2,4]triazolo[4,3-b]pyridazine and the appropriate 4-aryloxy piperidine:—

[Structure]

| Ex. | R | 1H NMR (399.9 MHz, CDCl3) | m/z [M + H]+ |
|---|---|---|---|
| 267 | OMe | δ 1.94-2.10 (4H, m), 3.62-3.68 (2H, m), 3.80 (3H, s), 3.82-3.86 (2H, m), 4.58-4.62 (1H, m), 6.49-6.56 (3H, m), 7.07 (1H, d), 7.00-7.26 (1H, m), 7.20 (1H, t), 7.91 (1H, d) | 376 |
| 268 | F | δ 1.94-2.11 (4H, m), 3.63-3.69 (2H, m), 3.79-3.85 (2H, m), 4.58-4.62 (1H, m), 6.63-6.73 (3H, m), 7.08 (1H, d), 7.13 (1H, t), 7.24 (1H, q), 7.91 (1H, d) | 364 |

EXAMPLE 269

Preparation of 3-(difluoromethyl)-6-[4-[(1R)-1-(4-fluorophenyl)ethyl]piperazin-1-yl][1,2,4]triazolo[4,3-b]pyridazine

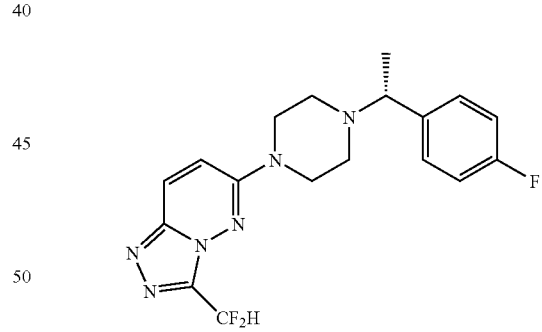

A stirred solution of 6-chloro-3-(difluoromethyl)-[1,2,4]triazolo[4,3-b]pyridazine (103 mg, 0.5 mmol), (R)-1-[1-(4-fluorophenyl)ethyl]piperazine (125 mg, 0.6 mmol) (prepared as described in J. Med. Chem. 2007, 50, 3528) and DIPEA (97 mg, 0.75 mmol, 129 µl) in DMF (2 mL) was heated at 100° C. for 2 hours. The crude product was purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to afford 3-(difluoromethyl)-6-[4-[(1R)-1-(4-fluorophenyl)ethyl]piperazin-1-yl][1,2,4]triazolo[4,3-b]pyridazine (158 mg, 84%) as a crisp foam.

1H NMR (399.9 MHz, CDCl3) δ 1.38 (3H, d), 2.48-2.54 (2H, m), 2.59-2.64 (2H, m), 3.43 (1H, q), 3.54-3.62 (4H, m), 6.99-7.05 (3H, m), 7.12 (1H, t), 7.28-7.31 (2H, m), 7.88 (1H, d); m/z=377 [M+H]+.

EXAMPLE 270

Preparation of 6-[4-[(1R)-1-(4-bromophenyl)ethyl]piperazin-1-yl]-3-(difluoromethyl)-[1,2,4]triazolo[4,3-b]pyridazine

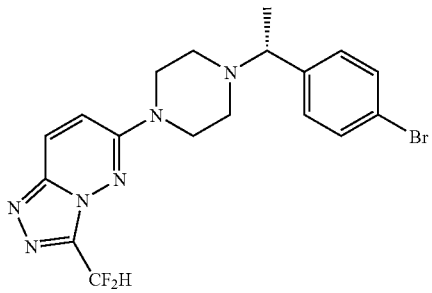

A mixture of (R)-1-[1-(4-bromophenyl)ethyl]piperazine and 6-chloro-3-difluoromethyl-[1,2,4]-triazolo[4,3-b]pyridazine was allowed to react by an analogous method to Example 269 to give 6-[4-[(1R)-1-(4-bromophenyl)ethyl]piperazin-1-yl]-3-(difluoromethyl)-[1,2,4]triazolo[4,3-b]pyridazine in 75% yield.

1H NMR (399.9 MHz, CDCl3) δ 1.37 (3H, d), 2.49-2.54 (2H, m), 2.60-2.65 (2H, m), 3.41 (1H, q), 3.53-3.62 (4H, m), 6.99 (1H, d), 7.12 (1H, t), 7.20-7.24 (2H, m), 7.44-7.48 (2H, m), 7.88 (1H, d); m/z=437 [M+H]+.

The (R)-1-[1-(4-bromphenyl)ethyl]piperazine used as starting material was prepared as follows:—

Preparation of (R)-1-[1-(4-bromophenyl)ethyl]-4-tosylpiperazine

N,N-Bis(2-chloroethyl)-4-methylbenzenesulfonamide (4.0 g, 13.50 mmol) and (R)-1-(4-bromophenyl)ethanamine (2.57 g, 12.83 mmol) in DIPEA (5 mL) were stirred and heated at 125° C. for 32 hours. The resulting dark mixture was cooled to 80° C. then a mixture of EtOH/water (70/30, 20 mL) added slowly to give a brown precipitate. The precipitate was collected by filtration, washed with EtOH/water (70/30) and iso-hexane and air dried to afford (R)-1-[1-(4-bromophenyl)ethyl]-4-tosylpiperazine (4.45 g, 78%) as a brown solid, which was used without further purification.

1H NMR (399.9 MHz, CDCl3) δ 1.27 (3H, d), 2.40-2.45 (5H, m), 2.52-2.57 (2H, m), 2.97 (4H, m), 3.32 (1H, q), 7.10 (2H, d), 7.32 (2H, d), 7.40 (2H, d), 7.62 (2H, d); m/z=423/425 [M+H]+.

Preparation of (R)-1-[1-(4-bromophenyl)ethyl]piperazine (R)-1-(1-(4-Bromophenyl)ethyl)-4-tosylpiperazine (4.44 g, 10.49 mmol) and 4-hydroxybenzoic acid (4.35 g, 31.46 mmol) in hydrobromic acid (33% in AcOH, 40 mL,) were stirred at room temperature for 48 hours. Water (40 mL) was then added to the dark mixture and stirring continued for a further 2 hours to give a beige solid, which was filtered off and washed with water (10 mL). The combined filtrate and washings were washed with toluene (3×50 mL) then cooled to 5° C. and basified to pH>10 with 40% NaOH. The resulting mixture was extracted with tert butyl methyl ether (2×50 mL) and the combined extracts washed with saturated brine, dried over MgSO4 and evaporated to give (R)-1-[1-(4-bromophenyl)ethyl]piperazine (2.69 g, 95%) as an orange, viscous oil.

1H NMR (399.9 MHz, CDCl3) δ 1.31 (3H, d), 2.29-2.35 (2H, m), 2.37-2.48 (2H, m), 2.85 (4H, t), 3.30 (1H, q), 7.19 (2H, d), 7.42 (2H, d); m/z=269/271 [M+H]+.

EXAMPLE 271

Preparation of 3-(difluoromethyl)-6-[4-[1-(4-fluorophenyl)-1-methylethyl]piperazin-1-yl][1,2,4]triazolo[4,3-b]pyridazine

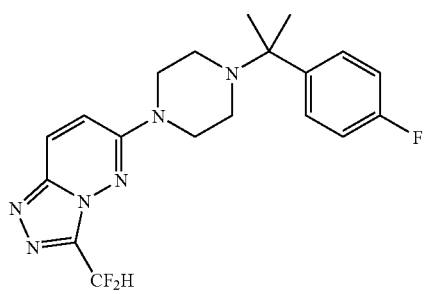

A mixture of 1-[1-(4-fluorophenyl)-1-methyl-ethyl]piperazine (obtained as described in J. Med. Chem. 2007, 50, 3528) and 6-chloro-3-(difluoromethyl)-[1,2,4]triazolo[4,3-b]pyridazine was allowed to react by an analogous method to Example 269 to give 3-(difluoromethyl)-6-[4-[1-(4-fluorophenyl)-1-methylethyl]piperazin-1-yl][1,2,4]triazolo[4,3-b]pyridazine in 62% yield.

1H NMR (399.9 MHz, CDCl3) δ 1.37 (6H, s), 2.61 (4H, t), 3.56 (4H, t), 6.98-7.02 (3H, m), 6.98-7.24 (1H, m), 7.49-7.53 (2H, m), 7.86-7.89 (1H, m); m/z=391 [M+H]+.

EXAMPLE 272

Preparation of 6-[1-(3-fluorobenzyl)-1,2,3,6-tetrahydropyridin-4-yl]-3-(trifluoromethyl)-[1,2,4]triazolo[4,3-b]pyridazine

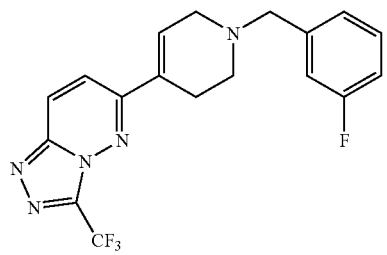

A mixture of 3-fluorobenzaldehyde and 6-(3,6-dihydro-2H-pyridin-4-yl)-3-(trifluoromethyl)-[1,2,4]triazolo[4,3-b]pyridazine was allowed to react by General Synthetic Method 5 to give 6-[1-(3-fluorobenzyl)-1,2,3,6-tetrahydropyridin-4-yl]-3-(trifluoromethyl)[1,2,4]triazolo[4,3-b]pyridazine in 46% yield.

1H NMR (399.9 MHz, CDCl3) δ 2.76 (4H, s), 3.29 (2H, d), 3.67 (2H, s), 6.72 (1H, t), 6.95-7.00 (1H, m), 7.10-7.15 (2H, m), 7.27-7.33 (1H, m), 7.54 (1H, d), 8.11 (1H, d); m/z=376 [M−H]−.

The 6-(3,6-dihydro-2H-pyridin-4-yl)-3-(trifluoromethyl)-[1,2,4]triazolo[4,3-b]pyridazine used as starting material was prepared as follows:—

Preparation of tert-butyl 4-(6-chloropyridazin-3-yl)-5,6-dihydropyridine-1(2H)-carboxylate Saturated aqueous NaHCO₃ solution (10 mL) was added to a stirred solution of 3,6-dichloropyridazine (0.968 g, 6.5 mmol), tert-butyl 4-(4,4,5,5-tetramethyl-1,3,2-dioxaborolan-2-yl)-5,6-dihydropyridine-1(2H)-carboxylate (2.010 g, 6.50 mmol) and tetrakis(triphenylphosphine)palladium(0) (0.376 g, 0.33 mmol) in DME (20 mL). The vessel was flushed with nitrogen and the initial suspension was heated at 80° C. for 9 hours. The reaction mixture was diluted with DCM and washed with water. The organic phase was dried over MgSO4 and evaporated. The crude product was purified by MPLC silica chromatography, elution gradient 35 to 45% EtOAc in isohexane. Pure fractions were evaporated to dryness to afford tert-butyl 4-(6-chloropyridazin-3-yl)-5,6-dihydropyridine-1(2H)-carboxylate (0.929 g, 48.3%) as a colourless crystalline solid.

1H NMR (399.9 MHz, CDCl3) δ 1.50 (9H, s), 2.77-2.78 (2H, m), 3.67 (2H, t), 4.18 (2H, q), 6.62 (1H, s), 7.45 (1H, d), 7.55 (1H, d); m/z=240 [M+H-butylene]+.

Preparation of tert-butyl 4-(6-hydrazinylpyridazin-3-yl)-5,6-dihydropyridine-1(2H)-carboxylate A stirred mixture of tert-butyl 4-(6-chloropyridazin-3-yl)-5,6-dihydropyridine-1(2H)-carboxylate (870 mg, 2.94 mmol) and hydrazine hydrate (4.29 mL, 88.25 mmol) in acetonitrile (15 mL) was heated at 80° C. for 4 hours. The mixture was partially evaporated (removing MeCN) and diluted with water (10 mL). The reaction mixture was extracted with DCM (3×50 mL). The organic layer was dried over Na₂SO₄, filtered and evaporated to afford crude product as a gum, which crystallised on trituration with ether. The precipitate was collected by filtration, washed with ether and dried under vacuum to afford tert-butyl 4-(6-hydrazinylpyridazin-3-yl)-5,6-dihydropyridine-1(2H)-carboxylate (503 mg, 58.7%) as a cream crystalline solid.

1H NMR (399.9 MHz, CDCl3) δ 1.49 (9H, s), 2.76-2.79 (2H, m), 3.65 (2H, t), 4.00 (2H, s), 4.13 (2H, q), 6.07 (1H, s), 6.33-6.35 (1H, m), 6.95 (1H, d), 7.43 (1H, d); m/z=292 [M+H]+.

Preparation of 6-(1,2,3,6-tetrahydropyridin-4-yl)-3-(trifluoromethyl)-[1,2,4]triazolo[4,3-b]pyridazine TFA (2 mL) was added in one portion to tert-butyl 4-(6-hydrazinylpyridazin-3-yl)-5,6-dihydropyridine-1(2H)-carboxylate (480 mg, 1.65 mmol) which dissolved with a vigorous effervescence. The solution was stirred for 24 hours at 70° C. The solution was evaporated and the residue was dissolved in methanol. It was run on an SCX cartridge, eluting with 2M ammonia in methanol. Product containing fractions were evaporated to dryness and triturated with ether to afford 6-(1,2,3,6-tetrahydropyridin-4-yl)-3-(trifluoromethyl)-[1,2,4]triazolo[4,3-b]pyridazine (90 mg, 20.29%) as a cream solid.

1H NMR (399.9 MHz, DMSO-d6) δ 2.79 (2H, s), 3.37 (2H, t), 3.91 (2H, s), 6.99 (1H, s), 7.96 (1H, d), 8.49 (1H, d), NH not observed; m/z=270 [M+H]+.

EXAMPLE 273

Preparation of 6-[4-[5-(3-chlorophenyl)-1,2,4-oxadiazol-3-yl]piperazin-1-yl]-3-(trifluoromethyl)[1,2,4]triazolo[4,3-b]pyridazine

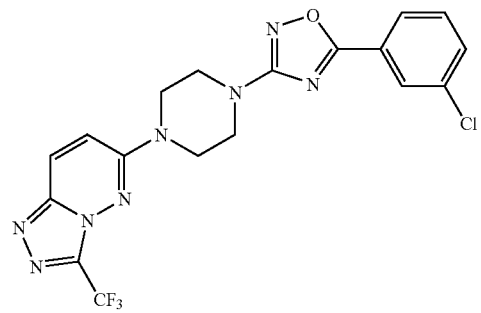

3-Chlorobenzoyl chloride (92 mg, 0.53 mmol) was added to a stirred partial solution of N-hydroxy-4-[3-(trifluoromethyl)-[1,2,4]triazolo[4,3-b]pyridazin-6-yl]piperazine-1-carboximidamide (165 mg, 0.5 mmol) and DIPEA (97 mg, 0.75 mmol) in THF (3 mL). The reaction mixture became a clear solution over 30 minutes and LCMS after 1 hour showed complete initial acylation. The reaction mixture was heated at 150° C. for 15 minutes by microwave after which LCMS showed complete cyclisation to the desired product. The reaction mixture was evaporated and the residue was boiled briefly with ethanol, cooled and filtered off to give 6-[4-[5-(3-chlorophenyl)-1,2,4-oxadiazol-3-yl]piperazin-1-yl]-3-(trifluoromethyl)[1,2,4]triazolo[4,3-b]pyridazine (104 mg, 46%) as a crystalline powder.

1H NMR (399.9 MHz, DMSO-d6) δ 3.60-3.63 (4H, m), 3.78-3.81 (4H, m), 7.65-7.69 (2H, m), 7.77-7.80 (1H, m), 8.01-8.06 (2H, m), 8.32 (1H, d); m/z=451 [M+H]+.

The N-hydroxy-4-[3-(trifluoromethyl)-[1,2,4]triazolo[4,3-b]pyridazin-6-yl]piperazine-1-carboximidamide used as starting material was prepared in as follows:—

Preparation of 4-[3-(trifluoromethyl)-[1,2,4]triazolo[4,3-b]pyridazin-6-yl]piperazine-1-carbonitrile A stirred solution of 6-chloro-3-(trifluoromethyl)-[1,2,4]triazolo[4,3-b]pyridazine (3.48 g, 15.65 mmol), piperazine-1-carbonitrile (2 g, 17.99 mmol) and DIPEA (3.54 mL, 20.34 mmol) in DMF (20 mL) was heated at 70° C. for 1 hour. The solution was evaporated and partitioned between DCM and 1M aqueous K₂CO₃. The organic phase was washed with brine, dried over MgSO4, evaporated and triturated with ether. The precipitate was collected by filtration, washed with ether and dried under vacuum to afford 4-[3-(trifluoromethyl)-[1,2,4]triazolo[4,3-b]pyridazin-6-yl]piperazine-1-carbonitrile (4.29 g, 92%) as a cream crystalline solid.

1H NMR (399.9 MHz, CDCl3) δ 3.41-3.43 (4H, m), 3.75 (4H, t), 7.05 (1H, d), 8.02 (1H, d); m/z=298 [M+H]+.

Preparation of N-hydroxy-4-[3-(trifluoromethyl)-[1,2,4]triazolo[4,3-b]pyridazin-6-yl]piperazine-1-carboximidamide Hydroxylamine (50% w/v aqueous solution) (0.667 mL, 10.09 mmol) was added to a stirred suspension of 4-[3-(trifluoromethyl)-[1,2,4]triazolo[4,3-b]pyridazin-6-yl]piperazine-1-carbonitrile (2.5 g, 8.41 mmol) in ethanol (16.82 mL) and the suspension was stirred at ambient temperature. Over 20 minutes the starting material largely dissolved and the product began to crystallise. The mixture was stirred for 2 hours and the precipitate was collected by filtration, washed with EtOH followed by ether and dried under vacuum to afford N-hydroxy-4-[3-(trifluoromethyl)-[1,2,4]triazolo[4,3-b]pyridazin-6-yl]piperazine-1-carboximidamide (2.410 g, 87%) as a colourless crystalline solid.

1H NMR (399.9 MHz, DMSO-d6) δ 3.15 (3H, t), 3.44-3.47 (1H, m), 3.58-3.63 (4H, m), 5.24-5.26 (1H, m), 6.09 & 8.37 (1H, 2S), 7.63 (1H, d), 8.26-8.29 (1H, m), 8.38 (1H, s), one exchangeable not observed; m/z=331 [M+H]+.

EXAMPLES 274-277

The following compounds were prepared in 43-55% yield by an analogous method to Example 273, starting from N-hydroxy-4-[3-(trifluoromethyl)-[1,2,4]triazolo[4,3-b]pyridazin-6-yl]piperazine-1-carboximidamide and the appropriate benzoyl chloride:—

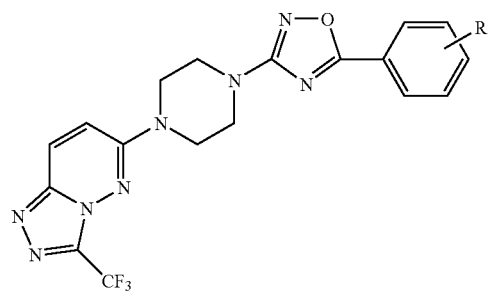

| Ex. | R | 1H NMR (399.9 MHz, DMSO-d6) | m/z [M + H]+ |
|---|---|---|---|
| 274 | 4-F | δ 3.59-3.62 (4H, m), 3.78-3.81 (4H, m), 7.45-7.50 (2H, m), 7.66 (1H, d), 8.11-8.15 (2H, m), 8.32 (1H, d) | 433 [M − H]− |
| 275 | H | 3.60-3.63 (4H, m), 3.78-3.81 (4H, m), 7.61-7.73 (4H, m), 8.05-8.08 (2H, m), 8.31-8.34 (1H, m) | 417 |
| 276 | 3-F | δ 3.60-3.63 (4H, m), 3.79-3.81 (4H, m), 7.58 (1H, d), 7.65-7.70 (2H, m), 7.82-7.85 (1H, m), 7.91-7.93 (1H, m), 8.33 (1H, s) | 435 |
| 277 | 4-CN | δ 3.61-3.64 (4H, m), 3.79-3.81 (4H, m), 7.67 (1H, d), 8.09-8.12 (2H, m), 8.21-8.24 (2H, m), 8.33 (1H, d) | 442 |

EXAMPLES 278-284

The following compounds were prepared in 9-71% yield by General Synthetic Method 5, starting from 6-(piperazin-1-yl)-3-(trifluoromethyl)-[1,2,4]triazolo[4,3-b]pyridazine and the appropriate indole-3-carboxaldehyde:—

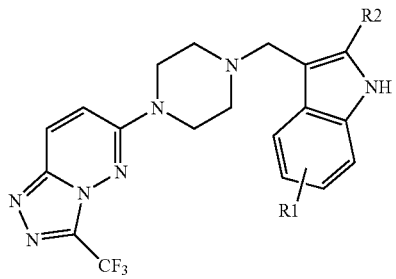

| Ex. | R1 | R2 | 1H NMR (399.9 MHz, DMSO-d6) | m/z [M + H]+ |
|---|---|---|---|---|
| 278 | 5-CN | H | δ 2.55 (4H, t), 3.61 (4H, t), 3.75 (2H, s), 7.42-7.45 (1H, m), 7.50 (1H, s), 7.53-7.55 (1H, m), 7.57 (1H, d), 8.20-8.20 (1H, m), 8.23 (1H, d), 11.55 (1H, s) | 427 |
| 279 | H | Me | [1] δ 2.44 (3H, s), 2.62 (4H, t), 3.60 (4H, t), 3.71 (2H, s), 7.04 (1H, d), 7.08-7.16 (2H, m), 7.28-7.31 (1H, m), 7.65 (1H, d), 7.89 (2H, m) | 416 |
| 280 | 5-Cl | H | δ 2.53-2.57 (4H, m), 3.60 (4H, t), 3.69 (2H, s), 7.07-7.10 (1H, m), 7.35-7.40 (2H, m), 7.57 (1H, d), 7.69 (1H, d), 8.23 (1H, d), 11.16 (1H, s) | 436 |
| 281 | 5-Br | H | δ 2.53-2.57 (4H, m), 3.60 (4H, t), 3.68 (2H, s), 7.18-7.21 (1H, m), 7.34-7.36 (2H, m), 7.58 (1H, d), 7.83 (1H, d), 8.23 (1H, d), 11.17 (1H, s) | 480 |
| 282 | 4-Cl | H | δ 2.56-2.61 (4H, m), 3.60 (4H, s), 3.86 (2H, s), 7.00-7.07 (2H, m), 7.34-7.37 (2H, m), 7.59 (1H, d), 8.24 (1H, d), 11.33 (1H, s) | 436 |
| 283 | 5-F | H | δ 2.54-2.57 (4H, m), 3.60 (4H, t), 3.68 (2H, s), 6.90-6.95 (1H, m), 7.34-7.41 (3H, m), 7.57 (1H, d), 8.23 (1H, d), 11.05 (1H, s) | 420 |
| 284 | 6-F | H | δ 2.54-2.57 (4H, m), 3.60 (4H, t), 3.69 (2H, s), 6.83-6.89 (1H, m), 7.12-7.15 (1H, m), 7.27 (1H, d), 7.57 (1H, d), 7.64-7.68 (1H, m), 8.23 (1H, d), 11.01 (1H, s) | 420 |

[1]Spectrum recorded in CDCl3

EXAMPLE 285

Preparation of 6-[4-(1H-indazol-3-ylmethyl)piperazin-1-yl]-3-(trifluoromethyl)[1,2,4]triazolo[4,3-b]pyridazine

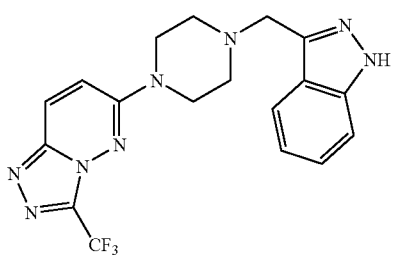

1H-Indazole-3-carboxaldehyde (75 mg, 0.51 mmol) and (polystyrylmethyl)trimethylammonium cyanoborohydride (125 mg, 0.51 mmol) were added to a solution of 6-(piperazin-1-yl)-3-(trifluoromethyl)-[1,2,4]triazolo[4,3-b]pyridazine (100 mg, 0.37 mmol) in DCM (2 mL)/acetic acid (0.2 mL). The mixture was stirred at ambient temperature for 18 hours. The resin was filtered off and the filtrate was evaporated. The crude product was purified by preparative HPLC (Waters XTerra C18 column, 5μ silica, 19 mm diameter, 100 mm length), using decreasingly polar mixtures of water (containing 1% ammonia) and MeCN as eluents. Fractions containing the desired compound were evaporated to dryness to afford 6-[4-(1H-indazol-3-ylmethyl)piperazin-1-yl]-3-(trifluoromethyl)[1,2,4]triazolo[4,3-b]pyridazine (89 mg, 60%) as a white solid.

1H NMR (399.9 MHz, DMSO-d6) δ 2.60 (4H, t), 3.61 (4H, t), 3.92 (2H, s), 7.09-7.13 (1H, m), 7.33-7.36 (1H, m), 7.50 (1H, d), 7.57 (1H, d), 7.90 (1H, d), 8.23 (1H, d), 12.85 (1H, s); m/z=403 [M+H]+.

EXAMPLES 286-292

The following compounds were prepared in 57-74% yield by General Synthetic Method 5, starting from 3-(difluoromethyl)-6-(piperazin-1-yl)-[1,2,4]triazolo[4,3-b]pyridazine and the appropriate indole-3-carboxaldehyde:—

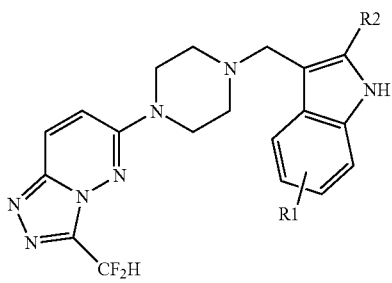

| Ex. | R1 | R2 | 1H NMR (399.9 MHz, DMSO-d6) | m/z [M + H]+ |
|---|---|---|---|---|
| 286 | 5-CN | H | δ 2.53-2.56 (4H, m), 3.61 (4H, t), 3.75 (2H, s), 7.43-7.45 (1H, m), 7.49-7.65 (4H, m), 8.15-8.21 (2H, m), 11.55 (1H, s) | 409 |
| 287 | 5-Cl | H | δ 2.53-2.57 (4H, m), 3.60 (4H, t), 3.69 (2H, s), 7.07-7.10 (1H, m), 7.37 (2H, t), 7.49-7.51 (1H, m), 7.52 (1H, t), 7.70 (1H, d), 8.15-8.18 (1H, m), 11.17 (1H, s). | 418 |
| 288 | 5-Br | H | δ 2.53-2.57 (4H, m), 3.60 (4H, t), 3.69 (2H, s), 7.18-7.21 (1H, m), 7.34 (2H, s), 7.52 (1H, t), 7.52 (1H, d), 7.84 (1H, d), 8.15-8.18 (1H, m), 11.17 (1H, s). | 462 |
| 289 | 4-Cl | H | δ 2.61 (4H, t), 3.60 (4H, t), 3.86 (2H, s), 7.00-7.08 (2H, m), 7.34-7.37 (2H, m), 7.50-7.53 (1H, m), 7.53 (1H, t), 8.17 (1H, d), 11.17 (1H, s). | 418 |
| 290 | 5-F | H | δ 2.53-2.57 (4H, m), 3.60 (4H, t), 3.69 (2H, s), 6.92 (1H, d), 7.34-7.42 (3H, m), 7.50 (1H, d), 7.52 (1H, t), 8.15-8.18 (1H, m), 11.05 (1H, s) | 402 |
| 291 | H | Cl | δ 2.56 (4H, t), 3.60 (4H, t), 3.69 (2H, s), 7.07 (1H, s), 7.13-7.14 (1H, m), 7.29-7.31 (1H, m), 7.48-7.51 (1H, m), 7.52 (1H, t), 7.66 (1H, s), 8.15-8.17 (1H, m), 11.79 (1H, s) | 418 |
| 292 | 6-F | H | δ 2.52 (4H, t), 3.59 (4H, s), 3.69 (2H, s), 6.83-6.89 (1H, m), 7.12-7.15 (1H, m), 7.27 (1H, s), 7.50 (1H, d), 7.39-7.64 (1H, m), 7.66-7.68 (1H, m), 8.17 (1H, d), 11.01 (1H, s) | 402 |

EXAMPLE 293

Preparation of 3-(difluoromethyl)-6-[4-(1H-indazol-3-ylmethyl)piperazin-1-yl][1,2,4]triazolo[4,3-b]pyridazine

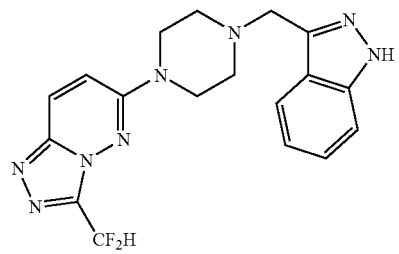

A mixture of indazole-3-carboxaldehyde and 3-(difluoromethyl)-6-(piperazin-1-yl)-[1,2,4]triazolo[4,3-b]pyridazine was allowed to react by General Synthetic Method 5 to give 3-(difluoromethyl)-6-[4-(1H-indazol-3-ylmethyl)piperazin-1-yl][1,2,4]triazolo[4,3-b]pyridazine in 65% yield.

1H NMR (399.9 MHz, DMSO-d6) δ 2.57-2.61 (4H, m), 3.61 (4H, t), 3.92 (2H, s), 7.11 (1H, t), 7.33-7.37 (1H, m), 7.48-7.52 (2H, m), 7.52 (1H, t), 7.91 (1H, s), 8.17 (1H, d), 12.85 (1H, s); m/z=385 [M+H]+.

EXAMPLE 294

Preparation of 6-[4-[(tetrahydro-2H-pyran-4-yloxy)methyl]piperidin-1-yl]-3-(trifluoromethyl)[1,2,4]triazolo[4,3-b]pyridazine

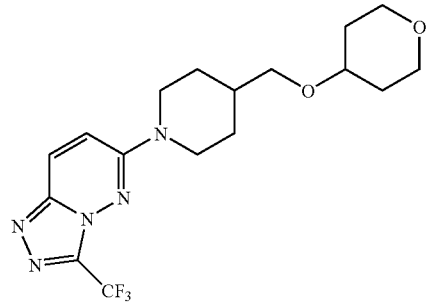

Sodium hydride (60% dispersion in oil, 42 mg, 1.05 mmol) was added to stirred tetrahydro-4H-pyran-4-ol (1 g). 6-[4-(Methanesulfonyloxymethyl)piperidin-1-yl]-3-(trifluoromethyl)-[1,2,4]triazolo[4,3-b]pyridazine (133 mg, 0.35 mmol) was added and the mixture was stirred at 80° C. for 3 hours. The reaction mixture was diluted with MeOH and run down a 20 g SCX cartridge, eluting with 2M ammonia in methanol. The solution was evaporated and the crude product was purified by preparative HPLC (Waters XTerra C18 column, 5μ silica, 19 mm diameter, 100 mm length), using decreasingly polar mixtures of water (containing 1% ammonia) and MeCN as eluents. Fractions containing the desired compound were evaporated to dryness to afford 66-[4-[(tetrahydro-2H-pyran-4-yloxy)methyl]piperidin-1-yl]-3-(trifluoromethyl)[1,2,4]triazolo[4,3-b]pyridazine (43 mg, 32%) as a white solid.

1H NMR (399.9 MHz, CDCl3) δ 1.25-1.33 (2H, m), 1.46-1.55 (2H, m), 1.78-1.87 (5H, m), 2.93-3.00 (2H, m), 3.27-

3.28 (2H, m), 3.34-3.42 (3H, m), 3.83-3.88 (2H, m), 4.16-4.20 (2H, m), 7.01 (1H, d), 7.83 (1H, d); m/z=386 [M+H]+.

The 6-[4-(methanesulfonyloxymethyl)piperidin-1-yl]-3-(trifluoromethyl)-[1,2,4]triazolo[4,3-b]pyridazine used as starting material was prepared as follows:—

Preparation of [1-[3-(trifluoromethyl)-[1,2,4]triazolo[4,3-b]pyridazin-6-yl]piperidin-4-yl]methanol A stirred solution of 6-chloro-3-(trifluoromethyl)-[1,2,4]triazolo[4,3-b]pyridazine (5.56 g, 25 mmol), piperidin-4-yl-methanol (3.17 g, 27.50 mmol) and DIPEA (5.66 mL, 32.50 mmol) in DMF (50 mL) was heated at 70° C. for 1 hour. The solution was evaporated and partitioned between DCM and 1M aqueous $K_2CO_3$. The organic phase was washed with brine, dried over MgSO4, evaporated and triturated with ether. The precipitate was collected by filtration, washed with ether and dried under vacuum to afford [1-[3-(trifluoromethyl)-[1,2,4]triazolo[4,3-b]pyridazin-6-yl]piperidin-4-yl]methanol (6.68 g, 89%) as a cream crystalline solid.

1H NMR (399.9 MHz, CDCl3) δ 1.31-1.41 (2H, m), 1.80-1.93 (3H, m), 3.00-3.07 (2H, m), 3.57 (2H, t), 4.25-4.29 (2H, m), 7.09 (1H, d), 7.90 (1H, d), OH not observed; m/z=302 [M+H]+.

Preparation of 6-[4-(methanesulfonyloxymethyl)piperidin-1-yl]-3-(trifluoromethyl)-[1,2,4]triazolo[4,3-b]pyridazine Methanesulfonyl chloride (2.83 mL, 36.51 mmol) in DCM (30 mL) was added dropwise to a stirred partial solution of [1-[3-(trifluoromethyl)-[1,2,4]triazolo[4,3-b]pyridazin-6-yl]piperidin-4-yl]methanol (10 g, 33.19 mmol) and triethylamine (5.09 mL, 36.51 mmol) in DCM (140 mL). The reaction was stirred for 20 minutes, quenched with water (100 mL) and extracted with DCM (2×75 mL). The organic layer was dried over MgSO4, filtered and evaporated to afford a yellow solid. The crude solid was triturated with ether to give a solid which was collected by filtration and dried under vacuum to give 6-[4-(methanesulfonyloxymethyl)piperidin-1-yl]-3-(trifluoromethyl)-[1,2,4]triazolo[4,3-b]pyridazine (7.60 g, 60.4%) as a white solid.

1H NMR (400.1 MHz, DMSO) δ 1.32 (2H, ddd), 1.82 (2H, d), 2.09-2.02 (1H, m), 3.05 (2H, t), 3.18 (3H, s), 4.11 (2H, d), 4.30 (2H, d), 7.61 (1H, d), 8.22 (1H, d); m/z=380 [M+H]+.

EXAMPLES 295-298

The following compounds were prepared in 17-71% yield by an analogous method to Example 294, starting from 6-[4-(methanesulfonyloxymethyl)piperidin-1-yl]-3-(trifluoromethyl)-[1,2,4]triazolo[4,3-b]pyridazine and the appropriate alcohol:—

| Ex. | R | 1H NMR (399.9 MHz, CDCl3) | m/z [M + H]+ |
|---|---|---|---|
| 295 | cyclopropylmethyl | δ 0.12-0.15 (2H, m), 0.45-0.49 (2H, m), 0.95-1.01 (1H, m), 1.22-1.32 (2H, m), 1.84-1.90 (3H, m), 2.92-2.99 (2H, m), 3.20-3.21 (2H, m), 3.26 (2H, d), 4.15-4.20 (2H, m), 7.01 (1H, d), 7.83 (1H, d) | 356 |
| 296 | 2-methoxyethyl | δ 1.21-1.31 (2H, m), 1.83-1.93 (3H, m), 2.91-2.98 (2H, m), 3.28-3.30 (2H, m), 3.32 (3H, s), 3.46-3.49 (2H, m), 3.49-3.54 (2H, m), 4.14-4.19 (2H, m), 7.01 (1H, d), 7.83 (1H, d) | 360 |
| 297 | 2-morpholinoethyl | δ 1.21-1.31 (2H, m), 1.80-1.89 (3H, m), 2.49-2.56 (6H, m), 2.91-2.98 (2H, m), 3.25-3.27 (2H, m), 3.54 (2H, s), 3.69 (4H, s), 4.15-4.19 (2H, m), 7.01 (1H, d), 7.83 (1H, d) | 415 |
| 298 | 2-propyl | δ 1.08 (6H, d), 1.20-1.30 (2H, m), 1.78-1.86 (3H, m), 2.92-2.99 (2H, m), 3.22 (2H, d), 3.44-3.50 (1H, m), 4.15-4.19 (2H, m), 7.01 (1H, d), 7.83 (1H, d) | 344 |

EXAMPLES 299-303

The following compounds were prepared in 1-84% yield by an analogous method to Example 273, starting from N-hydroxy-1-[3-(trifluoromethyl)-[1,2,4]triazolo[4,3-b]pyridazin-6-yl]piperidine-4-carboximidamide and the appropriate benzoyl chloride.

| Ex. | R | 1H NMR (399.9 MHz, CDCl3) | m/z [M + H]+ |
|---|---|---|---|
| 299 | 3-Cl | δ 2.01-2.10 (2H, m), 2.23-2.27 (2H, m), 3.20-3.27 (1H, m), 3.28-3.35 (2H, m), 4.24-4.29 (2H, m), 7.13 (1H, d), 7.47 (1H, t), 7.56-7.59 (1H, m), 7.95 (1H, d), 7.99-8.02 (1H, m), 8.12 (1H, t) | 450 |
| 300 | 4-F | δ 2.00-2.10 (2H, m), 2.22-2.27 (2H, m), 3.18-3.26 (1H, m), 3.28-3.35 (2H, m), 4.23-4.29 (2H, m), 7.13 (1H, d), 7.19-7.25 (2H, m), 7.95 (1H, d), 8.11-8.16 (2H, m) | 434 |
| 301 | H | δ 2.00-2.12 (2H, m), 2.23-2.28 (2H, m), 3.20-3.27 (1H, m), 3.28-3.35 (2H, m), 4.24-4.29 (2H, m), | 416 |

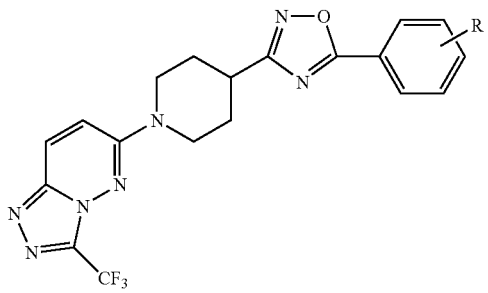

| Ex. | R | 1H NMR (399.9 MHz, CDCl3) | m/z [M + H]+ |
|---|---|---|---|
| 302 | 3-F | 7.13 (1H, d), 7.51-7.55 (2H, m), 7.58-7.62 (1H, m), 7.95 (1H, d), 8.11 -8.14 (2H,m) δ 2.01-2.11 (2H, m), 2.23 -2.28 (2H, m), 3.20-3.27 (1H, m), 3.28-3.35 (2H, m), 4.24-4.29 (2H, m), 7.13 (1H, d), 7.28-7.33 (1H, m), 7.49-7.54 (1H, m), 7.80-7.84 (1H, m), 7.91-7.96 (2H, m) | 434 |
| 303 | 3-CN | δ 2.00-2.10 (2H, m), 2.24-2.29 (2H, m), 3.21-3.28 (1H, m), 3.28-3.35 (2H, m), 4.24-4.30 (2H, m), 7.13 (1H, d), 7.67-7.71 (1H, m), 7.87-7.89 (1H, m), 7.96 (1H, d), 8.34-8.36 (1H, m), 8.42-8.43 (1H, m) | 441 |

The N-hydroxy-1-[3-(trifluoromethyl)-[1,2,4]triazolo[4,3-b]pyridazin-6-yl]piperidine-4-carboximidamide used as starting material was prepared as follows:—

Preparation of 1-[3-(trifluoromethyl)-[1,2,4]triazolo[4,3-b]pyridazin-6-yl]piperidine-4-carbonitrile A stirred solution of 6-chloro-3-(trifluoromethyl)-[1,2,4]triazolo[4,3-b]pyridazine (5.56 g, 25 mmol), piperidine-4-carbonitrile (3.03 g, 27.50 mmol) and DIPEA (5.66 mL, 32.50 mmol) in DMF (50 mL) was heated at 70° C. for 1 hour. The solution was evaporated and partitioned between DCM and 1M aqueous $K_2CO_3$. The organic phase was washed with brine, dried over MgSO4, evaporated and the residue was triturated with ether. The solid was collected by filtration, washed with ether and dried under vacuum to afford 1-[3-(trifluoromethyl)-[1,2,4]triazolo[4,3-b]pyridazin-6-yl]piperidine-4-carbonitrile (6.86 g, 93%) as a cream crystalline solid.

1H NMR (399.9 MHz, CDCl3) δ 1.97-2.12 (4H, m), 2.95-3.01 (1H, m), 3.62-3.68 (2H, m), 3.80-3.86 (2H, m), 7.08 (1H, d), 7.97 (1H, d); m/z=297 [M+H]+.

Preparation of N-hydroxy-1-[3-(trifluoromethyl)-[1,2,4]triazolo[4,3-b]pyridazin-6-yl]piperidine-4-carboximidamide Hydroxylamine (50% w/v aqueous solution) (0.669 mL, 10.13 mmol) was added to a stirred suspension of 1-(3-(trifluoromethyl)-[1,2,4]triazolo[4,3-b]pyridazin-6-yl)piperidine-4-carbonitrile (2.5 g, 8.44 mmol) in ethanol (16.88 mL) and the suspension was stirred at ambient temperature. Additional hydroxylamine (50% w/v aqueous solution) (3 mL) was added and stirring was continued for 18 hours. The mixture was then heated for 1 hour. The precipitate was collected by filtration, washed with EtOH and ether and dried under vacuum to afford N-hydroxy-1-[3-(trifluoromethyl)-[1,2,4]triazolo[4,3-b]pyridazin-6-yl]piperidine-4-carboximidamide (2.380 g, 86%) as a colourless crystalline solid.

1H NMR (399.9 MHz, DMSO-d6) δ 1.61-1.71 (2H, m), 1.81-1.86 (2H, m), 2.32-2.38 (1H, m), 3.01-3.08 (2H, m), 4.29 (2H, d), 5.32-5.34 (2H, m), 7.62 (1H, d), 8.23 (1H, d), 8.81 (1H, s); m/z=330 [M+H]+.

EXAMPLE 304

Preparation of 6-[4-(cyclopropylmethoxy)piperidin-1-yl]-3-(trifluoromethyl)[1,2,4]triazolo[4,3-b]pyridazine

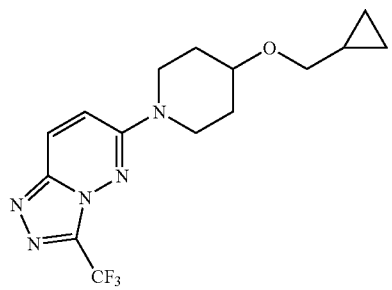

A mixture of 4-(cyclopropylmethoxy)piperidine and 6-(piperazin-1-yl)-3-(trifluoromethyl)-[1,2,4]triazolo[4,3-b]pyridazine was allowed to react by an analogous method to Example 216 to give 6-[4-(cyclopropylmethoxy)piperidin-1-yl]-3-(trifluoromethyl)[1,2,4]triazolo[4,3-b]pyridazine in 69% yield.

1H NMR (399.9 MHz, CDCl3) δ 0.20-0.24 (2H, m), 0.54-0.59 (2H, m), 1.02-1.12 (1H, m), 1.70-1.79 (2H, m), 1.94-2.00 (2H, m), 3.34 (2H, d), 3.40-3.44 (2H, m), 3.61-3.66 (1H, m), 3.87-3.93 (2H, m), 7.10 (1H, d), 7.91 (1H, d); m/z=342 [M+H]+.

EXAMPLE 305

Preparation of 6-[4-(1-Phenylethyl)piperazin-1-yl]-3-(trifluoromethyl)[1,2,4]triazolo[4,3-b]pyridazine

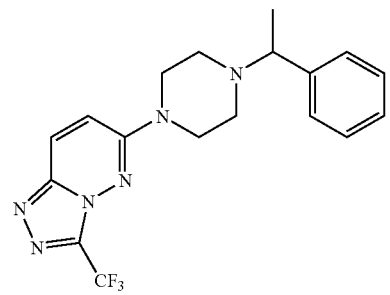

6-Chloro-3-(trifluoromethyl)-[1,2,4]triazolo[4,3-b]pyridazine (400 mg, 1.80 mmol), 1-(1-phenylethyl)piperazine (342 mg, 1.80 mmol) and DIPEA (0.34 mL, 1.98 mmol) in DMF (4 mL) were stirred and heated at 80° C. for 30 minutes. The mixture was cooled to ambient temperature then applied to an SCX column and eluted with methanol followed by 2M ammonia in methanol. Fractions containing pure product were evaporated to give a solid which was recrystallised from MTBE/isohexane to give 6-[4-(1-phenylethyl)piperazin-1-yl]-3-(trifluoromethyl)[1,2,4]triazolo[4,3-b]pyridazine (516 mg, 76%).

1H NMR (399.9 MHz, CDCl3) δ 1.41 (3H, d), 2.50-2.56 (2H, m), 2.60-2.66 (2H, m), 3.44 (1H, q), 3.55-3.64 (4H, m), 7.03 (1H, d), 7.24-7.35 (5H, m), 7.89 (1H, d); m/z=377 [M+H]+.

EXAMPLE 306

Preparation of 6-[4-[(1R)-1-(4-bromophenyl)ethyl]piperazin-1-yl]-3-(trifluoromethyl)[1,2,4]triazolo[4,3-b]pyridazine

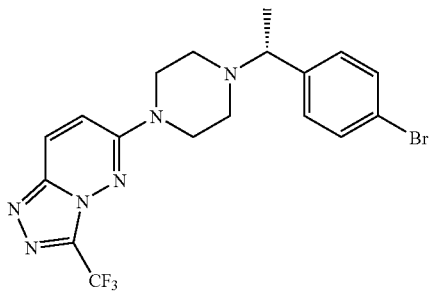

6-Chloro-3-(trifluoromethyl)-[1,2,4]triazolo[4,3-b]pyridazine (251 mg, 1.13 mmol), (R)-1-[1-(4-bromophenyl)ethyl]piperazine (obtained as described in Example 270, preparation of starting materials, 304 mg, 1.13 mmol) and DIPEA (0.20 mL, 1.13 mmol) in DMF (3 mL) were stirred and heated at 80° C. for 1 hour. The resulting solution was cooled to ambient temperature then quenched with water (10 mL) to give a pale brown precipitate. The precipitate was collected by filtration, washed sequentially with water, acetonitrile and ether and dried under vacuum to afford 6-[4-[(1R)-1-(4-bromophenyl)ethyl]piperazin-1-yl]-3-(trifluoromethyl)[1,2,4]triazolo[4,3-b]pyridazine (437 mg, 85%) as a pale brown solid.

1H NMR (399.9 MHz, CDCl3) δ 1.37 (3H, d), 2.48-2.54 (2H, m), 2.59-2.65 (2H, m), 3.40 (1H, q), 3.54-3.64 (4H, m), 7.03 (1H, d), 7.21 (2H, d), 7.46 (2H, d), 7.90 (1H, d); m/z=455/457 [M+H]+.

EXAMPLE 307

Preparation of 4-[(1R)-1-[4-[3-(trifluoromethyl)[1,2,4]triazolo[4,3-b]pyridazin-6-yl]piperazin-1-yl]ethyl]benzonitrile

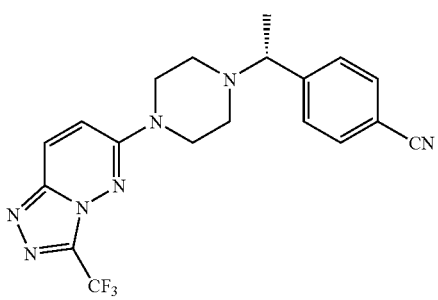

6-[4-[(1R)-1-(4-Bromophenyl)ethyl]piperazin-1-yl]-3-(trifluoromethyl)[1,2,4]triazolo[4,3-b]pyridazine (obtained as described in Example 306) (250 mg, 0.55 mmol), zinc cyanide (38.7 mg, 0.33 mmol), tris(dibenzylideneacetone)dipalladium(0) (5.0 mg, 5.49 μmol), 4,5-bis(diphenylphosphino)-9,9-dimethylxanthene (6.3 mg, 10.98 μmol) and N,N,N',N'-tetramethylethylenediamine (0.017 mL, 0.11 mmol) were suspended in DMF (2.5 mL) and sealed into a microwave tube. The reaction was heated to 160° C. for 5 minutes in a microwave reactor and cooled to ambient temperature. The resulting mixture was applied to an SCX column and eluted with methanol followed by 2M ammonia in methanol. Fractions containing product were combined and evaporated then purified by preparative HPLC (Waters XTerra C18 column, 5μ silica, 19 mm diameter, 100 mm length), using decreasingly polar mixtures of water (containing 1% ammonia) and MeCN as eluents. Fractions containing the desired compound were evaporated to dryness to afford 4-[(1R)-1-[4-[3-(trifluoromethyl)[1,2,4]triazolo[4,3-b]pyridazin-6-yl]piperazin-1-yl]ethyl]benzonitrile (168 mg, 76%) as a colourless solid.

1H NMR (399.9 MHz, CDCl3) δ 1.39 (3H, d), 2.48-2.53 (2H, m), 2.63-2.68 (2H, m), 3.49 (1H, q), 3.55-3.65 (4H, m), 7.04 (1H, d), 7.48 (2H, d), 7.64 (2H, d), 7.92 (1H, d); m/z=402 [M+H]+.

EXAMPLE 308

Preparation of 6-[4-[(1R)-1-(4-fluorophenyl)ethyl]piperazin-1-yl]-3-(trifluoromethyl)[1,2,4]triazolo[4,3-b]pyridazine

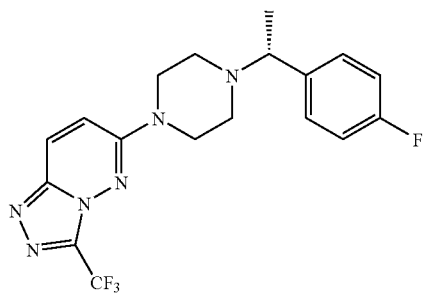

A mixture of (R)-1-[1-(4-fluorophenyl)ethyl]piperazine (obtained as described in J. Med. Chem. 2007, 50, 3528) and 6-chloro-3-(trifluoromethyl)-[1,2,4]triazolo[4,3-b]pyridazine was allowed to react by the method described in Example 306 to give 6-[4-[(1R)-1-(4-fluorophenyl)ethyl]piperazin-1-yl]-3-(trifluoromethyl)[1,2,4]triazolo[4,3-b]pyridazine in 87% yield.

1H NMR (399.9 MHz, CDCl3) δ 1.38 (3H, d), 2.49-2.54 (2H, m), 2.59-2.65 (2H, m), 3.43 (1H, q), 3.54-3.64 (4H, m), 6.99-7.04 (3H, m), 7.29 (2H, dd), 7.90 (1H, d); m/z=395 [M+H]+.

EXAMPLE 309

Preparation of 6-[4-[1'-(4-fluorophenyl)-1-methylethyl]piperazin-1-yl]-3-(trifluoromethyl)[1,2,4]triazolo[4,3-b]pyridazine

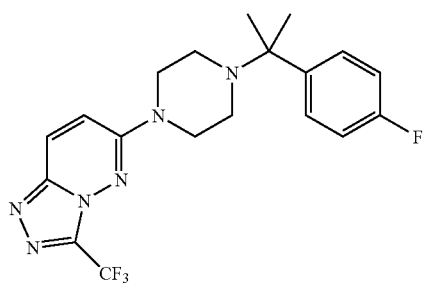

6-Chloro-3-(trifluoromethyl)-[1,2,4]triazolo[4,3-b]pyridazine (120 mg, 0.54 mmol), DIPEA (0.094 mL, 0.54 mmol) and 1-[2-(4-fluorophenyl)propan-2-yl]piperazine (obtained as described in J. Med. Chem. 2007, 50, 3528) (120 mg, 0.54 mmol) in DMF (1.5 mL) were stirred and heated at 80° C. for 1 hour. The resulting solution was cooled to room temperature then applied to an SCX column and eluted with MeOH followed by 2M ammonia in methanol. Fractions containing product were combined and evaporated, then purified by preparative HPLC (Waters XTerra C18 column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[1-(4-fluorophenyl)-1-methylethyl]piperazin-1-yl]-3-(trifluoromethyl)[1,2,4]triazolo[4,3-b]pyridazine (155 mg, 70%) as a colourless solid.

1H NMR (399.9 MHz, CDCl3) δ 1.37 (6H, s), 2.62 (4H, t), 3.57 (4H, t), 6.99 (2H, d), 7.04 (1H, d), 7.51 (2H, dd), 7.90 (1H, d); m/z=409 [M+H]+.

EXAMPLE 310

Preparation of 4-(3-fluorophenyl)-1-[3-(trifluoromethyl)[1,2,4]triazolo[4,3-b]pyridazin-6-yl]piperidin-4-ol

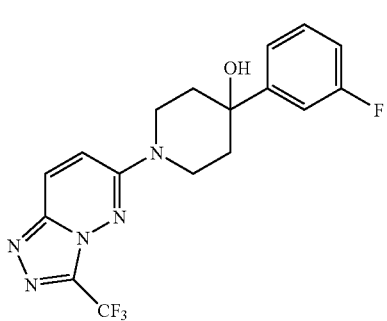

3-Fluorophenylmagnesium bromide (1.0M in THF, 1.68 mL, 1.68 mmol) was added dropwise to 1-[3-(trifluoromethyl)-[1,2,4]triazolo[4,3-b]pyridazin-6-yl]piperidin-4-one (400 mg, 1.40 mmol) in THF (10 mL) cooled to 0° C. over a period of 10 minutes. The resulting mixture was stirred at 0° C. for 20 minutes, then quenched with saturated ammonium chloride solution (20 mL) and extracted with ethyl acetate. The extract was washed with saturated brine, dried over MgSO4 and evaporated to a pale orange oil which was triturated with DCM to give a beige solid. The solid was filtered, washed with DCM and dried, then purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 4-(3-fluorophenyl)-1-[3-(trifluoromethyl)[1,2,4]triazolo[4,3-b]pyridazin-6-yl]piperidin-4-ol (96 mg, 18%) as a colourless solid.

1H NMR (399.9 MHz, DMSO-d6) δ 1.71-1.74 (2H, m), 2.00-2.08 (2H, m), 3.40-3.46 (2H, m), 4.20-4.24 (2H, m), 5.37 (1H, s), 7.02-7.08 (1H, m), 7.31-7.40 (3H, m), 7.66 (1H, d), 8.24 (1H, d).; m/z=382 [M+H]+.

The 1-[3-(trifluoromethyl)-[1,2,4]triazolo[4,3-b]pyridazin-6-yl]piperidin-4-one used as starting material was prepared as follows:—

6-Chloro-3-(trifluoromethyl)-[1,2,4]triazolo[4,3-b]pyridazine (10.0 g, 44.93 mmol), 4-piperidone monohydrate hydrochloride (8.48 g, 49.43 mmol) and DIPEA (16.3 mL, 98.85 mmol) in DMF (100 mL) were stirred and heated at 90° C. for 1 hour. The DMF was then evaporated in vacuo and the residue purified by flash silica chromatography, eluting with 2% MeOH in DCM. Pure fractions were concentrated to give a pale yellow precipitate. The precipitate was collected by filtration, washed with ether and air dried to afford 1-[3-(trifluoromethyl)-[1,2,4]triazolo[4,3-b]pyridazin-6-yl]piperidin-4-one (10.61 g, 83%) as a pale yellow solid.

1H NMR (399.9 MHz, CDCl3) δ 2.65 (4H, t), 3.98 (4H, t), 7.15 (1H, d), 8.02 (1H, d); m/z=286 [M+H]+.

EXAMPLES 311-314

The following compounds were prepared in 27-37% yield by an analogous method to Example 310, starting from 1-[3-(trifluoromethyl)-[1,2,4]triazolo[4,3-b]pyridazin-6-yl]piperidin-4-one and the appropriate aryl magnesium bromide:—

| Ex. | R | 1H NMR (399.9 MHz, DMSO-d6) | m/z [M + H]+ |
|---|---|---|---|
| 311 | 4-OMe | δ 1.71-1.74 (2H, m), 1.95-2.03 (2H, m), 3.40-3.46 (2H, m), 3.74 (3H, s), 4.17-4.20 (2H, m), 5.12 (1H, s), 6.88 (2H, d), 7.41 (2H, d), 7.65 (1H, d), 8.23 (1H, d). | 394 |
| 312 | 3-OMe | δ 1.71-1.74 (2H, m), 1.99-2.06 (2H, m), 3.40-3.46 (2H, m), 3.76 (3H, s), 4.19-4.22 (2H, m), 5.22 (1H, s), 6.80 (1H, dd), 7.05-7.09 (2H, m), 7.24 (1H, t), 7.66 (1H, d), 8.24 (1H, d). | 394 |
| 313 | 3-Cl | δ 1.70-1.73 (2H, m), 2.00-2.08 (2H, m), 3.40-3.46 (2H, m), 4.21-4.24 (2H, m), 5.39 (1H, s), 7.29 (1H, d), 7.36 (1H, t), 7.46 (1H, d), 7.57 (1H, m), 7.66 (1H, d), 8.24 (1H, d). | 398 |
| 314 | 2-OMe | δ 1.55-1.58 (2H, m), 2.52-2.58 (2H, m), 3.40-3.48 (2H, m), 3.63 (3H, s), 4.14-4.17 (2H, m), 5.10 (1H, s), 6.94-6.98 (2H, m), 7.21-7.25 (1H, m), 7.61 (1H, m), 7.67 (1H, d), 8.25 (1H, d). | 394 |

EXAMPLE 315

Preparation of 4-(2-chlorophenyl)-1-[3-(trifluoromethyl)[1,2,4]triazolo[4,3-b]pyridazin-6-yl]piperidin-4-ol

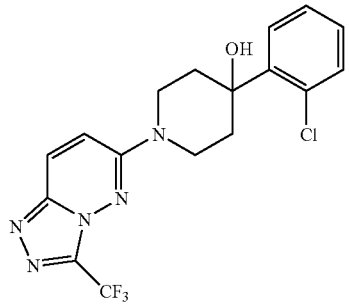

Isopropylmagnesium chloride-lithium chloride complex (1.0M in THF, 10 mL, 10.00 mmol) was added dropwise to 1-bromo-2-chlorobenzene (1.91 g, 9.98 mmol) in THF (2.0 mL) cooled to 0° C. over a period of 10 minutes. The resulting solution was stirred at 0° C. for 1 hour then a 2.0 mL aliquot was added dropwise to 1-[3-(trifluoromethyl)-[1,2,4]triazolo[4,3-b]pyridazin-6-yl]piperidin-4-one (400 mg, 1.40 mmol) in THF (10 mL) cooled to 0° C. over a period of 10 minutes. The resulting solution was stirred at 0° C. for 10 minutes then allowed to warm slowly to room temperature and stirred for a further hour. The reaction mixture was then quenched with saturated ammonium chloride (30 mL) and extracted with EtOAc. The extract was washed with saturated brine, dried over MgSO$_4$ and concentrated by evaporation, then purified by flash silica chromatography, eluting with EtOAc. Pure fractions were evaporated to dryness to afford 4-(2-chlorophenyl)-1-[3-(trifluoromethyl)[1,2,4]triazolo[4,3-b]pyridazin-6-yl]piperidin-4-ol (230 mg, 41%) as a colourless solid.

1H NMR (399.9 MHz, DMSO-d6) δ 1.68-1.71 (2H, m), 2.61-2.69 (2H, m), 3.44-3.51 (2H, m), 4.20-4.24 (2H, m), 5.47 (1H, s), 7.26-7.30 (1H, m), 7.36-7.40 (2H, m), 7.69 (1H, d), 7.84-7.86 (1H, m), 8.26 (1H, d); m/z=398 [M+H]+.

EXAMPLE 316

Preparation of 3-[4-hydroxy-1-[3-(trifluoromethyl)[1,2,4]triazolo[4,3-b]pyridazin-6-yl]piperidin-4-yl]benzonitrile

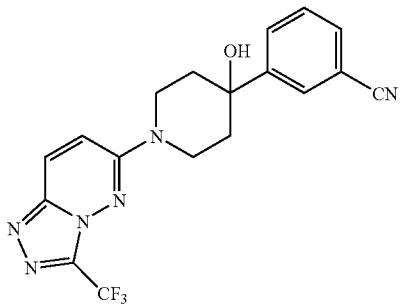

A mixture of 1-[3-(trifluoromethyl)-[1,2,4]triazolo[4,3-b]pyridazin-6-yl]piperidin-4-one and 3-bromobenzonitrile was allowed to react by the method of Example 315 to give 3-[4-hydroxy-1-[3-(trifluoromethyl)[1,2,4]triazolo[4,3-b]pyridazin-6-yl]piperidin-4-yl]benzonitrile in 26% yield.

1H NMR (399.9 MHz, DMSO-d6) δ 1.70-1.73 (2H, m), 2.04-2.11 (2H, m), 3.41-3.47 (2H, m), 4.22-4.25 (2H, m), 5.49 (1H, s), 7.55 (1H, t), 7.67 (1H, d), 7.71 (1H, m), 7.87 (1H, m), 7.95 (1H, m), 8.25 (1H, d); m/z=389 [M+H]+.

EXAMPLE 317

Preparation of 2-[4-hydroxy-1-[3-(trifluoromethyl)[1,2,4]triazolo[4,3-b]pyridazin-6-yl]piperidin-4-yl]benzonitrile

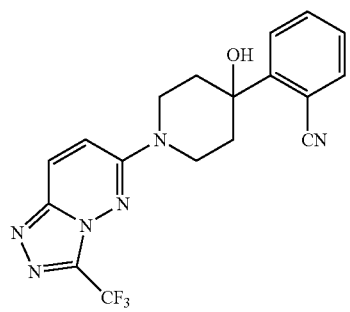

A mixture of 1-[3-(trifluoromethyl)-[1,2,4]triazolo[4,3-b]pyridazin-6-yl]piperidin-4-one and 2-bromobenzonitrile was allowed to react by the method of Example 315 to give 2-[4-hydroxy-1-[3-(trifluoromethyl)[1,2,4]triazolo[4,3-b]pyridazin-6-yl]piperidin-4-yl]benzonitrile in 24% yield.

1H NMR (399.9 MHz, DMSO-d6) δ 1.72-1.75 (2H, m), 2.23-2.30 (2H, m), 3.39-3.45 (2H, m), 4.39-4.43 (2H, m), 7.51-7.63 (4H, m), 7.72 (1H, d), 8.30 (1H, d), 8.04 (s) & 8.71 (s) (1H); m/z=389 [M+H]+.

EXAMPLE 318

Preparation of 4-(4-fluorophenyl)-1-[3-(trifluoromethyl)[1,2,4]triazolo[4,3-b]pyridazin-6-yl]piperidin-4-ol

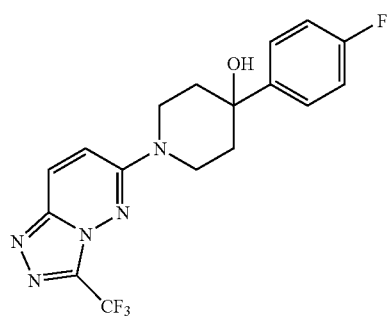

A mixture of 4-(4-fluorophenyl)piperidin-4-ol and 6-chloro-3-(trifluoromethyl)-[1,2,4]triazolo[4,3-b]pyridazine was allowed to react by the method of Example 306 to give 4-(4-fluorophenyl)-1-[3-(trifluoromethyl)[1,2,4]triazolo[4,3-b]pyridazin-6-yl]piperidin-4-ol in 74% yield.

1H NMR (399.9 MHz, DMSO-d6) δ 1.71-1.75 (2H, m), 1.98-2.06 (2H, m), 3.40-3.46 (2H, m), 4.19-4.22 (2H, m), 5.28 (1H, s), 7.14 (2H, t), 7.54 (2H, dd), 7.66 (1H, d), 8.24 (1H, d); m/z=382 [M+H]+.

EXAMPLE 319

Preparation of 4-pyridin-2-yl-1-[3-(trifluoromethyl)[1,2,4]triazolo[4,3-b]pyridazin-6-yl]piperidin-4-ol

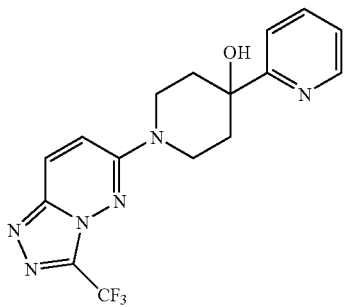

A mixture of 4-(pyridin-2-yl)piperidin-4-ol and 6-chloro-3-(trifluoromethyl)-[1,2,4]triazolo[4,3-b]pyridazine was allowed to react by the method of Example 306 to give 4-pyridin-2-yl-1-[3-(trifluoromethyl)[1,2,4]triazolo[4,3-b]pyridazin-6-yl]piperidin-4-ol in 77% yield.

1H NMR (399.9 MHz, DMSO-d6) δ 1.66-1.69 (2H, m), 2.18-2.25 (2H, m), 3.44-3.50 (2H, m), 4.20-4.23 (2H, m), 5.47 (1H, s), 7.24-7.27 (1H, m), 7.67 (1H, d), 7.72 (1H, d), 7.82 (1H, td), 8.25 (1H, d), 8.49 (1H, d); m/z=365 [M+H]+.

EXAMPLE 320

Preparation of 4-[5-(trifluoromethyl)pyridin-3-yl]-1-[3-(trifluoromethyl)[1,2,4]triazolo[4,3-b]pyridazin-6-yl]piperidin-4-ol

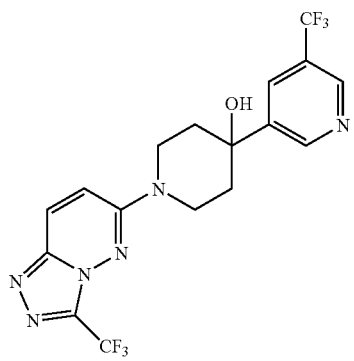

A mixture of 4-[5-(trifluoromethyl)pyridin-3-yl]piperidin-4-ol and 6-chloro-3-(trifluoromethyl)-[1,2,4]triazolo[4,3-b]pyridazine was allowed to react by the method of Example 306 to give 4-[5-(trifluoromethyl)pyridin-3-yl]-1-[3-(trifluoromethyl)[1,2,4]triazolo[4,3-b]pyridazin-6-yl]piperidin-4-ol in 75% yield.

1H NMR (399.9 MHz, DMSO-d6) δ 1.77-1.80 (2H, m), 2.12-2.20 (2H, m), 3.43-3.49 (2H, m), 4.25-4.28 (2H, m), 5.69 (1H, s), 7.68 (1H, d), 8.26 (2H, m), 8.87 (1H, d), 9.05 (1H, d); m/z=433 [M+H]+.

The 4-[5-(trifluoromethyl)pyridin-3-yl]piperidin-4-ol used as starting material was prepared as follows:—

Preparation of benzyl 4-hydroxy-4-[5-(trifluoromethyl)pyridin-3-yl]piperidine-1-carboxylate Isopropylmagnesium chloride-lithium chloride complex (1.0M in THF) (5.31 mL, 5.31 mmol) was added dropwise to 3-bromo-5-(trifluoromethyl)pyridine (1.20 g, 5.31 mmol) in THF (10 mL) cooled to 0° C. over a period of 10 minutes. The resulting solution was stirred at 0° C. for 1 hour then benzyl 4-oxo-1-piperidinecarboxylate (1.24 g, 5.31 mmol) in THF (5 mL) was added dropwise. The mixture was allowed to warm slowly to room temperature and stirred for a further 1 hour before quenching with aqueous ammonium chloride (25 mL). The mixture was then extracted with tert butyl methyl ether. The extract was washed with water followed by saturated brine, dried over MgSO4, concentrated by evaporation then purified by flash silica chromatography, elution gradient 20 to 50% EtOAc in isohexane. Pure fractions were evaporated to dryness to afford benzyl 4-hydroxy-4-[5-(trifluoromethyl)pyridin-3-yl]piperidine-1-carboxylate (1.32 g, 65%) as a pale yellow oil.

1H NMR (399.9 MHz, CDCl3) δ 1.76-1.79 (2H, m), 1.94-2.08 (2H, m), 3.26-3.37 (2H, m), 4.12-4.27 (2H, m), 5.16 (2H, s), 5.17 (1H, s), 7.32-7.38 (5H, m), 8.05 (1H, m), 8.79 (1H, d), 8.90 (1H, d); m/z=381 [M+H]+.

Preparation of 4-[5-(trifluoromethyl)pyridin-3-yl]piperidin-4-ol

Benzyl 4-hydroxy-4-[5-(trifluoromethyl)pyridin-3-yl]piperidine-1-carboxylate (1.30 g, 3.42 mmol), 5% palladium on activated carbon (50 mg) and ammonium formate (2.0 g) in ethanol (20 mL) were stirred and heated under reflux for 1 hour then cooled to ambient temperature and filtered through diatomaceous earth. The filtrate was applied to an SCX column and eluted with methanol followed by 2M ammonia in methanol. Fractions containing product were combined and evaporated then purified by flash silica chromatography, elution gradient 10 to 20% 2M ammonia in methanol in DCM. Pure fractions were evaporated to dryness to afford 4-[5-(trifluoromethyl)pyridin-3-yl]piperidin-4-ol (0.417 g, 50%) as a pale yellow solid.

1H NMR (399.9 MHz, DMSO-d6) δ 1.56-1.59 (2H, m), 1.86-1.93 (2H, m), 2.77-2.80 (2H, m), 2.92-2.98 (2H, m), 5.27 (1H, s), 8.17 (1H, s), 8.85 (1H, s), 8.98 (1H, s); m/z=247 [M+H]+.

EXAMPLE 321

Preparation of 4-(6-methoxypyridin-3-yl)-1-[3-(trifluoromethyl)[1,2,4]triazolo[4,3-b]pyridazin-6-yl]piperidin-4-ol

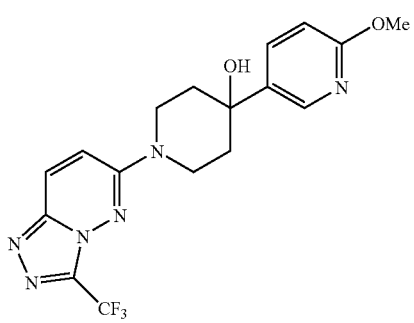

A mixture of 4-(6-methoxypyridin-3-yl)piperidin-4-ol and 6-chloro-3-(trifluoromethyl)-[1,2,4]triazolo[4,3-b]pyridazine was allowed to react by the method of Example 306 to give 4-(6-methoxypyridin-3-yl)-1-[3-(trifluoromethyl)[1,2,4]triazolo[4,3-b]pyridazin-6-yl]piperidin-4-ol in 58% yield.

1H NMR (399.9 MHz, DMSO-d6) δ 1.75-1.78 (2H, m), 1.99-2.04 (2H, m), 3.41-3.47 (2H, m), 3.84 (3H, s), 4.18-4.21 (2H, m), 5.30 (1H, s), 6.77 (1H, d), 7.66 (1H, d), 7.81 (1H, d), 8.24 (1H, d), 8.28 (1H, s); m/z=395 [M+H]+.

The 4-(6-methoxypyridin-3-yl)piperidin-4-ol used as starting material was prepared as follows:—

Preparation of benzyl 4-hydroxy-4-(6-methoxypyridin-3-yl)piperidine-1-carboxylate n-Butyllithium (1.6M in hexanes, 6.65 mL, 10.64 mmol) was added dropwise to 5-bromo-2-methoxypyridine (2.0 g, 10.64 mmol) in ether (30 mL) cooled to −78° C. over a period of 15 minutes. The resulting solution was stirred at −78° C. for 40 minutes then a solution of benzyl 4-oxo-1-piperidinecarboxylate (2.48 g, 10.64 mmol) in ether (10 mL) was added dropwise. The reaction was allowed to warm slowly to room temperature then quenched with ammonium chloride solution (50 mL) and extracted with EtOAc. The extract was washed sequentially with water and saturated brine, dried over $MgSO_4$ and concentrated by evaporation then purified by flash silica chromatography, elution gradient 50 to 80% EtOAc in isohexane. Pure fractions were evaporated to dryness to afford benzyl 4-hydroxy-4-(6-methoxypyridin-3-yl)piperidine-1-carboxylate (1.90 g, 52%) as a pale orange oil.

1H NMR (399.9 MHz, CDCl3) δ 1.75-1.79 (2H, m), 1.88-2.02 (2H, m), 3.29-3.35 (2H, m), 3.92 (3H, s), 4.03-4.16 (2H, m), 5.14 (2H, s), 6.72 (1H, d), 7.36 (5H, m), 7.66 (1H, dd), 8.24 (1H, d); m/z=343 [M+H]+.

Preparation of 4-(6-methoxypyridin-3-yl)piperidin-4-ol

Obtained in 39% yield by an analogous method to Example 320, preparation of starting materials, starting from benzyl 4-hydroxy-4-(6-methoxypyridin-3-yl)piperidine-1-carboxylate.

1H NMR (399.9 MHz, DMSO-d6) δ 1.65-1.68 (2H, m), 1.92-1.99 (2H, m), 2.92-2.95 (2H, m), 3.01-3.07 (2H, m), 3.84 (3H, s), 5.13 (1H, br s), 6.79 (1H, d), 7.76 (1H, dd), 8.23 (1H, d); m/z=209 [M+H]+.

EXAMPLE 322

Preparation of 4-(4-methylpyridin-2-yl)-1-[3-(trifluoromethyl)[1,2,4]triazolo[4,3-b]pyridazin-6-yl]piperidin-4-ol A mixture of 4-(4-methylpyridin-2-yl)piperidin-4-ol and 6-chloro-3-(trifluoromethyl)-[1,2,4]triazolo[4,3-b]pyridazine was allowed to react by the method of Example 306 to give 4-(4-methylpyridin-2-yl)-1-[3-(trifluoromethyl)[1,2,4]triazolo[4,3-b]pyridazin-6-yl]piperidin-4-ol in 81% yield.

1H NMR (399.9 MHz, DMSO-d6) δ 1.64-1.67 (2H, m), 2.20 (2H, td), 2.35 (3H, s), 3.42-3.49 (2H, m), 4.19-4.22 (2H, m), 5.43 (1H, s), 7.09 (1H, d), 7.55 (1H, s), 7.66 (1H, d), 8.24 (1H, d), 8.34 (1H, d); m/z=379 [M+H]+.

The 4-(4-methylpyridin-2-yl)piperidin-4-ol used as starting material was prepared as follows:—

Preparation of benzyl 4-hydroxy-4-(4-methylpyridin-2-yl)piperidine-1-carboxylate Obtained in 56% yield by an analogous method to Example 321, preparation of starting materials, starting from benzyl 4-oxo-1-piperidinecarboxylate and 2-bromo-4-methylpyridine.

1H NMR (399.9 MHz, CDCl3) δ 1.58-1.61 (2H, m), 1.87-2.00 (2H, m), 3.21 (3H, s), 3.29-3.45 (2H, m), 4.09-4.29 (2H, m), 5.17 (2H, s), 5.32 (1H, s), 7.03 (1H, d), 7.10 (1H, s), 7.30-7.41 (5H, m), 8.37 (1H, d); m/z=327 [M+H]+.

Preparation of 4-(4-methylpyridin-2-yl)piperidin-4-ol

Obtained in 56% yield by an analogous method to Example 321, preparation of starting materials, starting from benzyl 4-hydroxy-4-(4-methylpyridin-2-yl)piperidine-1-carboxylate.

1H NMR (399.9 MHz, DMSO-d6) δ 1.39-1.42 (2H, m), 2.01 (2H, td), 2.33 (3H, s), 2.73-2.76 (2H, m), 2.88-2.94 (2H, m), 4.96 (1H, s), 7.06 (1H, d), 7.47 (1H, s), 8.36 (1H, d); m/z=193 [M+H]+.

EXAMPLE 323

Preparation of 4-(6-chloropyridin-3-yl)-1-[3-(trifluoromethyl)[1,2,4]triazolo[4,3-b]pyridazin-6-yl]piperidin-4-ol

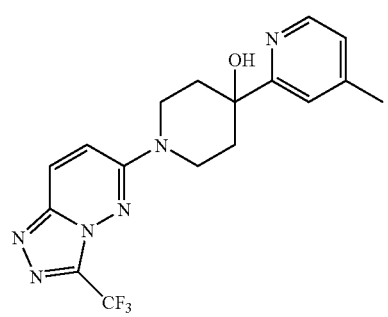

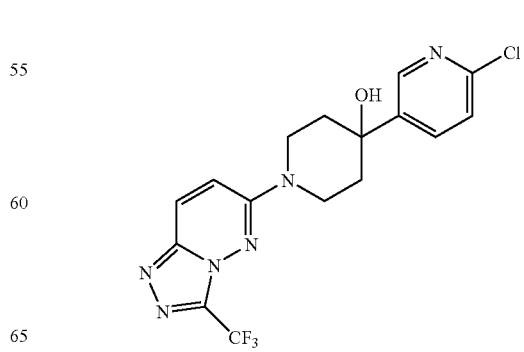

A mixture of 4-(6-chloropyridin-3-yl)piperidin-4-ol and 6-chloro-3-(trifluoromethyl)-[1,2,4]triazolo[4,3-b]pyridazine was allowed to react by the method of Example 306 to give 4-(6-chloropyridin-3-yl)-1-[3-(trifluoromethyl)[1,2,4]triazolo[4,3-b]pyridazin-6-yl]piperidin-4-ol in 80% yield.

1H NMR (399.9 MHz, DMSO-d6) δ 1.74-1.78 (2H, m), 2.06 (2H, td), 3.44 (2H, t), 4.21-4.25 (2H, m), 5.54 (1H, s), 7.47 (1H, d), 7.67 (1H, d), 7.96 (1H, dd), 8.25 (1H, d), 8.55 (1H, d); m/z=399 [M+H]+.

The 4-(6-chloropyridin-3-yl)piperidin-4-ol used as starting material was prepared as follows:—

Preparation of tert-butyl 4-hydroxy-4-(6-chloropyridin-3-yl)piperidine-1-carboxylate n-Butyl lithium (1.6M in hexanes, 6.50 mL, 10.39 mmol) was added dropwise to 5-bromo-2-chloropyridine (2.0 g, 10.39 mmol) in ether (30 mL) cooled to −78° C. over a period of 15 minutes. The resulting solution was stirred at −78° C. for 45 minutes then a solution of tert-butyl 4-oxo-1-piperidinecarboxylate (1.66 g, 8.31 mmol) in ether (10 mL) was added dropwise. The reaction was allowed to warm slowly to room temperature then quenched with ammonium chloride solution (50 mL) and extracted with EtOAc. The extract was washed sequentially with water and saturated brine, dried over MgSO4 and concentrated by evaporation, then purified by flash silica chromatography, elution gradient 20 to 50% EtOAc in isohexane. Pure fractions were evaporated to dryness to afford tert-butyl 4-(6-chloropyridin-3-yl)-4-hydroxypiperidine-1-carboxylate (1.33 g, 41%) as a cream solid.

1H NMR (399.9 MHz, CDCl3) δ 1.48 (9H, s), 1.72-1.76 (2H, m), 1.90-2.01 (2H, m), 3.16-3.27 (2H, m), 3.99-4.13 (2H, m), 7.31 (1H, d), 7.76 (1H, dd), 8.50 (1H, d); m/z=313 [M+H]+.

Preparation of 4-(6-chloropyridin-3-yl)piperidin-4-ol

HCl (4M in dioxan, 4.22 mL, 16.88 mmol) was added in one portion to a stirred suspension of tert-butyl 4-(6-chloropyridin-3-yl)-4-hydroxypiperidine-1-carboxylate (1.32 g, 4.22 mmol) in ethyl acetate (20 mL) at ambient temperature. The resulting mixture was stirred at 50° C. for 90 minutes then cooled to room temperature, diluted with ether (20 mL) and filtered. The filtered solid was washed with ether and dried then taken up in methanol, applied to an SCX column and eluted with methanol followed by 2M ammonia in methanol. Product-containing fractions were combined and evaporated then purified by flash silica chromatography, elution gradient 10 to 20% 2M ammonia in methanol in DCM. Pure fractions were evaporated to dryness to afford 4-(6-chloropyridin-3-yl)piperidin-4-ol (0.43 g, 48%) as a pale orange solid.

1H NMR (399.9 MHz, DMSO-d6) δ 1.53-1.56 (2H, m), 1.80 (2H, td), 2.72-2.75 (2H, m), 2.89-2.96 (2H, m), 5.09 (1H, s), 7.46 (1H, d), 7.90 (1H, dd), 8.49 (1H, d); m/z=213 [M+H]+.

EXAMPLE 324

Preparation of 4-(1,3-thiazol-2-yl)-1-[3-(trifluoromethyl)[1,2,4]triazolo[4,3-b]pyridazin-6-yl]piperidin-4-ol

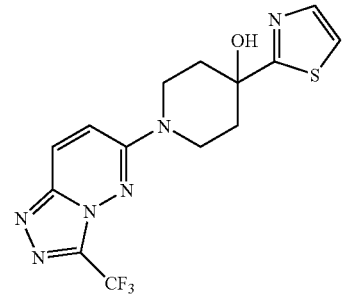

A mixture of 4-(1,3-thiazol-2-yl)piperidin-4-ol and 6-chloro-3-(trifluoromethyl)-[1,2,4]triazolo[4,3-b]pyridazine was allowed to react by the method of Example 306 to give 4-(1,3-thiazol-2-yl)-1-[3-(trifluoromethyl)[1,2,4]triazolo[4,3-b]pyridazin-6-yl]piperidin-4-ol in 65% yield.

1H NMR (399.9 MHz, DMSO-d6) δ 1.86-1.89 (2H, m), 2.15 (2H, td), 3.44-3.51 (2H, m), 4.16-4.19 (2H, m), 6.28 (1H, s), 7.62 (1H, d), 7.66 (1H, d), 7.72 (1H, d), 8.26 (1H, d); m/z=371 [M+H]+.

The 4-(1,3-thiazol-2-yl)piperidin-4-ol used as starting material was prepared as follows:—

Preparation of tert-butyl 4-hydroxy-4-(1,3-thiazol-2-yl)piperidine-1-carboxylate Obtained in 80% yield by an analogous method to Example 323, preparation of starting materials, starting from tert-butyl 4-oxo-1-piperidinecarboxylate and 2-bromothiazole.

1H NMR (399.9 MHz, CDCl3) δ 1.47 (9H, s), 1.85-1.88 (2H, m), 2.11 (2H, td), 3.24-3.35 (2H, m), 3.92-4.08 (2H, m), 7.30 (1H, d), 7.71 (1H, d); m/z=285 [M+H]+.

Preparation of 4-(1,3-thiazol-2-yl)piperidin-4-ol

Obtained in 82% yield by an analogous method to Example 323, preparation of starting materials, starting from tert-butyl 4-hydroxy-4-(2-thiazolyl)piperidine-1-carboxylate.

1H NMR (399.9 MHz, DMSO-d6) δ 1.77-1.80 (2H, m), 2.14 (2H, td), 3.02-3.04 (4H, m), 6.17 (1H, br s), 7.61 (1H, d), 7.74 (1H, d); m/z=185 [M+H]+.

EXAMPLE 325

Preparation of 6-[4-(1H-pyrrolo[2,3-b]pyridin-3-yl)piperidin-1-yl]-3-(trifluoromethyl)[1,2,4]triazolo[4,3-b]pyridazine

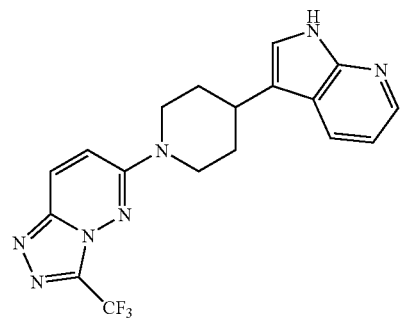

6-Chloro-3-(trifluoromethyl)-[1,2,4]triazolo[4,3-b]pyridazine (160 mg, 0.72 mmol), 3-(piperidin-4-yl)-1H-pyrrolo[2,3-b]pyridine (145 mg, 0.72 mmol) and DIPEA (0.14 mL, 0.79 mmol) in DMF (2.0 mL) were stirred and heated at 80° C. for 1 hour. The resulting mixture was then cooled to ambient temperature and quenched in water (10 mL) to give a beige solid. The solid was collected by filtration, washed sequentially with water, acetonitrile and ether, and air dried to give 6-[4-(1H-pyrrolo[2,3-b]pyridin-3-yl)piperidin-1-yl]-3-(trifluoromethyl)[1,2,4]triazolo[4,3-b]pyridazine (217 mg, 78%) as a colourless solid.

1H NMR (399.9 MHz, DMSO-d6) δ 1.70-1.81 (2H, m), 2.09-2.12 (2H, m), 3.12-3.26 (3H, m), 4.40-4.43 (2H, m), 7.03 (1H, dd), 7.25 (1H, d), 7.67 (1H, d), 8.04 (1H, d), 8.19 (1H, dd), 8.24 (1H, d), 11.34 (1H, s); m/z=388 [M+H]+.

The 4-(1H-pyrrolo[5,4-b]pyridin-3-yl)piperidine used as starting material was prepared as follows:—

Preparation of tert-butyl 4-(1H-pyrrolo[2,3-b]pyridin-3-yl)-5,6-dihydropyridine-1(2H)-carboxylate Potassium hydroxide (1.90 g, 33.86 mmol) was added to 1H-pyrrolo[2,3-b]pyridine (1.0 g, 8.46 mmol) and tert-butyl 4-oxopiperidine-1-carboxylate (3.37 g, 16.93 mmol) in methanol (25 mL) at ambient temperature, then the resulting solution was stirred at 65° C. for 18 hours. The mixture was cooled to ambient temperature, quenched in dilute aqueous ammonium chloride (80 mL) and extracted with ethyl acetate. The extract was washed sequentially with water and saturated brine, dried over MgSO$_4$, concentrated by evaporation and purified by flash silica chromatography, using 5% MeOH in DCM eluent. Pure fractions were combined and concentrated by evaporation, then triturated with ether to give a colourless precipitate. The precipitate was collected by filtration, washed with ether and air dried to afford tert-butyl 4-(1H-pyrrolo[2,3-b]pyridin-3-yl)-5,6-dihydropyridine-1(2H)-carboxylate (1.37 g, 54%) as a colourless solid.

1H NMR (399.9 MHz, CDCl3) δ 1.51 (9H, s), 2.57 (2H, m), 3.68 (2H, m), 4.14 (2H, m), 6.15 (1H, m), 7.13 (1H, dd), 7.33 (1H, s), 8.20 (1H, d), 8.34 (1H, d), 10.29 (1H, s); m/z=300 [M+H]+.

Preparation of tert-butyl 4-(1H-pyrrolo[2,3-b]pyridin-3-yl)piperidine-1-carboxylate tert-Butyl 4-(1H-pyrrolo[2,3-b]pyridin-3-yl)-5,6-dihydropyridine-1(2H)-carboxylate (1.35 g, 4.51 mmol), ammonium formate (1.42 g, 22.55 mmol) and 5% palladium on activated carbon (50 mg) in ethanol (25 mL) were stirred and refluxed for 1 hour. The resulting mixture was cooled to room temperature and filtered through diatomaceous earth. The filtrate was concentrated by evaporation then treated with dilute aqueous ammonium chloride (50 mL) and extracted with DCM. The extract was washed with water, dried over MgSO4 and evaporated to a colourless solid. The solid was triturated with ether then collected by filtration and dried under vacuum to give tert-butyl 4-(1H-pyrrolo[2,3-b]pyridin-3-yl)piperidine-1-carboxylate (1.088 g, 80%) as a colourless solid.

1H NMR (399.9 MHz, CDCl3) δ 1.49 (9H, s), 1.64-1.74 (2H, m), 2.00-2.03 (2H, m), 2.86-3.00 (3H, m), 4.16-4.34 (2H, m), 7.06-7.10 (2H, m), 7.96 (1H, d), 8.31 (1H, s), 9.73 (1H, s); m/z=302 [M+H]+.

Preparation of 4-(1H-pyrrolo[5,4-b]pyridin-3-yl)piperidine

TFA (5.0 mL, 3.58 mmol) was added in one portion at ambient temperature to a stirred suspension of tert-butyl 4-(1H-pyrrolo[2,3-b]pyridin-3-yl)piperidine-1-carboxylate (1.08 g, 3.58 mmol) in DCM (8 mL). The resulting solution was stirred for 30 minutes then applied to an SCX column and eluted with MeOH followed by 2M ammonia in methanol. Pure fractions were combined and concentrated by evaporation, then triturated with ether to give a solid which was collected by filtration and air-dried to give 3-(piperidin-4-yl)-1H-pyrrolo[2,3-b]pyridine (0.64 g, 88%) as a colourless solid.

1H NMR (399.9 MHz, DMSO-d6) δ 1.54-1.63 (2H, m), 1.86-1.89 (2H, m), 2.62-2.68 (2H, m), 2.81-2.87 (1H, m), 3.02-3.05 (2H, m), 7.01 (1H, dd), 7.18 (1H, s), 7.98 (1H, d), 8.17 (1H, d), 11.28 (1H, s); m/z=202 [M+H]+.

EXAMPLES 326-328

The following compounds were prepared in 40-60% yield by an analogous method to Example 325, starting from 6-chloro-3-(trifluoromethyl)-[1,2,4]triazolo[4,3-b]pyridazine and the appropriate 4-(1H-pyrrolopyridin-3-yl)piperidine:—

| Ex. | W | X | Y | 1H NMR (399.9 MHz, DMSO-d6) | m/z [M + H]+ |
|---|---|---|---|---|---|
| 326 | CH | N | CH | δ 1.72-1.82 (2H, m), 2.13-2.16 (2H, m), 3.18-3.27 (3H, m), 4.40-4.43 (2H, m), 7.22 (1H, dd), 7.32 (1H, d), 7.68 (1H, d), 8.14 (1H, d), 8.24 (1H, d), 8.93 (1H, s), 11.23 (1H, s). | 388 |
| 327 | N | CH | CH | δ 1.71-1.81 (2H, m), 2.09-2.12 (2H, m), 3.12-3.27 (3H, m), 4.40-4.43 (2H, m), 7.40 (1H, d), 7.60 (1H, d), 7.68 (1H, d), 8.07 (1H, d), 8.25 (1H, d), 8.70 (1H, d), 11.33 (1H, s). | 388 |
| 328 | CH | CH | N | δ 1.81-1.92 (2H, m), 2.17-2.20 (2H, m), 3.18-3.30 (3H, m), 4.40 (2H, d), 7.08 (1H, dd), 7.42 (1H, d), 7.67 (1H, d), 7.71 (1H, dd), 8.24 (1H, d), 8.29 (1H, dd), 11.02 (1H, s). | 388 |

The isomeric 4-(1H-pyrrolopyridin-3-yl)piperidines used as starting materials in Examples 326-328 were prepared in 3 steps as follows:—

Preparation of tert-butyl 4-(1H-pyrrolopyridin-3-yl)-3,6-dihydro-2H-pyridine-1-carboxylates Obtained in 49-54% yield by an analogous procedure to Example 325, preparation of starting materials, starting from tert-butyl 4-oxopiperidine-1-carboxylate and the appropriate 1H-pyrrolopyridine.

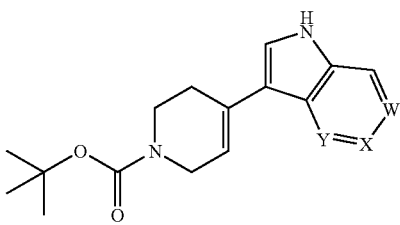

| Precursor to Ex. | W | X | Y | 1H NMR (399.9 MHz, CDCl3) | m/z [M + H]+ |
|---|---|---|---|---|---|
| 326 | CH | N | CH | δ 1.51 (9H, s), 2.55-2.61 (2H, m), 3.69 (2H, t), 4.16 (2H, m), 6.23 (1H, m), 7.22 (1H, s), 7.31 (1H, d), 8.33 (1H, d), 9.20 (2H, m). | 300 |
| 327 | N | CH | CH | δ 1.51 (9H, s), 2.54-2.62 (2H, m), 3.68-3.71 (2H, m), 4.12-4.19 (2H, m), 6.16 (1H, m), 7.38 (1H, s), 7.77 (1H, d), 8.29 (1H, d), 8.83 (1H, s), 9.63 (1H, br s). | 300 |
| 328 | CH | CH | N | δ 1.49 (9H, s), 2.57-2.60 (2H, m), 3.68-3.71 (2H, m), 4.17-4.19 (2H, m), 7.13 (1H, dd), 7.20 (1H, m), 7.36 (1H, d), 7.65 (1H, dd), 8.36 (1H, s), 8.53 (1H, dd). | 300 |

Preparation of tert-butyl 4-(1H-pyrrolopyridin-3-yl)piperidine-1-carboxylates

Obtained in 75-81% yield by an analogous procedure to Example 325, preparation of starting materials, starting from the appropriate tert-butyl 4-(1H-pyrrolopyridin-3-yl)-3,6-dihydro-2H-pyridine-1-carboxylate.

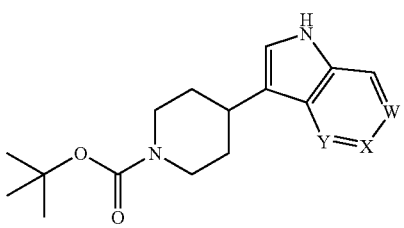

| Precursor to Ex. | W | X | Y | 1H NMR (399.9 MHz, CDCl3) | m/z [M + H]+ |
|---|---|---|---|---|---|
| 326 | CH | N | CH | δ 1.49 (9H, s), 1.63-1.74 (2H, m), 2.04-2.07 (2H, m), 2.88-2.95 (2H, m), 3.00-3.08 (1H, m), 4.16-4.34 (2H, m), 7.03 (1H, s), 7.31 (1H, dd), 8.29 (1H, d), 8.96 (1H, d), 9.04 (1H, br s). | 302 |
| 327 | N | CH | CH | δ 1.49 (9H, s), 1.64-1.74 (2H, m), 1.98-2.02 (2H, m), 2.86-2.92 (2H, m), 2.97-3.05 (1H, m), 4.16-4.37 (2H, m), 6.25 (1H, br s), 7.58 (1H, s), 7.76 (1H, d), 8.11 (1H, d), 9.26 (1H, s). | 302 |
| 328 | CH | CH | N | δ 1.48 (9H, s), 1.60-1.70 (2H, m), 2.14-2.17 (2H, m), 2.90-2.96 (2H, m), 3.22-3.30 (1H, m), 4.21 (2H, m), 7.11 (1H, dd), 7.18 (1H, d), 7.64 (1H, dd), 8.31 (1H, s), 8.47 (1H, dd). | 302 |

Preparation of 4-(1H-pyrrolopyridin-3-yl)piperidines

Obtained in 72-100% yield by an analogous procedure to Example 325, preparation of starting materials, starting from the appropriate tert-butyl 4-(1H-pyrrolopyridin-3-yl)piperidine-1-carboxylates.

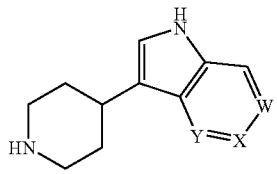

| Precursor to Ex. | W | X | Y | 1H NMR (399.9 MHz, DMSO-d6) | m/z [M + H]+ |
|---|---|---|---|---|---|
| 326 | CH | N | CH | δ 1.60-1.70 (2H, m), 1.92-1.95 (2H, m), 2.69-2.75 (2H, m), 2.91-2.99 (1H, m), 3.07-3.10 (2H, m), 7.17 (1H, s), 7.32 (1H, d), 8.13 (1H, d), 8.89 (1H, s), 11.20 (1H, s). | 202 |
| 327 | N | CH | CH | δ 1.53-1.64 (2H, m), 1.85-1.88 (2H, m), 2.63-2.68 (2H, m), 2.82-2.88 (1H, m), 3.02-3.05 (2H, m), 7.33 (1H, s), 7.55 (1H, d), 8.05 (1H, d), 8.69 (1H, s), 11.27 (1H, s). | 202 |
| 328 | CH | CH | N | δ 1.59-1.69 (2H, m), 1.96-2.00 (2H, m), 2.63-2.70 (2H, m), 2.96-3.06 (3H, m), 7.06 (1H, dd), 7.35 (1H, d), 7.69 (1H, dd), 8.28 (1H, dd), 10.96 (1H, s). | 202 |

EXAMPLE 329

Preparation of ethyl (2E)-3-[4-([4-[3-(trifluoromethyl)[1,2,4]triazolo[4,3-b]pyridazin-6-yl]piperazin-1-yl]methyl)phenyl]prop-2-enoate

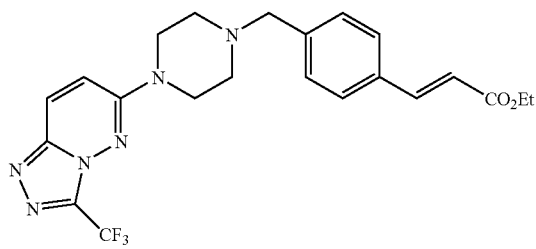

A mixture of ethyl (E)-3-(4-formylphenyl)prop-2-enoate and 6-(piperazin-1-yl)-3-(trifluoromethyl)[1,2,4]triazolo[4,3-b]pyridazine was allowed to react by General Synthetic Method 7 to give ethyl (2E)-3-[4-([4-[3-(trifluoromethyl)[1,2,4]triazolo[4,3-b]pyridazin-6-yl]piperazin-1-yl]methyl)phenyl]prop-2-enoate in 59% yield.

1H NMR (300.1 MHz, DMSO-d6) δ 1.27 (3H, t), 2.49-2.51 (4H, m), 3.58 (2H, s), 3.62 (4H, t), 4.20 (2H, q), 6.61 (1H, d), 7.39 (2H, d), 7.54-7.73 (4H, m), 8.24 (1H, d); m/z=461 [M+H]+.

EXAMPLE 330

Preparation of 4-[[4-[3-(trifluoromethyl)[1,2,4]triazolo[4,3-b]pyridazin-6-yl]piperazin-1-yl]methyl]aniline

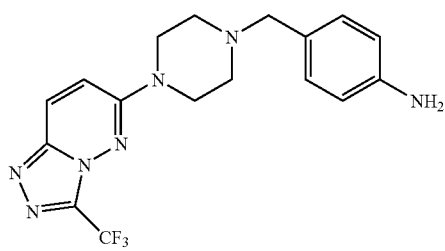

TFA (0.5 mL, 0.15 mmol) was added to tert-butyl N-[4-[[4-[3-(trifluoromethyl)-[1,2,4]triazolo[4,3-b]pyridazin-6-yl]piperazin-1-yl]methyl]phenyl]carbamate (obtained as described in Example 146, 72 mg, 0.15 mmol) in DCM (2 mL). The resulting solution was stirred at ambient temperature for 2 hours and then evaporated to dryness. The crude product was purified by preparative HPLC using decreasingly polar mixtures of water (containing 0.1% TFA) and MeCN as eluents. Fractions containing the desired compound were evaporated and further purified by ion exchange chromatography, using an SCX column. The desired product was eluted from the column using 7M ammonia in methanol and pure fractions were evaporated to dryness to afford 4-[[4-[3-(trifluoromethyl)[1,2,4]triazolo[4,3-b]pyridazin-6-yl]piperazin-1-yl]methyl]aniline (32 mg, 56%).

1H NMR (300.1 MHz, DMSO-d6) δ 2.29 (4H, t), 3.18 (2H, s), 3.42 (4H, t), 4.79 (2H, s), 6.36 (2H, d), 6.79 (2H, d), 7.41 (1H, d), 8.07 (1H, d); m/z=378 [M+H]+.

EXAMPLE 331

Preparation of 6-[3-(4-methoxyphenyl)pyrrolidin-1-yl]-3-(trifluoromethyl)[1,2,4]triazolo[4,3-b]pyridazine

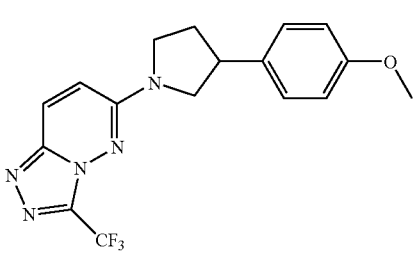

A solution of 6-chloro-3-(trifluoromethyl)-[1,2,4]triazolo[4,3-b]pyridazine (50 mg, 0.22 mmol) in ethanol (1 mL) was added to 3-(4-methoxyphenyl)pyrrolidine hydrochloride (71 mg, 0.33 mmol). The reaction mixture was treated with DIPEA (86 mg, 0.66 mmol) and the mixture was heated at 70° C. for 16 hours. The reaction mixture was evaporated to leave an involatile residue that was purified by preparative reverse phase chromatography to give 6-[3-(4-methoxyphenyl)pyrrolidin-1-yl]-3-(trifluoromethyl)[1,2,4]triazolo[4,3-b]pyridazine (45 mg, 55%).

1H NMR (300.1 MHz, DMSO-d6) δ 2.00-2.18 (1H, m), 2.30-2.42 (1H, m), 3.33-3.66 (3H, m), 3.68-3.83 (4H, m), 3.89-4.06 (1H, m), 6.88-6.96 (2H, m), 7.24-7.34 (3H, m), 8.23 (1H, d); m/z=364 [M+H]+.

EXAMPLES 332-334

The following compounds were prepared in 64-77% yield by an analogous method to Example 331, starting from 6-chloro-3-(trifluoromethyl)-[1,2,4]triazolo[4,3-b]pyridazine and the appropriate aryl pyrrolidine hydrochloride:—

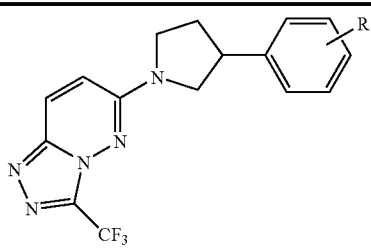

| Ex. | R | 1H NMR (300.1 MHz, DMSO-d6) | m/z [M + H]+ |
|---|---|---|---|
| 332 | 3-CN | 6-cδ 2.08-2.25 (1H, m), 2.37-2.48 (1H, m), 3.41-3.71 (3H, m), 3.72-3.86 (1H, m), 3.98-4.11 (1H, m), 7.31 (1H, d), 7.58 (1H, t), 7.72-7.77 (2H, m), 7.88 (1H, t), 8.26 (1H, d) | 359 |
| 333 | 2-CO2Me | 6-cδ 2.14-2.30 (1H, m), 2.31-2.44 (1H, m), 3.41-3.68 (2H, m), 3.71-3.83 (1H, m), 3.86 (3H, s), 3.97 (1H, t), 4.10-4.23 (1H, m), 7.31 | 392 |

-continued

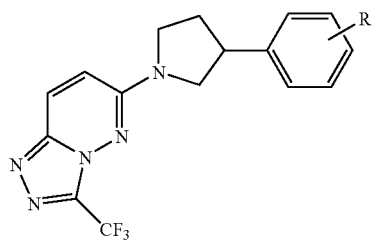

| Ex. | R | 1H NMR (300.1 MHz, DMSO-d6) | m/z [M + H]+ |
|---|---|---|---|
| | | (1H, d), 7.36-7.43 (1H, m), 7.55-7.61 (2H, m), 7.77 (1H, d), 8.24 (1H, d) | |
| 334 | 3-CO2Me | 6-cδ 2.15-2.33 (1H, m), 2.47-2.58 (1H, m), 3.47-3.81 (3H, m), 3.82-3.92 (1H, m), 3.94 (3H, s), 4.06-4.21 (1H, m), 7.41 (1H, d), 7.60 (1H, t), 7.73-7.79 (1H, m), 7.92-7.98 (1H, m), 8.03 (1H, t), 8.32 (1H, d) | 392 |

EXAMPLES 335-338

The following compounds were prepared in 52-74% yield by an analogous method to Example 331, starting from 6-chloro-3-[chloro(difluoro)methyl]-[1,2,4]triazolo[4,3-b]pyridazine and the appropriate aryl pyrrolidine hydrochloride:—

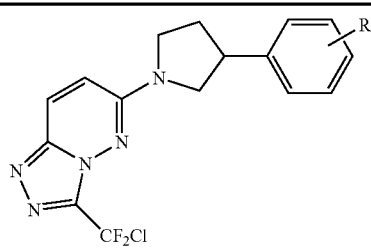

| Ex. | R | 1H NMR (300.1 MHz, CDCl3) | m/z [M + H]+ |
|---|---|---|---|
| 335 | 4-CF3 | δ 2.17-2.32 (1H, m), 2.49-2.61 (1H, m), 3.54-3.75 (3H, m), 3.81-3.91 (1H, m), 4.03-4.11 (1H, m), 6.89 (1H, d), 7.42 (2H, d), 7.64 (2H, d), 7.95 (1H, d) | 418 |
| 336 | 3-CF3 | δ 2.18-2.34 (1H, m), 2.49-2.61 (1H, m), 3.52-3.75 (3H, m), 3.83-3.93 (1H, m), 4.04-4.13 (1H, m), 6.89 (1H, d), 7.47-7.53 (2H, m), 7.53-7.60 (2H, m), 7.95 (1H, d) | 418 |
| 337 | H (S-enantiomer) | δ 2.16-2.32 (1H, m), 2.45-2.56 (1H, m), 3.52-3.72 (3H, m), 3.80-3.91 (1H, m), 3.98-4.11 (1H, m), 6.89 (1H, d), 7.27-7.33 (3H, m), 7.34-7.42 (2H, m), 7.93 (1H, d) | 350 |
| 338 | H (R-enantiomer) | δ 2.16-2.31 (1H, m), 2.45-2.56 (1H, m), 3.51-3.72 (3H, m), 3.79-3.90 (1H, m), 3.98-4.10 (1H, m), 6.89 (1H, d), 7.27-7.33 (3H, m), 7.34-7.42 (2H, m), 7.92 (1H, d) | 350 |

The 6-chloro-3-[chloro(difluoro)methyl]-[1,2,4]triazolo[4,3-b]pyridazine used as starting material was obtained in 70% yield by an analogous method to General Synthetic Method 1, preparation of starting materials, starting from 3-chloropyridazin-6-yl hydrazine and chlorodifluoroacetic acid.

1H NMR (300.1 MHz, DMSO) d 7.77 (d, 1H), 8.68 (d, 1H); m/z=239 [M+H]+.

EXAMPLE 339

Preparation of 3-[chloro(difluoro)methyl]-6-[4-(3,5-dichloropyridin-4-yl)piperazin-1-yl][1,2,4]triazolo[4,3-b]pyridazine

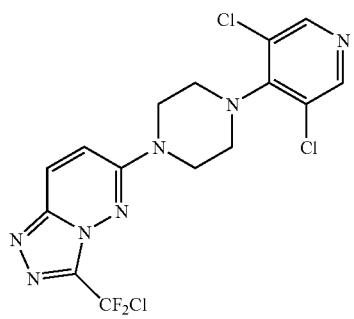

A solution of 6-chloro-3-[chloro(difluoro)methyl]-[1,2,4]triazolo[4,3-b]pyridazine (obtained as described in Examples 335-338, preparation of starting materials) (53 mg, 0.22 mmol) in ethanol (1 mL) was added to 1-(3,5-dichloropyridin-4-yl)piperazine (77 mg, 0.33 mmol). The reaction mixture was treated with DIPEA (43 mg, 0.33 mmol) and the mixture was heated at 70° C. for 4 hours. The reaction mixture was evaporated to leave an involatile residue that was purified by preparative reverse phase chromatography to give 3-[chloro(difluoro)methyl]-6-[4-(3,5-dichloropyridin-4-yl)piperazin-1-yl][1,2,4]triazolo[4,3-b]pyridazine (28 mg, 29%).

1H NMR (300.1 MHz, CDCl3) δ 3.48-3.54 (4H, m), 3.78-3.84 (4H, m), 7.13 (1H, d), 7.99 (1H, d), 8.41 (2H, s); m/z=434 [M+H]+.

EXAMPLES 340-343

The following compounds were prepared in 50-73% yield by an analogous method to Example 339, starting from 6-chloro-3-[chloro(difluoro)methyl]-[1,2,4]triazolo[4,3-b]pyridazine and the appropriate benzyl piperazine:—

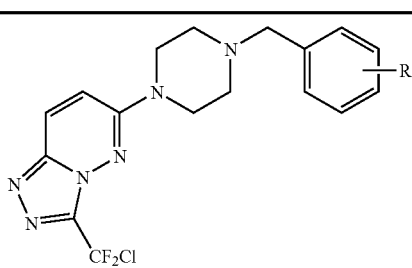

| Ex. | R | 1H NMR (300.1 MHz, CDCl3) | m/z [M + H]+ |
|---|---|---|---|
| 340 | H | δ 2.60 (4H, t), 3.58 (2H, s), 3.64 (4H, t), 7.06 (1H, d), 7.27-7.37 (5H, m), 7.92 (1H, d) | 379 |
| 341 | 4-F | δ 2.58 (4H, t), 3.54 (2H, s), 3.63 (4H, t), 6.98-7.09 (3H, m), 7.27-7.35 (2H, m), 7.92 (1H, d) | 397 |

-continued

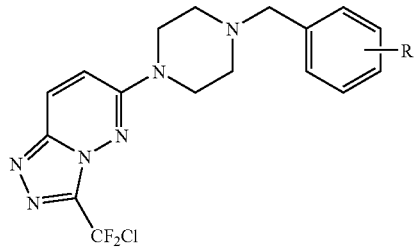

| Ex. | R | 1H NMR (300.1 MHz, CDCl3) | m/z [M + H]+ |
|---|---|---|---|
| 342 | 4-CN | δ 2.60 (4H, t), 3.60-3.69 (6H, m), 7.07 (1H, d), 7.49 (2H, d), 7.64 (2H, d), 7.94 (1H, d) | 404 |
| 343 | 3-CN | δ 2.60 (4H, t), 3.60 (2H, s), 3.66 (4H, t), 7.07 (1H, d), 7.46 (1H, t), 7.56-7.62 (2H, m), 7.70 (1H, s), 7.94 (1H, d) | 404 |

EXAMPLES 344-348

The following compounds were prepared in 24-76% yield by an analogous method to Example 339, starting from 6-chloro-3-[chloro(difluoro)methyl]-[1,2,4]triazolo[4,3-b]pyridazine and the appropriate benzyl piperazine:—

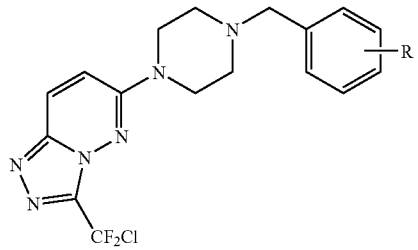

| Ex. | R | 1H NMR (300.1 MHz, DMSO-d6) | m/z [M + H]+ |
|---|---|---|---|
| 344 | 3-Br | δ 2.49-2.52 (4H, m), 3.56 (2H, s), 3.63 (4H, t), 7.28-7.38 (2H, m), 7.45-7.50 (1H, m), 7.53-7.55 (1H, m), 7.58 (1H, d), 8.24 (1H, d) | 459 |
| 345 | 3-F | δ 2.50-2.55 (4H, m), 3.57 (2H, s), 3.64 (4H, t), 7.05-7.21 (3H, m), 7.34-7.44 (1H, m), 7.58 (1H, d), 8.24 (1H, d) | 397 |
| 346 | 3-CF3 | δ 2.50-2.57 (4H, m), 3.60-3.69 (6H, m), 7.55-7.62 (3H, m), 7.68-7.75 (2H, m), 8.25 (1H, d) | 447 |
| 347 | 3-CF3 | δ 2.50-2.53 (4H, m), 3.60-3.68 (6H, m), 7.55-7.70 (5H, m), 8.24 (1H, d) | 447 |
| 348 | 4-Br | δ 2.49-2.52 (4H, m), 3.52 (2H, s), 3.62 (4H, t), 7.31 (2H, d), 7.50-7.61 (3H, m), 8.24 (1H, d) | 459 |

EXAMPLE 349

Preparation of 3-[chloro(difluoro)methyl]-6-[4-(2-phenylethyl)piperazin-1-yl][1,2,4]triazolo[4,3-b]pyridazine

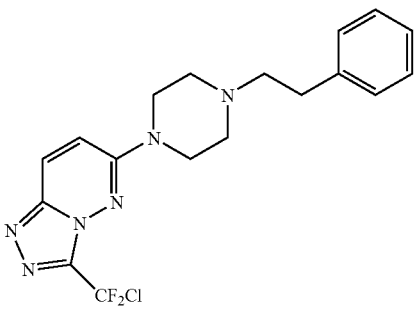

A mixture of 1-phenethylpiperazine and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-(2-phenylethyl)piperazin-1-yl][1,2,4]triazolo[4,3-b]pyridazine in 71% yield.

1H NMR (300.1 MHz, CDCl3) δ 2.64-2.73 (6H, m), 2.81-2.89 (2H, m), 3.67 (4H, t), 7.08 (1H, d), 7.19-7.34 (5H, m), 7.93 (1H, d); m/z=393 [M+H]+.

EXAMPLE 350

Preparation of 3-[chloro(difluoro)methyl]-6-[4-(1-Phenylethyl)piperazin-1-yl][1,2,4]triazolo[4,3-b]pyridazine

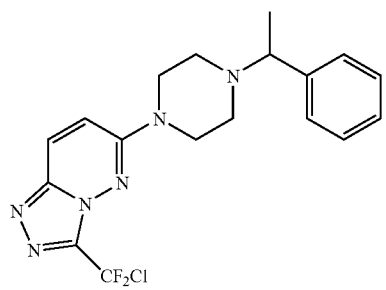

A mixture of 1-(1-phenylethyl)piperazine and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-(1-phenylethyl)piperazin-1-yl][1,2,4]triazolo[4,3-b]pyridazine in 64% yield.

1H NMR (499.8 MHz, DMSO-d6) δ 1.32 (3H, d), 2.39-2.57 (4H, m), 3.47 (1H, q), 3.58 (4H, t), 7.22-7.27 (1H, m), 7.30-7.35 (4H, m), 7.53 (1H, d), 8.20 (1H, d); m/z=393 [M+H]+.

EXAMPLE 351

Preparation of 3-[chloro(difluoro)methyl]-6-[4-[3-chloro-5-(trifluoromethyl)pyridin-2-yl]-1,4-diazepan-1-yl][1,2,4]triazolo[4,3-b]pyridazine

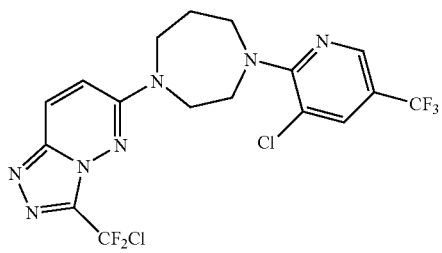

A mixture of 1-(3-chloro-5-trifluoromethyl-2-pyridyl)-1,4-diazepane and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-[3-chloro-5-(trifluoromethyl)pyridin-2-yl]-1,4-diazepan-1-yl][1,2,4]triazolo[4,3-b]pyridazine in 62% yield.

1H NMR (300.1 MHz, CDCl3) δ 2.09-2.19 (2H, m), 3.75 (2H, t), 3.81 (2H, t), 4.01 (4H, s), 7.04 (1H, d), 7.70-7.72 (1H, m), 7.94 (1H, d), 8.29-8.31 (1H, m); m/z=482 [M+H]+.

EXAMPLE 352

Preparation of 6-(4-benzyl-2-methylpiperazin-1-yl)-3-[chloro(difluoro)methyl][1,2,4]triazolo[4,3-b]pyridazine

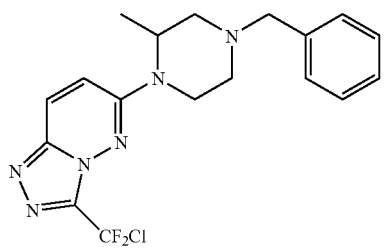

A mixture of 1-benzyl-3-methyl-piperazine and 6-chloro-3-[chloro(difluoro)methyl]-[1,2,4]triazolo[4,3-b]pyridazine was allowed to react by an analogous method to Example 339 to give 6-(4-benzyl-2-methylpiperazin-1-yl)-3-[chloro(difluoro)methyl][1,2,4]triazolo[4,3-b]pyridazine in 41% yield.

1H NMR (300.1 MHz, DMSO-d6) δ 1.26 (3H, d), 2.06-2.19 (1H, m), 2.22-2.30 (1H, m), 2.75 (1H, d), 2.94 (1H, d), 3.14-3.27 (1H, m), 3.53 (2H, q), 4.04 (1H, d), 4.41-4.53 (1H, m), 7.23-7.39 (5H, m), 7.56 (1H, d), 8.24 (1H, d); m/z=393 [M+H]+.

EXAMPLE 353

Preparation of 3-[chloro(difluoro)methyl]-6-[4-(2,6-dimethylphenyl)piperazin-1-yl][1,2,4]triazolo[4,3-b]pyridazine

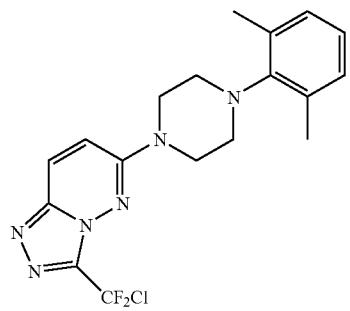

A mixture of 1-(2,6-dimethylphenyl)piperazine and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-(2,6-dimethylphenyl)piperazin-1-yl][1,2,4]triazolo[4,3-b]pyridazine in 64% yield.

1H NMR (300.1 MHz, CDCl3) δ 2.35 (6H, s), 3.26 (4H, t), 3.74 (4H, t), 7.00-7.05 (3H, m), 7.14 (1H, d), 7.95 (1H, d); m/z=393 [M+H]+.

EXAMPLE 354

Preparation of 6-(5-benzylhexahydropyrrolo[3,4-c]pyrrol-2(1H)-yl)-3-[chloro(difluoro)methyl][1,2,4]triazolo[4,3-b]pyridazine

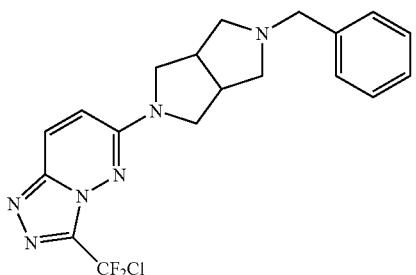

A mixture of 2-benzylhexahydropyrrolo[3,4-c]pyrrole hydrochloride and 6-chloro-3-[chloro(difluoro)methyl]-[1,2,4]triazolo[4,3-b]pyridazine was allowed to react by an analogous method to Example 331 to give 6-(5-benzylhexahydropyrrolo[3,4-c]pyrrol-2(1H)-yl)-3-[chloro(difluoro)methyl][1,2,4]triazolo[4,3-b]pyridazine in 66% yield.

1H NMR (300.1 MHz, CDCl3) δ 2.58-2.75 (4H, m), 3.04 (2H, s), 3.41-3.50 (2H, m), 3.63 (2H, s), 3.76-3.85 (2H, m), 6.88 (1H, d), 7.22-7.33 (5H, m), 7.90 (1H, d); m/z=405 [M+H]+.

EXAMPLE 355

Preparation of 3-[chloro(difluoro)methyl]-6-(4-phenylazepan-1-yl)[1,2,4]triazolo[4,3-b]pyridazine

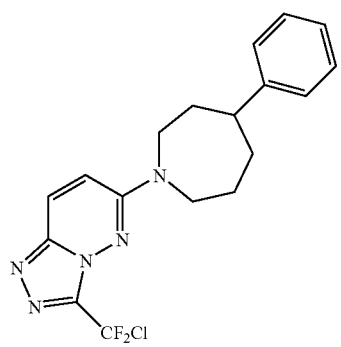

A mixture of 4-phenylazepane hydrochloride and 6-chloro-3-[chloro(difluoro)methyl]-[1,2,4]triazolo[4,3-b]pyridazine was allowed to react by an analogous method to Example 331 to give 3-[chloro(difluoro)methyl]-6-(4-phenylazepan-1-yl)[1,2,4]triazolo[4,3-b]pyridazine in 69% yield.

1H NMR (499.8 MHz, DMSO-d6) δ 1.64-1.90 (4H, m), 1.98-2.09 (2H, m), 2.68 (1H, t), 3.59-3.75 (2H, m), 3.76-3.86 (1H, m), 3.87-3.96 (1H, m), 7.10-7.20 (3H, m), 7.24 (2H, t), 7.49 (1H, d), 8.20 (1H, d); m/z=378 [M+H]+.

EXAMPLE 356

Preparation of 3-[chloro(difluoro)methyl]-6-[4-(thiophen-2-ylmethyl)piperazin-1-yl][1,2,4]triazolo[4,3-b]pyridazine

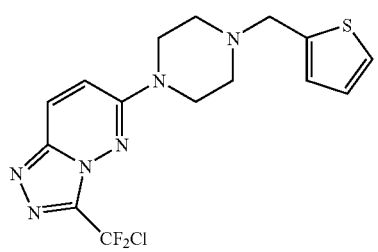

A mixture of 1-(thiophen-2-ylmethyl)piperazine and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-(thiophen-2-ylmethyl)piperazin-1-yl][1,2,4]triazolo[4,3-b]pyridazine in 74% yield.

1H NMR (300.1 MHz, DMSO-d6) δ 2.52-2.59 (4H, m), 3.63 (4H, t), 3.77 (2H, s), 6.97-7.01 (2H, m), 7.44-7.48 (1H, m), 7.58 (1H, d), 8.24 (1H, d); m/z=385 [M+H]+.

EXAMPLE 357

Preparation of 3-[chloro(difluoro)methyl]-6-[4-(thiophen-3-ylmethyl)piperazin-1-yl][1,2,4]triazolo[4,3-b]pyridazine

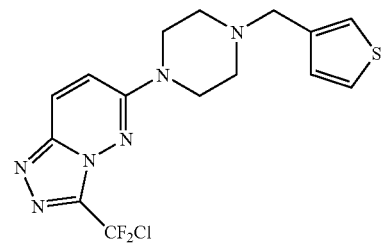

A mixture of 1-(thiophen-3-ylmethyl)piperazine and 6-chloro-3-[chloro(difluoro)methyl]-[1,2,4]triazolo[4,3-b]pyridazine was allowed to react by an analogous method to Example 339 to give 3-[chloro(difluoro)methyl]-6-[4-(thiophen-3-ylmethyl)piperazin-1-yl][1,2,4]triazolo[4,3-b]pyridazine in 70% yield.

1H NMR (300.1 MHz, DMSO-d6) δ 2.49-2.52 (4H, m), 3.56 (2H, s), 3.62 (4H, t), 7.06-7.10 (1H, m), 7.33-7.37 (1H, m), 7.49-7.52 (1H, m), 7.58 (1H, d), 8.24 (1H, d); m/z=385 [M+H]+.

EXAMPLE 358

Preparation of 6-[(2S)-2-methyl-4-(pyridin-4-ylmethyl)piperazin-1-yl]-3-(trifluoromethyl)[1,2,4]triazolo[4,3-b]pyridazine

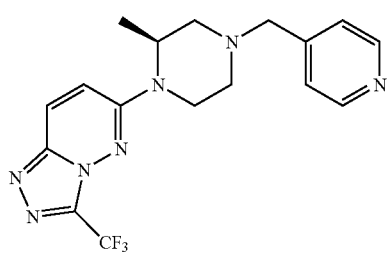

A mixture of pyridine-4-carboxaldehyde and 6-[(2S)-2-methylpiperazin-1-yl]-3-(trifluoromethyl)-[1,2,4]triazolo[4,3-b]pyridazine was allowed to react by General Synthetic Method 5 to give 6-[(2S)-2-methyl-4-(pyridin-4-ylmethyl)piperazin-1-yl]-3-(trifluoromethyl)[1,2,4]triazolo[4,3-b]pyridazine in 53% yield.

1H NMR (399.9 MHz, DMSO-d6) δ 1.29 (3H, d), 2.15-2.21 (1H, m), 2.30-2.34 (1H, m), 2.74 (1H, d), 2.94 (1H, d), 3.22-3.28 (1H, m), 3.52 (1H, d), 3.63 (1H, d), 4.04 (1H, d), 4.48 (1H, s), 7.39 (2H, d), 7.39 (1H, s), 7.58 (1H, d), 8.26 (1H, d), 8.54-8.55 (2H, m); m/z=378 [M+H]+.

The 6-[(2S)-2-methylpiperazin-1-yl]-3-(trifluoromethyl)-[1,2,4]triazolo[4,3-b]pyridazine used as starting material was prepared in 2 steps in 64% overall yield by an analogous method to Example 223, preparation of starting materials, starting from 6-chloro-3-(trifluoromethyl)-[1,2,4]-triazolo[4,3-b]pyridazine and (3S)-tert-butyl 3-methylpiperazine-1-carboxylate.

1H NMR (399.9 MHz, DMSO-d6) δ 1.23 (3H, d), 2.42 (1H, m), 2.65 (1H, m), 2.85 (2H, m), 3.04 (2H, m), 3.91 (1H, m), 4.35 (1H, m), 7.56 (1H, d), 8.23 (1H, d); m/z=387 [M+H]+.

EXAMPLES 359-360

The following compounds were prepared in 31-84% yield by General Synthetic Method 5, starting from 6-[(2S)-2-methylpiperazin-1-yl]-3-(trifluoromethyl)-[1,2,4]triazolo[4,3-b]pyridazine (obtained as described in Example 358, preparation of starting materials) and the appropriate aldehyde:—

| Ex | R | 1H NMR (399.9 MHz, DMSO-d6) | m/z [M + H]+ |
|---|---|---|---|
| 359 | H | δ 1.27-1.29 (3H, m), 2.18-2.25 (1H, m), 2.35-2.39 (1H, m), 2.79 (1H, d), 2.96-2.99 (1H, m), 3.21-3.27 (1H, m), 3.62 (1H, d), 3.70 (1H, d), 4.03 (1H, d), 4.48 (1H, s), 7.27-7.31 (1H, m), 7.52 (1H, s), 7.54 (1H, s), 7.58 (1H, d), 7.79-7.83 (1H, m), 8.26 (1H, d), 8.51-8.53 (1H, m) | 378 |
| 360 | Br | δ 1.28-1.30 (3H, m), 2.20-2.27 (1H, m), 2.37-2.41 (1H, m), 2.79 (1H, d), 3.22-3.27 (1H, m), 3.61 (1H, d), 3.69 (1H, d), 4.04 (1H, d), 4.49 (1H, s), 7.56 (2H, t), 7.58 (1H, d), 7.79 (1H, t), 8.26 (1H, d) | 456 |

EXAMPLES 361-366

The following compounds were prepared in 32-84% yield by General Synthetic Method 5, starting from 6-[(2S)-2-methylpiperazin-1-yl]-3-(trifluoromethyl)-[1,2,4]triazolo[4,3-b]pyridazine and the appropriate aldehyde:—

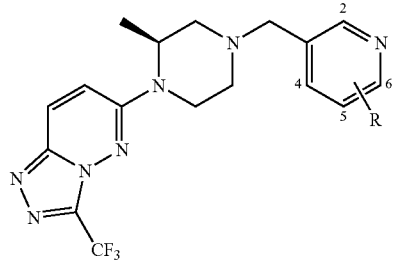

| Ex. | R | 1H NMR (399.9 MHz, DMSO-d6) | m/z [M + H]+ |
|---|---|---|---|
| 361 | 6-CF3 | δ 1.27-1.28 (3H, m), 2.16-2.23 (1H, m), 2.33-2.37 (1H, m), 2.77 (1H, d), 2.95 (1H, d), 3.20-3.27 (1H, m), 3.66 (1H, d), 3.74 (1H, d), 4.03 (1H, d), 4.49 (1H, d), 7.58 (1H, d), 7.91 (1H, d), 8.06-8.08 (1H, m), 8.26 (1H, d), 8.76 (1H, d) | |
| 362 | 2-Cl | δ 1.28-1.29 (3H, m), 2.22-2.29 (1H, m), 2.42-2.46 (1H, m), 2.80 (1H, d), 2.95 (1H, d), 3.20-3.27 (1H, m), 3.62 (2H, s), 4.04 (1H, d), 4.50 (1H, t), 7.46-7.49 (1H, m), 7.59 (1H, d), 7.99-8.01 (1H, m), 8.26 (1H, d), 8.34-8.36 (1H, m) | 421 |
| 363 | 2-Cl, 5-F | δ 1.29-1.31 (3H, m), 2.24-2.31 (1H, m), 2.46-2.49 (1H, m), 2.82 (1H, d), 2.97 (1H, d), 3.24-3.28 (1H, m), 3.63 (2H, s), 4.03 (1H, d), 4.50 (1H, t), 7.60 (1H, d), 7.91-7.94 (1H, m), 8.27 (1H, d), 8.41 (1H, d) | 430 |
| 364 | 6-OMe | δ 1.23 (3H, d), 2.24-2.27 (1H, m), 2.74 (1H, d), 3.43 (1H, d), 3.53 (1H, d), 3.86 (2H, s), 4.02 (1H, d), 4.47 (1H, d), 6.81-6.83 (1H, m), 7.57 (1H, d), 7.67-7.70 (1H, m), 8.10 (1H, d), 8.25 (1H, d) | 409 |
| 365 | 5-Br, 2-F | δ 1.25-1.27 (3H, m), 2.18-2.24 (1H, m), 2.36-2.40 (1H, m), 2.79 (1H, d), 2.96 (1H, d), 3.22-3.27 (1H, m), 3.56-3.64 (2H, m), 4.01-4.05 (1H, m), 4.49 (1H, d), 7.58 (1H, d), 8.20 (1H, d), 8.26 (1H, d), 8.32-8.33 (1H, m) | 476 |
| 366 | 5-F | δ 1.26-1.27 (3H, m), 2.14-2.21 (1H, m), 2.31-2.35 (1H, m), 2.76 (1H, d), 2.95 (1H, d), 3.20-3.27 (1H, m), 3.59 (1H, d), 3.67 (1H, d), 4.03 (1H, d), 4.48 (1H, s), 7.58 (1H, d), 7.67-7.71 (1H, m), 8.26 (1H, d), 8.45 (1H, t), 8.50 (1H, d) | 396 |

EXAMPLE 367

Preparation of 6-[4-[(6-bromopyridin-2-yl)methyl]piperazin-1-yl]-3-(trifluoromethyl)[1,2,4]triazolo[4,3-b]pyridazine

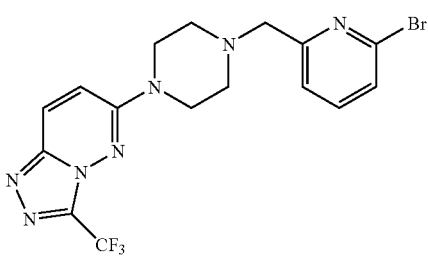

A mixture of 6-bromopyridine-2-carboxaldehyde and 6-(piperazin-1-yl)-3-(trifluoromethyl)-[1,2,4]triazolo[4,3-b]pyridazine was allowed to react by General Synthetic Method 5 to give 6-[4-[(6-bromopyridin-2-yl)methyl]piperazin-1-yl]-3-(trifluoromethyl)[1,2,4]triazolo[4,3-b]pyridazine in 66% yield.

1H NMR (399.9 MHz, DMSO-d6) δ 2.56-2.61 (4H, m), 3.64 (4H, t), 3.66 (2H, s), 7.53-7.54 (1H, m), 7.55-7.56 (1H, m), 7.60 (1H, d), 7.77 (1H, t), 8.26 (1H, d); m/z=444 [M+H]+.

EXAMPLES 368-377

The following compounds were prepared in 20-79% yield by General Synthetic Method 5, starting from 6-(piperazin-1-yl)-3-(trifluoromethyl)-[1,2,4]triazolo[4,3-b]pyridazine and the appropriate aldehyde:—

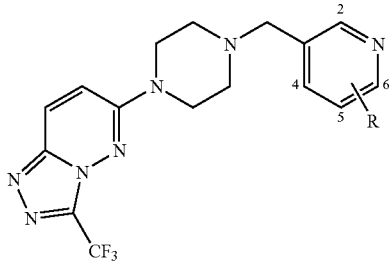

| Ex. | R | 1H NMR (399.9 MHz, DMSO-d6) | m/z [M + H]+ |
|---|---|---|---|
| 368 | 6-CF3 | δ 2.56 (4H, t), 3.64 (4H, t), 3.71 (2H, s), 7.60 (1H, d), 8.04-8.07 (1H, m), 8.26 (1H, d), 8.74 (1H, d) | 474 [1] |
| 369 | 2-Cl | δ 2.61 (4H, t), 3.66 (6H, s), 7.45-7.48 (1H, m), 7.61 (1H, d), 7.97-7.99 (1H, m), 8.27 (1H, d), 8.34-8.35 (1H, m) | 398 |
| 370 | 2-Cl, 5-F | δ 2.64 (4H, t), 3.66-3.67 (6H, m), 7.62 (1H, d), 7.90-7.93 (1H, m), 8.27 (1H, d), 8.40 (1H, d) | 416 |
| 371 | 5-F | δ 2.55 (4H, t), 3.63 (6H, t), 7.60 (1H, d), 7.67-7.71 (1H, m), 8.26 (1H, d), 8.44 (1H, t), 8.50 (1H, d) | 424 [1] |
| 372 | 5-Br, 2-F | δ 2.58 (4H, t), 3.62 (2H, s), 3.64 (4H, t), 7.59 (1H, d), 8.20 (1H, d), 8.26 (1H, d), 8.32-8.33 (1H, m) | 462 |
| 373 | 4-OMe | δ 2.56 (4H, t), 3.53 (2H, s), 3.63 (4H, t), 3.88 (3H, s), 6.99-7.02 (1H, m), 7.59 (1H, d), 7.72-7.75 (1H, m), 8.08-8.10 (1H, m), 8.25 (1H, d) | 394 |
| 374 | 6-Br | δ 2.54 (4H, s), 3.57-3.61 (2H, m), 3.62-3.63 (4H, m), 7.59 (1H, d), 7.64 (1H, d), 7.72-7.74 (1H, m), 8.26 (1H, d), 8.36 (1H, d) | 444 |
| 375 | 5-OMe | δ 2.53-2.56 (4H, m), 3.59-3.62 (2H, m), 3.63 (4H, d), 3.84 (3H, s), 7.33 (1H, q), 7.58 (1H, d), 8.14 (1H, d), 8.21-8.22 (1H, m), 8.23-8.25 (1H, m) | 394 |
| 376 | 2-Br | δ 2.53-2.57 (4H, m), 3.60-3.64 (6H, m), 7.59 (1H, d), 8.02 (1H, t), 8.26 (1H, d), 8.54 (1H, d), 8.63 (1H, d) | 444 |
| 377 | 4-Br | δ 2.59-2.63 (4H, m), 3.62-3.66 (4H, m), 3.68 (2H, s), 7.61 (1H, d), 7.72 (1H, d), 8.27 (1H, d), 8.36 (1H, d), 8.62 (1H, s) | 444 |

[1]Detected as adduct with acetonitrile used as solvent for mass spectral determination

EXAMPLES 378-379

The following compounds were prepared in 33-54% yield by an analogous method to Example 307, starting from the appropriate bromopyridine (obtained as described in the corresponding footnote):—

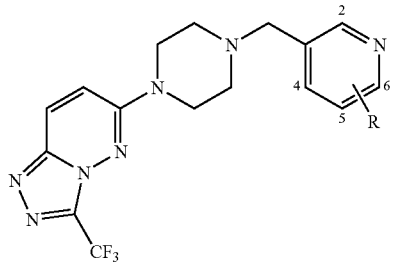

| Ex. | R | Note | H NMR (399.9 MHz, DMSO-d6) | m/z [M + H]+ |
|---|---|---|---|---|
| 378 | 2-CN | [1] | δ 2.61 (4H, t), 3.63 (4H, t), 3.78 (2H, s), 7.61 (1H, d), 7.74-7.77 (1H, m), 8.08-8.10 (1H, m), 8.27 (1H, d), 8.68-8.70 (1H, m) | 389 |
| 379 | 4-CN | [2] | δ 2.61 (4H, s), 3.63 (4H, s), 3.76 (2H, s), 7.60 (1H, d), 7.88 (1H, s), 8.26 (1H, d), 8.75 (1H, s), 8.85 (1H, s) | 389 |

[1]Starting form 6-[4-[(2-bromopyridin-3-yl)methyl]piperazin-1-yl]-3-(trifluoromethyl)[1,2,4]triazolo[4,3-b]pyridazine, obtained as described in Example 376.
[2]Starting form 6-[4-[(4-bromopyridin-3-yl)methyl]piperazin-1-yl]-3-(trifluoromethyl)[1,2,4]triazolo[4,3-b]pyridazine, obtained as described in Example 377.

EXAMPLES 380-393

The following compounds were prepared in 23-93% yield by General Synthetic Method 5, starting from 6-(piperazin-1-yl)-3-(trifluoromethyl)-[1,2,4]triazolo[4,3-b]pyridazine and the appropriate aldehyde:—

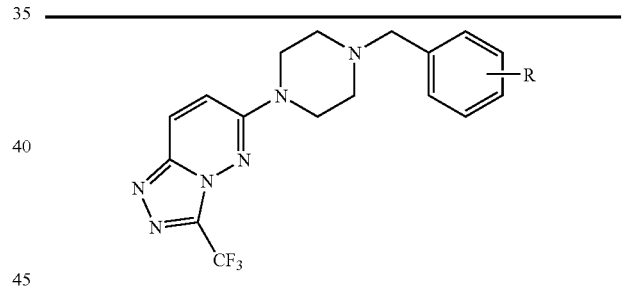

| Ex. | R | 1H NMR (399.9 MHz, DMSO-d6) | m/z [M + H]+ |
|---|---|---|---|
| 380 | 2,6-di-F, 4-CN | δ 2.65 (4H, m), 3.62 (4H, m), 3.78 (2H, s), 7.03 (1H, d), 7.25 (2H, m), 7.92 (1H, d) | 424 |
| 381 | 2,3-di-F | δ 2.64 (4H, m), 3.63 (4H, m), 3.69 (2H, s), 7.13 (4H, m), 7.92 (1H, d) | 399 |
| 382 | 2,4-di-F | 1H NMR (399.9 MHz, DMSO-d6) δ 2.52 (4H, m), 3.30 (2H, s), 3.61 (4H, m), 7.09 (1H, m), 7.22 (1H, m), 7.50 (1H, m), 7.58 (1H, d), 8.25 (1H, d) | 399 |
| 383 | 3,4-di-F | 1H NMR (399.9 MHz, DMSO-d6) δ 3.29 (4H, m), 3.55 (2H, s), 3.62 (4H, m), 7.19 (1H, m), 7.40 (2H, m), 7.59 (1H, d), 8.26 (1H, d) | 399 |
| 384 | 2,6-di-F | δ 2.76 (4H, m), 3.67 (4H, m), 3.85 (2H, s), 7.08 (2H, m), 7.44 (2H, m), 8.15 (1H, d) | 399 |
| 385 | 2-F, 4-OMe | δ 2.91 (4H, s), 3.74 (4H, s), 3.81 (3H, s), 3.91 (2H, s), 6.82 (2H, m), 7.40 (1H, m), 7.49 (1H, d), 8.18 (1H, d) | 411 |

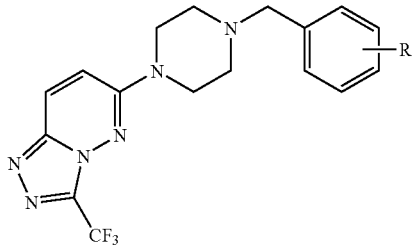

| Ex. | R | 1H NMR (399.9 MHz, DMSO-d6) | m/z [M + H]+ |
|---|---|---|---|
| 386 | 2,5-di-F | δ 2.78 (4H, m), 3.70 (4H, m), 3.80 (2H, s), 7.16 (1H, m), 7.22 (1H, m), 7.31 (1H, m), 7.49 (1H, d), 8.16 (1H, d) | 399 |
| 387 | 3-CN, 4-F | 1H NMR (399.9 MHz, DMSO-d6) δ 3.29 (4H, m), 3.60 (2H, s), 3.63 (4H, m), 7.52 (1H, m), 7.60 (1H, d), 7.77 (1H, m), 7.87 (1H, m), 8.26 (1H, d) | 406 |
| 388 | 3-F, 4-OMe | 1H NMR (399.9 MHz, DMSO-d6) δ 3.30 (4H, m), 3.49 (2H, s), 3.62 (4H, m), 3.84 (3H, s), 7.14 (3H, m), 7.59 (1H, d), 8.25 (1H, d) | 411 |
| 389 | 2-F, 4-CN | 1H NMR (399.9 MHz, DMSO-d6) δ 2.57 (4H, m), 3.30 (2H, s), 3.63 (4H, m), 7.60 (1H, d), 7.70 (2H, m), 7.85 (1H, m), 8.26 (1H, d) | 406 |
| 390 | 2-F, 5-OMe | 1H NMR (399.9 MHz, DMSO-d6) δ 2.55 (4H, m), 3.30 (3H, s), 3.62 (4H, m), 3.76 (2H, s), 6.88 (1H, m), 6.98 (1H, m), 7.12 (1H, m), 7.59 (1H, d), 8.25 (1H, d) | 411 |
| 391 | 3,5-di-F | 1H NMR (399.9 MHz, DMSO-d6) δ 3.30 (4H, m), 3.59 (2H, s), 3.64 (4H, m), 7.11 (3H, m), 7.60 (1H, d), 8.26 (1H, d) | 399 |
| 392 | 3-OMe, 4-F | 1H NMR (399.9 MHz, DMSO-d6) δ 2.52 (4H, m), 3.52 (2H, s), 3.63 (4H, m), 3.85 (3H, s), 6.90 (1H, m), 7.15 (2H, m), 7.59 (1H, d), 8.26 (1H, d) | 411 |
| 393 | 3-F, 4-CN | δ 2.55 (4H, m), 3.65 (4H, m), 3.67 (2H, s), 7.42 (1H, m), 7.51 (1H, m), 7.60 (1H, d), 7.91 (1H, m), 8.26 (1H, d) | 406 |

EXAMPLE 394

Preparation of 6-[4-(naphthalen-2-ylsulfonyl)piperazin-1-yl]-3-(trifluoromethyl)[1,2,4]triazolo[4,3-b]pyridazine

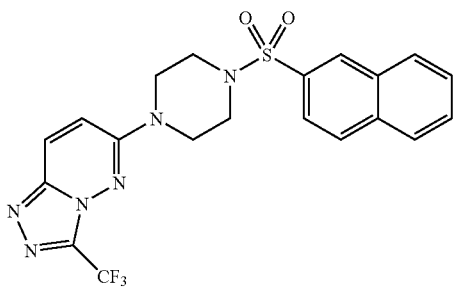

Naphthalene-2-sulfonyl chloride (175 mg, 0.77 mmol) was added to 6-(piperazin-1-yl)-3-(trifluoromethyl)-[1,2,4]triazolo[4,3-b]pyridazine (150 mg, 0.55 mmol) in pyridine (2 mL). The resulting solution was stirred at room temperature for 18 hours. The reaction mixture was evaporated to remove the pyridine. The crude product was purified by preparative HPLC (Phenomenex Gemini C18 110A (axia) column, 5μ silica, 19 mm diameter, 100 mm length), using decreasingly polar mixtures of water (containing 1% ammonia) and MeCN as eluents. Fractions containing the desired compound were evaporated to dryness to afford 6-[4-(naphthalen-2-ylsulfonyl)piperazin-1-yl]-3-(trifluoromethyl)[1,2,4]triazolo[4,3-b]pyridazine (168 mg, 66%) as a solid.

1H NMR (399.9 MHz, DMSO-d6) δ 3.15 (4H, m), 3.72 (4H, m), 7.49 (1H, d), 7.74 (3H, m), 8.07 (1H, d), 8.19 (3H, m), 8.49 (1H, s); m/z=463 [M+H]+.

EXAMPLE 395

Preparation of 6-[4-(pyridin-2-ylsulfonyl)piperazin-1-yl]-3-(trifluoromethyl)[1,2,4]triazolo[4,3-b]pyridazine

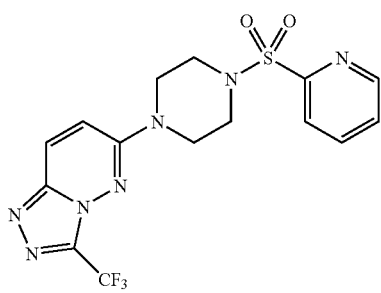

Obtained in 32% yield by an analogous method to Example 394, starting from pyridine-2-sulfonyl chloride and 6-(piperazin-1-yl)-3-(trifluoromethyl)-[1,2,4]triazolo[4,3-b]pyridazine.

1H NMR (399.9 MHz, DMSO-d6) δ 3.28 (4H, m), 3.63 (4H, m), 7.47 (1H, d), 7.64 (1H, m), 7.90 (1H, m), 8.06 (1H, m), 8.20 (1H, d), 8.68 (1H, m); m/z=414 [M+H]+.

EXAMPLES 396-405

The following compounds were prepared in 7-90% yield by an analogous method to Example 394, starting from 6-(piperazin-1-yl)-3-(trifluoromethyl)-[1,2,4]triazolo[4,3-b]pyridazine and the appropriate sulfonyl chloride:—

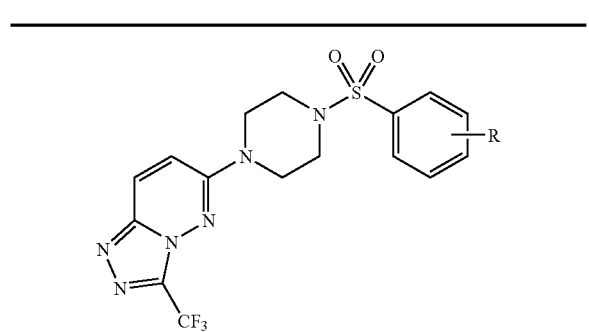

| Ex. | R | 1H NMR (399.9 MHz, DMSO-d6) | m/z [M + H]+ |
|---|---|---|---|
| 396 | 3-OMe | δ 3.09 (4H, m), 3.71 (4H, m), 3.85 (3H, s), 7.23 (1H, m), 7.32 (2H, m), 7.56 (2H, m), 8.25 (1H, d) | 443 |
| 397 | 2-OMe | δ 3.27 (4H, m), 3.67 (4H, m), 3.89 (3H, s), 7.12 (1H, m), 7.26 (1H, m), 7.56 (1H, d), 7.65 (1H, m), 7.78 (1H, m), 8.28 (1H, d) | 443 |
| 398 | 4-OMe | δ 2.96 (4H, m), 3.63 (4H, m), 3.76 (3H, s), 7.09 (2H, m), 7.44 (1H, d), 7.63 (2H, m), 8.17 (1H, d) | 443 |
| 399 | 2,5-di-OMe | δ 3.20 (4H, m), 3.59 (4H, m), 3.70 (3H, s), 3.76 (3H, s), 7.16 (3H, m), 7.48 (1H, d), 8.20 (1H, d) | 473 |
| 400 | 2-F | δ 3.16 (4H, m), 3.64 (4H, m), 7.42 (3H, m), 7.72 (2H, m), 8.19 (1H, d) | 431 |
| 401 | 3-F | δ 3.14 (4H, m), 3.72 (4H, m), 7.63 (5H, m), 8.26 (1H, d) | 431 |
| 402 | 3,4-di-OMe | δ 3.06 (4H, m), 3.71 (4H, m), 3.85 (6H, m), 7.18 (2H, m), 7.36 (1H, m), 7.53 (1H, d), 8.26 (1H, d) | 473 |
| 403 | 2-CN | δ 3.29 (4H, m), 3.74 (4H, m), 7.57 (1H, d), 7.94 (2H, m), 8.07 (1H, m), 8.18 (1H, m), 8.28 (1H, d) | 438 |
| 404 | 2,4-di-OMe | δ 3.21 (4H, m), 3.67 (4H, m), 3.85 (3H, s), 3.87 (3H, s), 6.68 (1H, m), 6.73 (1H, m), 7.56 (1H, d), 7.69 (1H, d), 8.27 (1H, d) | 473 |
| 405 | 4-F | δ 3.09 (4H, m), 3.72 (4H, m), 7.51 (3H, m), 7.86 (2H, m), 8.26 (1H, d) | 431 |

EXAMPLE 406

Preparation of N-methyl-N-(pyridin-3-ylmethyl)-1-[3-(trifluoromethyl)[1,2,4]triazolo[4,3-b]pyridazin-6-yl]piperidin-4-amine

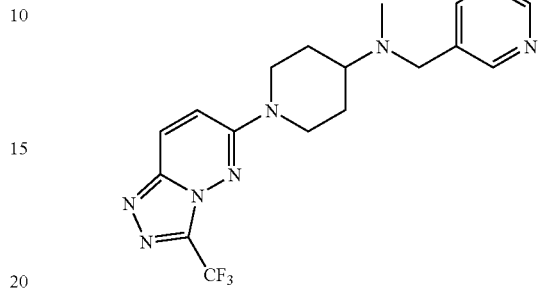

DIPEA (0.174 mL, 1.00 mmol) was added to N-methyl-1-[3-(trifluoromethyl)-[1,2,4]triazolo[4,3-b]pyridazin-6-yl]piperidin-4-amine (100 mg, 0.34 mmol) and 3-(bromomethyl)pyridine hydrobromide (127 mg, 0.50 mmol) in DMA (2 mL) and the mixture was sealed into a microwave tube. The reaction was heated to 150° C. for 15 minutes in the microwave reactor and cooled to ambient temperature. The crude product was purified by preparative HPLC (Waters XBridge Prep C18 OBD column, 5μ silica, 30 mm diameter, 100 mm length), using decreasingly polar mixtures of water (containing 1% ammonia) and MeCN as eluents. Fractions containing the desired compound were evaporated to dryness to afford N-methyl-N-(pyridin-3-ylmethyl)-1-[3-(trifluoromethyl)[1,2,4]triazolo[4,3-b]pyridazin-6-yl]piperidin-4-amine (113 mg, 78%) as a solid.

1H NMR (399.9 MHz, DMSO-d6) δ 1.59 (2H, m), 1.91 (2H, m), 2.12 (2H, s), 2.75 (1H, m), 3.03 (2H, m), 3.61 (3H, s), 4.34 (2H, m), 7.35 (1H, m), 7.63 (1H, d), 7.70 (1H, m), 8.23 (1H, d), 8.48 (2H, m); m/z=392 [M+H]+.

The N-methyl-1-[3-(trifluoromethyl)-[1,2,4]triazolo[4,3-b]pyridazin-6-yl]piperidin-4-amine used as starting material was prepared as follows:—

Preparation of tert-butyl methyl[1-(3-(trifluoromethyl)-[1,2,4]triazolo[4,3-b]pyridazin-6-yl)piperidin-4-yl]carbamate DIPEA (1.355 mL, 7.78 mmol) was added to 6-chloro-3-(trifluoromethyl)-[1,2,4]triazolo[4,3-b]pyridazine (0.865 g, 3.89 mmol) and tert-butyl methyl(piperidin-4-yl)carbamate (1 g, 4.67 mmol) in DMA (15 mL). The resulting solution was stirred at 50° C. for 2 hours. The reaction mixture was evaporated and diluted with DCM (100 mL), and washed sequentially with water (100 mL) and saturated brine (100 mL). The organic layer was dried over MgSO4, filtered and evaporated to afford crude product. The crude product was purified by flash silica chromatography, elution gradient 0 to 10% MeOH in DCM. Pure fractions were evaporated to dryness to afford tert-butyl methyl[1-(3-(trifluoromethyl)-[1,2,4]triazolo[4,3-b]pyridazin-6-yl)piperidin-4-yl]carbamate (1.500 g, 96%) as a solid.

1H NMR (399.9 MHz, DMSO-d6) δ 1.40 (9H, s), 1.71 (4H, m), 2.67 (3H, s), 3.05 (2H, m), 4.06 (1H, s), 4.38 (2H, m), 7.63 (1H, d), 8.24 (1H, d); m/z=401 [M+H]+.

Preparation of N-methyl-1-[3-(trifluoromethyl)-[1,2,4]triazolo[4,3-b]pyridazin-6-yl]piperidin-4-amine tert-Butyl methyl[1-(3-(trifluoromethyl)-[1,2,4]triazolo[4,3-b]pyridazin-6-yl]piperidin-4-yl]carbamate (1.5 g, 3.75 mmol) was dissolved in TFA (5 mL) and DCM (5 mL). The resulting solution was stirred at ambient temperature for 2 hours. The crude product was purified by ion exchange chromatography, using an SCX column. The desired product was eluted from the column using 2M ammonia in methanol and pure fractions were evaporated to dryness to afford N-methyl-1-[3-(trifluoromethyl)-[1,2,4]triazolo[4,3-b]pyridazin-6-yl]piperidin-4-amine (1.090 g, 97%) as a solid.

1H NMR (399.9 MHz, DMSO-d6) δ 1.30 (2H, m), 1.91 (2H, m), 2.59 (1H, m), 3.16 (2H, m), 3.30 (3H, s), 4.11 (2H, m), 7.61 (1H, d), 8.22 (1H, d); m/z=301 [M+H]+.

EXAMPLES 407-411

The following compounds were prepared in 39-78% yield by an analogous method to Example 406, starting from N-methyl-1-[3-(trifluoromethyl)-[1,2,4]triazolo[4,3-b]pyridazin-6-yl]piperidin-4-amine and the appropriate benzyl bromide:—

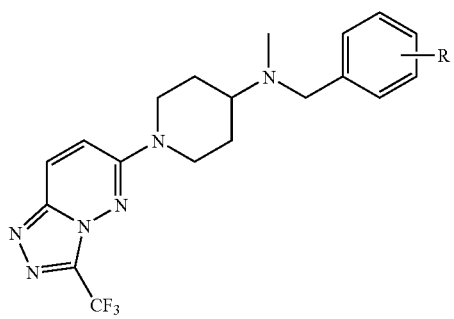

| Ex. | R | 1H NMR (399.9 MHz, DMSO-d6) | m/z [M + H]+ |
|---|---|---|---|
| 407 | 4-F | δ 1.58 (2H, m), 1.90 (2H, m), 2.11 (2H, s), 2.73 (1H, m), 3.02 (2H, m), 3.56 (3H, s), 4.32 (2H, m), 7.13 (2H, m), 7.34 (2H, m), 7.62 (1H, d), 8.23 (1H, d) | 409 |
| 408 | 3,4-di-F | δ 1.57 (2H, m), 1.89 (2H, m), 2.13 (2H, s), 2.73 (1H, m), 3.02 (2H, m), 3.56 (3H, s), 4.33 (2H, m), 7.16 (1H, m), 7.35 (2H, m), 7.63 (1H, d), 8.23 (1H, d) | 427 |
| 409 | 4-CN | δ 1.59 (2H, m), 1.90 (2H, m), 2.13 (2H, s), 2.65 (1H, m), 3.05 (2H, m), 3.66 (3H, s), 4.34 (2H, m), 7.65 (4H, m), 7.98 (1H, m), 8.27 (1H, m) | 416 |
| 410 | 3,5-di-F | δ 1.57 (2H, m), 1.89 (2H, m), 2.15 (2H, s), 2.73 (1H, m), 3.02 (2H, m), 3.61 (3H, s), 4.33 (2H, m), 7.06 (3H, m), 7.63 (1H, d), 8.23 (1H, d) | 427 |
| 411 | 3-CN, 4-F | δ 1.58 (2H, m), 1.89 (2H, m), 2.13 (2H, s), 2.74 (1H, m), 3.04 (2H, m), 3.60 (3H, s), 4.33 (2H, m), 7.48 (1H, m), 7.63 (1H, d), 7.73 (1H, m), 7.82 (1H, m), 8.23 (1H, d) | 434 |

EXAMPLE 412

Preparation of N-(2-hydroxyethyl)-N-methyl-4-[[1-[3-(trifluoromethyl)-[1,2,4]triazolo[4,3-b]pyridazin-6-yl]piperidin-4-yl]oxy]benzamide

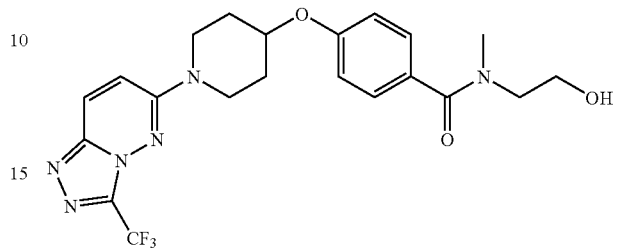

DIPEA (0.087 mL, 0.5 mmol) was added to 4-[[1-[3-(trifluoromethyl)-[1,2,4]triazolo[4,3-b]pyridazin-6-yl]piperidin-4-yl]oxy]benzoic acid (100 mg, 0.25 mmol), 2-(methylamino)ethanol (20.28 mg, 0.27 mmol) and HATU (114 mg, 0.3 mmol) in DMF (2 mL). The resulting solution was stirred at room temperature for 24 hours. The crude product was purified by preparative HPLC (Waters XBridge Prep C18 OBD column, 5μ silica, 21 mm diameter, 100 mm length), using decreasingly polar mixtures of water (containing 1% ammonia) and MeCN as eluents. Fractions containing the desired compound were evaporated to dryness to afford N-(2-hydroxyethyl)-N-methyl-4-[[1-[3-(trifluoromethyl)-[1,2,4]triazolo[4,3-b]pyridazin-6-yl]piperidin-4-yl]oxy]benzamide (64 mg, 55%).

1H NMR (399.9 MHz, DMSO-d6) δ 1.75 (2H, m), 2.10 (2H, m), 2.98 (3H, s), 3.56 (6H, m), 3.99 (2H, m), 4.76 (1H, m), 7.04 (2H, d), 7.39 (2H, d), 7.65 (1H, d), 8.27 (1H, d); m/z=465 [M+H]+.

The 4-[[1-[3-(trifluoromethyl)-[1,2,4]triazolo[4,3-b]pyridazin-6-yl]piperidin-4-yl]oxy]benzoic acid used as starting material was prepared as follows:—

Preparation of 1-[3-(trifluoromethyl)-[1,2,4]triazolo[4,3-b]pyridazin-6-yl]piperidin-4-ol 4-Hydroxypiperidine (10.91 g, 107.84 mmol) was added to 6-chloro-3-(trifluoromethyl)-[1,2,4]triazolo[4,3-b]pyridazine (20 g, 89.87 mmol) and DIPEA (23.48 mL, 134.80 mmol) in DMF (200 mL). The resulting solution was stirred at 125° C. for 2 hours. The reaction mixture was evaporated to dryness, redissolved in DCM and purified by flash silica chromatography, elution gradient 0 to 5% MeOH in DCM. Pure fractions were evaporated to dryness to give a beige solid which was stirred with ether then filtered to afford 1-[3-(trifluoromethyl)-[1,2,4]triazolo[4,3-b]pyridazin-6-yl]piperidin-4-ol (22.64 g, 88%) as a solid.

1H NMR (399.9 MHz, DMSO-d6) δ 1.46 (2H, m), 1.85 (2H, m), 3.32 (2H, m), 3.78 (1H, m), 3.96 (2H, m), 4.78 (1H, d), 7.61 (1H, d), 8.22 (1H, d); m/z=288 [M+H]+.

Preparation of ethyl 4-[[1-[3-(trifluoromethyl)-[1,2,4]triazolo[4,3-b]pyridazin-6-yl]piperidin-4-yl]oxy]benzoate DIAD (2.262 mL, 11.49 mmol) was added to 1-[3-(trifluoromethyl)-[1,2,4]triazolo[4,3-b]pyridazin-6-yl]piperidin-4-ol (3 g, 10.44 mmol), ethyl 4-hydroxybenzoate (1.909 g, 11.49 mmol) and triphenylphosphine (3.01 g, 11.49 mmol) in THF (50 mL) under nitrogen. The resulting solution was stirred at ambient temperature for 4 hours. The crude product was purified by ion exchange chromatography, using an SCX column. The desired product was eluted from the column using 2M ammonia in methanol. The crude solid was triturated with MeOH to give a solid which was collected by filtration and dried under vacuum to give ethyl 4-[[1-[3-(trifluoromethyl)-[1,2,4]triazolo[4,3-b]pyridazin-6-yl]piperidin-4-yl]oxy]benzoate (2.220 g, 49%) as a solid.

1H NMR (399.9 MHz, DMSO-d6) δ 1.33 (3H, t), 1.76 (2H, m), 2.11 (2H, m), 3.55 (2H, m), 3.98 (2H, m), 4.29 (2H, q), 4.83 (1H, m), 7.13 (2H, m), 7.66 (1H, d), 7.92 (2H, m), 8.27 (1H, d); m/z=436 [M+H]+.

Preparation of 4-[[1-[3-(trifluoromethyl)-[1,2,4]triazolo[4,3-b]pyridazin-6-yl]piperidin-4-yl]oxy]benzoic acid Lithium hydroxide monohydrate (0.488 g, 20.40 mmol) was added to ethyl 4-[[1-[3-(trifluoromethyl)-[1,2,4]triazolo[4,3-b]pyridazin-6-yl]piperidin-4-yl]oxy]benzoate (2.22 g, 5.10 mmol) in MeOH (80 mL) and water (40.0 mL). The resulting suspension was stirred at 50° C. for 2 days. The reaction was cooled to room temperature, the methanol was evaporated and the aqueous residues treated with citric acid until precipitation ceased. The precipitate was collected by filtration, washed with water and dried to afford 4-[[1-[3-(trifluoromethyl)-[1,2,4]triazolo[4,3-b]pyridazin-6-yl]piperidin-4-yl]oxy]benzoic acid (2.020 g, 97%) as a solid.

1H NMR (399.9 MHz, DMSO-d6) δ 1.76 (2H, m), 2.12 (2H, m), 3.54 (2H, m), 3.99 (2H, m), 4.82 (1H, m), 7.10 (2H, m), 7.66 (1H, d), 7.90 (2H, m), 8.26 (1H, d), 12.60 (1H, s); m/z=408 [M+H]+.

EXAMPLES 413-429

The following compounds were prepared in 9-62% yield by an analogous method to Example 412, starting from 4-[[1-[3-(trifluoromethyl)-[1,2,4]triazolo[4,3-b]pyridazin-6-yl]piperidin-4-yl]oxy]benzoic acid and the appropriate amine:—

| Ex. | NR1R2 | 1H NMR (399.9 MHz, DMSO-d6) | m/z [M + H]+ |
|---|---|---|---|
| 413 | HN-CH2CH2-pyrrolidinyl | δ 1.72 (6H, m), 2.10 (2H, m), 2.49 (4H, m), 2.57 (2H, m), 3.37 (2H, m), 3.55 (2H, m), 3.99 (2H, m), 4.79 (1H, m), 7.07 (2H, d), 7.65 (1H, d), 7.82 (2H, d), 8.26 (2H, m) | 504 |
| 414 | N-methylpiperazinyl | δ 1.75 (2H, m), 2.10 (2H, m), 2.20 (3H, s), 2.32 (4H, m), 3.50 (6H, m), 3.98 (2H, m), 4.76 (1H, m), 7.06 (2H, d), 7.35 (2H, d), 7.65 (1H, d), 8.26 (1H, d) | 490 |
| 415 | piperazinyl | δ 1.75 (2H, m), 2.10 (2H, m), 2.68 (4H, m), 3.41 (4H, m), 3.54 (2H, m), 3.98 (2H, m), 4.75 (1H, m), 7.05 (2H, m), 7.34 (2H, m), 7.65 (1H, d), 8.26 (1H, d) | 476 |
| 416 | HN-CH2CH2-OMe | 1H NMR (499.803 MHz, DMSO-d6) δ 1.72 (2H, m), 2.08 (2H, m), 3.26 (3H, s), 3.41 (4H, m), 3.51 (2H, m), 3.96 (2H, m), 4.77 (1H, m), 7.05 (2H, d), 7.63 (1H, d), 7.82 (2H, d), 8.24 (1H, d), 8.33 (1H, m) | 465 |
| 417 | NMe2 | δ 1.76 (2H, m), 2.11 (2H, m), 2.97 (6H, s), 3.53 (2H, m), 3.99 (2H, m), 4.76 (1H, m), 7.05 (2H, d), 7.38 (2H, d), 7.65 (1H, d), 8.26 (1H, d) | 435 |
| 418 | 3-hydroxypyrrolidinyl | δ 1.76 (3H, m), 1.94 (1H, m), 2.10 (2H, m), 3.53 (5H, m), 3.98 (2H, m), 4.28 (1H, m), 4.77 (1H, m), 4.94 (1H, m), 7.05 (2H, d), 7.51 (2H, d), 7.66 (1H, d), 8.26 (1H, d) | 477 |
| 419 | pyrrolidinyl | δ 1.80 (6H, m), 2.10 (2H, m), 3.50 (6H, m), 3.98 (2H, m), 4.76 (1H, m), 7.04 (2H, d), 7.51 (2H, d), 7.65 (1H, d), 8.26 (1H, d) | 461 |
| 420 | morpholinyl | δ 1.75 (2H, m), 2.10 (2H, m), 3.56 (10H, m), 3.98 (2H, m), 4.77 (1H, m), 7.07 (2H, m), 7.39 (2H, m), 7.65 (1H, d), 8.26 (1H, d) | 477 |
| 421 | NHMe | δ 1.75 (2H, m), 2.10 (2H, m), 2.77 (3H, m), 3.53 (2H, m), 3.98 (2H, m), 4.79 (1H, m), 7.06 (2H, d), 7.65 | 421 |

201
-continued

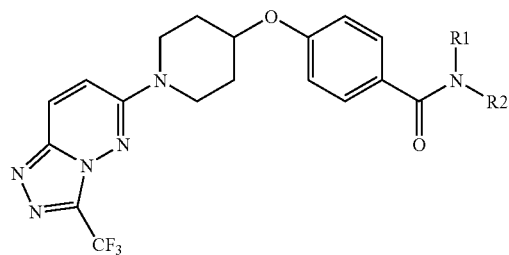

| Ex. | NR1R2 | 1H NMR (399.9 MHz, DMSO-d6) | m/z [M + H]+ |
|---|---|---|---|
| | | (1H, m), 7.81 (2H, d), 8.27 (2H, m) | |
| 422 | NHEt | δ 1.12 (3H, t), 1.75 (2H, m), 2.10 (2H, m), 3.30 (2H, m), 3.54 (2H, m), 3.98 (2H, m), 4.79 (1H, m), 7.06 (2H, d), 7.66 (1H, d), 7.82 (2H, d), 8.27 (2H, m) | 435 |
| 423 | H-N-CH2CH2-OH | δ 1.75 (2H, m), 2.11 (2H, m), 3.34 (2H, m), 3.53 (4H, m), 3.98 (2H, m), 4.69 (1H, t), 4.79 (1H, m), 7.07 (2H, d), 7.66 (1H, d), 7.84 (2H, d), 8.27 (2H, m) | 451 |
| 424 | H-N-CH2CH2-morpholine | δ 1.75 (2H, m), 2.10 (2H, m), 2.42 (4H, m), 2.57 (2H, m), 3.38 (2H, m), 3.55 (6H, m), 3.98 (2H, m), 4.79 (1H, m), 7.07 (2H, d), 7.65 (1H, d), 7.81 (2H, d), 8.25 (2H, m) | 520 |
| 425 | Me-N-CH2CH2-OMe | δ 1.74 (2H, m), 2.11 (2H, m), 2.98 (3H, s), 3.25 (3H, m), 3.52 (6H, m), 3.99 (2H, m), 4.75 (1H, m), 7.05 (2H, d), 7.36 (2H, d), 7.65 (1H, d), 8.26 (1H, d) | 479 |
| 426 | H-N-CH2-(5-methylisoxazol-3-yl) | δ 1.75 (2H, m), 2.11 (2H, m), 2.37 (3H, s), 3.54 (2H, m), 3.99 (2H, m), 4.45 (2H, d), 4.80 (1H, m), 6.14 (1H, s), 7.09 (2H, d), 7.66 (1H, d), 7.87 (2H, d), 8.26 (1H, d), 8.90 (1H, m) | 502 |
| 427 | H-N-(1-methylpiperidin-4-yl) | δ 1.63 (2H, m), 1.80 (4H, m), 1.99 (2H, m), 2.14 (2H, m), 2.22 (3H, s), 2.82 (2H, m), 3.60 (2H, m), 3.77 (1H, m), 4.02 (2H, m), 4.84 (1H, m), 7.11 (2H, d), 7.70 (1H, d), 7.88 (2H, d), 8.10 (1H, d), 8.31 (1H, d) | 504 |

202
-continued

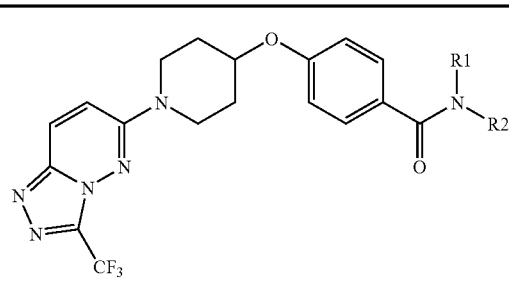

| Ex. | NR1R2 | 1H NMR (399.9 MHz, DMSO-d6) | m/z [M + H]+ |
|---|---|---|---|
| 428 | (3S)-3-hydroxypyrrolidin-1-yl | δ 1.76 (3H, m), 1.93 (1H, m), 2.10 (2H, m), 3.55 (5H, m), 3.98 (2H, m), 4.29 (1H, m), 4.77 (1H, m), 4.94 (1H, m), 7.05 (2H, d), 7.50 (2H, d), 7.65 (1H, d), 8.26 (1H, d) | 477 |
| 429 | H-N-CH2CH2-NMe2 | 1H NMR (500.13 MHz, DMSO-d6) δ 1.72 (2H, m), 2.08 (2H, m), 2.16 (6H, s), 2.37 (2H, m), 3.32 (2H, m), 3.51 (2H, m), 3.95 (2H, m), 4.77 (1H, m), 7.04 (2H, d), 7.63 (1H, d), 7.80 (2H, d), 8.19 (1H, m), 8.24 (1H, m) | 478 |

EXAMPLE 430

Preparation of N,N-dimethyl-3-[4-[[1-[3-(trifluoromethyl)-[1,2,4]triazolo[4,3-b]pyridazin-6-yl]piperidin-4-yl]oxy]phenoxy]propan-1-amine

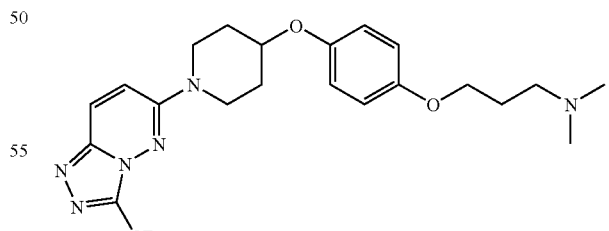

DIAD (0.05 mL, 0.29 mmol) was added to 4-[[1-[3-(trifluoromethyl)-[1,2,4]triazolo[4,3-b]pyridazin-6-yl]piperidin-4-yl]oxy]phenol, 3-dimethylamino-1-propanol (100 mg, 0.26 mmol (33 mg, 0.32 mmol) and triphenylphosphine (76 mg, 0.29 mmol) in THF (2 mL). The resulting solution was stirred at ambient temperature for 4 hours. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford the product (19.1 mg, 16%) as a gum.

1H NMR (399.9 MHz, DMSO-d6) δ 1.74 (2H, m), 1.86 (2H, m), 2.08 (2H, m), 2.19 (6H, s), 2.39 (2H, m), 3.57 (2H, m), 3.99 (4H, m), 4.58 (1H, m), 6.94 (4H, m), 7.69 (1H, d), 8.30 (1H, d); m/z=465 [M+H]+.

The 4-[[1-[3-(trifluoromethyl)-[1,2,4]triazolo[4,3-b]pyridazin-6-yl]piperidin-4-yl]oxy]phenol used as starting material was prepared as follows:—

Preparation of 6-[4-[4-(benzyloxy)phenoxy]piperidin-1-yl]-3-(trifluoromethyl)-[1,2,4]triazolo[4,3-b]pyridazine DIAD (2.262 mL, 11.49 mmol) was added to 1-[3-(trifluoromethyl)-[1,2,4]triazolo[4,3-b]pyridazin-6-yl]piperidin-4-ol (3 g, 10.44 mmol), 4-(benzyloxy)phenol (2.300 g, 11.49 mmol) and triphenylphosphine (3.01 g, 11.49 mmol) in THF (50 mL) under nitrogen. The resulting solution was stirred at ambient temperature for 4 hours. The crude oil was triturated with MeOH to give a solid which was collected by filtration and dried under vacuum to give 6-[4-[4-(benzyloxy)phenoxy]piperidin-1-yl]-3-(trifluoromethyl)-[1,2,4]triazolo[4,3-b]pyridazine (2.53 g, 52%) as a solid.

1H NMR (399.9 MHz, DMSO-d6) δ 1.75 (2H, m), 2.08 (2H, m), 3.56 (2H, m), 3.99 (2H, m), 4.60 (1H, m), 5.10 (2H, s), 7.00 (4H, m), 7.44 (5H, m), 7.69 (1H, d), 8.30 (1H, d); m/z=470 [M+H]+.

Preparation of 4-[[1-[3-(trifluoromethyl)-[1,2,4]triazolo[4,3-b]pyridazin-6-yl]piperidin-4yl]oxy]phenol 10% Palladium on carbon (0.574 g, 0.54 mmol) was added to 6-[4-[4-(benzyloxy)phenoxy]piperidin-1-yl]-3-(trifluoromethyl)-[1,2,4]triazolo[4,3-b]pyridazine (2.53 g, 5.39 mmol) in MeOH (30 mL) under an atmosphere of hydrogen. The resulting suspension was stirred at ambient temperature for 24 hours. The reaction mixture was evaporated. The crude product was purified by flash silica chromatography, elution gradient 0 to 3% MeOH in DCM. Pure fractions were evaporated to dryness to afford 4-[[1-[3-(trifluoromethyl)-[1,2,4]triazolo[4,3-b]pyridazin-6-yl]piperidin-4-yl]oxy]phenol (1.760 g, 86%) as a gum which crystallised on standing.

1H NMR (399.9 MHz, DMSO-d6) δ 1.69 (2H, m), 2.01 (2H, m), 3.51 (2H, m), 3.94 (2H, m), 4.46 (1H, m), 6.69 (2H, m), 6.83 (2H, m), 7.64 (1H, d), 8.25 (1H, d), 8.94 (1H, s); m/z=380 [M+H]+.

EXAMPLES 431-442

The following compounds were prepared in 8-43% yield by an analogous method to Example 430, starting from 4-[[1-[3-(trifluoromethyl)-[1,2,4]triazolo[4,3-b]pyridazin-6-yl]piperidin-4-yl]oxy]phenol and the appropriate alcohol:—

| Ex. | OR | 1H NMR (399.9 MHz, DMSO-d6) | m/z [M + H]+ |
|---|---|---|---|
| 431 |  | δ 1.70 (6H, m), 2.03 (2H, m), 2.52 (4H, m), 2.76 (2H, m), 3.52 (2H, m), 3.97 (4H, m), 4.54 (1H, m), 6.91 (4H, m), 7.64 (1H, d), 8.25 (1H, d) | 477 |
| 432 | 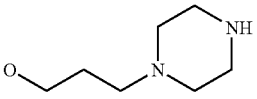 | δ 1.74 (2H, m), 2.08 (2H, m), 2.44 (2H, m), 2.67 (4H, m), 2.74 (4H, m), 3.23 (2H, m), 3.55 (2H, m), 4.05 (2H, m), 4.59 (1H, m), 6.74 (2H, m), 6.94 (4H, m), 7.69 (1H, d), 8.30 (1H, d) | 492 |
| 433 | 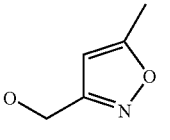 | δ 1.68 (2H, m), 1.81 (2H, m), 2.01 (2H, m), 2.27 (4H, m), 2.35 (2H, m), 2.66 (4H, m), 3.49 (2H, m), 3.92 (4H, m), 4.52 (1H, m), 6.84 (4H, m), 6.91 (2H, m), 7.62 (1H, d), 8.23 (1H, d) | 506 |
| 434 | 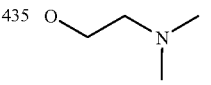 | δ 1.75 (2H, m), 2.08 (2H, m), 2.47 (3H, s), 3.57 (2H, m), 4.00 (2H, m), 4.61 (1H, m), 5.13 (2H, m), 6.37 (1H, m), 7.01 (4H, m), 7.69 (1H, d), 8.30 (1H, d) | 475 |
| 435 |  | δ 1.70 (2H, m), 2.03 (2H, m), 2.22 (6H, s), 2.61 (2H, m), 3.52 (2H, m), 3.96 (4H, m), 4.54 (1H, m), 6.91 (4H, m), 7.64 (1H, d), 8.25 (1H, d) | 451 |

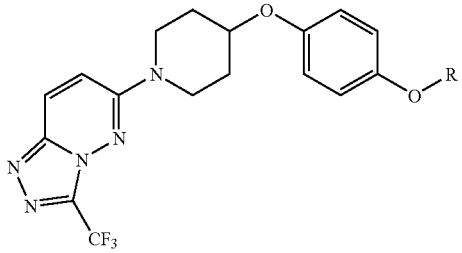

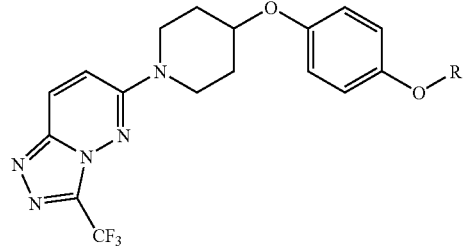

| Ex. | OR | 1H NMR (399.9 MHz, DMSO-d6) | m/z [M + H]+ |
|---|---|---|---|
| 436 | O-(4-methylpiperidine) | δ 1.68 (4H, m), 1.94 (2H, m), 2.08 (2H, m), 2.19 (3H, m), 2.64 (4H, m), 3.56 (2H, m), 3.99 (2H, m), 4.26 (1H, m), 4.59 (1H, m), 6.95 (4H, m), 7.69 (1H, d), 8.30 (1H, d) | 477 |
| 437 | O-propyl-(4-methylpiperazine) | δ 1.70 (2H, m), 1.84 (2H, m), 2.03 (2H, m), 2.15 (3H, s), 2.34 (10H, m), 3.52 (2H, m), 3.94 (4H, m), 4.53 (1H, m), 6.86 (2H, m), 6.94 (2H, m), 7.64 (1H, d), 8.25 (1H, d) | 520 |
| 438 | O-CH2-isoxazole | δ 1.68 (2H, m), 2.01 (2H, m), 3.49 (2H, m), 3.93 (2H, m), 4.54 (1H, m), 5.15 (2H, s), 6.67 (1H, d), 6.95 (4H, m), 7.62 (1H, d), 8.23 (1H, d), 8.92 (1H, d) | 461 |
| 439 | O-CH2-oxazole | δ 1.70 (2H, m), 2.04 (2H, m), 3.52 (2H, m), 3.95 (2H, m), 4.56 (1H, m), 5.12 (2H, s), 6.97 (4H, m), 7.31 (1H, s), 7.64 (1H, d), 8.25 (1H, d), 8.41 (1H, s) | 461 |
| 440 | O-CH2CH2-(4-methylpiperazine) | δ 1.70 (2H, m), 2.03 (2H, m), 2.15 (3H, s), 2.39 (8H, m), 2.66 (2H, m), 3.51 (2H, m), 3.97 (4H, m), 4.54 (1H, m), 6.91 (4H, m), 7.64 (1H, d), 8.25 (1H, d) | 506 |
| 441 | O-CH2CH2-(1-methylpyrazole) | δ 1.70 (2H, m), 2.03 (2H, m), 2.82 (2H, t), 3.52 (2H, m), 3.79 (3H, s), 3.95 (2H, m), 4.03 (2H, t), 4.54 (1H, m), 6.91 (4H, m), 7.56 (1H, s), 7.56 (1H, s), 7.64 (1H, d), 8.25 (1H, d) | 488 |
| 442 | O-CH2-(1-methylpyrazole) | δ 1.71 (2H, m), 2.04 (2H, m), 3.53 (2H, m), 3.84 (3H, s), 3.95 (2H, m), 4.58 (1H, m), 5.11 (2H, s), 6.35 (1H, m), 6.98 (4H, m), 7.38 (1H, m), 7.64 (1H, d), 8.25 (1H, d) | 474 |

EXAMPLES 443-446

The following compounds were prepared in 7-33% yield by an analogous method to Example 430, starting from 3-[[1-[3-(trifluoromethyl)-[1,2,4]triazolo[4,3-b]pyridazin-6-yl]piperidin-4-yl]oxy]phenol and the appropriate alcohol:—

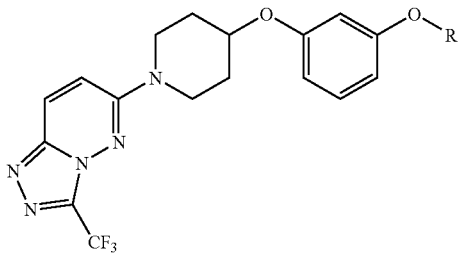

| Ex. | OR | 1H NMR (399.9 MHz, DMSO-d6) | m/z [M + H]+ |
|---|---|---|---|
| 443 | O-(CH2)3-N(CH3)2 | δ 1.72 (2H, m), 1.84 (2H, m), 2.06 (2H, m), 2.15 (6H, s), 2.35 (2H, m), 3.54 (2H, m), 3.97 (4H, m), 4.69 (1H, m), 6.55 (3H, m), 7.18 (1H, m), 7.64 (1H, d), 8.26 (1H, d) | 465 |
| 444 | O-(CH2)2-piperazine-NH | δ 1.73 (2H, m), 2.06 (2H, m), 2.40 (4H, m), 2.66 (6H, m), 3.53 (2H, m), 3.96 (2H, m), 4.06 (2H, m), 4.69 (1H, m), 6.56 (3H, m), 7.18 (1H, m), 7.64 (1H, d), 8.25 (1H, d) | 492 |
| 445 | O-(CH2)3-piperazine-NH | δ 1.69 (2H, m), 1.83 (2H, m), 2.04 (2H, m), 2.29 (4H, m), 2.36 (2H, m), 2.70 (4H, m), 3.51 (2H, m), 3.94 (4H, m), 4.66 (1H, m), 6.53 (3H, m), 7.16 (1H, m), 7.63 (1H, d), 8.24 (1H, d) | 506 |
| 446 | O-CH2-(5-methylisoxazol-3-yl) | δ 1.72 (2H, m), 2.07 (2H, m), 2.42 (3H, s), 3.52 (2H, m), 3.97 (2H, m), 4.69 (1H, m), 5.13 (2H, s), 6.33 (1H, s), 6.64 (3H, m), 7.21 (1H, m), 7.65 (1H, d), 8.26 (1H, d) | 475 |

The 3-[[1-[3-(trifluoromethyl)-[1,2,4]triazolo[4,3-b]pyridazin-6-yl]piperidin-4-yl]oxy]phenol used as starting material was prepared as follows:—

Preparation of 6-[4-[3-(benzyloxy)phenoxy]piperidin-1-yl]-3-(trifluoromethyl)-[1,2,4]triazolo[4,3-b]pyridazine Obtained in 40% yield by an analogous procedure to Example 430, preparation of starting materials, starting from 3-(benzyloxy)phenol and 1-[3-(trifluoromethyl)-[1,2,4]triazolo[4,3-b]pyridazin-6-yl]piperidin-4-ol.

1H NMR (399.9 MHz, DMSO-d6) δ 1.71 (2H, m), 2.05 (2H, m), 3.51 (2H, m), 3.96 (2H, m), 4.67 (1H, m), 5.10 (2H, s), 6.63 (3H, m), 7.19 (1H, m), 7.40 (5H, m), 7.64 (1H, d), 8.26 (1H, d); m/z=470 [M+H]+.

Preparation of 3-[[1-[3-(trifluoromethyl)-[1,2,4]triazolo[4,3-b]pyridazin-6-yl]piperidin-4-yl]oxy] phenol Obtained in 80% yield by an analogous procedure to Example 430, preparation of starting materials, starting from 6-[4-[3-(benzyloxy)phenoxy]piperidin-1-yl]-3-(trifluoromethyl)-[1,2,4]triazolo[4,3-b]pyridazine.

1H NMR (399.9 MHz, DMSO-d6) δ 1.71 (2H, m), 2.06 (2H, m), 3.53 (2H, m), 3.95 (2H, m), 4.60 (1H, m), 6.40 (3H, m), 7.07 (1H, m), 7.64 (1H, d), 8.25 (1H, d), 9.36 (1H, s); m/z=380 [M+H]+.

EXAMPLE 447

Preparation of 6-[4-[(6-methylpyridazin-3-yl)oxy]piperidin-1-yl]-3-(trifluoromethyl)[1,2,4]triazolo[4,3-b]pyridazine

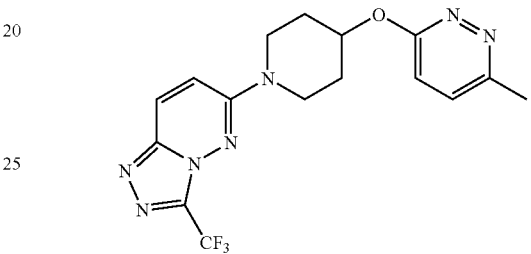

DIAD (0.102 mL, 0.52 mmol) was added to 1-[3-(trifluoromethyl)-[1,2,4]triazolo[4,3-b]pyridazin-6-yl]piperidin-4-ol (obtained as described in Example 310, preparation of starting materials) (135 mg, 0.47 mmol), 6-methylpyridazin-3(2H)-one (56.9 mg, 0.52 mmol) and triphenylphosphine (136 mg, 0.52 mmol) in THF (5 mL). The resulting solution was stirred at ambient temperature for 3 days. The crude product was purified by ion exchange chromatography, using an SCX column. The desired product was eluted from the column using 2M ammonia in methanol and evaporated to give crude product. The crude product was purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to afford 6-[4-[(6-methylpyridazin-3-yl)oxy]piperidin-1-yl]-3-(trifluoromethyl)[1,2,4]triazolo[4,3-b]pyridazine (22.00 mg, 12%) as a solid.

1H NMR (399.9 MHz, DMSO-d6) δ 1.91 (4H, m), 2.25 (3H, s), 3.22 (2H, m), 4.42 (2H, m), 5.10 (1H, m), 6.89 (1H, d), 7.32 (1H, d), 7.66 (1H, d), 8.27 (1H, d); m/z=380 [M+H]+.

EXAMPLE 448

Preparation of 5-[[1-[3-(trifluoromethyl)-[1,2,4]triazolo[4,3-b]pyridazin-6-yl]piperidin-4-yl]oxy]pyridine-2-carbonitrile

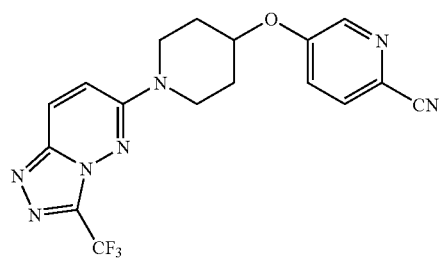

A solution of 1-[3-(trifluoromethyl)-[1,2,4]triazolo[4,3-b]pyridazin-6-yl]piperidin-4-ol (150 mg, 0.52 mmol) and sodium hydride (60% dispersion in oil, 22.98 mg, 0.57 mmol) in DMF (5 mL) was stirred for 30 minutes at ambient temperature under nitrogen. 5-Chloropicolinonitrile (80 mg, 0.57 mmol) was added to the reaction mixture. The resulting solution was stirred at 50° C. for 18 hours. The reaction mixture was diluted with a few drops of MeOH. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 5-[[1-[3-(trifluoromethyl)[1,2,4]triazolo[4,3-b]pyridazin-6-yl]piperidin-4-yl]oxy]pyridine-2-carbonitrile (55.0 mg, 27%) as a solid.

1H NMR (399.9 MHz, DMSO-d6) δ 1.78 (2H, m), 2.13 (2H, m), 3.53 (2H, m), 3.99 (2H, m), 4.95 (1H, m), 7.69 (2H, m), 8.02 (1H, d), 8.27 (1H, d), 8.50 (1H, m); m/z=390 [M+H]+.

EXAMPLE 449

Preparation of 4-[[1-[3-(trifluoromethyl)[1,2,4]triazolo[4,3-b]pyridazin-6-yl]piperidin-4-yl]oxy]pyridine-2-carbonitrile

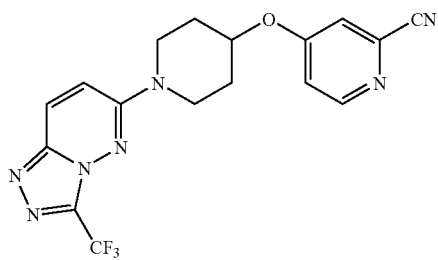

Obtained in 62% yield by an analogous procedure to Example 448, starting from 4-chloro-2-cyanopyridine and 1-[3-(trifluoromethyl)-[1,2,4]triazolo[4,3-b]pyridazin-6-yl]piperidin-4-ol.

1H NMR (399.9 MHz, DMSO-d6) δ 1.76 (2H, m), 2.14 (2H, m), 3.51 (2H, m), 4.01 (2H, m), 4.95 (1H, m), 7.37 (1H, m), 7.66 (1H, d), 7.81 (1H, m), 8.27 (1H, d), 8.55 (1H, m); m/z=390 [M+H]+.

EXAMPLES 450-455

The following compounds were prepared in 16-83% yield by an analogous method to Example 394, starting from 6-(hexahydropyrrolo[3,4-c]pyrrol-2(1H)-yl)-3-(trifluoromethyl)-[1,2,4]triazolo[4,3-b]pyridazine (obtained as described in General Synthetic Method 10, preparation of starting materials) and the appropriate sulfonyl chloride:—

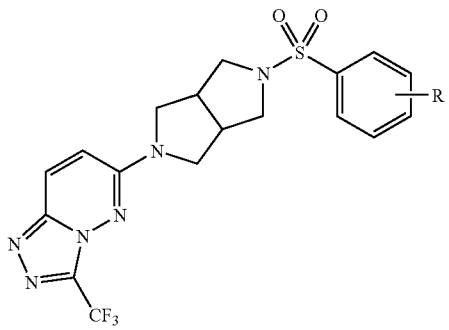

| Ex. | R | 1H NMR (399.9 MHz, CDCl₃) | m/z [M + H]+ |
|---|---|---|---|
| 450 | 3-F | δ 3.04-3.10 (2H, m), 3.28-3.32 (2H, m), 3.35-3.39 (2H, m), 3.46-3.50 (2H, m), 3.75-3.79 (2H, m), 6.79 (1H, d), 7.29-7.35 (1H, m), 7.51-7.57 (2H, m), 7.62-7.64 (1H, m), 7.93 (1H, d) | 457 |
| 451 | 2-OMe | δ 3.06-3.11 (2H, m), 3.38-3.44 (4H, m), 3.67-3.72 (2H, m), 3.76-3.80 (2H, m), 3.90 (3H, s), 6.81 (1H, d), 6.99-7.07 (2H, m), 7.50-7.54 (1H, m), 7.90-7.94 (2H, m) | 469 |
| 452 | 2-F | δ 3.09-3.13 (2H, m), 3.38-3.46 (4H, m), 3.66 (2H, q), 3.79 (2H, q), 6.81 (1H, d), 7.18-7.31 (2H, m), 7.55-7.61 (1H, m), 7.89-7.95 (2H, m) | 457 |
| 453 | 4-F | δ 3.03-3.10 (2H, m), 3.27-3.30 (2H, m), 3.36-3.46 (4H, m), 3.78 (2H, q), 6.78 (1H, d), 7.21-7.25 (2H, m), 7.83-7.87 (2H, m), 7.93 (1H, d) | 457 |
| 454 | 3-OMe | δ 3.01-3.06 (2H, m), 3.27-3.30 (2H, m), 3.34-3.38 (2H, m), 3.45-3.49 (2H, m), 3.73-3.77 (2H, m), 3.84 (3H, s), 6.77 (1H, d), 7.11-7.14 (1H, m), 7.33 (1H, t), 7.38-7.47 (2H, m), 7.92 (1H, d) | 469 |
| 455 | 4-OMe | δ 3.00-3.05 (2H, m), 3.23-3.27 (2H, m), 3.35-3.44 (4H, m), 3.73-3.77 (2H, m), 3.86 (3H, s), 6.77 (1H, d), 6.98-7.01 (2H, m), 7.75-7.79 (2H, m), 7.92 (1H, d) | 469 |

EXAMPLES 456-461

The following compounds were prepared in 54-96% yield by an analogous method to Example 394, starting from 6-(1,4-diazepan-1-yl)-3-(trifluoromethyl)-[1,2,4]triazolo[4,3-b]pyridazine (obtained as described in General Synthetic Method 8, preparation of starting materials) and the appropriate sulfonyl chloride:—

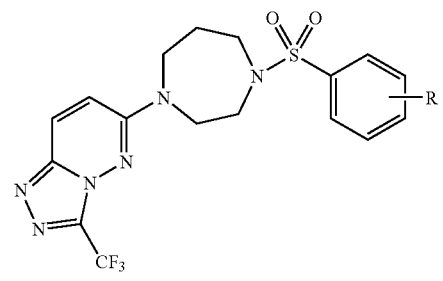

| Ex. | R | 1H NMR (399.9 MHz, CDCl₃) | m/z [M + H]+ |
|---|---|---|---|
| 456 | 3-F | δ 2.05-2.11 (2H, m), 3.36 (2H, t), 3.54 (2H, t), 3.82 (2H, t), 3.90 (2H, t), 6.94 (1H, d), 7.14-7.19 (1H, m), 7.36-7.41 | 445 |

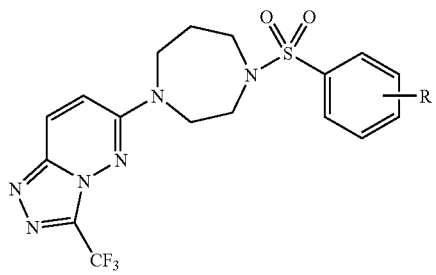

| Ex. | R | 1H NMR (399.9 MHz, CDCl₃) | m/z [M + H]+ |
|---|---|---|---|
| 457 | 4-F | (1H, m), 7.43-7.46 (1H, m), 7.52-7.55 (1H, m), 7.93 (1H, d)<br>δ 2.06-2.12 (2H, m), 3.29 (2H, t), 3.51 (2H, t), 3.83 (2H, t), 3.90 (2H, t), 6.95 (1H, d), 7.09-7.15 (2H, m), 7.75-7.80 (2H, m), 7.94 (1H, d) | 445 |
| 458 | 3-OMe | δ 2.03-2.09 (2H, m), 3.37 (2H, t), 3.54 (2H, t), 3.78-3.81 (5H, m), 3.88 (2H, t), 6.90-6.95 (2H, m), 7.22-7.23 (1H, m), 7.28-7.31 (2H, m), 7.90 (1H, d) | 457 |
| 459 | 2-OMe | δ 2.07-2.13 (2H, m), 3.31 (2H, t), 3.56-3.58 (2H, m), 3.87-3.91 (7H, m), 6.94-7.04 (3H, m), 7.46-7.50 (1H, m), 7.90-7.94 (2H, m) | 457 |
| 460 | 2-F | δ 2.06-2.12 (2H, m), 3.41 (2H, t), 3.60 (2H, t), 3.85 (2H, t), 3.90 (2H, t), 6.98 (1H, d), 7.03-7.08 (1H, m), 7.19-7.23 (1H, m), 7.44-7.50 (1H, m), 7.85-7.89 (1H, m), 7.94 (1H, d) | 445 |
| 461 | 4-OMe | δ 2.02-2.08 (2H, m), 3.34 (2H, t), 3.50 (2H, t), 3.78-3.81 (5H, m), 3.87 (2H, t), 6.81-6.84 (2H, m), 6.91 (1H, d), 7.64-7.67 (2H, m), 7.90 (1H, d) | 457 |

EXAMPLES 462-476

The following compounds were prepared in 15-70% yield by an analogous method to Example 447, starting from [1-[3-(trifluoromethyl)-[1,2,4]triazolo[4,3-b]pyridazin-6-yl]piperidin-4-yl]methanol (obtained as described in Example 294, preparation of starting materials) and the appropriate phenol:—

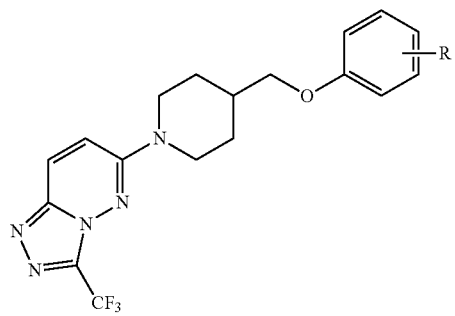

| Ex. | R | 1H NMR (399.9 MHz, DMSO-d₆) | m/z [M + H]+ |
|---|---|---|---|
| 462 | 2-OMe | δ 1.32-1.43 (2H, m), 1.90-1.94 (2H, m), 2.09-2.15 (1H, m), 3.05-3.12 (2H, m), 3.76 (3H, s), 3.85 (2H, d), 4.30-4.34 (2H, m), 6.85-6.92 (2H, m), 6.95-6.98 (2H, m), 7.63 (1H, d), 8.23 (1H, d) | 408 |

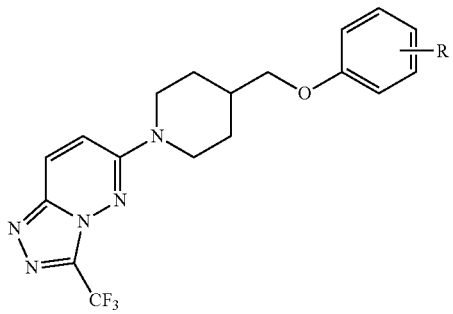

| Ex. | R | 1H NMR (399.9 MHz, DMSO-d₆) | m/z [M + H]+ |
|---|---|---|---|
| 463 | 4-F | δ 1.33-1.42 (2H, m), 1.89-1.92 (2H, m), 2.07-2.13 (1H, m), 3.03-3.11 (2H, m), 3.85 (2H, d), 4.30-4.34 (2H, m), 6.94-6.97 (2H, m), 7.09-7.13 (2H, m), 7.63 (1H, d), 8.23 (1H, d) | 396 |
| 464 | 3-F | δ 1.33-1.43 (2H, m), 1.89-1.92 (2H, m), 2.07-2.14 (1H, m), 3.04-3.11 (2H, m), 3.90 (2H, d), 4.30-4.34 (2H, m), 6.73-6.84 (2H, m), 7.28-7.34 (1H, m), 7.63 (1H, d), 8.23 (1H, d) | 396 |
| 465 | 4-OMe | δ 1.31-1.41 (2H, m), 1.88-1.92 (2H, m), 2.05-2.11 (1H, m), 3.03-3.10 (2H, m), 3.70 (3H, s), 3.81 (2H, d), 4.30-4.34 (2H, m), 6.84-7.89 (2H, m), 7.63 (1H, d), 8.23 (1H, d) | 408 |
| 466 | 3-OMe | δ 1.32-1.42 (2H, m), 1.89-1.93 (2H, m), 2.05-2.14 (1H, m), 3.04-3.11 (2H, m), 3.73 (3H, s), 3.86 (2H, d), 4.30-4.34 (2H, m), 6.49-6.54 (3H, m), 7.17 (1H, t), 7.63 (1H, d), 8.23 (1H, d) | 408 |
| 467 | 2-F | δ 1.34-1.44 (2H, m), 1.89-1.93 (2H, m), 2.11-2.18 (1H, m), 3.05-3.12 (2H, m), 3.96 (2H, d), 4.30-4.34 (2H, m), 6.91-6.97 (1H, m), 7.10-7.23 (3H, m), 7.63 (1H, d), 8.23 (1H, d) | 396 |
| 468 | 4-CF3 | δ 1.34-1.44 (2H, m), 1.89-1.94 (2H, m), 2.10-2.19 (1H, m), 3.05-3.12 (2H, m), 3.97 (2H, d), 4.31-4.34 (2H, m), 7.13 (2H, d), 7.62-7.66 (3H, m), 8.24 (1H, d) | 446 |
| 469 | 2-CN | δ 1.39-1.49 (2H, m), 2.15-2.22 (1H, m), 3.07-3.14 (2H, m), 4.06 (2H, d), 4.32-4.36 (2H, m), 7.08-7.12 (1H, m), 7.26 (1H, d), 7.63-7.68 (2H, m), 7.71-7.73 (1H, m), 8.24 (1H, d) | 403 |
| 470 | 4-Cl | δ 1.32-1.42 (2H, m), 1.88-1.92 (2H, m), 2.05-2.14 (1H, m), 3.03-3.10 (2H, m), 3.87 (2H, d), 4.29-4.33 (2H, m), 6.95-6.99 (2H, m), 7.29-7.34 (2H, m), 7.62 (1H, d), 8.23 (1H, d) | 412 |
| 471 | 2-CF3 | δ 1.39-1.49 (2H, m), 1.88-1.91 (2H, m), 2.12-2.19 (1H, m), 3.06-3.13 (2H, m), 4.02 (2H, d), 4.31-4.35 (2H, m), 7.09 (1H, t), 7.25 (1H, d), 7.60-7.65 (3H, m), 8.24 (1H, d) | 446 |
| 472 | 3-CF3 | δ 1.35-1.45 (2H, m), 1.91-1.94 (2H, m), 2.09-2.18 (1H, m), 3.05-3.12 (2H, m), 3.97 (2H, d), 4.31-4.34 (2H, m), 7.24-7.30 (3H, m), 7.53 (1H, t), 7.64 (1H, d), 8.24 (1H, d) | 446 |
| 473 | 3-Cl | δ 1.32-1.42 (2H, m), 1.87-1.92 (2H, m), 2.07-2.15 (1H, m), 3.04-3.11 (2H, m), 3.91 (2H, d), 4.30-4.33 (2H, m), 6.92-6.94 (1H, m), 6.98-7.00 (1H, m), 7.03 (1H, t), 7.31 (1H, t), 7.63 (1H, d), 8.23 (1H, d) | 412 |
| 474 | 4-CN | δ 1.33-1.44 (2H, m), 1.87-1.92 (2H, m), 2.08-2.17 (1H, m), 3.05-3.11 (2H, m), 3.99 (2H, d), 4.30-4.34 (2H, m), 7.11-7.14 (2H, m), 7.63 (1H, d), 7.75-7.78 (2H, m), 8.23 (1H, d) | 403 |

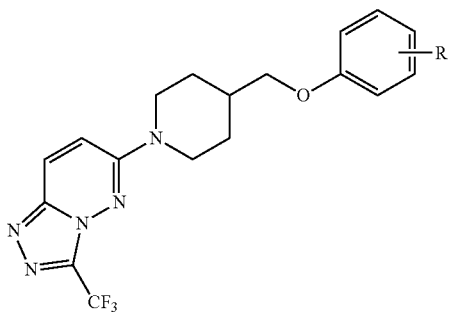

| Ex. | R | 1H NMR (399.9 MHz, DMSO-d$_6$) | m/z [M + H]+ |
|---|---|---|---|
| 475 | 2-Cl | δ 1.37-1.48 (2H, m), 1.92-1.96 (2H, m), 2.12-2.19 (1H, m), 3.06-3.13 (2H, m), 3.98 (2H, d), 4.31-4.35 (2H, m), 6.93-6.97 (1H, m), 7.14-7.16 (1H, d), 7.28-7.32 (1H, m), 7.41-7.43 (1H, m), 7.64 (1H, d), 8.24 (1H, d) | 412 |
| 476 | 3-CN | δ 1.34-1.43 (2H, m), 1.88-1.92 (2H, m), 2.10-2.16 (1H, m), 3.05-3.12 (2H, m), 3.96 (2H, d), 4.30-4.34 (2H, d), 7.29-7.32 (1H, m), 7.39-7.41 (1H, m), 7.43-7.44 (1H, m), 7.47-7.51 (1H, m), 7.63 (1H, d), 8.24 (1H, d) | 403 |

EXAMPLE 477

Preparation of 6-[4-(1H-pyrrolo[2,3-c]pyridin-3-yl)piperidin-1-yl]-3-(trifluoromethyl)[1,2,4]triazolo[4,3-b]pyridazine

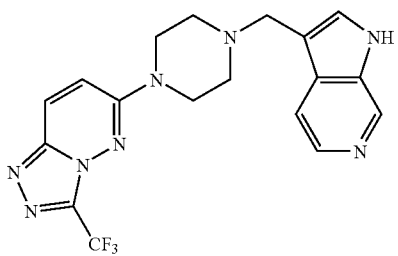

Obtained in 68% yield by General Synthetic Method 5, starting from 6-(piperazin-1-yl)-3-(trifluoromethyl)-[1,2,4]triazolo[4,3-b]pyridazine and 1H-pyrrolo[2,3-c]pyridine-3-carboxaldehyde (obtained as described in J. Chem. Soc. (C) 1970, 498).

1H NMR (399.9 MHz, DMSO-d6) δ 2.25 (4H, t), 3.60 (4H, t), 3.73 (2H, s), 7.53 (1H, s), 7.57 (1H, d), 7.63-7.65 (1H, m), 8.10 (1H, d), 8.23 (1H, d), 8.72 (1H, d), 11.47 (1H, s); m/z=403 [M+H]+.

EXAMPLES 478-480

The following compounds were prepared in 61-82% yield by General Synthetic Method 5, starting from 6-chloro-3-(trifluoromethyl)-[1,2,4]triazolo[4,3-b]pyridazine and the appropriate 1H-pyrrolopyridine-3-carboxaldehyde (obtained as described in the corresponding footnote):—

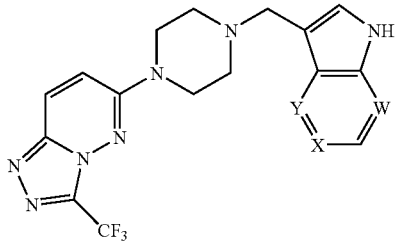

| Ex. | W | X | Y | Note | 1H NMR (399.9 MHz, DMSO-d6) | m/z [M + H]+ |
|---|---|---|---|---|---|---|
| 478 | N | CH | CH | [1] | δ 2.55 (4H, s), 3.60 (4H, s), 3.71 (2H, s), 7.04-7.07 (1H, m), 7.39 (1 H, s), 7.57 (1H, d), 8.07 (1H, d), 8.20-8.24 (2H, m), 11.48 (1H, s) | 403 |
| 479 | CH | CH | N | [2] | δ 2.59 (4H, t), 3.60 (4H, t), 3.81 (2H, s), 7.08-7.11 (1H, m), 7.55-7.58 (2H, m), 7.73-7.75 (1H, m), 8.22 (1H, d), 8.32-8.34 (1H, m), 11.21 (1H, s) | 403 |
| 480 | CH | N | CH | [3] | δ 2.56 (4H, t), 3.62 (4H, t), 3.77 (2H, s), 7.34-7.35 (1H, m), 7.36 (1 H, d), 7.58 (1H, d), 8.16 (1H, d), 8.23 (1H, d), 8.97 (1H, d), 11.34 (1H, s) | 403 |

Obtained from 1H-pyrrolo[2,3-b]pyridine-3-carboxaldehyde, prepared as described in Bioorg. Med. Chem. 2004, 12, 5505.

[2] Obtained from 1H-pyrrolo[3,2-b]pyridine-3-carboxaldehyde, prepared as described in US Pat Appl. 2007/0123535, page 35.

[3] Obtained from 1H-pyrrolo[3,2-c]pyridine-3-carboxaldehyde, prepared as follows:—

A solution of 1H-pyrrolo[3,2-c]pyridine (2.95 g, 25 mmol) and hexamethylenetetramine (5.26 g, 37.50 mmol) in acetic acid (25 mL) and water (50 mL) was heated under reflux for 4 hours. The reaction mixture was evaporated and the residue was purified by MPLC silica chromatography, elution gradient 5 to 10% ammonia-methanol in DCM. Product containing fractions were evaporated to dryness and triturated with MeCN to afford 1H-pyrrolo[3,2-c]pyridine-3-carbaldehyde (0.170 g, 4.65%) as a white crystalline solid.

1H NMR (399.9 MHz, DMSO-d6) δ 7.52-7.54 (1H, m), 8.36 (1H, d), 8.42 (1H, s), 9.30 (1H, d), 10.01 (1H, s), 12.41 (1H, s); m/z=188 [M+H]+ (detected as adduct with acetonitrile used in mass spectral determination).

EXAMPLES 481-482

The following compounds were prepared in 10-48% yield by an analogous method to Example 294, starting from 6-[4-(methanesulfonyloxymethyl)piperidin-1-yl]-3-(trifluoromethyl)-[1,2,4]triazolo[4,3-b]pyridazine and the appropriate alcohol:—

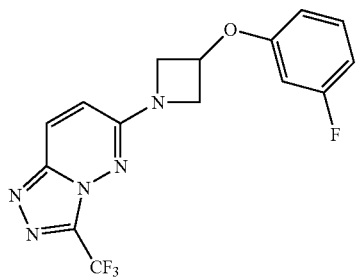

| Ex. | R | 1H NMR (399.9 MHz, CDCl3) | m/z [M + H]+ |
|---|---|---|---|
| 481 | oxetan-3-yl | δ 1.31-1.42 (2H, m), 1.86-1.97 (3H, m), 3.00-3.07 (2H, m), 3.24 (2H, d), 4.23-4.28 (2H, m), 4.50-4.55 (1H, m), 4.57-4.60 (2H, m), 4.75-4.78 (2H, m), 7.09 (1H, d), 7.90 (1H, d) | 358 |
| 482 | 2,2,2-trifluoroethyl | δ 1.35-1.39 (2H, m), 1.90-1.99 (3H, m), 2.99-3.06 (2H, m), 3.50-3.52 (2H, m), 3.83 (2H, q), 4.24-4.28 (2H, m), 7.09 (1H, d), 7.91 (1H, d) | 384 |

EXAMPLE 483

Preparation of 6-[3-(3-fluorophenoxy)azetidin-1-yl]-3-(trifluoromethyl)[1,2,4]triazolo[4,3-b]pyridazine A stirred partial solution of 6-[3-(methanesulfonyloxy)azetidin-1-yl]-3-(trifluoromethyl)-[1,2,4]triazolo[4,3-b]pyridazine (169 mg, 0.5 mmol), 3-fluorophenol (112 mg, 1.5 mmol) and potassium carbonate (207 mg, 1.5 mmol) in DMF (3 mL) was heated at 100° C. for 24 hours. The reaction mixture was filtered and the product was isolated by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to give 6-[3-(3-fluorophenoxy)azetidin-1-yl]-3-(trifluoromethyl)[1,2,4]triazolo[4,3-b]pyridazine (58 mg, 33%) as a solid.

1H NMR (399.9 MHz, CDCl3) δ 4.17-4.21 (2H, m), 4.50-4.54 (2H, m), 5.05-5.10 (1H, m), 6.44-6.47 (1H, m), 6.50-6.52 (1H, m), 6.60 (1H, d), 6.66-6.71 (1H, m), 7.18-7.24 (1H, m), 7.88 (1H, d); m/z=354 [M+H]+.

The starting 6-[3-(methanesulfonyloxy)azetidin-1-yl]-3-(trifluoromethyl)-[1,2,4]triazolo[4,3-b]pyridazine was prepared as follows:—

Preparation of 1-[3-(trifluoromethyl)-[1,2,4]triazolo[4,3-b]pyridazin-6-yl]azetidin-3-ol A stirred solution of 6-chloro-3-(trifluoromethyl)-[1,2,4]triazolo[4,3-b]pyridazine (5.56 g, 25 mmol), azetidin-3-ol hydrochloride (3.01 g, 27.50 mmol) and DIPEA (10.89 mL, 62.50 mmol) in DMF (50 mL) was heated at 70° C. for 1 hour. The solution was slowly diluted with water and the product crystallised. The precipitate was collected by filtration, washed with water, drained well and washed with ether. It was dried under vacuum to afford 1-[3-(trifluoromethyl)-[1,2,4]triazolo[4,3-b]pyridazin-6-yl]azetidin-3-ol (5.30 g, 82%) as a white crystalline solid.

1H NMR (399.9 MHz, DMSO-d6) δ 3.88 (2H, q), 4.32-4.36 (2H, m), 4.61-4.65 (1H, m), 5.82-5.83 (1H, m), 7.04 (1H, d), 8.22 (1H, d); m/z=260 [M+H]+.

Preparation of 6-[3-(methanesulfonyloxy)azetidin-1-yl]-3-(trifluoromethyl)-[1,2,4]triazolo[4,3-b]pyridazine Methanesulfonyl chloride (0.929 mL, 12 mmol) was added dropwise to a stirred partial solution of 1-(3-(trifluoromethyl)-[1,2,4]triazolo[4,3-b]pyridazin-6-yl)azetidin-3-ol (2.59 g, 10 mmol) and triethylamine (1.951 mL, 14 mmol) in DCM (17 mL) at 0° C. The solution was allowed to warm to ambient temperature and stirred for 30 minutes. The precipitate was collected by filtration, washed with a little DCM, a little ethanol and ether. It was dried under vacuum to afford 6-[3-(methanesulfonyloxy)azetidin-1-yl]-3-(trifluoromethyl)-[1,2,4]triazolo[4,3-b]pyridazine (2.400 g, 71.2%) as a white crystalline solid.

1H NMR (399.9 MHz, DMSO-d6) δ 3.32 (3H, s), 4.25-4.29 (2H, m), 4.54-4.59 (2H, m), 5.45-5.50 (1H, m), 7.11 (1H, d), 8.29 (1H, d); m/z=338 [M+H]+.

EXAMPLES 484-486

The following compounds were prepared in 49-56% yield by an analogous method to Example 483, starting from 6-[3-(methanesulfonyloxy)azetidin-1-yl]-3-(trifluoromethyl)-[1,2,4]triazolo[4,3-b]pyridazine and the appropriate phenol:—

| Ex. | R | 1H NMR (399.9 MHz, CDCl3) | m/z [M + H]+ |
|---|---|---|---|
| 484 | 4-F | δ 4.16-4.20 (2H, m), 4.48-4.52 (2H, m), 5.02-5.07 (1H, m), 6.60 (1H, d), 6.66-6.70 (2H, m), 6.92-6.98 (2H, m), 7.88 (1H, d) | 354 |
| 485 | 3-OMe | δ 3.74 (3H, s), 4.16-4.20 (2H, m), 4.48-4.53 (2H, m), 5.05-5.10 (1H, m), 6.29-6.32 (2H, m), 6.51-6.54 (1H, m), 6.60 (1H, d), 7.13-7.18 (1H, m), 7.88 (1H, d) | 366 |
| 486 | 4-OMe | δ 3.72 (3H, s), 4.15-4.19 (2H, m), 4.46-4.50 (2H, m), 5.00-5.05 (1H, m), 6.60 (1H, d), 6.65-6.69 (2H, m), 6.77-6.82 (2H, m), 7.88 (1H, d) | 366 |

EXAMPLE 487

Preparation of N,N-dimethyl-2-[[11-[3-(trifluoromethyl)[1,2,4]triazolo[4,3-b]pyridazin-6-yl]piperidin-4-yl]methoxy]acetamide

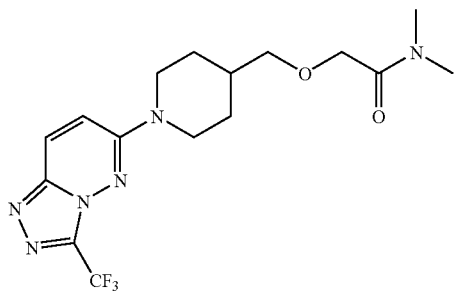

A stirred solution of methyl 2-[[1-[3-(trifluoromethyl)-[1,2,4]triazolo[4,3-b]pyridazin-6-yl]piperidin-4-yl]methoxy]acetate (95 mg, 0.25 mmol) in 2M dimethylamine in methanol (2.0 mL, 4.00 mmol) was heated at 120° C. in a microwave reactor for 1 hour. The reaction mixture was evaporated and the crude product was purified by preparative LCMS (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford N,N-dimethyl-2-[[1-[3-(trifluoromethyl)[1,2,4]triazolo[4,3-b]pyridazin-6-yl]piperidin-4-yl]methoxy]acetamide (48.0 mg, 48.8%) as a white solid.

1H NMR (399.9 MHz, CDCl3) δ 1.32-1.43 (2H, m), 1.93 (2H, d), 1.98-2.02 (1H, m), 2.96 (3H, s), 3.00 (3H, s), 3.03-3.07 (2H, m), 3.41-3.43 (2H, m), 4.15 (2H, s), 4.25 (2H, d), 7.09 (1H, d), 7.90 (1H, d); m/z=387 [M+H]+.

The methyl 2-[[1-[3-(trifluoromethyl)-[1,2,4]triazolo[4,3-b]pyridazin-6-yl]piperidin-4-yl]methoxy]acetate used as starting material was prepared as follows:—

Sodium hydride (60% dispersion in oil, 0.120 g, 3.0 mmol) was added to neat methyl glycolate (1.544 mL, 20.0 mmol). When the effervescence had subsided 6-[4-(methanesulfonyloxymethyl)piperidin-1-yl]-3-(trifluoromethyl)-[1,2,4]triazolo[4,3-b]pyridazine (0.759 g, 2.0 mmol) was added and the mixture was heated at 100° C. for 40 minutes. The reaction mixture was partitioned between DCM and water. The organic phase was washed with water and brine, dried over MgSO4 and evaporated. The product was isolated by MPLC silica chromatography, eluting with ethyl acetate. The product containing fractions were evaporated to an oil which crystallised from ether, giving methyl 2-[[1-[3-(trifluoromethyl)-[1,2,4]triazolo[4,3-b]pyridazin-6-yl]piperidin-4-yl]methoxy]acetate (0.130 g, 17%).

1H NMR (399.9 MHz, CDCl3) δ 1.33-1.43 (2H, m), 1.92-2.02 (3H, m), 3.00-3.07 (2H, m), 3.42-3.44 (2H, m), 3.76 (3H, s), 4.09 (2H, s), 4.23-4.26 (2H, m), 7.08 (1H, d), 7.90 (1H, d); m/z=374 [M+H]+.

EXAMPLE 488

Preparation of 6-[4-[(2-fluoroethoxy)methyl]piperidin-1-yl]-3-(trifluoromethyl)[1,2,4]triazolo[4,3-b]pyridazine

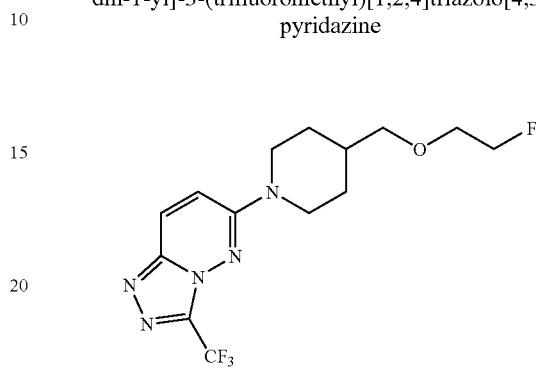

(Diethylamino)sulfur trifluoride (0.059 mL, 0.45 mmol) was added dropwise to a stirred solution of 2-[[1-(3-(trifluoromethyl)-[1,2,4]triazolo[4,3-b]pyridazin-6-yl]piperidin-4-yl)methoxy]ethanol (104 mg, 0.3 mmol) in DCM (3 mL) at −70° C. The solution was allowed to warm to ambient temperature and stir for 18 hours. The solution was diluted with DCM and washed with 2M aqueous K2CO3. The organic phase was dried over MgSO4 and evaporated. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[(2-fluoroethoxy)methyl]piperidin-1-yl]-3-(trifluoromethyl)[1,2,4]triazolo[4,3-b]pyridazine (22.0 mg, 21%) as a white solid.

1H NMR (399.9 MHz, CDCl3) δ 1.30-1.40 (2H, m), 1.90-2.01 (3H, m), 2.99-3.06 (2H, m), 3.40 (2H, d), 3.65-3.74 (2H, m), 4.23-4.27 (2H, m), 4.49-4.63 (2H, m), 7.09 (1H, d), 7.90 (1H, d); m/z=348 [M+H]+.

The starting 2-[[1-[3-(trifluoromethyl)[1,2,4]triazolo[4,3-b]pyridazin-6-yl]piperidin-4-yl]methoxy]ethanol was prepared as follows:—

Sodium hydride (60% dispersion in oil, 0.180 g, 4.5 mmol) was added to neat tetrahydropyranylethyleneglycol (3 g, 20.5 mmol). When the effervescence had subsided 6-[4-(methanesulfonyloxymethyl)piperidin-1-yl]-3-(trifluoromethyl)-[1,2,4]triazolo[4,3-b]pyridazine (obtained as described in Example 294, preparation of starting materials) (1.138 g, 3 mmol) was added and the mixture was heated at 100° C. for 40 minutes. The reaction mixture was partitioned between DCM and water. The organic phase was washed with water and brine, dried over MgSO4 and evaporated. The crude intermediate was disolved in methanol (20 mL) and p-toluenesulfonic acid monohydrate (0.855 g, 4.5 mmol) was added. The solution was stirred for 1 hour and then evaporated. The reaction mixture was partitioned between DCM and water and the organic phase was washed with water and brine, dried over MgSO4 and evaporated. The product was isolated by MPLC silica chromatography, eluting with 5% methanol/DCM. The product containing fractions were evaporated giving a crystalline solid which was triturated with ether, giving 2-[[1-[3-(trifluoromethyl)[1,2,4]triazolo[4,3-b]pyridazin-6-yl]piperidin-4-yl]methoxy]ethanol (0.563 g, 54%)

1H NMR (399.9 MHz, CDCl3) δ 1.31-1.41 (2H, m), 1.89-2.00 (3H, m), 2.99-3.06 (2H, m), 3.38-3.39 (2H, m), 3.55-3.57 (2H, m), 3.74-3.76 (2H, m), 4.23-4.27 (2H, m), 7.08 (1H, d), 7.90 (1H, d), OH not observed; m/z=346 [M+H]+.

EXAMPLE 489

Preparation of 6-[4-(tert-butoxymethyl)piperidin-1-yl]-3-(trifluoromethyl)[1,2,4]triazolo[4,3-b]pyridazine

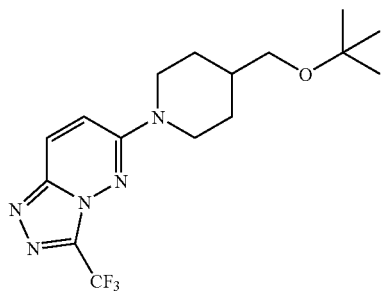

A stirred solution of [1-(3-(trifluoromethyl)-[1,2,4]triazolo[4,3-b]pyridazin-6-yl)piperidin-4-yl]methanol (obtained as described in Example 294, preparation of starting materials) (151 mg, 0.5 mmol) and p-toluenesulfonic acid monohydrate (190 mg, 1.0 mmol) in DCM (2 mL) was cooled to −70° C. and 2-methylpropene (1 mL, 10.48 mmol) was condensed in from a cylinder. The mixture was stirred for 2 days at ambient temperature in a sealed tube. The tube was re-cooled to open then allowed to warm to ambient temperature with stirring. The solution was diluted with DCM and washed with 2M aqueous K₂CO₃. The organic phase was dried over MgSO₄ and evaporated. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-(4-(tert-butoxymethyl)piperidin-1-yl)-3-(trifluoromethyl)-[1,2,4]triazolo[4,3-b]pyridazine (98 mg, 54%) as a white solid.

1H NMR (399.9 MHz, CDCl3) δ 1.18 (9H, s), 1.24-1.35 (2H, m), 1.79-1.84 (1H, m), 1.92 (2H, d), 2.98-3.05 (2H, m), 3.23 (2H, d), 4.25 (2H, d), 7.09 (1H, d), 7.89 (1H, d); m/z=358 [M+H]+.

EXAMPLES 490-493

The following compounds were prepared in 43-63% yield by an analogous method to Example 447, starting from [1-[3-(trifluoromethyl)-[1,2,4]triazolo[4,3-b]pyridazin-6-yl]azetidin-3-yl]methanol and the appropriate phenol:—

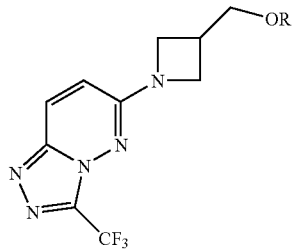

| Ex. | R | 1H NMR (399.9 MHz, CDCl3) | m/z [M + H]+ |
|---|---|---|---|
| 490 | 3-fluorophenyl | δ 3.26-3.33 (1H, m), 4.08-4.11 (2H, m), 4.18 (2H, d), 4.34 (2H, t), 6.61-6.66 (2 H, m), 6.68-6.73 (2H, m), 7.21-7.27 (1 H, m), 7.92 (1H, s) | 368 |
| 491 | 3-fluorophenyl | δ 3.25-3.32 (1H, m), 4.08-4.11 (2H, m), 4.15 (2H, d), 4.34 (2H, t), 6.64 (1H, d), 6.84-6.87 (2H, m), 6.96-7.02 (2H, m), 7.91 (1H, d) | 368 |
| 492 | pyridin-3-yl | δ 3.30-3.37 (1H, m), 4.10-4.13 (2H, m), 4.26 (2H, d), 4.37 (2H, t), 6.65 (1H, d), 7.20-7.26 (2H, m), 7.93 (1H, d), 8.27-8.28 (1H, m), 8.34 (1H, q) | 351 |
| 493 | pyrimidin-2-yl | δ 3.32-3.40 (1H, m), 4.10-4.13 (2H, m), 4.34 (2H, t), 4.61-4.63 (2H, m), 6.64 (1 H, d), 7.00 (1H, t), 7.90 (1H, d), 8.54 (2 H, d) | 352 |

The starting [1-[3-(trifluoromethyl)-[1,2,4]triazolo[4,3-b]pyridazin-6-yl]azetidin-3-yl]methanol was prepared as follows:—

A stirred solution of 6-chloro-3-(trifluoromethyl)-[1,2,4]triazolo[4,3-b]pyridazine (4.44 g, 20.0 mmol), azetidin-3-ylmethanol (2.25 g, 22.0 mmol) and DIPEA (5.21 mL, 30.0 mmol) in DMF (40 mL) was heated at 70° C. for 1 hour. The solution was evaporated and partitioned between water and 2M aqueous K₂CO₃. The organic phase was washed with water and brine and dried over MgSO₄. The crude product was purified by MPLC silica chromatography, eluting with 5% MeOH in DCM. Pure fractions were evaporated to dryness and triturated with ether, giving [1-[3-(trifluoromethyl)-[1,2,4]triazolo[4,3-b]pyridazin-6-yl]azetidin-3-yl]methanol (1.65 g, 30%) as a cream crystalline solid.

1H NMR (399.9 MHz, DMSO-d6) δ 2.87 (1H, t), 3.59 (2H, t), 3.86-3.89 (2H, m), 4.14 (2H, t), 4.88 (1H, t), 7.03 (1H, d), 8.21 (1H, d); m/z=274 [M+H]+.

EXAMPLE 494

Preparation of 6-[4-(5-methoxy-1H-indol-3-yl)piperidin-1-yl]-3-(trifluoromethyl)[1,2,4]triazolo[4,3-b]pyridazine

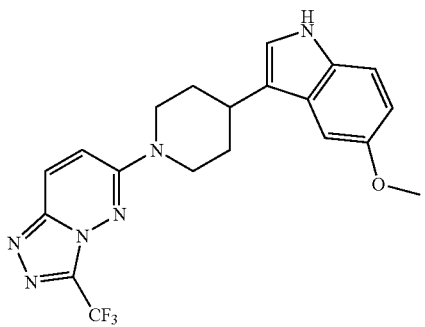

6-Chloro-3-(trifluoromethyl)-[1,2,4]triazolo[4,3-b]pyridazine (160 mg, 0.72 mmol), 5-methoxy-3-(piperidin-4-yl)-1H-indole (obtained as described in PCT Int. Appl. WO 2004006922, Intermediate 37) (166 mg, 0.72 mmol) and DIPEA (0.138 mL, 0.79 mmol) in DMF (2 mL) were stirred and heated at 80° C. for 1 hour. The resulting mixture was cooled to room temperature and quenched in water (10 mL) to give a precipitate. The solid was collected by filtration, washed sequentially with water, acetonitrile and ether, and air dried to give 6-[4-(5-methoxy-1H-indol-3-yl)piperidin-1-yl]-3-(trifluoromethyl)[1,2,4]triazolo[4,3-b]pyridazine (189 mg, 63%) as a colourless solid.

1H NMR (399.9 MHz, DMSO-d6) δ 1.67-1.75 (2H, m), 2.10-2.13 (2H, m), 3.08-3.14 (1H, m), 3.18-3.25 (2H, m), 3.76 (3H, s), 4.39-4.42 (2H, m), 6.73 (1H, d), 7.07 (2H, s), 7.23 (1H, d), 7.67 (1H, d), 8.24 (1H, d), 10.63 (1H, s); m/z 417 [M+H]+.

EXAMPLE 495

Preparation of 3-[1-[3-(trifluoromethyl)[1,2,4]triazolo[4,3-b]pyridazin-6-yl]piperidin-4-yl]-1H-indole-5-carbonitrile

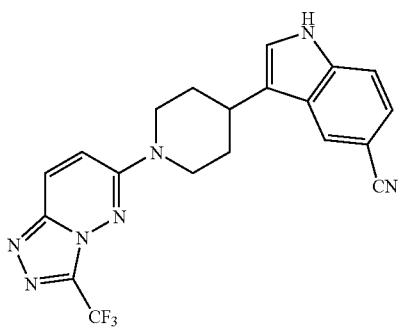

Obtained in 88% yield by an analogous procedure to Example 494, starting from 6-chloro-3-(trifluoromethyl)-[1,2,4]triazolo[4,3-b]pyridazine and 3-(piperidin-4-yl)-1H-indole-5-carbonitrile (obtained as described in PCT Int. Appl. WO 2001043740, Example 3).

1H NMR (399.9 MHz, DMSO-d6) δ 1.68-1.78 (2H, m), 2.11-2.13 (2H, m), 3.18-3.24 (3H, m), 4.40-4.43 (2H, m), 7.36 (1H, s), 7.42 (1H, d), 7.51 (1H, d), 7.68 (1H, d), 8.24 (2H, m), 11.43 (1H, s); m/z 410 [M−H]−.

EXAMPLE 496

Preparation of N-(2-hydroxyethyl)-N-methyl-3-[1-[3-(trifluoromethyl)[1,2,4]triazolo[4,3-b]pyridazin-6-yl]piperidin-4-yl]-1H-indole-5-carboxamide

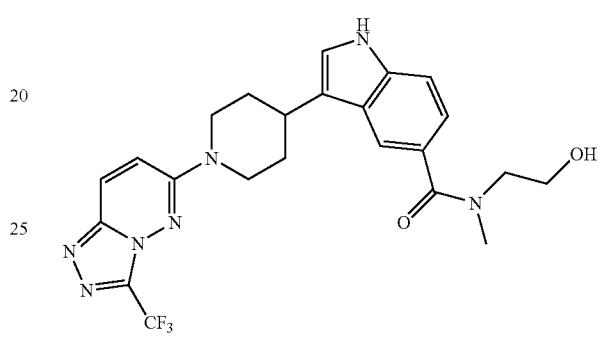

HATU (139 mg, 0.37 mmol) was added portionwise at ambient temperature to a stirred mixture of 3-[1-[3-(trifluoromethyl)[1,2,4]triazolo[4,3-b]pyridazin-6-yl]piperidin-4-yl]-1H-indole-5-carboxylic acid (150 mg, 0.35 mmol), 2-(methylamino)ethanol (0.034 mL, 0.42 mmol) and DIPEA (0.073 mL, 0.42 mmol) in DMF (2.0 mL). The resulting solution was stirred for 2 hours then purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford N-(2-hydroxyethyl)-N-methyl-3-[1-[3-(trifluoromethyl)[1,2,4]triazolo[4,3-b]pyridazin-6-yl]piperidin-4-yl]-1H-indole-5-carboxamide (155 mg, 91%) as a colourless solid.

1H NMR (399.9 MHz, DMSO-d6) δ 1.68-1.78 (2H, m), 2.09-2.13 (2H, m), 3.01 (3H, s), 3.13-3.24 (3H, m), 3.29-3.70 (4H, m), 4.40-4.43 (2H, m), 4.78 (1H, t), 7.14 (1H, dd), 7.21 (1H, d), 7.36 (1H, d), 7.68 (1H, d), 7.71 (1H, s), 8.25 (1H, d), 11.03 (1H, s); m/z=488 [M+H]+.

The 3-[1-[3-(trifluoromethyl)[1,2,4]triazolo[4,3-b]pyridazin-6-yl]piperidin-4-yl]-1H-indole-5-carboxylic acid used as starting material was prepared as follows:—

Preparation of 3-[1-(tert-butoxycarbonyl)-1,2,3,6-tetrahydropyridin-4-yl]-1H-indole-5-carboxylic acid Potassium hydroxide (5.17 g, 92.08 mmol) was added to 1H-indole-5-carboxylic acid (3.71 g, 23.02 mmol) and tert-butyl 4-oxopiperidine-1-carboxylate (9.17 g, 46.04 mmol) in methanol (80 mL) at ambient temperature and the resulting solution was stirred at 65° C. for 18 hours. The mixture was then cooled to ambient temperature, quenched in water (100 mL) and extracted with ethyl acetate (2×100 mL). The extracts were discarded and the aqueous phase acidified to pH 2-3 wth 2M hydrochloric acid to give a pale yellow solid. The solid was collected by filtration, washed sequentially with water and ether and air dried to give 3-[1-(tert-butoxycarbonyl)-1,2,3,6-tetrahydropyridin-4-yl]-1H-indole-5-carboxylic acid (5.62 g, 71.3%) as a colourless solid.

1H NMR (399.9 MHz, DMSO-d6) δ 1.45 (9H, s), 2.50-2.55 (2H, m), 3.59 (2H, t), 4.06-4.11 (2H, m), 6.16 (1H, m), 7.46 (1H, d), 7.55 (1H, d), 7.76 (1H, dd), 8.48 (1H, s), 11.51 (1H, s), 12.45 (1H, br s); m/z=341 [M−H]−.

Preparation of methyl 3-[1-(tert-butoxycarbonyl)-1,2,3,6-tetrahydropyridin-4-yl]-1H-indole-5-carboxylate Iodomethane (1.22 mL, 19.63 mmol) was added in one portion to 3-[1-(tert-butoxycarbonyl)-1,2,3,6-tetrahydropyridin-4-yl]-1H-indole-5-carboxylic acid (6.72 g, 19.63 mmol) and potassium carbonate (3.26 g, 23.55 mmol) in DMF (60 mL) at ambient temperature. The resulting mixture was stirred at ambient temperature for 3 hours then quenched in water (200 mL) and extracted with MTBE (2×100 mL). The extract was washed sequentially with water (3×100 mL) and saturated brine, dried over MgSO4 and concentrated by evaporation then purified by flash silica chromatography, elution gradient 20 to 35% EtOAc in isohexane. Pure fractions were evaporated to dryness to afford methyl 3-[1-(tert-butoxycarbonyl)-1,2,3,6-tetrahydropyridin-4-yl]-1H-indole-5-carboxylate (5.09 g, 73%) as a colourless solid.

1H NMR (399.9 MHz, CDCl3) δ 1.51 (9H, s), 2.55-2.58 (2H, m), 3.67-3.70 (2H, m), 3.95 (3H, s), 4.14-4.18 (2H, m), 6.23 (1H, m), 7.22 (1H, d), 7.38 (1H, d), 7.93 (1H, dd), 8.42 (1H, s), 8.63 (1H, s); m/z=355 [M−H]−.

Preparation of methyl 3-[1-(tert-butoxycarbonyl)piperidin-4-yl]-1H-indole-5-carboxylate Methyl 3-[1-(tert-butoxycarbonyl)-1,2,3,6-tetrahydropyridin-4-yl]-1H-indole-5-carboxylate (5.0 g, 14.03 mmol), ammonium formate (4.42 g, 70.14 mmol) and palladium (5% on activated carbon, 200 mg) in ethanol (80 mL) were stirred and refluxed for 1 hour. The resulting mixture was cooled to ambient temperature and filtered through diatomaceous earth. The filtrate was concentrated by evaporation then treated with dilute aqueous ammonium chloride (100 mL) and extracted with ethyl acetate. The extract was washed sequentially with water and saturated brine, dried over MgSO4 and evaporated to a colourless solid. The solid was triturated with ether, then collected by filtration and air dried to give methyl 3-[1-(tert-butoxycarbonyl)piperidin-4-yl]-1H-indole-5-carboxylate (4.59 g, 91%) as a colourless solid.

1H NMR (399.9 MHz, CDCl3) δ 1.49 (9H, s), 1.60-1.70 (2H, m), 2.03-2.06 (2H, m), 2.88-2.95 (2H, m), 3.03 (1H, tt), 3.94 (3H, s), 4.17-4.32 (2H, m), 7.01 (1H, d), 7.37 (1H, d), 7.90 (1H, dd), 8.26 (1H, s), 8.39 (1H, s); m/z=357 [M−H]−.

Preparation of methyl 3-(piperidin-4-yl)-1H-indole-5-carboxylate

TFA (10 mL) was added in one portion at ambient temperature to a stirred solution of methyl 3-[1-(tert-butoxycarbonyl)piperidin-4-yl]-1H-indole-5-carboxylate (4.58 g, 12.78 mmol) in DCM (30 mL). The resulting solution was stirred for 30 minutes then applied to an SCX column and eluted with methanol followed by 2M ammonia in methanol. Pure fractions were combined and concentrated by evaporation then triturated with ether to give a solid which was collected by filtration and air dried to give methyl 3-(piperidin-4-yl)-1H-indole-5-carboxylate (2.69 g, 81%) as a pale yellow solid.

1H NMR (399.9 MHz, DMSO-d6) δ 1.53-1.63 (2H, m), 1.86-1.89 (2H, m), 2.64-2.70 (2H, m), 2.86-2.92 (1H, m), 3.02-3.05 (2H, m), 3.85 (3H, s), 7.21 (1H, d), 7.42 (1H, d), 7.71 (1H, dd), 8.26 (1H, s), 11.20 (1H, s); m/z=257 [M−H]−.

Preparation of methyl 3-[1-[3-(trifluoromethyl)-[1,2,4]triazolo[4,3-b]pyridazin-6-yl]piperidin-4-yl]-1H-indole-5-carboxylate 6-Chloro-3-(trifluoromethyl)-[1,2,4]triazolo[4,3-b]pyridazine (1.8 g, 8.09 mmol), methyl 3-(piperidin-4-yl)-1H-indole-5-carboxylate (2.09 g, 8.09 mmol) and DIPEA (1.55 mL, 8.90 mmol) in DMF (25 mL) were stirred and heated at 80° C. for 1 hour. The resulting mixture was then cooled to ambient temperature and quenched in water (60 mL) to give a precipitate which was collected by filtration, washed sequentially with water, acetonitrile and ether and dried under vacuum to give methyl 3-[1-[3-(trifluoromethyl)-[1,2,4]triazolo[4,3-b]pyridazin-6-yl]piperidin-4-yl]-1H-indole-5-carboxylate (3.29 g, 92%) as a cream solid.

1H NMR (399.9 MHz, DMSO-d6) δ 1.70-1.80 (2H, m), 2.09-2.12 (2H, m), 3.21-3.28 (3H, m), 3.85 (3H, s), 4.40-4.43 (2H, m), 7.28 (1H, d), 7.44 (1H, d), 7.68 (1H, d), 7.73 (1H, dd), 8.25 (1H, d), 8.31 (1H, d), 11.26 (1H, s); m/z=445 [M+H]+.

Preparation of 3-[1-[3-(trifluoromethyl)[1,2,4]triazolo[4,3-b]pyridazin-6-yl]piperidin-4-yl]-1H-indole-5-carboxylic acid Methyl 3-[1-[3-(trifluoromethyl)-[1,2,4]triazolo[4,3-b]pyridazin-6-yl]piperidin-4-yl]-1H-indole-5-carboxylate (3.28 g, 7.38 mmol) and 2M NaOH (10 mL, 7.38 mmol) in methanol (80 mL) were heated under reflux for 40 hours. The resulting solution was concentrated by evaporation, then acidified to pH 2-3 with 2M hydrochloric acid to give a colourless precipitate. The precipitate was collected by filtration, washed sequentially with water, acetonitrile and ether and dried under vacuum to afford 3-[1-[3-(trifluoromethyl)[1,2,4]triazolo[4,3-b]pyridazin-6-yl]piperidin-4-yl]-1H-indole-5-carboxylic acid (2.83 g, 89%) as a colourless solid.

1H NMR (399.9 MHz, DMSO-d6) δ 1.69-1.79 (2H, m), 2.09-2.13 (2H, m), 3.18-3.26 (3H, m), 4.40-4.43 (2H, m), 7.23 (1H, d), 7.37 (1H, d), 7.68 (1H, d), 7.72 (1H, dd), 8.25 (1H, d), 8.29 (1H, s), 11.19 (1H, s); m/z=431 [M+H]+.

EXAMPLES 497-505

The following compounds were prepared in 75-98% yield by an analogous method to Example 496, starting from 3-[1-[3-(trifluoromethyl)[1,2,4]triazolo[4,3-b]pyridazin-6-yl]piperidin-4-yl]-1H-indole-5-carboxylic acid and the appropriate amine:—

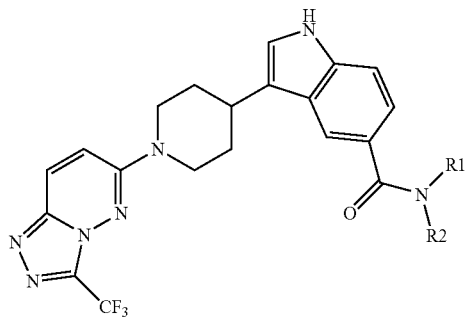

| Ex. | NR1R2 | 1H NMR (399.9 MHz, DMSO-d6) | m/z [M + H]+ |
|---|---|---|---|
| 497 | N-methylpiperazine | δ 1.68-1.78 (2H, m), 2.08-2.12 (2H, m), 2.18 (3H, s), 2.25-2.35 (4H, m), 3.15-3.24 (3H, m), 3.42-3.61 (4H, m), 4.40-4.43 (2H, m), 7.11 (1H, dd), 7.23 (1H, d), 7.38 (1H, d), 7.68 (1H, s), 7.69 (1H, d), 8.26 (1H, d), 11.07 (1H, s) | 513 |
| 498 | HN-CH2CH2-OMe | δ 1.70-1.81 (2H, m), 2.14-2.17 (2H, m), 3.15-3.25 (3H, m), 3.29 (3H, s), 3.44-3.50 (4H, m), 4.43-4.46 (2H, m), 7.22 (1H, d), 7.36 (1H, d), 7.64 (1H, dd), 7.70 (1H, d), 8.20 (1H, s), 8.27 (1H, d), 8.41 (1H, t), 11.09 (1H, s) | 488 |
| 499 | NMe2 | δ 1.68-1.78 (2H, m), 2.09-2.12 (2H, m), 2.99 (6H, s), 3.13-3.24 (3H, m), 4.40-4.43 (2H, m), 7.14 (1H, dd), 7.21 (1H, d), 7.37 (1H, d), 7.69 (1H, d), 7.70 (1H, s), 8.25 (1H, d), 11.05 (1H, s). | 458 |
| 500 | (S)-3-hydroxypyrrolidine | δ 1.66-2.01 (4H, m), 2.09-2.12 (2H, m), 3.16-3.29 (3H, m), 3.46-3.70 (4H, m), 4.22 (m) & 4.34 (m, 1H), 4.40-4.43 (2H, m), 4.91 (d) & 5.02 (d, 1H), 7.22 (1H, d), 7.27 (1H, d), 7.37 (1H, d), 7.69 (1H, d), 7.82 (1H, s), 8.25 (1H, d), 11.06 (1H, s) | 500 |
| 501 | pyrrolidine | δ 1.68-1.93 (6H, m), 2.08-2.12 (2H, m), 3.15-3.24 (3H, m), 3.43-3.51 (4H, m), 4.40-4.43 (2H, m), 7.21 (1H, d), 7.27 (1H, dd), 7.36 (1H, d), 7.69 (1H, d), 7.82 (1H, s), 8.26 (1H, d), 11.05 (1H, s) | 484 |
| 502 | morpholine | δ 1.68-1.78 (2H, m), 2.09-2.12 (2H, m), 3.15-3.24 (3H, m), 3.47-3.65 (8H, m), 4.40-4.43 (2H, m), 7.14 (1H, dd), 7.23 (1H, d), 7.39 (1H, d), 7.69 (1H, d), 7.71 (1H, s), 8.26 (1H, d), 11.08 (1H, s) | 500 |
| 503 | HN-CH2CH2-morpholine | δ 1.71-1.81 (2H, m), 2.14-2.16 (2H, m), 2.44 (4H, m), 2.47-2.50 (2H, m), 3.14-3.25 (3H, m), 3.42 (2H, q), 3.58 (4H, t), 4.43-4.46 (2H, m), 7.22 (1H, d), 7.37 (1H, d), 7.62 (1H, dd), 7.70 (1H, d), 8.16 (1H, s), 8.27 (1H, d), 8.28 (1H, t), 11.08 (1H, s) | 543 |
| 504 | MeN-CH2CH2-OMe | δ 1.69-1.79 (2H, m), 2.09-2.12 (2H, m), 2.99 (3H, s), 3.14-3.29 (6H, m), 3.40-3.64 (4H, m), 4.40-4.44 (2H, m), 7.12 (1H, dd), 7.21 (1H, d), 7.37 (1H, d), 7.69 (1H, d), 7.70 (1H, s), 8.25 (1H, d), 11.04 (1H, s) | 502 |
| 505 | (R)-3-hydroxypyrrolidine | δ 1.67-2.00 (4H, m), 2.09-2.12 (2H, m), 3.16-3.29 (3H, m), 3.45-3.70 (4H, m), 4.22 (m) & 4.34 (m, 1H), 4.40-4.43 (2H, m), 4.91 (d) & 5.02 (d, 1H), 7.22 (1H, d), 7.27 (1H, d), 7.37 (1H, d), 7.69 (1H, d), 7.82 (1H, s), 8.25 (1H, d), 11.06 (1H, s) | 500 |

EXAMPLE 506

Preparation of 6-[4-[5-(piperazin-1-ylcarbonyl)-1H-indol-3-yl]piperidin-1-yl]-3-(trifluoromethyl)[1,2,4]triazolo[4,3-b]pyridazine

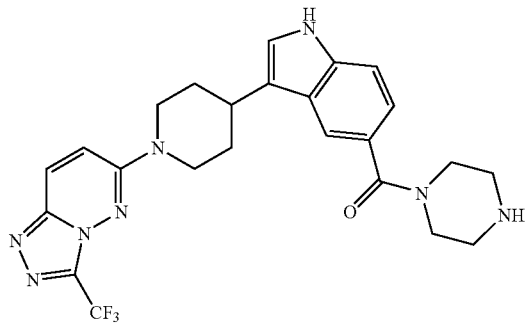

TFA (1 mL) was added in one portion at ambient temperature to a stirred solution of tert-butyl [4-[3-[1-(3-(trifluoromethyl)-[1,2,4]triazolo[4,3-b]pyridazin-6-yl]piperidin-4-yl]-1H-indole-5-carbonyl]piperazine-1-carboxylate (190 mg, 0.32 mmol) in DCM (2 mL). The resulting solution was stirred for 1 hour then applied to an SCX column and eluted with MeOH followed by 2M ammonia in MeOH. Pure fractions were combined and concentrated by evaporation then triturated with ether to give a solid which was collected by filtration and air dried to give 6-[4-[5-(piperazin-1-ylcarbonyl)-1H-indol-3-yl]piperidin-1-yl]-3-(trifluoromethyl)[1,2,4]triazolo[4,3-b]pyridazine (156 mg, 99%) as a colourless solid.

1H NMR (399.9 MHz, DMSO-d6) δ 1.68-1.78 (2H, m), 2.09-2.12 (2H, m), 2.83-2.93 (4H, m), 3.15-3.24 (3H, m), 3.50-3.64 (4H, m), 4.40-4.44 (2H, m), 7.14 (1H, dd), 7.23 (1H, d), 7.39 (1H, d), 7.69 (1H, d), 7.71 (1H, s), 8.26 (1H, d), 11.09 (1H, s); m/z=499 [M+H]+.

The tert-butyl [4-[3-[1-(3-(trifluoromethyl)-[1,2,4]triazolo[4,3-b]pyridazin-6-yl]piperidin-4-yl]-1H-indole-5-carbonyl]piperazine-1-carboxylate used as starting material was prepared in 91% yield by an analogous method to Example 496, starting from 3-[1-[3-(trifluoromethyl)[1,2,4]triazolo[4,3-b]pyridazin-6-yl]piperidin-4-yl]-1H-indole-5-carboxylic acid and tert-butyl 1-piperazinecarboxylate.

m/z=599 [M+H]+.

EXAMPLE 507

Preparation of 6-[4-(1H-indol-3-yl)piperidin-1-yl]-3-(trifluoromethyl)[1,2,4]triazolo[4,3-b]pyridazine

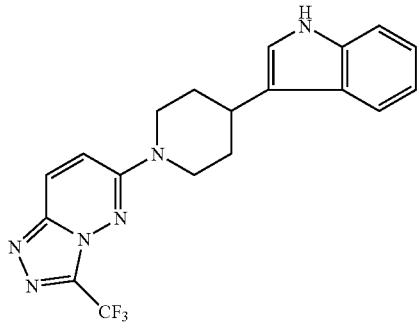

A stirred solution of 6-chloro-3-(trifluoromethyl)-[1,2,4]triazolo[4,3-b]pyridazine (0.223 g, 1.0 mmol), 3-(piperidin-4-yl)-1H-indole (0.240 g, 1.20 mmol) and DIPEA (0.257 mL, 1.50 mmol) in DMF (3 mL) was heated at 70° C. for 1 hour. The reaction mixture was run onto an SCX cartridge, which was washed with MeOH and eluted with 2M ammonia in methanol. The crude product was purified by MPLC silica chromatography, eluting with ethyl acetate. Pure fractions were evaporated to a gum which crystallised on trituration with ether to afford 6-[4-(1H-indol-3-yl)piperidin-1-yl]-3-(trifluoromethyl)[1,2,4]triazolo[4,3-b]pyridazine (0.119 g, 31%) as a colourless crystalline solid.

1H NMR (399.9 MHz, CDCl3) δ 1.81-1.92 (2H, m), 2.25 (2H, d), 3.15-3.27 (3H, m), 4.37 (2H, d), 6.99-6.99 (1H, m), 7.11-7.15 (2H, m), 7.19-7.24 (1H, m), 7.38-7.40 (1H, m), 7.64 (1H, d), 7.92 (1H, d), 8.02 (1H, s); m/z=387 [M+H]+.

EXAMPLE 508

Preparation of 6-[4-[1-(2-pyrrolidin-1-ylethyl)-1H-indol-3-yl]piperidin-1-yl]-3-(trifluoromethyl)[1,2,4]triazolo[4,3-b]pyridazine

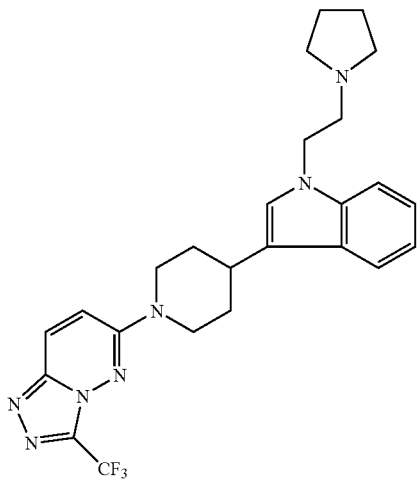

Sodium hydride (60% dispersion in oil, 31 mg, 0.75 mmol) was added to 6-[4-(1H-indol-3-yl)piperidin-1-yl]-3-(trifluoromethyl)[1,2,4]triazolo[4,3-b]pyridazine (obtained as described in Example 507) (150 mg, 0.39 mmol) suspended in DMF (2 mL) at 0° C. under nitrogen. The resulting mixture was stirred at 0° C. for 30 minutes, then 1-(2-chloroethyl)pyrrolidine hydrochloride (72.6 mg, 0.43 mmol) in DMF (1 mL) was added. The resulting mixture was stirred at ambient temperature for 18 hours. The reaction mixture was evaporated to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to give 6-[4-[1-(2-pyrrolidin-1-ylethyl)-1H-indol-3-yl]piperidin-1-yl]-3-(trifluoromethyl)[1,2,4]triazolo[4,3-b]pyridazine (52.0 mg, 27.7%) as a white solid.

1H NMR (399.9 MHz, DMSO-$d_6$) δ 1.63-1.67 (4H, m), 1.71-1.76 (2H, m), 2.09 (1H, d), 2.11 (1H, s), 2.45-2.48 (4H, m), 2.76 (2H, t), 3.15 (1H, t), 3.19-3.25 (2H, m), 3.38 (1H, s), 4.20 (2H, t), 4.40 (2H, d), 6.99-7.03 (1H, m), 7.10-7.14 (1H, m), 7.18 (1H, s), 7.42 (1H, d), 7.61 (1H, s), 7.67 (1H, d), 8.24 (1H, d); m/z 485 [M+H]+.

EXAMPLES 509-510

The following compounds were prepared in 26-32% yield by an analogous procedure to Example 508, starting from 6-[4-(1H-indol-3-yl)piperidin-1-yl]-3-(trifluoromethyl)-[1,2,4]triazolo[4,3-b]pyridazine and the appropriate alkyl chloride:—

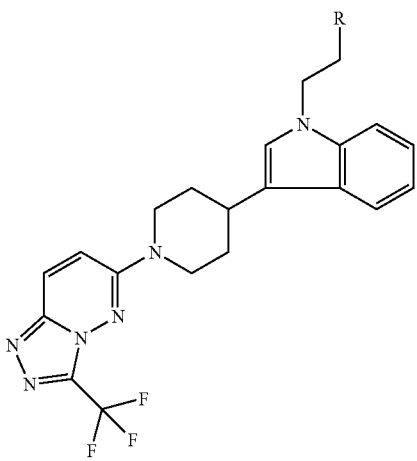

| Ex. | R | 1H NMR (399.9 MHz, DMSO-d6) | m/z [M + H]+ |
|---|---|---|---|
| 509 | Me2N | δ 1.70-1.74 (1H, m), 2.11 (2H, d), 2.18 (6H, s), 2.58 (2H, t), 3.15 (1H, t), 3.21 (1H, d), 3.25-3.26 (1H, m), 3.35 (1H, d), 4.18 (2H, t), 4.41 (2H, d), 7.00 (1H, t), 7.10-7.13 (1H, m), 7.18 (1H, s), 7.42 (1H, d), 7.63 (1H, s), 7.67 (1H, d), 8.24 (1H, d) | 459 |
| 510 | MeO | δ 1.70-1.74 (2H, m), 2.10 (1H, d), 2.12 (1H, s), 3.15-3.19 (1H, m), 3.22 (4H, s), 3.64 (2H, t), 4.26 (2H, t), 4.39-4.43 (2H, m), 6.99-7.03 (1H, m), 7.10-7.14 (1H, m), 7.15 (1H, s), 7.44 (1H, d), 7.61 (1H, s), 7.67 (1H, d), 8.25 (1H, d) | 446 |

EXAMPLE 511

Preparation of 4-pyridin-3-yl-1-[3-(trifluoromethyl)[1,2,4]triazolo[4,3-b]pyridazin-6-yl]piperidin-4-ol

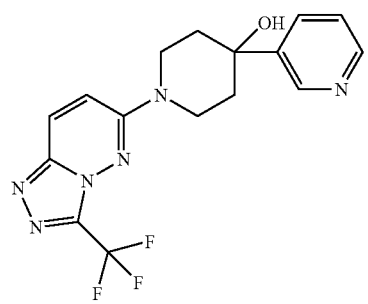

A stirred solution of 6-chloro-3-(trifluoromethyl)-[1,2,4]triazolo[4,3-b]pyridazine (0.445 g, 2.0 mmol), 4-(pyridin-3-yl)piperidin-4-ol (obtained as described in Canadian Patent Application CA2076191, Example 87 (see also Example 87 in EP0533344B1)) (0.392 g, 2.20 mmol) and DIPEA (0.453 mL, 2.60 mmol) in DMF (4 mL) was heated at 70° C. for 1 hour. The solution was evaporated and partitioned between DCM (20 mL) and 1M aqueous potassium carbonate (20 mL). The organic phase was washed with saturated aqueous sodium chloride, dried over MgSO$_4$ and evaporated to dryness, and the residue was triturated with ether. The precipitated solid was collected by filtration, washed with ether and dried under vacuum to afford 4-pyridin-3-yl-1-[3-(trifluoromethyl)[1,2,4]triazolo[4,3-b]pyridazin-6-yl]piperidin-4-ol (0.270 g, 37%) as a white crystalline solid.

1H NMR (399.9 MHz, DMSO-d6) δ 1.76-1.79 (2H, m), 2.03-2.11 (2H, m), 3.43-3.49 (2H, m), 4.23 (2H, d), 5.43 (1H, s), 7.33-7.37 (1H, m), 7.67 (1H, d), 7.87-7.90 (1H, m), 8.25 (1H, d), 8.45-8.46 (1H, m), 8.74 (1H, d); m/z=363 [M−H]−.

EXAMPLE 511.1

Large Scale Preparation of 4-pyridin-3-yl-1-[3-(trifluoromethyl)[1,2,4]triazolo[4,3-b]pyridazin-6-yl]piperidin-4-ol A stirred solution of 6-chloro-3-(trifluoromethyl)-[1,2,4]triazolo[4,3-b]pyridazine (24.29 g, 109.15 mmol), 4-(pyridin-3-yl)piperidin-4-ol (21.40 g, 120.07 mmol) and DIPEA (24.72 ml, 141.90 mmol) in DMF (95 ml) was heated at 80° C. for 1 hour. The solution was cooled to ambient temperature and slowly diluted with water, with seeding, to give a crystalline precipitate. The precipitate was collected by filtration, washed with water, acetonitrile and ether and dried under vacuum to afford 4-pyridin-3-yl-1-[3-(trifluoromethyl)[1,2,4]triazolo[4,3-b]pyridazin-6-yl]piperidin-4-ol (36.1 g, 91%) as a solid.

1H NMR (399.9 MHz, DMSO-d6) δ 1.76 (2H, d), 2.03-2.09 (2H, m), 3.41-3.47 (2H, m), 4.23 (2H, d), 5.47 (1H, s), 7.33-7.37 (1H, m), 7.68 (1H, d), 7.87-7.90 (1H, m), 8.26 (1H, d), 8.44-8.46 (1H, m), 8.74 (1H, d); m/z=365 [M+H]+.

The 4-(pyridin-3-yl)piperidin-4-ol used as starting material was prepared as follows:—

Preparation of benzyl 4-hydroxy-4-(pyridin-3-yl)piperidine-1-carboxylate

A solution of 3-bromopyridine (9.09 mL, 94.31 mmol) in diethyl ether (50 mL) was added dropwise to a stirred solution of 1.6M n-butyl lithium in hexane (58.9 mL, 94.31 mmol) in diethyl ether (500 mL) cooled to −78° C., over a period of 15 minutes under nitrogen. The resulting suspension was stirred at −78° C. for 1 hour. A solution of benzyl 4-oxopiperidine-1-carboxylate (20 g, 85.74 mmol) in diethyl ether (50 mL) and THF (50 mL) was added dropwise over 15 minutes. The reaction mixture was stirred at −78° C. for 1 hour, warmed to 0° C. over 2.5 hours and quenched with saturated ammonium chloride solution (500 ml). The mixture was extracted with ethyl acetate (2×500 mL) and the combined extracts were washed with brine (200 mL) then dried over MgSO$_4$ and filtered through a short pad of silica. The silica pad was washed through with ethyl acetate (4×250 mL) and the filtrate was concentrated under vacuum. The residue was purified by flash silica chromatography eluting with ethyl acetate. Pure fractions were evaporated to dryness to afford benzyl 4-hydroxy-4-(pyridin-3-yl)piperidine-1-carboxylate (12.8 g, 48%) as an oil.

1H NMR (400.1 MHz, CDCl3) δ 1.71-1.82 (2H, m), 1.84-2.02 (2H, m), 3.25-3.43 (2H, m), 3.48-3.66 (1H, m), 4.03-4.19 (2H, m), 5.15 (2H, s), 7.27-7.39 (6H, m), 7.79-7.82 (1H, m), 8.37-8.40 (1H, m), 8.69 (1H, d); m/z=313 [M+H]+.

Preparation of 4-(pyridin-3-yl)piperidin-4-ol

Benzyl 4-hydroxy-4-(pyridin-3-yl)piperidine-1-carboxylate (32.7 g, 104.69 mmol) was dissolved in ethanol (350 mL)

and hydrogenated over 10% palladium on carbon (3.2 g) at 2 bar pressure at 30° C. After hydrogen uptake was complete, the mixture was filtered through a pad of diatomaceous earth to remove the catalyst and the pad was washed with ethanol. The filtrate was concentrated to dryness under vacuum to give an oil which crystallised on standing overnight. The solid was triturated with MTBE (100 mL), collected by filtration, washed with MTBE (2×50 ml) and dried in a vacuum oven at 40° C. to afford 4-(pyridin-3-yl)piperidin-4-ol (14.9 g, 80%) as a solid.

1H NMR (400.1 MHz, DMSO-d6) δ 1.53-1.61 (2H, m), 1.86 (2H, m), 2.74-2.83 (2H, m), 2.96 (2H, m), 7.34 (1H, m), 7.83 (1H, m), 8.43 (1H, m), 8.69 (1H, d).

EXAMPLE 511.2

Preparation of crystalline 4-pyridin-3-yl-1-[3-(trifluoromethyl)[1,2,4]triazolo[4,3-b]pyridazin-6-yl]piperidin-4-ol Anhydrous Form A A stirred solution of 6-chloro-3-(trifluoromethyl)-[1,2,4]triazolo[4,3-b]pyridazine (16.69 g, 75 mmol), 4-(pyridin-3-yl)piperidin-4-ol (14.70 g, 82.50 mmol) and N-ethyldiisopropylamine (16.98 mL, 97.50 mmol) in DMF (75 mL) was heated at 80° C. for 1 hr. The solution was cooled to ambient temperature and slowly diluted with water, with seeding, giving a crystalline precipitate. The precipitate was collected by filtration, washed with water, acetonitrile and ether and dried under vacuum at 50° C. to afford 4-(pyridin-3-yl)-1-(3-(trifluoromethyl)-[1,2,4]triazolo[4,3-b]pyridazin-6-yl)piperidin-4-ol anhydrous Form A (25.2 g, 92%) as a cream crystalline solid, which was used without further purification. Approximately 30 mg of material was then slurried in approximately 1 ml of ethyl acetate and stirred using a magnetic stirrer bar for 3 days at ambient temperature. The resultant material was air dried and analysed.

4-Pyridin-3-yl-1-[3-(trifluoromethyl)[1,2,4]triazolo[4,3-b]pyridazin-6-yl]piperidin-4-ol Anhydrous Form A is characterised by providing an X-ray powder diffraction pattern substantially as shown in FIG. 1. The intensity of the peaks at the corresponding 2θ values are shown in Table A below.

4-Pyridin-3-yl-1-[3-(trifluoromethyl)[1,2,4]triazolo[4,3-b]pyridazin-6-yl]piperidin-4-ol Anhydrous Form A may thus also be characterised by providing at least one of the following 2θ values when measured using CuKa radiation: 9.18°, 15.51°, 16.01°, 18.94° and 24.59°.

TABLE A

| Angle 2-Theta ° (2θ) | Intensity % |
|---|---|
| 8.296 | 42 |
| 9.176 | 87.2 |
| 9.961 | 16.7 |
| 10.411 | 11.7 |
| 14.352 | 49 |
| 15.022 | 25.7 |
| 15.513 | 68.9 |
| 16.007 | 100 |
| 17.026 | 33.5 |
| 18.458 | 9.3 |
| 18.939 | 69.6 |
| 19.181 | 28 |
| 19.823 | 27.6 |
| 20.353 | 36.2 |
| 20.609 | 17.9 |
| 21.804 | 51.4 |
| 22.653 | 17.5 |
| 23.377 | 38.5 |

TABLE A-continued

| Angle 2-Theta ° (2θ) | Intensity % |
|---|---|
| 24.151 | 10.5 |
| 24.585 | 71.2 |
| 25.43 | 55.6 |
| 26.12 | 18.3 |
| 26.349 | 40.1 |
| 26.592 | 14.4 |
| 27.431 | 15.6 |
| 29.375 | 25.7 |
| 31.83 | 22.6 |
| 37.332 | 12.1 |

DSC analysis showed that 4-pyridin-3-yl-1-[3-(trifluoromethyl)[1,2,4]triazolo[4,3-b]pyridazin-6-yl]piperidin-4-ol Anhydrous Form A has an onset of melting at about 230° C. and a peak of melting at about 232° C.

EXAMPLE 512

Preparation of N-(2-methoxyethyl)-N-methyl-4-[1-[3-(trifluoromethyl)[1,2,4]triazolo[4,3-b]pyridazin-6-yl]piperidin-4-yl]benzamide

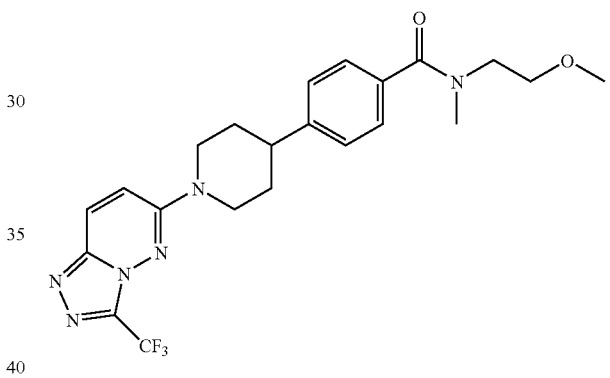

A mixture of 4-[1-[3-(trifluoromethyl)[1,2,4]triazolo[4,3-b]pyridazin-6-yl]piperidin-4-yl]benzoic acid (79 mg, 0.20 mmol), N-(2-methoxyethyl)methylamine (21 mg, 0.24 mmol), DIPEA (0.105 mL, 0.61 mmol) and HATU (92 mg, 0.24 mmol) in DMA (3 mL) was stirred at ambient temperature for 16 hours. The reaction mixture was purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to give N-(2-methoxyethyl)-N-methyl-4-[1-[3-(trifluoromethyl)[1,2,4]triazolo[4,3-b]pyridazin-6-yl]piperidin-4-yl]benzamide (77 mg, 82%) as a solid.

1H NMR (399.9 MHz, CDCl3) δ 1.81 (2H, m), 2.02 (2H, m), 2.86 (1H, m), 3.04-3.17 (5H, m), 3.29-3.48 (5H, m), 3.69 (2H, m), 4.39 (2H, m), 7.13 (1H, d), 7.24 (2H, d), 7.38 (2H, d), 7.94 (1H, d); m/z=463 [M+H]+.

The 4-[1-[3-(trifluoromethyl)[1,2,4]triazolo[4,3-b]pyridazin-6-yl]piperidin-4-yl]benzoic acid used as starting material was prepared as follows:—

Preparation of methyl 4-[1-[3-(trifluoromethyl)[1,2,4]triazolo[4,3-b]pyridazin-6-yl]piperidin-4-yl]benzoate 6-Chloro-3-(trifluoromethyl)-[1,2,4]triazolo[4,3-b]pyridazine (2 g, 8.99 mmol), methyl 4-(piperidin-4-yl)benzoate (CAS 281235-04-9, 2.168 g, 9.89 mmol) and DIPEA (3.91 mL, 22.47 mmol) were dissolved in DMA (10 mL) and sealed into a microwave tube. The mixture was heated to 110° C. for 5 minutes in the microwave reactor and cooled to room temperature. The reaction mixture was added dropwise to stirred water (30 mL), stirred for 10 minutes then the precipitate was collected by filtration, washed with ether (2×2 mL) and dried to give methyl 4-[1-[3-(trifluoromethyl)[1,2,4]triazolo[4,3-b]pyridazin-6-yl]piperidin-4-yl]benzoate (3.32 g, 91%) as a solid.

1H NMR (399.9 MHz, DMSO-d6) δ 1.73 (2H, m), 1.92 (2H, m), 2.98 (1H, m), 3.13 (2H, m), 3.84 (3H, s), 4.44 (2H, m), 7.44 (2H, d), 7.68 (1H, d), 7.91 (2H, d), 8.27 (1H, d); m/z=406 [M+H]+.

Preparation of 4-[1-[3-(trifluoromethyl)[1,2,4]triazolo[4,3-b]pyridazin-6-yl]piperidin-4-yl]benzoic acid Lithium hydroxide monohydrate (0.154 g, 3.66 mmol) was added to methyl 4-[1-[3-(trifluoromethyl)[1,2,4]triazolo[4,3-b]pyridazin-6-yl]piperidin-4-yl]benzoate (1.35 g, 3.33 mmol) in a mixture of methanol (30 mL) and water (15 mL). The resulting suspension was stirred at 50° C. for 16 hours. The mixture was cooled to room temperature, the methanol evaporated and the aqueous residue treated with 1M citric acid until precipitation ceased. The precipitate was collected by filtration, washed with water and dried to give 4-[1-[3-(trifluoromethyl)[1,2,4]triazolo[4,3-b]pyridazin-6-yl]piperidin-4-yl]benzoic acid (1.26 g, 97%) as a solid.

1H NMR (399.9 MHz, DMSO-d6) δ 1.69-1.79 (2H, m), 1.93 (2H, m), 2.94-3.02 (1H, m), 3.11-3.17 (2H, m), 4.44 (2H, m), 7.41 (2H, d), 7.67 (1H, d), 7.89 (2H, d), 8.25 (1H, d), 12.79 (1H, s); m/z=392 [M+H]+.

EXAMPLE 512.1

Alternative method for the preparation of N-(2-methoxyethyl)-N-methyl-4-[1-[3-(trifluoromethyl)[1,2,4]triazolo[4,3-b]pyridazin-6-yl]piperidin-4-yl]benzamide 4-Methylmorpholine (17.56 mL, 159.70 mmol) was added dropwise to 4-[1-[3-(trifluoromethyl)[1,2,4]triazolo[4,3-b]pyridazin-6-yl]piperidin-4-yl]benzoic acid (25 g, 63.88 mmol) and 2-chloro-4,6-dimethoxy-1,3,5-triazine (13.46 g, 76.66 mmol) suspended in DMF (250 mL) at 0° C. The resulting suspension was stirred for 10 minutes, then 2-methoxy-N-methylethanamine (5.69 g, 63.88 mmol) was added and the mixture warmed to ambient temperature and stirred for 16 hours. The reaction mixture was concentrated and diluted with DCM (1000 mL) and washed with water (500 mL). The aqueous phase was re-extracted with DCM (500 mL), then the combined organics were washed with saturated NaHCO3 (500 mL) and saturated brine (250 mL), and dried over MgSO4, filtered and evaporated to afford crude product. The crude product was triturated with ether, and the resulting solid was collected by filtration and dried under vacuum, then purified by flash silica chromatography, elution gradient 0 to 5% MeOH in DCM. Pure fractions were evaporated to dryness to afford N-(2-methoxyethyl)-N-methyl-4-[1-[3-(trifluoromethyl)[1,2,4]triazolo[4,3-b]pyridazin-6-yl]piperidin-4-yl]benzamide (23.45 g, 79%) as a solid.

1H NMR (399.9 MHz, CDCl3) δ 1.81 (2H, m), 2.02 (2H, m), 2.86 (1H, m), 3.04-3.17 (5H, m), 3.30-3.49 (5H, m), 3.69 (2H, m), 4.39 (2H, m), 7.13 (1H, d), 7.24 (2H, d), 7.39 (2H, d), 7.93 (1H, d); m/z=463 [M+H]+.

The 4-[1-[3-(trifluoromethyl)[1,2,4]triazolo[4,3-b]pyridazin-6-yl]piperidin-4-yl]benzoic acid used as starting material was prepared as follows:—

Preparation of sodium 4-(pyridin-4-yl)benzoate

A solution of sodium carbonate (830 g, 7834.20 mmol) in water (6800 mL) was added dropwise over 30 minutes to a stirred suspension of 4-boronobenzoic acid (520 g, 3133.68 mmol), 4-bromopyridine hydrochloride (622 g, 3196.35 mmol) and palladium(II) acetate (1.407 g, 6.27 mmol) in ethanol (2600 mL) and water (3600 mL) at 20° C. The reaction was stirred for 10 minutes then 3,3',3"-phosphinidynetris(benzenesulfonic acid) trisodium salt (30% w/w solution in water) (36.8 g, 18.80 mmol) was added and the mixture was heated to 85° C. for 4 hours. The reaction mixture was cooled to 55° C. and stirred for 2 hours, then the resulting suspension was stirred at 20° C. for 16 hours. The solid was collected by filtration, washed with acetone (3×1250 mL), and dried in a vacuum oven at 60° C. to afford sodium 4-(pyridin-4-yl)benzoate (690 g, 99%) as a solid.

1H NMR (400.1 MHz, DMSO-d6) δ 7.72 (4H, m), 7.97 (2H, d), 8.62 (2H, d); m/z=200 [M+H]+.

Preparation of methyl 4-(pyridin-4-yl)benzoate

Thionyl chloride (683 mL, 9358.59 mmol) was added dropwise over 20 minutes to a suspension of sodium 4-(pyridin-4-yl)benzoate (690 g, 3119.53 mmol) in methanol (15 L) at −10° C., keeping the temperature below 15° C. The mixture was stirred for 10 minutes then heated to 65° C. for 15 hours. The reaction mixture was cooled to 20° C. and the solvent was evaporated. The solid residue was partioned between ethyl acetate (14 L) and aqueous saturated sodium bicarbonate solution (14 L). The organic layer was separated and the aqueous layer extracted with ethyl acetate (7 L). The combined organics were washed with water (14 L), saturated brine (7 L) dried over magnesium sulfate, filtered and evaporated to dryness to afford methyl 4-(pyridin-4-yl)benzoate (570 g, 86%) as a solid.

1H NMR (400.1 MHz, DMSO-d6) δ 3.89 (3H, s), 7.78 (2H, d), 7.97 (2H, d), 8.09 (2H, d), 8.69 (2H, d); m/z=214 [M+H]+.

Preparation of methyl 4-(piperidin-4-yl)benzoate

Methyl 4-(pyridin-4-yl)benzoate (285 g, 1336.57 mmol) and palladium (5% on carbon, 50% wet, JM Type 87L) (57 g, 13.39 mmol) in methanol (2850 mL) were stirred under an atmosphere of hydrogen at 5 bar and 70° C. for 15 hours. The catalyst was removed by filtration and washed with methanol (2850 mL). The solvent was evaporated to dryness to afford methyl 4-(piperidin-4-yl)benzoate (291 g, 99%) as a solid.

1H NMR (400.1 MHz, DMSO-d6) δ 1.51 (2H, m), 1.68 (2H, m), 2.54-2.69 (3H, m), 3.02 (2H, m), 3.84 (3H, s), 7.37 (2H, d), 7.89 (2H, d); m/z=220 [M+H]+.

Preparation of methyl 4-[1-[3-(trifluoromethyl)[1,2,4]triazolo[4,3-b]pyridazin-6-yl]piperidin-4-yl]benzoate DIPEA (88 mL, 505.27 mmol) was added to 6-chloro-3-(trifluoromethyl)-[1,2,4]triazolo[4,3-b]pyridazine (45.0 g, 202.11 mmol) and methyl 4-(piperidin-4-yl)benzoate (48.75 g, 222.32 mmol) in DMA (250 mL). The resulting suspension was stirred at 100° C. for 1 hour then cooled to room temperature. The reaction mixture was added dropwise to water (1500 mL) with stirring. Stirring was continued for 10 minutes then the precipitate was collected by filtration, washed with water (300 mL) and ether (250 mL×2) and dried to afford methyl 4-[1-[3-(trifluoromethyl)[1,2,4]triazolo[4,3-b]pyridazin-6-yl]piperidin-4-yl]benzoate (76 g, 93%) as a solid.

1H NMR (400.1 MHz, DMSO-d6) δ 1.63-1.83 (2H, m), 1.85-2.01 (2H, m), 2.94-3.03 (1H, m), 3.08-3.18 (2H, m), 3.84 (3H, s), 4.36-4.52 (2H, m), 7.44 (2H, d), 7.68 (1H, d), 7.91 (2H, d), 8.27 (1H, d); m/z=406 [M+H]+.

Preparation of 4-[1-[3-(trifluoromethyl)[1,2,4]triazolo[4,3-b]pyridazin-6-yl]piperidin-4-yl]benzoic acid Lithium hydroxide monohydrate (9.06 g, 215.94 mmol) was added to methyl 4-[1-[3-(trifluoromethyl)[1,2,4]triazolo[4,3-b]pyridazin-6-yl]piperidin-4-yl]benzoate (79.58 g, 196.31 mmol) in a mixture of MeOH (800 mL) and water (400 mL). The resulting suspension was stirred at 65° C. for 16 hours. The mixture was cooled to room temperature, the methanol evaporated and the aqueous residues diluted with water (600 mL), filtered then treated with 1M citric acid until precipitation ceased. The precipitate was collected by filtration, washed with water and dried to afford 4-[1-[3-(trifluoromethyl)[1,2,4]triazolo[4,3-b]pyridazin-6-yl]piperidin-4-yl]benzoic acid (77 g, 101%) as a solid.

1H NMR (400.1 MHz, DMSO-d6) δ 1.67-1.79 (2H, m), 1.88-1.96 (2H, m), 2.91-3.02 (1H, m), 3.07-3.18 (2H, m), 4.39-4.48 (2H, m), 7.41 (2H, d), 7.68 (1H, d), 7.88 (2H, d), 8.26 (1H, d); m/z=392 [M+H]+.

EXAMPLE 512.2

Preparation of crystalline N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A
4-methylmorpholine (17.56 mL, 159.70 mmol) was added dropwise to 4-(1-(3-(trifluoromethyl)-[1,2,4]triazolo[4,3-b]pyridazin-6-yl)piperidin-4-yl)benzoic acid (25 g, 63.88 mmol) and 2-chloro-4,6-dimethoxy-1,3,5-triazine (13.46 g, 76.66 mmol) suspended in DMF (250 mL) cooled to 0° C. The resulting suspension was stirred for 10 minutes then 2-methoxy-N-methylethanamine (5.69 g, 63.88 mmol) was added and the mixture warmed to ambient temperature and stirred for 16 hours. The reaction mixture was concentrated and diluted with DCM (1 L) and washed with water (500 mL). The aqueous was reextracted with DCM (500 mL) then the combined organics were washed with saturated NaHCO3 (500 mL) followed by saturated brine (25 mL) then dried over MgSO4, filtered and evaporated to afford crude product. This was then triturated in ether, filtered off the solid and dried under vacuum. LCMS shows there to be 2.5% impurity. The crude product was purified by flash silica chromatography, elution gradient 0 to 5% MeOH in DCM. Pure fractions were evaporated to dryness to afford N-(2-methoxyethyl)-Nm-ethyl-4-(1-(3-(trifluoromethyl)-[1,2,4]triazolo[4,3-b]pyridazin-6-yl)piperidin-4-yl)benzamide anhydrous Form A (23.45 g, 79%) as an off-white solid.

N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A is characterised by providing an X-ray powder diffraction pattern substantially as shown in FIG. 2. The intensity of the peaks at the corresponding 2θ values are shown in Table B below.

N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A may thus also be characterised by providing at least one of the following 2θ values when measured using CuKa radiation: 12.34°, 15.78°, 20.42°, 23.75° and 24.73°.

TABLE B

| Angle 2-Theta ° (2θ) | Intensity % |
|---|---|
| 6.283 | 8.3 |
| 7.922 | 1.3 |
| 9.65 | 1.5 |
| 12.341 | 12.3 |
| 12.689 | 7.1 |
| 14.92 | 4.6 |
| 15.78 | 100 |
| 16.893 | 1.5 |
| 18.783 | 4 |
| 19.283 | 7.9 |
| 20.424 | 17.7 |
| 20.986 | 3.3 |
| 21.574 | 2.7 |
| 22.494 | 3.9 |
| 23.311 | 2.6 |
| 23.746 | 18.8 |
| 24.339 | 3.7 |
| 24.728 | 9.5 |
| 25.375 | 3.4 |
| 26.93 | 4.9 |
| 28.138 | 2.7 |
| 29.08 | 1.6 |
| 31.16 | 1.3 |
| 31.855 | 1.6 |
| 32.496 | 1.2 |
| 33.141 | 3.3 |
| 34.793 | 1.3 |
| 36.343 | 1.5 |
| 36.782 | 1.4 |
| 38.01 | 1.3 |
| 38.637 | 1.6 |

DSC analysis showed that N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A has an onset of melting at about 167° C. and a peak of melting at about 169° C.

EXAMPLE 513

Preparation of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine

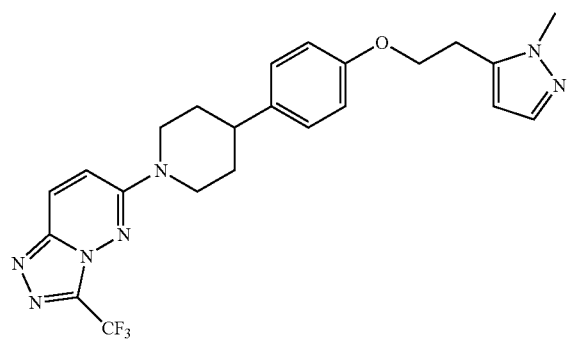

DIAD (78 μl, 0.386 mmol) was added dropwise to 4-[1-[3-(trifluoromethyl)[1,2,4]triazolo[4,3-b]pyridazin-6-yl]piperidin-4-yl]phenol (117 mg, 0.322 mmol), triphenylphosphine (101 mg, 0.386 mmol) and 2-(1-methyl-1H-pyrazol-5-yl)ethanol (obtained as described in PCT Int. Appl. WO 2007017222, Intermediate 1) (49 mg, 0.386 mmol) in THF (2 mL). The resulting mixture was stirred at ambient temperature for 16 hours and then added to a SCX column. The crude product was eluted using 2M ammonia in methanol and the product-containing fractions were evaporated. The product was purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to give 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine (79 mg, 52%) as a solid.

1H NMR (399.9 MHz, DMSO-d6) δ 1.67 (2H, m), 1.88 (2H, m), 2.77-2.84 (3H, m), 3.10 (2H, m), 3.78 (3H, s), 4.05 (2H, t), 4.41 (2H, m), 6.88 (2H, d), 7.18 (2H, d), 7.33 (1H, s), 7.55 (1H, s), 7.66 (1H, d), 8.24 (1H, d); m/z=472 [M+H]+.

The 4-[1-[3-(trifluoromethyl)[1,2,4]triazolo[4,3-b]pyridazin-6-yl]piperidin-4-yl]phenol used as starting material was prepared as follows:—

DIPEA (5.84 mL, 33.54 mmol) was added to 6-chloro-3-(trifluoromethyl)-[1,2,4]triazolo[4,3-b]pyridazine (2.99 g, 13.41 mmol) and 4-(piperidin-4-yl)phenol hydrochloride (CAS 263139-27-1, 3.01 g, 14.08 mmol) in DMF (30 mL). The resulting solution was stirred at 80° C. for 1 hour. The mixture was cooled to room temperature, evaporated to dryness and re-dissolved in DCM (200 mL). The solution was washed with water (200 mL) and saturated brine (200 mL), dried over MgSO4 and evaporated to afford crude product. The crude product was purified by flash silica chromatography, elution gradient 50 to 70% ethyl acetate in isohexane. Pure fractions were evaporated to dryness to afford 4-[1-[3-(trifluoromethyl)[1,2,4]triazolo[4,3-b]pyridazin-6-yl]piperidin-4-yl]phenol (4.47 g, 92%) as a solid.

1H NMR (399.9 MHz, DMSO-d6) δ 1.63 (2H, m), 1.86 (2H, m), 2.74 (1H, m), 3.08 (2H, m), 4.40 (2H, m), 6.69 (2H, d), 7.05 (2H, d), 7.66 (1H, d), 8.25 (1H, d), 9.19 (1H, s); m/z=364 [M+H]+.

EXAMPLE 513.1

Large scale preparation of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine DIAD (19.73 mL, 100.18 mmol) was added dropwise to 4-[1-[3-(trifluoromethyl)[1,2,4]triazolo[4,3-b]pyridazin-6-yl]piperidin-4-yl]phenol (28 g, 77.06 mmol), 2-(1-methyl-1H-pyrazol-5-yl)ethanol (14.53 g, 100.18 mmol) and triphenylphosphine (26.3 g, 100.18 mmol) in THF (250 mL). The resulting solution was stirred at ambient temperature for 3 days. The reaction mixture was evaporated to dryness and re-dissolved in DCM (1 L), and the solution was washed sequentially with 2M NaOH (300 mL×2) and saturated brine (250 mL). The organic layer was dried over MgSO4, filtered and evaporated to afford crude product. The crude product was purified by flash silica chromatography, eluting with 75% EtOAc in isohexane followed by a gradient of 0 to 3% MeOH in DCM. Fractions containing the desired product were evaporated to dryness then re-dissolved in DCM (500 mL) and the solution washed with 2M NaOH (300 mL×2) followed by brine (250 mL), then dried over MgSO4, filtered and evaporated. The residue was further purified by flash silica chromatography, elution gradient 80 to 100% EtOAc in isohexane. Pure fractions were evaporated to dryness to afford 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine (18.21 g, 50.1%) as a solid.

1H NMR (399.9 MHz, DMSO-d6) δ 1.67 (2H, m), 1.88 (2H, m), 2.81 (1H, m), 3.07-3.14 (4H, m), 3.79 (3H, s), 4.18 (2H, t), 4.41 (2H, m), 6.14 (1H, d), 6.89 (2H, d), 7.19 (2H, d), 7.30 (1H, d), 7.66 (1H, d), 8.24 (1H, d); m/z=472 [M+H]+.

The 2-(1-methyl-1H-pyrazol-5-yl)ethanol used as starting material was prepared as follows:—n-Butyl lithium (1.6M in hexanes) (1226 mL, 1961.78 mmol) was added dropwise to 1-methyl-1H-pyrazole (153.4 g, 1868.37 mmol) in THF (3000 mL) cooled to −78° C. over a period of 1 hour under nitrogen. The resulting solution was stirred at −60° C. for 30 minutes, then warmed to −10° C. and stirred for a further 40 minutes. A solution of oxirane (210 mL, 4203.82 mmol) in THF (600 mL) was added slowly at −10° C. followed by further THF (1000 mL) and the resulting slurry was stirred at −10° C. for 30 minutes, then at 0° C. for 30 minutes. The mixture was then allowed to gradually warm to room temp under nitrogen and stirred for 16 hours. The reaction mixture was quenched with saturated NH4Cl solution (2000 ml), the layers separated and the aqueous phase extracted with n-butanol (3×1000 ml). The combined organics were washed with saturated brine (1500 ml), dried over MgSO4, filtered and evaporated to give an oil, which was azeotroped with toluene (1000 ml) to leave an oil with some solid. The oil was dissolved in DCM and the insoluble solid was filtered off and washed with DCM. The filtrate was purified by chromatography using a silica Novasep prep HPLC column, eluting with a gradient of 5-10% methanol in DCM. Pure fractions were evaporated to dryness to afford 2-(1-methyl-1H-pyrazol-5-yl)ethanol (195 g, 83%) as an oil.

1H NMR (400.1 MHz, DMSO-d6) δ 2.77 (2H, t), 3.63 (2H, m), 3.74 (3H, s), 4.74 (1H, t), 6.04 (1H, m), 7.26 (1H, d).

The 4-[1-[3-(trifluoromethyl)[1,2,4]triazolo[4,3-b]pyridazin-6-yl]piperidin-4-yl]phenol used as starting material was prepared as follows:—

Preparation of benzyl 4-(trifluoromethylsulfonyloxy)-5,6-dihydropyridine-1(2H)-carboxylate A solution of benzyl 4-oxopiperidine-1-carboxylate (88.57 g, 379.70 mmol) in THF (300 mL) was added dropwise to lithium bis(trimethylsilyl)amide (1M in THF) (418 mL, 417.67 mmol) at −78° C., over a period of 1 hour under nitrogen. The resulting mixture was stirred at −78° C. for 90 minutes then a solution of 1,1,1-trifluoro-N-phenyl-N-(trifluoromethylsulfonyl)methanesulfonamide (142 g, 398.68 mmol) in THF (600 mL) was added dropwise over a period of 1 hour. The resulting mixture was stirred at −78° C. for 30 minutes, then allowed to warm to room temperature and stirred for 16 hours. The reaction mixture was quenched with 2M NaOH (450 mL). The layers were separated and the organic layer was washed with 2M NaOH (360 mL). The solvent was evaporated, then the residue was re-dissolved in diethyl ether (1500 mL) and the solution washed with water (500 mL). The organic layer was dried over MgSO4, filtered and evaporated to afford benzyl 4-(trifluoromethylsulfonyloxy)-5,6-dihydropyridine-1(2H)-carboxylate (124 g, 81%) as an oil.

1H NMR (399.9 MHz, DMSO-d6) δ 2.43 (2H, m), 3.62 (2H, m), 4.06 (2H, m), 5.10 (2H, s), 6.02 (1H, m), 7.34 (5H, m).

Preparation of benzyl 4-(4-hydroxyphenyl)-5,6-dihydropyridine-1(2H)-carboxylate

Sodium carbonate (96 g, 909.79 mmol) was added to benzyl 4-(trifluoromethylsulfonyloxy)-5,6-dihydropyridine-1

(2H)-carboxylate (123.1 g, 303.26 mmol) and 4-hydroxyphenylboronic acid (46.0 g, 333.59 mmol) in a mixture of dioxane (1000 mL) and water (250 mL). The resulting mixture was bubbled with nitrogen for 10 minutes then 1,1'-bis (diphenylphosphino)ferrocenedichloropalladium(II) (5.49 g, 7.58 mmol) was added and the reaction mixture was heated at 80° C. for 1 hour, then cooled to room temperature. The reaction mixture was diluted with DCM (2 L) and washed with water (2 L). The aqueous washing was re-extracted with DCM (1 L), then the combined organics were washed with saturated brine (500 mL), dried over MgSO4, filtered and evaporated to afford crude product. The crude product was purified by flash silica chromatography, elution gradient 10 to 30% EtOAc in isohexane. Fractions containing the desired product were evaporated to dryness then triturated with isohexane, filtered and dried to afford benzyl 4-(4-hydroxyphenyl)-5,6-dihydropyridine-1(2H)-carboxylate (62.3 g, 66.4%) as a solid.

1H NMR (399.9 MHz, DMSO-d6) δ 2.44 (2H, m), 3.61 (2H, m), 4.05 (2H, m), 5.12 (2H, s), 5.99 (1H, m), 6.73 (2H, d), 7.26 (2H, d), 7.32-7.40 (5H, m), 9.45 (1H, s); m/z=310 [M+H]+.

Preparation of 4-(piperidin-4-yl)phenol

Benzyl 4-(4-hydroxyphenyl)-5,6-dihydropyridine-1(2H)-carboxylate (37.7 g, 121.86 mmol) and 5% palladium on carbon (7.6 g, 3.57 mmol) in methanol (380 mL) were stirred under an atmosphere of hydrogen at 5 bar and 25° C. for 2 hours. The catalyst was removed by filtration, washed with MeOH and the solvents evaporated. The crude material was triturated with diethyl ether, then the desired product collected by filtration and dried under vacuum to afford 4-(piperidin-4-yl)phenol (20.36 g, 94%) as a solid.

1H NMR (399.9 MHz, DMSO-d6) δ 1.46 (2H, m), 1.65 (2H, m), 2.45 (1H, m), 2.58 (2H, m), 3.02 (2H, m), 6.68 (2H, d), 7.00 (2H, d), 9.15 (1H, s); m/z=178 [M+H]+.

Preparation of 4-[1-[3-(trifluoromethyl)[1,2,4]triazolo[4,3-b]pyridazin-6-yl]piperidin-4-yl]phenol DIPEA (48.2 mL, 276.86 mmol) was added to 6-chloro-3-(trifluoromethyl)-[1,2,4]triazolo[4,3-b]pyridazine (24.65 g, 110.74 mmol) and 4-(piperidin-4-yl)phenol (20.61 g, 116.28 mmol) in DMF (200 mL). The resulting solution was stirred at 80° C. for 1 hour. The reaction mixture was cooled to room temperature, then evaporated to dryness and re-dissolved in DCM (1 L) and washed with water (2×1 L). The organic layer was washed with saturated brine (500 mL), then dried over MgSO4, filtered and evaporated to afford crude product. The crude product was triturated with ether to afford 4-[1-[3-(trifluoromethyl)[1,2,4]triazolo[4,3-b]pyridazin-6-yl]piperidin-4-yl]phenol (36.6 g, 91%) as a solid.

1H NMR (399.9 MHz, DMSO-d6) δ 1.64 (2H, m), 1.87 (2H, m), 2.75 (1H, m), 3.09 (2H, m), 4.40 (2H, m), 6.69 (2H, d), 7.05 (2H, d), 7.65 (1H, d), 8.24 (1H, d), 9.15 (1H, s); m/z=364 [M+H]+.

EXAMPLE 513.2

Preparation of crystalline 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine Anhydrous Form A DIAD (3.70 mL, 18.77 mmol) was added to 4-(1-(3-(trifluoromethyl)[1,2,4]triazolo[4,3-b]pyridazin-6-yl)piperidin-4-yl)phenol (6.2 g, 17.06 mmol), 2-(1-methyl-1H-pyrazol-5-yl)ethanol (2.368 g, 18.77 mmol) and triphenylphosphine (4.92 g, 18.77 mmol) in THF (150 mL) under nitrogen. The resulting solution was stirred at ambient temperature for 1 day. The crude product was purified by ion exchange chromatography, using an SCX column. The desired product was eluted from the column using 2M NH3/MeOH and pure fractions were evaporated to dryness to afford crude product. The crude product was purified by flash silica chromatography, elution gradient 0 to 5% MeOH in DCM. Pure fractions were evaporated to dryness to afford crude product. Product was dissolved in DCM (100 mL) and washed with 2M NaOH (100 mL) twice. Organic layer was evaporated to afford 6-(4-(4-(2-(1-methyl-1H-pyrazol-5-yl)ethoxy)phenyl)piperidin-1-yl)-3-(trifluoromethyl)-[1,2,4]triazolo[4,3-b]pyridazine anhydrous Form A (4.95 g, 61.5%) as a white solid.

6-[4-[4-[2-(1-Methyl-1H-pyrazol-5-yl)ethoxy]phenyl]piperidin-1-yl]-3-(trifluoromethyl)[1,2,4]triazolo[4,3-b]pyridazine Anhydrous Form A is characterised by providing an X-ray powder diffraction pattern substantially as shown in FIG. 3. The intensity of the peaks at the corresponding 2θ values are shown in Table C below.

6-[4-[4-[2-(1-Methyl-1H-pyrazol-5-yl)ethoxy]phenyl]piperidin-1-yl]-3-(trifluoromethyl)[1,2,4]triazolo[4,3-b]pyridazine Anhydrous Form A may thus also be characterised by providing at least one of the following 2θ values when measured using CuKa radiation: 4.90°, 13.47°, 15.93°, 16.64° and 22.83°.

TABLE C

| Angle 2-Theta ° (2θ) | Intensity % |
| --- | --- |
| 4.898 | 100 |
| 9.784 | 8 |
| 11.503 | 17.1 |
| 11.942 | 2.7 |
| 12.966 | 4 |
| 13.473 | 24 |
| 14.719 | 13.8 |
| 15.934 | 26.6 |
| 16.642 | 33.4 |
| 17.359 | 6.5 |
| 18.322 | 1.8 |
| 18.669 | 6.5 |
| 19.195 | 22.1 |
| 19.666 | 4.9 |
| 20.257 | 2.8 |
| 20.581 | 11 |
| 20.866 | 2.2 |
| 21.334 | 3.4 |
| 21.641 | 2.4 |
| 22.834 | 24 |
| 23.7 | 3.1 |
| 24 | 13.5 |
| 24.396 | 14.8 |
| 25.985 | 6.4 |
| 26.752 | 6.5 |
| 27.146 | 6.5 |
| 28.104 | 1.8 |
| 28.545 | 2.7 |
| 29.016 | 2 |
| 29.461 | 8.7 |
| 29.737 | 5.8 |
| 30.121 | 4.7 |
| 30.654 | 3 |
| 31.371 | 1.3 |
| 31.853 | 1.8 |
| 33.656 | 3.4 |
| 34.28 | 1.4 |

TABLE C-continued

| Angle 2-Theta ° (2θ) | Intensity % |
|---|---|
| 35.851 | 2.2 |
| 36.424 | 2.3 |
| 37.617 | 1.8 |
| 38.531 | 1.3 |

DSC analysis showed that 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine Anhydrous Form A has an onset of melting at about 159° C. and a peak of melting at about 162° C.

EXAMPLE 514

Preparation of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine

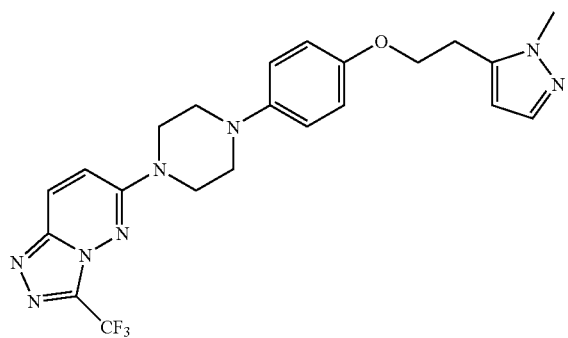

DIAD (0.162 mL, 0.82 mmol) was added to 4-[4-[3-(trifluoromethyl)[1,2,4]triazolo[4,3-b]pyridazin-6-yl]piperazin-1-yl]phenol (250 mg, 0.69 mmol), 2-(1-methyl-1H-pyrazol-5-yl)ethanol (obtained as described in PCT Int. Appl. WO 2007017222, Intermediate 1) (130 mg, 1.03 mmol) and triphenylphosphine (270 mg, 1.03 mmol) in THF (5 mL). The resulting solution was stirred at ambient temperature for 18 hours then added to a SCX column. The crude product was eluted using 2M ammonia in methanol and the product-containing fractions were evaporated. The product was purified by flash silica chromatography, elution gradient 0 to 3% methanol in DCM. Pure fractions were evaporated to dryness to afford 6-[4-[4-[2-(1H-methyl-1H-pyrazol-5-yl)ethoxy]phenyl]piperazin-1-yl]-3-(trifluoromethyl)[1,2,4]triazolo[4,3-b]pyridazine (111 mg, 34%) as a solid.

1H NMR (399.9 MHz, DMSO-d6) δ 2.81 (2H, t), 3.17 (4H, m), 3.75 (4H, m), 3.78 (3H, s), 4.02 (2H, t), 6.87 (2H, d), 6.96 (2H, d), 7.33 (1H, s), 7.56 (1H, s), 7.69 (1H, d), 8.30 (1H, d); m/z=473 [M+H]+.

The 4-[4-[3-(trifluoromethyl)[1,2,4]triazolo[4,3-b]pyridazin-6-yl]piperazin-1-yl]phenol used as starting material was prepared as follows:—

DIPEA (12.15 mL, 69.78 mmol) was added to 6-chloro-3-(trifluoromethyl)-[1,2,4]triazolo[4,3-b]pyridazine (10.35 g, 46.52 mmol) and 1-(4-hydroxyphenyl)piperazine (CAS 56621-48-8, 9.12 g, 51.17 mmol) in DMF (80 mL). The resulting solution was stirred at 80° C. for 1 hour. The reaction mixture was cooled to room temperature, evaporated to dryness and the residue re-dissolved in DCM (250 mL). The solution was washed with water (200 mL), dried over MgSO4 and evaporated to afford crude product, which was triturated with diethyl ether. The resulting solid was collected by filtration and dried under vacuum to give 4-[4-[3-(trifluoromethyl)[1,2,4]triazolo[4,3-b]pyridazin-6-yl]piperazin-1-yl]phenol (14.27 g, 84%) as a solid.

1H NMR (399.9 MHz, DMSO-d6) δ 3.12 (4H, m), 3.75 (4H, m), 6.69 (2H, d), 6.87 (2H, d), 7.67 (1H, d), 8.28 (1H, d), 8.87 (1H, s); m/z=365 [M+H]+.

EXAMPLE 514.1

Large scale preparation of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine DIAD (20.73 mL, 105.27 mmol) was added dropwise to 4-[4-[3-(trifluoromethyl)[1,2,4]triazolo[4,3-b]pyridazin-6-yl]piperazin-1-yl]phenol (32.0 g, 87.72 mmol), 2-(1-methyl-1H-pyrazol-5-yl)ethanol (prepared as described in Example 513, preparation of starting materials) (16.6 g, 131.58 mmol) and triphenylphosphine (34.5 g, 131.58 mmol) in THF (320 mL) at 0° C. under nitrogen. The resulting solution was stirred at ambient temperature for 3 days. The reaction mixture was evaporated to dryness and re-dissolved in DCM (700 mL), and the solution was washed sequentially with 2M NaOH (200 mL×2) and saturated brine (200 mL). The organic layer was dried over MgSO4, filtered and evaporated to afford crude product. The crude product was purified by flash silica chromatography, eluting with a gradient of 80 to 100% EtOAc in isohexane followed by EtOAc, then a gradient of 0 to 3% MeOH in DCM. Pure fractions were evaporated to dryness to afford 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine (28.7 g, 69.3%) as a solid.

1H NMR (399.9 MHz, DMSO-d6) δ 3.07 (2H, t), 3.18 (4H, m), 3.76 (4H, m), 3.79 (3H, s), 4.15 (2H, t), 6.14 (1H, d), 6.88 (2H, d), 6.97 (2H, d), 7.30 (1H, d), 7.67 (1H, d), 8.28 (1H, d); m/z=473 [M+H]+.

The 4-[4-[3-(trifluoromethyl)[1,2,4]triazolo[4,3-b]pyridazin-6-yl]piperazin-1-yl]phenol used as starting material was prepared as follows:—

DIPEA (52.4 mL, 300.84 mmol) was added to 6-chloro-3-(trifluoromethyl)-[1,2,4]triazolo[4,3-b]pyridazine (44.6 g, 200.56 mmol) and 1-(4-hydroxyphenyl)piperazine (39.32 g, 220.61 mmol) in DMF (450 mL). The resulting solution was stirred at 80° C. for 2 hours. The reaction mixture was cooled to room temperature, then evaporated to dryness and partitioned between DCM (2 L) and water (1 L) containing methanol (250 mL) to aid solubility. The insoluble material was collected by filtration, washed with methanol and dried to give the desired product. The organic filtrate was separated from the aqueous, then washed with saturated brine (500 mL), dried over MgSO4 and evaporated to a brown gum. This was triturated with ether, the resulting solid was collected by filtration, washed with DCM followed by methanol, combined with the previous precipitate and dried to afford 4-[4-[3-(trifluoromethyl)[1,2,4]triazolo[4,3-b]pyridazin-6-yl]piperazin-1-yl]phenol (63.8 g, 87%) as a solid.

1H NMR (399.9 MHz, DMSO-d6) δ 3.12 (4H, m), 3.75 (4H, m), 6.69 (2H, d), 6.87 (2H, d), 7.67 (1H, d), 8.28 (1H, d), 8.87 (1H, s); m/z=365 [M+H]+.

EXAMPLE 514.2

Preparation of crystalline 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine Anhydrous Form A DIAD (7.78 mL, 39.53 mmol) was added dropwise to 4-(4-(3-(trifluoromethyl)-[1,2,4]triazolo[4,3-b]pyridazin-6-yl)piperazin-1-yl)phenol (12 g, 32.94 mmol), 2-(1-methyl-1H-pyrazol-5-yl)ethanol (6.23 g, 49.41 mmol) and triphenylphosphine (12.96 g, 49.41 mmol) in THF (250 mL). The resulting solution was stirred at ambient temperature for 18 hours then split and added to a series of SCX columns (6). The crude product was eluted from the columns using 2M $NH_3$/MeOH and the solvents evaporated. The crude product was diluted with DCM (200 mL) and washed with 2M NaOH (200 mL×2). The organic layer was dried over $MgSO_4$, filtered and evaporated then purified by flash silica chromatography, elution gradient 0 to 3% MeOH in DCM. Pure fractions were evaporated to dryness giving a yellow solid, which was triturated with ether then dried to afford 6-(4-(4-(2-(1-methyl-1H-pyrazol-5-yl)ethoxy)phenyl)piperazin-1-yl)-3-(trifluoromethyl)-[1,2,4]triazolo[4,3-b]pyridazine anhydrous Form A (9.18 g, 59.0%) as a cream solid.

6-[4-[4-[2-(1-Methyl-1H-pyrazol-5-yl)ethoxy]phenyl]piperazin-1-yl]-3-(trifluoromethyl)[1,2,4]triazolo[4,3-b]pyridazine Anhydrous Form A is characterised by providing an X-ray powder diffraction pattern substantially as shown in FIG. 4. The intensity of the peaks at the corresponding 2θ values are shown in Table D below.

6-[4-[4-[2-(1-Methyl-1H-pyrazol-5-yl)ethoxy]phenyl]piperazin-1-yl]-3-(trifluoromethyl)[1,2,4]triazolo[4,3-b]pyridazine Anhydrous Form A may thus also be characterised by providing at least one of the following 2θ values when measured using CuKa radiation: 6.90°, 15.38°, 21.55°, 24.48° and 27.56°.

TABLE D

| Angle 2-Theta ° (2θ) | Intensity % |
|---|---|
| 6.903 | 23.4 |
| 9.6 | 8.6 |
| 10.776 | 11.2 |
| 12.818 | 13.3 |
| 13.162 | 3.3 |
| 13.845 | 10 |
| 14.436 | 3.1 |
| 15.376 | 19.2 |
| 16.436 | 11 |
| 17.457 | 4.1 |
| 18.247 | 3.6 |
| 18.916 | 14.9 |
| 19.266 | 3.4 |
| 20.182 | 3 |
| 21.03 | 4.3 |
| 21.545 | 100 |
| 22.36 | 12.4 |
| 22.625 | 3.3 |
| 23.552 | 5.6 |
| 23.76 | 4.7 |
| 24.479 | 40.9 |
| 25.2 | 2.2 |
| 25.755 | 7.2 |
| 26.465 | 2.7 |
| 27.561 | 17.1 |
| 27.833 | 11.8 |
| 28.206 | 6.2 |
| 29.098 | 2.1 |
| 29.928 | 2.1 |
| 30.587 | 1.6 |
| 31.201 | 4.8 |
| 32.489 | 1.8 |
| 33.326 | 1.8 |
| 34.042 | 2.3 |
| 34.618 | 3 |
| 36.18 | 1.7 |
| 36.538 | 1.7 |
| 37.448 | 1.3 |
| 38.17 | 1.5 |
| 39.324 | 2.4 |

DSC analysis showed that 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine Anhydrous Form A has an onset of melting at about 178° C. and a peak of melting at about 179° C.

EXAMPLE 514.3

Preparation of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate 3 ml of acetone was added to 50 mg of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine and heated to form a solution. 12.3 mg of fumaric acid was dissolved in 3 ml of acetone. The compound solution was added to the counter-ion solution and the resultant mixture shaken with heat. The solution was dried under air and once the volume had dramatically reduced, solid 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate precipitated out.

6-[4-[4-[2-(1-Methyl-1H-pyrazol-5-yl)ethoxy]phenyl]piperazin-1-yl]-3-(trifluoromethyl)[1,2,4]triazolo[4,3-b]pyridazine fumarate is characterised by providing an X-ray powder diffraction pattern substantially as shown in FIG. 5. The intensity of the peaks at the corresponding 2θ values are shown in Table E below.

6-[4-[4-[2-(1-Methyl-1H-pyrazol-5-yl)ethoxy]phenyl]piperazin-1-yl]-3-(trifluoromethyl)[1,2,4]triazolo[4,3-b]pyridazine fumarate may thus also be characterised by providing at least one of the following 2θ values when measured using CuKa radiation: 11.72°, 16.46°, 17.58° and 21.89°.

TABLE E

| Angle 2-Theta ° (2θ) | Intensity % |
|---|---|
| 4.514 | 20.3 |
| 5.897 | 14.2 |
| 11.724 | 56.6 |
| 12.215 | 12.3 |
| 13.225 | 6.9 |
| 16.464 | 73.5 |
| 17.582 | 61.3 |
| 19.738 | 17.4 |
| 20.261 | 15 |
| 21.18 | 21.1 |
| 21.894 | 100 |

TABLE E-continued

| Angle 2-Theta ° (2θ) | Intensity % |
| --- | --- |
| 23.863 | 13 |
| 24.174 | 12.7 |
| 25.826 | 8.6 |
| 26.752 | 8.8 |
| 28.776 | 7.8 |
| 30.541 | 18.9 |
| 31.509 | 8.1 |

DSC analysis showed that 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate has a melting endotherm with onset at about 153° C. and a peak at about 155° C. (this is followed by a recrystallisation event and subsequent melt).

EXAMPLE 515

Preparation of 6-(3-phenylpiperidin-1-yl)-3-(trifluoromethyl)[1,2,4]triazolo[4,3-b]pyridazine

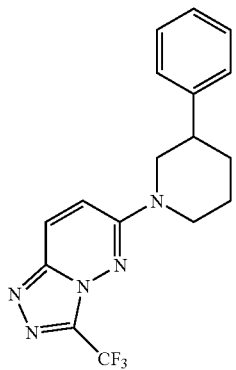

A solution of 6-chloro-3-(trifluoromethyl)-[1,2,4]triazolo[4,3-b]pyridazine (49 mg, 0.22 mmol) in EtOH (1.0 mL) was added to a mixture of 3-phenylpiperidine (53 mg, 0.33 mmol) and DIPEA (57 μL, 0.33 mmol) in EtOH (1.0 mL). The reaction mixture was heated to 70° C. overnight and the crude product was purified by preparative LCMS (Waters XBridge Prep C18 OBD column, 5μ silica, 19 mm diameter, 100 mm length), using decreasingly polar mixtures of water (containing 5% ammonia) and MeCN as eluents. Fractions containing the desired compound were evaporated to dryness to give 6-(3-phenylpiperidin-1-yl)-3-(trifluoromethyl)[1,2,4]triazolo[4,3-b]pyridazine (46 mg, 61%).

1H NMR (700.03 MHz, DMSO-$d_6$) δ 1.62-1.68 (1H, m), 1.82-1.88 (2H, m), 1.96-1.98 (1H, m), 2.83-2.87 (1H, m), 3.10-3.15 (1H, m), 4.30-4.36 (3H, m), 7.25-7.28 (1H, m), 7.33-7.38 (4H, m), 7.68 (1H, d), 8.23 (1H, d); m/z=348 [M+H]+.

EXAMPLE 516

Preparation of 6-[3-(Phenoxymethyl)piperidin-1-yl]-3-(trifluoromethyl)[1,2,4]triazolo[4,3-b]pyridazine

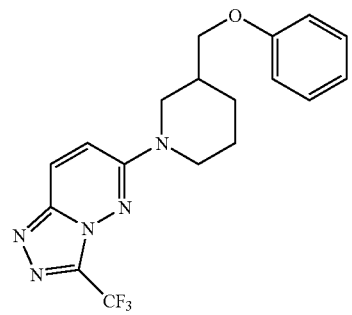

Obtained in 60% yield by an analogous method to Example 515, starting from 6-chloro-3-(trifluoromethyl)-[1,2,4]triazolo[4,3-b]pyridazine and 3-(phenoxymethyl)piperidine.

1H NMR (700.03 MHz, DMSO-$d_6$) δ 1.45-1.50 (1H, m), 1.56-1.61 (1H, m), 1.79-1.82 (1H, m), 1.90-1.92 (1H, m), 2.08-2.11 (1H, m), 3.07 (1H, dd), 3.16-3.20 (1H, m), 3.91 (1H, dd), 3.96 (1H, dd), 4.10-4.13 (1H, m), 4.31 (1H, dd), 6.93-6.97 (3H, m), 7.28-7.31 (2H, m), 7.60 (1H, d), 8.21 (1H, d); m/z=378 [M+H]+.

EXAMPLES 517-518

The following compounds were prepared in 45-46% yield by an analogous method to Example 515, starting from 6-chloro-3-(trifluoromethyl)-[1,2,4]triazolo[4,3-b]pyridazine and the appropriate 4-substituted piperidine:—

| Ex. | R | 1H NMR (700.03 MHz, DMSO-$d_6$) | m/z [M + H]+ |
| --- | --- | --- | --- |
| 517 | ethoxymethyl | δ 1.11 (3H, t), 1.21-1.27 (2H, m), 1.79 (2 H, d), 1.85-1.88 (1H, m), 3.00-3.04 (2H, m), 3.42 (2H, q), 4.27 (2H, d), 7.60 (1H, d), 8.21 (1H, d), (2H obscured by water) | 330 |
| 518 | propoxy | δ 0.89 (3H, t), 1.50-1.56 (4H, m), 1.91-1.95 (2H, m), 3.36-3.40 (1H, m), 3.41 (2 H, t), 3.55-3.59 (1H, m), 3.89-3.92 (2H, m), 7.62 (1H, d), 8.22 (1H, d), (1H obscured by water) | 330 |

EXAMPLES 519-526

The following compounds were prepared in 23-63% yield by an analogous method to Example 515, starting from 6-chloro-3-(trifluoromethyl)-[1,2,4]triazolo[4,3-b]pyridazine and the appropriate 4-aryl piperidine:—

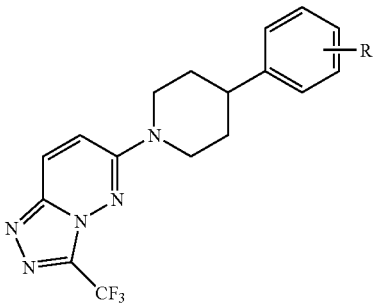

| Ex. | R | 1H NMR (700.3 MHz, DMSO-$d_6$) | m/z [M + H]+ |
|---|---|---|---|
| 519 | H | δ 1.69-1.75 (2H, m), 1.92 (2H, d), 2.85-2.90 (1H, m), 3.10-3.14 (2H, m), 4.42-4.44 (2H, m), 7.20-7.22 (1H, m), 7.27-7.28 (2H, m), 7.30-7.32 (2H, m), 7.66 (1H, d), 8.24 (1H, d) | 348 |
| 520 | 2-OMe | δ 1.67-1.73 (2H, m), 1.85 (2H, d), 3.10-3.14 (2H, m), 3.81 (3H, s), 4.42 (2H, d), 6.98-6.91 (1H, m), 6.99 (1H, d), 7.17-7.21 (2H, m), 7.65 (1H, d), 8.24 (1H, d), (2H obscured by water) | 378 |
| 521 | 4-SO2Me | δ 1.73-1.79 (2H, m), 1.94 (2H, d), 3.01-3.06 (1H, m), 4.45 (2H, d), 7.57 (2H, d), 7.67 (1H, d), 7.86-7.87 (2H, m), 8.26 (1H, d), (5H obscured by water) | 426 |
| 522 | 4-CONHMe | δ 1.70-1.76 (2H, m), 1.92 (2H, d), 2.78 (3H, d), 2.92-2.96 (1H, m), 3.11-3.15 (2H, m), 4.43 (2H, d), 7.36 (2H, d), 7.66 (1H, d), 7.76-7.78 (2H, m), 8.25 (1H, d), 8.32 (1H, q) | 405 |
| 523 | 4-OMe | δ 1.64-1.70 (2H, m), 1.87-1.89 (2H, m), 2.79-2.84 (1H, m), 3.08-3.12 (2H, m), 3.73 (3H, s), 4.41 (2H, d), 6.86-6.88 (2H, m), 7.18-7.20 (2H, m), 7.66 (1H, d), 8.24 (1H, d) | 378 |
| 524 | 4-CF3 | δ 1.72-1.78 (2H, m), 1.94 (2H, d), 2.99-3.03 (1H, m), 3.12-3.16 (2H, m), 4.44 (2H, d), 7.53 (2H, d), 7.66-7.68 (3H, m), 8.25 (1H, s) | 416 |
| 525 | 3-F | δ 1.69-1.75 (2H, m), 1.92 (2H, d), 2.90-2.94 (1H, m), 3.09-3.14 (2H, m), 4.42 (2H, d), 7.01-7.04 (1H, m), 7.13 (2H, t), 7.34-7.37 (1H, m), 7.66 (1H, d), 8.25 (1H, d) | 366 |
| 526 | 3-OMe | δ 1.69-1.75 (2H, m), 1.90-1.92 (2H, m), 2.83-2.87 (1H, m), 3.09-3.13 (2H, m), 3.74 (3H, s), 4.42 (2H, d), 6.77-6.79 (1H, m), 6.83 (1H, d), 6.84 (1H, t), 7.22 (1H, t), 7.66 (1H, d), 8.24 (1H, d) | 378 |

EXAMPLES 527-532

The following compounds were prepared in 56-65% yield by an analogous method to Example 515, starting from 6-chloro-3-(trifluoromethyl)-[1,2,4]triazolo[4,3-b]pyridazine and the appropriate 4-aryloxy piperidine:—

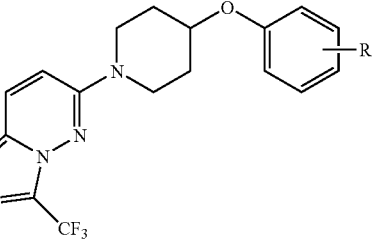

| Ex. | R | 1H NMR (700.03 MHz, DMSO-$d_6$) | m/z [M + H]+ |
|---|---|---|---|
| 527 | 3-OMe | δ 1.70-1.75 (2H, m), 2.05-2.08 (2H, m), 3.52-3.55 (2H, m), 3.74 (3H, s), 3.94-3.97 (2H, m), 4.67-4.70 (1H, m), 6.53 (1H, dd), 6.56 (1H, t), 6.60 (1H, dd), 7.20 (1H, t), 7.64 (1H, d), 8.25 (1H, d) | 394 |
| 528 | 4-OMe | δ 1.68-1.73 (2H, m), 2.01-2.05 (2H, m), 3.50-3.54 (2H, m), 3.72 (3H, s), 3.92-3.96 (2H, m), 4.52-4.56 (1H, m), 6.86-6.88 (2H, m), 6.94-6.97 (2H, m), 7.64 (1H, d), 8.25 (1H, d) | 394 |
| 529 | 2-F | δ 1.74-1.79 (2H, m), 2.07-2.10 (2H, m), 3.52-3.56 (2H, m), 3.94-3.98 (2H, m), 4.68-4.71 (1H, m), 6.98-7.01 (1H, m), 7.15 (1H, t), 7.22-7.25 (1H, m), 7.28-7.31 (1H, m), 7.64 (1H, d), 8.26 (1H, d) | 382 |
| 530 | 2-Cl | δ 1.78-1.83 (2H, m), 2.05-2.09 (2H, m), 3.62-3.66 (2H, m), 3.87-3.91 (2H, m), 4.79-4.82 (1H, m), 6.98-7.01 (1H, m), 7.29-7.30 (1H, m), 7.31-7.33 (1H, m), 7.44-7.46 (1H, m), 7.64 (1H, d), 8.26 (1H, d) | 398 |
| 531 | 2-OMe | δ 1.71-1.76 (2H, m), 2.01-2.04 (2H, m), 3.51-3.55 (2H, m), 3.77 (3H, s), 3.94-3.98 (2H, m), 4.55-4.58 (1H, m), 6.88-6.91 (1H, m), 6.95-6.97 (1H, m), 7.01 (1H, m), 7.08 (1H, m), 7.64 (1H, d), 8.25 (1H, d) | 394 |
| 532 | 3-F | δ 1.71-.175 (2H, m), 2.06-2.10 (2H, m), 3.51-3.54 (2H, m), 3.95-3.99 (2H, m), 4.71-4.74 (1H, m), 6.76-6.79 (1H, m), 6.86 (1H, dd), 6.90-6.93 (1H, m), 7.31-7.34 (1H, m), 7.64 (1H, d), 8.25 (1H, d) | 382 |

EXAMPLES 533-534

The following compounds were prepared in 43-62% yield by an analogous method to Example 515, starting from 6-chloro-3-(trifluoromethyl)-[1,2,4]triazolo[4,3-b]pyridazine and the appropriate 4-substituted piperidine:—

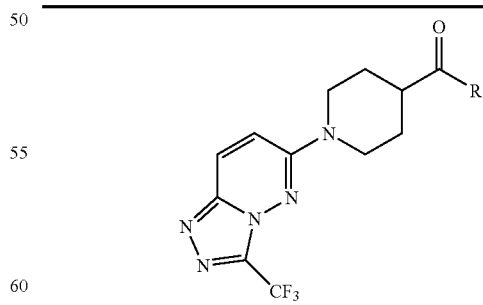

| Ex. | R | 1H NMR (700.03 MHz, DMSO-$d_6$) | m/z [M + H]+ |
|---|---|---|---|
| 533 | phenyl | δ 1.62-1.68 (2H, m), 1.93-1.96 (2H, m), 3.79-3.84 (1H, m), 4.30-4.31 (2H, m), 7.56-7.58 (2H, m), 7.63 (1H, d), 7.66-7.69 | 376 |

-continued

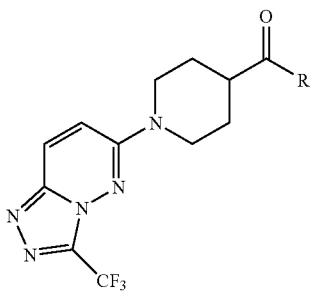

| Ex. | R | 1H NMR (700.03 MHz, DMSO-d$_6$) | m/z [M + H]+ |
|---|---|---|---|
| 534 | 4-fluorophenyl | (1H, m), 8.03-8.04 (2H, m), 8.24 (1H, d), (2H obscured by water) δ 1.61-1.67 (2H, m), 1.92-1.95 (2H, m), 3.78-3.82 (1H, m), 4.30 (2H, d), 7.37-7.40 (2H, m), 7.63 (1H, d), 8.11-8.14 (2H, m), 8.24 (1H, d), (2H obscured by water) | 394 |

EXAMPLES 535-539

The following compounds were prepared in 53-63% yield by an analogous method to Example 515, starting from 6-chloro-3-(trifluoromethyl)-[1,2,4]triazolo[4,3-b]pyridazine and the appropriate 4-substituted piperidine:—

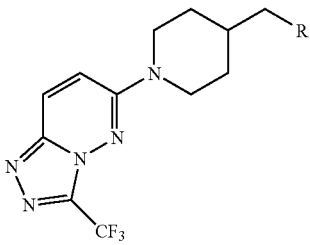

| Ex. | R | 1H NMR (700.03 MHz, DMSO-d$_6$) | m/z [M + H]+ |
|---|---|---|---|
| 535 | phenyl | δ 1.21-1.27 (2H, m), 1.68-1.71 (2H, m), 1.83-1.89 (1H, m), 2.55 (2H, d), 2.95-2.99 (2H, m), 4.25 (2H, d), 7.19-7.21 (3H, m), 7.29-7.31 (2H, m), 7.58 (1H, d), 8.21 (1H, d) | 362 |
| 536 | 4-fluorophenyl | δ 1.20-1.26 (2H, m), 1.67-1.69 (2H, m), 1.81-1.86 (1H, m), 2.55 (2H, d), 2.95-2.99 (2H, m), 4.25 (2H, d), 7.09-7.13 (2H, m), 7.21-7.24 (2H, m), 7.58 (1H, d), 8.21 (1H, d) | 380 |
| 537 | pyridin-2-yl | δ 1.26-1.32 (2H, m), 1.68-1.70 (2H, m), 2.08-2.13 (1H, m), 2.70 (2H, d), 2.98-3.02 (2H, m), 4.24 (2H, d), 7.20-7.22 (1H, m), 7.25 (1H, d), 7.59 (1H, d), 7.69-7.72 (1H, m), 8.21 (1H, d), 8.50-8.51 (1H, m) | 363 |
| 538 | pyridin-4-yl | δ 1.23-1.29 (2H, m), 1.67-1.69 (2H, m), 1.90-1.95 (1H, m), 2.58 (2H, d), 2.97-3.01 (2H, m), 4.25 (2H, d), 7.23-7.24 (2H, m), 7.59 (1H, d), 8.21 (1H, d), 8.47-8.48 (2H, m) | 363 |
| 539 | pyridin-3-yl | δ 1.23-1.29 (2H, m), 1.68-1.70 (2H, m), 1.86-1.91 (1H, m), 2.58 (2H, d), 2.96-3.00 (2H, m), 4.26 (2H, d), 7.33 (1H, dd), 7.59 (1H, d), 7.62-7.64 (1H, m), 8.21 (1H, d), 8.42-8.43 (2H, m) | 363 |

EXAMPLES 540-543

The following compounds were prepared in 40-63% yield by an analogous method to Example 515, starting from 6-chloro-3-(trifluoromethyl)-[1,2,4]triazolo[4,3-b]pyridazine and the appropriate 4-substituted piperidine:—

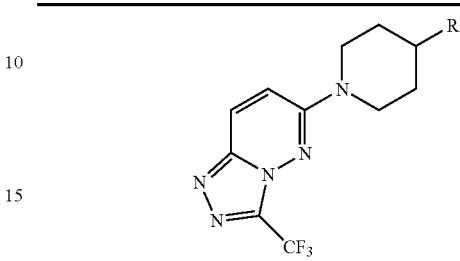

| Ex. | R | 1H NMR (700.03 MHz, DMSO-d$_6$) | m/z [M + H]+ |
|---|---|---|---|
| 540 | pyridin-4-yl | δ 1.69-1.75 (2H, m), 1.94 (2H, d), 2.90-2.94 (1H, m), 3.11-3.15 (2H, m), 4.43 (2H, d), 7.31-7.32 (2H, m), 7.67 (1H, d), 8.25 (1H, d), 8.48-8.49 (2H, m) | 349 |
| 541 | benzotriazol-1-yl | δ 2.27-2.32 (4H, m), 4.48 (2H, s), 5.27-5.32 (1H, m), 7.42-7.44 (1H, m), 7.57-7.59 (1H, m), 7.72 (1H, d), 7.98 (1H, d), 8.06 (1H, d), 8.30 (1H, d), (2H obscured by water) | 389 |
| 542 | indol-1-yl | δ 2.03-2.10 (4H, m), 4.49 (2H, d), 4.75-4.80 (1H, m), 6.45 (1H, d), 7.02-7.05 (1H, m), 7.14-7.17 (1H, m), 7.49 (1H, d), 7.55 (1H, d), 7.61 (1H, d), 7.70 (1H, d), 8.28 (1H, d), (2H obscured by water) | 387 |
| 543 | (3,5-dimethoxy)pyrimidin-2-yl | δ 1.81-1.87 (2H, m), 2.09-2.11 (2H, m), 3.00-3.04 (1H, m), 3.88 (6H, s), 4.31-4.33 (2H, m), 6.08 (1H, s), 7.65 (1H, d), 8.24 (1H, d), (2H obscured by water) | 410 |

EXAMPLES 544-546

The following compounds were prepared in 33-57% yield by an analogous method to Example 515, starting from 6-chloro-3-(trifluoromethyl)-[1,2,4]triazolo[4,3-b]pyridazine and the appropriate 4-substituted piperidine:—

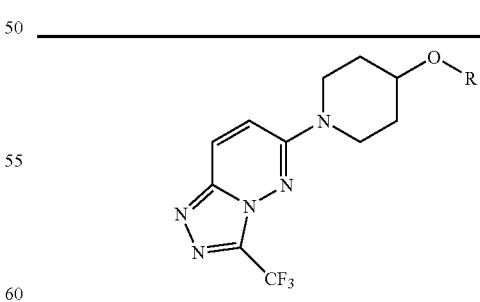

| Ex. | R | 1H NMR (700.03 MHz, DMSO-d$_6$) | m/z [M + H]+ |
|---|---|---|---|
| 544 | pyrazinyl | δ 1.79-1.84 (2H, m), 2.12-2.16 (2H, m), 3.54-3.57 (2H, m), 3.98-4.02 (2H, m), 5.30-5.34 (1H, m), 7.66 (1H, d), 8.22-8.23 (2H, m), 8.26 (1H, d), 8.31 (1H, d) | 366 |

-continued

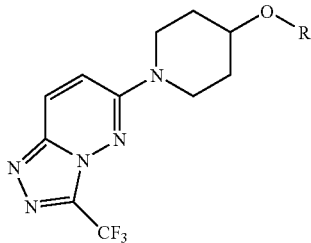

| Ex. | R | 1H NMR (700.03 MHz, DMSO-d$_6$) | m/z [M + H]+ |
|---|---|---|---|
| 545 | pyridin-4-yl | δ 1.73-1.78 (2H, m), 2.10-2.14 (2H, m), 3.51-3.55 (2H, m), 3.97-4.00 (2H, m), 4.84-4.87 (1H, m), 7.03-7.04 (2H, m), 7.65 (1H, d), 8.26 (1H, d), 8.39-8.40 (2H, m) | 365 |
| 546 | pyridin-2-yl | δ 1.74-1.79 (2H, m), 2.10-2.14 (2H, m), 3.51-3.54 (2H, m), 3.99-4.02 (2H, m), 5.30-5.33 (1H, m), 6.81 (1H, d), 6.97-6.99 (1H, m), 7.65 (1H, d), 7.70-7.73 (1H, m), 8.17-8.19 (1H, m), 8.25 (1H, d) | 365 |

EXAMPLES 547-550

The following compounds were prepared in 25-65% yield by an analogous method to Example 515, starting from 6-chloro-3-(trifluoromethyl)-[1,2,4]triazolo[4,3-b]pyridazine and the appropriate 4-substituted piperidin-4-ol:—

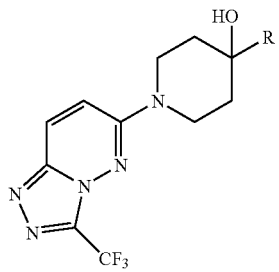

| Ex. | R | 1H NMR (700.03 MHz, DMSO-d$_6$) | m/z [M + H]+ |
|---|---|---|---|
| 547 | phenyl | δ 1.74 (2H, d), 2.01-2.05 (2H, m), 3.43-3.47 (2H, m), 4.20-4.22 (2H, m), 5.20 (1H, s), 7.22-7.24 (1H, m), 7.32-7.34 (2H, m), 7.50-7.52 (2H, m), 7.66 (1H, d), 8.24 (1H, d) | 364 |
| 548 | benzyl | δ 1.50 (2H, d), 1.56-1.60 (2H, m), 2.73 (2H, s), 4.01 (2H, d), 4.51 (1H, s), 7.19-7.21 (1H, m), 7.23-7.24 (2H, m), 7.27 (2H, t), 7.58 (1H, d), 8.19 (1H, d), (2H obscured by water) | 378 |
| 549 | 2-fluorophenyl | δ 1.76 (2H, d), 2.23-2.27 (2H, m), 3.45 (2H, t), 4.19-4.21 (2H, m), 5.47 (1H, s), 7.09-7.12 (1H, m), 7.21-7.23 (1H, m), 7.30-7.33 (1H, m), 7.66-7.70 (2H, m), 8.25 (1H, d) | 382 |
| 550 | pyridin-4-yl | δ 1.71 (2H, d), 2.01-2.06 (2H, m), 3.42-3.46 (2H, m), 4.22-4.24 (2H, m), 7.49-7.50 (2H, m), 7.67 (1H, d), 8.25 (1H, d), 8.51-8.52 (2H, m) | 365 |

EXAMPLES 551-552

The following compounds were prepared in 50-56% yield by an analogous method to Example 515, starting from 6-chloro-3-(trifluoromethyl)-[1,2,4]triazolo[4,3-b]pyridazine and the appropriate 4-aryl tetrahydropyridine:—

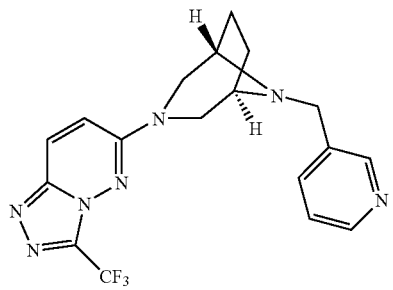

| Ex. | R | 1H NMR (700.03 MHz, DMSO-d$_6$) | m/z [M + H]+ |
|---|---|---|---|
| 551 | H | δ 2.67-2.69 (2H, m), 3.90 (2H, t), 4.27 (2H, q), 6.31-6.32 (1H, m), 7.29 (1H, t), 7.37-7.39 (2H, m), 7.49-7.51 (2H, m), 7.68 (1H, d), 8.29 (1H, d) | 346 |
| 552 | F | δ 2.66-2.67 (2H, m), 3.89 (2H, t), 4.26 (2H, q), 6.29-6.30 (1H, m), 7.19-7.22 (2H, m), 7.52-7.55 (2H, m), 7.68 (1H, d), 8.29 (1H, d) | 364 |

EXAMPLE 553

Preparation of 6-[(1R,5S)-8-(pyridin-3-ylmethyl)-3,8-diazabicyclo[3.2.1]oct-3-yl]-3-(trifluoromethyl)[1,2,4]triazolo[4,3-b]pyridazine A mixture of pyridine-3-carboxaldehyde and 6-[(1R,5S)-3,8-diazabicyclo[3.2.1]oct-3-yl]-3-(trifluoromethyl)[1,2,4]triazolo[4,3-b]pyridazine was allowed to react by General Synthetic Method 5 to give 6-[(1R,5S)-8-(pyridin-3-ylmethyl)-3,8-diazabicyclo[3.2.1]oct-3-yl]-3-(trifluoromethyl)[1,2,4]triazolo[4,3-b]pyridazine in 68% yield.

1H NMR (399.9 MHz, DMSO-d6) δ 1.64-1.68 (2H, m), 2.03-2.06 (2H, m), 3.19 (2H, d), 3.31-3.34 (2H, m, partially obscured by solvent peak), 3.64 (2H, s), 3.82-3.85 (2H, m), 7.36-7.40 (1H, m), 7.51 (1H, d), 7.81-7.84 (1H, m), 8.24 (1H, d), 8.48-8.49 (1H, m), 8.59 (1H, d); m/z=390 [M+H]+.

The 6-[(1R,5S)-3,8-diazabicyclo[3.2.1]oct-3-yl]-3-(trifluoromethyl)[1,2,4]triazolo[4,3-b]pyridazine used as starting material was prepared as follows:—

Preparation of (1R,5S)-tert-butyl 3-[3-(trifluoromethyl)-[1,2,4]triazolo[4,3-b]pyridazin-6-yl]-3,8-diazabicyclo[3.2.1]octane-8-carboxylate A stirred solution of 6-chloro-3-(trifluoromethyl)-[1,2,4]triazolo[4,3-b]pyridazine (312 mg, 1.40 mmol), (1R,5S)-tertbutyl 3,8-diazabicyclo[3.2.1]octane-8-carboxylate (312 mg, 1.47 mmol) and DIPEA (0.36 ml, 2.10 mmol) in ethanol (7.00 ml) was heated at 70° C. for 18 hours. On cooling a white precipitate formed which was collected by filtration, washed with ethanol (10 mL) and dried under vacuum to afford (1R, 5S)-tert-butyl 3-(3-(trifluoromethyl)-[1,2,4]triazolo[4,3-b]pyridazin-6-yl)-3,8-diazabicyclo[3.2.1]octane-8-carboxylate (384 mg, 69%) as a white crystalline solid.

1H NMR (399.9 MHz, DMSO-d6) δ 1.44 (9H, s), 1.71-1.72 (2H, m), 1.88-1.90 (2H, m), 3.13 (2H, d), 3.97 (2H, d), 4.29 (2H, s), 7.54 (1H, d), 8.28 (1H, d); m/z=399 [M+H]+.

Preparation of 6-((1R,5S)-3,8-diazabicyclo[3.2.1]octan-3-yl)-3-(trifluoromethyl)-[1,2,4]triazolo[4,3-b]pyridazine TFA (2.42 ml, 31.4 mmol) was added to a stirred solution of (1R,5S)-tert-butyl 3-(3-(trifluoromethyl)-[1,2,4]triazolo[4,3-b]pyridazin-6-yl)-3,8-diazabicyclo[3.2.1]octane-8-carboxylate (443 mg, 1.11 mmol) in DCM (4.50 ml) at 25° C. The resulting solution was stirred at ambient temperature for 18 hours. The reaction mixture was diluted with methanol and the crude product was purified by ion exchange chromatography, using an SCX column. The desired product was eluted using 7M ammonia in methanol and evaporated to dryness to afford 6-[(1R,5S)-3,8-diazabicyclo[3.2.1]oct-3-yl]-3-(trifluoromethyl)[1,2,4]triazolo[4,3-b]pyridazine (336 mg, 100%) as a white solid.

1H NMR (399.9 MHz, DMSO-d6) δ 1.61-1.71 (4H, m), 3.05-3.08 (2H, m), 3.55 (2H, s), 3.81-3.84 (2H, m), 7.50 (1H, d), 8.22 (1H, d), NH not observed; m/z=299 [M+H]+.

EXAMPLE 554

Preparation of (1α,5α,6α) N-(4-fluorobenzyl)-3-[3-(trifluoromethyl)[1,2,4]triazolo[4,3-b]pyridazin-6-yl]-3-azabicyclo[3.1.0]hexan-6-amine

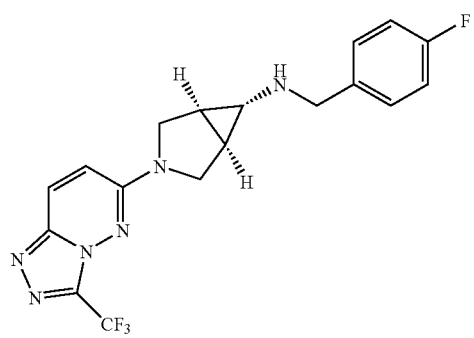

(1α,5α,6α) 3-[3-(Trifluoromethyl)[1,2,4]triazolo[4,3-b]pyridazin-6-yl]-3-azabicyclo[3.1.0]hexan-6-amine (150 mg, 0.53 mmol), magnesium sulphate monohydrate (361 mg, 2.64 mmol) and 4-fluorobenzaldehyde (98 mg, 0.79 mmol) were added to DCM (10 mL) and the mixture was stirred overnight at 25° C. The crude mixture was purified by flash silica chromatography, elution gradient 0 to 10% MeOH in DCM. The appropriate fractions were evaporated to dryness, and the intermediate imine and acetic acid (0.2 mL, 3.49 mmol) were added to MeOH (15 mL). Sodium cyanoborohydride (0.040 mL, 0.70 mmol) was added and the mixture was stirred for 20 minutes. The crude product was purified by ion exchange chromatography using an SCX column, eluting with 3.5M ammonia in methanol. The appropriate fractions were evaporated to dryness to afford a clear gum, which was purified by flash silica chromatography, elution gradient 0 to 10% MeOH in DCM. Product-containing fractions were evaporated to dryness and the residue was crystallised from a mixture of ether and isohexane to give (1α,5α,6α) N-(4-fluorobenzyl)-3-[3-(trifluoromethyl)[1,2,4]triazolo[4,3-b]pyridazin-6-yl]-3-azabicyclo[3.1.0]hexan-6-amine (125 mg, 60%).

1H NMR (400.1 MHz, CDCl3) δ 1.81 (2H, s), 1.84 (1H, s), 2.02 (1H, t), 3.59 (2H, d), 3.68 (2H, d), 3.81 (2H, s), 6.76 (1H, d), 7.01 (2H, t), 7.27 (2H, t), 7.87 (1H, d); m/z=393 [M+H]+.

The (1α,5α,6α) 3-[3-(trifluoromethyl)[1,2,4]triazolo[4,3-b]pyridazin-6-yl]-3-azabicyclo[3.1.0]hexan-6-amine used as starting material was prepared in 2 steps in 78% overall yield by an analogous method to Example 223, preparation of starting materials, starting from 6-chloro-3-(trifluoromethyl)-[1,2,4]-triazolo[4,3-b]pyridazine and (1α,5α,6α) tert-butyl 3-azabicyclo[3.1.0]hex-6-ylcarbamate (obtained as described in Synlett. 1996, 1097).

1H NMR (400.1 MHz, CDCl3) δ 1.60 (2H, s), 1.77 (2H, s), 2.21 (1H, s), 3.61 (2H, d), 3.72 (2H, d), 6.78 (1H, d), 7.87 (1H, d); m/z=285 [M+H]+.

EXAMPLES 555-557

The following compounds were prepared in 50-85% yield by an analogous method to Example 554, starting from (1α,5α,6α) 3-[3-(trifluoromethyl)[1,2,4]triazolo[4,3-b]pyridazin-6-yl]-3-azabicyclo[3.1.0]hexan-6-amine and the appropriate aldehyde:—

| Ex. | R | 1H NMR (400.1 MHz, CDCl3) | m/z [M + H]+ |
|---|---|---|---|
| 555 | 3-Cl | δ 1.82 (2H, s), 1.89 (1H, s), 2.02 (1H, t), 3.60 (2H, d), 3.68 (2H, d), 3.82 (2H, s), 6.76 (1H, d), 7.17 (1H, d), 7.28-7.24 (2H, m), 7.31 (1H, s), 7.87 (1H, d) | 409 |
| 556 | 3-F | δ 1.83 (2H, s), 1.89 (1H, s), 2.04 (1H, t), 3.59 (2H, d), 3.68 (2H, d), 3.84 (2H, s), 6.76 (1H, d), 6.95 (1H, t), 7.02 (1H, d), 7.07 (1H, d), 7.31-7.26 (1H, m), 7.87 (1H, d) | 393 |
| 557 | 4-CN | δ 1.82 (2H, s), 1.89 (1H, s), 2.05 (1H, t), 3.60 (2H, d), 3.68 (2H, d), 3.91 (2H, s), 6.76 (1H, d), 7.43 (2H, d), 7.62 (2H, d), 7.87 (1H, d) | 399 |

EXAMPLES 558-559

The following compounds were prepared in 5-36% yield by an analogous method to Example 448, starting from [1-[3-(trifluoromethyl)-[1,2,4]triazolo[4,3-b]pyridazin-6-yl]piperidin-4-yl]methanol (obtained as described in Example 294, preparation of starting materials) and the appropriate chloro heterocycle:—

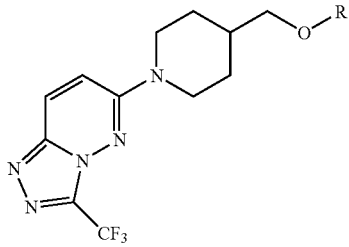

| Ex. | R | 1H NMR (399.9 MHz, DMSO-d6) | m/z [M + H]+ |
|---|---|---|---|
| 558 | pyrimidin-2-yl | δ 1.39 (2H, ddd), 1.91-1.87 (2H, m), 2.21-2.08 (1H, m), 3.07 (2H, t), 4.21 (2H, d), 4.34-4.31 (2H, m), 7.14 (1H, t), 7.63 (1H, d), 8.23 (1H, d), 8.60 (2H, d) | 380 |
| 559 | 3-bromopyrimidin-2-yl | δ 1.46-1.36 (2H, m), 1.91-1.87 (2H, m), 2.18-2.05 (1H, m), 3.11-3.04 (2H, m), 4.24 (2H, d), 4.34-4.31 (2H, m), 6.95 (1H, dd), 7.63 (1H, d), 8.03 (1H, d), 8.15 (1H, d), 8.23 (1H, d) | 458 |

EXAMPLES 560-561

The following compounds were prepared in 30-37% yield by an analogous method to Example 294, starting from 6-[4-(methanesulfonyloxymethyl)piperidin-1-yl]-3-(trifluoromethyl)-[1,2,4]triazolo[4,3-b]pyridazine and the appropriate pyridinol:—

| Ex. | R | 1H NMR (400.1 MHz, DMSO-d6) | m/z [M + H]+ |
|---|---|---|---|
| 560 | pyridin-3-yl | 1.38 (2H, ddd), 1.93-1.90 (2H, m), 2.16-2.10 (1H, m), 3.11-3.04 (2H, m), 3.96 (2H, d), 4.33-4.30 (2H, m), 7.32 (1H, dd), 7.39 (1H, ddd), 7.63 (1H, d), 8.16 (1H, dd), 8.23 (1H, d), 8.30 (1H, d) | 379 |
| 561 | pyridin-4-yl | δ 1.38 (2H, ddd), 1.91-1.88 (2H, m), 2.21-2.11 (1H, m), 3.11-3.04 (2H, m), 3.97 (2H, d), 4.33-4.30 (2H, m), 6.97-6.96 (2H, m), 7.62 (1H, d), 8.23 (1H, d), 8.38-8.37 (2H, m) | 379 |

EXAMPLE 562

Preparation of 6-[4-[[(6-chloropyridin-2-yl)oxy]methyl]piperidin-1-yl]-3-(trifluoromethyl)[1,2,4]triazolo[4,3-b]pyridazine

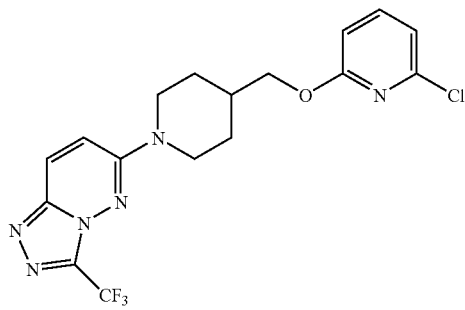

Obtained in 75% yield by an analogous method to Example 447, starting from [1-[3-(trifluoromethyl)-[1,2,4]triazolo[4,3-b]pyridazin-6-yl]piperidin-4-yl]methanol (obtained as described in Example 294, preparation of starting materials) and 6-chloropyridin-2-ol.

1H NMR (400.1 MHz, DMSO-d6) δ 1.37 (2H, ddd), 1.89-1.87 (2H, m), 2.14-2.08 (1H, m), 3.06 (2H, t), 4.14 (2H, d), 4.33-4.30 (2H, m), 6.84 (1H, d), 7.08 (1H, d), 7.62 (1H, d), 7.76 (1H, t), 8.22 (1H, d); m/z=413 [M+H]+.

EXAMPLE 563

Preparation of 6-[6,6-difluoro-4-(4-fluorobenzyl)-1,4-diazepan-1-yl]-3-(trifluoromethyl)[1,2,4]triazolo[4,3-b]pyridazine

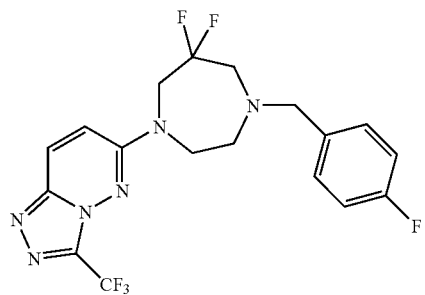

Sodium cyanotrihydroborate (58.5 mg, 0.93 mmol) was added to a stirred mixture of 6-(6,6-difluoro-1,4-diazepan-1-yl)-3-(trifluoromethyl)[1,2,4]triazolo[4,3-b]pyridazine (200 mg, 0.62 mmol), 4-fluorobenzaldehyde (93 mg, 0.75 mmol) and acetic acid (71.1 μl, 1.24 mmol) in methanol (10 mL) at room temperature. The resulting mixture was stirred at 21° C. for 20 hours. The reaction mixture was concentrated to dryness, diluted with methanol and a few drops of 7M ammonia in methanol were added. The mixture was concentrated to dryness, the residue was diluted with DCM and the salts were filtered off. The filtrate was concentrated and purified by flash chromatography on silica gel eluting with 0 to 20% acetonitrile in DCM. Product-containing fractions were concentrated to give to give 6-[6,6-difluoro-4-(4-fluorobenzyl)-1,4-diazepan-1-yl]-3-(trifluoromethyl)[1,2,4]triazolo[4,3-b]pyridazine (154 mg, 55%).

1H NMR (500 MHz, DMSO-d6) δ 2.82-2.88 (m, 2H), 3.02-3.11 (m, 2H), 3.73 (s, 2H), 3.79-3.84 (m, 2H), 4.28-4.36 (m, 2H), 6.95 (dd, 2H), 7.23 (dd, 2H), 7.61 (d, 1H), 8.32 (d, 1H); m/z=431[M+H]+.

The 6-(6,6-difluoro-1,4-diazepan-1-yl)-3-(trifluoromethyl)[1,2,4]triazolo[4,3-b]pyridazine used as starting material was prepared as follows:—

Preparation of tert-butyl 6,6-difluoro-1,4-diazepane-1-carboxylate

Di-tert-butyl dicarbonate (5.29 ml, 23.0 mmol) in DCM (50 mL) was added dropwise to a ice-cooled mixture of 6,6-difluoro-1,4-diazepane (3.6 g, 26.4 mmol, obtained as described in Synthesis, 2003, 223) and DIPEA (2.30 mL, 13.2 mmol) in DCM (100 mL). The resulting mixture was stirred at room temperature for 15 hours. The mixture was concentrated to dryness and diluted with water and ethyl acetate. Insoluble material was removed by filtration and the organic phase was separated, washed with brine, dried over magnesium sulfate and concentrated. The residue was purified by flash chromatography on silica gel eluting with 0 to 4% methanol in DCM. Product-containing fractions were concentrated to afford tert-butyl 6,6-difluoro-1,4-diazepane-1-carboxylate (3.45 g, 55.2%) as a white solid. 1H NMR (500 MHz, CDCl3) δ 1.47 (s, 9H), 2.90-3.00 (m, 2H), 3.05-3.15 (m, 2H), 3.41-3.54 (m, 2H), 3.78-3.94 (m, 2H).

Preparation of 6-(6,6-difluoro-1,4-diazepan-1-yl)-3-(trifluoromethyl)[1,2,4]triazolo[4,3-b]pyridazine A mixture of 6-chloro-3-(trifluoromethyl)-[1,2,4]triazolo[4,3-b]pyridazine (1 g, 4.49 mmol), tert-butyl 6,6-difluoro-1,4-diazepane-1-carboxylate (1.06 g, 4.49 mmol) and DIPEA (1.56 ml, 8.99 mmol) in DMA (15 mL) was stirred at 135° C. for 6 hours. The reaction mixture was concentrated to dryness and DCM (30 mL) was added. The solution was cooled in an ice bath and TFA (15 mL) was added. The resulting mixture was stirred at room temperature for 4 hours. The reaction mixture was concentrated to dryness, diluted with water, basified with 6M aqueous sodium hydroxide and extracted with DCM. The organic phase was washed with water and brine, dried over magnesium sulfate and concentrated. The residue was purified by flash chromatography on silica gel eluting with 0 to 4% methanol in DCM to give 6-(6,6-difluoro-1,4-diazepan-1-yl)-3-(trifluoromethyl)-[1,2,4]triazolo[4,3-b]pyridazine (0.820 g, 56.6%) as a beige solid.

1H NMR (500 MHz, DMSO-d6) δ 2.80 (bs, 1H), 2.94-3.07 (m, 4H), 3.74-3.81 (m, 2H), 4.24-4.31 (m, 2H), 7.58 (d, 1H), 8.30 (d, 1H); m/z=323 [M+H]+.

EXAMPLE 564

Preparation of 6-[(3R)-3-methyl-4-(pyridin-3-ylmethyl)piperazin-1-yl]-3-(trifluoromethyl)[1,2,4]triazolo[4,3-b]pyridazine

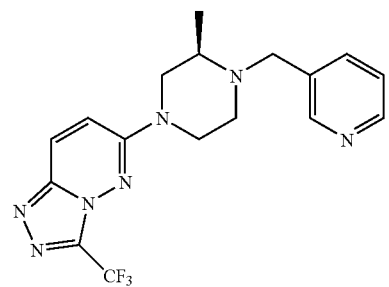

A mixture of pyridine-3-carboxaldehyde and 6-[(3R)-3-methylpiperazin-1-yl]-3-(trifluoromethyl)-[1,2,4]triazolo[4,3-b]pyridazine was allowed to react by General Synthetic Method 5, to give 6-[(3R)-3-methyl-4-(pyridin-3-ylmethyl)piperazin-1-yl]-3-(trifluoromethyl)[1,2,4]triazolo[4,3-b]pyridazine in 58% yield.

1H NMR (399.9 MHz, DMSO-d$_6$) δ 1.16 (3H, d), 2.24-2.30 (1H, m), 2.53-2.63 (1H, m), 2.72-2.76 (1H, m), 3.09-3.14 (1H, m), 3.28-3.32 (1H+H$_2$O, m), 3.35 (1H, d), 3.84-3.89 (1H, m), 3.92-4.00 (2H, m), 7.36-7.39 (1H, m), 7.61 (1H, d), 7.74-7.77 (1H, m), 8.25 (1H, d), 8.47-8.49 (1H, m), 8.54 (1H, d); m/z=378 [M+H]+.

The 6-[(3R)-3-methylpiperazin-1-yl]-3-(trifluoromethyl)-[1,2,4]triazolo[4,3-b]pyridazine used as starting material was prepared in 2 steps in 75% overall yield by an analogous method to Example 223, preparation of starting materials, starting from 6-chloro-3-(trifluoromethyl)-[1,2,4]triazolo[4,3-b]pyridazine and (3R)-tert-butyl 2-methylpiperazine-1-carboxylate.

1H NMR (399.9 MHz, DMSO-d$_6$) δ 1.04 (3H, d), 2.37 (1H, s), 2.54-2.60 (1H, m), 2.68-2.75 (2H, m), 2.87-3.00 (2H, m), 4.07-4.11 (2H, m), 7.61 (1H, d), 8.23 (1H, d).

EXAMPLES 565-569

The following compounds were prepared in 29-45% yield by General Synthetic Method 5, starting from 6-[(3R)-3-methylpiperazin-1-yl]-3-(trifluoromethyl)-[1,2,4]triazolo[4,3-b]pyridazine (obtained as described in Example 564, preparation of starting materials) and the appropriate aldehyde:—

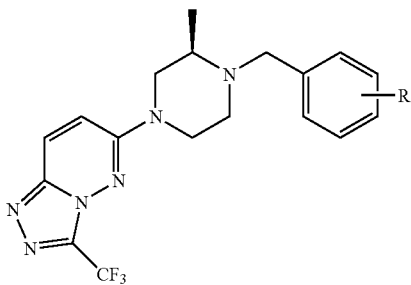

| Ex. R | 1H NMR (399.9 MHz, DMSO-d6) | m/z [M + H]+ |
|---|---|---|
| 565 4-CN | δ 1.13 (3H, d), 2.26-2.32 (1H, m), 2.61-2.65 (1H, m), 2.70-2.75 (1H, m), 3.10-3.15 (1H, m), 3.28-3.32 (1H +H$_2$O, m), 3.41 (1H, d), 3.85-3.89 (1H, m), 3.93-3.97 (1H, m), 4.03 (1H, d), 7.58 (2H, d), 7.60-7.63 (1H, m), 7.80-7.83 (2H, m), 8.26 (1H, d) | 402 |
| 566 3,4-di-F | δ 1.13 (3H, d), 2.24-2.29 (1H, m), 2.59-2.63 (1H, m), 2.71-2.76 (1H, m), 3.10-3.15 (1H, m), 3.28-3.32 (2H +H$_2$O, m), 3.84-3.89 (2H, m), 3.93 (1H, d), 7.18-7.21 (1H, m), 7.36-7.42 (2H, m), 7.61 (1H, d), 8.25 (1H, d) | 413 |
| 567 3,5-di-F | δ 1.12 (3H, d), 2.27-2.32 (1H, m), 2.59-2.62 (1H, m), 2.74-2.78 (1H, m), 3.11-3.16 (1H, m), 3.33-3.38 (2H, m), 3.86-3.97 (3H, m), 7.08-7.13 (3H, m), 7.62 (1H, d), 8.26 (1H, d) | 413 |
| 568 4-F | δ 1.14 (3H, d), 2.20-2.26 (1H, m), 2.56-2.61 (1H, m), 2.70-2.75 (1H, m), 3.08-3.14 (1H, m), 3.26-3.33 (2H, m), 3.84-3.96 (3H, m), 7.14-7.18 (2H, m), 7.36-7.40 (2H, m), 7.61 (1H, d), 8.25 (1H, d) | 395 |
| 569 3-CN, 4-F | δ 1.13 (3H, d), 2.24-2.30 (1H, m), 2.60-2.65 (1H, m), 2.71-2.76 (1H, m), 3.10-3.16 (1H, m), 3.28-3.32 (1H +H$_2$O, m), 3.36 (1H, d), 3.85-3.98 (3H, m), 7.49-7.53 (1H, m), 7.61 (1H, d), 7.75-7.79 (1H, m), 7.86-7.88 (1H, m), 8.26 (1H, d) | 420 |

EXAMPLE 570

Preparation of 6-[(3S)-3-methyl-4-(pyridin-3-ylmethyl)piperazin-1-yl]-3-(trifluoromethyl)[1,2,4]triazolo[4,3-b]pyridazine

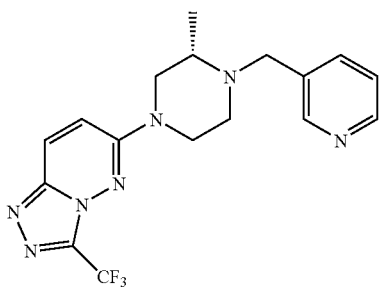

A mixture of pyridine-3-carboxaldehyde and 6-[(3S)-3-methylpiperazin-1-yl]-3-(trifluoromethyl)-[1,2,4]triazolo[4,3-b]pyridazine was allowed to react by General Synthetic Method 5 to give 6-[(3S)-3-methyl-4-(pyridin-3-ylmethyl)piperazin-1-yl]-3-(trifluoromethyl)[1,2,4]triazolo[4,3-b]pyridazine in 62% yield.

1H NMR (399.9 MHz, DMSO-d$_6$) δ 1.16 (3H, d), 2.24-2.30 (1H, m), 2.53-2.63 (1H, m), 2.72-2.76 (1H, m), 3.09-3.14 (1H, m), 3.28-3.32 (1H+H$_2$O, m), 3.35 (1H, d), 3.84-3.89 (1H, m), 3.92-4.00 (2H, m), 7.36-7.39 (1H, m), 7.61 (1H, d), 7.74-7.77 (1H, m), 8.25 (1H, d), 8.47-8.49 (1H, m), 8.54 (1H, d); m/z=378 [M+H]+.

The 6-[(3S)-3-methylpiperazin-1-yl]-3-(trifluoromethyl)-[1,2,4]triazolo[4,3-b]pyridazine used as starting material was prepared in 2 steps in 71.5% overall yield by an analogous method to Example 223, preparation of starting materials, starting from 6-chloro-3-(trifluoromethyl)-[1,2,4]triazolo[4,3-b]pyridazine and (3S)-tert-butyl 2-methylpiperazine-1-carboxylate.

1H NMR (399.9 MHz, DMSO-d$_6$) δ 1.04 (3H, d), 2.37 (1H, s), 2.54-2.60 (1H, m), 2.68-2.75 (2H, m), 2.87-3.00 (2H, m), 4.07-4.11 (2H, m), 7.61 (1H, d), 8.23 (1H, d).

EXAMPLES 571-575

The following compounds were prepared in 36-55% yield by General Synthetic Method 5, starting from 6-[(3S)-3-methylpiperazin-1-yl]-3-(trifluoromethyl)-[1,2,4]triazolo[4,3-b]pyridazine (obtained as described in Example 570, preparation of starting materials) and the appropriate aldehyde:—

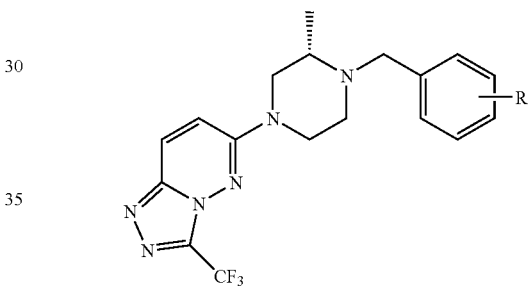

| Ex. R | 1H NMR (399.9 MHz, DMSO-d$_6$) | m/z [M + H]+ |
|---|---|---|
| 571 4-CN | δ 1.13 (3H, d), 2.26-2.32 (1H, m), 2.61-2.65 (1H, m), 2.70-2.75 (1H, m), 3.10-3.15 (1H, m), 3.28-3.32 (1H +H$_2$O, m), 3.41 (1H, d), 3.85-3.89 (1H, m), 3.93-3.97 (1H, m), 4.03 (1H, d), 7.58 (2H, d), 7.60-7.63 (1H, m), 7.80-7.83 (2H, m), 8.26 (1H, d) | 402 |
| 572 3,4-di-F | δ 1.13 (3H, d), 2.24-2.29 (1H, m), 2.59-2.63 (1H, m), 2.71-2.76 (1H, m), 3.10-3.15 (1H, m), 3.28-3.32 (2H +H$_2$O, m), 3.84-3.89 (2H, m), 3.93 (1H, d), 7.18-7.21 (1H, m), 7.36-7.42 (2H, m), 7.61 (1H, d), 8.25 (1H, d) | 413 |
| 573 3,5-di-F | δ 1.12 (3H, d), 2.27-2.32 (1H, m), 2.59-2.62 (1H, m), 2.74-2.78 (1H, m), 3.11-3.16 (1H, m), 3.33-3.38 (2H, m), 3.86-3.97 (3H, m), 7.08-7.13 (3H, m), 7.62 (1H, d), 8.26 (1H, d) | 413 |
| 574 4-F | δ 1.14 (3H, d), 2.20-2.26 (1H, m), 2.56-2.61 (1H, m), 2.70-2.75 (1H, m), 3.08-3.14 (1H, m), 3.26-3.33 (2H, m), 3.84-3.96 (3H, m), 7.14-7.18 (2H, m), 7.36-7.40 (2H, m), 7.61 (1H, d), 8.25 (1H, d) | 395 |
| 575 3-CN, 4-F | δ 1.13 (3H, d), 2.24-2.30 (1H, m), 2.60-2.65 (1H, m), 2.71-2.76 (1H, m), 3.10-3.16 (1H, m), 3.28-3.32 (1H +H$_2$O, m), 3.36 (1H, d), 3.85-3.98 (3H, m), 7.49-7.53 (1H, m), 7.61 (1H, d), 7.75-7.79 (1H, m), 7.86-7.88 (1H, m), 8.26 (1H, d) | 420 |

EXAMPLE 576

Preparation of 6-[(3R)-3-(pyridin-3-yloxy)pyrrolidin-1-yl]-3-(trifluoromethyl)[1,2,4]triazolo[4,3-b]pyridazine

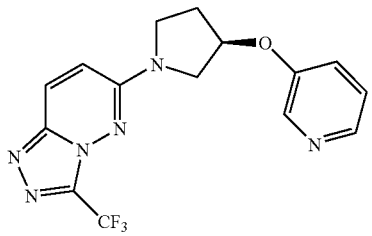

Obtained in 68% yield by an analogous procedure to Example 216, starting from 6-chloro-3-(trifluoromethyl)-[1,2,4]triazolo[4,3-b]pyridazine and (3R)-3-(pyridin-3-yloxy)pyrrolidine.

1H NMR (399.9 MHz, DMSO-$d_6$) δ 2.27-2.38 (2H, m), 3.63-3.88 (4H, m), 5.30-5.34 (1H, m), 7.32 (1H, d), 7.35-7.39 (1H, m), 7.47-7.50 (1H, m), 8.21-8.23 (1H, m), 8.25 (1H, d), 8.34 (1H, d); m/z=351 [M+H]+.

The (3R)-3-(pyridin-3-yloxy)pyrrolidine used as starting material was prepared as follows:—

DIAD (0.631 mL, 3.20 mmol) in DCM (5 ml) was added dropwise to a mixture of (S)-tert-butyl 3-hydroxypyrrolidine-1-carboxylate (500 mg, 2.67 mmol), pyridin-3-ol (305 mg, 3.20 mmol) and triphenylphosphine (840 mg, 3.20 mmol) in DCM (20 ml), cooled in an ice bath. The mixture was allowed to warm to room temperature, stirred for 1 hour and then concentrated. The residue was dissolved in dioxan (15 mL) and 4M HCl in dioxan (15 mL) was added. The mixture was stirred for 1 hour and concentrated. The crude product was purified by ion exchange chromatography, using an SCX column. The desired product was eluted from the column using 7M ammonia in methanol and pure fractions were evaporated to dryness to afford (3R)-3-(pyridin-3-yloxy)pyrrolidine (405 mg, 92%) as a colourless oil.

1H NMR (399.9 MHz, DMSO-$d_6$) δ 1.72-1.79 (1H, m), 1.99-2.08 (1H, m), 2.75-2.81 (1H, m), 2.84-2.95 (2H, m), 3.05-3.09 (1H, m), 4.90-4.95 (1H, m), 7.30-7.37 (2H, m), 8.15-8.16 (1H, m), 8.25 (1H, d); m/z=165 [M+H]+.

EXAMPLE 577

Preparation of 6-[(3R)-3-(pyridin-4-yloxy)pyrrolidin-1-yl]-3-(trifluoromethyl)[1,2,4]triazolo[4,3-b]pyridazine

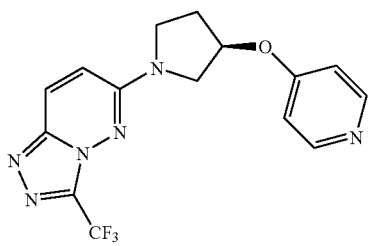

Obtained in 60% yield by an analogous procedure to Example 216, starting from 3-(trifluoromethyl)[1,2,4]triazolo[4,3-b]pyridazine and (3R)-3-(pyridin-4-yloxy)pyrrolidine.

1H NMR (399.9 MHz, DMSO-$d_6$) δ 2.25-2.30 (1H, m), 2.34-2.41 (1H, m), 3.61-3.90 (4H, m), 5.34-5.38 (1H, t), 7.03-7.04 (2H, m), 7.32 (1H, d), 8.25 (1H, d), 8.41-8.43 (2H, m); m/z=351 [M+H]+.

The (3R)-3-(pyridin-4-yloxy)pyrrolidine used as starting material was prepared in 61% yield by an analogous method to Example 576, preparation of starting materials, starting from (3S)-tert-butyl 3-hydroxypyrrolidine-1-carboxylate and pyridin-4-ol.

1H NMR (399.9 MHz, DMSO-$d_6$) δ 1.71-1.79 (1H, m), 2.01-2.10 (1H, m), 2.75-2.81 (1H, m), 2.86-2.93 (2H, m), 3.05-3.14 (1H, m), 4.93-4.97 (1H, m), 6.91-6.93 (2H, m), 8.36-8.38 (2H, m); m/z=165 [M+H]+.

EXAMPLE 578

Preparation of 6-[(3R)-3-(pyridin-2-yloxy)pyrrolidin-1-yl]-3-(trifluoromethyl)[1,2,4]triazolo[4,3-b]pyridazine

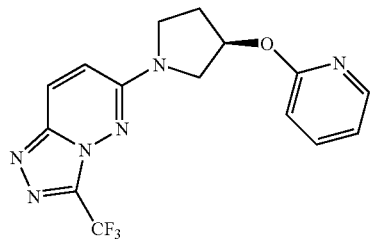

Obtained in 63% yield by an analogous procedure to Example 216, starting from 3-(trifluoromethyl)[1,2,4]triazolo[4,3-b]pyridazine and (3R)-3-(pyridin-2-yloxy)pyrrolidine.

1H NMR (399.9 MHz, DMSO-$d_6$) δ 2.25-2.30 (1H, m), 2.33-2.42 (1H, m), 3.65-3.76 (3H, m), 3.89 (1H, d), 5.69-5.72 (1H, m), 6.82-6.84 (1H, m), 7.00-7.04 (1H, m), 7.29-7.32 (1H, m), 7.71-7.75 (1H, m), 8.21-8.24 (2H, m); m/z=351 [M+H]+.

The (3R)-3-(pyridin-2-yloxy)pyrrolidine used as starting material was prepared in 65% yield by an analogous method to Example 576, preparation of starting materials, starting from tert-butyl (3S)-3-hydroxypyrrolidine-1-carboxylate and pyridin-2-ol.

1H NMR (399.9 MHz, DMSO-$d_6$) δ 1.72-1.80 (1H, m), 1.97-2.06 (1H, m), 2.75-2.84 (2H, m), 2.87-2.94 (1H, m), 3.05-3.10 (1H, m), 5.34-5.38 (1H, m), 6.75-6.77 (1H, m), 6.93-6.96 (1H, m), 7.66-7.70 (1H, m), 8.15-8.17 (1H, m); m/z=165 [M+H]+.

EXAMPLES 579-586

The following compounds were prepared in 29-45% yield by an analogous method to Example 447, starting from (3S)-1-[3-(trifluoromethyl)[1,2,4]triazolo[4,3-b]pyridazin-6-yl]pyrrolidin-3-ol and the appropriate phenol:—

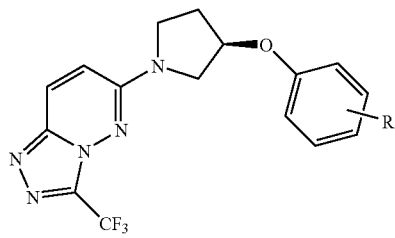

| Ex. | R | 1H NMR (399.9 MHz, DMSO-d$_6$) | m/z [M + H]+ |
|---|---|---|---|
| 579 | 4-CF3 | δ 2.26-2.42 (2H, m), 3.63-3.90 (4H, m), 5.33-5.37 (1H, m), 7.20 (2H, d), 7.32 (1H, d), 7.69 (2H, d), 8.25 (1H, d) | 418 |
| 580 | 4-CN | δ 2.25-2.29 (1H, m), 2.33-2.41 (1H, m), 3.62-3.90 (4H, m), 5.35-5.38 (1H, s), 7.17-7.21 (2H, m), 7.31 (1H, d), 7.79-7.82 (2H, m), 8.25 (1H, d) | 375 |
| 581 | 4-F | δ 2.22-2.34 (2H, m), 3.61-3.84 (4H, m), 5.17-5.20 (1H, m), 7.00-7.05 (2H, m), 7.12-7.18 (2H, m), 7.31 (1H, d), 8.24 (1H, d) | 368 |
| 582 | 4-OMe | δ 2.20-2.34 (2H, m), 3.54-3.89 (7H, m), 5.10-5.13 (1H, m), 6.87-6.90 (2H, m), 6.93-6.95 (2H, m), 7.31 (1H, d), 8.24 (1H, d) | 380 |
| 583 | 3-CF3 | δ 2.28-2.37 (2H, m), 3.63-3.86 (4H, m), 5.35-5.39 (1H, m), 7.31-7.34 (4H, m), 7.55-7.59 (1H, m), 8.25 (1H, d) | 418 |
| 584 | 3-CN | δ 2.23-2.29 (1H, m), 2.31-2.38 (1H, m), 3.62-3.89 (4H, m), 5.31-5.35 (1H, m), 7.32 (1H, d), 7.34-7.37 (1H, m), 7.45 (1H, d), 7.51-7.55 (2H, m), 8.25 (1H, d) | 375 |
| 585 | 3-F | δ 2.23-2.36 (2H, m), 3.61-3.87 (4H, m), 5.24-5.28 (1H, m), 6.78-6.86 (2H, m), 6.89-6.93 (1H, m), 7.30-7.38 (2H, m), 8.25 (1H, d) | 368 |
| 586 | 3-OMe | δ 2.23-2.37 (2H, m), 3.56-3.92 (7H, m), 5.20-5.24 (1H, m), 6.54-6.60 (3H, m), 7.22 (1H, t), 7.32 (1H, d), 8.24 (1H, d) | 380 |

The (3S)-1-[3-(trifluoromethyl)[1,2,4]triazolo[4,3-b]pyridazin-6-yl]pyrrolidin-3-ol used as starting material was prepared in 77% yield by an analogous method to Example 216, preparation of starting materials, starting from 6-chloro-3-(trifluoromethyl)-[1,2,4]-triazolo[4,3-b]pyridazine and (S)-pyrrolidin-3-ol.

1H NMR (399.9 MHz, DMSO-d$_6$) δ 1.93-1.98 (1H, m), 2.03-2.08 (1H, m), 3.42 (1H, d), 3.55-3.62 (3H, m), 4.43-4.45 (1H, m), 5.07 (1H, d), 7.26 (1H, d), 8.21 (1H, d); m/z=274 [M+H]+.

EXAMPLE 587

Preparation of 6-[(3S)-3-(pyridin-3-yloxy)pyrrolidin-1-yl]-3-(trifluoromethyl)[1,2,4]triazolo[4,3-b]pyridazine

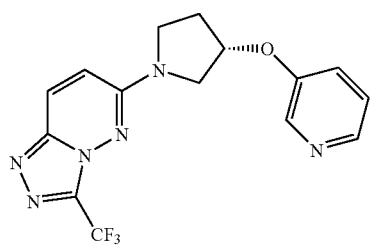

Obtained in 74% yield by an analogous procedure to Example 447, starting from (3R)-1-[3-(trifluoromethyl)[1,2,4]triazolo[4,3-b]pyridazin-6-yl]pyrrolidin-3-ol and pyridin-3-ol.

1H NMR (399.9 MHz, DMSO-d$_6$) δ 2.27-2.38 (2H, m), 3.63-3.88 (4H, m), 5.31-5.34 (1H, m), 7.32 (1H, d), 7.35-7.39 (1H, m), 7.47-7.50 (1H, m), 8.21-8.23 (1H, m), 8.25 (1H, d), 8.34 (1H, d); m/z=351 [M+H]+.

The (3R)-1-[3-(trifluoromethyl)[1,2,4]triazolo[4,3-b]pyridazin-6-yl]pyrrolidin-3-ol used as starting material was prepared in 81% yield by an analogous method to Example 216, preparation of starting materials, starting from 6-chloro-3-(trifluoromethyl)-[1,2,4]-triazolo[4,3-b]pyridazine and (R)-pyrrolidin-3-ol.

1H NMR (399.9 MHz, DMSO-d$_6$) δ 1.93-1.98 (1H, m), 2.03-2.08 (1H, m), 3.42 (1H, d), 3.55-3.62 (3H, m), 4.43-4.45 (1H, m), 5.07 (1H, d), 7.26 (1H, d), 8.21 (1H, d); m/z=274 [M+H]+.

EXAMPLE 588

Preparation of 6-[(3S)-3-(pyridin-4-yloxy)pyrrolidin-1-yl]-3-(trifluoromethyl)[1,2,4]triazolo[4,3-b]pyridazine

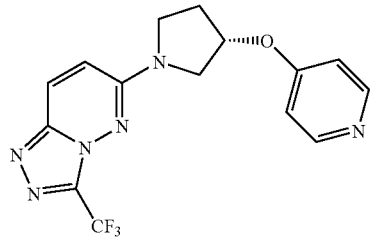

Obtained in 75% yield by an analogous procedure to Example 216, starting from 3-(trifluoromethyl)[1,2,4]triazolo[4,3-b]pyridazine and (3S)-3-(pyridin-4-yloxy)pyrrolidine.

1H NMR (399.9 MHz, DMSO-d$_6$) δ 2.25-2.30 (1H, m), 2.34-2.43 (1H, m), 3.61-3.90 (4H, m), 5.34-5.37 (1H, m), 7.03-7.04 (2H, m), 7.32 (1H, d), 8.25 (1H, d), 8.41-8.43 (2H, m); m/z=351 [M+H]+.

The (3S)-3-(pyridin-4-yloxy)pyrrolidine used as starting material was prepared in 61% yield by an analogous method to Example 576, preparation of starting materials, starting from tert-butyl (3R)-3-hydroxypyrrolidine-1-carboxylate and pyridin-4-ol.

1H NMR (399.9 MHz, DMSO-d$_6$) δ 1.71-1.79 (1H, m), 2.01-2.10 (1H, m), 2.75-2.81 (1H, m), 2.86-2.93 (2H, m), 3.05-3.14 (1H, m), 4.93-4.97 (1H, m), 6.91-6.93 (2H, m), 8.36-8.38 (2H, m); m/z=165 [M+H]+.

EXAMPLE 589

Preparation of 6-[(3S)-3-(pyridin-2-yloxy)pyrrolidin-1-yl]-3-(trifluoromethyl)[1,2,4]triazolo[4,3-b]pyridazine

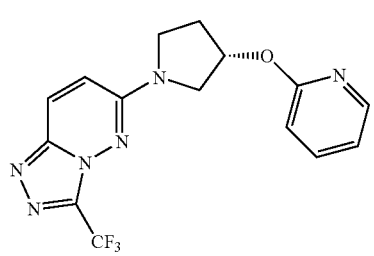

Obtained in 62% yield by an analogous procedure to Example 216, starting from 3-(trifluoromethyl)[1,2,4]triazolo[4,3-b]pyridazine and (3S)-3-(pyridin-2-yloxy)pyrrolidine.

1H NMR (399.9 MHz, DMSO-$d_6$) δ 2.25-2.30 (1H, m), 2.33-2.42 (1H, m), 3.65-3.76 (3H, m), 3.89 (1H, d), 5.70-5.72 (1H, m), 6.82-6.84 (1H, m), 7.01-7.04 (1H, m), 7.31 (1H, d), 7.71-7.75 (1H, m), 8.21-8.25 (2H, m); m/z=351 [M+H]+.

The (3S)-3-(pyridin-2-yloxy)pyrrolidine used as starting material was prepared in 62% yield by an analogous method to Example 576, preparation of starting materials, starting from tert-butyl (3R)-3-hydroxypyrrolidine-1-carboxylate and pyridin-2-ol.

1H NMR (399.9 MHz, DMSO-$d_6$) δ 1.72-1.80 (1H, m), 1.97-2.06 (1H, m), 2.75-2.84 (2H, m), 2.87-2.94 (1H, m), 3.05-3.10 (1H, m), 5.34-5.38 (1H, m), 6.75-6.77 (1H, m), 6.93-6.96 (1H, m), 7.66-7.70 (1H, m), 8.15-8.17 (1H, m); m/z=165 [M+H]+.

EXAMPLES 590-592

The following compounds were prepared in 22-51% yield by an analogous method to Example 447, starting from (3R)-1-[3-(trifluoromethyl)[1,2,4]triazolo[4,3-b]pyridazin-6-yl]pyrrolidin-3-ol (obtained as described in Example 587, preparation of starting materials) and the appropriate phenol:—

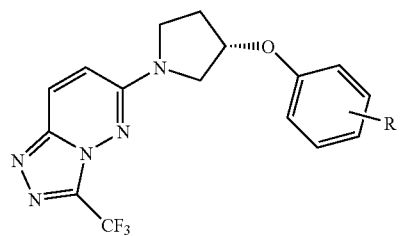

| Ex. R | 1H NMR (399.9 MHz, DMSO-$d_6$) | m/z [M + H]+ |
|---|---|---|
| 590 3-CN | δ 2.24-2.29 (1H, m), 2.31-2.39 (1H, m), 3.62-3.89 (4H, m), 5.33 (1H, s), 7.32 (1H, d), 7.34-7.37 (1H, m), 7.43-7.46 (1H, m), 7.51-7.55 (2H, m), 8.24-8.26 (1H, m) | 375 |
| 591 4-CN | δ 2.27-2.30 (1H, m), 2.33-2.39 (1H, m), 3.62-3.90 (4H, m), 5.37 (1H, s), 7.17-7.21 (2H, m), 7.31 (1H, d), 7.79-7.83 (2H, m), 8.25 (1H, d) | 375 |
| 592 4-CF3 | δ 2.26-2.31 (1H, m), 2.33-2.40 (1H, m), 3.63-3.90 (4H, m), 5.35 (1H, s), 7.20 (2H, d), 7.32 (1H, d), 7.69 (2H, d), 8.25 (1H, d) | 418 |

EXAMPLE 593

Preparation of 6-[(2S)-2-methyl-4-(pyridin-3-ylmethyl)piperazin-1-yl]-3-(trifluoromethyl)[1,2,4]triazolo[4,3-b]pyridazine

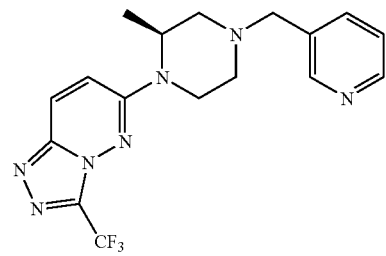

A mixture of pyridine-3-carboxaldehyde and 6-[(2S)-2-methylpiperazin-1-yl]-3-(trifluoromethyl)-[1,2,4]triazolo[4,3-b]pyridazine (obtained as described in Example 358, preparation of starting materials) was allowed to react by General Synthetic Method 5, to give 6-[(2S)-2-methyl-4-(pyridin-3-ylmethyl)piperazin-1-yl]-3-(trifluoromethyl)[1,2,4]triazolo[4,3-b]pyridazine in 76% yield.

1H NMR (500.1 MHz, DMSO-d6, 373K) δ 1.31 (3H, d), 2.42 (1H, m), 2.56 (1H, m), 2.88 (1H, m), 3.04 (1H, m), 3.33 (1H, m), 3.77 (2H, m), 4.05 (1H, m), 4.51 (1H, m), 7.47 (2H, m), 7.91 (1H, m), 8.15 (1H, d), 8.56 (1H, m), 8.63 (1H, m); m/z=378 [M+H]+.

EXAMPLES 594-598

The following compounds were prepared in 43-89% yield by General Synthetic Method 5, starting from 6-[(2S)-2-methylpiperazin-1-yl]-3-(trifluoromethyl)-[1,2,4]triazolo[4,3-b]pyridazine and the appropriate aldehyde:—

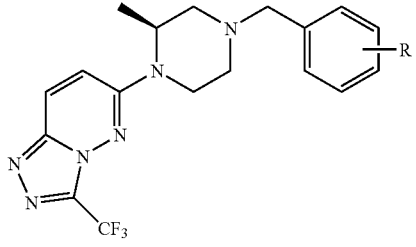

| Ex. R | 1H NMR (400.1 MHz, CDCl3) | m/z [M + H]+ |
|---|---|---|
| 594 4-CN | δ 1.47 (3H, d), 2.70 (1H, m), 2.86 (1H, m), 3.20 (1H, m), 3.50 (1H, m), 3.63 (1H, m), 4.01 (1H, d), 4.15 (2H, m), 4.55 (1H, m), 7.05 (1H, d), 7.60 (2H, d), 7.73 (2H, d), 8.05 (1H, d) | 402 |
| 595 3,4-di-F | δ 1.35 (3H, d), 2.22 (1H, m), 2.36 (1H, m), 2.76 (1H, m), 2.95 (1H, m), 3.33 (1H, m), 3.44 (1H, d), 3.55 (1H, d), 3.98 (1H, m), 4.33 (1H, m), 7.04-7.16 (3H, m), 7.23 (1H, m), 7.93 (1H, d) | 413 |
| 596 3,5-di-F | δ 1.48 (3H, d), 2.73 (1H, m), 2.90 (1H, m), 3.28 (1H, m), 3.57 (1H, m), 3.67 (1H, m), 4.00 (1H, d), 4.15 (2H, m), 4.58 (1H, m), 6.89 (1H, m), 7.01 (2H, d), 7.05 (1H, d), 8.06 (1H, d) | 413 |
| 597 4-F | δ 1.51 (3H, d), 2.83 (1H, m), 3.02 (1H, m), 3.41 (1H, m), 3.77 (2H, m), 4.18 (2H, m), 4.35 | 395 |

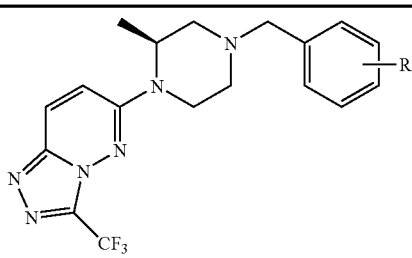

| Ex. | R | 1H NMR (400.1 MHz, CDCl3) | m/z [M + H]+ |
|---|---|---|---|
| 598 | 3-CN, 4-F | (1H, d), 4.64 (1H, m), 7.03 (1H, d), 7.15 (2H, m), 7.45 (2H, m), 8.05 (1H, d) δ 1.36 (3H, d), 2.25 (1H, m), 2.41 (1H, m), 2.74 (1H, m), 2.92 (1H, m), 3.33 (1H, m), 3.49 (1H, d), 3.58 (1H, d), 3.99 (1H, m), 4.34 (1H, m), 7.06 (1H, d), 7.21 (1H, m), 7.63 (2H, m), 7.94 (1H, d) | 420 |

EXAMPLE 599

Preparation of 6-[(2R)-2-methyl-4-(pyridin-3-ylmethyl)piperazin-1-yl]-3-(trifluoromethyl)[1,2,4]triazolo[4,3-b]pyridazine

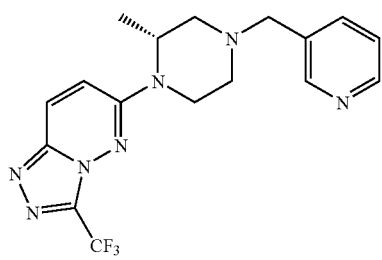

A mixture of pyridine-3-carboxaldehyde and 6-[(2R)-2-methylpiperazin-1-yl]-3-(trifluoromethyl)-[1,2,4]triazolo[4,3-b]pyridazine was allowed to react by General Synthetic Method 5 to give 6-[(2R)-2-methyl-4-(pyridin-3-ylmethyl)piperazin-1-yl]-3-(trifluoromethyl)[1,2,4]triazolo[4,3-b]pyridazine in quantitative yield.

1H NMR (500.1 MHz, DMSO-d6, 373K) δ 1.30 (3H, d), 2.37 (1H, m), 2.55 (1H, m), 2.85 (1H, m), 3.02 (1H, m), 3.32 (1H, m), 3.73 (2H, m), 4.04 (1H, m), 4.50 (1H, m), 7.45 (2H, m), 7.87 (1H, m), 8.15 (1H, d), 8.54 (1H, m), 8.61 (1H, m); m/z=378 [M+H]+.

The 6-[(2R)-2-methylpiperazin-1-yl]-3-(trifluoromethyl)-[1,2,4]triazolo[4,3-b]pyridazine used as starting material was prepared in 2 steps in 74% overall yield by an analogous method to Example 223, preparation of starting materials, starting from 6-chloro-3-(trifluoromethyl)-[1,2,4]triazolo[4,3-b]pyridazine and (3R)-tert-butyl 3-methylpiperazine-1-carboxylate.

1H NMR (399.1 MHz, DMSO-d6) δ 1.23 (3H, d), 2.43 (1H, m), 2.65 (1H, m), 2.85 (2H, m), 3.04 (2H, m), 3.91 (1H, m), 4.35 (1H, m), 7.56 (1H, d), 8.23 (1H, d); m/z=287 [M+H]+.

EXAMPLES 600-604

The following compounds were prepared in 56-93% yield by General Synthetic Method 5, starting from 6-[(2R)-2-methylpiperazin-1-yl]-3-(trifluoromethyl)-[1,2,4]triazolo[4,3-b]pyridazine and the appropriate aldehyde:—

| Ex. | R | 1H NMR (400.1 MHz, CDCl3) | m/z [M + H]+ |
|---|---|---|---|
| 600 | 4-CN | δ 1.46 (3H, d), 2.68 (1H, m), 2.84 (1H, m), 3.18 (1H, m), 3.48 (1H, m), 3.62 (1H, m), 3.99 (1H, d), 4.14 (2H, m), 4.54 (1H, m), 7.05 (1H, d), 7.59 (2H, d), 7.72 (2H, d), 8.04 (1H, d) | 402 |
| 601 | 3,4-di-F | δ 1.47 (3H, d), 2.70 (1H, m), 2.87 (1H, m), 3.25 (1H, m), 3.56 (1H, m), 3.66 (1H, m), 3.97 (1H, m), 4.14 (2H, m), 4.57 (1H, m), 7.02-7.33 (4H, m), 8.04 (1H, d) | 413 |
| 602 | 3,5-di-F | δ 1.47 (3H, d), 2.68 (1H, m), 2.85 (1H, m), 3.23 (1H, m), 3.52 (1H, m), 3.64 (1H, m), 3.95 (1H, d), 4.12 (2H, m), 4.56 (1H, m), 6.88 (1H, m), 7.00 (2H, m), 7.05 (1H, d), 8.05 (1H, d) | 413 |
| 603 | 4-F | δ 1.50 (3H, d), 2.82 (1H, m), 3.00 (1H, m), 3.39 (1H, m), 3.75 (2H, m), 4.17 (2H, m), 4.33 (1H, d), 4.63 (1H, m), 7.02 (1H, d), 7.15 (2H, m), 7.45 (2H, m), 8.05 (1H, d) | 395 |
| 604 | 3-CN, 4-F | δ 1.35 (3H, d), 2.25 (1H, m), 2.41 (1H, m), 2.74 (1H, m), 2.93 (1H, m), 3.33 (1H, m), 3.49 (1H, d), 3.58 (1H, d), 3.99 (1H, m), 4.35 (1H, m), 7.06 (1H, d), 7.21 (1H, m), 7.63 (2H, m), 7.94 (1H, d) | 420 |

EXAMPLE 605

Preparation of 1'-[3-(trifluoromethyl)[1,2,4]triazolo[4,3-b]pyridazin-6-yl]-1',2',3',6'-tetrahydro-3,4'-bipyridine

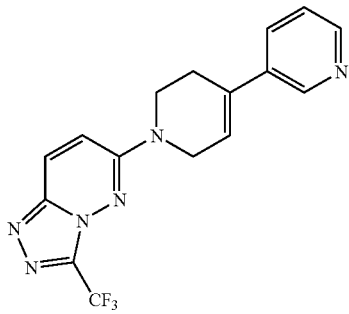

Sodium carbonate (114 mg, 1.08 mmol) was added to 1-[3-(trifluoromethyl)-[1,2,4]triazolo[4,3-b]pyridazin-6-yl]-1,2,3,6-tetrahydropyridin-4-yl trifluoromethanesulfonate (150 mg, 0.36 mmol) and 3-(4,4,5,5-tetramethyl-1,3,2-dioxaborolan-2-yl)pyridine (81 mg, 0.40 mmol) in a mixture of DME (2 mL) and water (0.5 mL). The mixture was bubbled with nitrogen for 10 minutes then tetrakis(triphenylphosphine)palladium(0) (20.77 mg, 0.02 mmol) was added and the mixture was stirred at 80° C. for 3 hours. The reaction mixture was cooled to room temperature and diluted with EtOAc (3 mL) and water (2 mL). The organic layer was separated and dried, and the solvent was evaporated to give crude product. Purification by flash silica chromatography, elution gradient 0 to 3% MeOH in DCM, gave 1'-[3-(trifluoromethyl)[1,2,4]triazolo[4,3-b]pyridazin-6-yl]-1',2',3',6'-tetrahydro-3,4'-bipyridine (100 mg, 80%).

1H NMR (399.1 MHz, DMSO-d6) δ 2.70 (2H, m), 3.91 (2H, m), 4.29 (2H, m), 6.44 (1H, m), 7.41 (1H, m), 7.69 (1H, d), 7.89 (1H, m), 8.30 (1H, d), 8.50 (1H, m), 8.74 (1H, m); m/z=347 [M+H]+.

The 1-[3-(trifluoromethyl)-[1,2,4]triazolo[4,3-b]pyridazin-6-yl]-1,2,3,6-tetrahydropyridin-4-yl trifluoromethanesulfonate used as starting material was prepared as follows:—

A solution of 1-(3-(trifluoromethyl)-[1,2,4]triazolo[4,3-b]pyridazin-6-yl)piperidin-4-one (obtained as described in Example 310, preparation of starting materials) (11.08 g, 38.85 mmol) in THF (200 mL) was added dropwise to 1M lithium bis(trimethylsilyl)amide in THF (42.7 mL, 42.73 mmol) at −78° C., over a period of 30 minutes under nitrogen. The resulting suspension was stirred at −78° C. for 20 minutes, then a solution of N-phenyltrifluoromethanesulfonimide (15.27 g, 42.73 mmol) in THF (150 ml) was added dropwise over a period of 10 minutes. The mixture was stirred at −78° C. for 30 minutes then allowed to warm to room temperature overnight. The reaction mixture was quenched with saturated aqueous ammonium chloride (5 mL), then concentrated and diluted with DCM (500 mL), washed with water (300 mL) then brine (300 mL) and evaporated to afford crude product. DCM (100 mL) was added to the crude product, the precipitate was collected by filtration and the filtrate was purified by flash silica chromatography, elution gradient 50 to 80% EtOAc in isohexane. Pure fractions were evaporated to dryness and combined with the previously collected precipitate to afford 1-(3-(trifluoromethyl)-[1,2,4]triazolo[4,3-b]pyridazin-6-yl)-1,2,3,6-tetrahydropyridin-4-yl trifluoromethanesulfonate (12.91 g, 80%).

1H NMR (399.9 MHz, DMSO-d6) δ 2.63 (2H, m), 3.90 (2H, m), 4.25 (2H, m), 6.19 (1H, m), 7.67 (1H, d), 8.33 (1H, d); m/z=418 [M+H]+.

EXAMPLES 606-609

The following compounds were prepared in 54-77% yield by an analogous method to Example 605, starting from 1-[3-(trifluoromethyl)-[1,2,4]triazolo[4,3-b]pyridazin-6-yl]-1,2,3,6-tetrahydropyridin-4-yl trifluoromethanesulfonate and the appropriate heteroaryl boronic acid or boronic acid pinacol ester:—

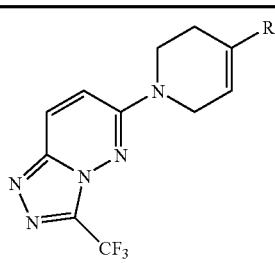

| Ex. R | 1H NMR (399.9 MHz, DMSO-d6) | m/z [M + H]+ |
|---|---|---|
| 606 3-fluoropyridin-4-yl | δ 2.68 (2H, m), 3.90 (2H, m), 4.31 (2H, m), 6.47 (1H, m), 7.49 (1H, m), 7.68 (1H, d), 8.31 (1H, d), 8.44 (1H, m), 8.57 (1H, d) | 365 |
| 607 5-fluoropyridin-3-yl | δ 2.71 (2H, m), 3.91 (2H, m), 4.30 (2H, m), 6.55-6.57 (1H, m), 7.70 (1H, d), 7.84-7.88 (1H, m), 8.30 (1H, d), 8.50 (1H, m), 8.63 (1H, m) | 365 |
| 608 5-(ethoxycarbonyl)pyridin-3-yl | δ 1.36 (3H, t), 2.75 (2H, m), 3.92 (2H, m), 4.31 (2H, m), 4.38 (2H, q), 6.56 (1H, m), 7.69 (1H, d), 8.29-8.32 (2H, m), 8.98-9.00 (2H, m) | 419 |
| 609 5-fluoro-6-methoxypyridin-3-yl | δ 2.66 (2H, m), 3.89 (2H, m), 3.97 (3H, s), 4.26-4.27 (2H, m), 6.38 (1H, m), 7.69 (1H, d), 7.87-7.91 (1H, m), 8.11 (1H, d), 8.29 (1H, d) | 395 |

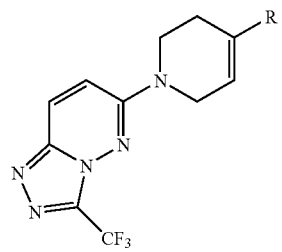

EXAMPLE 610

Preparation of 6-(4-pyridin-3-ylpiperidin-1-yl)-3-(trifluoromethyl)[1,2,4]triazolo[4,3-b]pyridazine

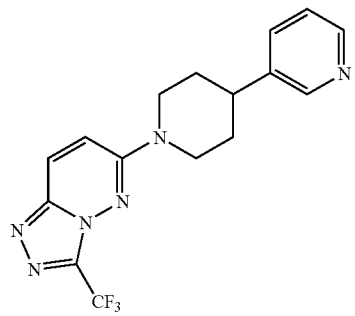

A mixture of 1'-[3-(trifluoromethyl)[1,2,4]triazolo[4,3-b]pyridazin-6-yl]-1',2',3',6'-tetrahydro-3,4'-bipyridine (obtained as described in Example 605) (82 mg, 0.24 mmol) and 10% palladium on carbon (25.2 mg, 0.02 mmol) in MeOH (10 mL) was stirred under an atmosphere of hydrogen at atmospheric pressure for 3 days. The catalyst was removed by filtration and the solvent evaporated to give crude product, which was purified by flash silica chromatography, elution gradient 0 to 3% MeOH in DCM. Fractions containing the desired product were evaporated to dryness to give 6-(4-pyridin-3-ylpiperidin-1-yl)-3-(trifluoromethyl)[1,2,4]triazolo[4,3-b]pyridazine (24 mg, 29%).

1H NMR (399.1 MHz, DMSO-d6) δ 1.75 (2H, m), 1.93 (2H, m), 2.94 (1H, m), 3.14 (2H, m), 4.44 (2H, m), 7.33 (1H, m), 7.69 (2H, m), 8.26 (1H, d), 8.43 (1H, m), 8.53 (1H, d); m/z=349 [M+H]+.

EXAMPLES 611-614

The following compounds were prepared in 13-57% yield by an analogous method to Example 610, starting from the appropriate tetrahydro bipyridine (obtained as described in Examples 606-609):—

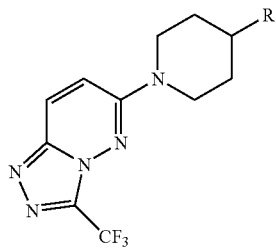

| Ex. | R | 1H NMR (399.9 MHz, DMSO-d6) | m/z [M + H]+ |
|---|---|---|---|
| 611 | 3-fluoropyridin-4-yl | δ 1.79 (2H, m), 1.91 (2H, m), 3.21 (3H, m), 4.44 (2H, m), 7.44 (1H, m), 7.67 (1H, d), 8.26 (1H, d), 8.38 (1H, d), 8.51 (1H, d) | 367 |
| 612 | 5-fluoropyridin-3-yl | δ 1.75-1.79 (2H, m), 1.94 (2H, m), 2.98-3.17 (3H, m), 4.43-4.46 (2H, m), 7.66-7.72 (2H, m), 8.26 (1H, d), 8.43 (2H, m) | 367 |
| 613 | 5-(ethoxycarbonyl)pyridin-3-yl | δ 1.34 (3H, t), 1.78-1.82 (2H, m), 1.96 (2H, m), 3.08-3.17 (3H, m), 4.36 (2H, q), 4.46 (2H, m), 7.67 (1H, d), 8.16 (1H, m), 8.26 (1H, d), 8.79 (1H, m), 8.96 (1H, m) | 462 [1] |
| 614 | 5-fluoro-6-methoxypyridin-3-yl | δ 1.70-1.74 (2H, m), 1.90 (2H, m), 2.92 (1H, m), 3.08-3.14 (2H, m), 3.92 (3H, s), 4.43 (2H, m), 7.65-7.69 (2H, m), 7.91 (1H, m), 8.25 (1H, d) | 397 |

[1] Detected as adduct with acetonitrile used as solvent in mass spectral determination

EXAMPLE 615

Preparation of 4-[1-[3-(trifluoromethyl)[1,2,4]triazolo[4,3-b]pyridazin-6-yl]piperidin-4-yl]aniline

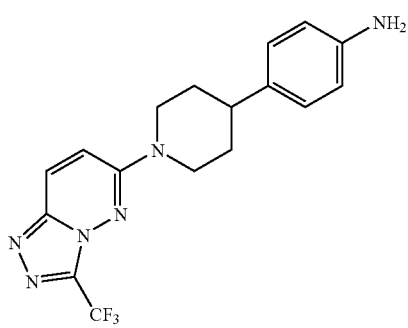

DIPEA (1.631 mL, 9.36 mmol) was added to 6-chloro-3-(trifluoromethyl)-[1,2,4]triazolo[4,3-b]pyridazine (1.389 g, 6.24 mmol) and 4-(piperidin-4-yl)aniline (1.21 g, 6.86 mmol) in DMF (30 mL). The resulting solution was stirred at 80° C. for 2 hours. The reaction mixture was evaporated to dryness, redissolved in DCM and purified by flash chromatography on silica gel, elution gradient 0 to 3% MeOH in DCM. Pure fractions were evaporated to dryness to give 4-[1-[3-(trifluoromethyl)[1,2,4]triazolo[4,3-b]pyridazin-6-yl]piperidin-4-yl]aniline (1.910 g, 84%) as a solid.

1H NMR (399.9 MHz, CDCl3) δ 1.72-1.79 (2H, m), 1.96-2.00 (2H, m), 2.70-2.73 (1H, m), 3.06-3.14 (2H, m), 3.60 (2H, s), 4.33-4.38 (2H, m), 6.65 (2H, d), 7.01 (2H, d), 7.12 (1H, d), 7.91 (1H, d); m/z=363 [M+H]+.

The 4-(piperidin-4-yl)aniline used as starting material was prepared as follows;

TFA (5 mL) was added to tert-butyl 4-(4-aminophenyl)piperidine-1-carboxylate (1.9 g, 6.87 mmol, CAS 170011-57-1) in DCM (5 mL). The resulting solution was stirred at ambient temperature for 2 hours then added to an SCX column. The desired product was eluted from the column using 2M ammonia in methanol and the solvent evaporated to dryness to give 4-(piperidin-4-yl)aniline (1.210 g, 100%) as a solid.

m/z=177 [M+H]+.

EXAMPLE 616

Preparation of 3-[1-[3-(trifluoromethyl)[1,2,4]triazolo[4,3-b]pyridazin-6-yl]piperidin-4-yl]aniline

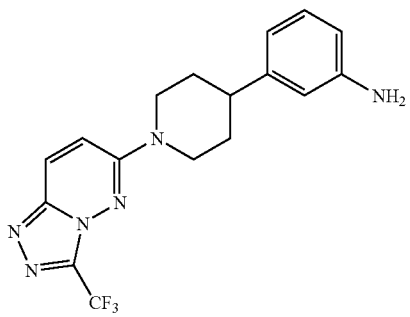

Obtained in 78% yield by an analogous procedure to Example 615, starting from 6-chloro-3-(trifluoromethyl)-[1,2,4]triazolo[4,3-b]pyridazine and 3-(piperidin-4-yl)aniline.

1H NMR (399.9 MHz, CDCl3) δ 1.76-1.80 (2H, m), 2.00 (2H, m), 2.74 (1H, m), 3.07-3.14 (2H, m), 3.64 (2H, s), 4.34-4.39 (2H, m), 6.54-6.63 (3H, m), 7.11 (2H, m), 7.92 (1H, d); m/z=363 [M+H]+.

The 3-(piperidin-4-yl)aniline used as starting material was prepared in 97% yield by an analogous procedure to Example 616, preparation of starting materials, starting from tert-butyl 4-(3-aminophenyl)piperidine-1-carboxylate (CAS 387827-19-2).

m/z=177 [M+H]+.

EXAMPLES 617-622

The following compounds were prepared in 9-67% yield by an analogous method to Example 447, starting from 1-[3-(trifluoromethyl)-[1,2,4]triazolo[4,3-b]pyridazin-6-yl]piperidin-4-ol (obtained as described in Example 412, preparation of starting materials) and the appropriate hydroxy heterocycle:—

| Ex. | R | 1H NMR (399.9 MHz, DMSO-d6) | m/z [M + H]+ |
|---|---|---|---|
| 617 | 5-chloropyridin-3-yl | δ 1.75 (2H, m), 2.10 (2H, m), 3.52 (2H, m), 3.99 (2H, m), 4.85 (1H, m), 7.65 (1H, d), 7.74 (1H, m), 8.25 (2H, m), 8.33 (1H, d) | 399 |
| 618 | 5-chloropyridin-2-yl | δ 1.73-1.81 (2H, m), 2.08-2.14 (2H, m), 3.49-3.56 (2H, m), 3.96-4.02 (2H, m), 5.25-5.28 (1H, m), 6.88 (1H, d), 7.65 (1H, d), 7.80-7.83 (1H, m), 8.22-8.27 (2H, m) | 399 |
| 619 | pyrimidin-4-yl | δ 1.78-1.83 (2H, m), 2.12-2.17 (2H, m), 3.51-3.58 (2H, m), 3.97-4.03 (2H, m), 5.41 (1H, m), 6.95-6.97 (1H, m), 7.66 (1H, d), 8.27 (1H, d), 8.53-8.55 (1H, m), 8.80 (1H, m) | 366 |
| 620 | 5-bromopyridin-2-yl | δ 1.80-1.86 (2H, m), 2.12-2.16 (2H, m), 3.51-3.58 (2H, m), 3.96-4.02 (2H, m), 5.22-5.25 (1H, m), 7.66 (1H, d), 8.26 (1H, d), 8.78 (2H, s) | 444 |
| 621 | 4-trifluoromethylpyridin-2-yl | δ 1.76-1.85 (2H, m), 2.11-2.16 (2H, m), 3.53-3.60 (2H, m), 3.97-4.03 (2H, m), 5.37-5.41 (1H, m), 7.20 (1H, d), 7.33-7.34 (1H, m), 7.66 (1H, d), 8.27 (1H, d), 8.46 (1H, d) | 433 |
| 622 | 4-methylpyrimidin-2-yl | δ 1.78-1.82 (2H, m), 2.10-2.15 (2H, m), 2.41 (3H, s), 3.53-3.59 (2H, m), 3.95-4.01 (2H, m), 5.26 (1H, m), 7.02 (1H, d), 7.66 (1H, d), 8.26 (1H, d), 8.45 (1H, d) | 380 |

EXAMPLES 623-627

The following compounds were prepared in 12-29% yield by an analogous method to Example 447, starting from 1-[3-(trifluoromethyl)-[1,2,4]triazolo[4,3-b]pyridazin-6-yl]piperidin-4-ol (obtained as described in Example 412, preparation of starting materials) and the appropriate phenol:—

| Ex. | R | 1H NMR (399.9 MHz, DMSO-d6) | m/z [M + H]+ |
|---|---|---|---|
| 623 | 3-CN | δ 1.72-1.75 (2H, m), 2.08-2.13 (2H, m), 3.48-3.55 (2H, m), 3.96-4.01 (2H, m), 4.80 (1H, m), 7.35-7.38 (1H, m), 7.40-7.43 (1H, m), 7.49-7.56 (2H, m), 7.65 (1H, d), 8.26 (1H, d) | 389 |
| 624 | 4-CF3 | δ 1.75-1.78 (2H, m), 2.09-2.11 (2H, m), 3.52-3.58 (2H, m), 3.96-4.00 (2H, m), 4.84 (1H, m), 7.21 (2H, d), 7.64-7.68 (3H, m), 8.27 (1H, d) | 432 |
| 625 | 4-F | δ 1.69-1.76 (2H, m), 2.03-2.09 (2H, m), 3.49-3.55 (2H, m), 3.93-3.99 (2H, m), 4.62-4.65 (1H, m), 7.02-7.06 (2H, m), 7.11-7.15 (2H, m), 7.64 (1H, d), 8.25 (1H, d) | 382 |
| 626 | 3-CF3 | δ 1.73-1.78 (2H, m), 2.07-2.12 (2H, m), 3.52-3.59 (2H, m), 3.95-4.00 (2H, m), 4.84 (1H, m), 7.30-7.35 (3H, m), 7.53-7.57 (1H, m), 7.65 (1H, d), 8.26 (1H, d) | 432 |
| 627 | 4-CN | δ 1.74-1.77 (2H, m), 2.09 (2H, m), 3.51-3.56 (2H, m), 3.96-4.00 (2H, m), 4.86 (1H, m), 7.20 (2H, d), 7.65 (1H, d), 7.79 (2H, d), 8.26 (1H, d) | 389 |

EXAMPLES 628-629

The following compounds were prepared in 23-48% yield by an analogous method to Example 448, starting from 1-[3-(trifluoromethyl)-[1,2,4]triazolo[4,3-b]pyridazin-6-yl]piperidin-4-ol (obtained as described in Example 412, preparation of starting materials) and the appropriate chloropyridine:—

| Ex. | R | 1H NMR (399.9 MHz, DMSO-d6) | m/z [M + H]+ |
|---|---|---|---|
| 628 | 5-CN | δ 1.78-1.84 (2H, m), 2.13-2.16 (2H, m), 3.51-3.57 (2H, m), 3.97-4.03 (2H, m), 5.39-5.42 (1H, m), 7.01 (1H, d), 7.66 (1H, d), 8.16-8.18 (1H, m), 8.27 (1H, d), 8.71 (1H, d) | 390 |
| 629 | 4-CN | δ 1.78-1.81 (2H, m), 2.11 (2H, m), 3.51-3.57 (2H, m), 3.98-4.02 (2H, m), 5.35 (1H, m), 7.38 (1H, m), 7.41-7.43 (1H, m), 7.66 (1H, d), 8.27 (1H, d), 8.42-8.43 (1H, m) | 390 |

EXAMPLES 630-635

The following compounds were prepared in 10-90% yield by an analogous method to Example 512, starting from 4-[1-[3-(trifluoromethyl)[1,2,4]triazolo[4,3-b]pyridazin-6-yl]piperidin-4-yl]benzoic acid and the appropriate amine:—

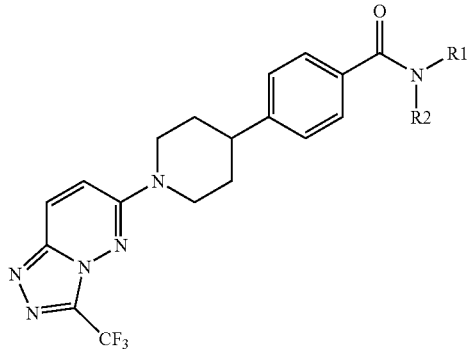
| Ex. | NR1R2 | 1H NMR (399.9 MHz, CDCl3) | m/z [M + H]+ |
|---|---|---|---|
| 630 | —N(Me)CH₂CH₂OH | δ 1.76-1.86 (2H, m), 2.03 (2H, m), 2.84-2.90 (1H, m), 3.08-3.17 (5H, m), 3.72-3.90 (4H, m), 4.37-4.41 (2H, m), 7.13 (1H, d), 7.26 (2H, d), 7.42 (2H, d), 7.94 (1H, d) | 449 |
| 631 | —NHCH₂CH₂-(pyrrolidin-1-yl) | δ 1.77-1.84 (6H, m), 2.02-2.05 (2H, m), 2.54-2.57 (4H, m), 2.70 (2H, m), 2.89 (1H, m), 3.10-3.18 (2H, m), 3.52-3.57 (2H, m), 4.38-4.41 (2H, m), 6.79 (1H, t), 7.13 (1H, d), 7.29 (2H, d), 7.75 (2H, d), 7.94 (1H, d) | 488 |
| 632 | 4-methylpiperazin-1-yl | δ 1.81 (2H, m), 2.02 (2H, m), 2.33 (3H, s), 2.43 (4H, m), 2.87 (1H, m), 3.13 (2H, m), 3.48-3.78 (4H, m), 4.39 (2H, m), 7.13 (1H, d), 7.26 (2H, d), 7.37 (2H, d), 7.94 (1H, d) | 474 |
| 633 | —NHCH₂CH₂OMe | δ 1.76-1.87 (2H, m), 2.01-2.05 (2H, m), 2.87-2.93 (1H, m), 3.10-3.18 (2H, m), 3.38 (3H, s), 3.56 (2H, m), 3.63-3.67 (2H, m), 4.38-4.41 (2H, m), 6.48 (1H, t), 7.14 (1H, d), 7.29 (2H, d), 7.75 (2H, d), 7.95 (1H, d) | 449 |
| 634 | NMe2 | δ 1.79-1.86 (2H, m), 2.00-2.04 (2H, m), 2.85 (1H, s), 2.98-3.17 (8H, m), 4.37-4.41 (2H, m), 7.13 (1H, d), 7.24 (2H, d), 7.38 (2H, d), 7.94 (1H, d) | 419 |
| 635 | morpholin-4-yl | δ 1.79-1.83 (2H, m), 2.00-2.04 (2H, m), 2.87 (1H, m), 3.10-3.17 (2H, m), 3.69 (8H, m), 4.37-4.41 (2H, m), 7.13 (1H, d), 7.27 (2H, d), 7.38 (2H, d), 7.95 (1H, d) | 461 |

EXAMPLES 636-642

The following compounds were prepared in 5-85% yield by an analogous method to Example 512, starting from 4-[1-[3-(trifluoromethyl)[1,2,4]triazolo[4,3-b]pyridazin-6-yl]piperidin-4-yl]benzoic acid and the appropriate amine:—

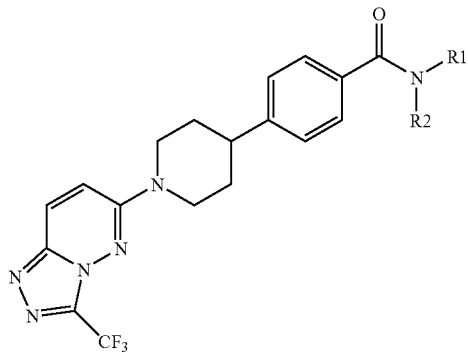

| Ex. | NR1R2 | 1H NMR (399.9 MHz, DMSO-d6) | m/z [M + H]+ |
|---|---|---|---|
| 636 | (piperazine) | δ 1.68-1.78(2H, m), 1.92-1.97(2H, m), 2.65 (4H, m), 2.89-2.97(1H, m), 3.09-3.16(2H, m), 3.44-3.52(4H, m), 4.47(2H, m), 7.38(2H, d), 7.67(1H, d), 7.81(2H, d), 8.26(1H, d) | 460 |
| 637 | NHEt | δ 1.14(3H, t), 1.68-1.79(2H, m), 1.92(2H, m), 2.91-2.97(1H, m), 3.10-3.16(2H, m), 4.44 (2H, d), 7.36(2H, d), 7.67(1H, d), 7.78(2H, d), 8.25(1H, d), 8.36(1H, t), (2H obscured by water) | 419 |
| 638 | (morpholinoethylamino) | δ 1.74(2H, m), 1.92(2H, m), 2.94(1H, m), 3.14 (2H, m), 3.40(2H, m), 3.60(4H, m), 4.44(2H, m), 7.37(2H, d), 7.67(1H, d), 7.78(2H, d), 8.26 (1H, d), 8.33(1H, t), (2H obscured by water, 4H obscured by DMSO) | 504 |
| 639 | (2-oxopyrrolidin-1-yl ethylamino) | δ 1.72-1.79(2H, m), 1.87-1.94(4H, m), 2.16-2.20(2H, m), 2.91-2.97(1H, m), 3.10-3.16 (2H, m), 3.33-3.43(6H, m), 4.44(2H, d), 7.37 (2H, d), 7.67(1H, d), 7.75(2H, d), 8.25(1H, d), 8.43(1H, t) | 502 |
| 640 | (5-methylisoxazol-3-ylmethylamino) | δ 1.72-1.78(2H, m), 1.92(2H, m), 2.37(3H, s), 2.96(1H, m), 3.11-3.17(2H, m), 4.42-4.46 (4H, m), 6.14(1H, s), 7.39(2H, d), 7.67(1H, d), 7.83(2H, d), 8.26(1H, d), 8.97(1H, t) | 486 |
| 641 | (1-methylpiperidin-4-ylamino) | δ 1.54-1.78(6H, m), 1.92(2H, m), 2.00-2.10 (2H, m), 2.21(3H, s), 2.81(2H, m), 2.91-2.98 (1H, m), 3.10-3.16(2H, m), 3.72-3.76(1H, m), 4.44(2H, m), 7.36(2H, d), 7.67(1H, d), 7.79 (2H, d), 8.14(1H, d), 8.25(1H, d) | 488 |
| 642 | (4-methylpiperazin-1-yl ethylamino) | δ 1.74(2H, m), 1.92(2H, m), 2.17(3H, s), 2.32-2.48(10H, m), 2.94(1H, m), 3.13(2H, m), 3.36 (2H, m), 4.44(2H, m), 7.36(2H, d), 7.67(1H, d), 7.77(2H, d), 8.27(2H, m) | 517 |

EXAMPLES 643-652

The following compounds were prepared in 16-73% yield by an analogous method to Example 512, starting from 3-[1-[3-(trifluoromethyl)[1,2,4]triazolo[4,3-b]pyridazin-6-yl]piperidin-4-yl]benzoic acid and the appropriate amine:—

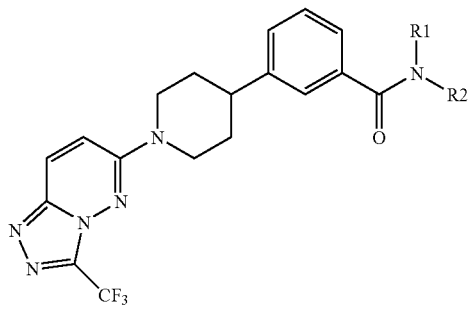

| Ex. | NR1R2 | 1H NMR (399.9 MHz, DMSO-d6) | m/z [M + H]+ |
|---|---|---|---|
| 643 | N–CH2CH2OH (N-methyl) | δ 1.69-1.77(2H, m), 1.93(2H, m), 2.89-2.97 (4H, m), 3.10-3.16(2H, m), 3.49-3.61(4H, m), 4.43(2H, m), 4.75(1H, t,), 7.23-7.24(1H, m), 7.30-7.35(3H, m), 7.67(1H, d), 8.25(1H, d) | 449 |
| 644 | HN-CH2CH2-pyrrolidinyl | δ 1.64-1.71(4H, m), 1.73-1.80(2H, m), 1.94 (2H, m), 2.46-2.49(4H, m), 2.56(2H, m), 2.91-2.97(1H, m), 3.11-3.17(2H, m), 3.35-3.39 (2H, m), 4.45(2H, m), 7.37-7.44(2H, m), 7.67-7.69(2H, m), 7.74(1H, s), 8.26(1H, d), 8.38 (1H, t) | 488 |
| 645 | 4-methylpiperazin-1-yl | δ 1.73(2H, m), 1.93(2H, m), 2.19(3H, s), 2.30 (4H, m), 2.94(1H, m), 3.13(2H, m), 3.33-3.66 (4H, m), 4.43(2H, m), 7.21(1H, m), 7.27(1H, s), 7.38(2H, m), 7.67(1H, d), 8.25(1H, d) | 474 |
| 646 | piperazin-1-yl | δ 1.68-1.78(2H, m), 1.92-1.97(2H, m), 2.69 (4H, m), 2.89-2.97(1H, m), 3.09-3.16(2H, m), 3.44-3.52(4H, m), 4.43(2H, m), 7.19-7.22 (1H, m), 7.26(1H, s), 7.31-7.40(2H, m), 7.67 (1H, d), 8.25(1H, d) | 460 |
| 647 | NMe2 | δ 1.68-1.79(2H, m), 1.93(2H, m), 2.88-2.97 (7H, m), 3.09-3.16(2H, m), 4.42-4.45(2H, m), 7.22-7.25(1H, m), 7.29(1H, s), 7.45-7.39(2H, m), 7.67(1H, d), 8.25(1H, d) | 419 |
| 648 | morpholin-4-yl | δ 1.69-1.78(2H, m), 1.93(2H, m), 2.90-2.96 (1H, m), 3.10-3.16(2H, m), 3.60(8H, m), 4.43 (2H, m), 7.23-7.26(1H, m), 7.31(1H, s), 7.36-7.41(2H, m), 7.67(1H, d), 8.25(1H, d) | 461 |
| 649 | NHMe | δ 1.75(2H, m), 1.94(2H, m), 2.78(3H, d), 2.94 (1H, m), 3.14(2H, m), 4.45(2H, m), 7.40(2H, m), 7.68(2H, m), 7.74(1H, s), 8.26(1H, d), 8.38 (1H, m) | 405 |
| 650 | HN-CH2CH2-morpholinyl | δ 1.75(2H, m), 1.94(2H, m), 2.44(6H, m), 2.95 (1H, m), 3.14(2H, m), 3.38(2H, m), 3.57(4H, m), 4.46(2H, m), 7.41(2H, m), 7.68(2H, m), 7.73(1H, s), 8.26(1H, d), 8.36(1H, t) | 504 |
| 651 | HN-(1-methylpiperidin-4-yl) | δ 1.58(2H, m), 1.76(4H, m), 1.94(4H, m), 2.16 (3H, s), 2.77(2H, m), 2.94(1H, m), 3.13(2H, m), 3.73(1H, m), 4.46(2H, m), 7.40(2H, m), 7.68 (2H, m), 7.74(1H, s), 8.18(1H, d), 8.26(1H, d) | 488 |

-continued

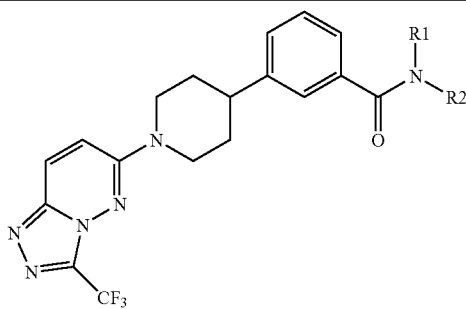

| Ex. | NR1R2 | 1H NMR (399.9 MHz, DMSO-d6) | m/z [M + H]+ |
|---|---|---|---|
| 652 | H N~~~N(N-methylpiperazinyl) | δ 1.75(2H, m), 1.94(2H, m), 2.14(3H, s), 2.30 (4H, m), 2.43(4H, m), 2.56(2H, m), 2.95(1H, m), 3.14(2H, m), 3.36(2H, m), 4.45(2H, m), 7.41(2H, m), 7.68(2H, m), 7.73(1H, s), 8.26 (1H, d), 8.33(1H, t) | 517 |

The 3-[1-[3-(trifluoromethyl)[1,2,4]triazolo[4,3-b]pyridazin-6-yl]piperidin-4-yl]benzoic acid used as starting material was prepared as follows:—

Preparation of ethyl 3-(pyridin-4-yl)benzoate

Obtained in 92% yield by an analogous procedure to Example 605, starting from 4-bromopyridine hydrochloride and 3-(ethoxycarbonyl)phenylboronic acid.

1H NMR (399.9 MHz, DMSO-d6) δ 1.37 (3H, t), 4.38 (2H, q), 7.71 (1H, m), 7.76 (2H, d), 8.08 (2H, m), 8.30 (1H, s), 8.69 (2H, d); m/z=228 [M+H]+.

Preparation of ethyl 3-(piperidin-4-yl)benzoate

Ethyl 3-(pyridin-4-yl)benzoate (1.46 g, 6.42 mmol), 5% palladium on carbon (50% wet) (0.301 g, 0.07 mmol) and citric acid monohydrate (0.601 g, 2.86 mmol) in a mixture of isopropanol (50 mL) and water (5 mL) were stirred under an atmosphere of hydrogen at 20 atmosphere and 70° C. for 15 hours. The reaction was cooled to room temperature, the catalyst removed by filtration and the solvent evaporated to give the crude product, which was purified by ion exchange chromatography, using an SCX column. The desired product was eluted from the column using 2M ammonia in methanol to give ethyl 3-(piperidin-4-yl)benzoate (1.190 g, 79%) as a liquid.

m/z=275 [M+H]+ (acetonitrile adduct).

Preparation of ethyl 3-[1-(3-(trifluoromethyl)-[1,2,4]triazolo[4,3-b]pyridazin-6-yl)piperidin-4-yl]benzoate Ethyl 3-(piperidin-4-yl)benzoate (1.195 g, 5.12 mmol) was added to 6-chloro-3-(trifluoromethyl)-[1,2,4]triazolo[4,3-b]pyridazine (1 g, 4.49 mmol) and DIPEA (1.174 mL, 6.74 mmol) in DMA (10 mL). The resulting solution was stirred at 125° C. for 2 hours. The reaction mixture was evaporated to dryness, redissolved in DCM and purified by flash silica chromatography, eluting with 50% EtOAc in isohexane. Pure fractions were evaporated to dryness to give a beige solid, which was triturated with ether to give ethyl 3-[1-(3-(trifluoromethyl)-[1,2,4]triazolo[4,3-b]pyridazin-6-yl)piperidin-4-yl]benzoate (0.805 g, 42.7%) as a solid.

1H NMR (399.9 MHz, DMSO-d6) δ 1.33 (3H, t), 1.74 (2H, m), 1.94 (2H, m), 2.99 (1H, m), 3.14 (2H, m), 4.32 (2H, q), 4.44 (2H, m), 7.47 (1H, m), 7.59 (1H, m), 7.67 (1H, d), 7.83 (2H, m), 8.25 (1H, d); m/z=420 [M+H]+.

Preparation of 3-[1-[3-(trifluoromethyl)[1,2,4]triazolo[4,3-b]pyridazin-6-yl]piperidin-4-yl]benzoic acid Obtained in 100% yield by an analogous procedure to Example 512, preparation of starting materials, starting from ethyl 3-[1-[3-(trifluoromethyl)[1,2,4]triazolo[4,3-b]pyridazin-6-yl]piperidin-4-yl]benzoate.

1H NMR (399.9 MHz, DMSO-d6) δ 1.69-1.79 (2H, m), 1.94 (2H, m), 2.95-3.01 (1H, m), 3.14 (2H, m), 4.44 (2H, m), 7.45 (1H, m), 7.54-7.56 (1H, m), 7.67 (1H, d), 7.79-7.82 (1H, m), 7.84 (1H, m), 8.25 (1H, d), 12.78 (1H, s); m/z=392 [M+H]+.

EXAMPLES 653-654

The following compounds were prepared in 25-37% yield by an analogous method to Example 447, starting from 1-[3-(trifluoromethyl)-[1,2,4]triazolo[4,3-b]pyridazin-6-yl]piperidin-4-ol (obtained as described in Example 412, preparation of starting materials) and the appropriate phenol:—

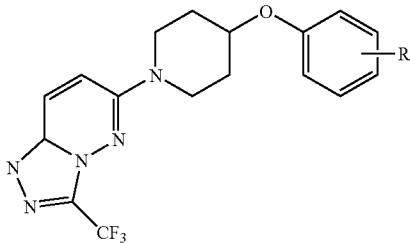

| Ex. | R | 1H NMR (399.9 MHz, DMSO-d6) | m/z [M + H]+ |
|---|---|---|---|
| 653 | 2-CF3 | δ 1.81(2H, m), 2.08(2H, m), 3.69(2H, m), 3.80(2H, m), 4.94(1H, m), 7.11(1H, m), 7.40(1H, m), 7.64(3H, m), 8.26(1H, d) | 432 |
| 654 | 2-CN | δ 1.82(2H, m), 2.11(2H, m), 3.65(2H, m), 3.90(2H, m), 4.94(1H, m), 7.12(1H, m), 7.41(1H, m), 7.68(2H, m), 7.75(1H, m), 8.27(1H, d) | 389 |

EXAMPLE 655

Preparation of N-[3-[1-[3-(trifluoromethyl)[1,2,4]triazolo[4,3-b]pyridazin-6-yl]piperidin-4-yl]phenyl]acetamide

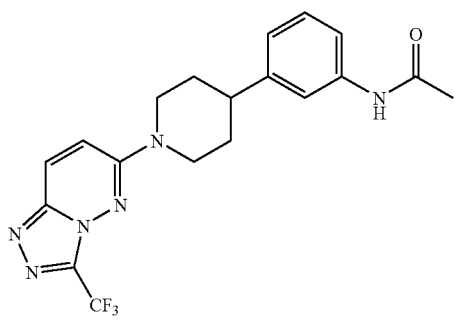

DIPEA (123 μl, 0.70 mmol) was added to 3-[1-(3-(trifluoromethyl)-[1,2,4]triazolo[4,3-b]pyridazin-6-yl)piperidin-4-yl]aniline (obtained as described in Example 616) (85 mg, 0.23 mmol), acetic acid (16 μl, 0.28 mmol) and HATU (107 mg, 0.28 mmol) in DMA (2 mL). The resulting solution was stirred at ambient temperature for 2 hours then purified by preparative HPLC (Waters XBridge Prep C18 OBD column, 5μ silica, 19 mm diameter, 100 mm length), using decreasingly polar mixtures of water (containing 1% ammonia) and acetonitrile as eluents. Fractions containing the desired compound were evaporated to dryness to give N-[3-[1-[3-(trifluoromethyl)[1,2,4]triazolo[4,3-b]pyridazin-6-yl]piperidin-4-yl]phenyl]acetamide (89 mg, 94%) as a solid.

1H NMR (399.9 MHz, DMSO-d6) δ 1.66 (2H, m), 1.91 (2H, m), 2.02 (3H, s), 2.84 (1H, m), 3.13 (2H, m), 4.42 (2H, m), 6.95 (1H, m), 7.22 (1H, m), 7.41 (1H, m), 7.49 (1H, s), 7.67 (1H, d), 8.25 (1H, d), 9.84 (1H, s); m/z=405 [M+H]+.

EXAMPLES 656-658

The following compounds were prepared in 71-86% yield by an analogous method to Example 655, starting from 3-[1-[3-(trifluoromethyl)[1,2,4]triazolo[4,3-b]pyridazin-6-yl]piperidin-4-yl]aniline and the appropriate carboxylic acid:—

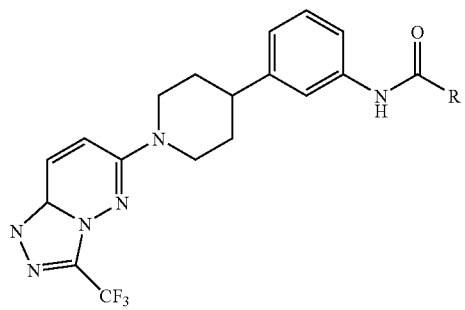

| Ex. | NHCOR | 1H NMR (399.9 MHz, DMSO-d6) | m/z [M + H]+ |
|---|---|---|---|
| 656 | ![piperidine-carboxamide with N-methyl] | δ 1.68(6H, m), 1.88(4H, m), 2.17(3H, s), 2.25 (1H, m), 2.83(3H, m), 3.13(2H, m), 4.42(2H, m), 6.94(1H, m), 7.21(1H, m), 7.42(1H, m), 7.56(1H, s), 7.67(1H, d), 8.25(1H, d), 9.77(1H, s) | 488 |

-continued

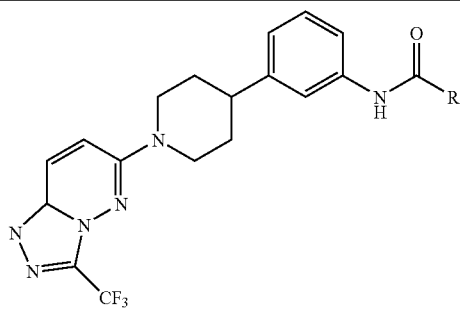

| Ex. | NHCOR | 1H NMR (399.9 MHz, DMSO-d6) | m/z [M + H]+ |
|---|---|---|---|
| 657 | (structure: HN-C(O)-CH2-O-CH3) | δ 1.67(2H, m), 1.92(2H, m), 2.85(1H, m), 3.14 (2H, m), 3.38(3H, s), 3.98(2H, s), 4.43(2H, m), 6.99(1H, m), 7.24(1H, m), 7.53(1H, m), 7.59 (1H, s), 7.67(1H, d), 8.25(1H, d), 9.64(1H, s) | 435 |
| 658 | (structure: HN-C(O)-tetrahydropyran-4-yl) | δ 1.66(6H, m), 1.91(2H, m), 2.58(1H, m), 2.84 (1H, m), 3.13(2H, m), 3.35(2H, m), 3.91(2H, m), 4.42(2H, m), 6.95(1H, m), 7.22(1H, m), 7.43(1H, m), 7.56(1H, s), 7.67(1H, d), 8.25 (1H, d), 9.80(1H, s) | 475 |

EXAMPLE 659

Preparation of 4-(4-methylpiperazin-1-yl)-N-[3-[1-[3-(trifluoromethyl)-[1,2,4]triazolo[4,3-b]pyridazin-6-yl]piperidin-4-yl]phenyl]butanamide

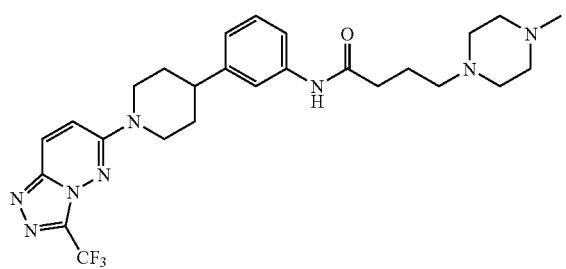

1-Methylpiperazine (152 µl, 1.37 mmol) was added to 4-chloro-N-[3-[1-[3-(trifluoromethyl)-[1,2,4]triazolo[4,3-b]pyridazin-6-yl]piperidin-4-yl]phenyl]butanamide (160 mg, 0.343 mmol) and sodium iodide (10 mg, 0.069 mmol) in a mixture of THF (2 mL) and DMA (0.5 mL). The resulting solution was heated at 60° C. for 16 hours, then cooled and evaporated to give the crude product, which was purified by flash chromatography on silica, eluting with a gradient of 0-10% 2M ammonia in methanol in DCM. The solvents were evaporated, then the resulting gum triturated with ether and the precipitate filtered and dried to give 4-(4-methylpiperazin-1-yl)-N-[3-[1-[3-(trifluoromethyl)-[1,2,4]triazolo[4,3-b]pyridazin-6-yl]piperidin-4-yl]phenyl]butanamide (87 mg, 48%) as a solid.

1H NMR (399.9 MHz, DMSO-d6) δ 1.60-1.76 (4H, m), 1.91 (2H, m), 2.12 (3H, s), 2.25-2.35 (12H, m), 2.84 (1H, m), 3.13 (2H, m), 4.42 (2H, m), 6.94 (1H, m), 7.21 (1H, m), 7.42 (1H, m), 7.52 (1H, m), 7.67 (1H, d), 8.25 (1H, d), 9.77 (1H, s); m/z=531 [M+H]+.

The 4-chloro-N-[3-[1-[3-(trifluoromethyl)-[1,2,4]triazolo[4,3-b]pyridazin-6-yl]piperidin-4-yl]phenyl]butanamide used as starting material was prepared as follows:—A solution of 4-chlorobutyryl chloride (175 mg, 1.24 mmol) in DCM (2 mL) was added dropwise to a stirred suspension of 3-[1-[3-(trifluoromethyl)[1,2,4]triazolo[4,3-b]pyridazin-6-yl]piperidin-4-yl]aniline (obtained as described in Example 616) (375 mg, 1.03 mmol) and pyridine (164 mg, 2.07 mmol) in DCM (3 mL) under nitrogen. The resulting solution was stirred at ambient temperature for 16 hours. The reaction mixture was diluted with DCM (5 mL), washed with saturated sodium bicarbonate (10 mL), dried and the solvents evaporated to a yellow gum, which was triturated with ether to give 4-chloro-N-[3-[1-[3-(trifluoromethyl)-[1,2,4]triazolo[4,3-b]pyridazin-6-yl]piperidin-4-yl]phenyl]butanamide (480 mg, 99%) as a solid.

m/z=467 [M+H]+.

EXAMPLES 660-661

The following compounds were prepared in 5-34% yield by an analogous method to Example 659, starting from 4-chloro-N-[3-[1-[3-(trifluoromethyl)-[1,2,4]triazolo[4,3-b]pyridazin-6-yl]piperidin-4-yl]phenyl]butanamide and the appropriate amine:—

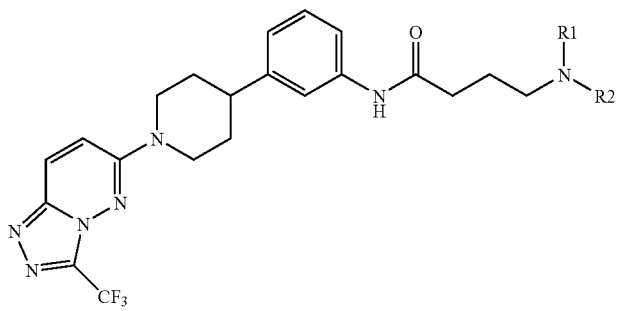

| Ex. | NR1R2 | 1H NMR (399.9 MHz, DMSO-d6) | m/z [M + H]+ |
|---|---|---|---|
| 660 | pyrrolidine | δ 1.66(2H, m), 1.85-1.95(8H, m), 2.40(2H, t), 2.85 (1H, m), 2.98-3.19(8H, m), 4.43(2H, m), 6.97(1H, m), 7.24(1H, m), 7.43(1H, m), 7.51(1H, m), 7.67(1H, d), 8.26(1H, d), 9.90(1H, s) | 502 |
| 661 | morpholine | δ 1.61-1.77(4H, m), 1.86(2H, m), 2.27-2.40(8H, m), 2.84(1H, m), 3.13(2H, m), 3.59(4H, m), 4.45(2H, m), 6.92(1H, m), 7.22(1H, m), 7.46(1H, m), 7.54(1H, m), 7.69(1H, d), 8.26(1H, d), 9.78(1H, s) | 518 |

EXAMPLE 662

Preparation of 4-methoxy-N-[3-[1-(3-(trifluoromethyl)-[1,2,4]triazolo[4,3-b]pyridazin-6-yl)piperidin-4-yl]phenyl]butanamide

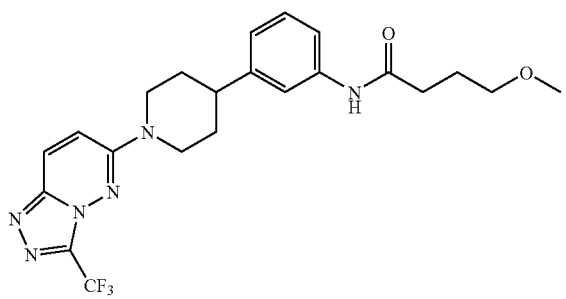

Obtained in 68% yield by an analogous procedure to Example 655, starting from 3-[1-[3-(trifluoromethyl)[1,2,4]triazolo[4,3-b]pyridazin-6-yl]piperidin-4-yl]aniline and 4-methoxybutanoic acid.

1H NMR (399.9 MHz, DMSO-d6) δ 1.66 (2H, m), 1.80 (2H, m), 1.91 (2H, m), 2.34 (2H, t), 2.84 (1H, m), 3.13 (2H, m), 3.24 (3H, s), 3.35 (2H, t), 4.42 (2H, m), 6.94 (1H, d), 7.22 (1H, m), 7.42 (1H, d), 7.53 (1H, s), 7.67 (1H, d), 8.25 (1H, d), 9.81 (1H, s); m/z=463 [M+H]+.

The 4-methoxybutanoic acid used as starting material was prepared as follows:—

Lithium hydroxide monohydrate (0.381 g, 9.08 mmol) was added to methyl 4-methoxybutanoate (1 g, 7.57 mmol) in a mixture of MeOH (20 mL) and water (10 mL). The resulting suspension was stirred at 50° C. for 16 hours. The reaction was cooled to room temperature, the MeOH evaporated and the aqueous residues diluted with water (50 mL) and washed with EtOAc (2×50 mL). The aqueous layer was then acidified to pH 4 with 1M citric acid and extracted with EtOAc (2×50 mL). The combined extracts were dried over MgSO₄ and the solvent evaporated to afford 4-methoxybutanoic acid (0.709 g, 79%) as a liquid.

1H NMR (399.9 MHz, CDCl3) δ 1.91 (2H, m), 2.46 (2H, t), 3.34 (3H, s), 3.44 (2H, t), 10.92 (1H, br s).

EXAMPLES 663-665

The following compounds were prepared in 22-68% yield by an analogous method to Example 655, starting from 4-[1-[3-(trifluoromethyl)[1,2,4]triazolo[4,3-b]pyridazin-6-yl]piperidin-4-yl]aniline (obtained as described in Example 615) and the appropriate carboxylic acid:—

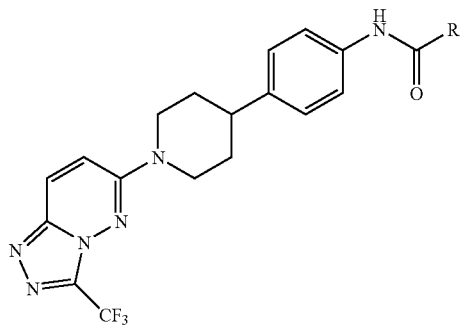

| Ex. | NHCOR | 1H NMR (399.9 MHz, DMSO-d6) | m/z [M + H]+ |
|---|---|---|---|
| 663 | ![HN-C(O)-piperidine-NMe] | δ 1.60-1.75(6H, m), 1.88(4H, m), 2.18(3H, s), 2.26(1H, m), 2.83(3H, m), 3.10(2H, m), 4.41 (2H, m), 7.18(2H, d), 7.52(2H, d), 7.66(1H, d), 8.24(1H, d), 9.75(1H, s) | 488 |
| 664 | ![HN-C(O)-CH2-OMe] | δ 1.68(2H, m), 1.89(2H, m), 2.83(1H, m), 3.11 (2H, m), 3.38(3H, s), 3.98(2H, s), 4.42(2H, m), 7.21(2H, d), 7.58(2H, d), 7.66(1H, d), 8.24(1H, d), 9.66(1H, s) | 435 |
| 665 | ![HN-C(O)-tetrahydropyran] | δ 1.67(6H, m), 1.89(2H, m), 2.82(1H, m), 3.11 (2H, m), 3.36(2H, m), 3.91(2H, m), 4.41(2H, m), 7.19(2H, d), 7.53(2H, d), 7.66(1H, d), 8.25 (1H, d), 9.79(1H, s), (1H obscured by DMSO) | 475 |

EXAMPLES 666-668

The following compounds were prepared in 27-68% yield by an analogous method to Example 659, starting from 4-chloro-N-[4-[1-(3-(trifluoromethyl)-[1,2,4]triazolo[4,3-b]pyridazin-6-yl)piperidin-4-yl]phenyl]butanamide and the appropriate amine:—

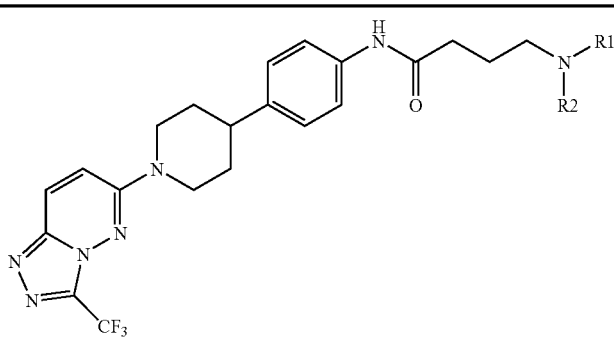

| Ex. | NR1R2 | 1H NMR (399.9 MHz, DMSO-d6) | m/z [M + H]+ |
|---|---|---|---|
| 666 | ![N-methylpiperazine] | δ 1.62-1.76(4H, m), 1.88(2H, m), 2.13(3H, s), 2.26-2.37(12H, m), 2.81(1H, m), 3.11(2H, m), 4.41(2H, m), 7.18(2H, d), 7.51(2H, d), 7.66(1H, d), 8.24(1H, d), 9.76(1H, s) | 531 |
| 667 | ![pyrrolidine] | δ 1.62-1.79(8H, m), 1.89(2H, m), 2.33(2H, m), 2.41-2.50(6H, m), 2.82(1H, m), 3.11(2H, m), 4.42(2H, m), 7.18(2H, d), 7.51(2H, d), 7.66(1H, d), 8.24(1H, d), 9.80(1H, s) | 502 |

-continued

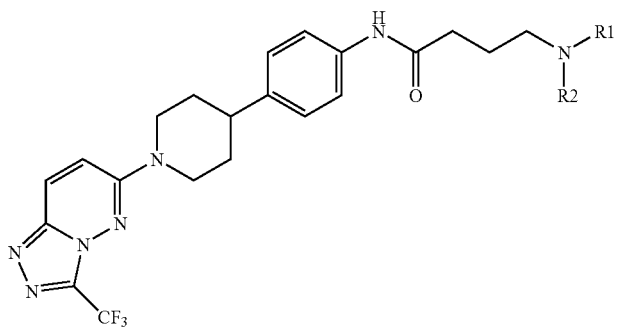

| Ex. | NR1R2 | 1H NMR (399.9 MHz, DMSO-d6) | m/z [M + H]+ |
|---|---|---|---|
| 668 | morpholine | δ 1.62-1.78(4H, m), 1.89(2H, m), 2.27-2.40(8H, m), 2.82(1H, m), 3.11(2H, m), 3.56(4H, m), 4.41 (2H, m), 7.19(2H, d), 7.51(2H, d), 7.66(1H, d), 8.24 (1H, d), 9.78(1H, s) | 518 |

The 4-chloro-N-[4-[1-(3-(trifluoromethyl)-[1,2,4]triazolo[4,3-b]pyridazin-6-yl)piperidin-4-yl]phenyl]butanamide used as starting material was obtained in 80% yield by an analogous procedure to Example 659, preparation of starting materials, starting from 4-[1-[3-(trifluoromethyl)[1,2,4]triazolo[4,3-b]pyridazin-6-yl]piperidin-4-yl]aniline (obtained as described in Example 615).
m/z=467 [M+H]+.

EXAMPLE 669

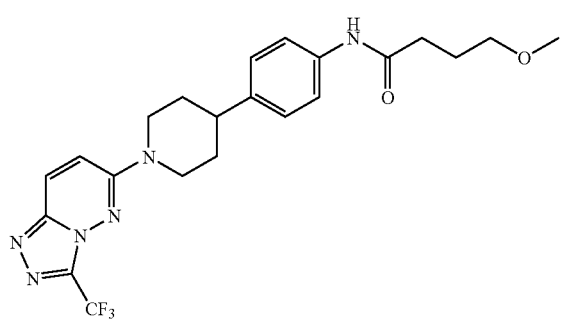

Obtained in 38% yield by an analogous procedure to Example 655, starting from 4-[1-[3-(trifluoromethyl)[1,2,4]triazolo[4,3-b]pyridazin-6-yl]piperidin-4-yl]aniline (obtained as described in Example 615) and 4-methoxybutanoic acid (obtained as described in Example 662, preparation of starting materials).

1H NMR (399.9 MHz, DMSO-d6) δ 1.68 (2H, m), 1.80 (2H, m), 1.89 (2H, m), 2.34 (2H, t), 2.82 (1H, m), 3.11 (2H, m), 3.24 (3H, s), 3.35 (2H, t), 4.41 (2H, m), 7.18 (2H, d), 7.51 (2H, d), 7.66 (1H, d), 8.24 (1H, d), 9.80 (1H, s); m/z=463 [M+H]+.

EXAMPLES 670-684

The following compounds were prepared in 17-64% yield by an analogous method to Example 513, starting from 3-[1-[3-(trifluoromethyl)[1,2,4]triazolo[4,3-b]pyridazin-6-yl]piperidin-4-yl]phenol and the appropriate alcohol:—

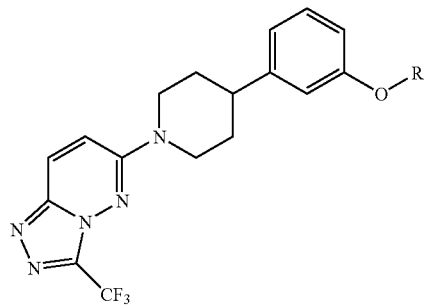

| Ex. | OR | 1H NMR (399.9 MHz, DMSO-d6) | m/z [M + H]+ |
|---|---|---|---|
| 670 | O-CH2CH2CH2-N(CH3)2 | δ 1.71(2H, m), 1.85(4H, m), 2.14(6H, s), 2.35 (2H, t), 2.84(1H, m), 3.10(2H, m), 3.98(2H, t), 4.42(2H, m), 6.76(1H, m), 6.83(2H, m), 7.20 (1H, m), 7.66(1H, d), 8.24(1H, d) | 449 |

-continued

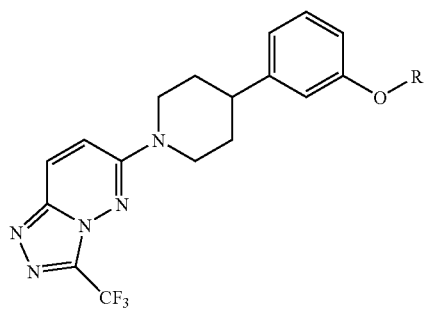

| Ex. | OR | 1H NMR (399.9 MHz, DMSO-d6) | m/z [M + H]+ |
| --- | --- | --- | --- |
| 671 | O-CH2CH2-N(pyrrolidine) | δ 1.66-1.77(6H, m), 1.90(2H, m), 2.59(4H, m), 2.85(3H, m), 3.11(2H, m), 4.07(2H, t), 4.42(2H, m), 6.78(1H, m), 6.85(2H, m), 7.21 (1H, m), 7.66(1H, d), 8.25(1H, d) | 461 |
| 672 | O-CH2CH2-N(piperazine)NH | δ 1.72(2H, m), 1.90(2H, m), 2.38(4H, m), 2.65 (6H, m), 2.84(1H, m), 3.10(2H, m), 4.05(2H, t), 4.42(2H, m), 6.77(1H, m), 6.84(2H, m), 7.20(1H, m), 7.66(1H, d), 8.24(1H, d) | 476 |
| 673 | O-CH2CH2CH2-N(piperazine)NH | δ 1.71(2H, m), 1.86(4H, m), 2.29(4H, m), 2.36 (2H, m), 2.67(4H, m), 2.84(1H, m), 3.10(2H, m), 3.98(2H, t), 4.42(2H, m), 6.76(1H, m), 6.83(2H, m), 7.20(1H, m), 7.66(1H, d), 8.24 (1H, d) | 490 |
| 674 | O-CH2-(5-methylisoxazol-3-yl) | δ 1.72(2H, m), 1.91(2H, m), 2.41(3H, s), 2.85 (1H, m), 3.11(2H, m), 4.42(2H, m), 5.12(2H, s), 6.32(1H, s0, 6.85-6.94(3H, m), 7.24(1H, m), 7.67(1H, d), 8.25(1H, d) | 459 |
| 675 | O-CH2CH2-N(CH3)2 | δ 1.71(2H, m), 1.90(2H, m), 2.21(6H, s), 2.61 (2H, t), 2.84(1H, m), 3.10(2H, m), 4.03(2H, t), 4.42(2H, m), 6.78(1H, m), 6.84(2H, m), 7.21 (1H, m), 7.66(1H, d), 8.24(1H, d) | 435 |
| 676 | O-CH2CH2-morpholine | δ 1.71(2H, m), 1.90(2H, m), 2.47(4H, m), 2.68 (2H, t), 2.84(1H, m), 3.11(2H, m), 3.57(4H, m), 4.07(2H, t), 4.42(2H, m), 6.78(1H, m), 6.84(2H, m), 7.21(1H, m), 7.66(1H, d), 8.25 (1H, d) | 477 |
| 677 | O-(1-methylpiperidin-4-yl) | δ 1.65-1.76(4H, m), 1.88-2.01(4H, m), 2.42 (3H, s), 2.86(3H, m), 3.10(2H, m), 4.44(3H, m), 6.83(3H, m), 7.21(1H, m), 7.66(1H, d), 8.25(1H, d), (2H obscured by DMSO) | 461 |
| 678 | O-CH2CH2CH2-N(4-methylpiperazine) | δ 1.71(2H, m), 1.87(4H, m), 2.14(3H, s), 2.25-2.42(10H, m), 2.84(1H, m), 3.10(2H, m), 3.98 (2H, t), 4.42(2H, m), 6.76(1H, m), 6.83(2H, m), 7.20(1H, m), 7.66(1H, d), 8.25(1H, d) | 504 |
| 679 | O-CH2-(1-methylpyrazol-5-yl) | δ 1.72(2H, m), 1.91(2H, m), 2.86(1H, m), 3.11 (2H, m), 4.43(2H, m), 5.22(2H, s), 6.69(1H, d), 6.89(2H, m), 6.95(1H, m), 7.24(1H, m), 7.67 (1H, d), 8.25(1H, d), 8.94(1H, d) | 445 |

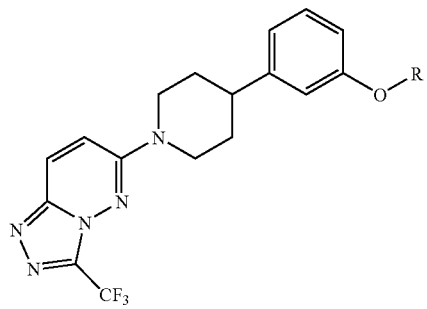

| Ex. | OR | 1H NMR (399.9 MHz, DMSO-d6) | m/z [M + H]+ |
|---|---|---|---|
| 680 | | δ 1.72(2H, m), 1.91(2H, m), 2.86(1H, m), 3.11 (2H, m), 4.43(2H, m), 5.17(2H, s), 6.89(2H, m), 6.94(1H, m), 7.24(1H, m), 7.32(1H, s), 7.67(1H, d), 8.25(1H, d), 8.40(1H, s) | 445 |
| 681 | | δ 1.72(2H, m), 1.90(2H, m), 2.14(3H, s), 2.30 (4H, m), 2.47(4H, m), 2.66(2H, t), 2.84(1H, m), 3.10(2H, m), 4.05(2H, t), 4.42(2H, m), 6.77(1H, m), 6.84(2H, m), 7.20(1H, m), 7.66 (1H, d), 8.24(1H, d) | 490 |
| 682 | | δ 1.71(2H, m), 1.90(2H, m), 2.81-2.88(3H, m), 3.10(2H, m), 3.78(3H, s), 4.07(2H, t), 4.42 (2H, m), 6.79(1H, m), 6.84(2H, m), 7.21(1H, m), 7.33(1H, s), 7.56(1H, s), 7.66(1H, d), 8.24 (1H, d) | 472 |
| 683 | | δ 1.72(2H, m), 1.91(2H, m), 2.86(1H, m), 3.11 (2H, m), 3.83(3H, s), 4.43(2H, m), 5.16(2H, s), 6.36(1H, d), 6.90(2H, m), 6.96(1H, m), 7.24 (1H, m), 7.37(1H, d), 7.67(1H, d0, 8.25(1H, d) | 458 |
| 684 | | δ 1.72(2H, m), 1.90(2H, m), 2.84(1H, m), 3.10 (2H, m), 3.31(3H, s), 3.65(2H, m), 4.08(2H, m), 4.42(2H, m), 6.78(1H, m), 6.85(2H, m), 7.21(1H, m), 7.66(1H, d), 8.24(1H, d) | 422 |

The 3-[1-[3-(trifluoromethyl)[1,2,4]triazolo[4,3-b]pyridazin-6-yl]piperidin-4-yl]phenol used as starting material was prepared as follows:—

Preparation of 3-[1-[3-(trifluoromethyl)-[1,2,4]triazolo[4,3-b]pyridazin-6-yl]-1,2,3,6-tetrahydropyridin-4-yl]phenol Obtained in 72% yield by an analogous procedure to Example 605, starting from 1-[3-(trifluoromethyl)-[1,2,4]triazolo[4,3-b]pyridazin-6-yl]-1,2,3,6-tetrahydropyridin-4-yl trifluoromethanesulfonate and 3-hydroxyphenylboronic acid.

1H NMR (399.9 MHz, DMSO-d6) δ 2.63 (2H, m), 3.88 (2H, m), 4.25 (2H, m), 6.24 (1H, m), 6.70 (1H, m), 6.86 (1H, m), 6.92 (1H, m), 7.17 (1H, m), 7.67 (1H, d), 8.29 (1H, d), 9.38 (1H, s); m/z=362 [M+H]+.

Preparation of 3-[1-[3-(trifluoromethyl)[1,2,4]triazolo[4,3-b]pyridazin-6-yl]piperidin-4-yl]phenol Obtained in 73% yield by an analogous procedure to Example 610, starting from 3-[1-[3-(trifluoromethyl)-[1,2,4]triazolo[4,3-b]pyridazin-6-yl]-1,2,3,6-tetrahydropyridin-4-yl]phenol.

1H NMR (399.9 MHz, DMSO-d6) δ 1.64-1.71 (2H, m), 1.89 (2H, m), 2.75-2.79 (1H, m), 3.07-3.14 (2H, m), 4.39-4.42 (2H, m), 6.59-6.70 (3H, m), 7.09 (1H, m), 7.66 (1H, d), 8.24 (1H, d), 9.24 (1H, s); m/z=364 [M+H]+.

EXAMPLES 685-707

The following compounds were prepared in 31-95% yield by an analogous method to Example 512, starting from 3-[[1-[3-(trifluoromethyl)[1,2,4]triazolo[4,3-b]pyridazin-6-yl]piperidin-4-yl]oxy]benzoic acid and the appropriate amine:—

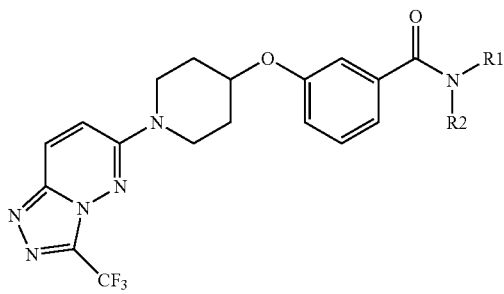

| Ex. | NR1R2 | 1H NMR (399.9 MHz, DMSO-d6) | m/z [M + H]+ |
|---|---|---|---|
| 685 | ⟨N-CH2CH2OH, NMe⟩ | δ 1.74(2H, m), 2.09(2H, m), 2.96(3H, m), 3.46-3.65(6H, m), 3.97(2H, m), 4.75(2H, m), 6.96(1H, m), 7.05(2H, m), 7.34(1H, m), 7.65(1H, d), 8.26(1H, d) | 465 |
| 686 | ⟨NH-CH2CH2-pyrrolidine⟩ | δ 1.66-1.80(6H, m), 2.10(2H, m), 2.48(4H, m), 2.57(2H, t), 3.38(2H, m), 3.56(2H, m), 3.96(2H, m), 4.75(1H, m), 7.17(1H, m), 7.36-7.44(3H, m), 7.65(1H, d), 8.26(1H, d), 8.39(1H, t) | 504 |
| 687 | N-methylpiperazine | δ 1.74(2H, m), 2.09(2H, m), 2.27(3H, s), 2.37-2.47(4H, m), 3.37-3.70(6H, m), 3.97(2H, m), 4.75(1H, m), 6.94(1H, m), 7.00(1H, m), 7.09(1H, m), 7.37(1H, m), 7.65(1H, d), 8.26(1H, d) | 490 |
| 688 | piperazine | δ 1.73(2H, m), 2.08(2H, m), 2.60-2.75(4H, m), 3.28(2H, m), 3.54(4H, m), 3.98(2H, m), 4.75(1H, m), 6.92(1H, m), 6.98(1H, m), 7.07(1H, m), 7.36(1H, m), 7.65(1H, d), 8.26(1H, d) | 476 |
| 689 | ⟨NH-CH2CH2OMe⟩ | δ 1.76(2H, m), 2.09(2H, m), 3.28(3H, s), 3.44(4H, m), 3.57(2H, m), 3.96(2H, m), 4.76(1H, m), 7.18(1H, m), 7.39(1H, m), 7.45(2H, m), 7.65(1H, d), 8.26(1H, d), 8.48(1H, t) | 465 |
| 690 | NMe2 | δ 1.73(2H, m), 2.08(2H, m), 2.91(3H, s), 2.98(3H, s), 3.53(2H, m), 3.97(2H, m), 4.75(1H, m), 6.95(1H, m), 7.02(1H, m), 7.07(1H, m), 7.36(1H, m), 7.65(1H, d), 8.26(1H, d) | 435 |
| 691 | (S)-3-hydroxypyrrolidine | δ 1.70-1.97(4H, m), 2.08(2H, m), 3.39(1H, m), 3.55(5H, m), 3.96(2H, m), 4.28(1H, m), 4.76(1H, m), 4.95(1H, m), 7.08(3H, m), 7.36(1H, m), 7.65(1H, d), 8.26(1H, d) | 477 |
| 692 | pyrrolidine | δ 1.69-1.89(6H, m), 2.08(2H, m), 3.37(2H, m), 3.47(2H, m), 3.54(2H, m), 3.97(2H, m), 4.75(1H, m), 7.08(3H, m), 7.35(1H, m), 7.65(1H, d), 8.26(1H, d) | 461 |
| 693 | morpholine | δ 1.74(2H, m), 2.09(2H, m), 3.32-3.67(10H, m), 3.97(2H, m), 4.75(1H, m), 6.97(1H, m), 7.02(1H, m), 7.09(1H, m), 7.37(1H, m), 7.65(1H, d), 8.26(1H, d) | 477 |
| 694 | NHMe | δ 1.75(2H, m), 2.10(2H, m), 2.79(3H, d), 3.56(2H, m), 3.97(2H, m), 4.75(1H, m), 7.16(1H, m), 7.36-7.44(3H, m), 7.66(1H, d), 8.26(1H, d), 8.39(1H, q) | 421 |
| 695 | NHEt | δ 1.13(3H, t), 1.75(2H, m), 2.09(2H, m), 3.28(2H, m), 3.57(2H, m), 3.96(2H, m), 4.76(1H, m), 7.17(1H, m), 7.38(1H, m), 7.44(2H, m), 7.65(1H, d), 8.26(1H, d), 8.42(1H, t) | 435 |
| 696 | ⟨NH-CH2CH2-NMe2⟩ | δ 1.76(2H, m), 2.09(2H, m), 2.22(6H, s), 2.45(2H, t), 3.37(2H, m), 3.57(2H, m), 3.96(2H, m), 4.76(1H, m), 7.18(1H, m), 7.37-7.44(3H, m), 7.66(1H, d), 8.26(1H, d), 8.36(1H, t) | 478 |

-continued

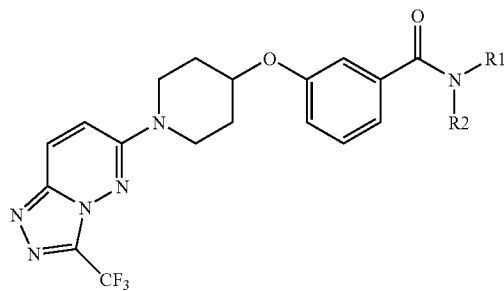

| Ex. | NR1R2 | 1H NMR (399.9 MHz, DMSO-d6) | m/z [M + H]+ |
|---|---|---|---|
| 697 | H-N-CH2CH2-OH | δ 1.76(2H, m), 2.09(2H, m), 3.33(2H, m), 3.55 (4H, m), 3.96(2H, m), 4.70(1H, t), 4.76(1H, m), 7.17(1H, m), 7.38(1H, m), 7.45(2H, m), 7.65 (1H, d), 8.26(1H, d), 8.39(1H, t) | 451 |
| 698 | H-N-CH2CH2-morpholine | δ 1.76(2H, m), 2.10(2H, m), 2.45(4H, m), 3.40 (2H, m), 3.57(6H, m), 3.96(2H, m), 4.76(1H, m), 7.18(1H, m), 7.41(3H, m), 7.65(1H, d), 8.26 (1H, d), 8.38(1H, t), (2H obscured by DMSO) | 520 |
| 699 | Me-N-CH2CH2-OMe | δ 1.74(2H, m), 2.08(2 h, m0, 2.95(3H, m), 3.21 (2H, m), 3.33-3.62(7H, m), 3.97(2H, m), 4.74 (1H, m), 6.94(1H, m), 7.00(1H, m), 7.06(1H, m), 7.35(1H, m), 7.65(1H, d), 8.26(1H, d) | 479 |
| 700 | (S)-3-hydroxypyrrolidine | δ 1.70-1.96(4H, m), 2.08(2H, m), 3.38(1H, m), 3.54(5H, m), 3.97(2H, m), 4.28(1H, m), 4.76 (1H, m), 4.95(1H, m), 7.08(3H, m), 7.36(1H, m), 7.65(1H, d), 8.26(1H, d) | 477 |
| 701 | H-N-CH2CH2-(2-oxopyrrolidin-1-yl) | δ 1.76(2H, m), 1.91(2H, m), 2.10(2H, m), 2.19 (2H, m), 3.39(6H, m) ,3.56(2H, m), 3.98(2H, m), 4.75(1H, m), 7.17(1H, m), 7.39(3H, m), 7.66(1H, d), 8.26(1H, d), 8.47(1H, t) | 518 |
| 702 | H-N-CH2-(5-methylisoxazol-3-yl) | δ 1.76(2H, m), 2.10(2H, m), 2.38(3H, s), 3.57 (2H, m), 3.96(2H, m), 4.46(2H, d), 4.76(1H, m), 6.16(1H, s), 7.20(1H, m), 7.41(1H, m), 7.48 (2H, m), 7.65(1H, d), 8.26(1H, d), 9.03(1H, t) | 502 |
| 703 | H-N-(1-methylpiperidin-4-yl) | δ 1.60(2H, m), 1.76(4H, m), 1.97(2H, m), 2.09 (2H, m), 2.19(3H, s), 2.79(2H, m), 3.57(2H, m), 3.73(1H, m), 3.95(2H, m), 4.76(1H, m), 7.18 (1H, m), 7.38(1H, m), 7.44(2H, m), 7.65(1H, d), 8.19(1H, d), 8.26(1H, d) | 504 |
| 704 | H-N-CH2CH2-(4-methylpiperazin-1-yl) | δ 1.75(2H, m), 2.10(2H, m), 2.24(3H, s), 2.40-2.51(10H, m), 3.38(2H, m), 3.56(2H, m), 3.96 (2H, m), 4.76(1H, m), 7.18(1H, m), 7.40(3H, m), 7.65(1H, d), 8.26(1H, d), 8.35(1H, t) | 533 |
| 705 | H-N-CH2CH2-(1H-pyrazol-1-yl) | δ 1.75(2H, m), 2.09(2H, m), 3.56(2H, m), 3.64 (2H, m), 3.97(2H, m), 4.31(2H, t), 4.74(1H, m), 6.23(1H, m), 7.18(1H, m), 7.39(3H, m), 7.46 (1H, m), 7.66(1H, d), 7.70(1H, m), 8.27(1H, d), 8.53(1H, t) | 501 |

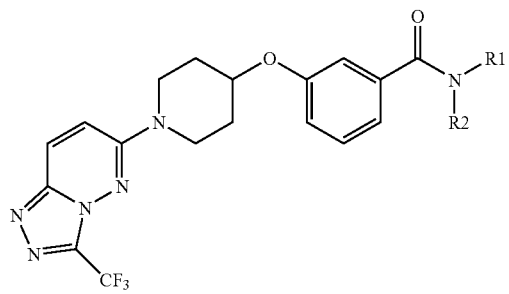

| Ex. | NR1R2 | 1H NMR (399.9 MHz, DMSO-d6) | m/z [M + H]+ |
|---|---|---|---|
| 706 | (pyrazole-methyl-amine structure) | δ 1.76(2H, m), 2.09(2H, m), 3.57(2H, m), 3.79 (3H, s), 3.96(2H, m), 4.41(2H, d), 4.76(1H, m), 6.13(1H, d), 7.17(1H, m), 7.38(1H, m), 7.48 (2H, m), 7.58(1H, d), 7.65(1H, d), 8.26(1H, d), 8.85(1H, t) | 501 |
| 707 | (oxazole-methyl-amine structure) | δ 1.75(2H, m), 2.10(2H, m), 3.57(2H, m), 3.96 (2H, m), 4.38(2H, d), 4.76(1H, m), 7.18(1H, m), 7.39(1H, m), 7.48(2H, m), 7.65(1H, d), 7.97 (1H, s), 8.26(1H, d), 8.32(1H, s), 8.90(1H, t) | 488 |

The 3-[[1-[3-(trifluoromethyl)[1,2,4]triazolo[4,3-b]pyridazin-6-yl]piperidin-4-yl]oxy]benzoic acid used as starting material was prepared in 2 steps in 38% overall yield by an analogous method to Example 412, preparation of starting materials, starting from 1-[3-(trifluoromethyl)-[1,2,4]triazolo[4,3-b]pyridazin-6-yl]piperidin-4-ol and methyl 4-hydroxy benzoate.

1H NMR (399.9 MHz, DMSO-d6) δ 1.74-1.78 (2H, m), 2.06-2.11 (2H, m), 3.54-3.60 (2H, m), 3.93-3.99 (2H, m), 4.78 (1H, m), 7.27-7.30 (1H, m), 7.44 (1H, m), 7.51-7.57 (2H, m), 7.65 (1H, d), 8.26 (1H, d), 12.97 (1H, s); m/z=408 [M+H]+.

EXAMPLE 708

Preparation of 2-(4-methylpiperazin-1-yl)-N-[4-[1-[3-(trifluoromethyl)[1,2,4]triazolo[4,3-b]pyridazin-6-yl]piperidin-4-yl]phenyl]acetamide

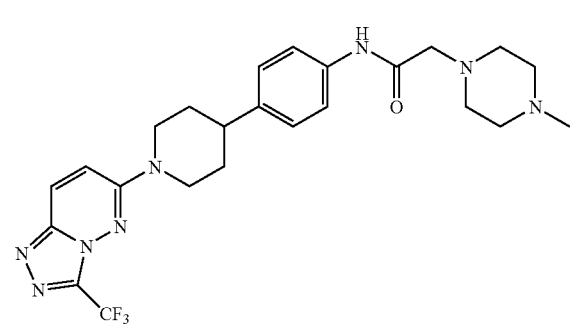

1-Methylpiperazine (140 μl, 1.27 mmol) was added to 2-chloro-N-[4-[1-(3-(trifluoromethyl)-[1,2,4]triazolo[4,3-b]pyridazin-6-yl]piperidin-4-yl]phenyl]acetamide (139 mg, 0.317 mmol) and sodium iodide (10 mg, 0.063 mmol) in a mixture of THF (2 mL) and DMA (0.5 mL). The resulting solution was heated at 60° C. for 2 hours, then cooled and evaporated to give the crude product which was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to give 2-(4-methylpiperazin-1-yl)-N-[4-[1-[3-(trifluoromethyl)[1,2,4]triazolo[4,3-b]pyridazin-6-yl]piperidin-4-yl]phenyl]acetamide (111 mg, 70%) as a solid.

1H NMR (399.9 MHz, DMSO-d6) δ 1.68 (2H, m), 1.89 (2H, m), 2.17 (3H, s), 2.37 (4H, m), 2.83 (1H, m), 3.11 (4H, m), 4.42 (2H, m), 7.21 (2H, d), 7.54 (2H, d), 7.66 (1H, d), 8.24 (1H, d), 9.58 (1H, s), (4H obscured by DMSO); m/z=503 [M+H]+.

The 2-chloro-N-[4-[1-(3-(trifluoromethyl)-[1,2,4]triazolo[4,3-b]pyridazin-6-yl]piperidin-4-yl]phenyl]acetamide used as starting material was prepared as follows:—

A solution of chloroacetyl chloride (140 mg, 1.24 mmol) in DCM (2 mL) was added dropwise to a stirred suspension of 4-[1-[3-(trifluoromethyl)[1,2,4]triazolo[4,3-b]pyridazin-6-yl]piperidin-4-yl]aniline (obtained as described in Example 615) (375 mg, 1.03 mmol) and pyridine (164 mg, 2.07 mmol) in DCM (3 mL) under nitrogen. The resulting solution was stirred at ambient temperature for 2 hours. The resulting precipitate was collected by filtration, washed with DCM (2 mL) and dried under vacuum to give 2-chloro-N-[4-[1-(3-(trifluoromethyl)-[1,2,4]triazolo[4,3-b]pyridazin-6-yl]piperidin-4-yl]phenyl]acetamide (418 mg, 92%) as a solid.

m/z=439 [M+H]+.

EXAMPLES 709-710

The following compounds were prepared in 41-61% yield by an analogous method to Example 708, starting from 2-chloro-N-[4-[1-(3-(trifluoromethyl)-[1,2,4]triazolo[4,3-b]pyridazin-6-yl]piperidin-4-yl]phenyl]acetamide and the appropriate amine:—

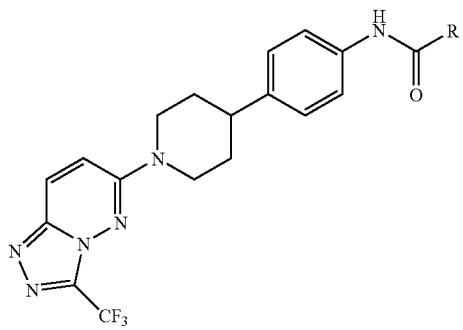

| Ex. | NHCOR | 1H NMR (399.9 MHz, DMSO-d6) | m/z [M + H]+ |
|---|---|---|---|
| 709 | (acetamide with pyrrolidine) | δ 1.63-1.76(6H, m), 1.89(2H, m), 2.59(4H, m), 2.83(1H, m), 3.11(2H, m), 3.22(2H, s), 4.42 (2H, m), 7.20(2H, d), 7.56(2H, d), 7.66(1H, d), 8.24(1H, d), 9.60(1H, s) | 474 |
| 710 | (acetamide with morpholine) | δ 1.68(2H, m), 1.89(2H, m), 2.55(4H, m), 2.83 (1H, m), 3.11(4H, m), 3.64(4H, m), 4.42(2H, m), 7.21(2H, d), 7.55(2H, d), 7.66(1H, d), 8.25 (1H, d), 9.64(1H, s) | 490 |

EXAMPLES 711-713

The following compounds were prepared in 26-33% yield by an analogous method to Example 708, starting from 2-chloro-N-[3-[1-(3-(trifluoromethyl)-[1,2,4]triazolo[4,3-b]pyridazin-6-yl]piperidin-4-yl]phenyl]acetamide and the appropriate amine:—

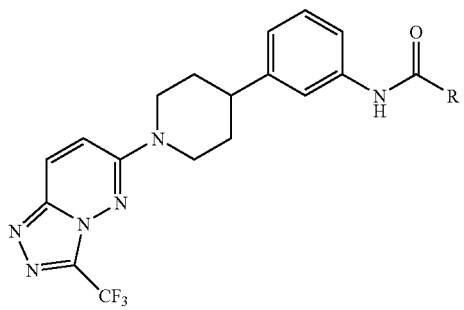

| Ex. | NHCOR | 1H NMR (399.9 MHz, DMSO-d6) | m/z [M + H]+ |
|---|---|---|---|
| 711 | (acetamide with N-methylpiperazine) | δ 1.68(2H, m), 1.92(2H, m), 2.17(3H, s), 2.37 (4H, m), 2.85(1H, m), 3.12(4H, m), 4.43(2H, m), 6.98(1H, m), 7.24(1H, m), 7.50(2H, m), 7.67(1H, d), 8.25(1H, d), 9.59(1H, s), (4H obscured by DMSO) | 503 |
| 712 | (acetamide with pyrrolidine) | δ 1.63-1.77(6H, m), 1.92(2H, m), 2.58(4H, m), 2.85(1H, m), 3.13(2H, m), 3.22(2H, s), 4.43(2H, m), 6.97(1H, m), 7.23(1H, m), 7.53 (2H, m), 7.67(1H, d), 8.25(1H, d), 9.69(1H, s) | 474 |
| 713 | (acetamide with morpholine) | δ 1.68(2H, m), 1.91(2H, m), 2.56(4H, m), 2.85(1H, m), 3.13(4H, m), 3.64(4H, m), 4.43 (2H, m), 6.98(1H, m), 7.24(1H, m), 7.52(2H, m), 7.67(1H, d), 8.25(1H, d), 9.64(1H, s), (4H partially obscured by DMSO) | 490 |

The 2-chloro-N-[3-[1-(3-(trifluoromethyl)-[1,2,4]triazolo[4,3-b]pyridazin-6-yl]piperidin-4-yl]phenyl]acetamide used as starting material was prepared in 100% yield by an analogous method to Example 708, preparation of starting materials, starting from 3-[1-[3-(trifluoromethyl)[1,2,4]triazolo[4,3-b]pyridazin-6-yl]piperidin-4-yl]aniline (obtained as described in Example 616) and chloroacetyl chloride.

m/z=439 [M+H]+.

EXAMPLES 714-723

The following compounds were prepared in 15-48% yield by an analogous method to Example 447, starting from 1-[3-(trifluoromethyl)-[1,2,4]triazolo[4,3-b]pyridazin-6-yl]piperidin-4-ol (obtained as described in Example 412, preparation of starting materials) and the appropriate hydroxy heterocycle:—

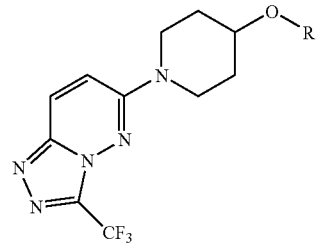

| Ex. | R | 1H NMR (399.9 MHz, DMSO-d6) | m/z [M + H]+ |
|---|---|---|---|
| 714 | 5-chloropyrimidin-2-yl | δ 1.82(2H, m), 2.14(2H, m), 3.55 (2H, m), 3.99(2H, m), 5.24(1H, m), 7.66(1H, d), 8.27(1H, d), 8.73 (2H, s) | 400 |
| 715 | 2-chloropyridin-3-yl | δ 1.81(2H, m), 2.09(2H, m), 3.64 (2H, m), 3.89(2H, m), 4.88(1H, m), 7.41(1H, m), 7.65(1H, d), 7.75 (1H, m), 8.01(1H, m), 8.26(1H, d) | 399 |
| 716 | 6-chloropyridin-2-yl | δ 1.78(2H, m), 2.12(2H, m), 3.56 (2H, m), 3.97(2H, m), 5.24(1H, m), 6.84(1H, m), 7.10(1H, m), 7.65(1H, d), 7.78(1H, m), 8.26 (1H, d) | 399 |
| 717 | 2-bromopyridin-3-yl | δ 1.83(2H, m), 2.07(2H, m), 3.69 (2H, m), 3.85(2H, m), 4.90(1H, m), 7.42(1H, m), 7.67(2H, m), 8.00(1H, m), 8.27(1H, d) | 443 |
| 718 | pyridin-3-yl | δ 1.75(2H, m), 2.10(2H, m), 3.53 (2H, m), 3.98(2H, m), 4.78(1H, m), 7.35(1H, m), 7.49(1H, m), 7.65(1H, d), 8.19(1H, m), 8.26 (1H, d), 8.35(1H, m) | 365 |
| 719 | 5-trifluromethylpyridin-2-yl | δ 1.81(2H, m), 2.14(2H, m), 3.55 (2H, m), 4.00(2H, m), 5.40(1H, m), 7.02(1H, d), 7.66(1H, d), 8.07 (1H, m), 8.26(1H, d), 8.59(1H, m) | 433 |
| 720 | 6-chloropyridin-3-yl | δ 1.74(2H, m), 2.10(2H, m), 3.52 (2H, m), 3.97(2H, m), 4.78(1H, m), 7.45(1H, m), 7.59(1H, m), 7.65 (1H, d), 8.19(1H, d), 8.26(1H, d) | 399 |
| 721 | 5-bromopyridin-2-yl | δ 1.76(2H, m), 2.11(2H, m), 3.52 (2H, m), 3.99(2H, m), 5.26(1H, m), 6.84(1H, d0, 7.65(1H, d), 7.91 (1H, m), 8.26(1H, d), 8.30(1H, d) | 443 |
| 722 | 5-bromopyridin-3-yl | δ 1.74(2H, m), 2.10(2H, m), 3.52 (2H, m), 3.99(2H, m), 4.85(1H, m), 7.65(1H, d), 7.85(1H, m), 8.25-8.36(3H, m) | 443 |
| 723 | 3-bromopyridin-2-yl | δ 1.82(2H, m), 2.10(2H, m), 3.67 (2H, m), 3.89(2H, m), 5.40(1H, m), 6.97(1H, m), 7.65(1H, d), 8.05 (1H, m), 8.18(1H, m), 8.26(1H, d) | 443 |

EXAMPLES 724-725

The following compounds were prepared in 18-26% yield by an analogous method to Example 447, starting from 1-[3-(trifluoromethyl)-[1,2,4]triazolo[4,3-b]pyridazin-6-yl]piperidin-4-ol (obtained as described in Example 412, preparation of starting materials) and the appropriate phenol:—

| Ex. | R | 1H NMR (399.9 MHz, DMSO-d6) | m/z [M + H]+ |
|---|---|---|---|
| 724 | 4-Cl | δ 1.72(2H, m), 2.07(2H, m), 3.52(2H, m), 3.96(2H, m), 4.68(1H, m), 7.05(2H, d), 7.34(2H, d), 7.64(1H, d), 8.25 (1H, d) | 398 |
| 725 | 3-Cl | δ 1.72(2H, m), 2.08(2H, m), 3.53(2H, m), 3.96(2H, m), 4.75(1H, m), 7.00(2H, m), 7.12(1H, m), 7.32(1H, m), 7.64(1H, d), 8.25(1H, d) | 398 |

EXAMPLES 726-736

The following compounds were prepared in 7-51% yield by an analogous method to Example 513, starting from 4-[1-[3-(trifluoromethyl)[1,2,4]triazolo[4,3-b]pyridazin-6-yl]piperidin-4-yl]phenol and the appropriate alcohol:—

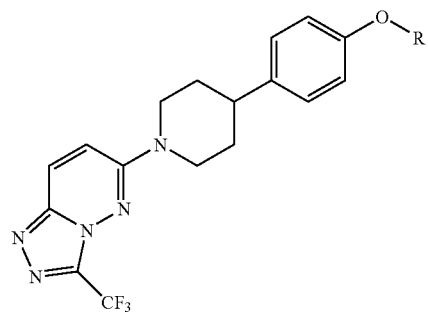

| Ex. | OR | 1H NMR (399.9 MHz, DMSO-d6) | m/z [M + H]+ |
|---|---|---|---|
| 726 | O\~\~\~N(CH3)2 | δ 1.66(2H, m), 1.79-1.91(4H, m), 2.14(6H, s), 2.34(2H, t), 2.81(1H, m), 3.10(2H, m), 3.96(2H, t), 4.41(2H, m), 6.85(2H, d), 7.17(2H, d), 7.66(1H, d), 8.24(1H, d) | 449 |
| 727 | O\~\~N(piperazine)NH | δ 1.66(2H, m), 1.88(2H, m), 2.39(4H, m), 2.63(2H, t), 2.68(4H, m), 2.81(1H, m), 3.10(2H, m), 4.03(2H, t), 4.41(2H, m), 6.87(2H, d), 7.17(2H, d), 7.66(1H, d), 8.24(1H, d) | 476 |
| 728 | O\~\~\~N(piperazine)NH | δ 1.66(2H, m), 1.85(4H, m), 2.38(6H, m), 2.78-2.84(5H, m), 3.10(2H, m), 3.97(2H, t), 4.41(2H, m), 6.85(2H, d), 7.17(2H, d), 7.66(1H, d), 8.24(1H, d) | 490 |
| 729 | O-CH2-(5-methylisoxazol-3-yl) | δ 1.67(2H, m), 1.88(2H, m), 2.41(3H, s), 2.82(1H, m), 3.10(2H, m), 4.41(2H, m), 5.11(2H, s), 6.31(1H, s), 6.95(2H, d), 7.20(2H, d), 7.66(1H, d), 8.24(1H, d) | 459 |
| 730 | O\~\~N(CH3)2 | δ 1.66(2H, m), 1.88(2H, m), 2.22(6H, s), 2.61(2H, t), 2.81(1H, m), 3.10(2H, m), 4.01(2H, t), 4.41(2H, m), 6.87(2H, d), 7.17(2H, d), 7.66(1H, d), 8.24(1H, d) | 435 |
| 731 | O\~\~N-morpholine | δ 1.66(2H, m), 1.88(2H, m), 2.47(4H, m), 2.68(2H, t), 2.81(1H, m), 3.10(2H, m), 3.58(4H, m), 4.06(2H, t), 4.41(2H, m), 6.87(2H, d), 7.17(2H, d), 7.66(1H, d), 8.24(1H, d) | 477 |
| 732 | O\~\~\~N(piperazine)N-CH3 | δ 1.66(2H, m), 1.80-1.90(4H, m), 2.15(3H, s), 2.25-2.42(10H, m), 2.81(1H, m), 3.10(2H, m), 3.96(2H, t), 4.41(2H, m), 6.85(2H, d), 7.17(2H, d), 7.66(1H, d), 8.24(1H, d) | 504 |
| 733 | O-CH2-(isoxazol-3-yl) | δ 1.67(2H, m), 1.89(2H, m), 2.82(1H, m), 3.10(2H, m), 4.41(2H, m), 5.20(2H, s), 6.68(1H, d), 6.97(1H, d), 7.21(2H, d), 7.66(1H, d), 8.24(1H, d), 8.94(1H, d) | 445 |
| 734 | O-CH2-(1,3,4-oxadiazol-2-yl) | δ 1.67(2H, m), 1.89(2H, m), 2.82(1H, m), 3.10(2H, m), 4.41(2H, m), 5.15(2H, s), 6.97(2H, d), 7.20(2H, d), 7.32(1H, s), 7.66(1H, d), 8.24(1H, d), 8.40(1H, s) | 445 |
| 735 | O\~\~N(piperazine)N-CH3 | δ 1.66(2H, m), 1.88(2H, m), 2.15(3H, s), 2.31(4H, m), 2.46(4H, m), 2.66(2H, t), 2.81(1H, m), 3.10(2H, m), 4.03(2H, t), 4.41(2H, m), 6.87(2H, d), 7.17(2H, d), 7.66(1H, d), 8.24(1H, d) | 490 |
| 736 | O-CH2-(1-methylpyrazol-5-yl) | δ 1.68(2H, m), 1.89(2H, m), 2.82(1H, m), 3.10(2H, m), 3.83(3H, s), 4.42(2H, m), 5.14(2H, s), 6.36(1H, d), 6.99(1H, d), 7.21(2H, d), 7.37(1H, d), 7.66(1H, d), 8.24(1H, d) | 458 |

EXAMPLE 737

Preparation of 2-[3-[1-[3-(trifluoromethyl)[1,2,4]triazolo[4,3-b]pyridazin-6-yl]piperidin-4-yl]phenoxy]ethanol

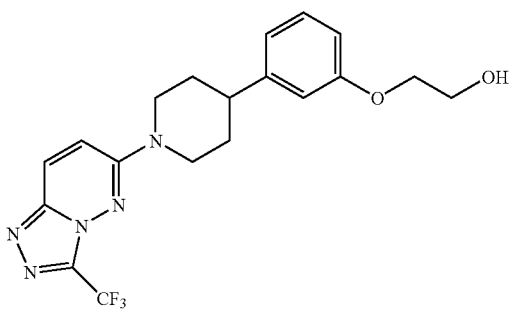

DIAD (0.081 mL, 0.41 mmol) was added dropwise to 3-[1-[3-(trifluoromethyl)-[1,2,4]triazolo[4,3-b]pyridazin-6-yl]piperidin-4-yl]phenol (obtained as described in Example 670, preparation of starting materials) (125 mg, 0.34 mmol), triphenylphosphine (108 mg, 0.41 mmol) and 2-(tetrahydro-2H-pyran-2-yloxy)ethanol (60.4 mg, 0.41 mmol) in THF (3 mL) under nitrogen. The resulting mixture was stirred at ambient temperature for 4 hours, then added to an SCX column. The crude product was eluted from the column using 2M ammonia in methanol and the solvents were evaporated. The crude product was purified by flash silica chromatography, elution gradient 80 to 100% EtOAc in isohexane. Fractions containing product were evaporated then further purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 2-(3-(1-(3-(trifluoromethyl)-[1,2,4]triazolo[4,3-b]pyridazin-6-yl)piperidin-4-yl)phenoxy)ethanol (74 mg, 53%) as a solid.

1H NMR (399.9 MHz, DMSO-d6) δ 1.71 (2H, m), 1.91 (2H, m), 2.85 (1H, m), 3.11 (2H, m), 3.70 (2H, m), 3.98 (2H, t), 4.42 (2H, m), 4.80 (1H, t), 6.78 (1H, m), 6.84 (2H, m), 7.21 (1H, m), 7.66 (1H, d), 8.24 (1H, d); m/z=408 [M+H]+.

EXAMPLES 738-741

The following compounds were prepared in 78-89% yield by an analogous method to Example 512, starting from 4-[1-[3-(trifluoromethyl)[1,2,4]triazolo[4,3-b]pyridazin-6-yl]piperidin-4-yl]benzoic acid and the appropriate amine:—

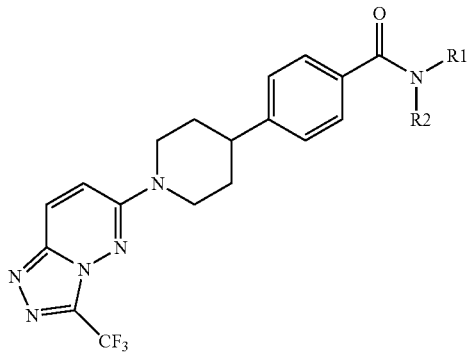

| Ex. | NR1R2 | 1H NMR (399.1 MHz, DMSO-d6) | m/z [M + H]+ |
|---|---|---|---|
| 738 | (S)-3-hydroxypyrrolidinyl | δ 1.68-1.95 (6H, m), 2.93 (1H, m), 3.13 (2H, m), 3.33-3.42 (1H, m), 3.47-3.62 (3H, m), 4.22-4.32 (1H, m), 4.44 (2H, m), 4.88-4.98 (1H, m), 7.34 (2H, d), 7.46 (2H, m), 7.67 (1H, d), 8.25 (1H, d) | 461 |
| 739 | (R)-3-hydroxypyrrolidinyl | δ 1.68-1.96 (6H, m), 2.93 (1H, m), 3.13 (2H, m), 3.35-3.42 (1H, m), 3.47-3.62 (3H, m), 4.22-4.32 (1H, m), 4.44 (2H, m), 4.88-4.98 (1H, m), 7.34 (2H, d), 7.46 (2H, m), 7.67 (1H, d), 8.25 (1H, d) | 461 |
| 740 | 4-hydroxypiperidinyl | δ (373 K) 1.38 (2H, m), 1.75 (4H, m), 1.97 (2H, m), 3.18 (4H, m), 3.75 (3H, m), 4.39 (3H, m), 7.31 (4H, m), 7.56 (1H, d), 8.14 (1H, d) | 475 |
| 741 | N-methyl-N-(2-(methylsulfonyl)ethyl)amino | δ 1.73 (2H, m), 1.94 (2H, m), 2.90-3.17 (9H, m), 3.48 (2H, t), 3.85 (2H, m), 4.44 (2H, m), 7.36 (4H, s), 7.67 (1H, d), 8.25 (1H, d) | 511 |

EXAMPLES 742-752

The following compounds were prepared in 39-84% yield by an analogous method to Example 512, starting from 4-[4-[3-(trifluoromethyl)[1,2,4]triazolo[4,3-b]pyridazin-6-yl]piperazin-1-yl]benzoic acid and the appropriate amine:—

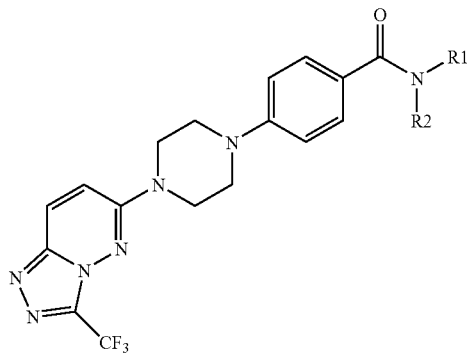

| Ex. | NR1R2 | 1H NMR (399.9 MHz, DMSO-d6) | m/z [M + H]+ |
|---|---|---|---|
| 742 | piperazine (NH) | δ 2.67 (4H, m), 3.41 (8H, m), 3.78 (4H, m), 7.02 (2H, d), 7.30 (2H, d), 7.69 (1H, d), 8.31 (1H, d) | 461 |
| 743 | N-methyl-N-(2-hydroxyethyl) | δ 2.98 (3H, s), 3.41 (6H, m), 3.55 (2H, m), 3.78 (4H, m), 4.79 (1H, t), 7.02 (2H, d), 7.35 (2H, d), 7.69 (1H, d), 8.31 (1H, d) | 450 |
| 744 | 4-methylpiperazin-1-yl | δ 2.20 (3H, s), 2.30 (4H, m), 3.42 (4H, m), 3.49 (4H, m), 3.78 (4H, m), 7.03 (2H, d), 7.31 (2H, d), 7.69 (1H, d), 8.31 (1H, d) | 475 |
| 745 | NH-CH2CH2-OMe | δ 3.27 (3H, s), 3.39-3.47 (8H, m), 3.78 (4H, m), 7.03 (2H, d), 7.69 (1H, d), 7.78 (2H, d), 8.27 (1H, t), 8.31 (1H, d) | — |
| 746 | NMe2 | δ 2.97 (6H, s), 3.42 (4H, m), 3.78 (4H, m), 7.02 (2H, d), 7.34 (2H, d), 7.69 (1H, d), 8.31 (1H, d) | 420 |
| 747 | (R)-3-hydroxypyrrolidin-1-yl | δ 1.77-1.95 (2H, m), 3.29 (1H, m), 3.42-3.66 (7H, m), 3.78 (4H, m), 4.27 (1H, m), 4.95 (1H, m), 7.02 (2H, d), 7.46 (2H, d), 7.69 (1H, d), 8.31 (1H, d) | 462 |
| 748 | pyrrolidin-1-yl | δ 1.83 (4H, m), 3.43 (8H, m), 3.78 (4H, m), 7.01 (2H, d), 7.47 (2H, d), 7.69 (1H, d), 8.31 (1H, d) | 446 |
| 749 | morpholin-4-yl | δ 3.42 (4H, m), 3.50 (4H, m), 3.59 (4H, m), 3.78 (4H, m), 7.03 (2H, d), 7.34 (2H, d), 7.69 (1H, d), 8.31 (1H, d) | 462 |
| 750 | NH-CH2CH2-morpholin-4-yl | δ 2.39-2.46 (6H, m), 3.36 (2H, m), 3.46 (4H, m), 3.57 (4H, m), 3.78 (4H, m), 7.03 (2H, d), 7.69 (1H, d), 7.76 (2H, d), 8.16 (1H, t), 8.31 (1H, d) | 505 |
| 751 | N-methyl-N-(2-methoxyethyl) | δ 2.97 (3H, s), 3.24 (3H, s), 3.41 (4H, m), 3.50 (4H, m), 3.78 (4H, m), 7.02 (2H, d), 7.32 (2H, d), 7.69 (1H, d), 8.31 (1H, d) | 464 |
| 752 | (S)-3-hydroxypyrrolidin-1-yl | δ 1.76-1.95 (2H, m), 3.29 (1H, m), 3.42-3.66 (7H, m), 3.78 (4H, m), 4.27 (1H, m), 4.96 (1H, m), 7.02 (2H, d), 7.46 (2H, d), 7.69 (1H, d), 8.31 (1H, d) | 462 |

The 4-[4-[3-(trifluoromethyl)[1,2,4]triazolo[4,3-b]pyridazin-6-yl]piperazin-1-yl]benzoic acid used as starting material was prepared as follows:—

Preparation of ethyl 4-[4-[3-(trifluoromethyl)[1,2,4]triazolo[4,3-b]pyridazin-6-yl]piperazin-1-yl]benzoate DIPEA (2.348 mL, 13.48 mmol) was added to 6-chloro-3-(trifluoromethyl)-[1,2,4]triazolo[4,3-b]pyridazine (2 g, 8.99 mmol) and ethyl 4-(piperazin-1-yl)benzoate (2.316 g, 9.89 mmol, CAS 80518-57-6) in DMF (20 mL). The resulting solution was stirred at 80° C. for 2 hours. The reaction mixture was cooled to room temperature, then evaporated to dryness and redissolved in DCM (150 mL) and washed with water (100 mL). The organic layer was dried over MgSO4, filtered and evaporated to afford crude product which was triturated with ether. The solid was collected by filtration and dried under vacuum to give ethyl 4-[4-[3-(trifluoromethyl)[1,2,4]triazolo[4,3-b]pyridazin-6-yl]piperazin-1-yl]benzoate (3.40 g, 90%) as a solid.

1H NMR (399.9 MHz, DMSO-d6) δ 1.30 (3H, t), 3.54 (4H, m), 3.79 (4H, m), 4.26 (2H, q), 7.04 (2H, d), 7.66 (1H, d), 7.83 (2H, d), 8.30 (1H, d); m/z=421 [M+H]+.

Preparation of 4-[4-[3-(trifluoromethyl)[1,2,4]triazolo[4,3-b]pyridazin-6-yl]piperazin-1-yl]benzoic acid Lithium hydroxide monohydrate (0.373 g, 8.90 mmol) was added to ethyl 4-[4-[3-(trifluoromethyl)[1,2,4]triazolo[4,3-b]pyridazin-6-yl]piperazin-1-yl]benzoate (3.40 g, 8.09 mmol) in a mixture of MeOH (60 mL) and water (30 mL). The resulting suspension was stirred at 50° C. for 16 hours. Further lithium hydroxide monohydrate (0.373 g, 8.90 mmol) was added, the temperature was increased to 65° C. and the suspension was stirred for a further 6 hours. The reaction mixture was cooled to room temperature and the MeOH evaporated. The residues were dissolved in water (200 mL) and filtered. The filtrate was acidified with 1M citric acid until precipitation ceased, and the precipitate was collected by filtration, washed with water and dried under vacuum to afford 4-[4-[3-(trifluoromethyl)[1,2,4]triazolo[4,3-b]pyridazin-6-yl]piperazin-1-yl]benzoic acid (3.17 g, 100%) as a solid.

1H NMR (399.9 MHz, DMSO-d6) δ 3.52 (4H, m), 3.79 (4H, m), 7.03 (2H, d), 7.67 (1H, d), 7.81 (2H, d), 8.30 (1H, d), 12.20 (1H, s); m/z=393 [M+H]+.

EXAMPLE 753

Preparation of N-methyl-N-[2-(2-oxopyrrolidin-1-yl)ethyl]-4-[1-[3-(trifluoromethyl)[1,2,4]triazolo[4,3-b]pyridazin-6-yl]piperidin-4-yl]benzamide

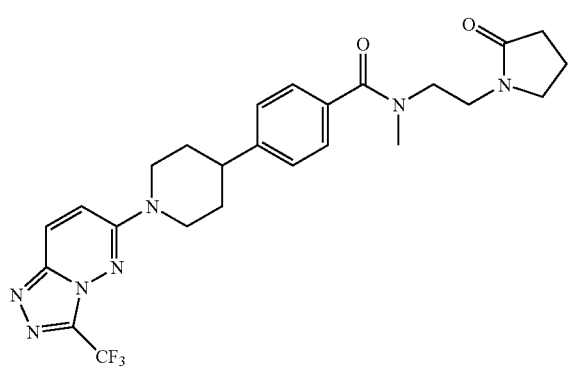

A solution of N-[2-(2-oxopyrrolidin-1-yl)ethyl]-4-[1-[3-(trifluoromethyl)[1,2,4]triazolo[4,3-b]pyridazin-6-yl]piperidin-4-yl]benzamide (obtained as described in Example 639) (150 mg, 0.30 mmol) in DMF (2 mL) was added dropwise to a stirred suspension of sodium hydride (60% in mineral oil) (13.16 mg, 0.33 mmol) in DMF (1 mL) under nitrogen. The resulting suspension was stirred at ambient temperature for 5 minutes, then iodomethane (0.028 mL, 0.45 mmol) was added and the mixture was stirred at ambient temperature for a further 10 minutes. The reaction was quenched with MeOH (0.5 mL) and purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford N-methyl-N-[2-(2-oxopyrrolidin-1-yl)ethyl]-4-[1-[3-(trifluoromethyl)[1,2,4]triazolo[4,3-b]pyridazin-6-yl]piperidin-4-yl]benzamide (84 mg, 55%) as a solid.

1H NMR (399.9 MHz, DMSO-d6) δ 1.67-1.94 (6H, m), 2.17 (2H, m), 2.87-2.98 (4H, m), 3.12 (2H, m), 3.44 (4H, m), 3.62 (2H, m), 4.44 (2H, m), 7.25-7.35 (4H, m), 7.68 (1H, d), 8.26 (1H, d); m/z=516 [M+H]+.

EXAMPLE 754

Preparation of N-methyl-N-(2-morpholin-4-ylethyl)-4-[1-[3-(trifluoromethyl)[1,2,4]triazolo[4,3-b]pyridazin-6-yl]piperidin-4-yl]benzamide

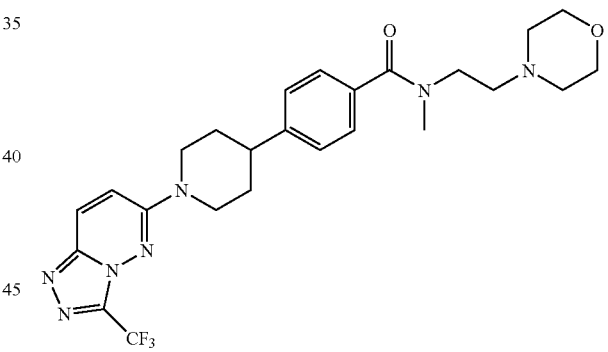

Obtained in 74% yield by an analogous method to Example 753, starting from N-(2-morpholin-4-ylethyl)-4-[1-[3-(trifluoromethyl)[1,2,4]triazolo[4,3-b]pyridazin-6-yl]piperidin-4-yl]benzamide (obtained as described in Example 638).

1H NMR (399.9 MHz, DMSO-d6) δ 1.72 (2H, m), 1.92 (2H, m), 2.14 (2H, m), 2.41 (4H, m), 2.88-2.97 (4H, m), 3.13 (2H, m), 3.43-3.59 (6H, m), 4.44 (2H, m), 7.33 (4H, m), 7.68 (1H, d), 8.26 (1H, d); m/z=518 [M+H]+.

EXAMPLES 755-758

The following compounds were prepared in 9-24% yield by an analogous method to Example 514, starting from 4-[4-[3-(trifluoromethyl)[1,2,4]triazolo[4,3-b]pyridazin-6-yl]piperazin-1-yl]phenol and the appropriate alcohol:—

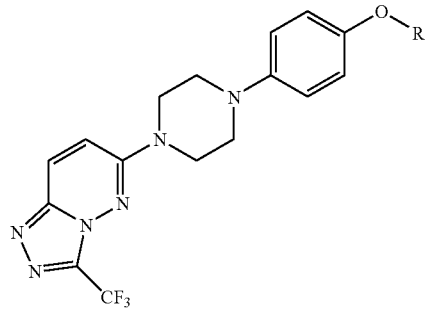

| Ex. | OR | 1H NMR (399.9 MHz, DMSO-d6) | m/z [M + H]+ |
|---|---|---|---|
| 755 | O-CH2CH2-pyrrolidine | δ 1.70 (4H, m), 2.58 (4H, m), 2.82 (2H, m), 3.17 (4H, m), 3.76 (4H, m), 4.02 (2H, m), 6.87 (2H, d), 6.97 (2H, d), 7.69 (1H, d), 8.30 (1H, d) | 462 |
| 756 | O-(N-methylpiperidin-4-yl) | δ 1.61 (2H, m), 1.89 (2H, m), 2.19 (5H, m), 2.64 (2H, m), 3.17 (4H, m), 3.75 (4H, m), 4.23 (1H, m), 6.87 (2H, d), 6.96 (2H, d), 7.69 (1H, d), 8.30 (1H, d) | 462 |
| 757 | O-CH2-isoxazol-3-yl | δ 3.19 (4H, m), 3.76 (4H, m), 5.17 (2H, s), 6.69 (1H, d), 6.97 (4H, m), 7.69 (1H, d), 8.30 (1H, d), 8.95 (1H, d) | 446 |
| 758 | O-CH2-oxazol-5-yl | δ 3.19 (4H, m), 3.76 (4H, m), 5.11 (2H, s), 6.97 (4H, m), 7.31 (1H, s), 7.69 (1H, d), 8.30 (1H, d), 8.41 (1H, s) | 446 |

EXAMPLES 759-768

The following compounds were prepared in 15-49% yield by General Synthetic Method 5, starting from 6-(piperazin-1-yl)-3-(trifluoromethyl)-[1,2,4]triazolo[4,3-b]pyridazine and the appropriate aldehyde:—

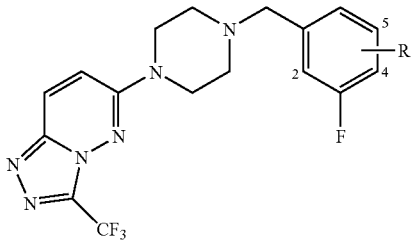

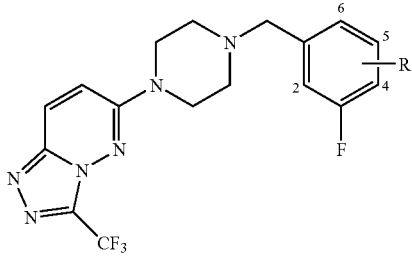

| Ex. | R | 1H NMR (400.1 MHz, DMSO-d6) | m/z [M + H]+ |
|---|---|---|---|
| 759 | 5-Cl | δ 2.52-2.56 (4H, m), 3.59 (2H, s), 3.62-3.66 (4H, m), 7.18-7.22 (1H, m), 7.29 (1H, s), 7.32-7.36 (1H, m), 7.59 (1H, d), 8.26 (1H, d) | 415 |
| 760 | 5-CF3 | δ 2.53-2.57 (4H, m), 3.62-3.66 (4H, m), 3.68 (2H, s), 7.56-7.61 (4H, m), 8.26 (1H, d) | 449 |
| 761 | 2-CF3 | δ 2.54-2.58 (4H, m), 3.60-3.64 (4H, m), 3.73 (2H, s), 7.38-7.44 (1H, m), 7.58-7.61 (2H, m), 7.69-7.72 (1H, m), 8.27 (1H, d) | 449 |
| 762 | 6-CF3 | δ 2.57-2.61 (4H, m), 3.65-3.69 (4H, m), 3.72 (2H, s), 7.32-7.36 (1H, m), 7.61 (1H, d), 7.64-7.67 (1H, m), 7.80-7.83 (1H, m), 8.27 (1H, d) | 449 |
| 763 | 2,5-F | δ 2.55-2.58 (4H, m), 3.62-3.65 (4H, m), 3.67 (2H, d), 7.17-7.20 (1H, m), 7.45-7.48 (1H, m), 7.59 (1H, d), 8.26 (1H, d) | 417 |
| 764 | 2,6-F | δ 2.55-2.59 (4H, m), 3.59-3.63 (4H, m), 3.71 (2H, s), 7.15-7.18 (1H, m), 7.48-7.53 (1H, m), 7.57 (1H, d), 8.24 (1H, d) | 417 |
| 765 | 6-SO2Me | δ 2.59-2.63 (4H, m), 3.42 (3H, s), 3.62-3.66 (4H, m), 3.96 (2H, s), 7.43-7.47 (1H, m), 7.56-7.59 (1H, m), 7.62 (1H, d), 8.04-8.08 (1H, m), 8.28 (1H, d) | 459 |
| 766 | 2,4-F | δ 2.54-2.58 (4H, m), 3.60-3.64 (6H, m), 7.30-7.34 (2H, m), 7.59 (1H, d), 8.25 (1H, d) | 417 |
| 767 | 4,5-F | δ 2.53-2.56 (4H, m), 3.56 (2H, s), 3.61-3.65 (4H, m), 7.28-7.32 (2H, m), 7.60 (1H, d), 8.26 (1H, d) | 417 |
| 768 | 2-Cl | δ 2.59-2.63 (4H, m), 3.62-3.66 (4H, m), 3.69 (2H, s), 7.35-7.42 (3H, m), 7.60 (1H, d), 8.26 (1H, d) | 415 |

EXAMPLE 769

Preparation of 6-[4-[(2-methylpyridin-4-yl)methyl]piperazin-1-yl]-3-(trifluoromethyl)[1,2,4]triazolo[4,3-b]pyridazine

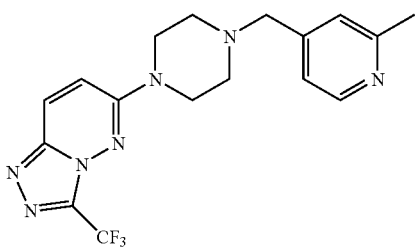

Obtained in 61% yield by General Synthetic Method 5, starting from 6-(piperazin-1-yl)-3-(trifluoromethyl)-[1,2,4]triazolo[4,3-b]pyridazine and 2-methylpyridine-4-carboxaldehyde 1H NMR (399.9 MHz, DMSO-d6) δ 2.47 (3H, s), 2.54-2.58 (4H, m), 3.55 (2H, s), 3.62-3.66 (4H, m), 7.15-7.17 (1H, m), 7.22 (1H, s), 7.59 (1H, d), 8.26 (1H, d), 8.39-8.40 (1H, m); m/z=378 [M+H]+.

EXAMPLES 770-777

The following compounds were prepared in 19-69% yield by General Synthetic Method 5 starting from 6-(piperazin-1-yl)-3-(trifluoromethyl)-[1,2,4]triazolo[4,3-b]pyridazine and the appropriate aldehyde:—

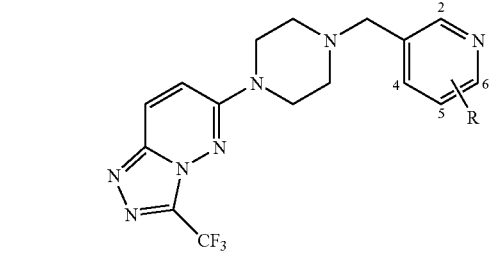

| Ex. | R | 1H NMR (400.1 MHz, DMSO-d6) | m/z [M + H]+ |
|---|---|---|---|
| 770 | 5-Cl | δ 2.54-2.58 (4H, m), 3.62-3.65 (6H, m), 7.59 (1H, d), 7.89 (1H, t), 8.26 (1H, d), 8.51 (1H, d), 8.56 (1H, d) | 398 |
| 771 | 4-CF3 | δ 2.56-2.60 (4H, m), 3.62-3.66 (4H, m), 3.76 (2H, s), 7.60 (1H, d), 7.74 (1H, d), 8.27 (1H, d), 8.78 (1H, d), 8.99 (1H, s) | 432 |
| 772 | 2-Me | δ 2.53-2.57 (7H, m), 3.54 (2H, s), 3.60-3.64 (4H, m), 7.19-7.22 (1H, m), 7.60 (1H, d), 7.65 (1H, d), 8.26 (1H, d), 8.35-8.37 (1H, m) | 378 |
| 773 | 4-Cl | δ 2.58-2.62 (4H, m), 3.61-3.65 (4H, m), 3.70 (2H, s), 7.56 (1H, d), 7.60 (1H, d), 8.26 (1H, d), 8.47 (1H, d), 8.66 (1H, s) | 398 |
| 774 | 5-Br | δ 2.49-2.53 (4H, m), 3.60-3.90 (6H, m), 7.54-7.57 (1H, m), 7.63 (1H, d), 8.04-8.06 (1H, m), 8.34 (1H, d), 8.43 (1H, s) | 442 |
| 775 | 2-OMe | δ 2.54 (2H, d), 2.56 (1H, t), 3.59-3.62 (3H, m), 3.64 (3H, d), 3.85 (3H, s), 7.33 (1H, q), 7.59 (1H, d), 8.14 (1H, d), 8.21-8.22 (1H, m), 8.26 (1H, d) | 394 |

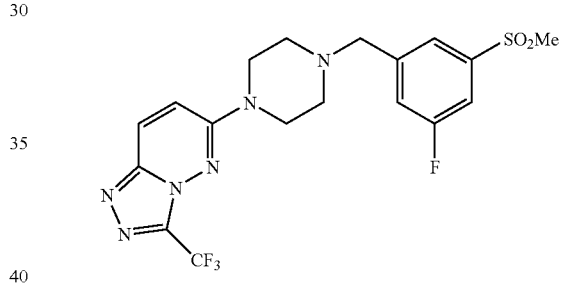

| Ex. | R | 1H NMR (400.1 MHz, DMSO-d6) | m/z [M + H]+ |
|---|---|---|---|
| 776 | 6-Me | δ 2.46 (3H, s), 2.52-2.55 (4H, m), 3.54 (2H, s), 3.60-3.63 (4H, m), 7.23-7.24 (1H, m), 7.57-7.63 (2H, m), 8.25 (1H, d), 8.39 (1H, s) | 378 |
| 777 | 2-CF3 | δ 2.56-2.60 (4H, m), 3.62-3.66 (4H, m), 3.75 (2H, s), 7.61 (1H, d), 7.73-7.76 (1H, m), 8.26-8.29 (2H, m), 8.65-8.66 (1H, m) | 432 |

EXAMPLE 778

Preparation of 6-[4-[3-fluoro-5-(methylsulfonyl)benzyl]piperazin-1-yl]-3-(trifluoromethyl)[1,2,4]triazolo[4,3-b]pyridazine Obtained in 45% yield by General Synthetic Method 5, starting from 6-(piperazin-1-yl)-3-(trifluoromethyl)-[1,2,4]triazolo[4,3-b]pyridazine and 3-fluoro-5-methylsulfonyl-benzaldehyde.

1H NMR (399.9 MHz, DMSO-d6) δ 2.55-2.59 (4H, m), 3.30 (3H, s), 3.63-3.67 (4H, m), 3.70 (2H, s), 7.58-7.62 (2H, m), 7.70-7.73 (1H, m), 7.77 (1H, d), 8.26 (1H, d); m/z=459 [M+H]+.

The 3-fluoro-5-methylsulfonylbenzaldehyde used as starting material was prepared as follows:—

Preparation of [3-fluoro-5-(methylsulfonyl)phenyl]methanol

Methanesulphinic acid sodium salt (748 mg, 7.33 mmol) was added to (3-bromo-5-fluorophenyl)methanol (501 mg, 2.44 mmol) and copper(I) iodide (0.248 mL, 7.33 mmol) in DMSO (12 mL) under nitrogen. The resulting mixture was stirred at 90° C. for 3 days. The reaction mixture was diluted with EtOAc (300 mL), then filtered. The filtrate was washed sequentially with water (200 mL) and saturated brine (2×200 mL). The organic layer was dried over Na2SO4, filtered and evaporated to afford crude product. The crude product was purified by flash silica chromatography, elution gradient 70 to 100% EtOAc in isohexane. Pure fractions were evaporated to dryness to afford [3-fluoro-5-(methylsulfonyl)phenyl]methanol (240 mg, 48.1%) as a white solid.

1H NMR (399.9 MHz, CDCl3) δ 2.49 (1H, t), 3.07 (3H, s), 4.79 (2H, d), 7.36-7.40 (1H, m), 7.51-7.54 (1H, m), 7.72 (1H, s); m/z=203 [M−H]−.

Preparation of 3-fluoro-5-methylsulfonylbenzaldehyde 1,1,1-Triacetoxy-1,1-dihydro-1,2-benziodoxol-3(1H)-one (530 mg, 1.21 mmol) was added in one portion to [3-fluoro-5-(methylsulfonyl)phenyl]methanol (225 mg, 1.10 mmol) in DCM (20 mL) at 22° C. The resulting solution was stirred at ambient temperature for 2 hours. The reaction mixture was diluted with DCM (50 ml) and poured into saturated aqueous sodium bicarbonate (30 mL) containing sodium thiosulfate (1219 mg, 7.71 mmol). The resulting suspension was stirred for 10 minutes before separating the layers. The organic layer was washed with water (1×50 mL), dried over MgSO4 and evaporated to afford crude product. The crude product was purified by flash silica chromatography, elution gradient 30 to 40% EtOAc in isohexane. Pure fractions were evaporated to dryness to afford 3-fluoro-5-(methylsulfonyl)benzaldehyde (168 mg, 75%) as a white solid.

1H NMR (399.9 MHz, CDCl3) δ 3.13 (3H, s), 7.85-7.88 (1H, m), 7.91-7.93 (1H, m), 8.26 (1H, t), 10.07 (1H, d); m/z=201 [M−H]−.

EXAMPLE 779

Preparation of 6-[4-[2-(difluoromethyl)-5-fluorobenzyl]piperazin-1-yl]-3-(trifluoromethyl)[1,2,4]triazolo[4,3-b]pyridazine

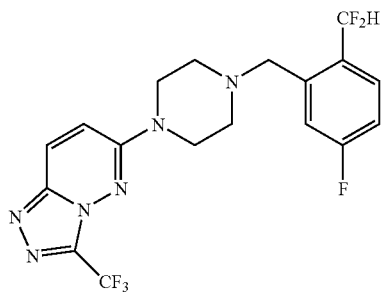

Obtained in 61% yield by General Synthetic Method 5, starting from 6-(piperazin-1-yl)-3-(trifluoromethyl)-[1,2,4]triazolo[4,3-b]pyridazine and 2-difluoromethyl-5-fluorobenzaldehyde.

1H NMR (399.9 MHz, DMSO-d6) δ 2.55-2.59 (4H, m), 3.60-3.64 (4H, m), 3.70 (2H, s), 7.26-7.32 (1H, m), 7.36 (1H, t), 7.36-7.41 (1H, m), 7.60 (1H, d), 7.67-7.71 (1H, m), 8.26 (1H, d); m/z=431 [M+H]+.

The 2-difluoromethyl-5-fluorobenzaldehyde used as starting material was prepared as follows:—

Isopropylmagnesium chloride-lithium chloride complex in THF (1M, 21.46 mL, 21.46 mmol) was added to 2-bromo-1-(difluoromethyl)-4-fluorobenzene (4.39 g, 19.51 mmol) in THF (120 mL) cooled to −20° C. under nitrogen. The resulting solution was stirred at −20° C. for 1 hour. N,N-Dimethylformamide (1.813 mL, 23.41 mmol) was added, and the mixture stirred for a further 1 hour, maintaining the temperature in the range −15 to −20° C. The mixture was allowed to warm to ambient temperature, then 2M hydrochloric acid (100 mL) was added and the mixture was extracted with EtOAc (150 mL). The organic layer was washed with saturated sodium bicarbonate (120 mL) and concentrated to yield crude product. The crude product was purified by flash silica chromatography, elution gradient 5 to 10% EtOAc in isohexane. Pure fractions were evaporated to dryness to afford 2-(difluoromethyl)-5-fluorobenzaldehyde (1.250 g, 36.8%) as a colourless liquid.

1H NMR (399.9 MHz, CDCl3) δ 7.26 (1H, t), 7.37-7.43 (1H, m), 7.63-7.67 (1H, m), 7.78-7.82 (1H, m), 10.19 (1H, d); m/z=173 [M−H]−.

EXAMPLE 780

Preparation of 3-(difluoromethyl)-6-[4-[2-(difluoromethyl)-5-fluorobenzyl]piperazin-1-yl][1,2,4]triazolo[4,3-b]pyridazine

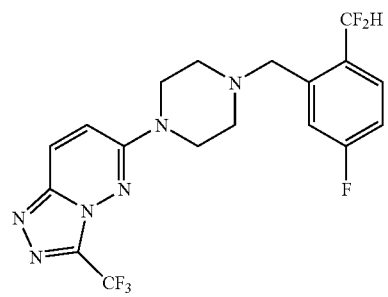

Obtained in 58% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and 2-difluoromethyl-5-fluorobenzaldehyde (obtained as described in Example 779, preparation of starting materials).

1H NMR (399.9 MHz, DMSO-d6) δ 2.54-2.57 (4H, m), 3.60-3.63 (4H, m), 3.70 (2H, s), 7.27-7.31 (1H, m), 7.36 (1H, t), 7.36-7.41 (1H, m), 7.51-7.53 (1H, m), 7.53 (1H, t), 7.67-7.71 (1H, m), 8.19 (1H, d); m/z=413 [M+H]+.

EXAMPLE 781

Preparation of 6-[4-[2-(difluoromethyl)-3-fluorobenzyl]piperazin-1-yl]-3-(trifluoromethyl)[1,2,4]triazolo[4,3-b]pyridazine

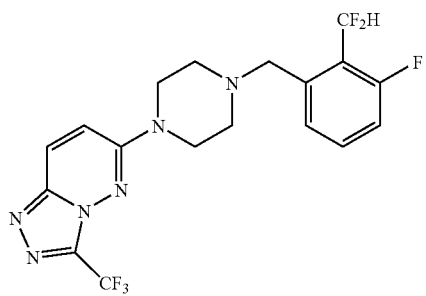

Obtained in 33% yield by General Synthetic Method 5, starting from 6-(piperazin-1-yl)-3-(trifluoromethyl)-[1,2,4]triazolo[4,3-b]pyridazine and 2-difluoromethyl-3-fluorobenzaldehyde.

1H NMR (399.9 MHz, DMSO-d6) δ 2.57-2.57 (4H, m), 3.56-3.60 (4H, m), 3.73 (2H, s), 7.28-7.32 (2H, m), 7.42 (1H, t), 7.55-7.60 (2H, m), 8.26 (1H, d); m/z=431 [M+H]+.

The 2-difluoromethyl-3-fluorobenzaldehyde used as starting material was obtained in 32% yield by an analogous method to Example 779, preparation of starting materials, starting from 1-bromo-2-(difluoromethyl)-3-fluorobenzene.

1H NMR (399.9 MHz, CDCl3) δ 7.20-7.43 (2H, m), 7.61-7.67 (1H, m), 7.86 (1H, d), 10.38-10.48 (1H, m); m/z=173 [M–H]–.

EXAMPLE 782

Preparation of 3-(difluoromethyl)-6-[4-[2-(difluoromethyl)-3-fluorobenzyl]piperazin-1-yl][1,2,4]triazolo[4,3-b]pyridazine

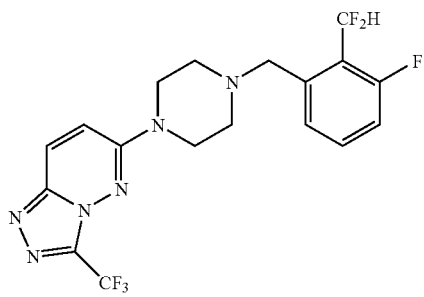

Obtained in 39% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and 2-difluoromethyl-3-fluorobenzaldehyde (obtained as described in Example 781, preparation of starting materials).

1H NMR (399.9 MHz, DMSO-d6) δ 2.52-2.56 (4H, m), 3.56-3.60 (4H, m), 3.73 (2H, s), 7.28-7.32 (2H, m), 7.34-7.57 (4H, m), 8.20 (1H, d); m/z=413 [M+H]+.

EXAMPLE 783

Preparation of 6-[4-[3-(difluoromethyl)-5-fluorobenzyl]piperazin-1-yl]-3-(trifluoromethyl)[1,2,4]triazolo[4,3-b]pyridazine

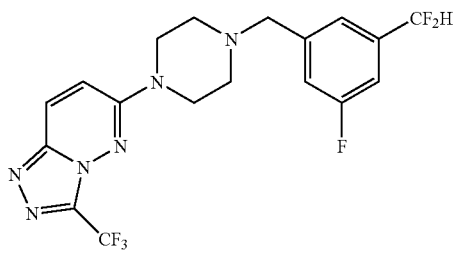

Obtained in 73% yield by General Synthetic Method 5, starting from 6-(piperazin-1-yl)-3-(trifluoromethyl)-[1,2,4]triazolo[4,3-b]pyridazine and 3-difluoromethyl-5-fluorobenzaldehyde.

1H NMR (399.9 MHz, DMSO-d6) δ 2.53-2.58 (4H, m), 3.62-3.66 (6H, m), 7.07 (1H, t), 7.33-7.43 (3H, m), 7.60 (1H, d), 8.26 (1H, d); m/z=431 [M+H]+.

The 3-difluoromethyl-5-fluorobenzaldehyde used as starting material was obtained in 44% yield by an analogous method to Example 779, preparation of starting materials, starting from 1-bromo-3-(difluoromethyl)-5-fluorobenzene.

1H NMR (399.9 MHz, CDCl3) δ 6.72 (1H, t), 7.49-7.52 (1H, m), 7.68-7.71 (1H, m), 7.83 (1H, d), 10.03 (1H, d); m/z=173 [M–H]–.

EXAMPLE 784

Preparation of 3-(difluoromethyl)-6-[4-[3-(difluoromethyl)-5-fluorobenzyl]piperazin-1-yl][1,2,4]triazolo[4,3-b]pyridazine

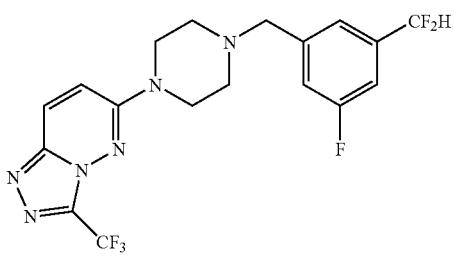

Obtained in 66% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and 3-difluoromethyl-5-fluorobenzaldehyde (obtained as described in Example 783, preparation of starting materials).

1H NMR (399.9 MHz, DMSO-d6) δ 2.53-2.57 (4H, m), 3.61-3.65 (6H, m), 7.07 (1H, t), 7.33-7.67 (5H, m), 8.19 (1H, d); m/z=413 [M+H]+.

EXAMPLE 785

Preparation of 6-[5-[(2-methylpyridin-4-yl)methyl]hexahydropyrrolo[3,4-c]pyrrol-2(1H)-yl]-3-(trifluoromethyl)[1,2,4]triazolo[4,3-b]pyridazine

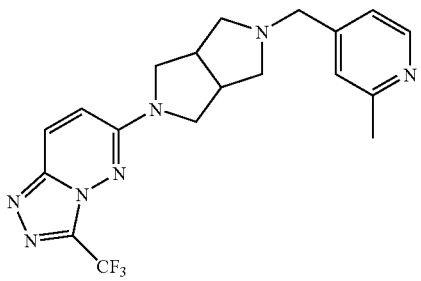

Obtained in 47% yield by General Synthetic Method 10, starting from 6-[(hexahydropyrrolo[3,4-c]pyrrol-2(1H)-yl)-3-(trifluoromethyl)]-[1,2,4]triazolo[4,3-b]pyridazine and 2-methylpyridine-4-carboxaldehyde.

1H NMR (399.9 MHz, DMSO-d6) δ 2.43 (3H, s), 2.55-2.63 (4H, m), 2.97-2.99 (2H, m), 3.41-3.44 (2H, m), 3.57 (2H, s), 3.73-3.78 (2H, m), 7.10 (1H, d), 7.15 (1H, s), 7.32 (1H, d), 8.23 (1H, d), 8.34 (1H, d); m/z=404 [M+H]+.

EXAMPLES 786-787

The following compounds were prepared in 22-57% yield by General Synthetic Method 10, starting from 6-[(hexahydropyrrolo[3,4-c]pyrrol-2(1H)-yl)-3-(trifluoromethyl)]-[1,2,4]triazolo[4,3-b]pyridazine and the appropriate aldehyde:—

| Ex. | R | 1H NMR (399.9 MHz, DMSO-d6) | m/z [M + H]+ |
|---|---|---|---|
| 786 | H | δ 2.61-2.67 (4H, m), 2.96-3.00 (2H, m), 3.39-3.42 (2H, m), 3.71 (2H, s), 3.74-3.79 (2H, m), 7.23-7.26 (1H, m), 7.31 (1H, d), 7.39 (1H, d), 7.71-7.75 (1H, m), 8.22 (1H, d), 8.47-8.49 (1H, m) | 390 |
| 787 | Br | δ 2.62-2.68 (4H, m), 2.97-3.00 (2H, m), 3.40-3.44 (2H, m), 3.69 (2H, s), 3.75-3.79 (2H, m), 7.31 (1H, d), 7.45 (1H, d), 7.51 (1H, d), 7.71 (1H, t), 8.22 (1H, d) | 469 |

EXAMPLES 788-805

The following compounds were prepared in 12-86% yield by General Synthetic Method 10, starting from 6-[hexahydropyrrolo[3,4-c]pyrrol-2(1H)-yl]-3-(trifluoromethyl)]-[1,2,4]triazolo[4,3-b]pyridazine and the appropriate aldehyde:—

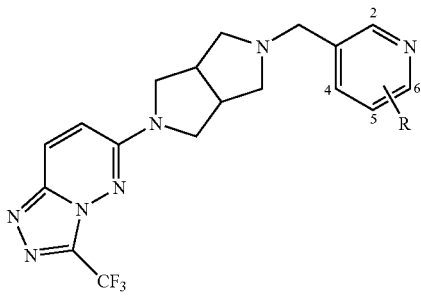

| Ex. | R | 1H NMR (399.9 MHz, DMSO-d6) | m/z [M + H]+ |
|---|---|---|---|
| 788 | 2-OMe | δ 2.56-2.65 (4H, m), 2.95-2.99 (2H, m), 3.40-3.44 (2H, m), 3.56 (2H, s), 3.73-3.78 (2H, m), 3.86 (3H, s), 6.93-6.96 (1H, m), 7.32 (1H, d), 7.63-7.66 (1H, m), 8.04-8.05 (1H, m), 8.22 (1H, d) | 420 |
| 789 | 5-F | δ 2.58-2.64 (4H, m), 2.96-3.00 (2H, m), 3.40-3.44 (2H, m), 3.67 (2H, s), 3.73-3.77 (2H, m), 7.31 (1H, d), 7.60-7.64 (1H, m), 8.22 (1H, d), 8.39 (1H, d), 8.46 (1H, d) | 408 |
| 790 | 2-Cl | δ 2.63-2.70 (4H, m), 2.98-3.01 (2H, m), 3.41-3.44 (2H, m), 3.70 (2H, s), 3.75-3.80 (2H, m), 7.32 (1H, d), 7.39-7.42 (1H, m), 7.88-7.90 (1H, m), 8.23 (1H, d), 8.29-8.31 (1H, m) | 424 |
| 791 | 6-Cl | δ 2.54-2.62 (4H, m), 2.96-2.98 (2H, m), 3.36-3.41 (2H, m), 3.62 (2H, s), 3.72-3.77 (2H, m), 7.30 (1H, d), 7.44-7.47 (1H, m), 7.76-7.78 (1H, m), 8.22 (1H, d), 8.32 (1H, d) | 424 |
| 792 | 2-Cl, 5-F | δ 2.63-2.68 (4H, m), 2.98-3.01 (2H, m), 3.42-3.46 (2H, m), 3.70 (2H, s), 3.75-3.80 (2H, m), 7.32 (1H, d), 7.79-7.82 (1H, m), 8.23 (1H, d), 8.36 (1H, d) | 442 |
| 793 | 6-OMe | δ 2.53-2.60 (4H, m), 2.95-2.98 (2H, m), 3.36-3.40 (2H, m), 3.52 (2H, s), 3.71-3.75 (2H, m), 3.83 (3H, s), 6.75 (1H, d), 7.30 (1H, d), 7.59-7.62 (1H, m), 8.05 (1H, d), 8.22 (1H, d) | 420 |
| 794 | 5-Br | δ 2.53-2.56 (2H, m), 2.60-2.65 (2H, m), 2.95-2.99 (2H, m), 3.39-3.43 (2H, m), 3.63 (2H, s), 3.71-3.76 (2H, m), 7.31 (1H, d), 7.94 (1H, t), 8.22 (1H, d), 8.49 (1H, d), 8.59 (1H, d) | 468 |
| 795 | 5-Br, 2-F | δ 2.53-2.59 (2H, m), 2.65-2.69 (2H, m), 2.96-2.99 (2H, m), 3.40-3.44 (2H, m), 3.64 (2H, s), 3.71-3.75 (2H, m), 7.31 (1H, d), 8.10-8.13 (1H, m), 8.22 (1H, d), 8.27-8.29 (1H, m) | 486 |
| 796 | 2-Br | δ 2.62-2.68 (4H, m), 2.99-3.01 (2H, m), 3.40-3.44 (2H, m), 3.67 (2H, s), 3.76-3.80 (2H, m), 7.32 (1H, d), 7.41-7.44 (1H, m), 7.82-7.85 (1H, m), 8.22 (1H, d), 8.26-8.28 (1H, m) | 468 |
| 797 | 5-OMe | δ 2.54-2.63 (4H, m), 2.97-2.99 (2H, m), 3.41-3.44 (2H, m), 3.61 (2H, s), 3.71-3.76 (2H, m), 3.79 (3H, s), 7.26 (1H, s), 7.31 (1H, d), 8.10 (1H, d), 8.17-8.18 (1H, m), 8.22 (1H, d) | 420 |
| 798 | 6-Br | δ 2.53-2.62 (4H, m), 2.96-2.98 (2H, m), 3.36-3.41 (2H, m), 3.59 (2H, s), 3.72-3.75 (2H, m), 7.30 (1H, d), 7.57-7.60 (1H, m), 7.66-7.68 (1H, m), 8.22 (1H, d), 8.31 (1H, d) | 468 |
| 799 | 2-Me | δ 2.46 (3H, s), 2.56-2.62 (4H, m), 2.96-2.98 (2H, m), 3.38-3.41 (2H, m), 3.58 (2H, s), 3.73-3.77 (2H, m), 7.14-7.17 (1H, m), 7.30 (1H, d), 7.58-7.61 (1H, m), 8.22 (1H, d), 8.30-8.31 (1H, m) | 404 |
| 800 | 4-Cl | δ 2.59-2.63 (2H, m), 2.66-2.70 (2H, m), 2.97-2.99 (2H, m), 3.39-3.43 (2H, m), 3.72-3.76 (4H, m), 7.31 (1H, d), 7.51 (1H, d), 8.22 (1H, d), 8.43 (1H, d), 8.58 (1H, s) | 424 |
| 801 | 4-Br | δ 2.61-2.68 (4H, m), 2.97-2.99 (2H, m), 3.40-3.44 (2H, m), 3.73-3.76 (4H, m), 7.31 (1H, d), 7.67 (1H, d), 8.22 (1H, d), 8.31 (1H, d), 8.54 (1H, s) | 469 |
| 802 | 4-CF3 | δ 2.60-2.64 (4H, m), 2.97-3.00 (2H, m), 3.36-3.41 (3H, m), 3.75-3.78 (2H, m), 3.79 (2H, s), 7.31 (1H, d), 7.68 (1H, d), 8.22 (1H, d), 8.73 (1H, d), 8.89 (1H, s) | 458 |
| 803 | 4-OMe | δ 2.53-2.68 (4H, m), 2.96-2.99 (2H, m), 3.41-3.44 (2H, m), 3.62 (2H, s), 3.71-3.75 (2H, m), 3.84 (3H, s), 7.02 (1H, d), 7.31 (1H, d), 8.22 (1H, d), 8.33-8.36 (2H, m) | 420 |
| 804 | 5-Cl | δ 2.54-2.58 (2H, m), 2.60-2.65 (2H, m), 2.97-2.99 (2H, m), 3.41-3.44 (2H, m), 3.64 (2H, s), 3.72-3.76 (2H, m), 7.31 (1H, d), 7.82 (1H, t), 8.22 (1H, d), 8.46-8.47 (1H, m), 8.51 (1H, d) | 424 |

-continued

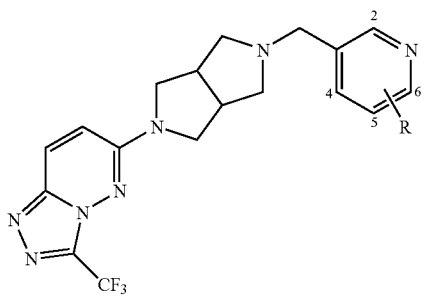

| Ex. | R | 1H NMR (399.9 MHz, DMSO-d6) | m/z [M + H]+ |
|---|---|---|---|
| 805 | 2-CF3 | δ 2.60-2.64 (4H, m), 2.97-3.00 (2H, m), 3.38-3.41 (2H, m), 3.76-3.79 (4H, m), 7.32 (1H, d), 7.66-7.69 (1H, m), 8.14 (1H, d), 8.23 (1H, d), 8.61 (1H, d) | 458 |

EXAMPLE 806

Preparation of 6-[4-(3-methoxyphenoxy)piperidin-1-yl]-3-(trifluoromethyl)[1,2,4]triazolo[4,3-a]pyridine

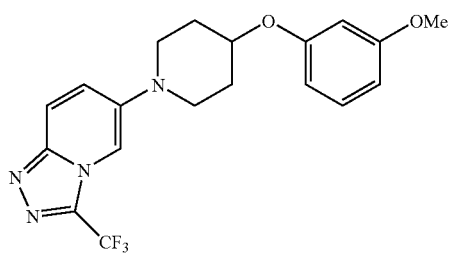

A mixture of 6-bromo-3-(trifluoromethyl)-[1,2,4]triazolo[4,3-a]pyridine (obtained as described in General Synthetic Method 9, preparation of starting materials) (100 mg, 0.38 mmol) and 4-(3-methoxyphenoxy)piperidine hydrochloride (110 mg, 0.45 mmol), rac-2,2'-bis(diphenylphosphino)-1,1'-binaphthyl (17.56 mg, 0.03 mmol) and sodium tert-butoxide (0.161 mL, 1.32 mmol) was suspended in xylenes (5 mL), then de-gassed and purged with nitrogen. Bis(dibenzylideneacetone)palladium (11 mg, 0.02 mmol) was added, and the mixture was sealed into a microwave tube. The reaction was heated to 100° C. for 20 minutes in the microwave reactor and cooled to ambient temperature. The reaction mixture was diluted with EtOAc (25 mL) and washed with water (25 mL). The organic layer was purified by ion exchange chromatography, using an SCX column. The desired product was eluted from the column using 7M ammonia in methanol and pure fractions were evaporated to dryness to afford crude product. The crude product was purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to afford 6-[4-(3-methoxyphenoxy)piperidin-1-yl]-3-(trifluoromethyl)[1,2,4]triazolo[4,3-a]pyridine (45.0 mg, 30.5%) as a white solid.

1H NMR (399.9 MHz, DMSO-d6) δ 1.77-1.83 (2H, m), 2.07-2.12 (2H, m), 3.11-3.17 (2H, m), 3.47-3.53 (2H, m), 3.74 (3H, s), 4.59-4.63 (1H, m), 6.51-6.55 (2H, m), 6.54-6.59 (1H, m), 7.20 (1H, t), 7.59 (1H, s), 7.75-7.78 (1H, m), 7.94 (1H, d); m/z=393 [M+H]+.

EXAMPLES 807-809

The following compounds were prepared in 61-70% yield by General Synthetic Method 9, starting from 6-(piperazin-1-yl)-3-(trifluoromethyl)-[1,2,4]triazolo[4,3-a]pyridine and the appropriate indole-3-carboxaldehyde:—

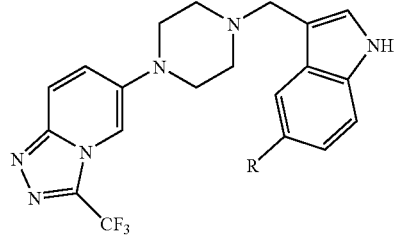

| Ex. | R | 1H NMR (399.9 MHz, DMSO-d6) | m/z [M + H]+ |
|---|---|---|---|
| 807 | H | δ 2.56-2.60 (4H, m), 3.16-3.19 (4H, m), 3.72 (2H, s), 6.97-7.01 (1H, m), 7.06-7.10 (1H, m), 7.28 (1H, d), 7.36 (1H, d), 7.51 (1H, s), 7.66-7.69 (1H, m), 7.71-7.74 (1H, m), 7.92 (1H, d), 10.96 (1H, s) | 401 |
| 808 | F | δ 2.55-2.59 (4H, m), 3.16-3.20 (4H, m), 3.69 (2H, s), 6.90-6.95 (1H, m), 7.34-7.37 (2H, m), 7.38-7.42 (1H, m), 7.51 (1H, s), 7.71-7.74 (1H, m), 7.92 (1H, d), 11.07-11.08 (1H, m) | 419 |
| 809 | CN | δ 2.56-2.60 (4H, m), 3.17-3.21 (4H, m), 3.76 (2H, s), 7.43-7.45 (1H, m), 7.51-7.56 (3H, m), 7.71-7.74 (1H, m), 7.92 (1H, d), 8.20 (1H, t), 11.57 (1H, d) | 426 |

EXAMPLE 810

Preparation of 6-[4-[2-(difluoromethyl)-5-fluorobenzyl]piperazin-1-yl]-3-(trifluoromethyl)[1,2,4]triazolo[4,3-a]pyridine

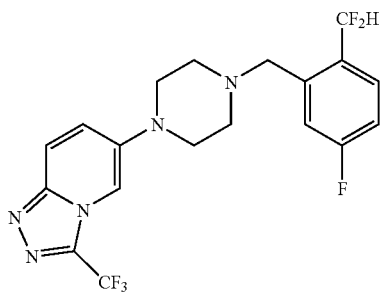

Obtained in 39% yield by General Synthetic Method 9, starting from 6-(piperazin-1-yl)-3-(trifluoromethyl)-[1,2,4]triazolo[4,3-a]pyridine and 2-difluoromethyl-5-fluorobenzaldehyde (obtained as described in Example 779, preparation of starting materials).

1H NMR (399.9 MHz, DMSO-d6) δ 2.56-2.60 (4H, m), 3.18-3.22 (4H, m), 3.72 (2H, s), 7.28-7.32 (1H, m), 7.37 (1H, t), 7.37-7.41 (1H, m), 7.54 (1H, s), 7.68-7.75 (2H, m), 7.94 (1H, d); m/z=430 [M+H]+.

EXAMPLE 811

Preparation of 6-[4-[4-[2-(1-methyl-1H-pyrazol-5-yl)ethoxy]phenyl]piperidin-1-yl]-3-(trifluoromethyl)[1,2,4]triazolo[4,3-a]pyridine

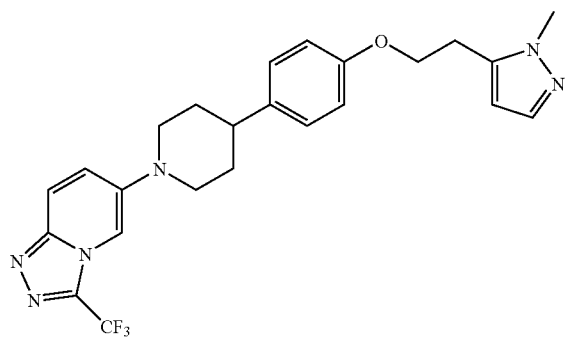

4-[4-[2-(1-Methyl-1H-pyrazol-5-yl)ethoxy]phenyl]piperidine (69 mg, 0.24 mmol), 6-bromo-3-(trifluoromethyl)-[1,2,4]triazolo[4,3-a]pyridine (obtained as described in General Synthetic Method 9, preparation of starting materials) (65 mg, 0.24 mmol), rac-2,2'-bis(diphenylphosphino)-1,1'-binaphthyl (11.41 mg, 0.02 mmol) and sodium tert-butoxide (0.060 mL, 0.49 mmol) were suspended in xylenes (5 mL), then de-gassed and purged with nitrogen. Bis(dibenzylideneacetone)palladium (7.02 mg, 0.01 mmol) was added, and the mixture was sealed into a microwave tube. The reaction was heated to 110° C. for 30 minutes in the microwave reactor and cooled to ambient temperature. The reaction mixture was diluted with EtOAc (25 mL), and washed with water (25 mL). The aqueous layer was extraced with further EtOAc (25 mL). The combined organic layers were purified by ion exchange chromatography, using an SCX column. The desired product was eluted from the column using 7M ammonia in methanol and pure fractions were evaporated to dryness to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[4-[2-(1-methyl-1H-pyrazol-5-yl)ethoxy]phenyl]piperidin-1-yl]-3-(trifluoromethyl)[1,2,4]triazolo[4,3-a]pyridine (22.00 mg, 19.14%) as a colourless gum.

1H NMR (399.9 MHz, DMSO-d6) δ 1.75-1.82 (2H, m), 1.84-1.90 (2H, m), 2.66-2.70 (1H, m), 2.80-2.85 (4H, m), 3.79 (3H, s), 3.80-3.83 (2H, s), 4.06 (2H, t), 6.90 (2H, d), 7.21 (2H, d), 7.34 (1H, s), 7.57 (2H, s), 7.77-7.80 (1H, m), 7.94 (1H, d); m/z=471 [M+H]+.

The 4-[4-[2-(1-methyl-1H-pyrazol-5-yl)ethoxy]phenyl]piperidine used as starting material was prepared as follows:—

DIAD (64.8 μl, 0.33 mmol) was added to 4-(piperidin-4-yl)phenol (CAS 263139-27-1, 53 mg, 0.30 mmol), 2-(1-methyl-1H-pyrazol-5-yl)ethanol (obtained as described in PCT Int. Appl. WO 2007017222, Intermediate 1) (37.7 mg, 0.30 mmol) and triphenylphosphine (86 mg, 0.33 mmol) in DCM (3 mL) at 20° C. under nitrogen. The resulting mixture was stirred at 22° C. for 3 days. The reaction mixture was purified by ion exchange chromatography, using an SCX column. The desired product was eluted from the column using 7M ammonia in methanol and pure fractions were evaporated to dryness to afford 4-[4-[2-(1-methyl-1H-pyrazol-5-yl)ethoxy]phenyl]piperidine (85 mg, 96%) as a yellow oil.

m/z=286 [M+H]+.

EXAMPLES 812-820

The following compounds were prepared in 11-72% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and the appropriate aldehyde:—

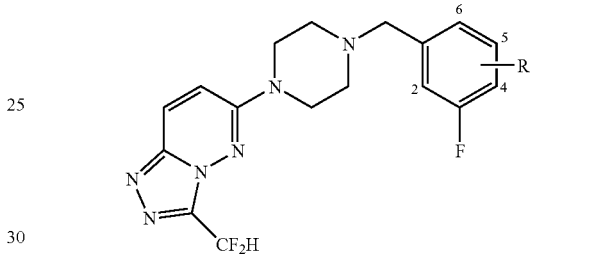

| Ex. | R | 1H NMR (399.9 MHz, CDCl3) | m/z [M + H]+ |
|---|---|---|---|
| 8121 | 2-CF3 | δ 2.54 (4H, t), 3.54 (4H, t), 3.66 (2H, s), 6.96 (1H, d), 7.02-7.07 (1H, m), 7.05 (1H, t), 7.39-7.45 (2H, m), 7.83 (1H, d) | 432 |
| 813 | 5-Cl | δ 2.59 (4H, t), 3.54 (2H, s), 3.64 (4H, t), 7.00-7.26 (5H, m), 7.91 (1H, d) | 398 |
| 814 | 5-CF3 | δ 2.61 (4H, t), 3.62 (2H, s), 3.64 (4H, t), 7.03 (1H, d), 7.13 (1H, t), 7.25 (1H, d), 7.31 (1H, d), 7.42 (1H, s), 7.91 (1H, dd) | 432 |
| 815 | 6-Cl | δ 2.67 (4H, t), 3.64-3.67 (6H, m), 6.94 (1H, td), 7.04 (1H, d), 7.13 (1H, t), 7.26-7.35 (2H, m), 7.91 (1H, d) | 398 |
| 816 | 6-CF3 | δ 2.65 (4H, s), 3.66 (4H, s), 3.73 (2H, s), 7.03-7.07 (2H, m), 7.13 (1H, t), 7.59 (1H, d), 7.65 (1H, dd), 7.92 (1H, d) | 432 |
| 817 | 2,6-F | δ 2.68 (4H, s), 3.63 (4H, t), 3.81 (2H, s), 6.83-6.89 (1H, m), 7.00 (1H, d), 7.08-7.16 (1H, m), 7.12 (1H, t), 7.89 (1H, d) | 400 |
| 818 | 4,5-F | δ 2.59 (4H, s), 3.50 (2H, s), 3.64 (4H, s), 6.95-7.05 (3H, m), 7.15 (1H, t), 7.92 (1H, d) | 399 |
| 819 | 6-SO2Me | δ 2.73-2.81 (4H, m), 3.31 (3H, s), 3.65 (4H, t), 4.07 (2H, s), 7.04 (1H, d), 7.12 (1H, t), 7.18-7.23 (1H, m), 7.36 (1H, s), 7.94 (1H, d), 8.15 (1H, dd) | 441 |
| 820 | 2,5-F | δ 2.58-2.71 (4H, m), 3.56-3.72 (6H, m), 6.80-6.91 (1H, m), 6.95-7.03 (1H, m), 7.02 (1H, d), 7.13 (1H, t), 7.91 (1H, d) | 400 |

EXAMPLES 821-823

The following compounds were prepared in 19-45% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and the appropriate aldehyde:—

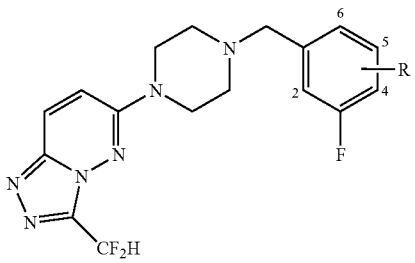

| Ex. | R | 1H NMR (399.9 MHz, DMSO-d6) | m/z [M + H]+ |
|---|---|---|---|
| 821 | 4,6-F | δ 3.18-3.80 (10H, m), 7.41-7.67 (4H, m), 8.21 (1H, d) | 400 |
| 822 | 2-Cl | δ 3.38-4.41 (10H, m), 7.47-7.54 (4H, m), 7.56 (1H, t), 8.27 (1H, d) | 397 |
| 823 | 2,4-F | δ 3.39-4.25 (10H, m), 7.34-7.69 (4H, m), 8.28 (1H, d) | 399 |

EXAMPLE 824

Preparation of 3-(difluoromethyl)-6-[4-[2-(difluoromethyl)benzyl]piperazin-1-yl][1,2,4]triazolo[4,3-b]pyridazine

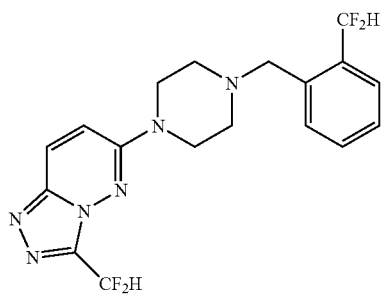

Obtained in 70% yield by General Synthetic Method 5, starting from 3-(difluoromethyl)-6-(piperazin-1-yl)-[1,2,4]triazolo[4,3-b]pyridazine (obtained as described in Examples 248-263, preparation of starting materials) and 2-difluoromethylbenzaldehyde.

1H NMR (399.9 MHz, CDCl3) δ 2.51 (4H, t), 3.53 (4H, t), 3.62 (2H, s), 6.95 (1H, d), 7.05 (1H, t), 7.18 (1H, t), 7.27-7.37 (3H, m), 7.59 (1H, t), 7.83 (1H, d); m/z=396 [M+H]+.

The 2-difluoromethylbenzaldehyde used as starting material was obtained in 19% yield by an analogous method to Example 779, preparation of starting materials, starting from 1-bromo-2-(difluoromethyl)benzene.

1H NMR (399.9 MHz, CDCl3) δ 7.36 (1H, t), 7.61-7.68 (2H, m), 7.75 (1H, d), 7.87 (1H, d), 10.12 (1H, s); m/z=155 (M−H)−.

EXAMPLE 825

Preparation of 3-(difluoromethyl)-6-[4-[3-(difluoromethyl)benzyl]piperazin-1-yl][1,2,4]triazolo[4,3-b]pyridazine

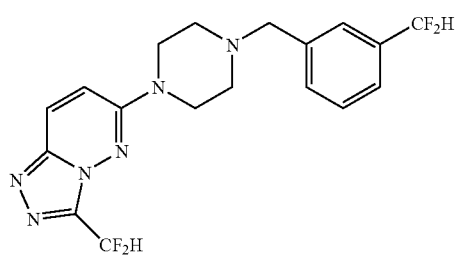

Obtained in 20% yield by General Synthetic Method 5, starting from 3-(difluoromethyl)-6-(piperazin-1-yl)-[1,2,4]triazolo[4,3-b]pyridazine and 3-difluoromethylbenzaldehyde.

1H NMR (399.9 MHz, CDCl3) δ 2.53 (4H, t), 3.55-3.57 (6H, m), 6.58 (1H, t), 6.95 (1H, d), 7.06 (1H, t), 7.36-7.44 (4H, m), 7.83 (1H, d); m/z=396 [M+H]+.

The 3-difluoromethylbenzaldehyde used as starting material was obtained in 10% yield by an analogous method to Example 779, preparation of starting materials, starting from 1-bromo-3-(difluoromethyl)benzene.

1H NMR (399.9 MHz, CDCl3) δ 6.66 (1H, t), 7.59 (1H, t), 7.72 (1H, d), 7.94 (1H, d), 7.97 (1H, s), 10.01 (1H, s)

EXAMPLE 826

Preparation of 3-(difluoromethyl)-6-[4-[4-(difluoromethyl)benzyl]piperazin-1-yl][1,2,4]triazolo[4,3-b]pyridazine

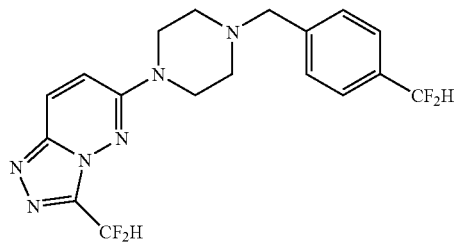

Obtained in 20% yield by General Synthetic Method 5, starting from 3-(difluoromethyl)-6-(piperazin-1-yl)-[1,2,4]triazolo[4,3-b]pyridazine and 4-difluoromethylbenzaldehyde.

1H NMR (399.9 MHz, CDCl3) δ 2.54-2.69 (4H, m), 3.55-3.72 (6H, m), 6.65 (1H, t), 7.02 (1H, d), 7.12 (1H, t), 7.43-7.52 (4H, m), 7.91 (1H, d); m/z=396 [M+H]+.

The 4-difluoromethylbenzaldehyde used as starting material was obtained in 34% yield by an analogous method to Example 779, preparation of starting materials, starting from 1-bromo-3-(difluoromethyl)benzene.

1H NMR (399.9 MHz, CDCl3) δ 6.71 (1H, t), 7.69 (2H, d), 7.98 (2H, d), 10.08 (1H, s); m/z=155 [M–H]–.

EXAMPLE 827

Preparation of 6-[4-[4-(difluoromethyl)benzyl]piperazin-1-yl]-3-(trifluoromethyl)[1,2,4]triazolo[4,3-b]pyridazine

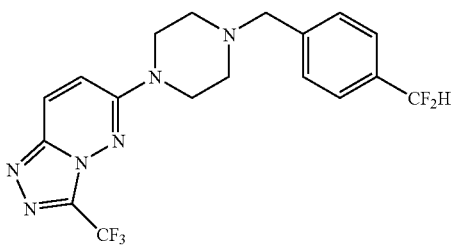

Obtained in 23% yield by General Synthetic Method 5, starting from 6-(piperazin-1-yl)-3-(trifluoromethyl)-[1,2,4]triazolo[4,3-b]pyridazine and 4-difluoromethylbenzaldehyde (obtained as described in Example 826, preparation of starting materials).

1H NMR (399.9 MHz, CDCl3) δ 2.57-2.70 (4H, m), 3.61-3.73 (6H, m), 6.65 (1H, t), 7.05 (1H, d), 7.45-7.51 (4H, m), 7.93 (1H, d); m/z=414 [M+H]+.

EXAMPLES 828

Preparation of 6-[(3R)-3-methyl-4-(pyridin-4-ylmethyl)piperazin-1-yl]-3-(trifluoromethyl)[1,2,4]triazolo[4,3-b]pyridazine

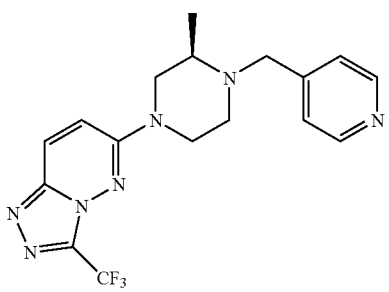

Obtained in 58% yield by General Synthetic Method 5, starting from 6-[(3R)-3-methylpiperazin-1-yl]-3-(trifluoromethyl)-[1,2,4]triazolo[4,3-b]pyridazine (obtained as described in Example 564, preparation of starting materials) and pyridine-4-carboxaldehyde.

1H NMR (399.9 MHz, CDCl3) δ 1.21 (3H, d), 2.34 (1H, ddd), 2.66-2.73 (1H, m), 2.81 (1H, ddd), 3.15 (1H, dd), 3.29 (1H, d), 3.37 (1H, ddd), 3.81-3.91 (2H, m), 4.04 (1H, d), 7.05 (1H, d), 7.32 (2H, d), 7.93 (1H, dd), 8.57 (2H, dd); m/z=378 [M+H]+.

EXAMPLES 829-830

The following compounds were prepared in 19-28% yield by General Synthetic Method 5, starting from 6-[(3R)-3-methylpiperazin-1-yl]-3-(trifluoromethyl)-[1,2,4]triazolo[4,3-b]pyridazine and the appropriate aldehyde:—

| Ex. | R | 1H NMR (399.9 MHz, CDCl3) | m/z [M + H]+ |
|---|---|---|---|
| 829 | H | δ 1.22-1.33 (3H, m), 2.37-2.58 (1H, m), 2.66-2.84 (1H, m), 2.84-3.01 (1H, m), 3.08-3.27 (1H, m), 3.30-3.62 (2H, m), 3.84-3.94 (2H, m), 4.16 (1H, d), 7.05 (1H, d), 7.18-7.23 (1H, m), 7.44-7.52 (1H, m), 7.69 (1H, t), 7.92 (1H, d), 8.58 (1H, dd) | 378 |
| 830 | Br | δ 1.21 (3H, d), 2.42-2.52 (1H, m), 2.66-2.81 (1H, m), 2.89-2.91 (1H, m), 3.13 (1H, t), 3.37 (1H, t), 3.58 (1H, d), 3.87 (2H, d), 4.07 (1H, d), 7.05 (1H, d), 7.38 (1H, d), 7.48-7.56 (2H, m), 7.93 (1H, d) | 456 |

EXAMPLES 831-836

The following compounds were prepared in 8-30% yield by General Synthetic Method 5, starting from 6-[(3R)-3-methylpiperazin-1-yl]-3-(trifluoromethyl)-[1,2,4]triazolo[4,3-b]pyridazine and the appropriate aldehyde:—

| Ex. | R | 1H NMR (399.9 MHz, CDCl3) | m/z [M + H]+ |
|---|---|---|---|
| 831 | 6-CF3 | δ 1.24 (3H, d), 2.36 (1H, t), 2.67-2.81 (2H, m), 3.17 (1H, t), 3.34-3.40 (2H, m), 3.81-3.90 (2H, m), 4.11 (1H, d), 7.05 (1H, dd), 7.67 (1H, d), 7.86-7.92 (1H, m), 7.93 (1H, d), 8.71 (1H, s) | 446 |
| 832 | 2-Cl | δ 1.22 (3H, d), 2.45 (1H, t), 2.71-2.87 (2H, m), 3.17 (1H, t), 3.39 (1H, t), 3.48 (1H, d), 3.86 (2H, t), 4.03 (1H, d), 7.06 (1H, d), 7.85-7.95 (2H, m), 8.26-8.36 (1H, m) (1H obscured by CHCl3) | 412 |
| 833 | 6-Cl | δ 1.20-1.27 (3H, m), 2.25-2.41 (1H, m), 2.69-2.78 (2H, m), 3.09-3.20 (1H, m), 3.26-3.34 (2H, m), 3.80-3.88 (2H, m), 4.00-4.03 (1H, m), 7.04 (1H, d), 7.31-7.36 (1H, m), 7.64-7.71 (1H, m), 7.93 (1H, d), 8.35 (1H, d) | 412 |
| 834 | 6-OMe | δ 1.24 (3H, d), 2.25-2.30 (1H, m), 2.59-2.69 (1H, m), 2.79-2.82 (1H, m), 3.12 (1H, t), 3.22 (1H, d), 3.27-3.35 (1H, m), 3.79-3.87 (2H, m), 3.94 (3H, s), 3.94-3.99 (1H, m), 6.74 (1H, d), | 409 |

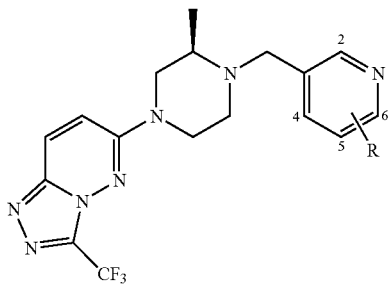

| Ex. | R | 1H NMR (399.9 MHz, CDCl3) | m/z [M + H]+ |
|---|---|---|---|
| | | 7.04 (1H, d), 7.57-7.59 (1H, m), 7.91 (1H, d), 8.07 (1H, s) | |
| 835 | 5-Br, 2-F | δ 1.21-1.24 (3H, m), 2.39-2.47 (1H, m), 2.68-2.80 (1H, m), 2.85-2.87 (1H, m), 3.11-3.20 (1H, m), 3.39-3.42 (2H, m), 3.82-3.97 (3H, m), 7.06 (1H, d), 7.94 (1H, d), 7.99-8.08 (1H, m), 8.18 (1H, s) | 475 |
| 836 | 5-F | δ 1.16 (3H, d), 2.22-2.35 (1H, m), 2.65-2.76 (2H, m), 3.04-3.16 (1H, m), 3.35-3.34 (2H, m), 3.75-3.83 (2H, m), 3.99 (1H, d), 6.98 (1H, d), 7.34-7.49 (1H, m), 7.86 (1H, d), 8.33 (2H, s) | 397 |

EXAMPLE 837

Preparation of 5-[[5-[3-(trifluoromethyl)[1,2,4]triazolo[4,3-b]pyridazin-6-yl]hexahydropyrrolo[3,4-c]pyrrol-2(1H)-yl]methyl]pyridine-2-carbonitrile

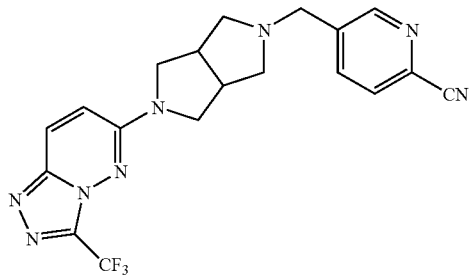

Obtained in 76% yield by an analogous method to Example 307, starting from 6-[5-[(6-bromopyridin-3-yl)methyl]hexahydropyrrolo[3,4-c]pyrrol-2(1H)-yl]-3-(trifluoromethyl)[1,2,4]triazolo[4,3-b]pyridazine (obtained as described in Example 797).

1H NMR (399.9 MHz, CDCl3) δ 2.63-2.70 (4H, m), 3.43 (2H, dd), 3.45 (2H, s), 3.71 (2H, s), 3.83 (2H, dd), 6.87 (1H, d), 7.65 (1H, d), 7.78 (1H, d), 7.91 (1H, d), 8.65 (1H, s); m/z=416 [M+H]+.

EXAMPLE 838

Preparation of 5-[[4-[3-(trifluoromethyl)[1,2,4]triazolo[4,3-b]pyridazin-6-yl]piperazin-1-yl]methyl]pyridine-2-carbonitrile

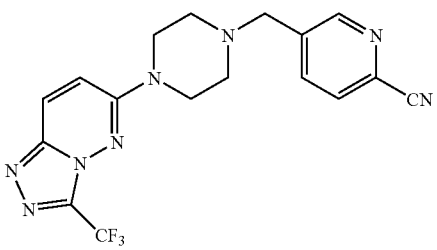

Obtained in 49% yield by an analogous method to Example 307, starting from 6-[4-[(6-bromopyridin-3-yl)methyl]piperazin-1-yl]-3-(trifluoromethyl)[1,2,4]triazolo[4,3-b]pyridazine (obtained as described in Example 374).

1H NMR (399.9 MHz, CDCl3) δ 2.58-2.69 (4H, m), 3.60-3.75 (6H, m), 7.06 (1H, d), 7.70 (1H, d), 7.83-7.90 (1H, m), 7.95 (1H, d), 8.71 (1H, s); m/z=390 [M+H]+.

EXAMPLES 839-841

The following compounds were prepared in 62-77% yield by General Synthetic Method 5, starting from 6-[(1R,5S)-3,8-diazabicyclo[3.2.1]oct-3-yl]-3-(trifluoromethyl)[1,2,4]triazolo[4,3-b]pyridazine (obtained as described in Example 553, preparation of starting materials) and the appropriate aldehyde:—

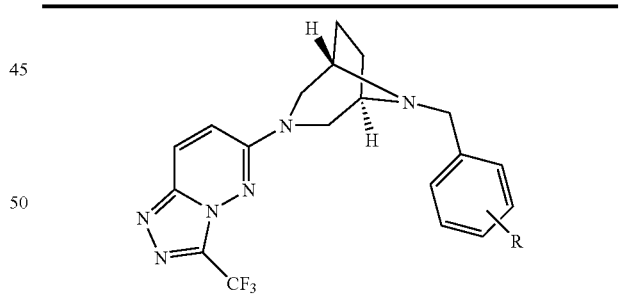

| Ex. | R | 1H NMR (399.9 MHz, DMSO-d6) | m/z [M + H]+ |
|---|---|---|---|
| 839 | 4-F | δ 1.64 (2H, m), 2.00-2.04 (2H, m), 3.16-3.19 (2H, m), 3.58 (2H, s), 3.81-3.84 (2H, m), 7.14-7.18 (2H, m), 7.43-7.47 (2H, m), 7.50 (1H, d), 8.24 (1H, d) | 407 |
| 840 | 3-CN | δ 1.65-1.67 (2H, m), 2.02-2.05 (2H, m), 3.20-3.23 (2H, m), 3.33 (2H, d), 3.67 (2H, s), 3.82-3.85 (2H, m), 7.51 (1H, d), 7.55-7.59 (1H, m), 7.73-7.76 (1H, m), 7.77-7.79 (1H, m), 7.86 (1H, s), 8.25 (1H, d) | 414 |
| 841 | 4-CN | δ 1.65-1.68 (2H, m), 2.01-2.04 (2H, m), 3.19-3.22 (2H, m), 3.31-3.34 (2H, m, partially obscured by solvent peak), 3.71 (2H, s), 3.82-3.86 (2H, m), | 414 |

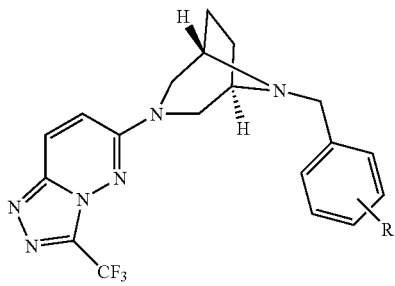

| Ex. | R | 1H NMR (399.9 MHz, DMSO-d6) | m/z [M + H]+ |
|---|---|---|---|
| | | 7.51 (1H, d), 7.63-7.65 (2H, m), 7.80-7.83 (2H, m), 8.25 (1H, d) | |

EXAMPLES 842-844

The following compounds were prepared in 42-55% yield by an analogous method to Example 563, starting from 6-(6,6-difluoro-1,4-diazepan-1-yl)-3-(trifluoromethyl)[1,2,4]triazolo[4,3-b]pyridazine and the appropriate aldehyde:—

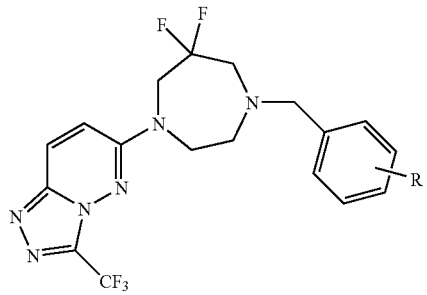

| Ex. | R | 1H NMR (500 MHz, DMSO-d6) | m/z [M + H]+ |
|---|---|---|---|
| 842 | 3-F | δ 2.84-2.91 (m, 2H), 3.06-3.16 (m, 2H), 3.78 (s, 2H), 3.80-3.87 (m, 2H), 4.29-4.38 (m, 2H), 6.95-7.05 (m, 3H), 7.16-7.22 (m, 1H), 7.62 (d, 1H), 8.32 (d, 1H) | 431 |
| 843 | 4-CN | δ 2.83-2.89 (m, 2H), 3.07-3.17 (m, 2H), 3.79-3.85 (m, 2H), 3.85 (s, 2H), 4.29-4.38 (m, 2H), 7.39 (d, 2H), 7.58 (d, 2H), 7.62 (d, 1H), 8.33 (d, 1H) | 438 |
| 844 | 3-CN | δ 2.84-2.91 (m, 2H), 3.06-3.17 (m, 2H), 3.82 (s, 2H), 3.82-3.86 (m, 2H), 4.29-4.39 (m, 2H), 7.33 (dd, 1H), 7.53 (d, 1H), 7.59-7.66 (m, 2H), 7.68 (s, 1H), 8.32 (d, 1H) | 438 |

EXAMPLE 845

Preparation of 6-[4-[4-[2-(1H-imidazol-1-yl)ethoxy]phenyl]piperazin-1-yl]-3-(trifluoromethyl)[1,2,4]triazolo[4,3-b]pyridazine

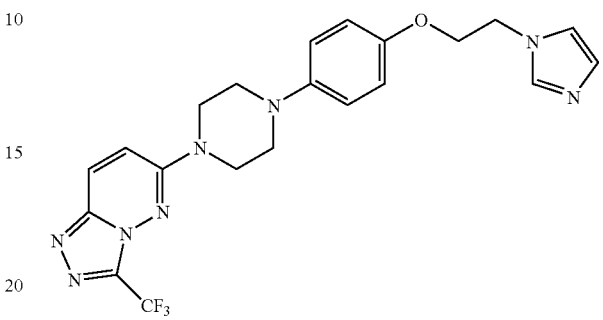

Obtained in 6% yield by an analogous method to Example 514, starting from 4-[4-[3-(trifluoromethyl)[1,2,4]triazolo[4,3-b]pyridazin-6-yl]piperazin-1-yl]phenol and 1-(2-hydroxyethyl)imidazole.

1H NMR (399.9 MHz, DMSO-d6) δ 3.18 (4H, t), 3.76 (1H, t), 4.18 (2H, t), 4.33 (2H, t), 6.82-6.99 (5H, m), 7.26 (1H, s), 7.53-7.72 (2H, m), 8.29 (1H, d); m/z=459 [M+H]+.

EXAMPLE 846

Preparation of 6-[4-[4-[2-(1H-imidazol-1-yl)ethoxy]phenyl]piperidin-1-yl]-3-(trifluoromethyl)[1,2,4]triazolo[4,3-b]pyridazine

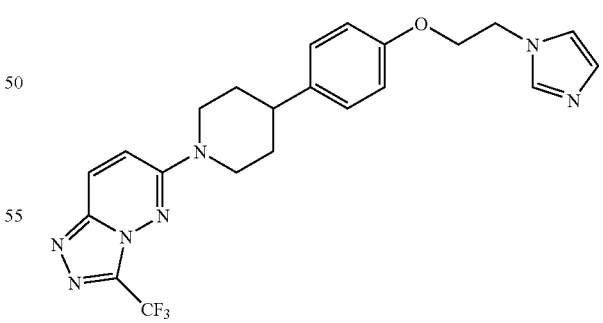

Obtained in 38% yield by an analogous method to Example 513, starting from 4-[4-[3-(trifluoromethyl)[1,2,4]triazolo[4,3-b]pyridazin-6-yl]piperidin-1-yl]phenol and 1-(2-hydroxyethyl)imidazole.

1H NMR (399.9 MHz, DMSO-d6) δ 1.58-1.73 (2H, m), 1.86 (2H, d), 2.76-2.88 (1H, m), 3.04-3.17 (2H, m), 4.18-4.29

(2H, m), 4.32-4.47 (4H, m), 6.83-6.93 (3H, m), 7.15-7.27 (3H, m), 7.62-7.70 (2H, m), 8.26 (1H, d); m/z=458 [M+H]+.

EXAMPLE 847

Preparation of 6-[4-[4-[2-(1H-pyrazol-1-yl)ethoxy]phenyl]piperazin-1-yl]-3-(trifluoromethyl)[1,2,4]triazolo[4,3-b]pyridazine

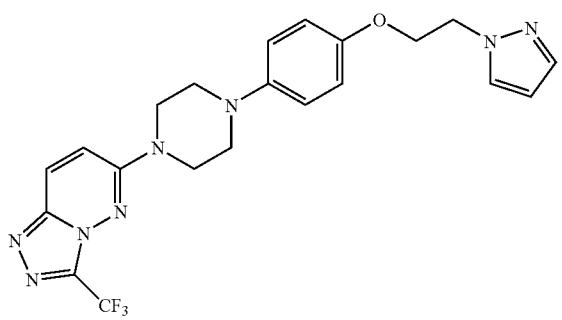

Sodium hydride (60% dispersion in oil, 16.97 mg, 0.42 mmol) was added to 1H-pyrazole (28.9 mg, 0.42 mmol) in DMF (2 mL) at 20° C. under nitrogen. The resulting suspension was stirred at 20° C. for 20 minutes. 6-[4-[4-(2-Bromoethoxy)phenyl]piperazin-1-yl]-3-(trifluoromethyl)-[1,2,4]triazolo[4,3-b]pyridazine (100 mg, 0.21 mmol) was added and the reaction stirred at 20° C. for 1 hour. Water (25 mL) was then added and the resulting precipitate filtered off, washed with ether and dried overnight under vacuum at 50° C. to give 6-[4-[4-[2-(1H-pyrazol-1-yl)ethoxy]phenyl]piperazin-1-yl]-3-(trifluoromethyl)[1,2,4]triazolo[4,3-b]pyridazine (66.0 mg, 68%) as a pale yellow solid.

1H NMR (399.9 MHz, DMSO-d6) δ 3.17 (4H, t), 3.73 (4H, t), 4.27 (2H, t), 4.46 (2H, t), 6.25 (1H, d), 6.84 (2H, d), 6.96 (2H, d), 7.48 (1H, d), 7.68 (1H, d), 7.79 (1H, d), 8.29 (1H, d); m/z=459 [M+H]+.

The starting 6-[4-[4-(2-bromoethoxy)phenyl]piperazin-1-yl]-3-(trifluoromethyl)-[1,2,4]triazolo[4,3-b]pyridazine was prepared as follows:

DIAD (1.625 mL, 8.25 mmol) was added to 4-[4-[3-(trifluoromethyl)[1,2,4]triazolo[4,3-b]pyridazin-6-yl]piperazin-1-yl]phenol (obtained as described in Example 514, preparation of starting materials) (3.01 g, 8.25 mmol), 2-bromoethanol (0.645 mL, 9.08 mmol) and triphenylphosphine (2.165 g, 8.25 mmol) in THF (150 mL) at 20° C. under nitrogen. The resulting solution was stirred at 20° C. for 16 hours. The crude product was purified by flash silica chromatography, elution gradient 0 to 3% MeOH in DCM to afford 6-[4-[4-(2-bromoethoxy)phenyl]piperazin-1-yl]-3-(trifluoromethyl)-[1,2,4]triazolo[4,3-b]pyridazine (0.765 g, 19.67%) as a pale yellow solid.

1H NMR (399.9 MHz, CDCl₃) δ 3.22 (4H, t), 3.62 (2H, t), 3.79 (4H, t), 4.26 (2H, t), 6.87-6.96 (4H, m), 7.11 (1H, d), 7.98 (1H, d); m/z=473 [M+H]+

EXAMPLE 848

Preparation of 1-[2-[4-[4-[3-(trifluoromethyl)[1,2,4]triazolo[4,3-b]pyridazin-6-yl]piperazin-1-yl]phenoxy]ethyl]-1H-pyrazole-4-carbonitrile

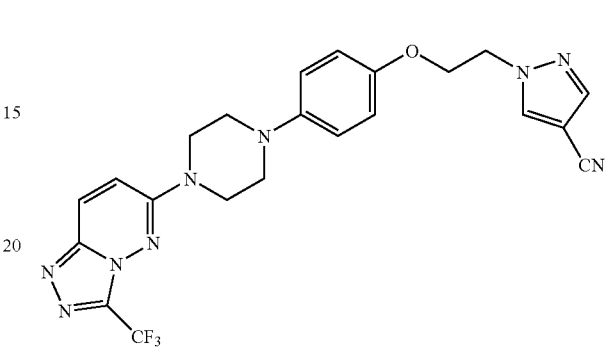

Obtained in 75% yield by an analogous method to Example 847, starting from 6-[4-[4-(2-bromoethoxy)phenyl]piperazin-1-yl]-3-(trifluoromethyl)-[1,2,4]triazolo[4,3-b]pyridazine and 4-cyanopyrazole.

1H NMR (399.9 MHz, DMSO-d6) δ 3.19 (4H, t), 3.76 (4H, t), 4.32 (2H, t), 4.56 (2H, t), 6.85 (2H, d), 6.97 (2H, d), 7.67 (1H, d), 8.09 (1H, s), 8.29 (1H, d), 8.64 (1H, s); m/z=484 [M+H]+.

EXAMPLE 849

Preparation of 6-[4-[4-[2-(1H-pyrazol-1-yl)ethoxy]phenyl]piperidin-1-yl]-3-(trifluoromethyl)[1,2,4]triazolo[4,3-b]pyridazine

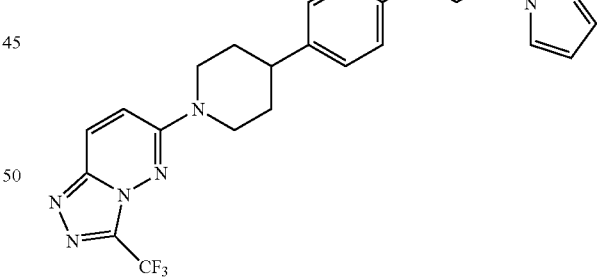

Obtained in 67% yield by an analogous method to Example 847, starting from 6-[4-[4-(2-bromoethoxy)phenyl]piperidin-1-yl]-3-(trifluoromethyl)-[1,2,4]triazolo[4,3-b]pyridazine and pyrazole.

1H NMR (399.9 MHz, DMSO-d6) δ 1.59-1.74 (2H, m), 1.86 (2H, d), 2.76-2.86 (1H, m), 3.07 (2H, t), 4.31 (2H, t), 4.36-4.44 (2H, m), 4.47 (2H, t), 6.25 (1H, d), 6.85 (2H, d), 7.18 (2H, d), 7.46 (1H, d), 7.65 (1H, d), 7.79 (1H, d), 8.24 (1H, d); m/z=458 [M+H]+.

The starting 6-[4-[4-(2-bromoethoxy)phenyl]piperidin-1-yl]-3-(trifluoromethyl)-[1,2,4]triazolo[4,3-b]pyridazine was obtained in 29% yield by an analogous method to Example 847, preparation of starting materials, starting from 4-[4-[3-(trifluoromethyl)[1,2,4]triazolo[4,3-b]pyridazin-6-yl]piperidin-1-yl]phenol (obtained as described in Example 513, preparation of starting materials).

1H NMR (399.9 MHz, DMSO-d6) δ 1.61-1.74 (2H, m), 1.87 (2H, d), 2.77-2.88 (1H, m), 3.09 (2H, t), 3.79 (2H, t), 4.29 (2H, t), 4.40 (2H, d), 6.89 (2H, d), 7.19 (2H, d), 7.68 (1H, d), 8.24 (1H, d); m/z=472 [M+H]+.

EXAMPLE 850

Preparation of 1-[2-[4-[4-[3-(trifluoromethyl)[1,2,4]triazolo[4,3-b]pyridazin-6-yl]piperidin-1-yl]phenoxy]ethyl]-1H-pyrazole-4-carbonitrile

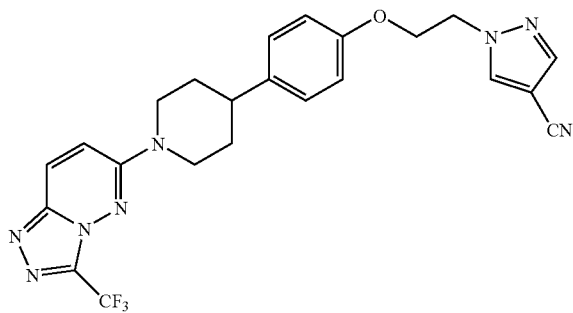

Obtained in 50% yield by an analogous method to Example 847, starting from 6-[4-[4-(2-bromoethoxy)phenyl]piperidin-1-yl]-3-(trifluoromethyl)-[1,2,4]triazolo[4,3-b]pyridazine (obtained as described in Example 849, preparation of starting materials) and 4-cyanopyrazole.

1H NMR (399.9 MHz, DMSO-d6) δ 1.58-1.74 (2H, m), 1.86 (2H, d), 2.76-2.87 (1H, m), 3.11 (2H, t), 4.31-4.47 (4H, m), 4.58 (2H, t), 6.86 (2H, d), 7.17 (2H, d), 7.68 (1H, d), 8.07 (1H, s), 8.23 (1H, d), 8.65 (1H, s); m/z=484 [M+H]+.

EXAMPLE 851

Preparation of N-(2-methoxyethyl)-N-methyl-2-[4-[1-[3-(trifluoromethyl)[1,2,4]triazolo[4,3-b]pyridazin-6-yl]piperidin-4-yl]phenoxy]acetamide

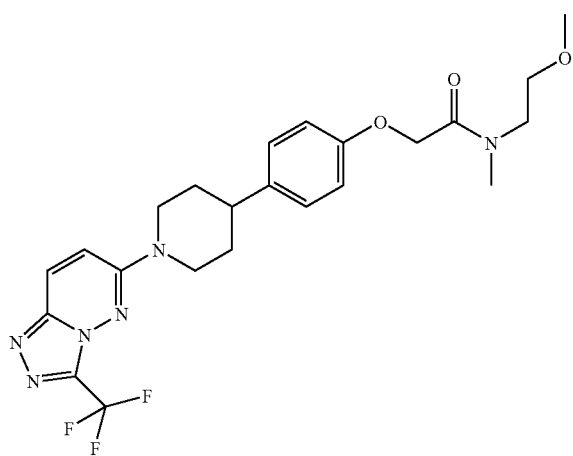

N-(2-methoxyethyl)methylamine (25 mg, 0.28 mmol) was added to 2-[4-[1-[3-(trifluoromethyl)-[1,2,4]triazolo[4,3-b]pyridazin-6-yl]piperidin-4-yl]phenoxy]acetic acid (100 mg, 0.24 mmol), HATU (108 mg, 0.28 mmol) and DIPEA (0.124 mL, 0.71 mmol) in DMF (2 mL). The resulting solution was stirred at ambient temperature for 3 hours then purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to give N-(2-methoxyethyl)-N-methyl-2-[4-[1-[3-(trifluoromethyl)[1,2,4]triazolo[4,3-b]pyridazin-6-yl]piperidin-4-yl]phenoxy]acetamide (26 mg, 22%).

1H NMR (499.8 MHz, DMSO-d6) δ 1.69 (2H, m), 1.93 (2H, m), 2.83 (1H, m), 3.14 (2H, m), 3.28 (3H, s), 3.48 (4H, m), 4.37 (2H, m), 4.72 (2H, s), 6.86 (2H, d), 7.16 (2H, d), 7.55 (1H, d), 8.13 (1H, d), 3H obscured by water peak; m/z=493 [M+H]+.

The starting 2-[4-[1-[3-(trifluoromethyl)-[1,2,4]triazolo[4,3-b]pyridazin-6-yl]piperidin-4-yl]phenoxy]acetic acid was prepared as follows:

Preparation of methyl 2-[4-[1-[3-(trifluoromethyl)-[1,2,4]triazolo[4,3-b]pyridazin-6-yl]piperidin-4-yl]phenoxy]acetate Methyl 2-bromoacetate (0.418 mL, 4.42 mmol) was added to 4-[1-[3-(trifluoromethyl)-[1,2,4]triazolo[4,3-b]pyridazin-6-yl]piperidin-4-yl]phenol (obtained as described in Example 513, preparation of starting materials) (1.07 g, 2.94 mmol) and potassium carbonate (0.814 g, 5.89 mmol) in DMF (20 mL). The resulting suspension was stirred at ambient temperature for 16 hours. The reaction mixture was evaporated to dryness then water (50 mL) added and stirring continued for 20 minutes. The resulting precipitate was collected by filtration, washed with water then ether and dried to afford methyl 2-[4-[1-[3-(trifluoromethyl)-[1,2,4]triazolo[4,3-b]pyridazin-6-yl]piperidin-4-yl]phenoxy]acetate (1.290 g, 100%).

1H NMR (399.9 MHz, DMSO-d6) δ 1.67 (2H, m), 1.88 (2H, m), 2.81 (1H, m), 3.09 (2H, m), 3.70 (3H, s), 4.42 (2H, m), 4.77 (2H, s), 6.86 (2H, d), 7.19 (2H, d), 7.67 (1H, d), 8.25 (1H, d); m/z=436 [M+H]+.

Preparation of 2-[4-[1-[3-(trifluoromethyl)-[1,2,4]triazolo[4,3-b]pyridazin-6-yl]piperidin-4-yl]phenoxy]acetic acid Lithium hydroxide monohydrate (0.622 g, 14.81 mmol) was added to 2-[4-[1-[3-(trifluoromethyl)-[1,2,4]triazolo[4,3-b]pyridazin-6-yl]piperidin-4-yl]phenoxy]acetate (1.29 g, 2.96 mmol) in a mixture of THF (20 mL), water (10 mL) and MeOH (5 mL). The resulting mixture was stirred at ambient temperature for 16 hours. The solvents were evaporated then the residues were suspended in water and acidified to pH 4 with 1M citric acid. The resulting precipitate was collected by filtration, washed with water and dried to afford 2-[4-[1-[3-(trifluoromethyl)-[1,2,4]triazolo[4,3-b]pyridazin-6-yl]piperidin-4-yl]phenoxy]acetic acid (1.020 g, 82%).

1H NMR (399.9 MHz, DMSO-d6) δ 1.66 (2H, m), 1.88 (2H, m), 2.78 (1H, m), 3.09 (2H, m), 4.17 (2H, s), 4.41 (2H, m), 6.74 (2H, d), 7.12 (2H, d), 7.66 (1H, d), 8.23 (1H, d); m/z=422 [M+H]+.

EXAMPLE 852

Preparation of 6-[4-[4-[2-(4-acetylpiperazin-1-yl)ethoxy]phenyl]piperidin-1-yl]-3-(trifluoromethyl)[1,2,4]triazolo[4,3-b]pyridazine

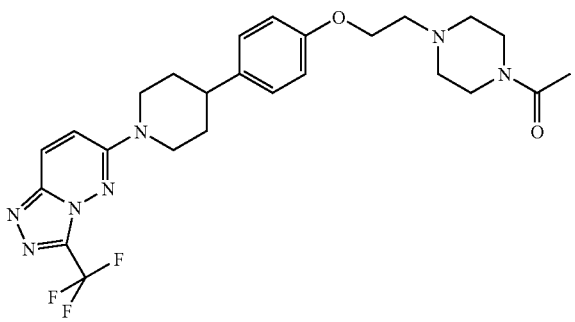

A solution of acetyl chloride (0.029 mL, 0.40 mmol) in DCM (0.5 mL) was added dropwise to 6-[4-[4-(2-piperazin-1-ylethoxy)phenyl]piperidin-1-yl]-3-(trifluoromethyl)[1,2,4]triazolo[4,3-b]pyridazine (obtained as described in Example 727) (160 mg, 0.34 mmol) and triethylamine (0.094 mL, 0.67 mmol) in DCM (1 mL) cooled to 0° C. under nitrogen. The resulting solution was stirred at 0° C. for 5 minutes then allowed to warm to room temperature and stirred for 15 minutes. The reaction mixture was diluted with water (2 mL), passed through a phase separating cartridge and the organic layer evaporated to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[4-[2-(4-acetylpiperazin-1-yl)ethoxy]phenyl]piperidin-1-yl]-3-(trifluoromethyl)[1,2,4]triazolo[4,3-b]pyridazine (60.0 mg, 35%).

1H NMR (399.9 MHz, CDCl3) δ 1.76 (2H, m), 2.00 (2H, m), 2.08 (3H, s), 2.53-2.59 (4H, m), 2.75-2.84 (3H, m), 3.12 (2H, m), 3.48 (2H, m), 3.63 (2H, m), 4.10 (2H, t), 4.37 (2H, m), 6.87 (2H, d), 7.13 (3H, m), 7.92 (1H, d); m/z=518 [M+H]+.

EXAMPLE 853

Preparation of 6-[4-[4-[2-[4-(methylsulfonyl)piperazin-1-yl]ethoxy]phenyl]piperidin-1-yl]-3-(trifluoromethyl)[1,2,4]triazolo[4,3-b]pyridazine

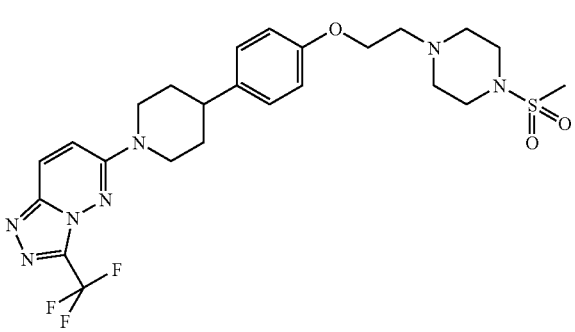

A solution of methanesulfonyl chloride (0.034 mL, 0.44 mmol) in DCM (0.5 mL) was added dropwise to 6-[4-[4-(2-piperazin-1-ylethoxy)phenyl]piperidin-1-yl]-3-(trifluoromethyl)[1,2,4]triazolo[4,3-b]pyridazine (obtained as described in Example 727) (175 mg, 0.37 mmol) and triethylamine (0.103 mL, 0.74 mmol) in DCM (1 mL) cooled to 0° C. under nitrogen. The resulting solution was stirred at 0° C. for 5 minutes then allowed to warm to room temperature and stirred for a further 15 minutes. The reaction mixture was diluted with water (2 mL), passed through a phase separating cartridge then the organic layer evaporated to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-[4-[2-[4-(methylsulfonyl)piperazin-1-yl]ethoxy]phenyl]piperidin-1-yl]-3-(trifluoromethyl)[1,2,4]triazolo[4,3-b]pyridazine (122 mg, 60%).

1H NMR (399.9 MHz, CDCl3) δ 1.76 (2H, m), 2.00 (2H, m), 2.70 (4H, m), 2.75-2.83 (4H, m), 2.86 (2H, t), 3.12 (2H, m), 3.26 (4H, m), 4.09 (2H, t), 4.37 (2H, m), 6.86 (2H, d), 7.13 (3H, m), 7.92 (1H, d); m/z=554 [M+H]+.

EXAMPLE 854

Preparation of 6-[4-[4-[3-(4-acetylpiperazin-1-yl)propoxy]phenyl]piperidin-1-yl]-3-(trifluoromethyl)[1,2,4]triazolo[4,3-b]pyridazine

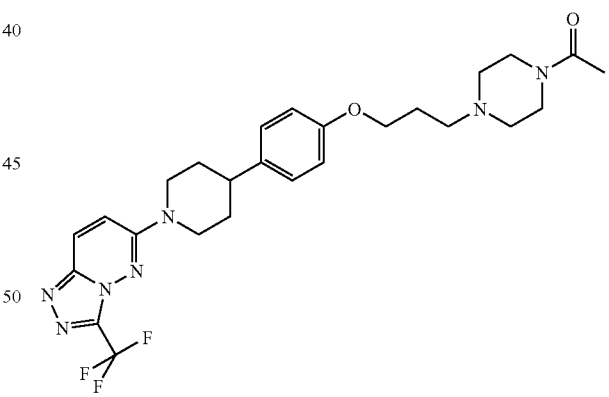

Obtained in 28% yield by an analogous method to Example 852, starting from 6-[4-[4-(3-piperazin-1-ylpropoxy)phenyl]piperidin-1-yl]-3-(trifluoromethyl)[1,2,4]triazolo[4,3-b]pyridazine (obtained as described in Example 728).

1H NMR (399.9 MHz, CDCl3) δ 1.76 (2H, m), 1.92-2.02 (4H, m), 2.08 (3H, s), 2.44 (4H, m), 2.54 (2H, t), 2.78 (1H, m), 3.11 (2H, m), 3.46 (2H, m), 3.62 (2H, m), 4.01 (2H, t), 4.37 (2H, m), 6.86 (2H, d), 7.13 (3H, m), 7.92 (1H, d); m/z=532 [M+H]+.

EXAMPLE 855

Preparation of 6-[4-[4-[3-[4-(methylsulfonyl)piperazin-1-yl]propoxy]phenyl]piperidin-1-yl]-3-(trifluoromethyl)[1,2,4]triazolo[4,3-b]pyridazine

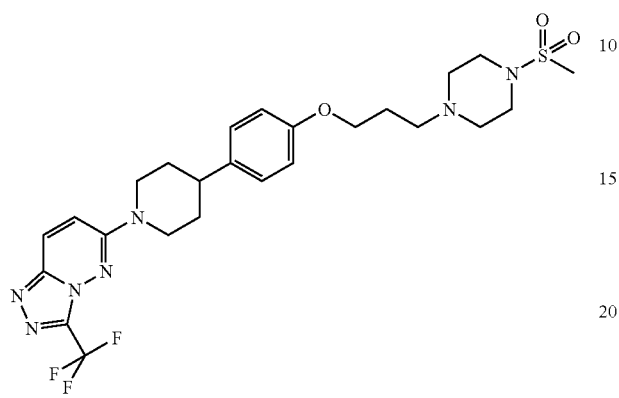

Obtained in 31% yield by an analogous method to Example 853, starting from 6-[4-[4-(3-piperazin-1-ylpropoxy)phenyl]piperidin-1-yl]-3-(trifluoromethyl)[1,2,4]triazolo[4,3-b]pyridazine (obtained as described in Example 728).
1H NMR (399.9 MHz, CDCl3) δ 1.76 (2H, m), 1.92-2.01 (4H, m), 2.57 (6H, m), 2.74-2.82 (4H, m), 3.11 (2H, m), 3.25 (4H, m), 4.00 (2H, t), 4.37 (2H, m), 6.85 (2H, d), 7.12 (3H, m), 7.93 (1H, d); m/z=568 [M+H]+.

EXAMPLE 856

Preparation of 3-(difluoromethyl)-6-[4-[4-[2-(1-methyl-1H-pyrazol-5-yl)ethoxy]phenyl]piperazin-1-yl][1,2,4]triazolo[4,3-b]pyridazine

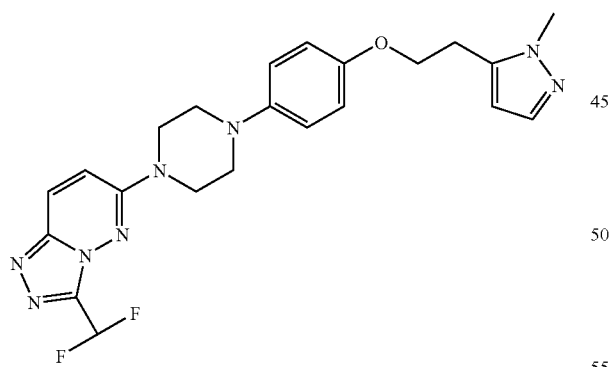

Obtained in 32% yield by an analogous method to Example 514, starting from 4-[4-[3-(difluoromethyl)[1,2,4]triazolo[4,3-b]pyridazin-6-yl]piperazin-1-yl]phenol.
1H NMR (399.9 MHz, DMSO-d6) δ 3.07 (2H, t), 3.17 (4H, m), 3.75 (4H, m), 3.79 (3H, s), 4.15 (2H, t), 6.14 (1H, d), 6.88 (2H, d), 6.97 (2H, d), 7.31 (1H, d), 7.43-7.69 (2H, m), 8.22 (1H, d); m/z=455 [M+H]+.
The 4-[4-[3-(difluoromethyl)[1,2,4]triazolo[4,3-b]pyridazin-6-yl]piperazin-1-yl]phenol used as starting material was prepared in 95% yield by an analogous method to Example 514, preparation of starting materials, starting from 3-(difluoromethyl)[1,2,4]triazolo[4,3-b]pyridazine (obtained as described in General Synthetic Method 1, preparation of starting materials).
1H NMR (399.9 MHz, DMSO-d6) δ 3.11 (4H, m), 3.74 (4H, m), 6.69 (2H, d), 6.87 (2H, d), 7.43-7.69 (2H, m), 8.22 (1H, d), 8.87 (1H, s); m/z=347 [M+H]+.

EXAMPLE 857

Preparation of 4-[4-[3-(trifluoromethyl)-[1,2,4]triazolo[3,4-f]pyridazin-6-yl]piperazin-1-yl]sulfonyl-benzonitrile

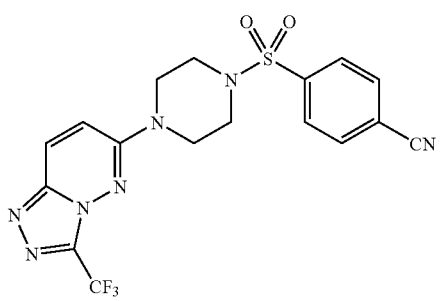

Obtained in 32% yield by an analogous procedure to Example 394, starting from 4-cyanobenzenesulfonyl chloride and 6-(piperazin-1-yl)-3-(trifluoromethyl)-[1,2,4]triazolo[4,3-b]pyridazine.
1H NMR (399.9 MHz, DMSO-d6) δ 3.07 (4H, m), 3.64 (4H, m), 7.46 (1H, d), 7.89 (2H, d), 8.06 (2H, d), 8.18 (1H, d); m/z=438 [M+H]+.

EXAMPLE 858

Preparation of 4-[(1R)-1-[4-[3-(difluoromethyl)-[1,2,4]triazolo[3,4-f]pyridazin-6-yl]piperazin-1-yl]ethyl]benzonitrile

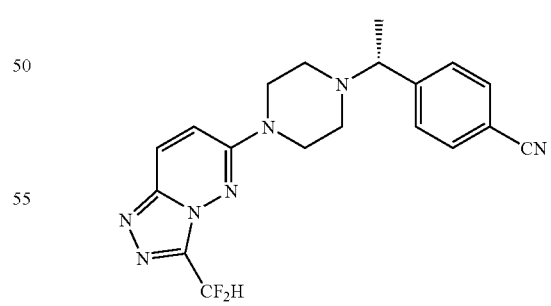

Obtained in 35% yield by an analogous procedure to Example 307, starting from 6-[4-[(1R)-1-(4-bromophenyl)ethyl]piperazin-1-yl]-3-(difluoromethyl)-[1,2,4]triazolo[4,3-b]pyridazine (obtained as described in Example 270).
1H NMR (399.9 MHz, CDCl3) δ 1.39 (3H, d), 2.48-2.53 (2H, m), 2.62-2.68 (2H, m), 3.49 (1H, q), 3.54-3.64 (4H, m), 7.00 (1H, d), 7.12 (1H, t), 7.47-7.49 (2H, m), 7.62-7.65 (2H, m), 7.89 (1H, d); m/z=384 [M+H]+.

EXAMPLE 859

Preparation of 3-(difluoromethyl)-6-[4-[3-fluoro-5-(methylsulfonyl)benzyl]piperazin-1-yl][1,2,4]triazolo[4,3-b]pyridazine

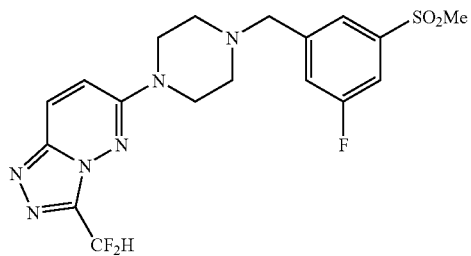

Obtained in 55% yield by General Synthetic Method 5, starting from 6-chloro-3-difluoromethyl-[1,2,4]triazolo[4,3-b]pyridazine and 3-fluoro-5-methylsulfonylbenzaldehyde (obtained as described in Example 778, preparation of starting materials).

1H NMR (399.9 MHz, DMSO) δ 2.53-2.57 (4H, m), 3.30 (3H, s), 3.62-3.66 (4H, m), 3.70 (2H, s), 7.51-7.54 (1H, m), 7.53 (1H, t), 7.58-7.60 (1H, m), 7.70-7.73 (1H, m), 7.77 (1H, d), 8.18-8.21 (1H, m); m/z=441 [M+H]+.

EXAMPLE 860

Preparation of 4-[4-[2-(1-methyl-1H-pyrazol-5-yl)ethoxy]phenyl]-1-[3-(trifluoromethyl)[1,2,4]triazolo[4,3-b]pyridazin-6-yl]piperidin-4-ol

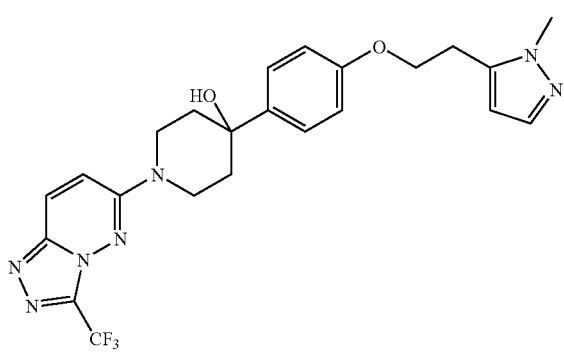

DIAD (0.311 mL, 1.58 mmol) was added dropwise to 4-(4-hydroxyphenyl)-1-[3-(trifluoromethyl)[1,2,4]triazolo[4,3-b]pyridazin-6-yl]piperidin-4-ol (500 mg, 1.32 mmol), 2-(1-methyl-1H-pyrazol-5-yl)ethanol (obtained as described in Example 513, preparation of starting materials) (249 mg, 1.98 mmol) and triphenylphosphine (519 mg, 1.98 mmol) in THF (10 mL) under nitrogen. The resulting suspension was stirred at ambient temperature for 16 hours then the solvents were evaporated to give crude product. The crude product was purified by flash silica chromatography, eluting with EtOAc then a gradient of 3 to 5% MeOH in DCM. Pure fractions were evaporated to dryness to give a solid which was triturated with ether, filtered and dried to give 4-[4-[2-(1-methyl-1H-pyrazol-5-yl)ethoxy]phenyl]-1-[3-(trifluoromethyl)[1,2,4]triazolo[4,3-b]pyridazin-6-yl]piperidin-4-ol (464 mg, 72.2%) as a solid.

1H NMR (399.9 MHz, DMSO-d6) δ 1.72 (2H, m), 1.99 (2H, m), 3.09 (2H, t), 3.43 (2H, m), 3.79 (3H, s), 4.18 (4H, m), 5.12 (1H, s), 6.13 (1H, d), 6.90 (2H, d), 7.30 (1H, d), 7.41 (2H, d), 7.65 (1H, d), 8.23 (1H, d); m/z=488 [M+H]+.

The starting 4-(4-hydroxyphenyl)-1-[3-(trifluoromethyl)[1,2,4]triazolo[4,3-b]pyridazin-6-yl]piperidin-4-ol was prepared as follows:—

Preparation of benzyl 4-[4-(benzyloxy)phenyl]-4-hydroxypiperidine-1-carboxylate n-Butyllithium (1.6M in hexane, 42.9 ml, 107.18 mmol) was added dropwise to 1-(benzyloxy)-4-bromobenzene (28.2 g, 107.18 mmol, CAS 6793-92-6) in THF (367 ml) at −78° C. over a period of 15 minutes under nitrogen. The resulting solution was stirred at −78° C. for 1 hour then benzyl 4-oxopiperidine-1-carboxylate (20 g, 85.74 mmol) in THF (122 ml) was added dropwise. The resulting mixture was stirred at −78° C. for 10 minutes, then allowed to warm to room temperature and stirred for 16 hours. The reaction mixture was evaporated to dryness and quenched with saturated ammonium chloride (50 mL), then then extracted with EtOAc (500 mL). The organic layer was dried over MgSO$_4$, filtered and evaporated to afford crude product. The crude product was purified by flash silica chromatography, elution gradient 1 to 100% EtOAc in isohexane. Pure fractions were evaporated to dryness to afford crude product. The crude product was further purified by flash silica chromatography, elution gradient 0 to 3% MeOH in DCM. Pure fractions were evaporated to dryness to afford benzyl 4-[4-(benzyloxy)phenyl]-4-hydroxypiperidine-1-carboxylate (13.49 g, 30.1%) as a gum.

1H NMR (399.9 MHz, DMSO-d6) δ 1.58 (2H, m), 1.80 (2H, m), 3.27 (2H, m), 3.71 (1H, m), 3.92 (2H, m), 5.10 (4H, m), 6.95 (2H, m), 7.39 (12H, m); m/z=416 [M−H]+.

Preparation of 4-(4-hydroxyphenyl)piperidin-4-ol

10% Palladium on carbon (3.44 g, 3.23 mmol) was added to benzyl 4-[4-(benzyloxy)phenyl]-4-hydroxypiperidine-1-carboxylate (13.49 g, 32.31 mmol) in MeOH (146 mL). The resulting mixture was stirred at room temperature for 20 hours under an atmosphere of hydrogen. The reaction mixture was filtered and evaporated to afford crude product. The crude material was triturated with DCM (100 mL) and MeOH (50 mL) to give a solid which was collected by filtration and dried under vacuum to give 4-(4-hydroxyphenyl)piperidin-4-ol (4.16 g, 66.6%).

1H NMR (399.9 MHz, DMSO-d6) δ 1.50 (2H, m), 1.73 (2H, m), 2.70 (2H, m), 2.90 (2H, m), 4.52 (1H, s), 6.69 (2H, m), 7.25 (2H, m), 9.21 (1H, s); m/z=192 [M−H]+.

Preparation of 4-(4-hydroxyphenyl)-1-[3-(trifluoromethyl)[1,2,4]triazolo[4,3-b]pyridazin-6-yl]piperidin-4-ol DIPEA (1.174 mL, 6.74 mmol) was added to 6-chloro-3-(trifluoromethyl)-[1,2,4]triazolo[4,3-b]pyridazine (1 g, 4.49 mmol) and 4-(4-hydroxyphenyl)piperidin-4-ol (0.955 g, 4.94 mmol) in DMF (10 mL). The resulting solution was stirred at 80° C. for 1 hour. The reaction mixture was cooled to room temperature then evaporated to dryness. The residues were triturated with water and the resulting solid collected by filtration, washed with further water followed by ether, then dried under vacuum to afford 4-(4-hydroxyphenyl)-1-[3-(trifluoromethyl)[1,2,4]triazolo[4,3-b]pyridazin-6-yl]piperidin-4-ol (1.680 g, 99%) as a solid.

1H NMR (399.9 MHz, DMSO-d6) δ 1.72 (2H, m), 1.95 (2H, m), 3.42 (2H, m), 4.17 (2H, m), 5.01 (1H, s), 6.70 (2H, d), 7.28 (2H, d), 7.65 (1H, d), 8.23 (1H, d), 9.20 (1H, s); m/z=380 [M+H]+.

EXAMPLE 861

Preparation of 4-[4-[(1-methyl-1H-pyrazol-5-yl)methoxy]phenyl]-1-[3-(trifluoromethyl)[1,2,4]triazolo[4,3-b]pyridazin-6-yl]piperidin-4-ol

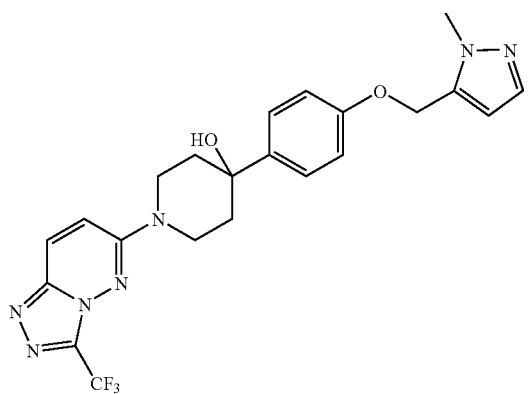

Obtained in 76% yield by an analogous method to Example 860, starting from 4-(4-hydroxyphenyl)-1-[3-(trifluoromethyl)[1,2,4]triazolo[4,3-b]pyridazin-6-yl]piperidin-4-ol and 2-(1-methyl-1H-pyrazol-5-yl)methanol.

1H NMR (399.9 MHz, DMSO-d6) δ 1.73 (2H, d), 1.95-2.07 (2H, m), 3.39-3.50 (2H, m), 3.83 (3H, s), 4.19 (2H, d), 5.13 (1H, s), 5.17 (2H, s), 6.37 (1H, d), 7.00 (2H, d), 7.38 (1H, d), 7.44 (2H, d), 7.66 (1H, d), 8.12 (1H, d); m/z=474 [M+H]+.

EXAMPLE 862

Preparation of 4-[4-[2-(dimethylamino)ethoxy]phenyl]-1-[3-(trifluoromethyl)[1,2,4]triazolo[4,3-b]pyridazin-6-yl]piperidin-4-ol

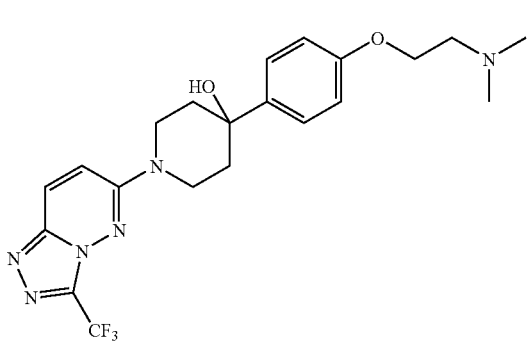

Obtained in 74% yield by an analogous method to Example 860, starting from 4-(4-hydroxyphenyl)-1-[3-(trifluoromethyl)[1,2,4]triazolo[4,3-b]pyridazin-6-yl]piperidin-4-ol and 2-(dimethylamino)ethanol.

1H NMR (399.9 MHz, DMSO-d6) δ 1.73 (2H, d), 1.95-2.06 (2H, m), 2.23 (6H, s), 2.61 (2H, t), 3.88-3.49 (2H, m), 4.04 (2H, t), 4.18 (2H, d), 5.11 (1H, s), 6.89 (2H, d), 7.39 (2H, d), 7.66 (1H, d), 8.23 (1H, d); m/z=451 [M+H]+.

EXAMPLE 863

Preparation of 4-[4-[2-(4-acetylpiperazin-1-yl)ethoxy]phenyl]-1-[3-(trifluoromethyl)[1,2,4]triazolo[4,3-b]pyridazin-6-yl]piperidin-4-ol

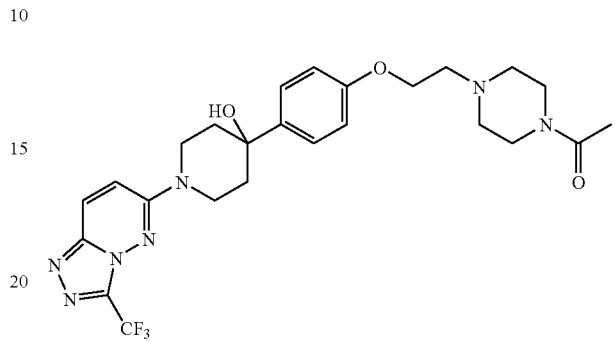

Obtained in 55% yield by an analogous method to Example 860, starting from 4-(4-hydroxyphenyl)-1-[3-(trifluoromethyl)[1,2,4]triazolo[4,3-b]pyridazin-6-yl]piperidin-4-ol and 2-(4-acetylpiperazine-1-yl)ethanol (obtained as described in PCT Int. Appl. WO2003064413, Example 28, preparation of starting materials).

1H NMR (499.8 MHz, DMSO-d6, spectrum recorded at 100° C.) δ 1.79 (2H, d), 1.97-2.07 (8H, m), 2.75 (2H, t), 3.39-3.48 (7H, m), 4.08-4.16 (4H, m), 6.89 (2H, d), 7.41 (2H, d), 7.55 (1H, d), 8.12 (1H, d); m/z=534 [M+H]+.

EXAMPLE 864

Preparation of 2-[4-[4-hydroxy-1-[3-(trifluoromethyl)[1,2,4]triazolo[4,3-b]pyridazin-6-yl]piperidin-4-yl]phenoxy]-N-(2-methoxyethyl)-N-methylacetamide

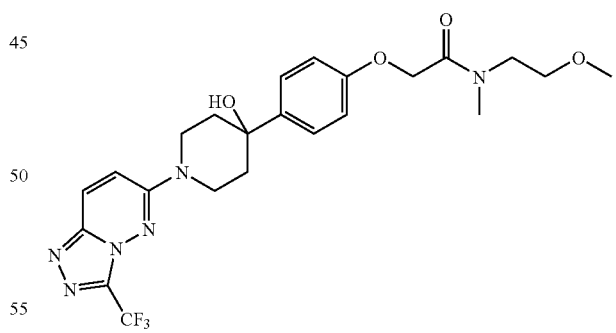

DIPEA (0.321 mL, 1.94 mmol) was added to 2-[4-[4-hydroxy-1-[3-(trifluoromethyl)-[1,2,4]triazolo[4,3-b]pyridazin-6-yl]piperidin-4-yl]phenoxy]acetic acid (283 mg, 0.65 mmol), N-(2-methoxyethyl)methylamine (63 mg, 0.71 mmol) and HATU (270 mg, 0.71 mmol) in DMF (5 mL) at 20° C. under nitrogen. The resulting solution was stirred at 20° C. for 4 hours. Water (50 mL) was then added and the mixture was extracted with DCM (2×50 mL). The combined organics were dried (Na2SO4), filtered and evaporated to give a orange oil. The crude product was purified by flash silica chromatography, elution gradient 0 to 100% EtOAc in isohexane then 0 to 10% MeOH in EtOAc. Pure fractions were evaporated to dryness then tritutated with isohexane, filtered and dried to afford 2-[4-[4-hydroxy-1-[3-(trifluoromethyl)[1,2,4]triazolo [4,3-b]pyridazin-6-yl]piperidin-4-yl]phenoxy]-N-(2-methoxyethyl)-N-methylacetamide (161 mg, 48.9%) as a white solid.

1H NMR (499.8 MHz, DMSO-d6, spectrum recorded at 100° C.) δ 1.79 (2H, d), 1.98-2.06 (2H, m), 2.89-2.99 (6H, m), 3.47-3.54 (6H, m), 3.46-3.54 (6H, m), 4.12 (2H, d), 4.71-4.79 (3H, m), 6.87 (2H, d), 7.39 (2H, d), 7.54 (1H, d), 8.12 (1H, d); m/z=509 [M+H]+.

The starting 2-[4-[4-hydroxy-1-[3-(trifluoromethyl)-[1,2,4]triazolo[4,3-b]pyridazin-6-yl]piperidin-4-yl]phenoxy] acetic acid was prepared as follows:—

Preparation of methyl 2-[4-[4-hydroxy-1-[3-(trifluoromethyl)-[1,2,4]triazolo[4,3-b]pyridazin-6-yl]piperidin-4-yl]phenoxy]acetate Methyl 2-bromoacetate (0.121 mL, 1.28 mmol) was added to 4-(4-hydroxyphenyl)-1-[3-(trifluoromethyl)[1,2,4]triazolo[4,3-b]pyridazin-6-yl]piperidin-4-ol (323 mg, 0.85 mmol) and potassium carbonate (235 mg, 1.70 mmol) in DMF (5 mL). The resulting suspension was stirred at ambient temperature for 16 hours. The reaction mixture was evaporated to dryness, then water (50 mL) was added and the mixture was stirred for 20 minutes. The resulting precipitate was collected by filtration, washed with water then ether and dried to afford methyl 2-[4-[4-hydroxy-1-[3-(trifluoromethyl)-[1,2,4]triazolo[4,3-b]pyridazin-6-yl]piperidin-4-yl]phenoxy]acetate (384 mg, 100%) as a beige solid.

1H NMR (399.9 MHz, CDCl₃) δ 1.93 (2H, d), 2.08-2.18 (2H, m), 3.58 (2H, t), 3.82 (3H, s), 4.14 (2H, d), 4.65 (2H, s), 6.91 (2H, d), 7.13 (1H, d), 7.42 (2H, d), 7.92 (1H, d); m/z=452 [M+H]+.

Preparation of 2-[4-[4-hydroxy-1-[3-(trifluoromethyl)-[1,2,4]triazolo[4,3-b]pyridazin-6-yl]piperidin-4-yl]phenoxy]acetic acid Lithium hydroxide monohydrate (177 mg, 4.21 mmol) was added to 2-[4-[4-hydroxy-1-[3-(trifluoromethyl)-[1,2,4]triazolo[4,3-b]pyridazin-6-yl]piperidin-4-yl]phenoxy]acetate (380 mg, 0.84 mmol) in a mixture of THF (7 mL), water (3.5 mL) and MeOH (3.5 mL). The resulting mixture was stirred at ambient temperature for 16 hours. The solvents were evaporated, then the residues were suspended in water and acidified to pH 4 with 1M citric acid. The resulting precipitate was collected by filtration, washed with water and dried to afford 2-[4-[4-hydroxy-1-[3-(trifluoromethyl)-[1,2,4]triazolo[4,3-b]pyridazin-6-yl]piperidin-4-yl]phenoxy]acetic acid (297 mg, 81%) as a white solid.

1H NMR (399.9 MHz, DMSO-d6) δ 1.73 (2H, d), 1.95-2.06 (2H, m), 3.43 (2H, t), 4.18 (2H, d), 4.67 (2H, s), 5.14 (1H, s), 6.87 (2H, d), 7.42 (2H, d), 7.67 (1H, d), 8.23 (1H, d), 12.94 (1H, bs); m/z=438 [M+H]+.

LIST OF FIGURES

FIG. 1: X-Ray Powder Diffraction Pattern for 4-pyridin-3-yl-1-[3-(trifluoromethyl)[1,2,4]triazolo[4,3-b]pyridazin-6-yl]piperidin-4-ol Anhydrous Form A when measured using CuKa radiation.

FIG. 2: X-Ray Powder Diffraction Pattern for N-(2-methoxyethyl)-N-methyl-4-[1-[3-(trifluoromethyl)[1,2,4]triazolo[4,3-b]pyridazin-6-yl]piperidin-4-yl]benzamide Anhydrous Form A when measured using CuKa radiation.

FIG. 3: X-Ray Powder Diffraction Pattern for 6-[4-[4-[2-(1-Methyl-1H-pyrazol-5-yl)ethoxy]phenyl]piperidin-1-yl]-3-(trifluoromethyl)[1,2,4]triazolo[4,3-b]pyridazine Anhydrous Form A when measured using CuKa radiation.

FIG. 4: X-Ray Powder Diffraction Pattern for 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine Anhydrous Form A when measured using CuKa radiation.

FIG. 5: X-Ray Powder Diffraction Pattern for 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine fumarate when measured using CuKa radiation.

The invention claimed is:

1. A compound of Formula (If), or a pharmaceutically acceptable salt thereof:

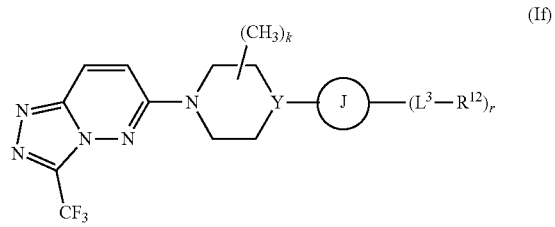

(If)

wherein
Y represents CH, COH or N;
k represents 0, 1 or 2;
J represents:
  phenyl or naphthyl;
  a totally saturated monocyclic 3 to 6 membered carbocyclic ring;
  furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl or thiadiazolyl; or
  a bicyclic 9 membered heteroaryl ring system which comprises 1 or 2 nitrogen atoms, 1 or 2 oxygen atoms, 1 sulphur atom, or 1 nitrogen atom and 1 sulphur atom;
$L^3$ represents a direct bond, $-(CR^9R^{10})_t-$, $-C(O)N(R^{11})-(CH_2)_q-$, $-C(O)N(R^{11})-(CH_2)_q-S(O)_2-$, $-C(O)-(CH_2)_q-$, $-O-(CH_2)_q-$, $-O-(CH_2)_q-NR^{11}-(CH_2)_q-$, $-O-(CH_2)_q-C(O)NR^{11}-(CH_2)_q-$, $-S-$, $-S(O)-$ or $-S(O)_2-$;
$R^9$ and $R^{10}$, identically or differently on each occurrence, represent hydrogen or methyl;
q, identically or differently on each occurrence, represents 0, 1, 2 or 3;
t represents 1, 2 or 3;
$R^{11}$ represents hydrogen or methyl;
$R^{12}$ represents:
  halo, $C_{1-6}$alkyl, $C_{2-6}$alkenyl, $C_{2-6}$alkynyl, carboxy, $C_{1-6}$alkoxy, fluoro$C_{1-6}$alkyl, hydroxy, amino, $N-C_{1-4}$ alkylamino or N,N-di-$C_{1-4}$alkylamino;
  phenyl or naphthyl, wherein the phenyl or naphthyl ring is optionally substituted with 1, 2 or 3 substituents selected from $R^{13}$;
  a monocylic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^{13}$; or a monocylic 4, 5, 6 or 7 membered heterocylic ring which comprises 1, 2, 3 or 4 heteroatoms independently selected from O, N or S and wherein the heterocyclic ring is optionally substituted with 1, 2 or 3 substituents selected from $R^{13}$;

$R^{13}$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, N—$C_{1-4}$alkylamino, N,N-di-$C_{1-4}$alkylamino or —C(O)N$R^{14}R^{15}$ wherein $R^{14}$ and $R^{15}$ independently represent hydrogen or methyl;

r represents 1, 2 or 3 when J represents phenyl or naphthyl;

r represents 0 when J represents a totally saturated monocyclic 3 to 6 membered carbocyclic ring; and r represents 0, 1, 2 or 3 when J represents furanyl, imidazolyl, isothiazolyl, morpholinyl, oxadiazolyl, oxazolyl, isoxazolyl, oxetanyl, tetrahydro-2H-pyranyl, pyrazolyl, pyridazinyl, pyridinyl, pyrrolyl, thiadiazolyl, or a bicyclic 9 membered heteroaryl ring system which comprises 1 or 2 nitrogen atoms, 1 or 2 oxygen atoms, 1 sulphur atom, or 1 nitrogen atom and 1 sulphur atom;

with the proviso that the compound of Formula (If) is other than:

4-{4-[3-(trifluoromethyl)[1,2,4]triazolo[4,3-b]pyridazin-6-yl]piperazin-1-yl}phenol;

6-[4-(1H-indol-3-yl)piperidin-1-yl]-3-(trifluoromethyl)[1,2,4]triazolo[4,3-b]pyridazine;

6-[4-(2,6-dimethylphenyl)piperazin-1-yl]-3-(trifluoromethyl)[1,2,4]triazolo[4,3-b]pyridazine;

6-[4-(4-methoxyphenyl)piperazin-1-yl]-3-(trifluoromethyl)[1,2,4]triazolo[4,3-b]pyridazine;

6-[4-(3-chlorophenyl)piperazin-1-yl]-3-(trifluoromethyl)[1,2,4]triazolo[4,3-b]pyridazine; or 6-[4-(4-fluorophenyl)piperazin-1-yl]-3-(trifluoromethyl)[1,2,4]triazolo[4,3-b]pyridazine.

2. A compound according to claim 1, or a pharmaceutically acceptable salt thereof, wherein Y represents CH or COH.

3. A compound according to claim 1 or a pharmaceutically acceptable salt thereof, wherein Y represents N.

4. A compound according to any one of claims 1 to 3, or a pharmaceutically acceptable salt thereof, wherein J represents phenyl, pyridinyl, indolyl, indazolyl or pyrrolopyridinyl.

5. A compound according to any one of claims 1 to 3, or a pharmaceutically acceptable salt thereof, wherein $L^3$ represents —C(O)N($R^{11}$)—(CH$_2$)$_q$—, —N$R^{11}$C(O)—(CH$_2$)$_q$—, —C(O)—(CH$_2$)$_q$—, or —O—(CH$_2$)$_q$—.

6. A compound according to claim 5, or a pharmaceutically acceptable salt thereof, wherein $R^{11}$ represents methyl.

7. A compound according to claim 5, or a pharmaceutically acceptable salt thereof, wherein $L^3$ represents —O—CH$_2$—CH$_2$—.

8. A compound according to any one of claims 1 to 3, or a pharmaceutically acceptable salt thereof, wherein $R^{12}$ represents fluoro, chloro, methyl, methoxy, difluoromethyl, trifluoromethyl, cyano, hydroxy, pyrrolidinyl, piperidinyl, piperazinyl, methylsulphonyl, morpholinyl or pyrazolyl.

9. A compound according to any one of claims 1 to 3, or a pharmaceutically acceptable salt thereof, wherein $R^{12}$ represents pyrazolyl.

10. A compound according to any one of claims 1 to 3, or a pharmaceutically acceptable salt thereof, wherein $R^{13}$ represents methyl, oxo or hydroxy.

11. A compound according to any one of claims 1 to 3, or a pharmaceutically acceptable salt thereof, wherein r represents 1.

12. A compound according to any one of claims 1 to 3, or a pharmaceutically acceptable salt thereof, wherein J does not represent phenyl or naphthyl and r represents 0.

13. A compound according to claim 1 selected from:
4-pyridin-3-yl-1-[3-(trifluoromethyl)[1,2,4]triazolo[4,3-b]pyridazin-6-yl]piperidin-4-ol;
N-(2-methoxyethyl)-N-methyl-4-[1-[3-(trifluoromethyl)[1,2,4]triazolo[4,3-b]pyridazin-6-yl]piperidin-4-yl]benzamide;
6-[4-[4-[2-(1-methyl-1H-pyrazol-5-yl)ethoxy]phenyl]piperidin-1-yl]-3-(trifluoromethyl)[1,2,4]triazolo[4,3-b]pyridazine;
6-[4-[4-[2-(1-methyl-1H-pyrazol-5-yl)ethoxy]phenyl]piperazin-1-yl]-3-(trifluoromethyl)[1,2,4]triazolo[4,3-b]pyridazine; and
4-[4-[2-(1-methyl-1H-pyrazol-5-yl)ethoxy]phenyl]-1-[3-(trifluoromethyl)[1,2,4]triazolo[4,3-b]pyridazin-6-yl]piperidin-4-ol;
and pharmaceutically acceptable salts thereof.

14. A pharmaceutical composition which comprises a compound according to any one of claims 1 to 3 or 13, or a pharmaceutically acceptable salt thereof, in association with a pharmaceutically acceptable diluent or carrier.

15. A process for the preparation of compounds of Formula (If) which comprises reacting a compound of Formula (IIb), wherein G represents halogen, with an amine of Formula (IIIb), wherein Y, J, $L^3$, $R^{12}$, k and r are as defined hereinbefore in relation to Formula (If):

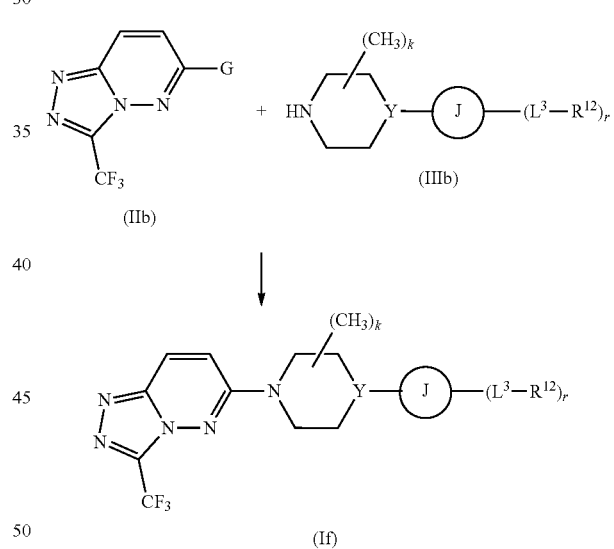

and thereafter, if necessary:
(i) converting a functional group of one compound of the invention into another functional group;
(ii) introducing a new functional group into one compound of the invention;
(iii) removing any protecting groups;
(iv) for compounds of the invention in the form of a single enantiomer separating a racemic compound of the invention into separate enantiomers;
(v) preparing a pharmaceutically acceptable salt thereof; and/or
(vi) preparing a crystalline form thereof.

* * * * *